(12) United States Patent
Wu et al.

(10) Patent No.: US 10,781,218 B2
(45) Date of Patent: Sep. 22, 2020

(54) SUBSTITUTED INHIBITORS OF MENIN-MLL AND METHODS OF USE

(71) Applicants: Kura Oncology, Inc., San Diego, CA (US); The Regents of The University of Michigan, Ann Arbor, MI (US)

(72) Inventors: Tao Wu, Carlsbad, CA (US); Liansheng Li, San Diego, CA (US); Yi Wang, San Diego, CA (US); Pingda Ren, San Diego, CA (US); Jolanta Grembecka, Ann Arbor, MI (US); Tomasz Cierpicki, Ann Arbor, MI (US); Szymon Klossowski, Ann Arbor, MI (US); Jonathan Pollock, Ann Arbor, MI (US); Dmitry Borkin, Ann Arbor, MI (US)

(73) Assignees: KURA ONCOLOGY, INC., San Diego, CA (US); THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 16/082,649

(22) PCT Filed: Mar. 15, 2017

(86) PCT No.: PCT/US2017/022564
§ 371 (c)(1),
(2) Date: Sep. 6, 2018

(87) PCT Pub. No.: WO2017/161028
PCT Pub. Date: Sep. 21, 2017

(65) Prior Publication Data
US 2019/0092784 A1    Mar. 28, 2019

Related U.S. Application Data

(60) Provisional application No. 62/309,372, filed on Mar. 16, 2016, provisional application No. 62/334,369, filed on May 10, 2016, provisional application No. 62/431,389, filed on Dec. 7, 2016, provisional application No. 62/446,640, filed on Jan. 16, 2017.

(51) Int. Cl.
*A61K 31/519* (2006.01)
*C07D 495/04* (2006.01)
*A61P 35/00* (2006.01)

(52) U.S. Cl.
CPC ............ *C07D 495/04* (2013.01); *A61P 35/00* (2018.01)

(58) Field of Classification Search
CPC .......................... A61K 31/519; C07D 487/04
USPC ....................... 514/259.3; 544/281
See application file for complete search history.

(56) References Cited

U.S. PATENT DOCUMENTS

| | | | |
|---|---|---|---|
| 5,445,764 A | 8/1995 | Poetsch et al. | |
| 5,866,562 A | 2/1999 | Schohe-Loop et al. | |
| 6,849,638 B2 | 2/2005 | Stolle et al. | |
| 7,030,240 B2 | 4/2006 | Dhanoa et al. | |
| 7,744,968 B2 | 6/2010 | Reiffenrath et al. | |
| 8,207,174 B2 | 6/2012 | Tasler et al. | |
| 8,507,491 B2 | 8/2013 | Cheng et al. | |
| 8,993,552 B2 | 3/2015 | Grembecka et al. | |
| 9,216,993 B2 * | 12/2015 | Grembecka ........... | C07D 495/04 |
| 9,505,781 B2 * | 11/2016 | Grembecka ........... | C07D 495/04 |
| 9,505,782 B2 | 11/2016 | Grembecka et al. | |
| 10,077,271 B2 | 9/2018 | Grembecka et al. | |
| 2003/0119829 A1 | 6/2003 | Stolle et al. | |
| 2003/0153556 A1 | 8/2003 | Levy et al. | |
| 2005/0123906 A1 | 6/2005 | Rana | |
| 2005/0222175 A1 | 10/2005 | Dhanoa et al. | |
| 2005/0222176 A1 | 10/2005 | Dhanoa et al. | |

(Continued)

FOREIGN PATENT DOCUMENTS

EP          1382603 A1      1/2004
JP       H10330377 A       12/1998

(Continued)

OTHER PUBLICATIONS

AC1MFIB7, Pubchem, [Online], 2005, [searched on Mar. 29, 2016], Internet,< url,< a="" href="https://pubchem.ncbi.nlm.nih.gov/compounds/2894865#section=Top">https://pubchem.ncbi.nlm.nih.gov/compounds/2894865#section=Top</url,>.

(Continued)

*Primary Examiner* — Jeffrey H Murray
(74) *Attorney, Agent, or Firm* — Wilson Sonsini Goodrich & Rosati

(57) ABSTRACT

The present disclosure provides compounds of Formula (II-A),

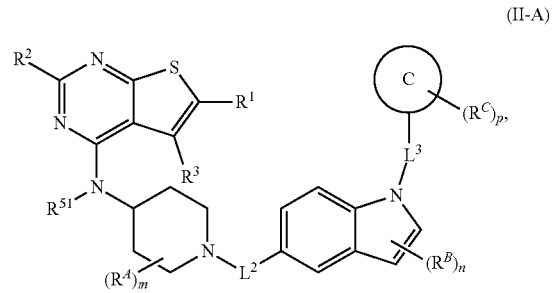

which inhibit the interaction of menin with one or more of MLL1, MLL2 and MLL-fusion oncoproteins. Also disclosed are methods for the treatment of leukemia, solid cancers, diabetes and other diseases dependent on activity of MLL1, MLL2, MLL fusion proteins, and/or menin.

20 Claims, 13 Drawing Sheets

(56) References Cited

U.S. PATENT DOCUMENTS

| | | |
|---|---|---|
| 2006/0025406 A1 | 2/2006 | Zembower et al. |
| 2006/0281769 A1 | 12/2006 | Baumann et al. |
| 2006/0281771 A1 | 12/2006 | Baumann et al. |
| 2007/0078133 A1 | 4/2007 | Liu et al. |
| 2008/0249114 A1 | 10/2008 | Tasler et al. |
| 2008/0293699 A1 | 11/2008 | Reed et al. |
| 2009/0163545 A1 | 6/2009 | Goldfarb |
| 2009/0298772 A1 | 12/2009 | Thirman |
| 2010/0063047 A1 | 3/2010 | Borchardt et al. |
| 2011/0065690 A1 | 3/2011 | Grembecka et al. |
| 2012/0322742 A1 | 12/2012 | Thirman |
| 2013/0210831 A1 | 8/2013 | Su et al. |
| 2014/0275070 A1 | 9/2014 | Grembecka et al. |
| 2014/0371239 A1 | 12/2014 | Grembecka et al. |
| 2016/0045504 A1 | 2/2016 | Grembecka et al. |
| 2016/0046647 A1 | 2/2016 | Grembecka et al. |
| 2017/0247391 A1 | 8/2017 | Grembecka et al. |
| 2017/0253611 A1 | 9/2017 | Grembecka et al. |
| 2018/0243303 A1 | 8/2018 | Grembecka et al. |
| 2019/0092784 A1 | 3/2019 | Wu et al. |

FOREIGN PATENT DOCUMENTS

| | | |
|---|---|---|
| JP | 2009507004 A | 2/2009 |
| JP | 2013503906 A | 2/2013 |
| WO | WO-9005719 A1 | 5/1990 |
| WO | WO-9627583 A1 | 9/1996 |
| WO | WO-9633172 A1 | 10/1996 |
| WO | WO-9803516 A1 | 1/1998 |
| WO | WO-9807697 A1 | 2/1998 |
| WO | WO-9830566 A1 | 7/1998 |
| WO | WO-9833768 A1 | 8/1998 |
| WO | WO-9834915 A1 | 8/1998 |
| WO | WO-9834918 A1 | 8/1998 |
| WO | WO-9929667 A1 | 6/1999 |
| WO | WO-9943675 A1 | 9/1999 |
| WO | WO-9952889 A1 | 10/1999 |
| WO | WO-9952910 A1 | 10/1999 |
| WO | WO-9965909 A1 | 12/1999 |
| WO | WO-02088138 A1 | 11/2002 |
| WO | WO-03022214 A2 | 3/2003 |
| WO | WO-2004030671 A2 | 4/2004 |
| WO | WO-2004030672 A1 | 4/2004 |
| WO | WO-2005020897 A2 | 3/2005 |
| WO | WO-2006135630 A1 | 12/2006 |
| WO | WO-2006135636 A2 | 12/2006 |
| WO | WO-2007026024 A2 | 3/2007 |
| WO | WO-2007042669 A2 | 4/2007 |
| WO | WO-2007076034 A2 | 7/2007 |
| WO | WO-2007115822 A1 | 10/2007 |
| WO | WO-2008070303 A2 | 6/2008 |
| WO | WO-2008090140 A1 | 7/2008 |
| WO | WO-2008099019 A1 | 8/2008 |
| WO | WO-2008107320 A1 | 9/2008 |
| WO | WO-2008114275 A2 | 9/2008 |
| WO | WO-2008135232 A1 | 11/2008 |
| WO | WO-2009017838 A2 | 2/2009 |
| WO | WO-2009064388 A2 | 5/2009 |
| WO | WO-2009143058 A1 | 11/2009 |
| WO | WO-2010030757 A2 | 3/2010 |
| WO | WO-2011003418 A1 | 1/2011 |
| WO | WO-2011014128 A1 | 2/2011 |
| WO | WO-2011029054 A1 | 3/2011 |
| WO | WO-2011101069 A2 | 8/2011 |
| WO | WO-2013024291 A2 | 2/2013 |
| WO | WO-2013072694 A1 | 5/2013 |
| WO | WO-2014164543 A1 | 10/2014 |
| WO | WO-2015154039 A2 | 10/2015 |
| WO | WO-2015191701 A1 | 12/2015 |
| WO | WO-2016040330 A1 | 3/2016 |
| WO | WO-2016195776 A1 | 12/2016 |
| WO | WO-2016197027 A1 | 12/2016 |
| WO | WO-2017112768 A1 | 6/2017 |
| WO | WO-2017132398 A1 | 8/2017 |
| WO | WO-2017161002 A1 | 9/2017 |
| WO | WO-2017161028 A1 | 9/2017 |
| WO | WO-2017192543 A1 | 11/2017 |
| WO | WO-2017207387 A1 | 12/2017 |
| WO | WO-2017214367 A1 | 12/2017 |
| WO | WO-2018024602 A1 | 2/2018 |
| WO | WO-2018050684 A1 | 3/2018 |
| WO | WO-2018050686 A1 | 3/2018 |
| WO | WO-2018053267 A1 | 3/2018 |

OTHER PUBLICATIONS

AC1N5DGQ, PubChem, [Online], 2005, [searched on Mar. 29, 2016], Internet,< url,< a="" href="https://pubchem.ncbi.nlm.nih.gov/compound/4143243">https://pubchem.ncbi.nlm.nih.gov/compound/4143243</url,>.

Arkin, et al. Small-molecule inhibitors of protein-protein interactions: progressing toward the reality. Chem Biol. Sep. 18, 2014;21(9):1102-14. doi: 10.1016/j.chembiol.2014.09.001.

Sorensen, et al. Molecular rearrangements of the MLL gene are present in most cases of infant acute myeloid leukemia and are strongly correlated with monocytic or myelomonocytic phenotypes. J Clin Invest, 93(1), pp. 429-437 (1994).

Bhaskar, et al. Synthesis, Antimicrobial and Antihyperlipidemic Activities of Some 4-Substituted-5,6,7,8-tetrhydrol. Asian J Chemistry 2007, 19(7):5187-5194.

Blackburn, et al. Identification and characterization of aminopiperidinequinolones and quinazolinones as MCHr1 antagonists. Bioorg Med Chem Lett. May 15, 2006;16(10):2621-7. Epub Mar. 9, 2006.

Borkin et al. Pharmacologic inhibition of the Menin-MLL interaction blocks progression of MLL leukemia in vivo. Cancer Cell. Apr. 13, 2015;27(4):589-602. doi: 10.1016/j.ccell.2015.02.016. Epub Mar. 26, 2015.

Borkin et al. Property Focused Structure-Based Optimization of Small Molecule Inhibitors of the Protein-Protein Interaction between Menin and Mixed Lineage Leukemia (MLL). J Med Chem. Feb. 11, 2016;59(3):892-913.

Chen, et al. The tumor suppressor menin regulates hematopoiesis and myeloid transformation by influencing Hox gene expression. Proc Natl Acad Sci USA, 103(4), pp. 1018-1023 (2006).

Co-pending U.S. Appl. No. 16/185,673, filed Nov. 9, 2018.

Cox, et al. Chromosomal aberration of the 11q23 locus in acute leukemia and frequency of MLL gene translocation: results in 378 adult patients. Am J Clin Pathol, 122(2), pp. 298-306 (2004).

Eguchi, et al. The role of the MLL gene in infant leukemia. Int J Hematol, 78(5), pp. 390-401 (2003).

F1174-09147, Pubchem, http://pubchem.ncbi.nlm.nih.govisummary/summary.cgi?cid=711090, 2007, 13 pages.

Grembecka, et al. Menin-MLL inhibitors reverse oncogenic activity of MLL fusion proteins in leukemia. Nature Chemical Biology. 2012 No. 8. pp. 277-284.

International Search Report and Written Opinion dated Aug. 2, 2017 for International PCT Patent Application No. PCT/US2017/022564.

Kim, et al. Chemical Biology Investigation of Cell Death Pathways Activated by Endoplasmic Reticulum Stress Cytoprotective Modulators of ASK1. J Biological Chemistry Jan. 2009, 284(3):1593-1603.

Kym, et al. Screening for cardiovascular safety: a structure-activity approach for guiding lead selection of melanin concentrating hormone receptor 1 antagonists. J Med Chem. Apr. 6, 2006;49(7):2339-52.

Marx, Stephen J. Molecular genetics of multiple endocrine neoplasia types 1 and 2. Nat Rev Cancer, 5(5), pp. 367-375 (2005).

Mayer, et al. Group epitope mapping by saturation transfer difference NMR to identify segments of a ligand in direct contact with a protein receptor. J Am Chem Soc, 123(25), pp. 6108-6117 (2001).

Mosmann, et al. Rapid colorimetric assay for cellular growth and survival: application to proliferation and cytotoxicity assays. J Immunol Methods, 65, (1-2), pp. 55-63 (1983).

Nairn, J.G. Solutions, Emulsions, Suspensions and Extracts. Chapter 83 of Remington's Pharmaceutical Sciences. 18th Ed. Gennaro, Alfonso R. Mack Publishing Company, Pennsylvania. 1990. 35 pages.

(56) References Cited

OTHER PUBLICATIONS

National Center for Biotechnology Information. PubChem Substance Database; SID=25433807, https://pubchem.ncbi.nlm.nih.gov/substance/25433807, deposit date Jul. 30, 2007.
Pollock et al. Rational Design of Orthogonal Multipolar Interactions with Fluorine in Protein-Ligand Complexes. J Med Chem. Sep. 24, 2015;58(18):7465-74.
Pubchem. CID 10631635. Oct. 25, 2006, pp. 1-12.
Pubchem CID 88912571. Create Date: Feb. 13, 2015. Date Accessed: Jul. 10, 2017; p. 4, compound listed.
Pubchem. CID10614048. Oct. 25, 2006, pp. 1-9. Retrieved from the Internet< url:<a href="https://pubchem.ncbi.nlm.nih.gov/compound/10614048>">https://pubchem.ncbi.nlm.nih.gov/compound/10614048.</url:<a>.
Sharma, et al. Synthesis of Thienopyrimidines and their Antipsychotic Activity. E Journal of Chemistry. 2010. 7(2):655-664.
Shi, et al. Structural insights into inhibition of the bivalent menin-MLL interaction by small molecules in leukemia. Blood. Nov. 29, 2012;120(23):4461-9.
Slany, Robert K. When epigenetics kills: MLL fusion proteins in leukemia. Hematol Oncol, 23(1), pp. 1-9 (2005).
SMR00018765, Pubchem, http://pubchem.ncbi.nlm.nih.gov/summary/summary.cgi?cid=1323703, 2007, 16 pages.

\* cited by examiner

FIG. 1

Amino acid sequence of human menin, isoform 1 (SEQ ID NO: 1):

```
MGLKAAQKTLFPLRSIDDVVRLFAAELGREEPDLVLLSLVLGFVEHFLAVNRVIPTNVPE
LTFQPSPAPDPPGGLTYFPVADLSIIAALYARFTAQIRGAVDLSLYPREGGVSSRELVKK
VSDVIWNSLSRSYFKDRAHIQSLFSFITGWSPVGTKLDSSGVAFAVVGACQALGLRDVHL
ALSEDHAWVVFGPNGEQTAEVTWHGKGNEDRRGQTVNAGVAERSWLYLKGSYMRCDRKME
VAFMVCAINPSIDLHTDSLELLQLQQKLLWLLYDLGHLERYPMALGNLADLEELEPTPGR
PDPLTLYHKGIASAKTYYRDEHIYPYMYLAGYHCRNRNVREALQAWADTATVIQDYNYCR
EDEEIYKEFFEVANDVIPNLLKEAASLLEAGEERPGEQSQGTQSQGSALQDPECFAHLLR
FYDGICKWEEGSPTPVLHVGWATFLVQSLGRFEGQVRQKVRIVSREAEAAEAEEPWGEEA
REGRRRGPRRESKPEEPPPPKKPALDKGLGTGQGAVSGPPRKPPGTVAGTARGPEGGSTA
QVPAPTASPPPEGPVLTFQSEKMKGMKELLVATKINSSAIKLQLTAQSQVQMKKQKVSTP
SDYTLSFLKRQRKGL
```

FIG. 2

Amino acid sequence of human menin, isoform 2 (SEQ ID NO: 2):

```
MGLKAAQKTLFPLRSIDDVVRLFAAELGREEPDLVLLSLVLGFVEHFLAVNRVIPTNVPE
LTFQPSPAPDPPGGLTYFPVADLSIIAALYARFTAQIRGAVDLSLYPREGGVSSRELVKK
VSDVIWNSLSRSYFKDRAHIQSLFSFITGTKLDSSGVAFAVVGACQALGLRDVHLALSED
HAWVVFGPNGEQTAEVTWHGKGNEDRRGQTVNAGVAERSWLYLKGSYMRCDRKMEVAFMV
CAINPSIDLHTDSLELLQLQQKLLWLLYDLGHLERYPMALGNLADLEELEPTPGRPDPLT
LYHKGIASAKTYYRDEHIYPYMYLAGYHCRNRNVREALQAWADTATVIQDYNYCREDEEI
YKEFFEVANDVIPNLLKEAASLLEAGEERPGEQSQGTQSQGSALQDPECFAHLLRFYDGI
CKWEEGSPTPVLHVGWATFLVQSLGRFEGQVRQKVRIVSREAEAAEAEEPWGEEAREGRR
RGPRRESKPEEPPPPKKPALDKGLGTGQGAVSGPPRKPPGTVAGTARGPEGGSTAQVPAP
TASPPPEGPVLTFQSEKMKGMKELLVATKINSSAIKLQLTAQSQVQMKKQKVSTPSDYTL
SFLKRQRKGL
```

FIG. 3

Amino acid sequence of human menin, isoform 3 (SEQ ID NO: 3):

```
MGLKAAQKTLFPLRSIDDVVRLFAAELGREEPDLVLLSLVLGFVEHFLAVNRVIPTNVPE
LTFQPSPAPDPPGGLTYFPVADLSIIAALYARFTAQIRGAVDLSLYPREGGVSSRELVKK
VSDVIWNSLSRSYFKDRAHIQSLFSFITGTKLDSSGVAFAVVGACQALGLRDVHLALSED
HAWSWLYLKGSYMRCDRKMEVAFMVCAINPSIDLHTDSLELLQLQQKLLWLLYDLGHLER
YPMALGNLADLEELEPTPGRPDPLTLYHKGIASAKTYYRDEHIYPYMYLAGYHCRNRNVR
EALQAWADTATVIQDYNYCREDEEIYKEFFEVANDVIPNLLKEAASLLEAGEERPGEQSQ
GTQSQGSALQDPECFAHLLRFYDGICKWEEGSPTPVLHVGWATFLVQSLGRFEGQVRQKV
RIVSREAEAAEAEEPWGEEAREGRRRGPRRESKPEEPPPPKKPALDKGLGTGQGAVSGPP
RKPPGTVAGTARGPEGGSTAQVPAPTASPPPEGPVLTFQSEKMKGMKELLVATKINSSAI
KLQLTAQSQVQMKKQKVSTPSDYTLSFLKRQRKGL
```

FIG. 11
Day 0
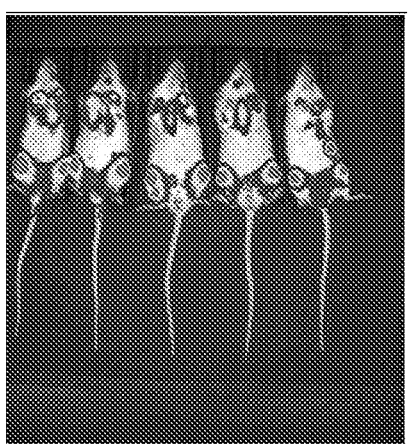
Treatment Day 6
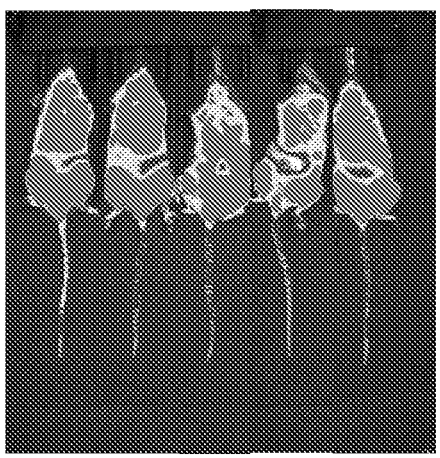 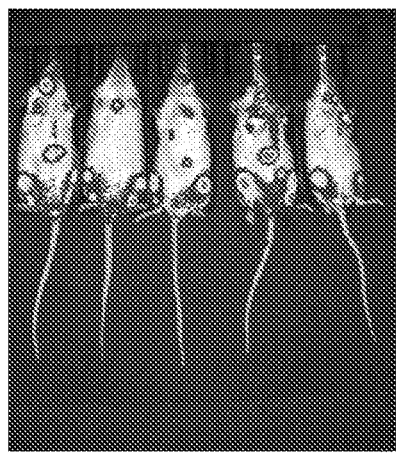
Vehicle          Compound D
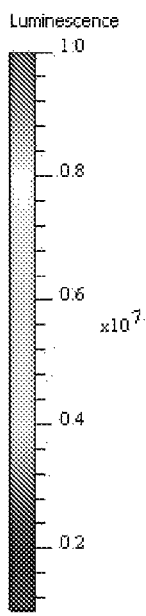

SUBSTITUTED INHIBITORS OF MENIN-MLL AND METHODS OF USE

CROSS-REFERENCE

This application is a National Stage Entry of PCT/US2017/022564, filed Mar. 15, 2017, which claims the benefit of U.S. Provisional Application No. 62/309,372, filed Mar. 16, 2016; U.S. Provisional Application No. 62/334,369, filed May 10, 2016; U.S. Provisional Application No. 62/431,389, filed Dec. 7, 2016; and U.S. Provisional Application No. 62/446,640, filed Jan. 16, 2017, each of which is incorporated herein by reference.

BACKGROUND OF THE INVENTION

The mixed-lineage leukemia (MLL) protein is a histone methyltransferase critical for the epigenetic regulation of gene transcription. Many acute leukemias, including acute myeloblastic leukemia (AML), acute lymphoblastic leukemia (ALL) and mixed-lineage leukemia (MLL), are characterized by the presence of chimeric MLL fusion proteins that result from chromosomal translocations of the MLL gene located at chromosome 11, band q23 (11q23). Chimeric MLL fusion proteins retain approximately 1,400 amino acids of the N-terminus of MLL, but are fused with one of approximately 80 partner proteins (e.g., AF4, AF9, ENL, AF10, ELL, AF6, AF1p, GAS7). MLL fusion proteins lack the original histone methyltransferase activity of the C-terminus of MLL and gain the ability to regulate transcription of numerous oncogenes, including HOX and MEIS1, resulting in increased cell proliferation and decreased cell differentiation, ultimately leading to leukemogenesis.

The menin protein, which is encoded by the Multiple Endocrine Neoplasia (MEN) gene, is a ubiquitously expressed nuclear protein that engages in interactions with DNA processing and repair proteins, chromatin modifying proteins and numerous transcription factors (Agarwal, et al.; *Horm Metab Res*, 2005, 37(6): 369-374). The association of menin with the N-terminus of MLL fusion proteins is necessary for the observed oncogenic activity of MLL fusion proteins. This association has been shown to constitutively up-regulate the expression of HOX and MEIS1 oncogenes and impairs proliferation and differentiation of hematopoietic cells leading to leukemia development. Since menin has been shown to function as a general oncogenic cofactor in MLL-related leukemias, the interaction between menin and MLL fusion proteins and MLL represents a potential chemotherapeutic target.

Patients, especially infants, with leukemias harboring chromosomal translocations of the MLL gene have a dismal prognosis, with less than a 40% five year survival rate (Slany; *Haematologica*, 2009, 94(7): 984-993). A novel therapeutic strategy is urgently needed to treat these leukemias. Small molecule inhibitors that block the menin-MLL interaction are thus valuable targets for treating diseases involving the MLL fusion proteins.

SUMMARY OF THE INVENTION

The present disclosure addresses a need in the art by providing compositions and methods for inhibiting the protein-protein interaction of menin with MLL1, MLL2 and MLL-fusion oncoproteins. The compositions and methods herein may be useful for treating diseases dependent on the activity of MLL1, MLL2, MLL fusion proteins, and/or menin such as leukemia, solid cancers, and diabetes. In some embodiments, a compound of the disclosure interacts non-covalently with menin and inhibits the interaction of menin with MLL. In some embodiments, a compound of the disclosure covalently binds menin and inhibits the interaction of menin with MLL.

In some embodiments of a compound provided herein, the compound non-covalently or covalently binds to any one or more isoforms of menin, for example, isoform 1 (SEQ ID NO: 1), isoform 2 (SEQ ID NO: 2) or isoform 3 (SEQ ID NO: 3) of menin. In certain embodiments, the menin protein shares 60% or more, 70% or more, 75% or more, 80% or more, 85% or more, 90% or more, 95% or more, or 99% or more sequence identity with isoform 1 (SEQ ID NO: 1), isoform 2 (SEQ ID NO: 2) or isoform 3 (SEQ ID NO: 3).

In one aspect, the present disclosure provides a compound of Formula (I):

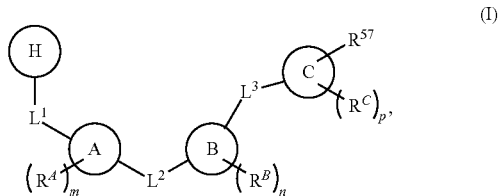

or a pharmaceutically acceptable salt, isotopic form, or prodrug thereof, wherein:

H is selected from $C_{5-12}$ carbocycle and 5- to 12-membered heterocycle, each of which is optionally substituted with one or more $R^{50}$;

A is selected from bond, $C_{3-12}$ carbocycle and 3- to 12-membered heterocycle;

B is selected from $C_{3-12}$ carbocycle and 3- to 12-membered heterocycle;

C is 3- to 12-membered heterocycle;

$L^1$, $L^2$ and $L^3$ are each independently selected from bond, —O—, —S—, —N($R^{51}$)—, —N($R^{51}$)CH$_2$—, —C(O)—, —C(O)O—, —OC(O)—, —OC(O)O—, —C(O)N($R^{51}$)—, —C(O)N($R^{51}$)C(O)—, —C(O)N($R^{51}$)C(O)N($R^{51}$)—, —N($R^{51}$)C(O)—, —N($R^{51}$)C(O)N($R^{51}$)—, —N($R^{51}$)C(O)O—, —OC(O)N($R^{51}$)—, —C(N$R^{51}$)—, —N($R^{51}$)C(N$R^{51}$)—, —C(N$R^{51}$)N($R^{51}$)—, —N($R^{51}$)C(N$R^{51}$)N($R^{51}$)—, —S(O)$_2$—, —OS(O)—, —S(O)O—, —S(O)—, —OS(O)$_2$—, —S(O)$_2$O—, —N($R^{51}$)S(O)$_2$—, —S(O)$_2$N($R^{51}$)—, —N($R^{51}$)S(O)—, —S(O)N($R^{51}$)—, —N($R^{51}$)S(O)$_2$N($R^{51}$)—, —N($R^{51}$)S(O)N($R^{51}$)—; alkylene, alkenylene, alkynylene, heteroalkylene, heteroalkenylene, and heteroalkynylene, each of which is optionally substituted with one or more $R^{50}$, wherein two $R^{50}$ groups attached to the same atom or different atoms of any one of $L^1$, $L^2$ or $L^3$ can together optionally form a bridge or ring;

$R^A$, $R^B$ and $R^C$ are each independently selected at each occurrence from $R^{50}$, or two $R^A$ groups, two $R^B$ groups or two $R^C$ groups attached to the same atom or different atoms can together optionally form a bridge or ring;

m, n and p are each independently an integer from 0 to 6;

$R^{50}$ is independently selected at each occurrence from: halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$);

C$_{1-10}$ alkyl, C$_{2-10}$ alkenyl, and C$_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{3-12}$ carbocycle, and 3- to 12-membered heterocycle; and C$_{3-12}$ carbocycle and 3- to 12-membered heterocycle, wherein each C$_{3-12}$ carbocycle and 3- to 12-membered heterocycle in R$^{50}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;

R$^{51}$ is independently selected at each occurrence from: hydrogen, —C(O)R$^{52}$, —C(O)OR$^{52}$, —C(O)N(R$^{52}$)$_2$, —C(O)NR$^{53}$R$^{54}$;

C$_{1-6}$ alkyl, C$_{2-6}$ alkenyl, and C$_{2-6}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{3-12}$ carbocycle and 3- to 12-membered heterocycle; and C$_{3-12}$ carbocycle and 3- to 12-membered heterocycle, wherein each C$_{3-12}$ carbocycle and 3- to 12-membered heterocycle in R$^{51}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;

R$^{52}$ is independently selected at each occurrence from hydrogen; and C$_{1-20}$ alkyl, C$_{2-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle;

R$^{53}$ and R$^{54}$ are taken together with the nitrogen atom to which they are attached to form a heterocycle, optionally substituted with one or more R$^{50}$;

R$^{57}$ is selected from:

halogen, —NO$_2$, —CN, —SR$^{52}$, —NR$^{53}$R$^{54}$, —S(=O)R$^{52}$, —S(=O)$_2$R$^{58}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)OR$^{52}$, —NR$^{52}$C(O)N(R$^{52}$)$_2$, —NR$^{52}$C(O)NR$^{53}$R$^{54}$, —C(O)NH(C$_{1-6}$ alkyl), —C(O)NR$^{53}$R$^{54}$, —P(O)(OR$^{52}$)$_2$, —P(O)(R$^{52}$)$_2$, =S, =N(R$^{52}$); and C$_{1-10}$ alkyl, C$_{2-10}$ alkenyl, and C$_{2-10}$ alkynyl, each of which is independently substituted at each occurrence with one or more substituents selected from —NO$_2$, —CN, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —P(O)(OR$^{52}$)$_2$, —P(O)(R$^{52}$)$_2$, =S, and =N(R$^{52}$); and R$^{58}$ is selected from hydrogen; and C$_{1-20}$ alkyl, C$_{3-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle, wherein for a compound or salt of Formula (I), when C is azetidinylene, piperidinylene or piperazinylene and R$^{57}$ is —S(=O)$_2$R$^{58}$, —S(=O)$_2$N(R$^{52}$)$_2$, or —NR$^{52}$S(=O)$_2$R$^{52}$:

p is an integer from 1 to 6; and/or

L$^3$ is substituted with one or more R$^{50}$, wherein L$^3$ is not —CH$_2$CH(OH)—.

In one aspect, the present disclosure provides a compound of Formula (II):

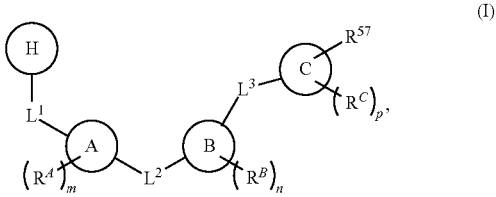

(I)

or a pharmaceutically acceptable salt thereof, wherein:

H is selected from C$_{5-12}$ carbocycle and 5- to 12-membered heterocycle, each of which is optionally substituted with one or more R$^{50}$;

A, B and C are each independently selected from C$_{3-12}$ carbocycle and 3- to 12-membered heterocycle;

L$^1$ and L$^2$ are each independently selected from bond, —O—, —S—, —N(R$^{51}$)—, —N(R$^{51}$)CH$_2$—, —C(O)—, —C(O)O—, —OC(O)—, —OC(O)O—, —C(O)N(R$^{51}$)—, —C(O)N(R$^{51}$)C(O)—, —C(O)N(R$^{51}$)C(O)N(R$^{51}$)—, —N(R$^{51}$)C(O)—, —N(R$^{51}$)C(O)N(R$^{51}$)—, —N(R$^{51}$)C(O)O—, —OC(O)N(R$^{51}$)—, —C(NR$^{51}$)—, —N(R$^{51}$)C(NR$^{51}$)—, —C(NR$^{51}$)N(R$^{51}$)—, —N(R$^{51}$)C(NR$^{51}$)N $(R^{51})$—, —S(O)$_2$—, —OS(O)—, —S(O)O—, —S(O)—, —OS(O)$_2$—, —S(O)$_2$O—, —N($R^{51}$)S(O)$_2$—, —S(O)$_2$N($R^{51}$)—, —N($R^{51}$)S(O)—, —S(O)N($R^{51}$)—, —N($R^{51}$)S(O)$_2$N($R^{51}$)—, —N($R^{51}$)S(O)N($R^{51}$)—; alkylene, alkenylene, alkynylene, heteroalkylene, heteroalkenylene, and heteroalkynylene, each of which is optionally substituted with one or more $R^{50}$;

$L^3$ is selected from alkylene, alkenylene, and alkynylene, each of which is substituted with one or more $R^{56}$ and optionally further substituted with one or more $R^{50}$;

$R^A$, $R^B$ and $R^C$ are each independently selected at each occurrence from $R^{50}$, or two $R^A$ groups, two $R^B$ groups or two $R^C$ groups attached to the same atom or different atoms can together optionally form a bridge or ring;

m, n and p are each independently an integer from 0 to 6;

$R^{50}$ is independently selected at each occurrence from:
halogen, —NO$_2$, —CN, —O$R^{52}$, —S$R^{52}$, —N($R^{52}$)$_2$, —N$R^{53}R^{54}$, —S(=O)$R^{52}$, —S(=O)$_2R^{52}$, —S(=O)$_2$N($R^{52}$)$_2$, —S(=O)$_2$N$R^{53}R^{54}$, —N$R^{52}$S(=O)$_2R^{52}$, —N$R^{52}$S(=O)$_2$N($R^{52}$)$_2$, —N$R^{52}$S(=O)$_2$N$R^{53}R^{54}$, —C(O)$R^{52}$, —C(O)O$R^{52}$, —OC(O)$R^{52}$, —OC(O)O$R^{52}$, —OC(O)N($R^{52}$)$_2$, —OC(O)N$R^{53}R^{54}$, —N$R^{52}$C(O)$R^{52}$, —N$R^{52}$C(O)O$R^{52}$, —N$R^{52}$C(O)N($R^{52}$)$_2$, —N$R^{52}$C(O)N$R^{53}R^{54}$, —C(O)N($R^{52}$)$_2$, —C(O)N$R^{53}R^{54}$, —P(O)(O$R^{52}$)$_2$, —P(O)($R^{52}$)$_2$, =O, =S, =N($R^{52}$);

C$_{1-10}$ alkyl, C$_{2-10}$ alkenyl, and C$_{2-10}$ alkynyl, each of which is independently optionally substituted at each occurrence with one or more substituents selected from halogen, —NO$_2$, —CN, —O$R^{52}$, —S$R^{52}$, —N($R^{52}$)$_2$, —N$R^{53}R^{54}$, —S(=O)$R^{52}$, —S(=O)$_2R^{52}$, —S(=O)$_2$N($R^{52}$)$_2$, —S(=O)$_2$N$R^{53}R^{54}$, —N$R^{52}$S(=O)$_2R^{52}$, —N$R^{52}$S(=O)$_2$N($R^{52}$), —N$R^{52}$S(=O)$_2$N$R^{53}R^{54}$, —C(O)$R^{52}$, —C(O)O$R^{52}$, —OC(O)$R^{52}$, —OC(O)O$R^{52}$, —OC(O)N($R^{52}$)$_2$, —OC(O)N$R^{53}R^{54}$, —N$R^{52}$C(O)$R^{52}$, —N$R^{52}$C(O)O$R^{52}$, —N$R^{52}$C(O)N($R^{52}$)$_2$, —N$R^{52}$C(O)N$R^{53}R^{54}$, —C(O)N($R^{52}$)$_2$, —C(O)N$R^{53}R^{54}$, —P(O)(O$R^{52}$)$_2$, —P(O)($R^{52}$)$_2$, =O, =S, =N($R^{52}$), C$_{3-12}$ carbocycle, and 3- to 12-membered heterocycle; and C$_{3-12}$ carbocycle and 3- to 12-membered heterocycle, wherein each C$_{3-12}$ carbocycle and 3- to 12-membered heterocycle in $R^{50}$ is independently optionally substituted with one or more substituents selected from halogen, —NO$_2$, —CN, —O$R^{52}$, —S$R^{52}$, —N($R^{52}$)$_2$, —N$R^{53}R^{54}$, —S(=O)$R^{52}$, —S(=O)$_2R^{52}$, —S(=O)$_2$N($R^{52}$)$_2$, —S(=O)$_2$N$R^{53}R^{54}$, —N$R^{52}$S(=O)$_2R^{52}$, —N$R^{52}$S(=O)$_2$N($R^{52}$)$_2$, —N$R^{52}$S(=O)$_2$N$R^{53}R^{54}$, —C(O)$R^{52}$, —C(O)O$R^{52}$, —OC(O)$R^{52}$, —OC(O)O$R^{52}$, —OC(O)N($R^{52}$)$_2$, —OC(O)N$R^{53}R^{54}$, —N$R^{52}$C(O)$R^{52}$, —N$R^{52}$C(O)O$R^{52}$, —N$R^{52}$C(O)N($R^{52}$)$_2$, —N$R^{52}$C(O)N$R^{53}R^{54}$, —C(O)N($R^{52}$)$_2$, —C(O)N$R^{53}R^{54}$, —P(O)(O$R^{52}$)$_2$, —P(O)($R^{52}$)$_2$, =O, =S, =N($R^{52}$), C$_{1-6}$ alkyl, C$_{1-6}$ haloalkyl, C$_{2-6}$ alkenyl, and C$_{2-6}$ alkynyl;

$R^{51}$ is independently selected at each occurrence from:
hydrogen, —C(O)$R^{52}$, —C(O)O$R^{52}$, —C(O)N($R^{52}$)$_2$, —C(O)N$R^{53}R^{54}$;

C$_{1-6}$ alkyl, C$_{2-6}$ alkenyl, and C$_{2-6}$ alkynyl, each of which is independently optionally substituted at each occurrence with one or more substituents selected from halogen, —NO$_2$, —CN, —O$R^{52}$, —S$R^{52}$, —N($R^{52}$)$_2$, —N$R^{53}R^{54}$, —S(=O)$R^{52}$, —S(=O)$_2R^{52}$, —S(=O)$_2$N($R^{52}$)$_2$, —S(=O)$_2$N$R^{53}R^{54}$, —N$R^{52}$S(=O)$_2R^{52}$, —N$R^{52}$S(=O)$_2$N($R^{52}$)$_2$, —N$R^{52}$S(=O)$_2$N$R^{53}R^{54}$, —C(O)$R^{52}$, —C(O)O$R^{52}$, —OC(O)$R^{52}$, —OC(O)O$R^{52}$, —OC(O)N($R^{52}$)$_2$, —OC(O)N$R^{53}R^{54}$, —N$R^{52}$C(O)$R^{52}$, —N$R^{52}$C(O)O$R^{52}$, —N$R^{52}$C(O)N($R^{52}$)$_2$, —N$R^{52}$C(O)N$R^{53}R^{54}$, —C(O)N($R^{52}$)$_2$, —C(O)N$R^{53}R^{54}$, —P(O)(O$R^{52}$)$_2$, —P(O)($R^{52}$)$_2$, =O, =S, =N($R^{52}$), C$_{3-12}$ carbocycle and 3- to 12-membered heterocycle; and C$_{3-12}$ carbocycle and 3- to 12-membered heterocycle, wherein each C$_{3-12}$ carbocycle and 3- to 12-membered heterocycle in $R^{51}$ is independently optionally substituted with one or more substituents selected from halogen, —NO$_2$, —CN, —O$R^{52}$, —S$R^{52}$, —N($R^{52}$)$_2$, —N$R^{53}R^{54}$, —S(=O)$R^{52}$, —S(=O)$_2R^{52}$, —S(=O)$_2$N($R^{52}$)$_2$, —S(=O)$_2$N$R^{53}R^{54}$, —N$R^{52}$S(=O)$_2R^{52}$, —N$R^{52}$S(=O)$_2$N($R^{52}$)$_2$, —N$R^{52}$S(=O)$_2$N$R^{53}R^{54}$, —C(O)$R^{52}$, —C(O)O$R^{52}$, —OC(O)$R^{52}$, —OC(O)O$R^{52}$, —OC(O)N($R^{52}$)$_2$, —OC(O)N$R^{53}R^{54}$, —N$R^{52}$C(O)$R^{52}$, —N$R^{52}$C(O)O$R^{52}$, —N$R^{52}$C(O)N($R^{52}$)$_2$, —N$R^{52}$C(O)N$R^{53}R^{54}$, —C(O)N($R^{52}$)$_2$, —C(O)N$R^{53}R^{54}$, —P(O)(O$R^{52}$)$_2$, —P(O)($R^{52}$)$_2$, =O, =S, =N($R^{52}$), C$_{1-6}$ alkyl, C$_{1-6}$ haloalkyl, C$_{2-6}$ alkenyl, and C$_{2-6}$ alkynyl;

$R^{52}$ is independently selected at each occurrence from hydrogen; and C$_{1-20}$ alkyl, C$_{2-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle;

$R^{53}$ and $R^{54}$ are taken together with the nitrogen atom to which they are attached to form a heterocycle, optionally substituted with one or more $R^{50}$;

$R^{56}$ is independently selected at each occurrence from:
—NO$_2$, —O$R^{59}$, —S$R^{52}$, —N$R^{53}R^{54}$, —S(=O)$R^{52}$, —S(=O)$_2R^{52}$, —S(=O)$_2$N($R^{52}$)$_2$, —S(=O)$_2$N$R^{53}R^{54}$, —N$R^{52}$S(=O)$_2R^{52}$, —N$R^{52}$S(=O)$_2$N($R^{52}$)$_2$, —N$R^{52}$S(=O)$_2$N$R^{53}R^{54}$, —C(O)$R^{52}$, —C(O)O$R^{52}$, —OC(O)$R^{52}$, —OC(O)O$R^{52}$, —OC(O)N($R^{52}$)$_2$, —OC(O)N$R^{53}R^{54}$, —N$R^{52}$C(O)$R^{52}$, —N$R^{52}$C(O)O$R^{52}$, —N$R^{52}$C(O)N($R^{52}$)$_2$, —N$R^{52}$C(O)N$R^{53}R^{54}$, —C(O)N($R^{52}$)$_2$, —C(O)N$R^{53}R^{54}$, —P(O)(O$R^{52}$)$_2$, —P(O)($R^{52}$)$_2$, =O, =S, =N($R^{52}$), C$_{1-10}$ alkyl, C$_{2-10}$ alkenyl, C$_{2-10}$ alkynyl, C$_{3-12}$ carbocycle and 3- to 12-membered heterocycle, wherein each C$_{1-10}$ alkyl, C$_{2-10}$ alkenyl, and C$_{2-10}$ alkynyl in $R^{56}$ is independently optionally substituted at each occurrence with one or more substituents selected from halogen, —NO$_2$, —CN, —O$R^{59}$, —S$R^{52}$, —N($R^{52}$)$_2$, —N$R^{53}R^{54}$, —S(=O)$R^{52}$, —S(=O)$_2R^{52}$, —S(=O)$_2$N($R^{52}$)$_2$, —S(=O)$_2$N$R^{53}R^{54}$, —N$R^{52}$S(=O)$_2R^{52}$, —N$R^{52}$S(=O)$_2$N($R^{52}$)$_2$, —N$R^{52}$S(=O)$_2$N$R^{53}R^{54}$, —C(O)$R^{52}$, —C(O)O$R^{52}$, —OC(O)$R^{52}$, —OC(O)O$R^{52}$, —OC(O)N($R^{52}$)$_2$, —OC(O)N$R^{53}R^{54}$, —N$R^{52}$C(O)$R^{52}$, —N$R^{52}$C(O)O$R^{52}$, —N$R^{52}$C(O)N($R^{52}$)$_2$, —N$R^{52}$C(O)N$R^{53}R^{54}$, —C(O)N($R^{52}$)$_2$, —C(O)N$R^{53}R^{54}$, —P(O)(O$R^{52}$)$_2$, —P(O)($R^{52}$)$_2$, =O, =S, =N($R^{52}$), C$_{3-12}$ carbocycle, and 3- to 12-membered heterocycle;

wherein each C$_{3-12}$ carbocycle and 3- to 12-membered heterocycle in $R^{56}$ is independently optionally substituted with one or more substituents selected from halogen, —NO$_2$, —CN, —O$R^{52}$, —S$R^{52}$, —N($R^{52}$)$_2$, —N$R^{53}R^{54}$, —S(=O)$R^{52}$, —S(=O)$_2R^{52}$, —S(=O)$_2$N($R^{52}$)$_2$, —S(=O)$_2$N$R^{53}R^{54}$, —N$R^{52}$S(=O)$_2R^{52}$, —N$R^{52}$S(=O)$_2$N($R^{52}$)$_2$, —N$R^{52}$S(=O)$_2$N$R^{53}R^{54}$, —C(O)$R^{52}$, —C(O)O$R^{52}$, —OC(O)$R^{52}$, —OC(O)O$R^{52}$, —OC(O)N($R^{52}$)$_2$, —OC(O)N$R^{53}R^{54}$, —N$R^{52}$C(O)$R^{52}$, —N$R^{52}$C(O)O$R^{52}$, —N$R^{52}$C(O)N($R^{52}$)$_2$, —N$R^{52}$C(O)N$R^{53}R^{54}$, —C(O)N($R^{52}$)$_2$, —C(O)

NR$^{53}$R$^{54}$, —P(O)(OR$^{52}$)$_2$, —P(O)(R$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl; and further wherein R$^{56}$ optionally forms a bond to ring C; and R$^{59}$ is independently selected at each occurrence from C$_{1-20}$ alkyl, C$_{2-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle, wherein for a compound or salt of Formula (II), when R$^{56}$ is —CH$_3$, L$^3$ is not further substituted with —OH, —NH$_2$, or —CN.

In some embodiments, for a compound of Formula (II), R$^C$ is selected from —C(O)R$^{52}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, =O, C$_{1-3}$ alkyl, and C$_{1-3}$ haloalkyl, or two R$^C$ groups attached to different atoms can together form a C$_{1-3}$ bridge.

For a compound of Formula (I) or (II), C may be 5- to 12-membered heterocycle, wherein the heterocycle comprises at least one nitrogen atom. In some embodiments, the heterocycle is saturated. In some embodiments, the heterocycle is selected from piperidinyl and piperazinyl.

In some embodiments, for a compound of Formula (I), C is selected from

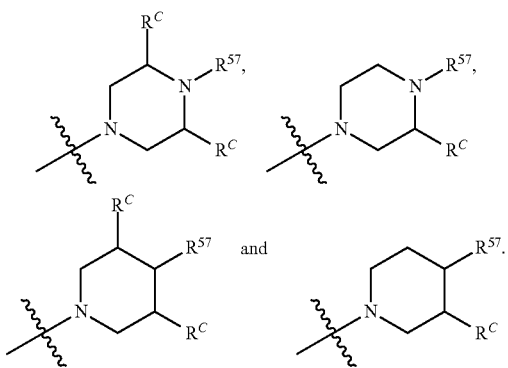

In some embodiments, R$^{57}$ is selected from —S(=O)R$^{51}$, —S(=O)$_2$R$^{58}$, —S(=O)$_2$N(R$^{52}$)$_2$, and —NR$^{52}$S(=O)$_2$R$^{52}$.

In some embodiments, for a compound of Formula (II), C is selected from

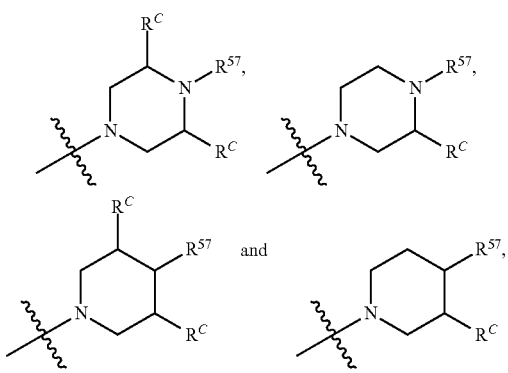

wherein R$^{57}$ is selected from —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$; and C$_{1-10}$ alkyl substituted with one or more substituents selected from —S(=O)R$^{52}$, —S(=O)$_2$R$^{52}$, —S(=O)$_2$N(R$^{52}$)$_2$, —S(=O)$_2$NR$^{53}$R$^{54}$, and —NR$^{52}$S(=O)$_2$R$^{52}$. In some embodiments, R$^{57}$ is selected from —S(=O)R$^{52}$, —S(=O)$_2$R$^{52}$, —S(=O)$_2$N(R$^{52}$)$_2$, and —NR$^{52}$S(=O)$_2$R$^{52}$. In some embodiments, R$^{57}$ is selected from —S(=O)CH$_3$, —S(=O)$_2$CH$_3$, —S(=O)$_2$NH$_2$, —NHS(=O)$_2$CH$_3$, and —S(=O)$_2$NHCH$_3$.

For a compound of Formula (I) or (II), R$^C$ may be selected from C$_{1-3}$ alkyl and C$_{1-3}$ haloalkyl.

In some embodiments, for a compound of Formula (I) or (II), H is 5- to 12-membered heterocycle, optionally substituted with one or more R$^{50}$; A is 3- to 12-membered heterocycle; and B is 3- to 12-membered heterocycle.

For a compound of Formula (I) or (II), H may be 6- to 12-membered bicyclic heterocycle, optionally substituted with one or more R$^{50}$. In some embodiments, H is thienopyrimidinyl, optionally substituted with one or more R$^{50}$. In some embodiments, H is

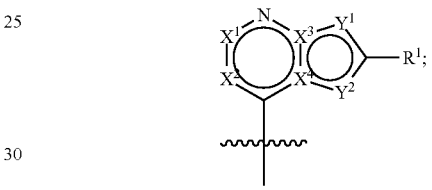

X$^1$ and X$^2$ are each independently selected from CR$^2$ and N; X$^3$ and X$^4$ are each independently selected from C and N; Y$^1$ and Y$^2$ are each independently selected from CR$^3$, N, NR$^4$, O, and S; R$^1$, R$^2$ and R$^3$ are each independently selected at each occurrence from hydrogen and R$^{50}$; and R$^4$ is selected from R$^{51}$. In some embodiments, X$^3$ and X$^4$ are each C. In some embodiments, X$^1$ is CR$^{52}$, and R$^2$ is selected from hydrogen, halogen, —OH, —OR$^{52}$, —NH$_2$, —N(R$^{52}$)$_2$, —CN, C$_{1-3}$ alkyl, C$_{1-3}$ alkyl-N(R$^{52}$)$_2$, C$_{1-3}$ haloalkyl, C$_{2-3}$ alkenyl, and C$_{2-3}$ alkynyl. In some embodiments, X$^1$ is CR$^{52}$, and R$^2$ is selected from hydrogen, halogen, —OH, —OR$^{52}$, —NH$_2$, —N(R$^{52}$)$_2$, —CN, C$_{1-3}$ alkyl, —CH$_2$OH, —CH$_2$OR$^{52}$, —CH$_2$NH$_2$, —CH$_2$N(R$^{52}$)$_2$, C$_{1-3}$ alkyl-N(R$^{52}$)$_2$, C$_{1-3}$ haloalkyl, C$_{2-3}$ alkenyl, and C$_{2-3}$ alkynyl. In some embodiments, X$^2$ is N. In some embodiments, Y$^2$ is CR$^3$, and R$^3$ is selected from hydrogen, halogen, —OH, —N(R$^{52}$)$_2$, —CN, —C(O)OR$^{52}$, C$_{1-3}$ alkyl, and C$_{1-3}$ haloalkyl. In some embodiments, R$^1$ is C$_{1-3}$ haloalkyl.

For a compound of Formula (I) or (II), A may be 5- to 8-membered heterocycle, such as 6-membered monocyclic heterocycle. In some embodiments, the heterocycle comprises at least one nitrogen atom. In some embodiments, A is selected from piperidinylene and piperazinylene, such as

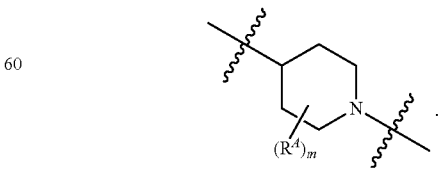

For a compound of Formula (I) or (II), B may be 6- to 12-membered bicyclic heterocycle. In some embodiments, the heterocycle comprises at least one nitrogen atom. In some embodiments, B is indolylene, such as

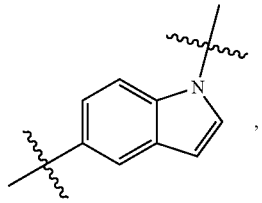 [SMILES: *c1ccc2c(ccn2*)c1]

optionally substituted with one or more $R^B$.

In some embodiments, for a compound of Formula (I) or (II), H is thienopyrimidinyl substituted with one or more $R^{50}$; A is selected from piperidinylene and piperazinylene; and B is indolylene.

For a compound of Formula (I) or (II), H may be substituted with —$CH_2CF_3$. In some embodiments, m is 0. In some embodiments, n is an integer from 1 to 3. In some embodiments, $L^1$ comprises less than 10 atoms. In some embodiments, $L^1$ is —$N(R^{51})$—. In some embodiments, $L^2$ comprises less than 10 atoms. In some embodiments, $L^2$ is $C_{1-4}$ alkylene, optionally substituted with one or more $R^{50}$. In some embodiments, $L^2$ is selected from —$CH_2$—, —$N(R^{51})$—, —$N(R^{51})CH_2$—, —$N(R^{51})C(O)$—, and —$N(R^{51})S(O)_2$—. In some embodiments, $L^3$ comprises less than 20 atoms. In some embodiments, $L^3$ is $C_{1-6}$ alkylene, optionally substituted with one or more $R^{50}$. In some embodiments, $L^3$ is $C_2$ alkylene substituted with at least one $C_{1-3}$ alkyl or $C_{1-3}$ haloalkyl, and optionally further substituted with one or more $R^{50}$. In some embodiments, $L^3$ is substituted with =O, $C_{1-6}$ alkyl, $C_{1-6}$ haloalkyl, $C_{1-3}$ alkyl (cyclopropyl), $C_{1-3}$ alkyl($NR^{52}C(O)R^{52}$) or —O($C_{1-6}$ alkyl). In some embodiments, $L^3$ is substituted with —$CH_3$. In some embodiments, a compound of Formula (I) or (II) is selected from Table 1.

For a compound of Formula (I), $L^3$ may be selected from

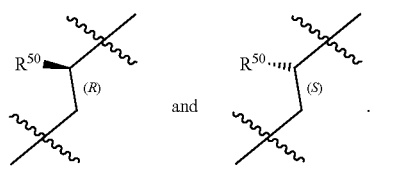

Optionally, $R^{50}$ is methyl. In some embodiments, for a compound of Formula (II), $L^3$ is selected from

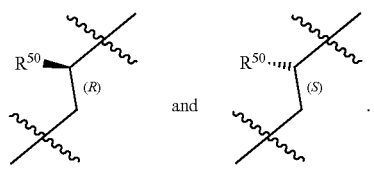

Optionally, $R^{56}$ is methyl. In certain aspects, the present disclosure provides a substantially pure stereoisomer of a compound of Formula (I) or (II). Optionally, the stereoisomer is provided in at least 90% enantiomeric excess.

In some embodiments, for a compound of Formula (I) or (II), H is thienopyrimidinyl, optionally substituted with one or more $R^{50}$; A is 3- to 12-membered heterocycle; B is 6- to 12-membered bicyclic heterocycle; m is an integer from 0 to 3; and n is an integer from 1 to 3.

In some embodiments, for a compound of Formula (I):
H is thienopyrimidinyl, optionally substituted with one or more $R^{50}$;
A is selected from piperidinylene and piperazinylene;
B is indolylene;
$L^1$ and $L^2$ are each independently selected from —O—, —S—, —NH—, and —$CH_2$—;
$L^3$ is selected from bond, —O—, —S—, —$N(R^{51})$—, —$N(R^{51})CH_2$—, —C(O)—, —C(O)O—, —OC(O)—, —OC(O)O—, —$C(O)N(R^{51})$—, —$C(O)N(R^{51})C(O)$—, —$C(O)N(R^{51})C(O)N(R^{51})$—, —$N(R^{51})C(O)$—, —$N(R^{51})C(O)N(R^{51})$—, —$N(R^{51})C(O)O$—, —$OC(O)N(R^{51})$—, —$C(NR^{51})$—, —$N(R^{51})C(NR^{51})$—, —$C(NR^{51})N(R^{51})$—, —$N(R^{51})C(NR^{51})N(R^{51})$—, —$S(O)_2$—, —OS(O)—, —S(O)O—, —S(O)—, —$OS(O)_2$—, —$S(O)_2O$—, —$N(R^{51})S(O)_2$—, —$S(O)_2N(R^{51})$—, —$N(R^{51})S(O)$—, —$S(O)N(R^{51})$—, —$N(R^{51})S(O)_2N(R^{51})$—, —$N(R^{51})S(O)N(R^{51})$—; alkylene, alkenylene, alkynylene, heteroalkylene, heteroalkenylene, and heteroalkynylene, each of which is optionally substituted with one or more $R^{50}$, wherein two $R^{50}$ groups attached to the same atom or different atoms of $L^3$ can together optionally form a ring;
$R^A$, $R^B$ and $R^C$ are each independently selected at each occurrence from $R^{50}$, or two $R^A$ groups, two $R^B$ groups or two $R^C$ groups attached to the same atom or different atoms can together optionally form a ring;
m is an integer from 0 to 3;
n is an integer from 1 to 3;
p is an integer from 0 to 6;
$R^{57}$ is selected from:
—$S(=O)R^{52}$, —$S(=O)_2R^{58}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$NR^{52}C(O)N(R^{52})_2$, —$NR^{52}C(O)NR^{53}R^{54}$, —C(O)NH($C_{1-6}$ alkyl), —$C(O)NR^{53}R^{54}$, —$P(O)(OR^{52})_2$, —$P(O)(R^{52})_2$; and $C_{1-10}$ alkyl, $C_{2-10}$ alkenyl, and $C_{2-10}$ alkynyl, each of which is independently substituted at each occurrence with one or more substituents selected from —$S(=O)R^{52}$, —$S(=O)_2R^{58}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$NR^{52}C(O)N(R^{52})_2$, —$NR^{52}C(O)NR^{53}R^{54}$, —C(O)NH($C_{1-6}$ alkyl), —$C(O)NR^{53}R^{54}$, —$P(O)(OR^{52})_2$, and —$P(O)(R^{52})_2$; and $R^{58}$ is selected from hydrogen; and $C_{1-20}$ alkyl, $C_{3-20}$ alkenyl, $C_{2-20}$ alkynyl, 1- to 6-membered heteroalkyl, $C_{3-12}$ carbocycle, and 3- to 12-membered heterocycle, each of which is optionally substituted by halogen, —CN, —$NO_2$, —$NH_2$, —$NHCH_3$, —$NHCH_2CH_3$, =O, —OH, —$OCH_3$, —$OCH_2CH_3$, $C_{3-12}$ carbocycle, or 3- to 6-membered heterocycle.

In some embodiments, for a compound of Formula (II):
H is thienopyrimidinyl, optionally substituted with one or more $R^{50}$;
A is selected from piperidinylene and piperazinylene;
B is indolylene;
$L^1$ and $L^2$ are each independently selected from —O—, —S—, —NH—, and —$CH_2$—;
$L^3$ is selected from $C_{1-6}$ alkylene, $C_{2-6}$ alkenylene, and $C_{2-6}$ alkynylene, each of which is substituted with one or more $R^{56}$ and optionally further substituted with one or more $R^{50}$;
$R^A$, $R^B$ and $R^C$ are each independently selected at each occurrence from $R^{50}$, or two $R^A$ groups, two $R^B$ groups or two $R^C$ groups attached to the same atom or different atoms can together optionally form a bridge or ring;

m is an integer from 0 to 3;

n is an integer from 1 to 3;

p is an integer from 0 to 6;

$R^{56}$ is independently selected at each occurrence from: —$OR^{59}$, =O, $C_{1-10}$ alkyl, $C_{2-10}$ alkenyl, and $C_{2-10}$ alkynyl, wherein each $C_{1-10}$ alkyl, $C_{2-10}$ alkenyl, and $C_{2-10}$ alkynyl in $R^{56}$ is independently optionally substituted at each occurrence with one or more substituents selected from halogen, —$NO_2$, —CN, —$OR^{59}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, =O, =S, =$N(R^{52})$, $C_{3-12}$ carbocycle, and 3- to 12-membered heterocycle;

wherein each $C_{3-12}$ carbocycle and 3- to 12-membered heterocycle in $R^{56}$ is independently optionally substituted with one or more substituents selected from halogen, —$NO_2$, —CN, —$OR^{52}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, =O, =S, =$N(R^{52})$, $C_{1-6}$ alkyl, $C_{1-6}$ haloalkyl, $C_{2-6}$ alkenyl, and $C_{2-6}$ alkynyl; and further wherein $R^{56}$ optionally forms a bond to ring C; and $R^{59}$ is independently selected at each occurrence from $C_{1-20}$ alkyl, $C_{2-20}$ alkenyl, $C_{2-20}$ alkynyl, 1- to 6-membered heteroalkyl, $C_{3-12}$ carbocycle, and 3- to 12-membered heterocycle, each of which is optionally substituted by halogen, —CN, —$NO_2$, —$NH_2$, —$NHCH_3$, —$NHCH_2CH_3$, =O, —OH, —$OCH_3$, —$OCH_2CH_3$, $C_{3-12}$ carbocycle, or 3- to 6-membered heterocycle.

For a compound of Formula (I), $R^{57}$ may be selected from —$S(=O)_2R^{58}$, —$S(=O)_2N(R^{52})_2$, and —$S(=O)_2NR^{53}R^{54}$, such as —$S(=O)_2CH_3$ and —$S(=O)_2NHCH_3$. For a compound of Formula (II), C may be substituted with —$S(=O)_2R^{58}$, —$S(=O)_2N(R^{52})_2$, or —$S(=O)_2NR^{53}R^{54}$.

In some embodiments, for a compound of Formula (I) or (II), H is

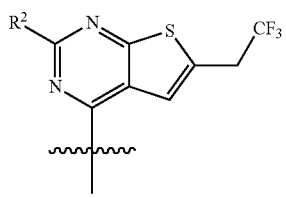

and $R^2$ is selected from hydrogen, halogen, —OH, —$OR^{52}$, —$NH_2$, —$N(R^{52})_2$, —CN, $C_{1-3}$ alkyl, $C_{1-3}$ alkyl-$N(R^{52})_2$, $C_{1-3}$ haloalkyl, $C_{2-3}$ alkenyl, and $C_{2-3}$ alkynyl. Optionally, $R^2$ is selected from —$NH_2$, —$CH_3$, and —$NHCH_3$. In some embodiments, for a compound of Formula (I) or (II), H is

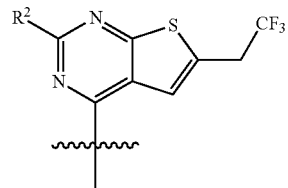

and $R^2$ is selected from hydrogen, halogen, —OH, —$OR^{52}$, —$NH_2$, —$N(R^{52})_2$, —CN, $C_{1-3}$ alkyl, $C_{1-3}$ alkyl-$OR^{52}$, $C_{1-3}$ alkyl-$N(R^{52})_2$, $C_{1-3}$ haloalkyl, $C_{2-3}$ alkenyl, and $C_{2-3}$ alkynyl. Optionally, $R^2$ is selected from —$NH_2$, —$CH_3$, —$OCH_3$, —$CH_2OH$, and —$NHCH_3$. For a compound of Formula (I) or (II), $L^3$ may be selected from

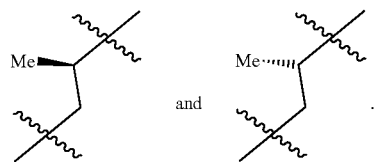

In certain aspects, the present disclosure provides a pharmaceutical composition comprising a compound or salt of Formula (I) or (II) and a pharmaceutically acceptable carrier. In some embodiments, the pharmaceutical composition is formulated for oral administration. In some embodiments, the pharmaceutical composition is formulated for injection.

In certain aspects, the present disclosure provides a method of inhibiting an interaction of menin with one or more of MLL1, MLL2, an MLL fusion protein, and an MLL Partial Tandem Duplication, comprising contacting menin with an effective amount of a compound or salt of Formula (I) or (II). In certain aspects, the present disclosure provides a method of inhibiting a menin-MLL interaction, comprising contacting menin with an effective amount of a compound or salt of Formula (I) or (II), wherein inhibition of the interaction is evidenced by a reduction in expression of an MLL fusion protein target gene. In certain aspects, the present disclosure provides a method of stabilizing menin, comprising contacting menin with a compound or salt of Formula (I) or (II).

In practicing any of the subject methods, the MLL fusion protein target gene may be HOXA9, DLX2, or MEIS1. The contacting may comprise contacting a cell that expresses menin. In some embodiments, the method comprises administering a second therapeutic agent. In some embodiments, the contacting takes place in vivo. In some embodiments, the contacting takes place in vitro.

In certain aspects, the present disclosure provides a method of treating a disease or condition associated with MLL fusion proteins, comprising administering to a subject in need thereof an effective amount of a compound or salt of Formula (I) or (II). In certain aspects, the present disclosure provides a method of treating a disease or condition in a subject, comprising administering to the subject a therapeutically effective amount of a pharmaceutical composition of a compound or salt of Formula (I) or (II). In some embodiments, the disease or condition comprises a leukemia, hematologic malignancy, solid tumor cancer, prostate cancer, breast cancer, liver cancer, brain tumor, or diabetes. In some embodiments, the leukemia comprises AML, ALL, Mixed Lineage Leukemia or a leukemia with Partial Tandem Duplications of MLL.

In certain aspects, the present disclosure provides a method of treating a disorder mediated by chromosomal rearrangement on chromosome 11q23 in a subject in need thereof, the method comprising administering to the subject a therapeutically effective amount of a compound or salt of Formula (I) or (II). In certain aspects, the present disclosure provides a method of treating a disorder mediated by an interaction between menin and another protein, comprising administering to a subject in need thereof a therapeutically effective amount of a compound or salt of Formula (I) or (II). In some embodiments, the subject is a human.

In certain aspects, the present disclosure provides a kit comprising a pharmaceutical composition described herein and instructions for using the composition to treat a subject suffering from a disease or condition mediated by an interaction between menin and another protein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 is an amino acid sequence of human menin, isoform 1 (SEQ ID NO: 1).

FIG. 2 is an amino acid sequence of human menin, isoform 2 (SEQ ID NO: 2).

FIG. 3 is an amino acid sequence of human menin, isoform 3 (SEQ ID NO: 3).

FIG. 11 depicts the luminescence of MV4;11-luc tumors in vehicle and compound treated xenotransplantation mouse models of MLL leukemia after 6 days of treatment.

DETAILED DESCRIPTION OF THE INVENTION

Figure 4:
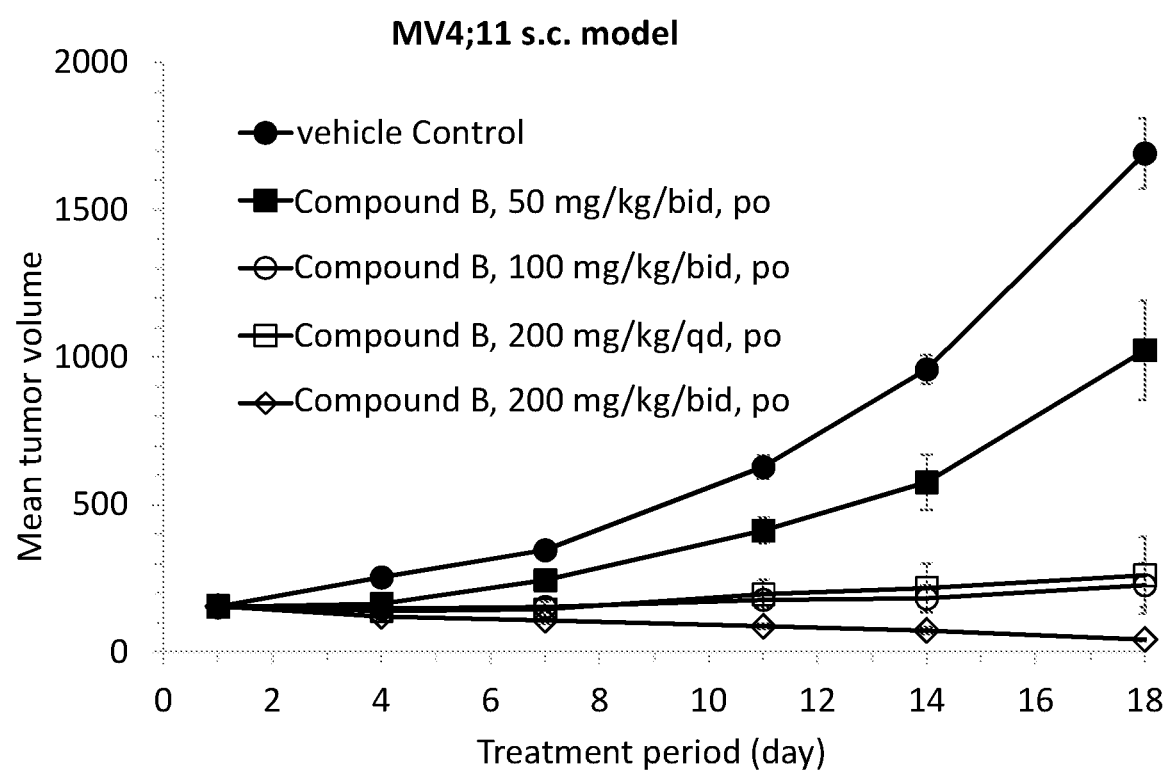
FIG. 4 depicts the change in volume of MV4;11 tumors in vehicle and compound treated mice.

Unless defined otherwise, all technical and scientific terms used herein have the same meaning as is commonly understood by one of skill in the art to which this invention belongs.

"MLL fusion protein" refers to a protein with an N-terminal fragment of MLL fused with a partner protein. Non-limiting examples of a partner protein include 11q23, 11q23.3, 11q24, 1p13.1, 1p32 (EPS15), 21q22, 9p13.3, 9p22 (MLLT3/AF9), ABI1, ABI2, ACACA, ACTN4, AFF1/AF4, AFF3/LAF4, AFF4/AF5, AKAP13, AP2A2, ARHGEF12, ARHGEF17, BCL9L, BTBD18, BUD13, C2CD3, CASC5, CASP8AP2, CBL, CEP164, CEP170B, CREBBP, DCP1A, DCPS, EEFSEC/SELB, ELL, EPS15, FLNA, FNBP1, FOXO3, GAS7, GMPS, KIAA1524, LAMC3, LOC100131626, MAML2, ME2, MLLT1/ENL, MLLT10/AF10, MLLT11/AF1Q, MLLT3/AF9, MLLT4/AF6, MLLT6/AF17, MYH 11, MYO1F, NA, NEBL, NRIP3, PDS5A, PICALM, PRPF19, PTD, RUNDC3B, SEPT11, SEPT2, SEPT5, SEPT6, SEPT9, SMAP1, TET1, TNRC18, TOP3A, VAV1, and Xq26.3 (CT45A2). MLL fusion proteins may be created through the joining of a gene that codes for an MLL protein and a gene that codes for a partner protein creating a fusion gene. Translation of this fusion gene may result in a single or multiple polypeptides with functional properties derived from each of the original proteins.

The term "$C_{x-y}$" or "$C_x$-$C_y$" when used in conjunction with a chemical moiety, such as alkyl, alkenyl, or alkynyl is meant to include groups that contain from x to y carbons in the chain. For example, the term "$C_{x-y}$ alkyl" refers to substituted or unsubstituted saturated hydrocarbon groups, including straight-chain alkyl and branched-chain alkyl groups that contain from x to y carbons in the chain. The terms "$C_{x-y}$ alkenyl" and "$C_{x-y}$ alkynyl" refer to substituted or unsubstituted straight-chain or branched-chain unsaturated hydrocarbon groups that contain at least one double or triple bond respectively. Unless stated otherwise specifically in the specification, a $C_{x-y}$ alkyl, $C_{x-y}$ alkenyl, or $C_{x-y}$ alkynyl is optionally substituted by one or more substituents such as those substituents described herein.

"Carbocycle" refers to a saturated, unsaturated or aromatic ring in which each atom of the ring is a carbon atom. Carbocycle may include 3- to 10-membered monocyclic rings, 6- to 12-membered bicyclic rings, and 6- to 12-membered bridged rings. Each ring of a bicyclic carbocycle may be selected from saturated, unsaturated, and aromatic rings. In some embodiments, the carbocycle is an aryl. In some embodiments, the carbocycle is a cycloalkyl. In some embodiments, the carbocycle is a cycloalkenyl. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, are included in the definition of carbocyclic. Exemplary carbocycles include cyclopentyl, cyclohexyl, cyclohexenyl, adamantyl, phenyl, indanyl, and naphthyl. Unless stated otherwise specifically in the specification, a carbocycle is optionally substituted by one or more substituents such as those substituents described herein.

"Heterocycle" refers to a saturated, unsaturated or aromatic ring comprising one or more heteroatoms. Exemplary heteroatoms include N, O, Si, P, B, and S atoms. Heterocycles include 3- to 10-membered monocyclic rings, 6- to 12-membered bicyclic rings, and 6- to 12-membered bridged rings. Each ring of a bicyclic heterocycle may be selected from saturated, unsaturated, and aromatic rings. The heterocycle may be attached to the rest of the molecule through any atom of the heterocycle, valence permitting, such as a carbon or nitrogen atom of the heterocycle. In some embodiments, the heterocycle is a heteroaryl. In some embodiments, the heterocycle is a heterocycloalkyl. In an exemplary embodiment, a heterocycle, e.g., pyridyl, may be fused to a saturated or unsaturated ring, e.g., cyclohexane, cyclopentane, or cyclohexene.

"Heteroaryl" refers to a 3- to 12-membered aromatic ring that comprises at least one heteroatom wherein each heteroatom may be independently selected from N, O, and S. As used herein, the heteroaryl ring may be selected from monocyclic or bicyclic and fused or bridged ring systems rings wherein at least one of the rings in the ring system is aromatic, i.e., it contains a cyclic, delocalized (4n+2) π-electron system in accordance with the Hickel theory. The heteroatom(s) in the heteroaryl may be optionally oxidized. One or more nitrogen atoms, if present, are optionally quaternized. The heteroaryl may be attached to the rest of the molecule through any atom of the heteroaryl, valence permitting, such as a carbon or nitrogen atom of the heteroaryl. Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, isoindolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryls as defined above which are optionally substituted by one or more substituents such as those substituents described herein.

Compounds of the present disclosure also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof.

The compounds described herein may exhibit their natural isotopic abundance, or one or more of the atoms may be artificially enriched in a particular isotope having the same atomic number, but an atomic mass or mass number different from the atomic mass or mass number predominantly found in nature. All isotopic variations of the compounds of the present disclosure, whether radioactive or not, are encompassed within the scope of the present disclosure. For example, hydrogen has three naturally occurring isotopes, denoted $^1$H (protium), $^2$H (deuterium), and $^3$H (tritium). Protium is the most abundant isotope of hydrogen in nature. Enriching for deuterium may afford certain therapeutic advantages, such as increased in vivo half-life and/or exposure, or may provide a compound useful for investigating in vivo routes of drug elimination and metabolism. Isotopically-enriched compounds may be prepared by conventional techniques well known to those skilled in the art.

"Isomers" are different compounds that have the same molecular formula. "Stereoisomers" are isomers that differ only in the way the atoms are arranged in space. "Enantiomers" are a pair of stereoisomers that are non superimposable mirror images of each other. A 1:1 mixture of a pair of enantiomers is a "racemic" mixture. The term "(+)" is used to designate a racemic mixture where appropriate. "Diastereoisomers" or "diastereomers" are stereoisomers that have at least two asymmetric atoms but are not mirror images of each other. The absolute stereochemistry is specified according to the Cahn-Ingold-Prelog R-S system. When a compound is a pure enantiomer, the stereochemistry at each chiral carbon can be specified by either R or S. Resolved compounds whose absolute configuration is unknown can be designated (+) or (−) depending on the direction (dextro- or levorotatory) in which they rotate plane polarized light at the wavelength of the sodium D line. Certain compounds described herein contain one or more asymmetric centers and can thus give rise to enantiomers, diastereomers, and other stereoisomeric forms, the asymmetric centers of which can be defined, in terms of absolute stereochemistry, as (R)- or (S)-. The present chemical entities, pharmaceutical compositions and methods are meant to include all such possible stereoisomers, including racemic mixtures, optically pure forms, mixtures of diastereomers and intermediate mixtures. Optically active (R)- and (S)-isomers can be prepared using chiral synthons or chiral reagents, or resolved using conventional techniques. The optical activity of a compound can be analyzed via any suitable method, including but not limited to chiral chromatography and polarimetry, and the degree of predominance of one stereoisomer over the other isomer can be determined.

Chemical entities having carbon-carbon double bonds or carbon-nitrogen double bonds may exist in Z- or E-form (or cis- or trans-form). Furthermore, some chemical entities may exist in various tautomeric forms. Unless otherwise specified, chemical entities described herein are intended to include all Z-, E- and tautomeric forms as well.

The term "substituted" refers to moieties having substituents replacing a hydrogen on one or more carbons or heteroatoms of the structure. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, a carbocycle, a heterocycle, a cycloalkyl, a heterocycloalkyl, an aromatic and heteroaromatic moiety. In some embodiments, substituents may include any substituents described herein, for example: halogen, hydroxy, oxo (=O), thioxo (=S), cyano (—CN), nitro (—NO$_2$), imino (=N—H), oximo (=N—OH), hydrazino (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2), and —R$^b$—S(O)$_t$N(R$^a$)$_2$ (where t is 1 or 2); and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl any of which may be optionally substituted by alkyl, alkenyl, alkynyl, halogen, hydroxy, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2), —R$^b$—S(O)$_t$R$^a$ (where t is 1 or 2); wherein each R$^a$ is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each R$^a$, valence permitting, may be optionally substituted with alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); and wherein each R$^b$ is independently selected from a direct bond or a straight or branched alkylene, alkenylene, or alkynylene chain, and each R$^c$ is a straight or branched alkylene, alkenylene or alkynylene chain.

It will be understood by those skilled in the art that substituents can themselves be substituted, if appropriate. Unless specifically stated as "unsubstituted," references to chemical moieties herein are understood to include substituted variants. For example, reference to a "heteroaryl" group or moiety implicitly includes both substituted and unsubstituted variants.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "salt" or "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

The term "effective amount" or "therapeutically effective amount" refers to that amount of a compound described herein that is sufficient to affect the intended application, including but not limited to disease treatment, as defined below. The therapeutically effective amount may vary depending upon the intended treatment application (in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment" or "treating" refers to an approach for obtaining beneficial or desired results with respect to a disease, disorder, or medical condition including but not limited to a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, encompass administration of two or more agents to an animal, including humans, so that both agents and/or their metabolites are present in the subject at the same time. Co-administration includes simultaneous administration in separate compositions, administration at different times in separate compositions, or administration in a composition in which both agents are present.

The terms "antagonist" and "inhibitor" are used interchangeably, and they refer to a compound having the ability to inhibit a biological function (e.g., activity, expression, binding, protein-protein interaction) of a target protein (e.g., menin, MLL1, MLL2, and/or an MLL fusion protein). Accordingly, the terms "antagonist" and "inhibitor" are defined in the context of the biological role of the target protein. While preferred antagonists herein specifically interact with (e.g., bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor.

The term "agonist" as used herein refers to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g., bind to) the target, compounds that initiate or enhance a biological activity of the target polypeptide by interacting with other members of the signal transduction pathway of which the target polypeptide is a member are also specifically included within this definition.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

"Subject" refers to an animal, such as a mammal, for example a human. The methods described herein can be useful in both human therapeutics and veterinary applications. In some embodiments, the subject is a mammal, and in some embodiments, the subject is human. "Mammal" includes humans and both domestic animals such as laboratory animals and household pets (e.g., cats, dogs, swine, cattle, sheep, goats, horses, rabbits), and non-domestic animals such as wildlife and the like.

"Prodrug" is meant to indicate a compound that may be converted under physiological conditions or by solvolysis to a biologically active compound described herein (e.g., compound of Formula (I) or (II)). Thus, the term "prodrug" refers to a precursor of a biologically active compound that is pharmaceutically acceptable. In some aspects, a prodrug is inactive when administered to a subject but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam); Higuchi, T., et al., "Pro-drugs as Novel Delivery Systems," (1987) A.C.S. Symposium Series, Vol. 14; and Bioreversible Carriers in Drug Design, ed. Edward B. Roche, American Pharmaceutical Association and Pergamon Press) each of which is incorporated in full by reference herein. The term "prodrug" is also meant to include any covalently bonded carriers, which release the active compound in vivo when such prodrug is administered to a mammalian subject. Prodrugs of an active compound, as described herein, are typically prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of a hydroxy functional group, or acetamide, formamide and benzamide derivatives of an amine functional group in the active compound and the like.

The term "in vivo" refers to an event that takes place in a subject's body.

The term "in vitro" refers to an event that takes places outside of a subject's body. For example, an in vitro assay encompasses any assay run outside of a subject. In vitro assays encompass cell-based assays in which cells alive or dead are employed. In vitro assays also encompass a cell-free assay in which no intact cells are employed.

"Optional" or "optionally" means that the subsequently described event of circumstances may or may not occur, and that the description includes instances where the event or circumstance occurs and instances in which it does not. For example, "optionally substituted aryl" means that the aryl group may or may not be substituted and that the description includes both substituted aryl groups and aryl groups having no substitution.

"Pharmaceutically acceptable carrier, diluent or excipient" includes without limitation any adjuvant, carrier, excipient, glidant, sweetening agent, diluent, preservative, dye, colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

The present disclosure provides compounds for modulating the interaction of menin with proteins such as MLL1, MLL2 and MLL-fusion oncoproteins. In certain embodiments, the disclosure provides compounds and methods for inhibiting the interaction of menin with its upstream or downstream signaling molecules including but not limited to MLL1, MLL2 and MLL-fusion oncoproteins. Compounds of the disclosure may be used in methods for the treatment of a wide variety of cancers and other diseases associated with one or more of MLL1, MLL2, MLL fusion proteins, and menin. In certain embodiments, a compound of the disclosure covalently binds menin and inhibits the interaction of menin with MLL. In certain embodiments, a compound of the disclosure interacts non-covalently with menin and inhibits the interaction of menin with MLL.

Compounds of the disclosure may be used in methods for treating a wide variety of diseases associated with MLL1, MLL2, MLL fusion proteins, and menin. In certain embodiments, a compound of the disclosure interacts non-covalently with menin and inhibits the interaction of menin with MLL. In certain embodiments, a compound of the disclosure covalently binds menin and inhibits the interaction of menin with MLL.

In some aspects, the present disclosure provides a compound or salt that selectively binds to the menin protein and/or modulates the interaction of menin with an MLL protein (e.g., MLL1, MLL2, or an MLL fusion protein). In certain embodiments, the compound modulates the menin protein by binding to or interacting with one or more amino acids and/or one or more metal ions. Certain compounds may occupy the F9 and/or P13 pocket of menin. The binding of a compound disclosed herein may disrupt menin or MLL (e.g., MLL1, MLL2, or an MLL fusion protein) downstream signaling.

In certain aspects, the present disclosure provides a compound of Formula (I):

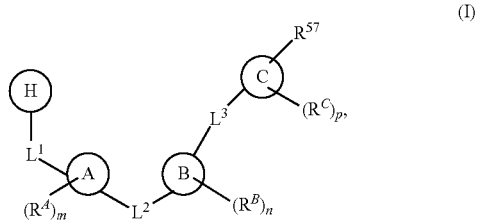

(I)

or a pharmaceutically acceptable salt, isotopic form, or prodrug thereof, wherein:

H is selected from $C_{5-12}$ carbocycle and 5- to 12-membered heterocycle, each of which is optionally substituted with one or more $R^{50}$;

A is selected from bond, $C_{3-12}$ carbocycle and 3- to 12-membered heterocycle;

B is selected from $C_{3-12}$ carbocycle and 3- to 12-membered heterocycle;

C is 3- to 12-membered heterocycle;

$L^1$, $L^2$ and $L^3$ are each independently selected from bond, —O—, —S—, —N($R^{51}$)—, —N($R^{51}$)CH$_2$—, —C(O)—, —C(O)O—, —OC(O)—, —OC(O)O—, —C(O)N($R^{51}$)—, —C(O)N($R^{51}$)C(O)—, —C(O)N($R^{51}$)C(O)N($R^{51}$)—, —N($R^{51}$)C(O)—, —N($R^{51}$)C(O)N($R^{51}$)—, —N($R^{51}$)C(O)O—, —OC(O)N($R^{51}$)—, —C(N$R^{51}$)—, —N($R^{51}$)C(N$R^{51}$)—, —C(N$R^{51}$)N($R^{51}$)—, —N($R^{51}$)C(N$R^{51}$)N($R^{51}$)—, —S(O)$_2$—, —OS(O)—, —S(O)O—, —S(O)—, —OS(O)$_2$—, —S(O)$_2$O—, —N($R^{51}$)S(O)$_2$—, —S(O)$_2$N($R^{51}$)—, —N($R^{51}$)S(O)—, —S(O)N($R^{51}$)—, —N($R^{51}$)S(O)$_2$N($R^{51}$)—, —N($R^{51}$)S(O)N($R^{51}$)—; alkylene, alkenylene, alkynylene, heteroalkylene, heteroalkenylene, and heteroalkynylene, each of which is optionally substituted with one or more $R^{50}$, wherein two $R^{50}$ groups attached to the same atom or different atoms of any one of $L^1$, $L^2$ or $L^3$ can together optionally form a bridge or ring;

$R^A$, $R^B$ and $R^C$ are each independently selected at each occurrence from $R^{50}$, or two $R^A$ groups, two $R^B$ groups or two $R^C$ groups attached to the same atom or different atoms can together optionally form a bridge or ring;

m, n and p are each independently an integer from 0 to 6;

$R^{50}$ is independently selected at each occurrence from: halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$);

$C_{1-10}$ alkyl, $C_{2-10}$ alkenyl, and $C_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{50}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{1-6}$ alkyl, $C_{1-6}$ haloalkyl, $C_{2-6}$ alkenyl, and $C_{2-6}$ alkynyl;

$R^{51}$ is independently selected at each occurrence from: hydrogen, —C(O)R$^{52}$, —C(O)OR$^{52}$, —C(O)N(R$^{52}$)$_2$, —C(O)NR$^{53}$R$^{54}$;

$C_{1-6}$ alkyl, $C_{2-6}$ alkenyl, and $C_{2-6}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{3-12}$ carbocycle and 3- to 12-membered heterocycle; and $C_{3-12}$ carbocycle and 3- to 12-membered heterocycle, wherein each $C_{3-12}$ carbocycle and 3- to 12-membered heterocycle in $R^{51}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;

R$^{52}$ is independently selected at each occurrence from hydrogen; and C$_{1-20}$ alkyl, C$_{2-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle;

R$^{53}$ and R$^{54}$ are taken together with the nitrogen atom to which they are attached to form a heterocycle, optionally substituted with one or more R$^{50}$;

R$^{57}$ is selected from:
halogen, —NO$_2$, —CN, —SR$^{52}$, —NR$^{53}$R$^{54}$, —S(=O)R$^{52}$, —S(=O)$_2$R$^{58}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)OR$^{52}$, —NR$^{52}$C(O)N(R$^{52}$)$_2$, —NR$^{52}$C(O)NR$^{53}$R$^{54}$, —C(O)NH(C$_{1-6}$ alkyl), —C(O)NR$^{53}$R$^{54}$, —P(O)(OR$^{52}$)$_2$, —P(O)(R$^{52}$)$_2$, =S, =N(R$^{52}$); and C$_{1-10}$ alkyl, C$_{2-10}$ alkenyl, and C$_{2-10}$ alkynyl, each of which is independently substituted at each occurrence with one or more substituents selected from —NO$_2$, —CN, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —P(O)(OR$^{52}$)$_2$, —P(O)(R$^{52}$)$_2$, =S, and =N(R$^{52}$); and R$^{58}$ is selected from hydrogen; and C$_{1-20}$ alkyl, C$_{3-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle, wherein for a compound or salt of Formula (I), when C is azetidinylene, piperidinylene or piperazinylene and R$^{57}$ is —S(=O)$_2$R$^{58}$, —S(=O)$_2$N(R$^{52}$)$_2$, or —NR$^{52}$S(=O)$_2$R$^{52}$:
p is an integer from 1 to 6; and/or
L$^3$ is substituted with one or more R$^{50}$, wherein L$^3$ is not —CH$_2$CH(OH)—.

In certain aspects, the present disclosure provides a compound of Formula (II):

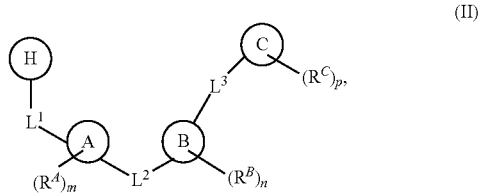

(II)

or a pharmaceutically acceptable salt thereof, wherein:
H is selected from C$_{5-12}$ carbocycle and 5- to 12-membered heterocycle, each of which is optionally substituted with one or more R$^{50}$;

A, B and C are each independently selected from C$_{3-12}$ carbocycle and 3- to 12-membered heterocycle;

L$^1$ and L$^2$ are each independently selected from bond, —O—, —S—, —N(R$^{51}$)—, —N(R$^{51}$)CH$_2$—, —C(O)—, —C(O)O—, —OC(O)—, —OC(O)O—, —C(O)N(R$^{51}$)—, —C(O)N(R$^{51}$)C(O)—, —C(O)N(R$^{51}$)C(O)N(R$^{51}$)—, —N(R$^{51}$)C(O)—, —N(R$^{51}$)C(O)N(R$^{51}$)—, —N(R$^{51}$)C(O)O—, —OC(O)N(R$^{51}$)—, —C(NR$^{51}$)—, —N(R$^{51}$)C(NR$^{51}$)—, —C(NR$^{51}$)N(R$^{51}$)—, —N(R$^{51}$)C(NR$^{51}$)N(R$^{51}$)—, —S(O)$_2$—, —OS(O)—, —S(O)O—, —S(O)—, —OS(O)$_2$—, —S(O)$_2$O—, —N(R$^{51}$)S(O)$_2$—, —S(O)$_2$N(R$^{51}$)—, —N(R$^{51}$)S(O)—, —S(O)N(R$^{51}$)—, —N(R$^{51}$)S(O)$_2$N(R$^{51}$)—, —N(R$^{51}$)S(O)N(R$^{51}$)—; alkylene, alkenylene, alkynylene, heteroalkylene, heteroalkenylene, and heteroalkynylene, each of which is optionally substituted with one or more R$^{50}$, wherein two R$^{50}$ groups attached to the same atom or different atoms of L or L$^2$ can together optionally form a ring;

L$^3$ is selected from alkylene, alkenylene, and alkynylene, each of which is substituted with one or more R$^{56}$ and optionally further substituted with one or more R$^{50}$;

R$^A$, R$^B$ and R$^C$ are each independently selected at each occurrence from R$^{50}$, or two R$^A$ groups, two R$^B$ groups or two R$^C$ groups attached to the same atom or different atoms can together optionally form a bridge or ring;

m, n and p are each independently an integer from 0 to 6;

R$^{50}$ is independently selected at each occurrence from:
halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$);

C$_{1-10}$ alkyl, C$_{2-10}$ alkenyl, and C$_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{3-12}$ carbocycle, and 3- to 12-membered heterocycle; and C$_{3-12}$ carbocycle and 3- to 12-membered heterocycle, wherein each C$_{3-12}$ carbocycle and 3- to 12-membered heterocycle in R$^{50}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)

$NR^{53}R^{54}$, —$P(O)(OR^{52})_2$, —$P(O)(R^{52})_2$, =O, =S, =$N(R^{52})$, $C_{1-6}$ alkyl, $C_{1-6}$ haloalkyl, $C_{2-6}$ alkenyl, and $C_{2-6}$ alkynyl;

$R^{51}$ is independently selected at each occurrence from: hydrogen, —$C(O)R^{52}$, —$C(O)OR^{52}$, —$C(O)N(R^{52})_2$, —$C(O)NR^{53}R^{54}$;

$C_{1-6}$ alkyl, $C_{2-6}$ alkenyl, and $C_{2-6}$ alkynyl, each of which is independently optionally substituted at each occurrence with one or more substituents selected from halogen, —$NO_2$, —CN, —$OR^{52}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, =O, =S, =$N(R^{52})$, $C_{3-12}$ carbocycle and 3- to 12-membered heterocycle; and $C_{3-12}$ carbocycle and 3- to 12-membered heterocycle, wherein each $C_{3-12}$ carbocycle and 3- to 12-membered heterocycle in $R^{51}$ is independently optionally substituted with one or more substituents selected from halogen, —$NO_2$, —CN, —$OR^{52}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, =O, =S, =$N(R^{52})$, $C_{1-6}$ alkyl, $C_{1-6}$ haloalkyl, $C_{2-6}$ alkenyl, and $C_{2-6}$ alkynyl;

$R^{52}$ is independently selected at each occurrence from hydrogen; and $C_{1-20}$ alkyl, $C_{2-20}$ alkenyl, $C_{2-20}$ alkynyl, 1- to 6-membered heteroalkyl, $C_{3-12}$ carbocycle, and 3- to 12-membered heterocycle, each of which is optionally substituted by halogen, —CN, —$NO_2$, —$NH_2$, —$NHCH_3$, —$NHCH_2CH_3$, =O, —OH, —$OCH_3$, —$OCH_2CH_3$, $C_{3-12}$ carbocycle, or 3- to 6-membered heterocycle;

$R^{53}$ and $R^{54}$ are taken together with the nitrogen atom to which they are attached to form a heterocycle, optionally substituted with one or more $R^{50}$;

$R^{56}$ is independently selected at each occurrence from: —$NO_2$, —$OR^{59}$, —$SR^{52}$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, =O, =S, =$N(R^{52})$, $C_{1-10}$ alkyl, $C_{2-10}$ alkenyl, $C_{2-10}$ alkynyl, $C_{3-12}$ carbocycle and 3- to 12-membered heterocycle, wherein each $C_{1-10}$ alkyl, $C_{2-10}$ alkenyl, and $C_{2-10}$ alkynyl in $R^{56}$ is independently optionally substituted at each occurrence with one or more substituents selected from halogen, —$NO_2$, —CN, —$OR^{59}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, =O, =S, =$N(R^{52})$, $C_{3-12}$ carbocycle, and 3- to 12-membered heterocycle;

wherein each $C_{3-12}$ carbocycle and 3- to 12-membered heterocycle in $R^{56}$ is independently optionally substituted with one or more substituents selected from halogen, —$NO_2$, —CN, —$OR^{52}$, —$SR^{52}$, —$N(R^{52})_2$, —$NR^{53}R^{54}$, —$S(=O)R^{52}$, —$S(=O)_2R^{52}$, —$S(=O)_2N(R^{52})$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, =O, =S, =$N(R^{52})$, $C_{1-6}$ alkyl, $C_{1-6}$ haloalkyl, $C_{2-6}$ alkenyl, and $C_{2-6}$ alkynyl; and further wherein $R^{56}$ optionally forms a bond to ring C; and $R^{59}$ is independently selected at each occurrence from $C_{1-20}$ alkyl, $C_{2-20}$ alkenyl, $C_{2-20}$ alkynyl, 1- to 6-membered heteroalkyl, $C_{3-12}$ carbocycle, and 3- to 12-membered heterocycle, each of which is optionally substituted by halogen, —CN, —$NO_2$, —$NH_2$, —$NHCH_3$, —$NHCH_2CH_3$, =O, —OH, —$OCH_3$, —$OCH_2CH_3$, $C_{3-12}$ carbocycle, or 3- to 6-membered heterocycle, wherein for a compound or salt of Formula (II), when $R^{56}$ is —$CH_3$, $L^3$ is not further substituted with —OH, —$NH_2$, or —CN.

In certain aspects, the present disclosure provides a compound of Formula (I):

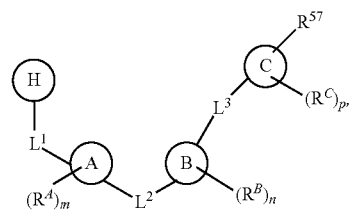

(I)

or a pharmaceutically acceptable salt, isotopic form, or prodrug thereof, wherein:

H is selected from $C_{5-12}$ carbocycle and 5- to 12-membered heterocycle, each of which is optionally substituted with one or more $R^{50}$;

A is selected from bond, $C_{3-12}$ carbocycle and 3- to 12-membered heterocycle;

B is selected from $C_{3-12}$ carbocycle and 3- to 12-membered heterocycle;

C is 3- to 12-membered heterocycle;

$L^1$, $L^2$ and $L^3$ are each independently selected from bond, —O—, —S—, —$N(R^{51})$—, —$N(R^{51})CH_2$—, —C(O)—, —C(O)O—, —OC(O)—, —OC(O)O—, —$C(O)N(R^{51})$—, —$C(O)N(R^{51})C(O)$—, —$C(O)N(R^{51})C(O)N(R^{51})$—, —$N(R^{51})C(O)$—, —$N(R^{51})C(O)N(R^{51})$—, —$N(R^{51})C(O)O$—, —$OC(O)N(R^{51})$—, —$C(NR^{51})$—, —$N(R^{51})C(NR^{51})$—, —$C(NR^{51})N(R^{51})$—, —$N(R^{51})C(NR^{51})N(R^{51})$—, —$S(O)_2$—, —OS(O)—, —S(O)O—, —S(O)—, —$OS(O)_2$—, —$S(O)_2O$—, —$N(R^{51})S(O)_2$—, —$S(O)_2N(R^{51})$—, —$N(R^{51})S(O)$—, —$S(O)N(R^{51})$—, —$N(R^{51})S(O)_2N(R^{51})$—, —$N(R^{51})S(O)N(R^{51})$—; alkylene, alkenylene, alkynylene, heteroalkylene, heteroalkenylene, and heteroalkynylene, each of which is optionally substituted with one or more $R^{50}$, wherein two $R^{50}$ groups attached to the same atom or different atoms of any one of $L^1$, $L^2$ or $L^3$ can together optionally form a bridge or ring;

$R^A$, $R^B$ and $R^C$ are each independently selected at each occurrence from $R^{50}$, or two $R^A$ groups, two $R^B$ groups or two $R^C$ groups attached to the same atom or different atoms can together optionally form a bridge or ring;

m, n and p are each independently an integer from 0 to 6;

$R^{50}$ is independently selected at each occurrence from:

halogen, —$NO_2$, —CN, —$OR^{52}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, —$P(O)(OR^{52})(R^{52})$, —$P(O)(NR^{52})(R^{52})$, —$NR^{52}P(O)(R^{52})$, —$P(O)(NR^{52})(OR^{52})$, —$P(O)(NR^{52})_2$, =O, =S, =$N(R^{52})$;

$C_{1-10}$ alkyl, $C_{2-10}$ alkenyl, and $C_{2-10}$ alkynyl, each of which is independently optionally substituted at each occurrence with one or more substituents selected from halogen, —$NO_2$, —CN, —$OR^{52}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, —$P(O)(OR^{52})(R^{52})$, —$P(O)(NR^{52})(R^{52})$, —$NR^{52}P(O)(R^{52})$, —$P(O)(NR^{52})(OR^{52})$, —$P(O)(NR^{52})_2$, =O, =S, =$N(R^{52})$, $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{50}$ is independently optionally substituted with one or more substituents selected from halogen, —$NO_2$, —CN, —$OR^{52}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, —$P(O)(OR^{52})(R^{52})$, —$P(O)(NR^{52})(R^{52})$, —$NR^{52}P(O)(R^{52})$, —$P(O)(NR^{52})(OR^{52})$, —$P(O)(NR^{52})_2$, =O, =S, =$N(R^{52})$, $C_{1-6}$ alkyl, $C_{1-6}$ haloalkyl, $C_{2-6}$ alkenyl, and $C_{2-6}$ alkynyl;

$R^{51}$ is independently selected at each occurrence from:

hydrogen, —$C(O)R^{52}$, —$C(O)OR^{52}$, —$C(O)N(R^{52})_2$, —$C(O)NR^{53}R^{54}$;

$C_{1-6}$ alkyl, $C_{2-6}$ alkenyl, and $C_{2-6}$ alkynyl, each of which is independently optionally substituted at each occurrence with one or more substituents selected from halogen, —$NO_2$, —CN, —$OR^{52}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, —$P(O)(OR^{52})(R^{52})$, —$P(O)(NR^{52})(R^{52})$, —$NR^{52}P(O)(R^{52})$, —$P(O)(NR^{52})(OR^{52})$, —$P(O)(NR^{52})_2$, =O, =S, =$N(R^{52})$, $C_{3-12}$ carbocycle and 3- to 12-membered heterocycle; and $C_{3-12}$ carbocycle and 3- to 12-membered heterocycle, wherein each $C_{3-12}$ carbocycle and 3- to 12-membered heterocycle in $R^{51}$ is independently optionally substituted with one or more substituents selected from halogen, —$NO_2$, —CN, —$OR^{52}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, —$P(O)(OR^{52})(R^{52})$, —$P(O)(NR^{52})(R^{52})$, —$NR^{52}P(O)(R^{52})$, —$P(O)(NR^{52})(OR^{52})$, —$P(O)(NR^{52})_2$, =O, =S, =$N(R^{52})$, $C_{1-6}$ alkyl, $C_{1-6}$ haloalkyl, $C_{2-6}$ alkenyl, and $C_{2-6}$ alkynyl;

$R^{52}$ is independently selected at each occurrence from hydrogen; and $C_{1-20}$ alkyl, $C_{2-20}$ alkenyl, $C_{2-20}$ alkynyl, 1- to 6-membered heteroalkyl, $C_{3-12}$ carbocycle, and 3- to 12-membered heterocycle, each of which is optionally substituted by halogen, —CN, —$NO_2$, —$NH_2$, —$NHCH_3$, —$NHCH_2CH_3$, =O, —OH, —$OCH_3$, —$OCH_2CH_3$, $C_{3-12}$ carbocycle, or 3- to 6-membered heterocycle;

$R^{53}$ and $R^{54}$ are taken together with the nitrogen atom to which they are attached to form a heterocycle, optionally substituted with one or more $R^{50}$;

$R^{57}$ is selected from:

halogen, —$NO_2$, —CN, —$SR^{52}$, —$NR^{53}R^{54}$, —$S(=O)R^{52}$, —$S(=O)_2R^{58}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)OR^{52}$, —$NR^{52}C(O)N(R^{52})_2$, —$NR^{52}C(O)NR^{53}R^{54}$, —$C(O)NH(C_{1-6}$ alkyl), —$C(O)NR^{53}R^{54}$, —$P(O)(OR^{52})_2$, —$P(O)(R^{52})_2$, —$P(O)(OR^{52})(R^{52})$, —$P(O)(NR^{52})(R^{52})$, —$NR^{52}P(O)(R^{52})$, —$P(O)(NR^{52})(OR^{52})$, —$P(O)(NR^{52})_2$, =S, =$N(R^{52})$; and $C_{1-10}$ alkyl, $C_{2-10}$ alkenyl, and $C_{2-10}$ alkynyl, each of which is independently substituted at each occurrence with one or more substituents selected from —$NO_2$, —CN, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$P(O)(OR^{52})_2$, —$P(O)(R^{52})_2$, —$P(O)(OR^{52})(R^{52})$, —$P(O)(NR^{52})(R^{52})$, —$NR^{52}P(O)(R^{52})$, —$P(O)(NR^{52})(OR^{52})$, —$P(O)(NR^{52})_2$, =S, and =$N(R^{52})$; and $R^{58}$ is selected from hydrogen; and $C_{1-20}$ alkyl, $C_{3-20}$ alkenyl, $C_{2-20}$ alkynyl, 1- to 6-membered heteroalkyl, $C_{3-12}$ carbocycle, and 3- to 12-membered heterocycle, each of which is optionally substituted by halogen, —CN, —$NO_2$, —$NH_2$, —$NHCH_3$, —$NHCH_2CH_3$, =O, —OH, —$OCH_3$, —$OCH_2CH_3$, $C_{3-12}$ carbocycle, or 3- to 6-membered heterocycle, wherein for a compound or salt of Formula (I), when C is azetidinylene, piperidinylene or piperazinylene and $R^{57}$ is —$S(=O)_2R^{58}$, —$S(=O)_2N(R^{52})_2$, or —$NR^{52}S(=)_2R^{52}$:

p is an integer from 1 to 6; and/or $L^3$ is substituted with one or more $R^{50}$, wherein $L^3$ is not —$CH_2CH(OH)$—.

In certain aspects, the present disclosure provides a compound of Formula (II):

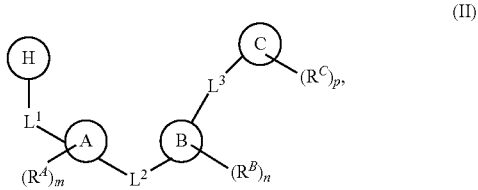

(II)

or a pharmaceutically acceptable salt thereof, wherein:

H is selected from $C_{5-12}$ carbocycle and 5- to 12-membered heterocycle, each of which is optionally substituted with one or more $R^{50}$;

A, B and C are each independently selected from $C_{3-12}$ carbocycle and 3- to 12-membered heterocycle;

$L^1$ and $L^2$ are each independently selected from bond, —O—, —S—, —N($R^{51}$)—, —N($R^{51}$)CH$_2$—, —C(O)—, —C(O)O—, —OC(O)—, —OC(O)O—, —C(O)N($R^{51}$)—, —C(O)N($R^{51}$)C(O)—, —C(O)N($R^{51}$)C(O)N($R^{51}$)—, —N($R^{51}$)C(O)—, —N($R^{51}$)C(O)N($R^{51}$)—, —N($R^{51}$)C(O)O—, —OC(O)N($R^{51}$)—, —C(N$R^{51}$)—, —N($R^{51}$)C(N$R^{51}$)—, —C(N$R^{51}$)N($R^{51}$)—, —N($R^{51}$)C(N$R^{51}$)N($R^{51}$)—, —S(O)$_2$-, —OS(O)—, —S(O)O—, —S(O)—, —OS(O)$_2$—, —S(O)$_2$O—, —N($R^{51}$)S(O)$_2$—, —S(O)$_2$N($R^{51}$)—, —N($R^{51}$)S(O)—, —S(O)N($R^{51}$)—, —N($R^{51}$)S(O)$_2$N($R^{51}$)—, —N($R^{51}$)S(O)N($R^{51}$)—; alkylene, alkenylene, alkynylene, heteroalkylene, heteroalkenylene, and heteroalkynylene, each of which is optionally substituted with one or more $R^{50}$, wherein two $R^{50}$ groups attached to the same atom or different atoms of L or $L^2$ can together optionally form a ring;

$L^3$ is selected from alkylene, alkenylene, and alkynylene, each of which is substituted with one or more $R^{56}$ and optionally further substituted with one or more $R^{50}$;

$R^A$, $R^B$ and $R^C$ are each independently selected at each occurrence from $R^{50}$, or two $R^A$ groups, two $R^B$ groups or two $R^C$ groups attached to the same atom or different atoms can together optionally form a bridge or ring;

m, n and p are each independently an integer from 0 to 6;

$R^{50}$ is independently selected at each occurrence from:
halogen, —NO$_2$, —CN, —OR$^{52}$, —SR$^{52}$, —N($R^{52}$)$_2$, —NR$^{53}$R$^{54}$, —S(=O)R$^{52}$, —S(=O)$_2$R$^{52}$, —S(=O)$_2$N($R^{52}$)$_2$, —S(=O)$_2$NR$^{53}$R$^{54}$, —NR$^{52}$S(=O)$_2$R$^{52}$, —NR$^{52}$S(=O)$_2$N($R^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N($R^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N($R^{52}$)$_2$, —NR$^{52}$C(O)NR$^{53}$R$^{54}$, —C(O)N($R^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N($R^{52}$);

$C_{1-10}$ alkyl, $C_{2-10}$ alkenyl, and $C_{2-10}$ alkynyl, each of which is independently optionally substituted at each occurrence with one or more substituents selected from halogen, —NO$_2$, —CN, —OR$^{52}$, —SR$^{52}$, —N($R^{52}$)$_2$, —NR$^{53}$R$^{54}$, —S(=O)R$^{52}$, —S(=O)$_2$R$^{52}$, —S(=O)$_2$N($R^{52}$)$_2$, —S(=O)$_2$NR$^{53}$R$^{54}$, —NR$^{52}$S(=O)$_2$R$^{52}$, —NR$^{52}$S(=O)$_2$N($R^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N($R^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N($R^{52}$)$_2$, —NR$^{52}$C(O)NR$^{53}$R$^{54}$, —C(O)N($R^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N($R^{52}$), $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{50}$ is independently optionally substituted with one or more substituents selected from halogen, —NO$_2$, —CN, —OR$^{52}$, —SR$^{52}$, —N($R^{52}$)$_2$, —NR$^{53}$R$^{54}$, —S(=O)R$^{52}$, —S(=O)$_2$R$^{52}$, —S(=O)$_2$N($R^{52}$)$_2$, —S(=O)$_2$NR$^{53}$R$^{54}$, —NR$^{52}$S(=O)$_2$R$^{52}$, —NR$^{52}$S(=O)$_2$N($R^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N($R^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N($R^{52}$)$_2$, —NR$^{52}$C(O)NR$^{53}$R$^{54}$, —C(O)N($R^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N($R^{52}$), $C_{1-6}$ alkyl, $C_{1-6}$ haloalkyl, $C_{2-6}$ alkenyl, and $C_{2-6}$ alkynyl;

$R^{51}$ is independently selected at each occurrence from: hydrogen, —C(O)R$^{52}$, —C(O)OR$^{52}$, —C(O)N($R^{52}$)$_2$, —C(O)NR$^{53}$R$^{54}$;

$C_{1-6}$ alkyl, $C_{2-6}$ alkenyl, and $C_{2-6}$ alkynyl, each of which is independently optionally substituted at each occurrence with one or more substituents selected from halogen, —NO$_2$, —CN, —OR$^{52}$, —SR$^{52}$, —N($R^{52}$)$_2$, —NR$^{53}$R$^{54}$, —S(=O)R$^{52}$, —S(=O)$_2$R$^{52}$, —S(=O)$_2$N($R^{52}$)$_2$, —S(=O)$_2$NR$^{53}$R$^{54}$, —NR$^{52}$S(=O)$_2$R$^{52}$, —NR$^{52}$S(=O)$_2$N($R^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N($R^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N($R^{52}$)$_2$, —NR$^{52}$C(O)NR$^{53}$R$^{54}$, —C(O)N($R^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N($R^{52}$), $C_{3-12}$ carbocycle and 3- to 12-membered heterocycle; and $C_{3-12}$ carbocycle and 3- to 12-membered heterocycle, wherein each $C_{3-12}$ carbocycle and 3- to 12-membered heterocycle in $R^{51}$ is independently optionally substituted with one or more substituents selected from halogen, —NO$_2$, —CN, —OR$^{52}$, —SR$^{52}$, —N($R^{52}$)$_2$, —NR$^{53}$R$^{54}$, —S(=O)R$^{52}$, —S(=O)$_2$R$^{52}$, —S(=O)$_2$N($R^{52}$)$_2$, —S(=O)$_2$NR$^{53}$R$^{54}$, —NR$^{52}$S(=O)$_2$R$^{52}$, —NR$^{52}$S(=O)$_2$N($R^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N($R^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N($R^{52}$)$_2$, —NR$^{52}$C(O)NR$^{53}$R$^{54}$, —C(O)N($R^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N($R^{52}$), $C_{1-6}$ alkyl, $C_{1-6}$ haloalkyl, $C_{2-6}$ alkenyl, and $C_{2-6}$ alkynyl;

$R^{52}$ is independently selected at each occurrence from hydrogen; and $C_{1-20}$ alkyl, $C_{2-20}$ alkenyl, $C_{2-20}$ alkynyl, 1- to 6-membered heteroalkyl, $C_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, $C_{3-12}$ carbocycle, or 3- to 6-membered heterocycle;

$R^{53}$ and $R^{54}$ are taken together with the nitrogen atom to which they are attached to form a heterocycle, optionally substituted with one or more $R^{50}$;

$R^{56}$ is independently selected at each occurrence from:
—$NO_2$, —$OR^{59}$, —$SR^{52}$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, —$P(O)(OR^{52})(R^{52})$, —$P(O)(NR^{52})(R^{52})$, —$NR^{52}P(O)(R^{52})$, —$P(O)(NR^{52})(OR^{52})$, —$P(O)(NR^{52})_2$, =O, =S, =$N(R^{52})$, $C_{1-10}$ alkyl, $C_{2-10}$ alkenyl, $C_{2-10}$ alkynyl, $C_{3-12}$ carbocycle and 3- to 12-membered heterocycle, wherein each $C_{1-10}$ alkyl, $C_{2-10}$ alkenyl, and $C_{2-10}$ alkynyl in $R^{56}$ is independently optionally substituted at each occurrence with one or more substituents selected from halogen, —$NO_2$, —CN, —$OR^{59}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, —$P(O)(OR^{52})(R^{52})$, —$P(O)(NR^{52})(R^{52})$, —$NR^{52}P(O)(R^{52})$, —$P(O)(NR^{52})(OR^{52})$, —$P(O)(NR^{52})_2$, =O, =S, =$N(R^{52})$, $C_{3-12}$ carbocycle, and 3- to 12-membered heterocycle;

wherein each $C_{3-12}$ carbocycle and 3- to 12-membered heterocycle in $R^{56}$ is independently optionally substituted with one or more substituents selected from halogen, —$NO_2$, —CN, —$OR^{52}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, —$P(O)(OR^{52})(R^{52})$, —$P(O)(NR^{52})(R^{52})$, —$NR^{52}P(O)(R^{52})$, —$P(O)(NR^{52})(OR^{52})$, —$P(O)(NR^{52})_2$, =O, =S, =$N(R^{52})$, $C_{1-6}$ alkyl, $C_{1-6}$ haloalkyl, $C_{2-6}$ alkenyl, and $C_{2-6}$ alkynyl; and further wherein $R^{56}$ optionally forms a bond to ring C; and $R^{59}$ is independently selected at each occurrence from $C_{1-20}$ alkyl, $C_{2-20}$ alkenyl, $C_{2-20}$ alkynyl, 1- to 6-membered heteroalkyl, $C_{3-12}$ carbocycle, and 3- to 12-membered heterocycle, each of which is optionally substituted by halogen, —CN, —$NO_2$, —$NH_2$, —$NHCH_3$, —$NHCH_2CH_3$, =O, —OH, —$OCH_3$, —$OCH_2CH_3$, $C_{3-12}$ carbocycle, or 3- to 6-membered heterocycle, wherein for a compound or salt of Formula (II), when $R^{56}$ is —$CH_3$, $L^3$ is not further substituted with —OH, —$NH_2$, or —CN.

In some embodiments, for a compound of Formula (I) or (II), H is 5- to 12-membered heterocycle, such as 6- to 12-membered bicyclic heterocycle, optionally substituted with one or more $R^{50}$. In some embodiments, H contains one or more heteroatoms, such as 1, 2, 3, 4, 5 or 6 ring heteroatoms. In some embodiments, H contains at least 1, 2, 3, 4 or 5 ring nitrogen atoms. In some embodiments, H is thienopyrimidinyl, optionally substituted with one or more $R^{50}$. In some embodiments, H is substituted with $C_{1-4}$ haloalkyl, such as —$CH_2CF_3$. In some embodiments, H is substituted with one or more $R^{50}$ (e.g., by replacing a hydrogen connected to a ring atom with a bond to $R^{50}$). H may be substituted with 0, 1, 2, 3, 4, 5, 6 or more $R^{50}$ groups. H may be substituted with 1, 2, 3, 4, 5 or 6 $R^{50}$ groups, such as H substituted with 1 or 2 $R^{50}$ groups. In some embodiments, H is substituted with at least 1, 2, 3, 4, 5 or 6 $R^{50}$ groups. In some embodiments, H is substituted with up to 6, 5, 4, 3, 2 or 1 $R^{50}$ groups.

In some embodiments, for a compound of Formula (I) or (II), H is

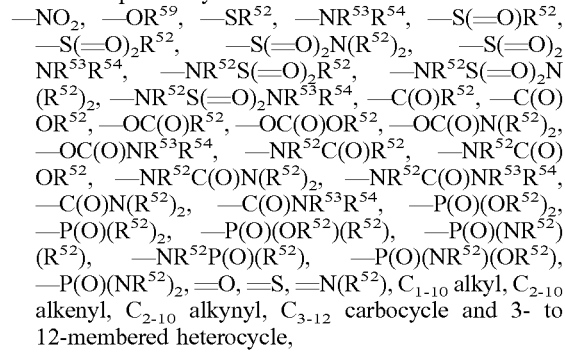

wherein $X^1$ and $X^2$ are each independently selected from $CR^2$ and N; $X^3$ and $X^4$ are each independently selected from C and N; $Y^1$ and $Y^2$ are each independently selected from $CR^3$, N, $NR^4$, O, and S; R, $R^2$ and $R^3$ are each independently selected at each occurrence from hydrogen and $R^{50}$; and $R^4$ is selected from $R^{51}$. In some embodiments, $X^3$ and $X^4$ are each C. In some embodiments, $X^1$ is $CR^2$, and $R^2$ is selected from hydrogen, halogen, —OH, —$OR^{52}$, —$NH_2$, —$N(R^{52})_2$, —CN, $C_{1-3}$ alkyl, —$CH_2OH$, —$CH_2OR^{52}$, —$CH_2NH_2$, —$CH_2N(R^{52})_2$, $C_{1-3}$ alkyl-$N(R^{52})_2$, $C_{1-3}$ haloalkyl, $C_{2-3}$ alkenyl, and $C_{2-3}$ alkynyl, such as $R^2$ is selected from —OH, —$OR^{52}$, —$NH_2$, —$N(R^{52})_2$, —CN, and $C_{1-2}$ alkyl. In some embodiments, $R^2$ is methyl or —$NHCH_3$. In some embodiments, $R^2$ is H. In some embodiments, $X^2$ is N. In some embodiments, $Y^2$ is $CR^3$, and $R^3$ is selected from hydrogen, halogen, —OH, —$N(R^{52})_2$, —CN, —$C(O)OR^{52}$, $C_{1-3}$ alkyl, and $C_{1-3}$ haloalkyl. In some embodiments, $Y^1$ is S. In some embodiments, at least one of $Y^1$ and $Y^2$ is selected from N, $NR^4$, O and S. In some embodiments, $R^1$ is $C_{1-3}$ haloalkyl, such as —$CH_2CF_3$. In some embodiments, $X^1$ is $CR^2$, $X^2$ is N, $X^3$ and $X^4$ are each C, $Y^1$ is S, $Y^2$ is $CR^3$, and $R^1$ is selected from $R^{50}$. In some embodiments, $X^1$ is $CR^2$; $X^2$ is N; $X^3$ and $X^4$ are each C; $Y^1$ is S; $Y^2$ is CH; $R^1$ is $C_{1-3}$ haloalkyl; and $R^2$ is selected from hydrogen, halogen, —OH, —$OR^{52}$, —$NH_2$, —$N(R^{52})_2$, —CN, $C_{1-3}$ alkyl, —$CH_2OH$, —$CH_2OR^{52}$, —$CH_2NH_2$, —$CH_2N(R^{52})_2$, $C_{1-3}$ alkyl-$N(R^{52})_2$, $C_{1-3}$ haloalkyl, $C_{2-3}$ alkenyl, and $C_{2-3}$ alkynyl. In some embodiments, H is

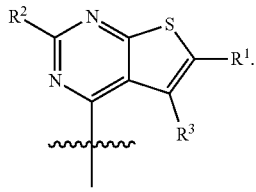

In some embodiments, H is

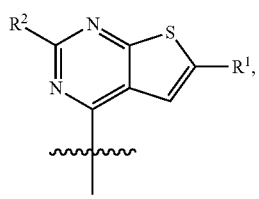

such as

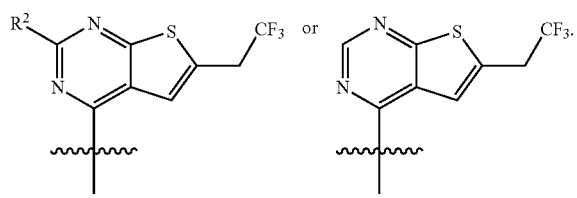

In some embodiments, H is

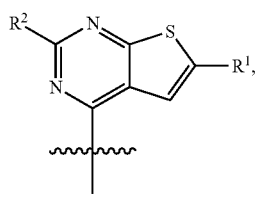

and $R^2$ is selected from hydrogen, halogen, —OH, —OR$^{52}$, —NH$_2$, —N(R$^{52}$)$_2$, —CN, C$_{1-3}$ alkyl, —CH$_2$OH, —CH$_2$OR$^{52}$, —CH$_2$NH$_2$, —CH$_2$N(R$^{52}$)$_2$, C$_{1-3}$ alkyl-N(R$^{52}$)$_2$, C$_{1-3}$ haloalkyl, C$_{2-3}$ alkenyl, and C$_{2-3}$ alkynyl. In some embodiments, $R^2$ is selected from hydrogen, halogen, —OH, alkoxy (e.g., —OR$^{52}$, —OCH$_3$, —OCH$_2$CH$_3$), aminoalkyl, alkylamino, —N(R$^{52}$)$_2$ (e.g., —NH$_2$, —NHCH$_3$, —NHCH$_2$CH$_3$), —N(CH$_3$)$_2$, —CN, C$_{1-3}$ alkyl (e.g., —CH$_3$), cyclopropyl, C$_{1-3}$ alkyl-OR$^{52}$ (e.g., —CH$_2$OH, —CH$_2$OC(O)CH$_3$), C$_{1-3}$ alkyl-N(R$^{52}$)$_2$, C$_{1-3}$ haloalkyl, C$_{2-3}$ alkenyl, and C$_{2-3}$ alkynyl.

In some embodiments, for a compound of Formula (I) or (II), H is

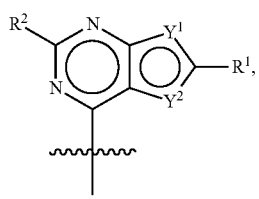

wherein $R^1$ is selected from H, halo, hydroxyl, amino, cyano, dialkylphosphine oxide, oxo, carboxyl, amido, acyl, alkyl, cycloalkyl, heteroalkyl, and haloalkyl, such as from alkyl and haloalkyl; $R^2$ is selected from H, halo, hydroxyl, amino, cyano, dialkylphosphine oxide, oxo, carboxyl, amido, acyl, alkyl, cycloalkyl, heteroalkyl, haloalkyl, aminoalkyl, hydroxyalkyl, alkoxy, and alkylamino, such as from H, halo, hydroxyl, and amino; and each of $Y^1$ and $Y^2$ is independently selected from S, CR$^3$, N, NR$^4$ and O. In certain embodiments, up to one of $Y^1$ and $Y^2$ is O or S.

In some embodiments, for a compound of Formula (I) or (II), $L^1$ comprises less than 20 atoms, such as less than 10 atoms. In some embodiments, $L^1$ comprises less than 20, 15, 10, 9, 8, 7, 6, 5, 4, or less than 3 atoms. In some embodiments, $L^1$ comprises at least 1, 2, 3, 4, 5, 6, 7, 8, 9, 10, 15 or at least 20 atoms. In some embodiments, $L^1$ comprises at least one heteroatom, such as $L^1$ comprises at least one nitrogen. In some embodiments, $L^1$ is substituted with one or more R$^{50}$. In some embodiments, $L^1$ is unsubstituted. In some embodiments, $L^1$ is selected from bond, —O—, —S—, —N(R$^{51}$)—, —N(R$^{51}$)CH$_2$—, —C(O)—, —C(O)O—, —OC(O)—, —C(O)N(R$^{51}$)—, —N(R$^{51}$)C(O)—, —N(R$^{51}$)C(O)N(R$^{51}$)—, —S(O)$_2$-, —S(O)—, —N(R$^{51}$)S(O)$_2$—, —S(O)$_2$N(R$^{51}$)—, —N(R$^{51}$)S(O)$_2$N(R$^{51}$)—, alkylene, alkenylene, heteroalkylene, and heteroalkenylene. In some embodiments, $L^1$ is selected from bond, —O—, —S—, —N(R$^{51}$)—, —N(R$^{51}$)CH$_2$—, —C(O)—, —C(O)O—, —OC(O)—, —C(O)N(R$^{51}$)—, —N(R$^{51}$)C(O)—, —N(R$^{51}$)C(O)N(R$^{51}$)—, —S(O)$_2$-, —S(O)—, —N(R$^{51}$)S(O)$_2$—, —S(O)$_2$N(R$^{51}$)—, —N(R$^{51}$)S(O)$_2$N(R$^{51}$)—, C$_{1-6}$ alkylene and C$_{2-6}$ alkenylene, wherein the C$_{1-6}$ alkylene and C$_{2-6}$ alkenylene are each optionally substituted with one or more R$^{50}$. In some embodiments, $L^1$ is —N(R$^{51}$)—, such as —NH—. In some embodiments, $L^1$ is selected from —O—, —N(R$^{51}$)—, —N(R$^{51}$)CH$_2$—, —C(O)—, —C(O)N(R$^{51}$)—, —N(R$^{51}$)C(O)—, —N(R$^{51}$)S(O)$_2$—, —S(O)$_2$N(R$^{51}$)—, C$_{1-4}$ alkylene, C$_{2-4}$ alkenylene, and C$_{1-4}$ heteroalkylene. In some embodiments, $L^1$ is —N(R$^{51}$)—, wherein R$^{51}$ is selected from hydrogen and alkyl.

In some embodiments, for a compound of Formula (I) or (II), A is 3- to 12-membered heterocycle, such as 5- to 8-membered heterocycle. In some embodiments, A is 6-membered monocyclic heterocycle. In some embodiments, the heterocycle comprises at least one nitrogen atom. In some embodiments, A comprises at least one ring nitrogen. In some embodiments, A is selected from piperidinylene and piperazinylene, such as

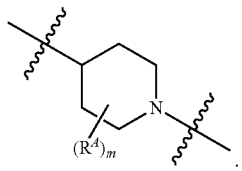

In some embodiments, A is

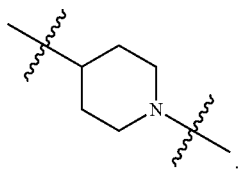 [SMILES: *C1CCN(*)CC1 ; "."]

In some embodiments, A is an aromatic, non-aromatic, saturated or unsaturated ring. In some embodiments, A is selected from arylene, cycloalkylene, heterocycloalkylene, N-heterocycloalkylene, heteroarylene, and N-heteroarylene. In some embodiments, A is 5- to 8-membered heterocycle, wherein the heterocycle comprises at least 1, 2, 3 or 4 ring heteroatoms selected from N, O and S.

In some embodiments, A is selected from

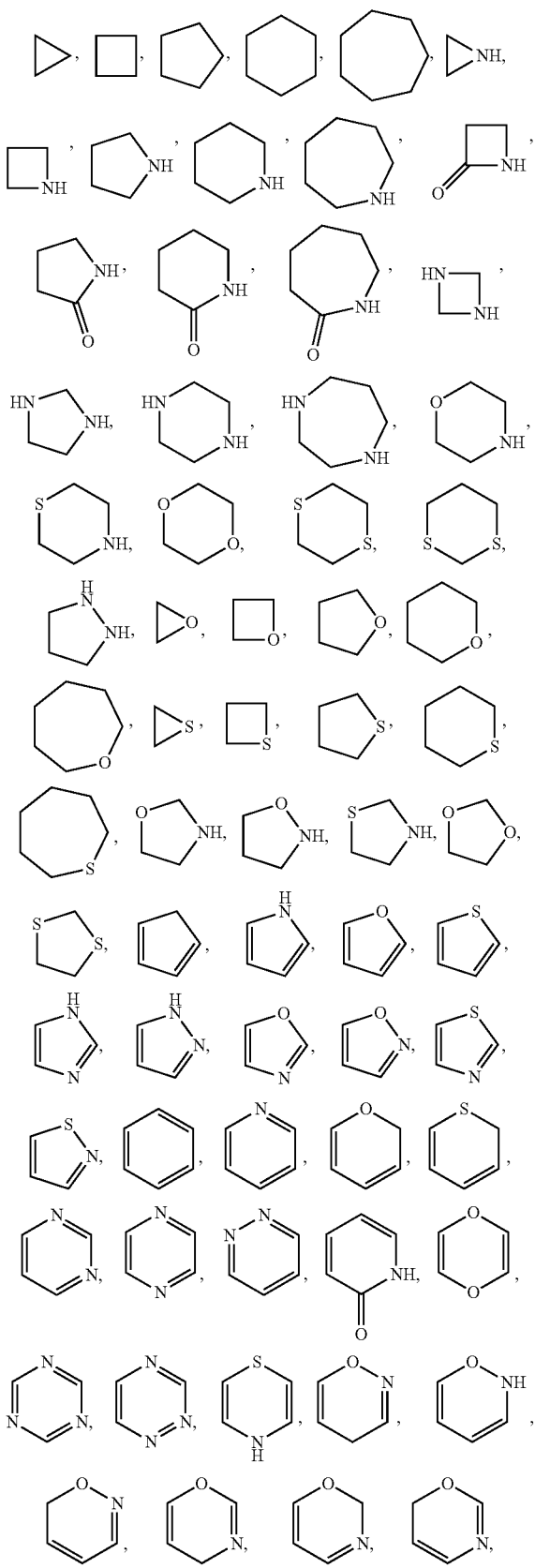
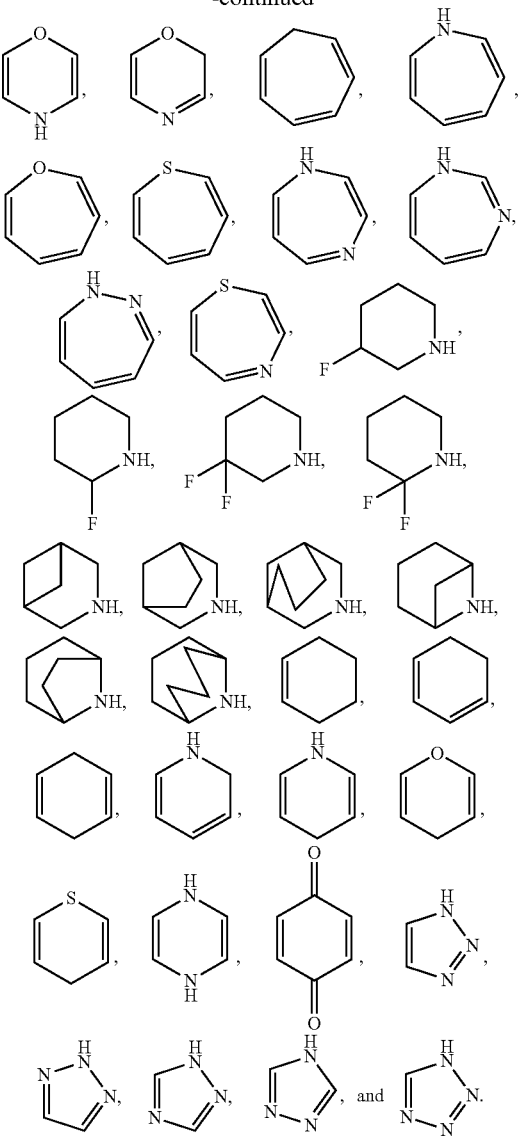

In some embodiments, A is substituted with one or more $R^A$ (e.g., by replacing a hydrogen connected to a ring atom with a bond to $R^A$). A may be substituted with 0, 1, 2, 3, 4, 5, 6 or more $R^A$ groups. A may be substituted with 1, 2, 3, 4, 5 or 6 $R^A$ groups, such as A substituted with 1 or 2 $R^A$ groups. In some embodiments, A is substituted with at least 1, 2, 3, 4, 5 or 6 $R^A$ groups. In some embodiments, A is unsubstituted. In some embodiments, A is substituted with m $R^A$ groups, wherein m is an integer from 0 to 6. In some embodiments, m is 0, 1, 2, 3, 4, 5 or 6. In some embodiments, m is at least 1, 2, 3, 4, 5 or 6. In some embodiments, m is up to 6, 5, 4, 3, 2, or 1. In some embodiments, m is 0.

In some embodiments, $R^A$ is independently selected at each occurrence from halo, hydroxyl, amino, cyano, dialkylphosphine oxide, oxo, carboxyl, amido, acyl, alkyl, cycloalkyl, heteroalkyl, haloalkyl, aminoalkyl, hydroxyalkyl, alkoxy, alkylamino, cycloalkylalkyl, cycloalkyloxy, cycloalkylalkyloxy, cycloalkylamino, cycloalkylalkylamino, heterocyclyl, heterocyclylalkyl, heterocyclyloxy, heterocyclylalkyloxy, heterocyclylamino, heterocyclylalkylamino, aryl, aralkyl, aryloxy, aralkyloxy, arylamino, aralkylamino, heteroaryl, heteroarylalkyl, heteroaryloxy, heteroarylalkyloxy, heteroarylamino, and heteroarylalkylamino. In some embodiments, two $R^4$ groups attached to the same atom or different atoms can together form a ring.

In some embodiments, for a compound of Formula (I) or (II), $L^2$ comprises less than 20 atoms, such as less than 10 atoms. In some embodiments, $L^2$ comprises less than 20, 15, 10, 9, 8, 7, 6, 5, 4, or less than 3 atoms. In some embodiments, $L^2$ comprises at least 1, 2, 3, 4, 5, 6, 7, 8, 9, 10, 15 or at least 20 atoms. In some embodiments, $L^2$ comprises at least one heteroatom, such as $L^2$ comprises at least one nitrogen. In some embodiments, $L^2$ is $C_{1-10}$ alkylene, such as $C_{1-4}$ alkylene, optionally substituted with one or more $R^{50}$. In some embodiments, $L^2$ is substituted with one or more $R^{50}$. In some embodiments, $L^2$ is unsubstituted. In some embodiments, $L^2$ is selected from bond, —O—, —S—, —N($R^{51}$)—, —N($R^{51}$)CH$_2$—, —C(O)—, —C(O)O—, —OC(O)—, —C(O)N($R^{51}$)—, —N($R^{51}$)C(O)—, —N($R^{51}$)C(O)N($R^{51}$)—, —S(O)$_2$-, —S(O)—, —N($R^{51}$)S(O)$_2$—, —S(O)$_2$N($R^{51}$)—, —N($R^{51}$)S(O)$_2$N($R^{51}$)—, alkylene, alkenylene, heteroalkylene, and heteroalkenylene. In some embodiments, $L^2$ is selected from bond, —O—, —S—, —N($R^{51}$)—, —N($R^{51}$)CH$_2$—, —C(O)—, —C(O)O—, —OC(O)—, —C(O)N($R^{51}$)—, —N($R^{51}$)C(O)—, —N($R^{51}$)C(O)N($R^{51}$)—, —S(O)$_2$-, —S(O)—, —N($R^{51}$)S(O)$_2$—, —S(O)$_2$N($R^{51}$)—, —N($R^{51}$)S(O)$_2$N($R^{51}$)—, $C_{1-6}$ alkylene and $C_{2-6}$ alkenylene, wherein the $C_{1-6}$ alkylene and $C_{2-6}$ alkenylene are each optionally substituted with one or more $R^{50}$. In some embodiments, $L^2$ is selected from —O—, —N($R^{51}$)—, —N($R^{51}$)CH$_2$—, —C(O)N($R^{51}$)—, —N($R^{51}$)C(O)—, —N($R^{51}$)S(O)$_2$—, —S(O)$_2$N($R^{51}$)—, $C_{1-4}$ alkylene and $C_{1-4}$ heteroalkylene. In some embodiments, $L^2$ is selected from —CH$_2$—, —N($R^{51}$)—, —N($R^{51}$)CH$_2$—, —N($R^{51}$)C(O)—, and —N($R^{51}$)S(O)$_2$—. In some embodiments, $L^2$ is —CH$_2$—.

In some embodiments, for a compound of Formula (I) or (II), B is 3- to 12-membered heterocycle, such as 6- to 12-membered bicyclic heterocycle. In some embodiments, the heterocycle comprises at least one nitrogen atom. In some embodiments, B is 6- to 12-membered heterocycle, wherein the heterocycle comprises at least 1, 2, 3 or 4 ring heteroatoms selected from N, O and S. In some embodiments, B is a 6,5- or 6,6-bicyclic heterocycle. In some embodiments, B comprises at least one ring nitrogen. In some embodiments, B is indolylene, such as

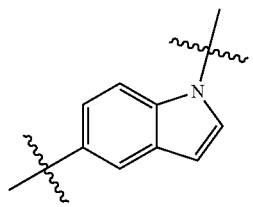 [SMILES: *c1ccc2c(ccn2*)c1]

optionally substituted with one or more $R^B$. In some embodiments, B is

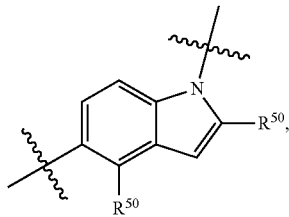

such as

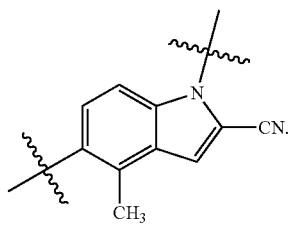 [SMILES: *c1ccc2c(cc(C#N)n2*)c1C]

In some embodiments, B is selected from

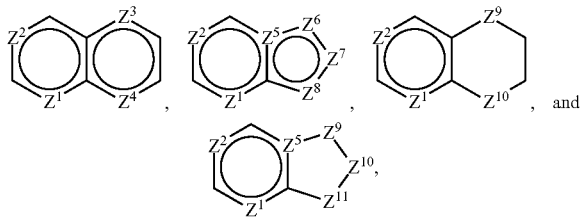

wherein $Z^1$, $Z^2$, $Z^3$ and $Z^4$ are each independently selected from $CR^7$, N and $NR^9$; $Z^5$ is selected from C and N; $Z^6$, $Z^7$ and $Z^8$ are each independently selected from $CR^8$, N, $NR^9$, O and S; $Z^9$, $Z^{10}$ and $Z^{11}$ are each independently selected from $CR^{10}$, $CR^{11}R^{12}$, $NR^{13}$, O and S; $R^7$, $R^8$, $R^{10}$, $R^{11}$, and $R^{12}$ are each independently selected from hydrogen and $R^{50}$; and $R^9$ and $R^{13}$ are each independently selected from $R^{51}$, wherein B may be connected at any ring atom to $L^2$ or $L^3$ (e.g., by replacing a hydrogen connected to a ring atom with a bond to $L^2$ or $L^3$).

In some embodiments, B is selected from

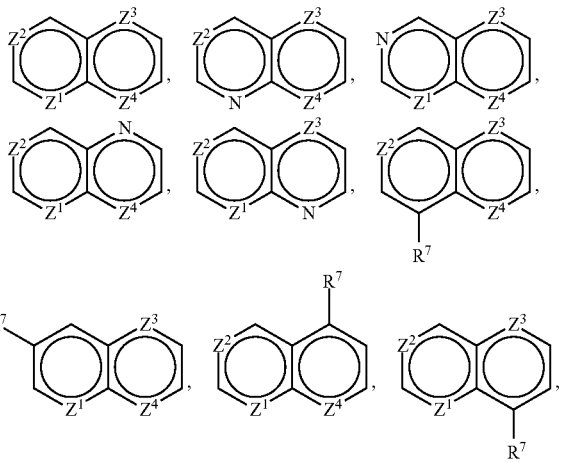

-continued
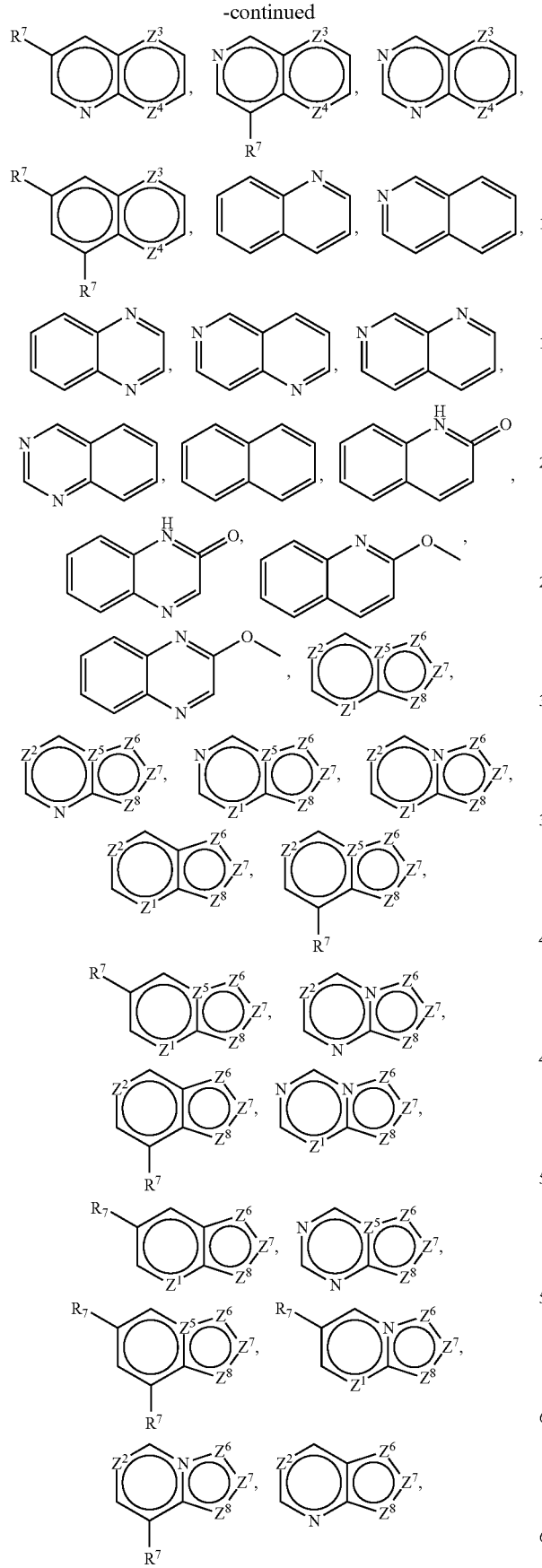
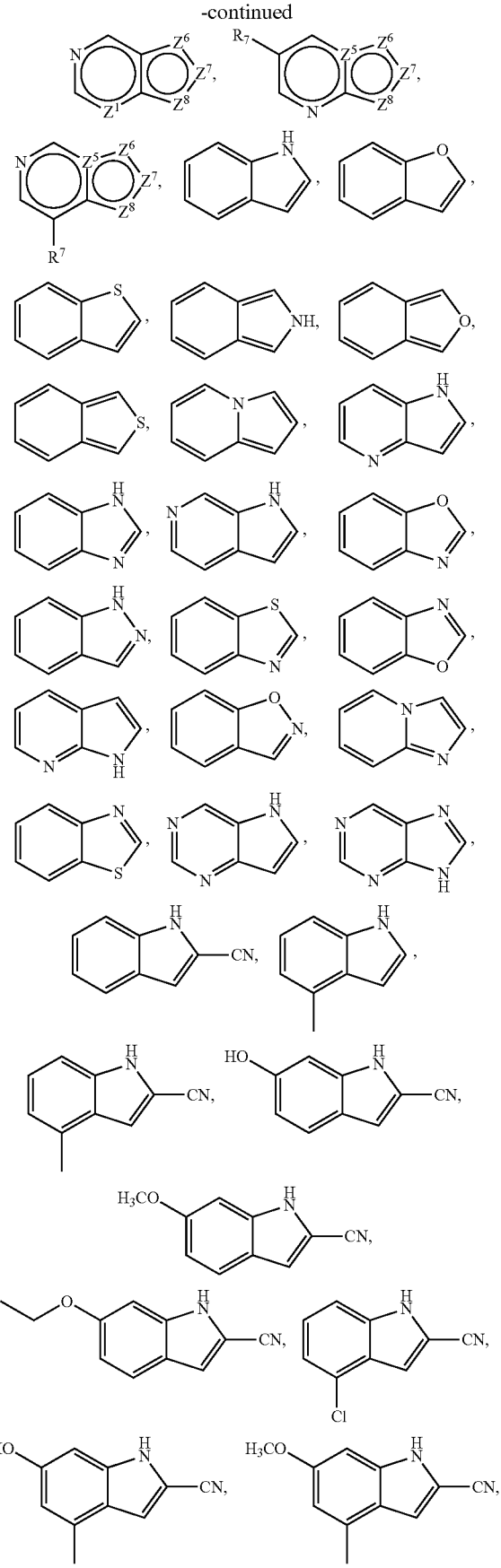

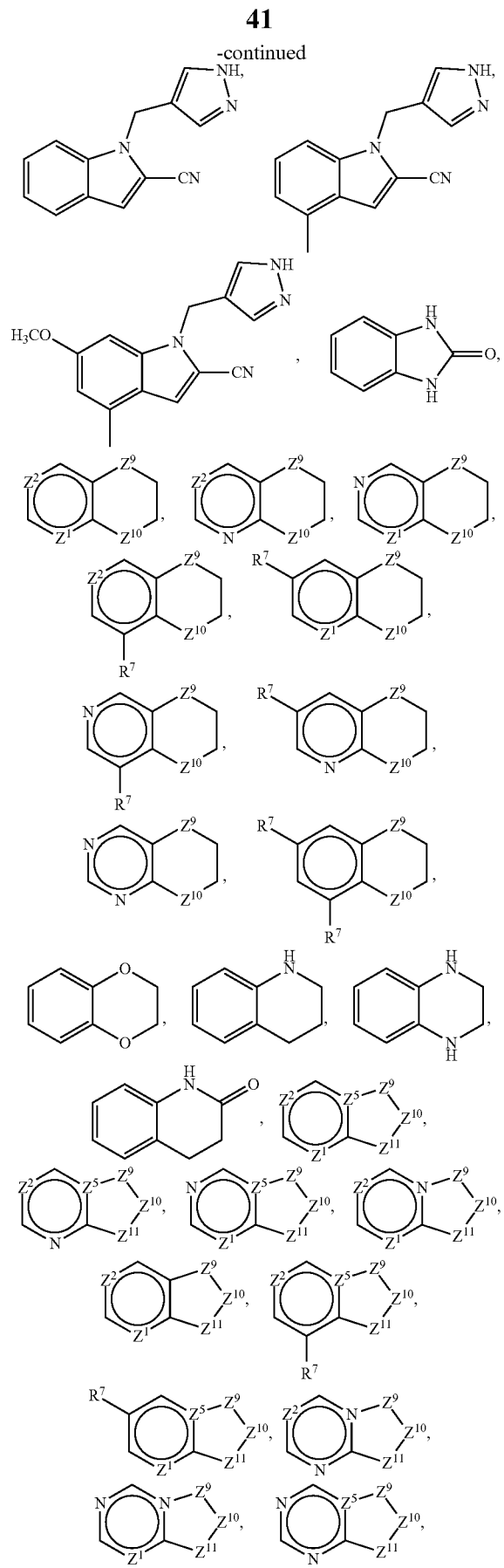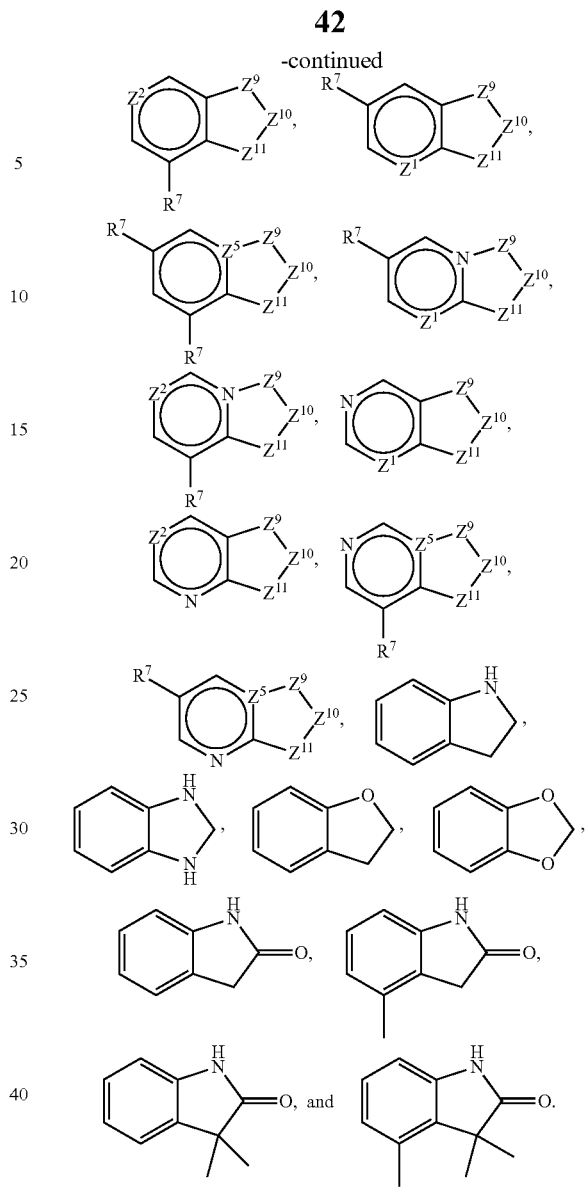

In some embodiments, B is substituted with one or more $R^B$ (e.g., by replacing a hydrogen connected to a ring atom with a bond to $R^B$). B may be substituted with 0, 1, 2, 3, 4, 5, 6 or more $R^B$ groups. B may be substituted with 1, 2, 3, 4, 5 or 6 $R^B$ groups, such as B substituted with 1 or 2 $R^B$ groups. In some embodiments, B is substituted with at least 1, 2, 3, 4, 5 or 6 $R^B$ groups. In some embodiments, B is substituted with n $R^B$ groups, wherein n is an integer from 0 to 6. In some embodiments, n is 0, 1, 2, 3, 4, 5 or 6. In some embodiments, n is at least 1, 2, 3, 4, 5 or 6. In some embodiments, n is up to 6, 5, 4, 3, 2, or 1. In some embodiments, n is an integer from 1 to 3.

In some embodiments, $R^B$ is independently selected at each occurrence from halo, hydroxyl, amino, cyano, dialkylphosphine oxide, oxo, carboxyl, amido, acyl, alkyl, cycloalkyl, heteroalkyl, haloalkyl, aminoalkyl, hydroxyalkyl, alkoxy, alkylamino, cycloalkylalkyl, cycloalkyloxy, cycloalkylalkyloxy, cycloalkylamino, cycloalkylalkylamino, heterocyclyl, heterocyclylalkyl, heterocyclyloxy, heterocyclylalkyloxy, heterocyclylamino, heterocyclylalkylamino, aryl, aralkyl, aryloxy, aralkyloxy, arylamino, aralkylamino, heteroaryl, heteroarylalkyl, heteroaryloxy, heteroarylalkyloxy, heteroarylamino, and heteroarylalkylamino. In some embodiments, $R^B$ is independently selected at each occurrence from halo, hydroxyl, amino, cyano, dialkylphosphine oxide, oxo, carboxyl, amido, acyl, alkyl, cycloalkyl, heteroalkyl, haloalkyl, aminoalkyl, hydroxyalkyl, alkoxy, alkylamino, heterocyclylalkyl, and heteroarylalkyl. In some embodiments, two $R^B$ groups attached to the same atom or different atoms can together form a ring.

In some embodiments, for a compound of Formula (I), $L^3$ comprises less than 30 atoms, such as less than 20 atoms. In some embodiments, $L^3$ comprises less than 30, 25, 20, 15, 10, 9, 8, 7, 6, 5, 4, or less than 3 atoms. In some embodiments, $L^3$ comprises at least 1, 2, 3, 4, 5, 6, 7, 8, 9, 10, 15 or at least 20 atoms. In some embodiments, $L^3$ comprises at least one heteroatom, such as $L^3$ comprises at least one nitrogen. In some embodiments, $L^3$ is $C_{1-10}$ alkylene, such as $C_{1-4}$ alkylene, optionally substituted with one or more $R^{50}$. In some embodiments, $L^3$ is substituted with one or more $R^{50}$. In some embodiments, $L^3$ is unsubstituted. In some embodiments, $L^3$ is selected from bond, —O—, —S—, —N($R^{51}$)—, —N($R^{51}$)$CH_2$—, —C(O)—, —C(O)O—, —OC(O)—, —C(O)N($R^{51}$)—, —N($R^{51}$)C(O)—, —N($R^{51}$)C(O)N($R^{51}$)—, —S(O)$_2$—, —S(O)—, —N($R^{51}$)S(O)$_2$—, —S(O)$_2$N($R^{51}$)—, —N($R^{51}$)S(O)$_2$N($R^{51}$)—, alkylene, alkenylene, heteroalkylene, and heteroalkenylene. In some embodiments, $L^3$ is $C_{1-6}$ alkylene, optionally substituted with one or more $R^{50}$, wherein $R^{50}$ is selected from deuterium, $C_{1-4}$ alkyl, $C_{1-4}$ haloalkyl, and —OR$^{52}$. In some embodiments, $L^3$ is -CH$_2$CH(R$^{50}$)—, such as —CH$_2$CH(CH$_3$)—. In some embodiments, two $R^{50}$ groups attached to the same atom or different atoms of $L^3$ optionally form a bridge or ring, such as a cyclopropyl ring. In some embodiments, $L^3$ is substituted with $R^{50}$, wherein $R^{50}$ forms a bond to ring C. In some embodiments, $L^3$ is substituted with one or more groups selected from deuterium, $C_{1-4}$ alkyl, $C_{1-4}$ haloalkyl, and —OR$^{52}$. In some embodiments, $L^3$ is substituted with —CH$_3$. In some embodiments, $L^3$ is $C_2$ alkylene substituted with at least one $C_{1-3}$ alkyl or $C_{1-3}$ haloalkyl, and optionally further substituted with one or more $R^{50}$. In some embodiments, $L^3$ is substituted with =O, $C_{1-6}$ alkyl, $C_{1-6}$ haloalkyl, $C_{1-3}$ alkyl(cyclopropyl), $C_{1-3}$ alkyl(NR$^{52}$C(O)R$^{52}$) or —O($C_{1-6}$ alkyl).

In some embodiments, for a compound of Formula (I), $L^3$ is selected from

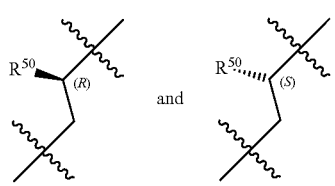

Optionally, $R^{50}$ is methyl. $L^3$ may be selected from

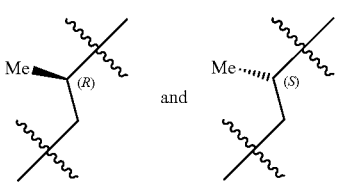

In some embodiments, $L^3$ is

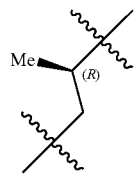

In some embodiments, $L^3$ is

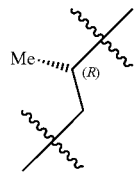

In some embodiments, $L^3$ comprises a stereocenter. In some embodiments, the stereocenter is in the R-configuration. In some embodiments, the stereocenter is in the S-configuration. In some embodiments, the R-isomer of $L^3$ is provided in at least 20%, 30%, 40%, 50%, 55%, 60%, 65%, 70%, 75%, 80%, 85%, 88%, 90%, 91%, 92%, 93%, 94%, 95%, 96%, 97%, 98%, 99%, 99.5%, or 99.9% excess over the S-isomer. In some embodiments, the S-isomer of $L^3$ is provided in at least 20%, 30%, 40%, 50%, 55%, 60%, 65%, 70%, 75%, 80%, 85%, 88%, 90%, 91%, 92%, 93%, 94%, 95%, 96%, 97%, 98%, 99%, 99.5%, or 99.9% excess over the R-isomer.

In some embodiments, for a compound of Formula (I), C is azetidinylene, piperidinylene or piperazinylene; $R^{57}$ is —S(=O)$_2$R$^{58}$, —S(=O)$_2$N(R$^{52}$)$_2$, or —NR$^{52}$S(=O)$_2$R$^{52}$; and $L^3$ is substituted with one or more $R^{50}$, wherein $L^3$ is not —CH$_2$CH(OH)—. In some embodiments, C is azetidinylene, piperidinylene or piperazinylene; $R^{57}$ is —S(=O)$_2$R$^{58}$, —S(=O)$_2$N(R$^{52}$)$_2$, or —NR$^{52}$S(=O)$_2$R$^{52}$; and $L^3$ is substituted with $C_{1-4}$ alkyl or $C_{1-4}$ haloalkyl.

In some embodiments, for a compound of Formula (I), $L^3$ is selected from

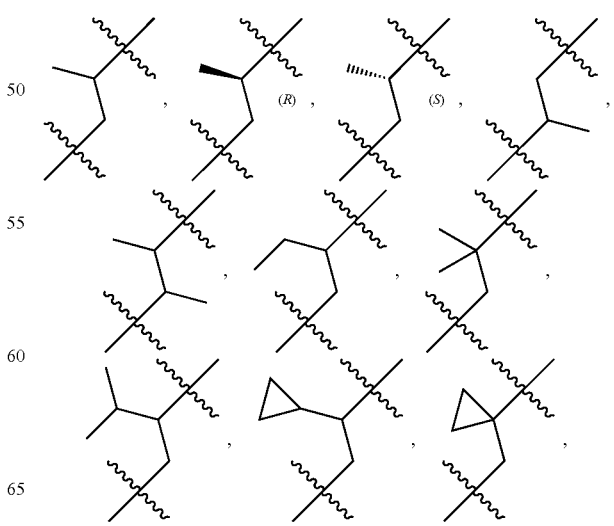

-continued

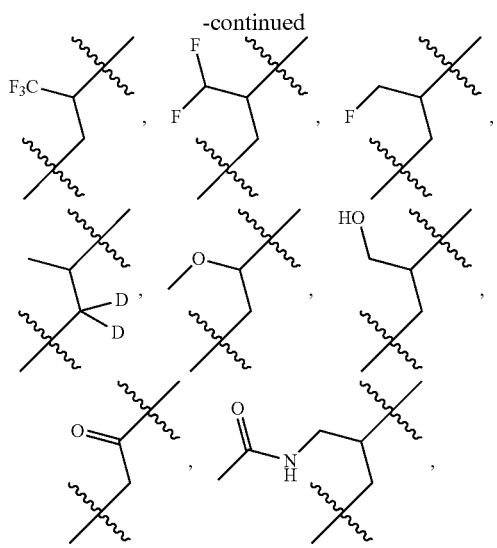

and any combination thereof. In some embodiments, for a compound of Formula (I), $L^3$ is selected from

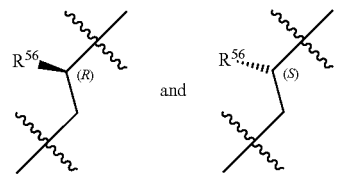

In some embodiments, for a compound of Formula (II), $L^3$ comprises less than 30 atoms, such as less than 20 atoms. In some embodiments, $L^3$ comprises less than 30, 25, 20, 15, 10, 9, 8, 7, 6, 5, 4, or less than 3 atoms. In some embodiments, $L^3$ comprises at least 1, 2, 3, 4, 5, 6, 7, 8, 9, 10, 15 or at least 20 atoms. In some embodiments, $L^3$ is $C_{1-10}$ alkylene, such as $C_{1-4}$ alkylene, substituted with one or more $R^{56}$ and optionally further substituted with one or more $R^{50}$. In some embodiments, $L^3$ is substituted with one or more $R^{50}$. In some embodiments, $L^3$ is substituted with $R^{56}$. In some embodiments, $L^3$ is selected from alkylene and alkenylene. In some embodiments, $L^3$ is $C_{1-6}$ alkylene substituted with one or more $R^{56}$, wherein $R^{56}$ is selected from deuterium, $C_{1-4}$ alkyl, $C_{1-4}$ haloalkyl, and —$OR^{59}$. In some embodiments, $L^3$ is $C_{1-4}$ alkylene substituted with $R^{56}$, wherein $R^{56}$ forms a bond to ring C. In some embodiments, $L^3$ is -$CH_2CH(R^{56})$—, such as —$CH_2CH(CH_3)$—. In some embodiments, two $R^{56}$ groups attached to the same atom or different atoms of $L^3$ optionally form a bridge or ring, such as a cyclopropyl ring. In some embodiments, $L^3$ is substituted with $R^{56}$, wherein $R^{56}$ forms a bond to ring C. In some embodiments, $L^3$ is substituted with one or more groups selected from $C_{1-4}$ alkyl, $C_{1-4}$ haloalkyl, and —$OR^{59}$. In some embodiments, $L^3$ is substituted with —$CH_3$. In some embodiments, $L^3$ is $C_{1-4}$ alkylene substituted with —$CH_3$ and optionally further substituted with $R^{50}$, wherein $R^{50}$ is not —OH, —$NH_2$, or —CN. In some embodiments, $L^3$ is $C_2$ alkylene substituted with at least one $C_{1-3}$ alkyl or $C_{1-3}$ haloalkyl, and optionally further substituted with one or more $R^{50}$. In some embodiments, $L^3$ is substituted with =O, $C_{1-6}$ alkyl, $C_{1-6}$ haloalkyl, $C_{1-3}$ alkyl(cyclopropyl), $C_{1-3}$ alkyl ($NR^{52}C(O)R^{52}$) or —$O(C_{1-6}$ alkyl).

In some embodiments, for a compound of Formula (II), $L^3$ is selected from

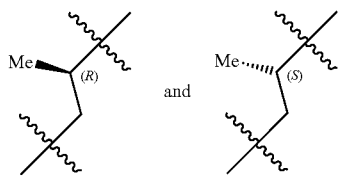

Optionally, $R^{56}$ is methyl. $L^3$ may be selected from

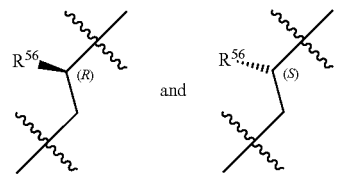

In some embodiments, $L^3$ is

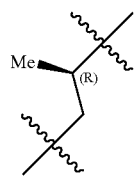

In some embodiments, $L^3$ is

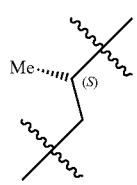

In some embodiments, $L^3$ comprises a stereocenter. In some embodiments, the stereocenter is in the R-configuration. In some embodiments, the stereocenter is in the S-configuration. In some embodiments, the R-isomer of $L^3$ is provided in at least 20%, 30%, 40%, 50%, 55%, 60%, 65%, 70%, 75%, 80%, 85%, 88%, 90%, 91%, 92%, 93%, 94%, 95%, 96%, 97%, 98%, 99%, 99.5%, or 99.9% excess over the S-isomer. In some embodiments, the S-isomer of $L^3$ is provided in at least 20%, 30%, 40%, 50%, 55%, 60%, 65%, 70%, 75%, 80%, 85%, 88%, 90%, 91%, 92%, 93%, 94%, 95%, 96%, 97%, 98%, 99%, 99.5%, or 99.9% excess over the R-isomer.

In some embodiments, for a compound of Formula (II), $L^3$ is selected from

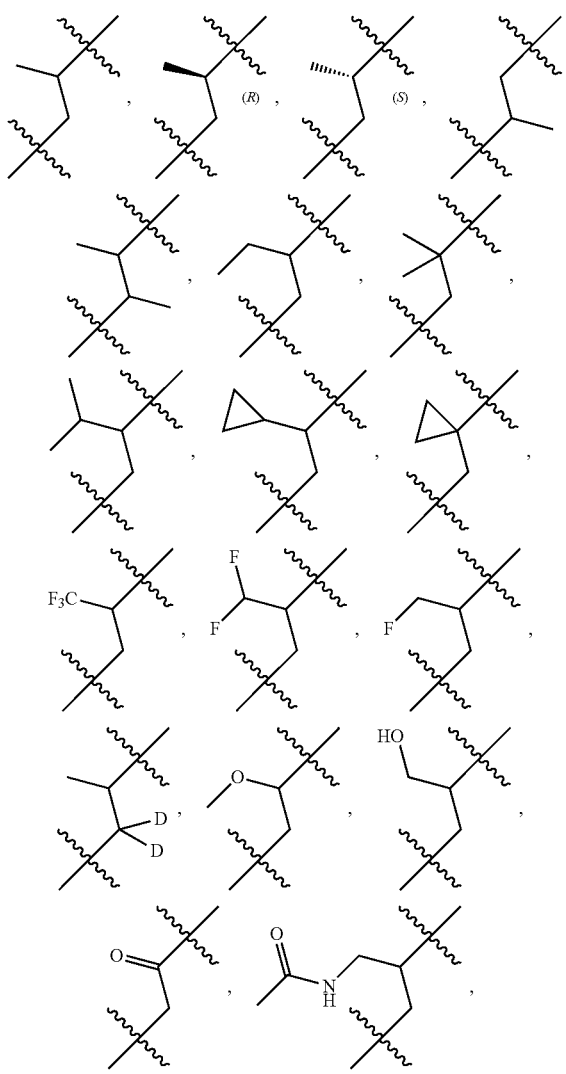

and any combination thereof. In some embodiments, for a compound of Formula (II), L³ is selected from

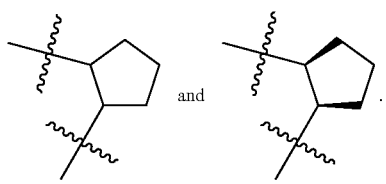 [SMILES: *C1CCCC1* ; *[C@@H]1CCC[C@@H]1*]

In some embodiments, for a compound of Formula (I), C is 3- to 12-membered heterocycle, such as 5- to 12-membered heterocycle. In some embodiments, the heterocycle is saturated. In some embodiments, C is selected from 5- to 7-membered monocyclic heterocycle, 8- to 10-membered fused bicyclic heterocycle, and 7- to 12-membered spirocyclic heterocycle. In some embodiments, the heterocycle comprises at least one nitrogen atom, such as one or two nitrogen atoms. In some embodiments, C comprises at least one ring nitrogen. In some embodiments, C is selected from piperidinyl and piperazinyl, such as

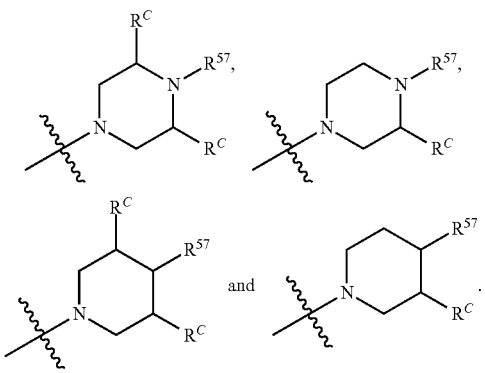

In some embodiments, C is selected from

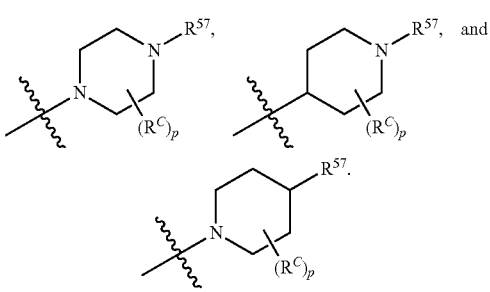

In some embodiments, C is selected from

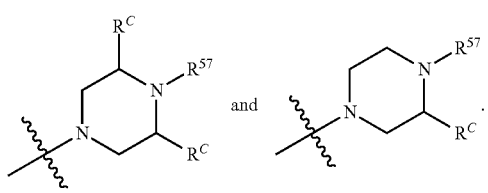

In some embodiments, C is selected from

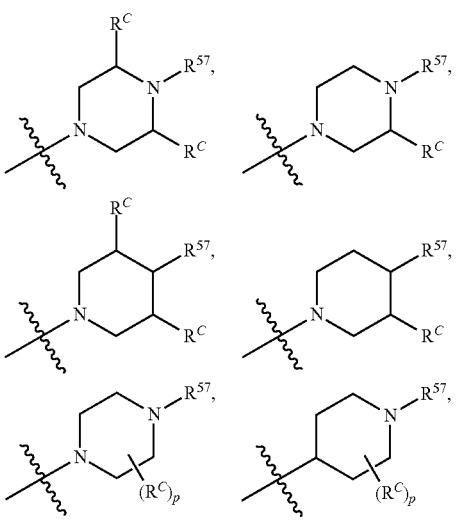

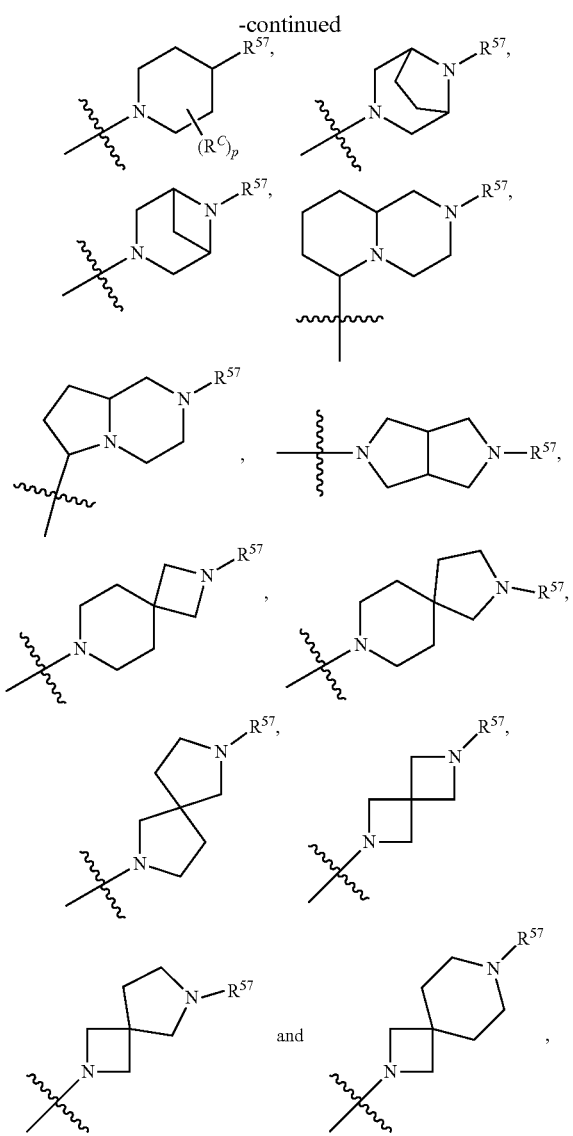

optionally substituted with one or more $R^C$. In some embodiments, C is selected from

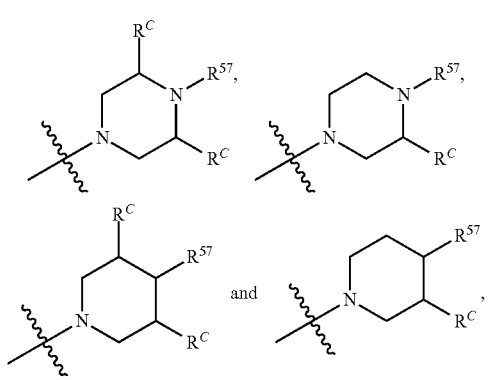

wherein $R^{57}$ is selected from —S(=O)$R^{52}$, —S(=O)$_2R^{52}$, —S(=O)$_2$N($R^{52}$)$_2$, —S(=O)$_2$N$R^{53}R^{54}$, —N$R^{52}$S(=O)$_2$ $R^{52}$; and $C_{1-10}$ alkyl substituted with one or more substituents selected from —S(=O)$R^{52}$, —S(=O)$_2R^{52}$, —S(=O)$_2$ N($R^{52}$)$_2$, —S(=O)$_2$N$R^{53}R^{54}$, and —N$R^{52}$S(=O)$_2R^{52}$. In some embodiments, $R^{57}$ is selected from —S(=O)$R^{52}$, —S(=O)$_2R^{58}$, —S(=O)$_2$N($R^{52}$)$_2$, and —N$R^{52}$S(=O)$_2$ $R^{52}$, such as $R^{57}$ is selected from —S(=O)CH$_3$, —S(=O)$_2$ CH$_3$, —S(=O)$_2$NH$_2$, —NHS(=O)$_2$CH$_3$, and —S(=O)$_2$ NHCH$_3$.

In some embodiments, for a compound of Formula (I), C is selected from

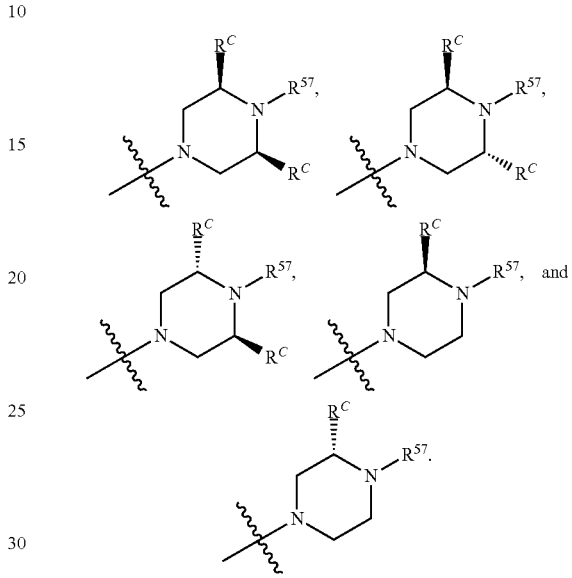

In some embodiments, for a compound of Formula (I), $R^{57}$ is selected from —S(=O)$_2R^{58}$, —S(=O)$_2$N($R^{52}$)$_2$, —S(=O)$_2$N$R^{53}R^{54}$, —N$R^{52}$S(=O)$_2R^{52}$, —N$R^{52}$S(=O)$_2$ N($R^{52}$)$_2$, —N$R^{52}$S(=O)$_2$N$R^{53}R^{54}$, —C(O)NH(C$_{1-6}$ alkyl), —C(O)N$R^{53}R^{54}$; and C$_{1-6}$ alkyl and C$_{2-6}$ alkenyl, each of which is independently substituted at each occurrence with one or more substituents selected from —S(=O)$_2R^{58}$, —S(=O)$_2$N($R^{52}$)$_2$, —S(=O)$_2$N$R^{53}R^{54}$, —N$R^{52}$S(=O)$_2$ $R^{52}$, —N$R^{52}$S(=O)$_2$N($R^{52}$)$_2$, —N$R^{52}$S(=O)$_2$N$R^{53}R^{54}$, —C(O)NH(C$_{1-6}$ alkyl), —C(O)N$R^{53}R^{54}$. In some embodiments, $R^{57}$ is selected from —S(=O)$_2R^{58}$, —S(=O)$_2$N ($R^{52}$)$_2$, —S(=O)$_2$N$R^{53}R^{54}$, —N$R^{52}$S(=O)$_2R^{52}$, —N$R^{52}$S(=O)$_2$N($R^{52}$)$_2$, —N$R^{52}$S(=O)$_2$N$R^{53}R^{54}$, and C$_{1-6}$ alkyl substituted with one or more substituents selected from —S(=O)$_2R^{58}$, —S(=O)$_2$N($R^{52}$)$_2$, —S(=O)$_2$N$R^{53}R^{54}$, —N$R^{52}$S(=O)$_2R^{52}$, —N$R^{52}$S(=O)$_2$N($R^{52}$)$_2$, and —N$R^{52}$S (=O)$_2$N$R^{53}R^{54}$. In some embodiments, $R^{57}$ is selected from —S(=O)$R^{52}$, —S(=O)$_2R^{58}$, —S(=O)$_2$N($R^{52}$)$_2$, and —N$R^{52}$S(=O)$_2R^{52}$. In some embodiments, $R^{57}$ is selected from —S(=O)CH$_3$, —S(=O)$_2$CH$_3$, —S(=O)$_2$NH$_2$, —NHS(=O)$_2$CH$_3$, and —S(=O)$_2$NHCH$_3$.

In some embodiments, for a compound of Formula (I) or (II), C is substituted with one or more $R^C$ (e.g., by replacing a hydrogen connected to a ring atom with a bond to $R^C$). C may be substituted with 0, 1, 2, 3, 4, 5, 6 or more $R^C$ groups. C may be substituted with 1, 2, 3, 4, 5 or 6 $R^C$ groups, such as C substituted with 1 or 2 $R^C$ groups. In some embodiments, C is substituted with at least 1, 2, 3, 4, 5 or 6 $R^C$ groups. In some embodiments, C is unsubstituted. In some embodiments, C is substituted with p $R^C$ groups, wherein p is an integer from 0 to 6. In some embodiments, p is 0, 1, 2, 3, 4, 5 or 6. In some embodiments, p is at least 1, 2, 3, 4, 5 or 6. In some embodiments, p is up to 6, 5, 4, 3, 2, or 1. In some embodiments, p is 0. In some embodiments, p is 1 or 2. In some embodiments, for a compound of Formula (I), C is azetidinylene, piperidinylene or piperazinylene; $R^{57}$ is $-S(=O)_2R^{58}$, $-S(=O)_2N(R^{52})_2$, or $-NR^{52}S(=O)_2R^{52}$; and p is an integer from 1 to 6.

In some embodiments, $R^C$ is selected from $-C(O)R^{52}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $=O$, $C_{1-3}$ alkyl, and $C_{1-3}$ haloalkyl, or two $R^C$ groups attached to different atoms can together form a $C_{1-3}$ bridge. In some embodiments, $R^C$ is selected from $C_{1-3}$ alkyl and $C_{1-3}$ haloalkyl, such as $-CH_3$.

In some embodiments, for a compound of Formula (II), C is selected from $C_{3-12}$ carbocycle and 3- to 12-membered heterocycle, such as 5- to 12-membered heterocycle. In some embodiments, the heterocycle is saturated. In some embodiments, C is selected from 5- to 7-membered monocyclic heterocycle, 8- to 10-membered fused bicyclic heterocycle, and 7- to 12-membered spirocyclic heterocycle. In some embodiments, the heterocycle comprises at least one nitrogen atom, such as one or two nitrogen atoms. In some embodiments, C comprises at least one ring nitrogen. In some embodiments, C is selected from piperidinyl and piperazinyl, such as

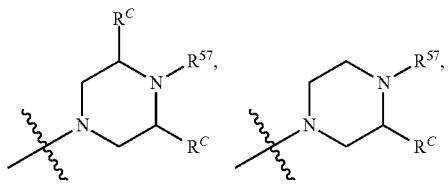

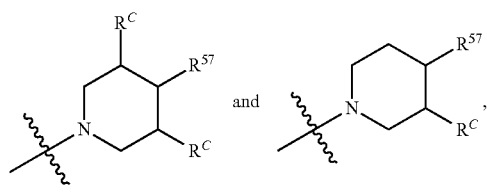

wherein $R^{57}$ is selected from hydrogen and $R^{50}$. In some embodiments, C is selected from

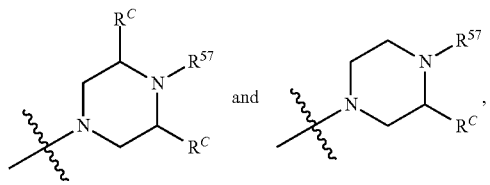

wherein $R^{57}$ is selected from hydrogen and $R^{50}$. In some embodiments, C is selected from

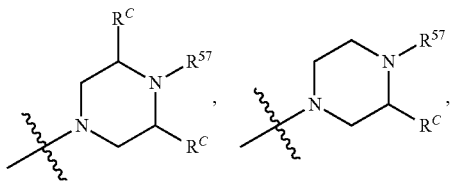

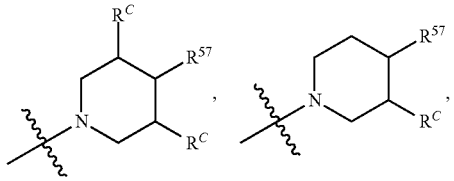

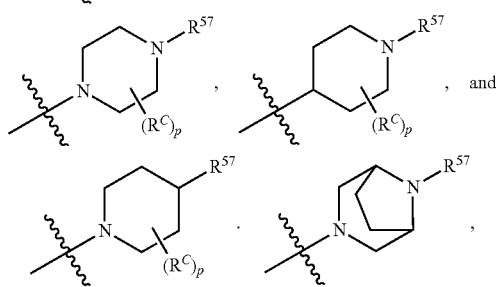

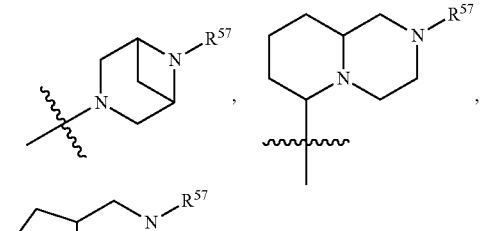

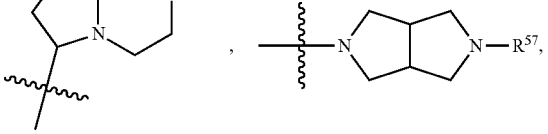

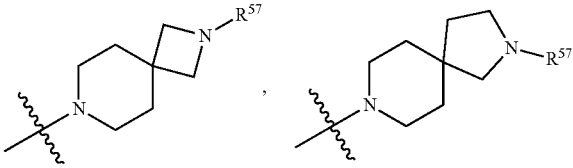

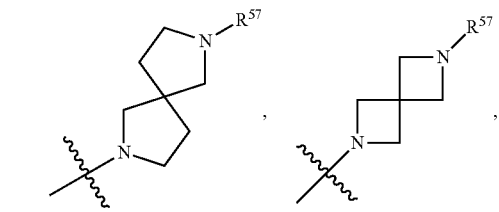

-continued

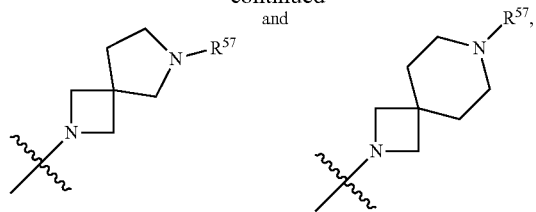

optionally substituted with one or more $R^C$, wherein $R^{57}$ is selected from hydrogen and $R^{50}$. In some embodiments, C is selected from

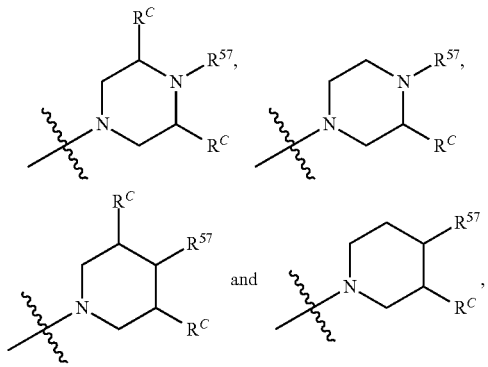

wherein $R^{57}$ is selected from —S(=O)$R^{52}$, —S(=O)$_2R^{52}$, —S(=O)$_2$N(R$^{52}$)$_2$, —S(=O)$_2$NR$^{53}$R$^{54}$, —NR$^{52}$S(=O)$_2$R$^{52}$; and $C_{1-10}$ alkyl substituted with one or more substituents selected from —S(=O)$R^{52}$, —S(=O)$_2$R$^{52}$, —S(=O)$_2$N(R$^{52}$)$_2$, —S(=O)$_2$NR$^{53}$R$^{54}$, and —NR$^{52}$S(=O)$_2$R$^{52}$. In some embodiments, $R^{57}$ is selected from —S(=O)$R^{52}$, —S(=O)$_2$R$^{52}$, —S(=O)$_2$N(R$^{52}$)$_2$, and —NR$^{52}$S(=O)$_2$R$^{52}$, such as $R^{57}$ is selected from —S(=O)CH$_3$, —S(=O)$_2$CH$_3$, —S(=O)$_2$NH$_2$, —NHS(=O)$_2$CH$_3$, and —S(=O)$_2$NHCH$_3$.

In some embodiments, for a compound of Formula (II), C is selected from

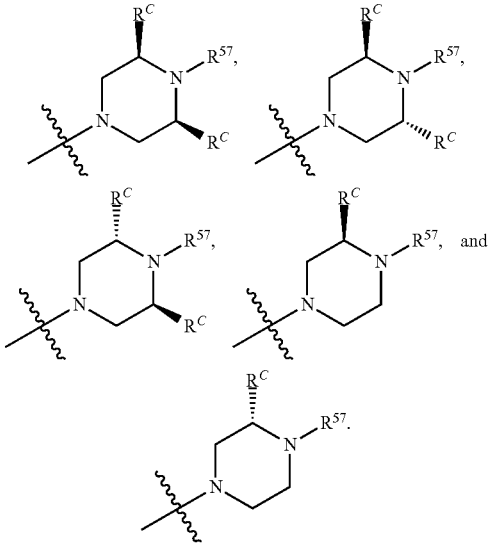

In some embodiments, for a compound of Formula (I) or (II), $R^C$ is selected from:

halogen, —OR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$; and $C_{1-10}$ alkyl, $C_{2-10}$ alkenyl, and $C_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{3-12}$ carbocycle, and 3- to 12-membered heterocycle;

wherein each $C_{3-12}$ carbocycle and 3- to 12-membered heterocycle in $R^C$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{1-6}$ alkyl, $C_{1-6}$ haloalkyl, $C_{2-6}$ alkenyl, and $C_{2-6}$ alkynyl.

In some embodiments, $R^C$ is selected from —N(R$^{52}$)$_2$, —NR$^{53}$R$^{54}$, —NR$^{52}$S(=O)$_2$R$^{52}$, —C(O)R$^{52}$, —C(O)OR$^{52}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, and —C(O)NR$^{53}$R$^{54}$. In some embodiments, $R^C$ is selected from —N(R$^{52}$)$_2$, —NR$^{53}$R$^{54}$, —NR$^{52}$S(=O)$_2$R$^{52}$, —C(O)R$^{52}$, —C(O)OR$^{52}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, $C_{1-6}$ alkyl, and $C_{1-6}$ alkyl substituted with —N(R$^{52}$)$_2$, —NR$^{53}$R$^{54}$, —NR$^{52}$S(=O)$_2$R$^{52}$, —C(O)R$^{52}$, —C(O)OR$^{52}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, or —C(O)NR$^{53}$R$^{54}$.

In some embodiments, C is selected from

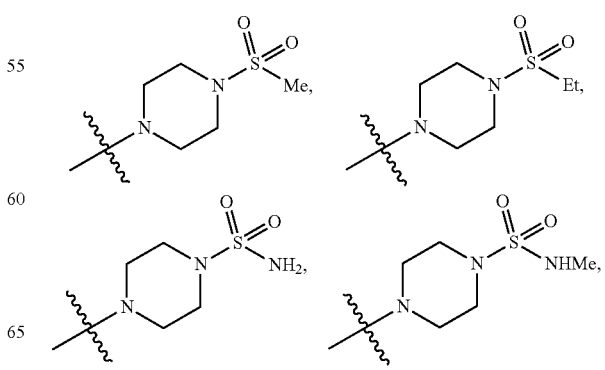

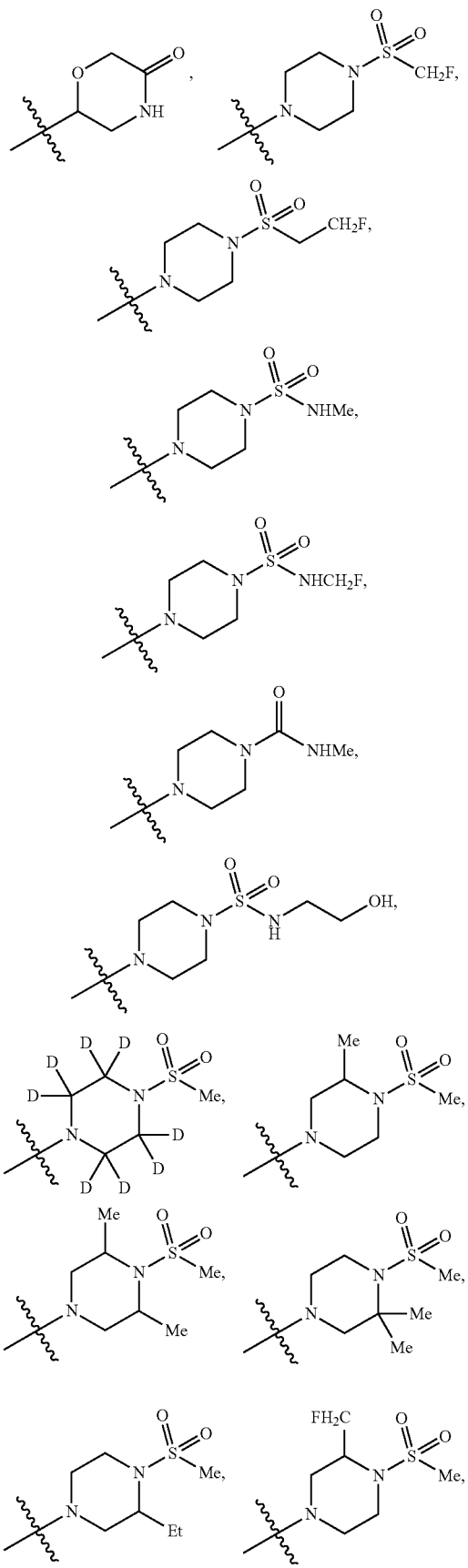
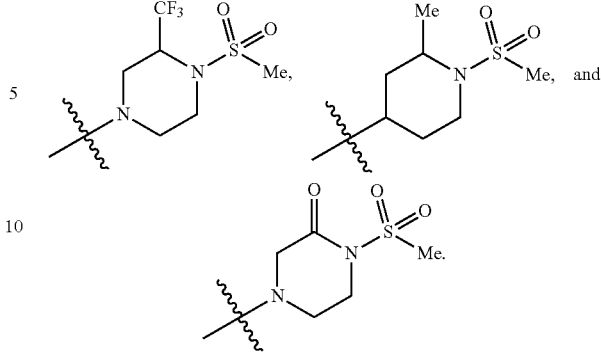

In some embodiments, for a compound of Formula (I) or (II), H is 5- to 12-membered heterocycle, optionally substituted with one or more $R^{50}$; A is 3- to 12-membered heterocycle; and B is 3- to 12-membered heterocycle. In some embodiments, H is 6- to 12-membered bicyclic heterocycle, optionally substituted with one or more $R^{50}$; A is 3- to 12-membered heterocycle; and B is 3- to 12-membered heterocycle. In some embodiments, H is 6- to 12-membered bicyclic heterocycle, optionally substituted with one or more $R^{50}$; A is 3- to 12-membered heterocycle; and B is 6- to 12-membered bicyclic heterocycle. In some embodiments, H is 5- to 12-membered heterocycle, optionally substituted with one or more $R^{50}$; A is 3- to 12-membered heterocycle; and B is 6- to 12-membered bicyclic heterocycle. In some embodiments, H is thienopyrimidinyl, optionally substituted with one or more $R^{50}$; A is 3- to 12-membered heterocycle; and B is 3- to 12-membered heterocycle. In some embodiments, H is 5- to 12-membered heterocycle, optionally substituted with one or more $R^{50}$; A is selected from piperidinylene and piperazinylene; and B is 3- to 12-membered heterocycle. In some embodiments, H is 5- to 12-membered heterocycle, optionally substituted with one or more $R^{50}$; A is 3- to 12-membered heterocycle; and B is indolylene. In some embodiments, H is thienopyrimidinyl substituted with one or more $R^{50}$; A is selected from piperidinylene and piperazinylene; and B is indolylene.

In some embodiments, for a compound of Formula (I) or (II), H is 5- to 12-membered heterocycle, optionally substituted with one or more $R^{50}$; A is 3- to 12-membered heterocycle; B is 3- to 12-membered heterocycle; C is 3- to 12-membered heterocycle; m is an integer from 0 to 3; and n is an integer from 1 to 3. In some embodiments, H is 6- to 12-membered bicyclic heterocycle, optionally substituted with one or more $R^{50}$; A is 3- to 12-membered heterocycle; B is 6- to 12-membered bicyclic heterocycle; C is 3- to 12-membered heterocycle; m is an integer from 0 to 3; and n is an integer from 1 to 3. In some embodiments, H is 5- to 12-membered heterocycle, optionally substituted with one or more $R^{50}$; A is 3- to 12-membered heterocycle; B is 3- to 12-membered heterocycle; and C is 3- to 12-membered heterocycle. In some embodiments, H is 6- to 12-membered bicyclic heterocycle, optionally substituted with one or more $R^{50}$; A is 3- to 12-membered heterocycle; B is 6- to 12-membered bicyclic heterocycle; and C is 3- to 12-membered heterocycle. In some embodiments, H is 6- to 12-membered bicyclic heterocycle, optionally substituted with one or more $R^{50}$; A is selected from piperidinylene and piperazinylene; B is 6- to 12-membered bicyclic heterocycle; and C is 3- to 12-membered heterocycle. In some embodiments, H is 6- to 12-membered bicyclic heterocycle, optionally substituted with one or more $R^{50}$; A is selected from piperidinylene and piperazinylene; B is 6- to 12-membered bicyclic heterocycle; m is an integer from 0 to 3; and n is an integer from 1 to 3. In some embodiments, H is thienopyrimidinyl, optionally substituted with one or more $R^{50}$; A is 3- to 12-membered heterocycle; and B is 6- to 12-membered bicyclic heterocycle. In some embodiments, H is thienopyrimidinyl, optionally substituted with one or more $R^0$; A is 3- to 12-membered heterocycle; B is 6- to 12-membered bicyclic heterocycle; m is an integer from 0 to 3; and n is an integer from 1 to 3. In some embodiments, H is 9- to 10-membered bicyclic heterocycle, optionally substituted with one or more $R^0$; A is 5- to 7-membered heterocycle; and B is 9-membered bicyclic heterocycle, wherein each of said heterocycles comprises at least one nitrogen atom. In some embodiments, H is 9- to 10-membered bicyclic heterocycle, optionally substituted with one or more $R^{50}$; A is 5- to 7-membered heterocycle; B is 9-membered bicyclic heterocycle; and n is an integer from 1 to 3, wherein each of said heterocycles comprises at least one nitrogen atom.

In some embodiments, for a compound of Formula (I), $L^1$ comprises less than 10 atoms, $L^2$ comprises less than 10 atoms, and $L^3$ comprises less than 20 atoms. In some embodiments, $L^1$, $L^2$ and $L^3$ each comprise at least 1 atom, such as at least 2 atoms. In some embodiments, $L^1$, $L^2$ and $L^3$ are each independently selected from bond, —O—, —S—, —N($R^{51}$)—, —N($R^{51}$)CH$_2$—, —C(O)—, —C(O)O—, —OC(O)—, —C(O)N($R^{51}$)—, —N($R^{51}$)C(O)—, —N($R^{51}$)C(O)N($R^{51}$)—, —S(O)$_2$—, —S(O)—, —N($R^{51}$)S(O)$_2$—, —S(O)$_2$N($R^{51}$)—, —N($R^{51}$)S(O)$_2$N($R^{51}$)—, alkylene, alkenylene, heteroalkylene, and heteroalkenylene. In some embodiments, $L^1$, $L^2$ and $L^3$ are each independently selected from —CH$_2$—, —CH$_2$CH$_2$—, —CH$_2$CH(CH$_3$)—, —N($R^{51}$)—, —N($R^{51}$)CH$_2$—, —N($R^{51}$)C(O)—, and —N($R^{51}$)S(O)$_2$—. In some embodiments, $L^1$ is selected from —O—, —S—, —N($R^{51}$)—, —N($R^{51}$)CH$_2$—, —C(O)—, —C(O)O—, —OC(O)—, —C(O)N($R^{51}$)—, —N($R^{51}$)C(O)—, —N($R^{51}$)C(O)N($R^{51}$)—, —S(O)$_2$—, —S(O)—, —N($R^{51}$)S(O)$_2$—, —S(O)$_2$N($R^{51}$)—, —N($R^{51}$)S(O)$_2$N($R^{51}$)—, alkylene, alkenylene, heteroalkylene, and heteroalkenylene; and $L^2$ and $L^3$ are independently selected from $C_{1-4}$ alkylene, optionally substituted with one or more $R^{50}$. In some embodiments, $L^1$, $L^2$ and $L^3$ are each independently selected from —O—, —S—, —N($R^{51}$)—; $C_{1-4}$ alkylene and 1- to 4-membered heteroalkylene, each of which is optionally substituted with one or more $R^{50}$. In some embodiments, $L^1$ is —NH—, $L^2$ is —CH$_2$—, and $L^3$ is $C_{1-4}$ alkylene, optionally substituted with one or more $R^{50}$.

In some embodiments, for a compound of Formula (II), $L^1$ comprises less than 10 atoms, $L^2$ comprises less than 10 atoms, and $L^3$ comprises less than 20 atoms. In some embodiments, $L^1$, $L^2$ and $L^3$ each comprise at least 1 atom, such as at least 2 atoms. In some embodiments, $L^1$ and $L^2$ are each independently selected from bond, —O—, —S—, —N($R^{51}$)—, —N($R^{51}$)CH$_2$—, —C(O)—, —C(O)O—, —OC(O)—, —C(O)N($R^{51}$)—, —N($R^{51}$)C(O)—, —N($R^{51}$)C(O)N($R^{51}$)—, —S(O)$_2$—, —S(O)—, —N($R^{51}$)S(O)$_2$—, —S(O)$_2$N($R^{51}$)—, —N($R^{51}$)S(O)$_2$N($R^{51}$)—, alkylene, alkenylene, heteroalkylene, and heteroalkenylene, and $L^3$ is selected from $C_{1-10}$ alkylene and $C_{2-10}$ alkenylene, substituted with one or more $R^{56}$ and optionally further substituted with one or more $R^{50}$. In some embodiments, $L^1$ and $L^2$ are each independently selected from —CH$_2$—, —N($R^{51}$)—, —N($R^{51}$)CH$_2$—, —N($R^{51}$)C(O)—, and —N($R^{51}$)S(O)$_2$—, and $L^3$ is selected from $C_{1-10}$ alkylene and $C_{2-10}$ alkenylene, substituted with one or more $R^{56}$ and optionally further substituted with one or more $R^{50}$. In some embodiments, $L^1$ is selected from —O—, —S—, —N($R^{51}$)—, —N($R^{51}$)CH$_2$—, —C(O)—, —C(O)O—, —OC(O)—, —C(O)N($R^{51}$)—, —N($R^{51}$)C(O)—, —N($R^{51}$)C(O)N($R^{51}$)—, —S(O)$_2$—, —S(O)—, —N($R^{51}$)S(O)$_2$—, —S(O)$_2$N($R^{51}$)—, —N($R^{51}$)S(O)$_2$N($R^{51}$)—, alkylene, alkenylene, heteroalkylene, and heteroalkenylene; and $L^2$ is $C_{1-4}$ alkylene, optionally substituted with one or more $R^{50}$, and $L^3$ is $C_{1-4}$ alkylene substituted with one or more $R^{56}$ and optionally further substituted with one or more $R^{50}$. In some embodiments, $L^1$ and $L^2$ are each independently selected from —O—, —S—, —N($R^{51}$)—; $C_{1-4}$ alkylene and 1- to 4-membered heteroalkylene, each of which is optionally substituted with one or more $R^{50}$, and $L^3$ is $C_{1-4}$ alkylene substituted with one or more $R^{56}$ and optionally further substituted with one or more $R^{50}$. In some embodiments, $L^1$ is —NH—, $L^2$ is —CH$_2$—, and $L^3$ is $C_{1-4}$ alkylene substituted with one or more $R^{56}$ and optionally further substituted with one or more $R^{50}$.

In certain aspects, for a compound of Formula (I):

H is 5- to 12-membered heterocycle, optionally substituted with one or more $R^{50}$;

A, B, and C are each independently selected from 3- to 12-membered heterocycle;

$L^1$, $L^2$ and $L^3$ are each independently selected from bond, —O—, —S—, —N($R^{51}$)—, —N($R^{51}$)CH$_2$—, —C(O)—, —C(O)O—, —OC(O)—, —OC(O)O—, —C(O)N($R^{51}$)—, —C(O)N($R^{51}$)C(O)—, —C(O)N($R^{51}$)C(O)N($R^{51}$)—, —N($R^{51}$)C(O)—, —N($R^{51}$)C(O)N($R^{51}$)—, —N($R^{51}$)C(O)O—, —OC(O)N($R^{51}$)—, —C(N$R^{51}$)—, —N($R^{51}$)C(N$R^{51}$)—, —C(N$R^{51}$)N($R^{51}$)—, —N($R^{51}$)C(N$R^{51}$)N($R^{51}$)—, —S(O)$_2$—, —OS(O)—, —S(O)O—, —S(O)—, —OS(O)$_2$—, —S(O)$_2$O—, —N($R^{51}$)S(O)$_2$—, —S(O)$_2$N($R^{51}$)—, —N($R^{51}$)S(O)—, —S(O)N($R^{51}$)—, —N($R^{51}$)S(O)N($R^{51}$)—, —N($R^{51}$)S(O)N($R^{51}$)—; alkylene, alkenylene, alkynylene, heteroalkylene, heteroalkenylene, and heteroalkynylene, each of which is optionally substituted with one or more $R^{50}$, wherein two $R^{50}$ groups attached to the same atom or different atoms of any one of $L^1$, $L^2$ or $L^3$ can together optionally form a ring;

$R^A$, $R^B$ and $R^C$ are each independently selected at each occurrence from $R^{50}$, or two $R^A$ groups, two $R^B$ groups or two $R^C$ groups attached to the same atom or different atoms can together optionally form a ring;

m is an integer from 0 to 3;

n is an integer from 1 to 3;

p is an integer from 0 to 6;

$R^{50}$ is independently selected at each occurrence from:

halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$);

$C_{1-10}$ alkyl, $C_{2-10}$ alkenyl, and $C_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)

NR$^{53}$R$^{54}$, —P(O)(OR$^{52}$)$_2$, —P(O)(R$^{52}$)$_2$, =O, =S, =N(R$^{52}$), C$_{3-12}$ carbocycle, and 3- to 12-membered heterocycle; and C$_{3-12}$ carbocycle and 3- to 12-membered heterocycle, wherein each C$_{3-12}$ carbocycle and 3- to 12-membered heterocycle in R$^{50}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;

R$^{51}$ is independently selected at each occurrence from: hydrogen, —C(O)R$^{52}$, —C(O)OR$^{52}$, —C(O)N(R$^{52}$)$_2$, —C(O)NR$^{53}$R$^{54}$;

C$_{1-6}$ alkyl, C$_{2-6}$ alkenyl, and C$_{2-6}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{3-12}$ carbocycle and 3- to 12-membered heterocycle; and C$_{3-12}$ carbocycle and 3- to 12-membered heterocycle, wherein each C$_{3-12}$ carbocycle and 3- to 12-membered heterocycle in R$^{51}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;

R$^{52}$ is independently selected at each occurrence from hydrogen; and C$_{1-20}$ alkyl, C$_{2-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle;

R$^{53}$ and R$^{54}$ are taken together with the nitrogen atom to which they are attached to form a heterocycle, optionally substituted with one or more R$^{50}$;

R$^{57}$ is selected from:
—S(=O)R$^{52}$, —S(=O)$_2$R$^{58}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —NR$^{52}$C(O)N(R$^{52}$)$_2$, —NR$^{52}$C(O)NR$^{53}$R$^{54}$, —C(O)NH(C$_{1-6}$ alkyl), —C(O)NR$^{53}$R$^{54}$, —P(O)(OR$^{52}$)$_2$, —P(O)(R$^{52}$)$_2$; and C$_{1-10}$ alkyl, C$_{2-10}$ alkenyl, and C$_{2-10}$ alkynyl, each of which is independently substituted at each occurrence with one or more substituents selected from —S(=O)R$^{52}$, —S(=O)$_2$R$^{58}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —NR$^{52}$C(O)N(R$^{52}$)$_2$, —NR$^{52}$C(O)NR$^{53}$R$^{54}$, —C(O)NH(C$_{1-6}$ alkyl), —C(O)NR$^{53}$R$^{54}$, —P(O)(OR$^{52}$)$_2$, and —P(O)(R$^{52}$)$_2$; and R$^{58}$ is selected from hydrogen; and C$_{1-20}$ alkyl, C$_{3-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle, wherein for a compound or salt of Formula (I), when C is azetidinylene, piperidinylene or piperazinylene and R$^{57}$ is —S(=O)$_2$R$^{58}$, —S(=O)$_2$N(R$^{52}$)$_2$, or —NR$^{52}$S(=O)$_2$R$^{52}$:

p is an integer from 1 to 6; and/or

L$^3$ is substituted with one or more R$^{50}$, wherein L$^3$ is not —CH$_2$CH(OH)—.

In certain aspects, for a compound of Formula (II):

H is 5- to 12-membered heterocycle, optionally substituted with one or more R$^{50}$;

A, B and C are each independently selected from 3- to 12-membered heterocycle;

L$^1$ and L$^2$ are each independently selected from bond, —O—, —S—, —N(R$^{51}$)—, —N(R$^{51}$)CH$_2$—, —C(O)—, —C(O)O—, —OC(O)—, —OC(O)O—, —C(O)N(R$^{51}$)—, —C(O)N(R$^{51}$)C(O)—, —C(O)N(R$^{51}$)C(O)N(R$^{51}$)—, —N(R$^{51}$)C(O)—, —N(R$^{51}$)C(O)N(R$^{51}$)—, —N(R$^{51}$)C(O)O—, —OC(O)N(R$^{51}$)—, —C(NR$^{51}$)—, —N(R$^{51}$)C(NR$^{51}$)—, —C(NR$^{51}$)N(R$^{51}$)—, —N(R$^{51}$)C(NR$^{51}$)N(R$^{51}$)—, —S(O)$_2$—, —OS(O)—, —S(O)O—, —S(O)—, —OS(O)$_2$—, —S(O)$_2$O—, —N(R$^{51}$)S(O)$_2$—, —S(O)$_2$N(R$^{51}$)—, —N(R$^{51}$)S(O)—, —S(O)N(R$^{51}$)—, —N(R$^{51}$)S(O)$_2$N(R$^{51}$)—, —N(R$^{51}$)S(O)N(R$^{51}$)—; alkylene, alkenylene, alkynylene, heteroalkylene, heteroalkenylene, and heteroalkynylene, each of which is optionally substituted with one or more R$^{50}$, wherein two R$^{50}$ groups attached to the same atom or different atoms of L or L$^2$ can together optionally form a ring;

L$^3$ is selected from C$_{1-6}$ alkylene, C$_{2-6}$ alkenylene, and C$_{2-6}$ alkynylene, each of which is substituted with one or more R$^{56}$ and optionally further substituted with one or more R$^{50}$;

R$^A$, R$^B$ and R$^C$ are each independently selected at each occurrence from R$^{50}$, or two R$^A$ groups, two R$^B$ groups or two R$^C$ groups attached to the same atom or different atoms can together optionally form a bridge or ring;

m is an integer from 0 to 3;

n is an integer from 1 to 3;

p is an integer from 0 to 6;

R$^{50}$ is independently selected at each occurrence from: halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$);

C$_{1-10}$ alkyl, C$_{2-10}$ alkenyl, and C$_{2-10}$ alkynyl, each of which is independently optionally substituted at each occurrence with one or more substituents selected from halogen, —$NO_2$, —CN, —$OR^{52}$, —$SR^{52}$, —$N(R^{52})_2$, —$NR^{53}R^{54}$, —S(=O)$R^{52}$, —S(=O)$_2R^{52}$, —S(=O)$_2$N($R^{52}$)$_2$, —S(=O)$_2$N$R^{53}R^{54}$, —$NR^{52}$S(=O)$_2R^{52}$, —$NR^{52}$S(=O)$_2$N($R^{52}$)$_2$, —$NR^{52}$S(=O)$_2$N$R^{53}R^{54}$, —C(O)$R^{52}$, —C(O)O$R^{52}$, —OC(O)$R^{52}$, —OC(O)O$R^{52}$, —OC(O)N($R^{52}$)$_2$, —OC(O)N$R^{53}R^{54}$, —$NR^{52}$C(O)$R^{52}$, —$NR^{52}$C(O)O$R^{52}$, —$NR^{52}$C(O)N($R^{52}$)$_2$, —$NR^{52}$C(O)N$R^{53}R^{54}$, —C(O)N($R^{52}$)$_2$, —C(O)N$R^{53}R^{54}$, —P(O)(O$R^{52}$)$_2$, —P(O)($R^{52}$)$_2$, =O, =S, =N($R^{52}$), $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{50}$ is independently optionally substituted with one or more substituents selected from halogen, —$NO_2$, —CN, —$OR^{52}$, —$SR^{52}$, —$N(R^{52})_2$, —$NR^{53}R^{54}$, —S(=O)$R^{52}$, —S(=O)$_2R^{52}$, —S(=O)$_2$N($R^{52}$)$_2$, —S(=O)$_2$N$R^{53}R^{54}$, —$NR^{52}$S(=O)$_2R^{52}$, —$NR^{52}$S(=O)$_2$N($R^{52}$)$_2$, —$NR^{52}$S(=O)$_2$N$R^{53}R^{54}$, —C(O)$R^{52}$, —C(O)O$R^{52}$, —OC(O)$R^{52}$, —OC(O)O$R^{52}$, —OC(O)N($R^{52}$)$_2$, —OC(O)N$R^{53}R^{54}$, —$NR^{52}$C(O)$R^{52}$, —$NR^{52}$C(O)O$R^{52}$, —$NR^{52}$C(O)N($R^{52}$)$_2$, —$NR^{52}$C(O)N$R^{53}R^{54}$, —C(O)N($R^{52}$)$_2$, —C(O)N$R^{53}R^{54}$, —P(O)(O$R^{52}$)$_2$, —P(O)($R^{52}$)$_2$, =O, =S, =N($R^{52}$), $C_{1-6}$ alkyl, $C_{1-6}$ haloalkyl, $C_{2-6}$ alkenyl, and $C_{2-6}$ alkynyl;

$R^{51}$ is independently selected at each occurrence from: hydrogen, —C(O)$R^{52}$, —C(O)O$R^{52}$, —C(O)N($R^{52}$)$_2$, —C(O)N$R^{53}R^{54}$;

$C_{1-6}$ alkyl, $C_{2-6}$ alkenyl, and $C_{2-6}$ alkynyl, each of which is independently optionally substituted at each occurrence with one or more substituents selected from halogen, —$NO_2$, —CN, —$OR^{52}$, —$SR^{52}$, —$N(R^{52})_2$, —$NR^{53}R^{54}$, —S(=O)$R^{52}$, —S(=O)$_2R^{52}$, —S(=O)$_2$N($R^{52}$)$_2$, —S(=O)$_2$N$R^{53}R^{54}$, —$NR^{52}$S(=O)$_2R^{52}$, —$NR^{52}$S(=O)$_2$N($R^{52}$)$_2$, —$NR^{52}$S(=O)$_2$N$R^{53}R^{54}$, —C(O)$R^{52}$, —C(O)O$R^{52}$, —OC(O)$R^{52}$, —OC(O)O$R^{52}$, —OC(O)N($R^{52}$)$_2$, —OC(O)N$R^{53}R^{54}$, —$NR^{52}$C(O)$R^{52}$, —$NR^{52}$C(O)O$R^{52}$, —$NR^{52}$C(O)N($R^{52}$)$_2$, —$NR^{52}$C(O)N$R^{53}R^{54}$, —C(O)N($R^{52}$)$_2$, —C(O)N$R^{53}R^{54}$, —P(O)(O$R^{52}$)$_2$, —P(O)($R^{52}$)$_2$, =O, =S, =N($R^{52}$), $C_{3-12}$ carbocycle and 3- to 12-membered heterocycle; and $C_{3-12}$ carbocycle and 3- to 12-membered heterocycle, wherein each $C_{3-12}$ carbocycle and 3- to 12-membered heterocycle in $R^{51}$ is independently optionally substituted with one or more substituents selected from halogen, —$NO_2$, —CN, —$OR^{52}$, —$SR^{52}$, —$N(R^{52})_2$, —$NR^{53}R^{54}$, —S(=O)$R^{52}$, —S(=O)$_2R^{52}$, —S(=O)$_2$N($R^{52}$)$_2$, —S(=O)$_2$N$R^{53}R^{54}$, —$NR^{52}$S(=O)$_2R^{52}$, —$NR^{52}$S(=O)$_2$N($R^{52}$)$_2$, —$NR^{52}$S(=O)$_2$N$R^{53}R^{54}$, —C(O)$R^{52}$, —C(O)O$R^{52}$, —OC(O)$R^{52}$, —OC(O)O$R^{52}$, —OC(O)N($R^{52}$)$_2$, —OC(O)N$R^{53}R^{54}$, —$NR^{52}$C(O)$R^{52}$, —$NR^{52}$C(O)O$R^{52}$, —$NR^{52}$C(O)N($R^{52}$)$_2$, —$NR^{52}$C(O)N$R^{53}R^{54}$, —C(O)N($R^{52}$)$_2$, —C(O)N$R^{53}R^{54}$, —P(O)(O$R^{52}$)$_2$, —P(O)($R^{52}$)$_2$, =O, =S, =N($R^{52}$), $C_{1-6}$ alkyl, $C_{1-6}$ haloalkyl, $C_{2-6}$ alkenyl, and $C_{2-6}$ alkynyl;

$R^{52}$ is independently selected at each occurrence from hydrogen; and $C_{1-20}$ alkyl, $C_{2-20}$ alkenyl, $C_{2-20}$ alkynyl, 1- to 6-membered heteroalkyl, $C_{3-12}$ carbocycle, and 3- to 12-membered heterocycle, each of which is optionally substituted by halogen, —CN, —$NO_2$, —$NH_2$, —$NHCH_3$, —$NHCH_2CH_3$, =O, —OH, —$OCH_3$, —$OCH_2CH_3$, $C_{3-12}$ carbocycle, or 3- to 6-membered heterocycle;

$R^{53}$ and $R^{54}$ are taken together with the nitrogen atom to which they are attached to form a heterocycle, optionally substituted with one or more $R^{50}$;

$R^{56}$ is independently selected at each occurrence from: —$OR^{59}$, =O, $C_{1-10}$ alkyl, $C_{2-10}$ alkenyl, $C_{2-10}$ alkynyl, wherein each $C_{1-10}$ alkyl, $C_{2-10}$ alkenyl, and $C_{2-10}$ alkynyl in $R^{56}$ is independently optionally substituted at each occurrence with one or more substituents selected from halogen, —$NO_2$, —CN, —$OR^{59}$, —$SR^{52}$, —$N(R^{52})_2$, —$NR^{53}R^{54}$, —S(=O)$R^{52}$, —S(=O)$_2R^{52}$, —S(=O)$_2$N($R^{52}$)$_2$, —S(=O)$_2$N$R^{53}R^{54}$, —$NR^{52}$S(=O)$_2R^{52}$, —$NR^{52}$S(=O)$_2$N($R^{52}$)$_2$, —$NR^{52}$S(=O)$_2$N$R^{53}R^{54}$, —C(O)$R^{52}$, —C(O)O$R^{52}$, —OC(O)$R^{52}$, —OC(O)O$R^{52}$, —OC(O)N($R^{52}$)$_2$, —OC(O)N$R^{53}R^{54}$, —$NR^{52}$C(O)$R^{52}$, —$NR^{52}$C(O)O$R^{52}$, —$NR^{52}$C(O)N($R^{52}$)$_2$, —$NR^{52}$C(O)N$R^{53}R^{54}$, —C(O)N($R^{52}$)$_2$, —C(O)N$R^{53}R^{54}$, —P(O)(O$R^{52}$)$_2$, —P(O)($R^{52}$)$_2$, =O, =S, =N($R^{52}$), $C_{3-12}$ carbocycle, and 3- to 12-membered heterocycle;

wherein each $C_{3-12}$ carbocycle and 3- to 12-membered heterocycle in $R^{56}$ is independently optionally substituted with one or more substituents selected from halogen, —$NO_2$, —CN, —$OR^{52}$, —$SR^{52}$, —$N(R^{52})_2$, —$NR^{53}R^{54}$, —S(=O)$R^{52}$, —S(=O)$_2R^{52}$, —S(=O)$_2$N($R^{52}$)$_2$, —S(=O)$_2$N$R^{53}R^{54}$, —$NR^{52}$S(=O)$_2R^{52}$, —$NR^{52}$S(=O)$_2$N($R^{52}$)$_2$, —$NR^{52}$S(=O)$_2$N$R^{53}R^{54}$, —C(O)$R^{52}$, —C(O)O$R^{52}$, —OC(O)$R^{52}$, —OC(O)O$R^{52}$, —OC(O)N($R^{52}$)$_2$, —OC(O)N$R^{53}R^{54}$, —$NR^{52}$C(O)$R^{52}$, —$NR^{52}$C(O)O$R^{52}$, —$NR^{52}$C(O)N($R^{52}$)$_2$, —$NR^{52}$C(O)N$R^{53}R^{54}$, —C(O)N($R^{52}$)$_2$, —C(O)N$R^{53}R^{54}$, —P(O)(O$R^{52}$)$_2$, —P(O)($R^{52}$)$_2$, =O, =S, =N($R^{52}$), $C_{1-6}$ alkyl, $C_{1-6}$ haloalkyl, $C_{2-6}$ alkenyl, and $C_{2-6}$ alkynyl; and further wherein $R^{56}$ optionally forms a bond to ring C; and $R^{59}$ is independently selected at each occurrence from $C_{1-20}$ alkyl, $C_{2-20}$ alkenyl, $C_{2-20}$ alkynyl, 1- to 6-membered heteroalkyl, $C_{3-12}$ carbocycle, and 3- to 12-membered heterocycle, each of which is optionally substituted by halogen, —CN, —$NO_2$, —$NH_2$, —$NHCH_3$, —$NHCH_2CH_3$, =O, —OH, —$OCH_3$, —$OCH_2CH_3$, $C_{3-12}$ carbocycle, or 3- to 6-membered heterocycle, wherein for a compound or salt of Formula (II), when $R^{56}$ is —$CH_3$, $L^3$ is not further substituted with —OH, —$NH_2$, or —CN.

In certain aspects, for a compound of Formula (I):

H is thienopyrimidinyl, optionally substituted with one or more $R^{50}$;

A is selected from piperidinylene and piperazinylene;

B is indolylene;

$L^1$ and $L^2$ are each independently selected from —O—, —S—, —NH—, and —$CH_2$—;

$L^3$ is selected from bond, —O—, —S—, —N($R^{51}$)—, —N($R^{51}$)$CH_2$—, —C(O)—, —C(O)O—, —OC(O)—, —OC(O)O—, —C(O)N($R^{51}$)—, —C(O)N($R^{51}$)C(O)—, —C(O)N($R^{51}$)C(O)N($R^{51}$)—, —N($R^{51}$)C(O)—, —N($R^{51}$)C(O)N($R^{51}$)—, —N($R^{51}$)C(O)O—, —OC(O)N($R^{51}$)—, —C(N$R^{51}$)—, —N($R^{51}$)C(N$R^{51}$)—, —C(N$R^{51}$)N($R^{51}$)—, —N($R^{51}$)C(N$R^{51}$)N($R^{51}$)—, —S(O)$_2$-, —OS(O)—, —S(O)O—, —S(O)—, —OS(O)$_2$—, —S(O)$_2$O—, —N($R^{51}$)S(O)$_2$—, —S(O)$_2$N($R^{51}$)—, —N($R^{51}$)S(O)—, —S(O)N($R^{51}$)—, —N($R^{51}$)S(O)$_2$N($R^{51}$)—, —N($R^{51}$)S(O)N($R^{51}$)—; alkylene, alkenylene, alkynylene, heteroalkylene, heteroalkenylene, and heteroalkynylene, each of which is optionally substituted with one or more $R^{50}$, wherein two $R^{50}$ groups attached to the same atom or different atoms of $L^3$ can together optionally form a ring;

R$^A$, R$^B$ and R$^C$ are each independently selected at each occurrence from R$^{50}$, or two R$^A$ groups, two R$^B$ groups or two R$^C$ groups attached to the same atom or different atoms can together optionally form a ring;

m is an integer from 0 to 3;
n is an integer from 1 to 3;
p is an integer from 0 to 6;
R$^{57}$ is selected from:
—S(=O)R$^{52}$, —S(=O)$_2$R$^{58}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —NR$^{52}$C(O)N(R$^{52}$)$_2$, —NR$^{52}$C(O)NR$^{53}$R$^{54}$, —C(O)NH(C$_{1-6}$ alkyl), —C(O)NR$^{53}$R$^{54}$, —P(O)(OR$^{52}$)$_2$, —P(O)(R$^{52}$)$_2$; and C$_{1-10}$ alkyl, C$_{2-10}$ alkenyl, and C$_{2-10}$ alkynyl, each of which is independently substituted at each occurrence with one or more substituents selected from —S(=O)R$^{52}$, —S(=O)$_2$R$^{58}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —NR$^{52}$C(O)N(R$^{52}$)$_2$, —NR$^{52}$C(O)NR$^{53}$R$^{54}$, —C(O)NH(C$_{1-6}$ alkyl), —C(O)NR$^{53}$R$^{54}$, —P(O)(OR$^{52}$)$_2$, and —P(O)(R$^{52}$)$_2$; and R$^{58}$ is selected from hydrogen; and C$_{1-20}$ alkyl, C$_{3-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle, wherein for a compound or salt of Formula (I), when C is azetidinylene, piperidinylene or piperazinylene and R$^{57}$ is —S(=O)$_2$R$^{58}$, —S(=O)$_2$N(R$^{52}$)$_2$, or —NR$^{52}$S(=O)$_2$R$^{52}$:
p is an integer from 1 to 6; and/or
L$^3$ is substituted with one or more R$^{50}$, wherein L$^3$ is not —CH$_2$CH(OH)—.

In certain aspects, for a compound of Formula (II):
H is thienopyrimidinyl, optionally substituted with one or more R$^{50}$;
A is selected from piperidinylene and piperazinylene;
B is indolylene;
L and L$^2$ are each independently selected from —O—, —S—, —NH—, and —CH$_2$—;
L$^3$ is selected from C$_{1-6}$ alkylene, C$_{2-6}$ alkenylene, and C$_{2-6}$ alkynylene, each of which is substituted with one or more R$^{56}$ and optionally further substituted with one or more R$^{50}$;
R$^A$, R$^B$ and R$^C$ are each independently selected at each occurrence from R$^{50}$, or two R$^A$ groups, two R$^B$ groups or two R$^C$ groups attached to the same atom or different atoms can together optionally form a bridge or ring;
m is an integer from 0 to 3;
n is an integer from 1 to 3;
p is an integer from 0 to 6;
R$^{56}$ is independently selected at each occurrence from:
—OR$^{59}$, =O, C$_{1-10}$ alkyl, C$_{2-10}$ alkenyl, and C$_{2-10}$ alkynyl,
wherein each C$_{1-10}$ alkyl, C$_{2-10}$ alkenyl, and C$_{2-10}$ alkynyl in R$^{56}$ is independently optionally substituted at each occurrence with one or more substituents selected from halogen, —NO$_2$, —CN, —OR$^{59}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{3-12}$ carbocycle, and 3- to 12-membered heterocycle;

wherein each C$_{3-12}$ carbocycle and 3- to 12-membered heterocycle in R$^{56}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl; and further wherein R$^{56}$ optionally forms a bond to ring C; and
R$^{59}$ is independently selected at each occurrence from C$_{1-20}$ alkyl, C$_{2-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle, wherein for a compound or salt of Formula (II), when R$^{56}$ is —CH$_3$, L$^3$ is not further substituted with —OH, —NH$_2$, or —CN.

In certain aspects, a compound of Formula (I) may be represented by:

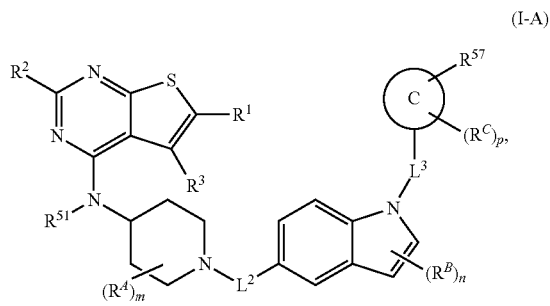

(I-A)

such as

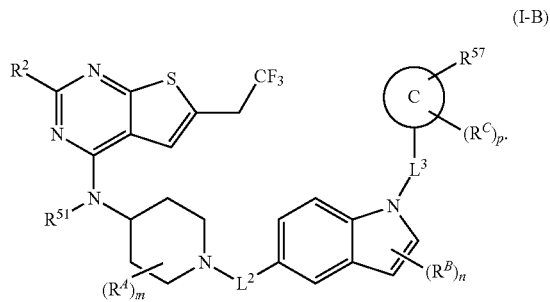

(I-B)

some embodiments, R$^1$ is selected from R$^{50}$. In some embodiments, R$^1$ is C$_{1-3}$ haloalkyl, such as —CH$_2$CF$_3$. In some embodiments, R$^2$ is selected from R$^{50}$. In some embodiments, R$^2$ is selected from hydrogen, halogen, —OH, —OR$^{52}$, —NH$_2$, —N(R$^{52}$)$_2$, —CN, C$_{1-3}$ alkyl, C$_{1-3}$ alkyl-OR$^{52}$, C$_{1-3}$ alkyl-N(R$^{52}$)$_2$, C$_{1-3}$ haloalkyl, C$_{2-3}$ alkenyl, and C$_{2-3}$ alkynyl. In some embodiments, R$^2$ is selected from halogen, —OH, —OR$^{52}$, —NH$_2$, —N(R$^{52}$)$_2$, —CN, C$_{1-3}$ alkyl, —CH$_2$OH, —CH$_2$OR$^{52}$, —CH$_2$NH$_2$, —CH$_2$N(R$^{52}$)$_2$, C$_{1-3}$ alkyl-N(R$^{52}$)$_2$, C$_{1-3}$ haloalkyl, C$_{2-3}$ alkenyl, and C$_{2-3}$ alkynyl, such as R$^2$ is selected from —OH, —OR$^{52}$, —NH$_2$, —N(R$^{52}$)$_2$, —CN, and C$_{1-2}$ alkyl. Optionally, R$^2$ is selected from —NH$_2$, —CH$_3$, —OCH$_3$, —CH$_2$OH, and —NHCH$_3$. In some embodiments, R$^3$ is selected from hydrogen, halogen, —OH, —N(R$^{52}$)$_2$, —CN, —C(O)OR$^{52}$, C$_{1-3}$ alkyl, and C$_{1-3}$ haloalkyl. In some embodiments, R$^{51}$ is selected from selected from hydrogen and alkyl, such as R$^{51}$ is hydrogen. In some embodiments, R$^A$ is selected from halogen, —CN, —OR$^{52}$, —N(R$^{52}$)$_2$, —NR$^{53}$R$^{54}$, —C(O)R$^{52}$, —C(O)OR$^{52}$, —OC(O)R$^{52}$, —NR$^{52}$C(O)R$^{52}$, —C(O)N(R$^{52}$)$_2$, —C(O)NR$^{53}$R$^{54}$, =O, C$_{1-10}$ alkyl, C$_{2-10}$ alkenyl, C$_{2-10}$ alkynyl, optionally substituted C$_{1-10}$ alkyl, optionally substituted C$_{2-10}$ alkenyl, and optionally substituted C$_{2-10}$ alkynyl. In some embodiments, m is 0. In some embodiments, L$^2$ is selected from —O—, —N(R$^{51}$)—, —N(R$^{51}$)CH$_2$—, —C(O)N(R$^{51}$)—, —N(R$^{51}$)C(O)—, —N(R$^{51}$)S(O)$_2$—, —S(O)$_2$N(R$^{51}$)—, C$_{1-4}$ alkylene and C$_{1-4}$ heteroalkylene. In some embodiments, L$^2$ is C$_{1-4}$ alkylene, optionally substituted with one or more R$^{50}$. In some embodiments, L$^2$ is C$_{1-2}$ alkylene, optionally substituted with one or more R$^{50}$. In some embodiments, L$^2$ is selected from —CH$_2$—, —N(R$^{51}$)—, —N(R$^{51}$)CH$_2$—, —N(R$^{51}$)C(O)—, and —N(R$^{51}$)S(O)$_2$—. In some embodiments, L$^2$ is —CH$_2$—. In some embodiments, R$^B$ is present at one or more positions of the indole, such as at position 2, 3, 4, or 6 of the indole. In some embodiments, R$^B$ is selected from halogen, —CN, —OR$^{52}$, —N(R$^{52}$)$_2$, —NR$^{53}$R$^{54}$, —C(O)R$^{52}$, —C(O)OR$^{52}$, —OC(O)R$^{52}$, —NR$^{52}$C(O)R$^{52}$, —C(O)N(R$^{52}$)$_2$, —C(O)NR$^{53}$R$^{54}$, =O, C$_{1-10}$ alkyl, C$_{2-10}$ alkenyl, C$_{2-10}$ alkynyl, optionally substituted C$_{1-10}$ alkyl, optionally substituted C$_{2-10}$ alkenyl, and optionally substituted C$_{2-10}$ alkynyl. In some embodiments, R$^B$ is selected from halogen, —CN, —OR$^{52}$, —N(R$^{52}$)$_2$, —NR$^{53}$R$^{54}$, C$_{1-3}$ alkyl, and optionally substituted C$_{1-3}$ alkyl, such as R$^B$ is selected from halogen, —CN, —OR$^{52}$, —N(R$^{52}$)$_2$, —NR$^{53}$R$^{54}$, and C$_{1-2}$ alkyl. In some embodiments, n is an integer from 1 to 4, such as an integer from 2 to 3. In some embodiments, n is 2. In some embodiments, L$^3$ is selected from C$_{1-6}$ alkylene, C$_{2-6}$ alkenylene, and C$_{2-6}$ alkynylene, each of which is substituted with one or more R$^{50}$. In some embodiments, L$^3$ is C$_{1-6}$ alkylene, optionally substituted with one or more R$^{50}$. In some embodiments, L$^3$ is C$_2$ alkylene substituted with at least one C$_{1-3}$ alkyl or C$_{1-3}$ haloalkyl, and optionally further substituted with one or more R$^{50}$. In some embodiments, L$^3$ is substituted with =O, C$_{1-6}$ alkyl, C$_{1-6}$ haloalkyl, C$_{1-3}$ alkyl(cyclopropyl), C$_{1-3}$ alkyl(NR$^{52}$C(O)R$^{52}$) or —O(C$_{1-6}$ alkyl). In some embodiments, L$^3$ is substituted with —CH$_3$. In some embodiments, L$^3$ is selected from

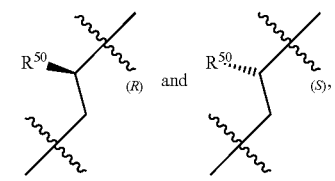

where R$^{50}$ is optionally methyl. In some embodiments, C is 3- to 12-membered heterocycle, such as 5- to 12-membered heterocycle. In some embodiments, the heterocycle is saturated. In some embodiments, C is selected from 5- to 7-membered monocyclic heterocycle, 8- to 10-membered fused bicyclic heterocycle, and 7- to 12-membered spirocyclic heterocycle. In some embodiments, the heterocycle comprises at least one nitrogen atom, such as one or two nitrogen atoms. In some embodiments, C comprises at least one ring nitrogen. In some embodiments, C is selected from piperidinyl and piperazinyl, such as

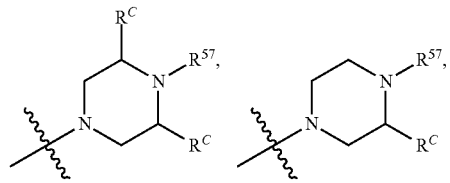

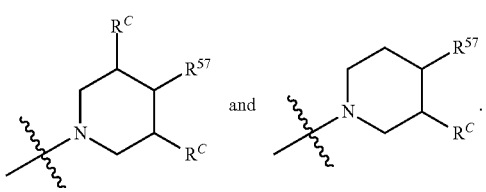

In some embodiments, C is selected from

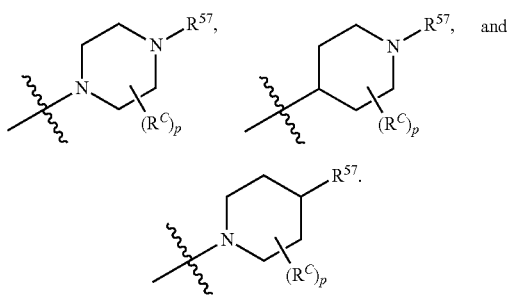

In some embodiments, C is selected from

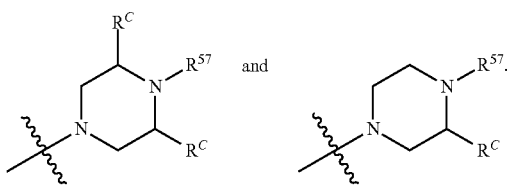

In some embodiments, C is selected from

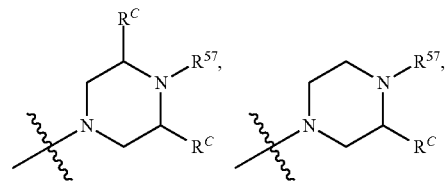

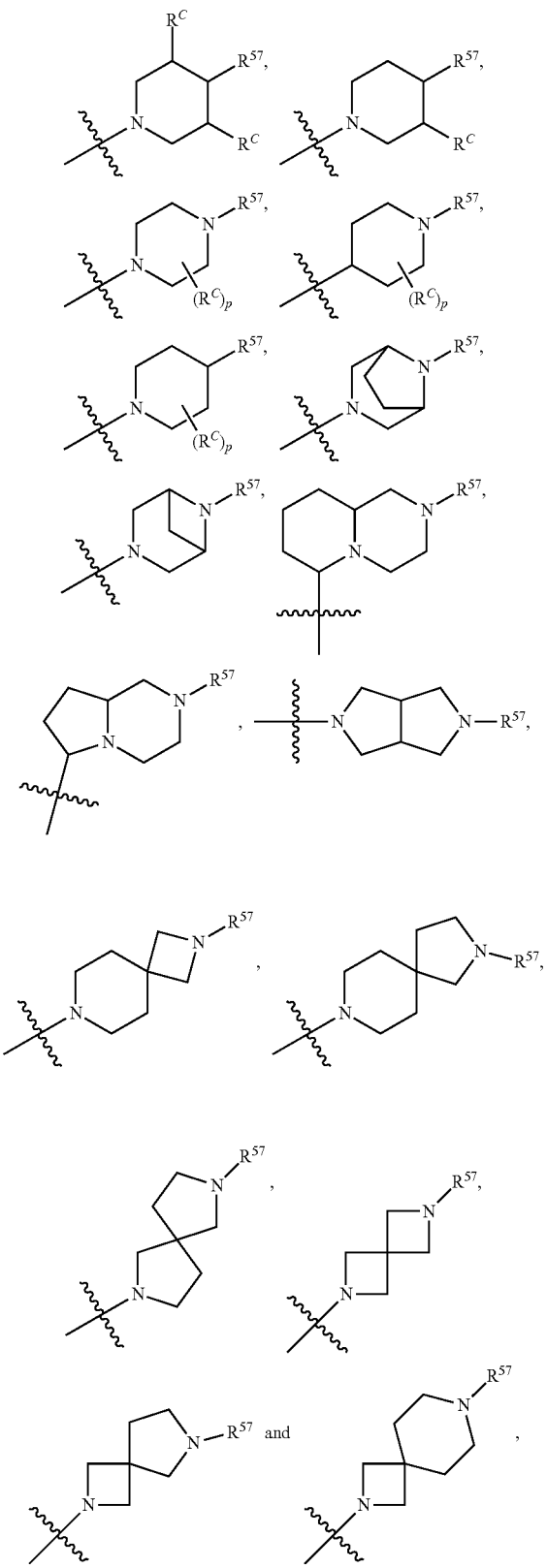

optionally substituted with one or more $R^C$. In some embodiments, C is selected from

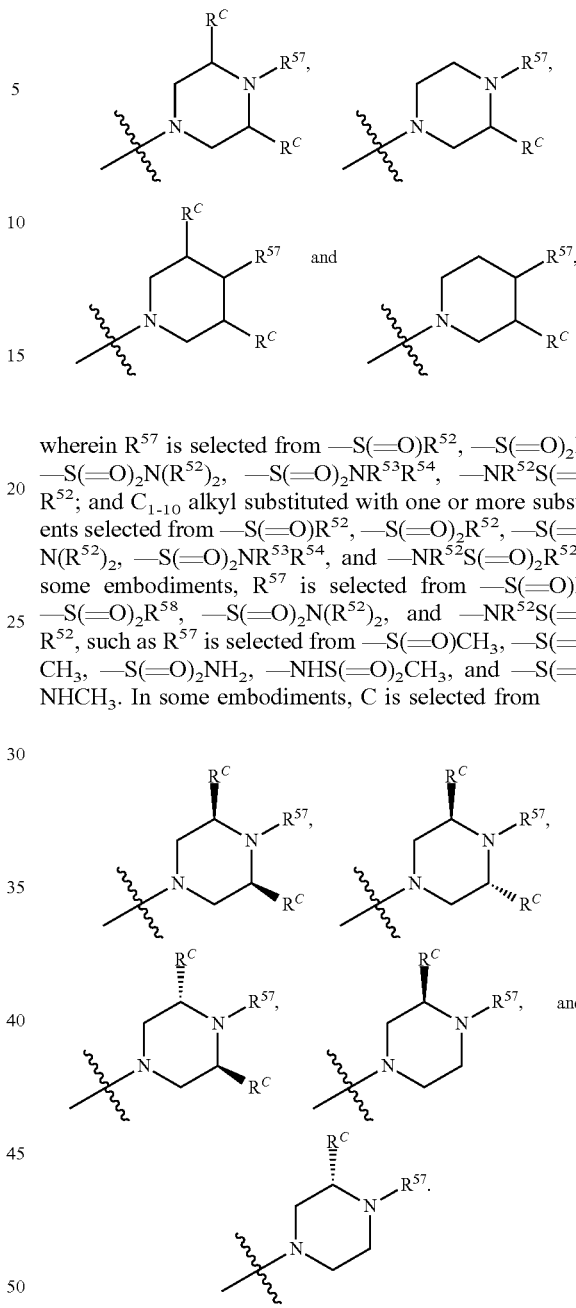

wherein $R^{57}$ is selected from —S(=O)$R^{52}$, —S(=O)$_2R^{52}$, —S(=O)$_2$N($R^{52}$)$_2$, —S(=O)$_2$N$R^{53}R^{54}$, —N$R^{52}$S(=O)$_2$ $R^{52}$; and $C_{1-10}$ alkyl substituted with one or more substituents selected from —S(=O)$R^{52}$, —S(=O)$_2R^{52}$, —S(=O)$_2$N($R^{52}$)$_2$, —S(=O)$_2$N$R^{53}R^{54}$, and —N$R^{52}$S(=O)$_2R^{52}$. In some embodiments, $R^{57}$ is selected from —S(=O)$R^{52}$, —S(=O)$_2R^{58}$, —S(=O)$_2$N($R^{52}$)$_2$, and —N$R^{52}$S(=O)$_2$ $R^{52}$, such as $R^{57}$ is selected from —S(=O)CH$_3$, —S(=O)$_2$ CH$_3$, —S(=O)$_2$NH$_2$, —NHS(=O)$_2$CH$_3$, and —S(=O)$_2$ NHCH$_3$. In some embodiments, C is selected from In some embodiments, $R^C$ is selected from —N($R^{52}$)$_2$, —N$R^{53}R^{54}$, —N$R^{52}$S(=O)$_2R^{52}$, —C(O)$R^{52}$, —C(O)O$R^{52}$, —N$R^{52}$C(O)$R^{52}$, —N$R^{52}$C(O)O$R^{52}$, —N$R^{52}$C(O)N($R^{52}$)$_2$, —N$R^{52}$C(O)N$R^{53}R^{54}$, —C(O)N($R^{52}$)$_2$, and —C(O) N$R^{53}R^{54}$. In some embodiments, $R^C$ is selected from —N($R^{52}$)$_2$, —N$R^{53}R^{54}$, —N$R^{52}$S(=O)$_2R^{52}$, —C(O)$R^{52}$, —C(O)O$R^{52}$, —N$R^{52}$C(O)$R^{52}$, —N$R^{52}$C(O)O$R^{52}$, —N$R^{52}$C(O)N($R^{52}$)$_2$, —N$R^{52}$C(O)N$R^{53}R^{54}$, —C(O)N ($R^{52}$)$_2$, —C(O)N$R^{53}R^{54}$, $C_{1-6}$ alkyl, and $C_{1-6}$ alkyl substituted with —N($R^{52}$)$_2$, —N$R^{53}R^{54}$, —N$R^{52}$S(=O)$_2R^{52}$, —C(O)$R^{52}$, —C(O)O$R^{52}$, —N$R^{52}$C(O)$R^{52}$, —N$R^{52}$C(O) O$R^{52}$, —N$R^{52}$C(O)N($R^{52}$)$_2$, —N$R^{52}$C(O)N$R^{53}R^{54}$, —C(O) N($R^{52}$)$_2$, or —C(O)N$R^{53}R^{54}$. In some embodiments, C is selected from

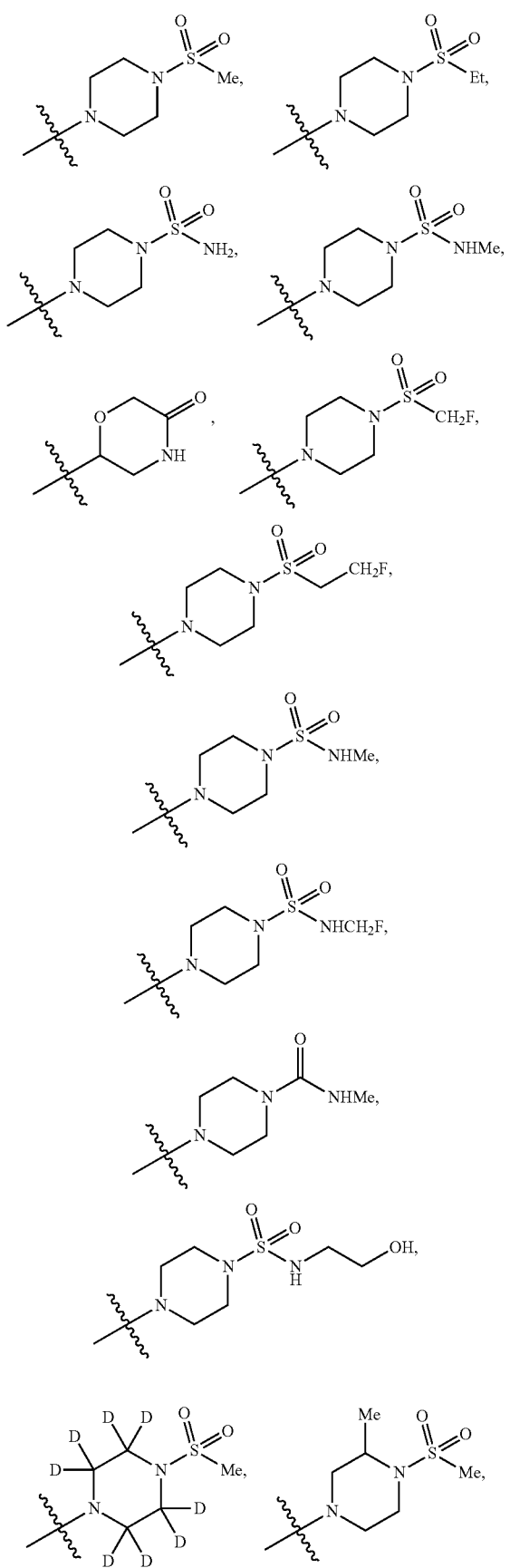
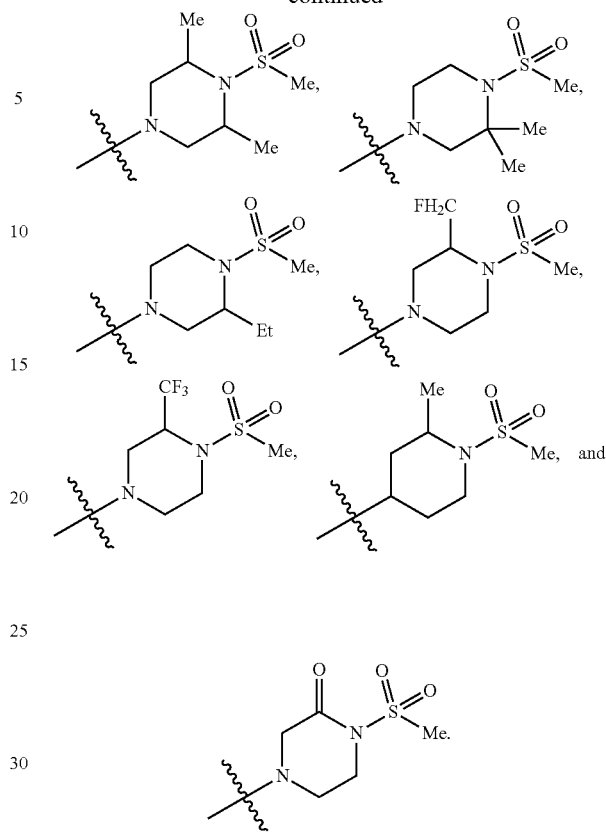

In some embodiments, $R^C$ is selected from $-C(O)R^{52}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, =O, $C_{1-3}$ alkyl, and $C_{1-3}$ haloalkyl, or two $R^C$ groups attached to different atoms can together form a $C_{1-3}$ bridge. In some embodiments, $R^C$ is selected from $C_{1-3}$ alkyl and $C_{1-3}$ haloalkyl, such as $-CH_3$. In some embodiments, p is selected from an integer 0 to 4, such as p is selected from an integer 0 to 2. In some embodiments, p is 0. In some embodiments, $R^{57}$ is selected from $-S(=O)_2R^{58}$, $-S(=O)_2N(R^{52})_2$, $-S(=O)_2 NR^{53}R^{54}$, $-NR^{52}S(=O)_2R^{52}$, $-NR^{52}S(=O)_2 N(R^{52})_2$, $-NR^{52}S(=O)_2NR^{53}R^{54}$, $-C(O)NH(C_{1-6}$ alkyl), $-C(O)NR^{53}R^{54}$; and $C_{1-6}$ alkyl and $C_{2-6}$ alkenyl, each of which is independently substituted at each occurrence with one or more substituents selected from $-S(=O)_2R^{58}$, $-S(=O)_2 N(R^{52})_2$, $-S(=O)_2NR^{53}R^{54}$, $-NR^{52}S(=O)_2 R^{52}$, $-NR^{52}S(=O)_2N(R^{52})_2$, $-NR^{52}S(=O)_2NR^{53}R^{54}$, $-C(O)NH(C_{1-6}$ alkyl), $-C(O)NR^{53}R^{54}$. In some embodiments, $R^{57}$ is selected from $-S(=O)_2R^{58}$, $-S(=O)_2N(R^{52})_2$, $-S(=O)_2NR^{53}R^{54}$, $-NR^{52}S(=O)_2R^{52}$, $-NR^{52}S(=O)_2 N(R^{52})_2$, $-NR^{52}S(=O)_2NR^{53}R^{54}$, and $C_{1-6}$ alkyl substituted with one or more substituents selected from $-S(=O)_2 R^{58}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, and $-NR^{52}S(=O)_2 NR^{53}R^{54}$. In some embodiments, $R^{57}$ is selected from $-S(=O)R^{52}$, $-S(=O)_2R^{58}$, $-S(=O)_2N(R^{52})_2$, and $-NR^{52}S(=O)_2R^{52}$. In some embodiments, $R^{57}$ is selected from $-S(=O)CH_3$, $-S(=O)_2CH_3$, $-S(=O)_2NH_2$, $-NHS(=O)_2CH_3$, and $-S(=O)_2NHCH_3$.

In certain aspects, a compound of Formula (I) may be represented by:

(I-C)

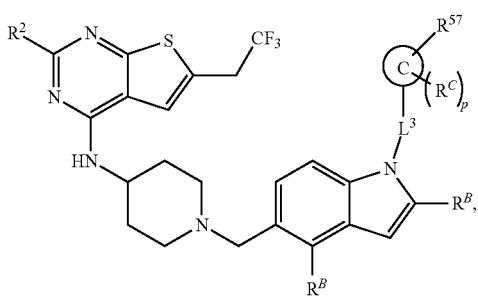

such as (I-D)

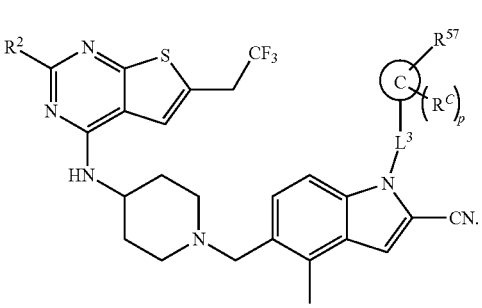

In some embodiments, R² is selected from R⁵⁰. In some embodiments, R² is selected from hydrogen, halogen, —OH, —OR⁵², —NH₂, —N(R⁵²)₂, —CN, $C_{1-3}$ alkyl, $C_{1-3}$ alkyl-OR⁵², $C_{1-3}$ alkyl-N(R⁵²)₂, $C_{1-3}$ haloalkyl, $C_{2-3}$ alkenyl, and $C_{2-3}$ alkynyl. In some embodiments, R² is selected from halogen, —OH, —OR⁵², —NH₂, —N(R⁵²)₂, —CN, $C_{1-3}$ alkyl, —CH₂OH, —CH₂OR⁵², —CH₂NH₂, —CH₂N(R⁵²)₂, $C_{1-3}$ alkyl-N(R⁵²)₂, $C_{1-3}$ haloalkyl, $C_{2-3}$ alkenyl, and $C_{2-3}$ alkynyl, such as R² is selected from —OH, —OR⁵², —NH₂, —N(R⁵²)₂, —CN, and $C_{1-2}$ alkyl. Optionally, R² is selected from —NH₂, —CH₃, —OCH₃, —CH₂OH, and —NHCH₃. In some embodiments, R$^B$ is selected from halogen, —CN, —OR⁵², —N(R⁵²)₂, —NR⁵³R⁵⁴, —C(O)R⁵², —C(O)OR⁵², —OC(O)R⁵², —NR⁵²C(O)R⁵², —C(O)N(R⁵²)₂, —C(O)NR⁵³R⁵⁴, =O, $C_{1-10}$ alkyl, $C_{2-10}$ alkenyl, $C_{2-10}$ alkynyl, optionally substituted $C_{1-10}$ alkyl, optionally substituted $C_{2-10}$ alkenyl, and optionally substituted $C_{2-10}$ alkynyl. In some embodiments, R$^B$ is selected from halogen, —CN, —OR⁵², —N(R⁵²)₂, —NR⁵³R⁵⁴, $C_{1-3}$ alkyl, and optionally substituted $C_{1-3}$ alkyl, such as R$^B$ is selected from halogen, —CN, —OR⁵², —N(R⁵²)₂, —NR⁵³R⁵⁴, and $C_{1-2}$ alkyl. In some embodiments, L³ is selected from $C_{1-6}$ alkylene, $C_{2-6}$ alkenylene, and $C_{2-6}$ alkynylene, each of which is substituted with one or more R⁵⁰. In some embodiments, L³ is $C_{1-6}$ alkylene, optionally substituted with one or more R⁵⁰. In some embodiments, L³ is $C_2$ alkylene substituted with at least one $C_{1-3}$ alkyl or $C_{1-3}$ haloalkyl, and optionally further substituted with one or more R⁵⁰. In some embodiments, L³ is substituted with =O, $C_{1-6}$ alkyl, $C_{1-6}$ haloalkyl, $C_{1-3}$ alkyl(cyclopropyl), $C_{1-3}$ alkyl(NR⁵²C(O)R⁵²) or —O($C_{1-6}$ alkyl). In some embodiments, L³ is substituted with —CH₃. In some embodiments, L³ is selected from

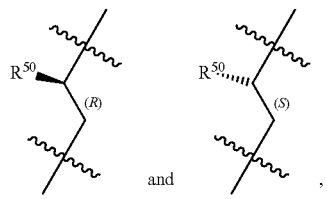

and where R⁵⁰ is optionally methyl. In some embodiments, C is 3- to 12-membered heterocycle, such as 5- to 12-membered heterocycle. In some embodiments, the heterocycle is saturated. In some embodiments, C is selected from 5- to 7-membered monocyclic heterocycle, 8- to 10-membered fused bicyclic heterocycle, and 7- to 12-membered spirocyclic heterocycle. In some embodiments, the heterocycle comprises at least one nitrogen atom, such as one or two nitrogen atoms. In some embodiments, C comprises at least one ring nitrogen. In some embodiments, C is selected from piperidinyl and piperazinyl, such as

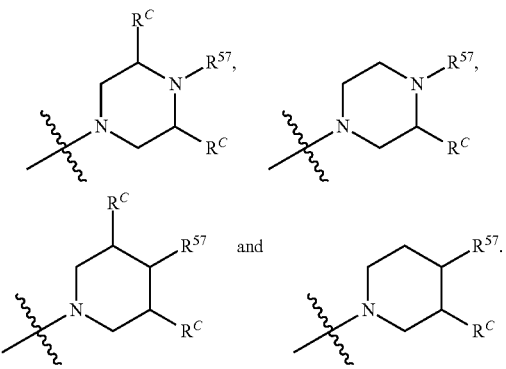

In some embodiments, C is selected from

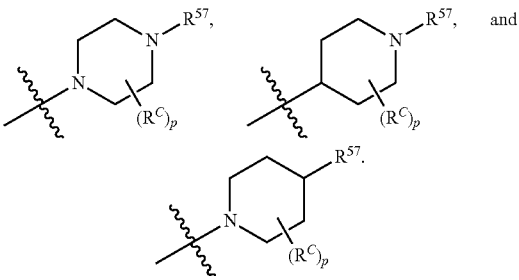

In some embodiments, C is selected from

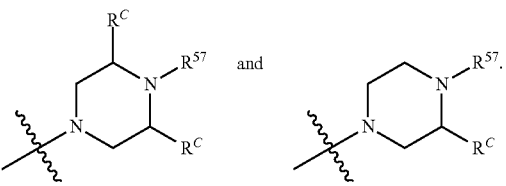

In some embodiments, C is selected from

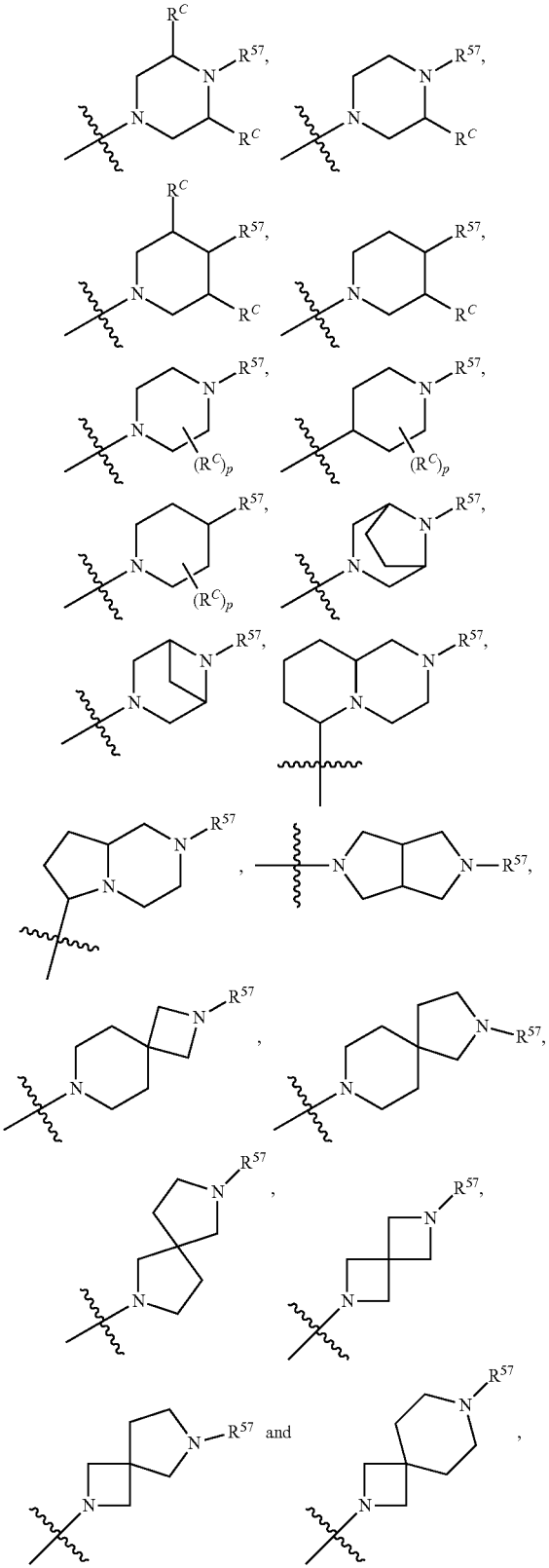

optionally substituted with one or more $R^C$. In some embodiments, C is selected from

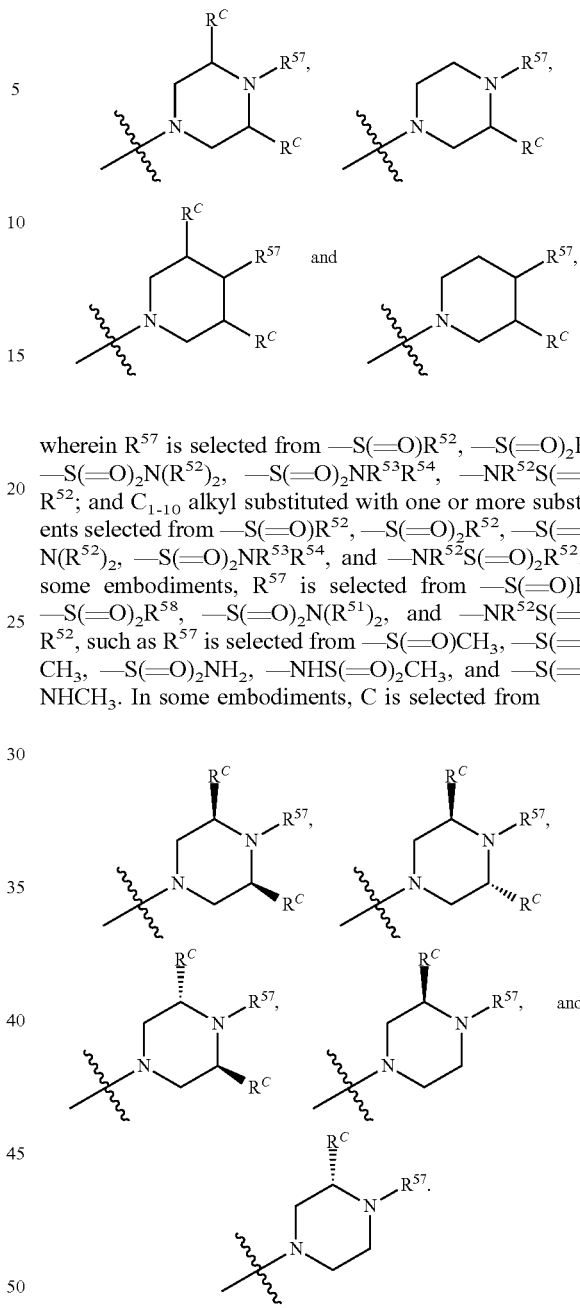

wherein $R^{57}$ is selected from —S(=O)$R^{52}$, —S(=O)$_2R^{52}$, —S(=O)$_2$N($R^{52}$)$_2$, —S(=O)$_2$N$R^{53}R^{54}$, —N$R^{52}$S(=O)$_2$ $R^{52}$; and $C_{1-10}$ alkyl substituted with one or more substituents selected from —S(=O)$R^{52}$, —S(=O)$_2R^{52}$, —S(=O)$_2$ N($R^{52}$)$_2$, —S(=O)$_2$N$R^{53}R^{54}$, and —N$R^{52}$S(=O)$_2R^{52}$. In some embodiments, $R^{57}$ is selected from —S(=O)$R^{52}$, —S(=O)$_2R^{58}$, —S(=O)$_2$N($R^{51}$)$_2$, and —N$R^{52}$S(=O)$_2$ $R^{52}$, such as $R^{57}$ is selected from —S(=O)CH$_3$, —S(=O)$_2$ CH$_3$, —S(=O)$_2$NH$_2$, —NHS(=O)$_2$CH$_3$, and —S(=O)$_2$ NHCH$_3$. In some embodiments, C is selected from In some embodiments, $R^C$ is selected from —N($R^{52}$)$_2$, —N$R^{53}R^{54}$, —N$R^{52}$S(=O)$_2R^{52}$, —C(O)$R^{52}$, —C(O)O$R^{52}$, —N$R^{52}$C(O)$R^{52}$, —N$R^{52}$C(O)O$R^{52}$, —N$R^{52}$C(O)N($R^{52}$)$_2$, —N$R^{52}$C(O)N$R^{52}R^{54}$, —C(O)N($R^{52}$)$_2$, and —C(O) N$R^{52}R^{54}$. In some embodiments, $R^C$ is selected from —N($R^{52}$)$_2$, —N$R^{53}R^{54}$, —N$R^{52}$S(=O)$_2R^{52}$, —C(O)$R^{52}$, —C(O)O$R^{52}$, —N$R^{52}$C(O)O$R^{52}$, —N$R^{52}$C(O)O$R^{52}$, —N$R^{52}$C(O)N($R^{51}$)$_2$, —N$R^{52}$C(O)N$R^{53}R^{54}$, —C(O)N ($R^{52}$)$_2$, —C(O)N$R^{53}R^{54}$, $C_{1-6}$ alkyl, and $C_{1-6}$ alkyl substituted with —N($R^{52}$)$_2$, —N$R^{53}R^{54}$, —N$R^{52}$S(=O)$_2R^{52}$, —C(O)$R^{52}$, —C(O)O$R^{52}$, —N$R^{52}$C(O)$R^{52}$, —N$R^{52}$C(O) O$R^{52}$, —N$R^{52}$C(O)N($R^{52}$)$_2$, —N$R^{52}$C(O)N$R^{53}R^{54}$, —C(O) N($R^{52}$)$_2$, or —C(O)N$R^{53}R^{54}$. In some embodiments, C is selected from

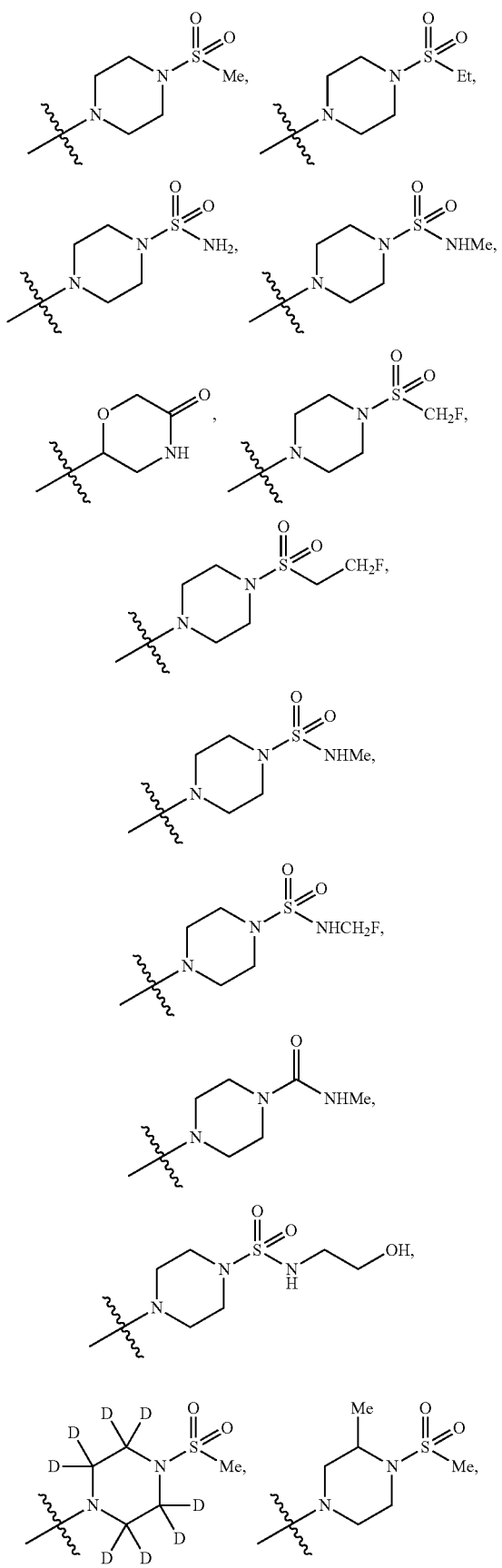

In some embodiments, $R^C$ is selected from —C(O)$R^{52}$, —S(=O)$R^{52}$, —S(=O)$_2R^{52}$, —S(=O)$_2$N($R^{52}$)$_2$, —S(=O)$_2$N$R^{53}R^{54}$, —N$R^{52}$S(=O)$_2R^{52}$, =O, $C_{1-3}$ alkyl, and $C_{1-3}$ haloalkyl, or two $R^C$ groups attached to different atoms can together form a $C_{1-3}$ bridge. In some embodiments, $R^C$ is selected from $C_{1-3}$ alkyl and $C_{1-3}$ haloalkyl, such as —CH$_3$. In some embodiments, p is selected from an integer 0 to 4, such as p is selected from an integer 0 to 2. In some embodiments, p is 0. In some embodiments, $R^{57}$ is selected from —S(=O)$_2R^{58}$, —S(=O)$_2$N($R^{52}$)$_2$, —S(O)$_2$N$R^{53}R^{54}$, —N$R^{52}$S(=O)$_2R^{52}$, —N$R^{52}$S(=O)$_2$N($R^{52}$)$_2$, —N$R^{52}$S(=O)$_2$N$R^{53}R^{54}$, —C(O)NH(C$_{1-6}$ alkyl), —C(O)N$R^{53}R^{54}$; and $C_{1-6}$ alkyl and $C_{2-6}$ alkenyl, each of which is independently substituted at each occurrence with one or more substituents selected from —S(=O)$_2R^{58}$, —S(=O)$_2$N($R^{52}$)$_2$, —S(=O)$_2$N$R^{53}R^{54}$, —N$R^{52}$S(=O)$_2R^{52}$, —N$R^{52}$S(=O)$_2$N($R^{52}$)$_2$, —N$R^{52}$S(=O)$_2$N$R^{53}R^{54}$, —C(O)NH(C$_{1-6}$ alkyl), —C(O)N$R^{53}R^{54}$. In some embodiments, $R^{57}$ is selected from —S(=O)$_2R^{58}$, —S(=O)$_2$N($R^{52}$)$_2$, —S(=O)$_2$N$R^{53}R^{54}$, —N$R^{52}$S(=O)$_2R^{52}$, —N$R^{52}$S(=O)$_2$N($R^{52}$)$_2$, —N$R^{52}$S(=O)$_2$N$R^{53}R^{54}$, and $C_{1-6}$ alkyl substituted with one or more substituents selected from —S(=O)$_2R^{58}$, —S(=O)$_2$N($R^{52}$)$_2$, —S(=O)$_2$N$R^{53}R^{54}$, —N$R^{52}$S(=O)$_2R^{52}$, —N$R^{52}$S(=O)$_2$N($R^{52}$)$_2$, and —N$R^{52}$S(=O)$_2$N$R^{53}R^{54}$. In some embodiments, $R^{57}$ is selected from —S(=O)$R^{52}$, —S(=O)$_2R^{58}$, —S(=O)$_2$N($R^{52}$)$_2$, and —N$R^{52}$S(=O)$_2R^{52}$. In some embodiments, $R^{57}$ is selected from —S(=O)CH$_3$, —S(=O)$_2$CH$_3$, —S(=O)$_2$NH$_2$, —NHS(=O)$_2$CH$_3$, and —S(=O)$_2$NHCH$_3$.

In certain aspects, a compound of Formula (I) may be represented by:

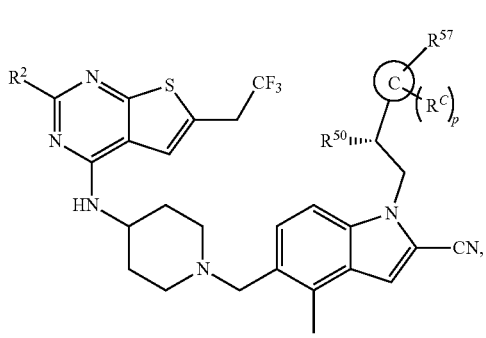

(I-E)

such as

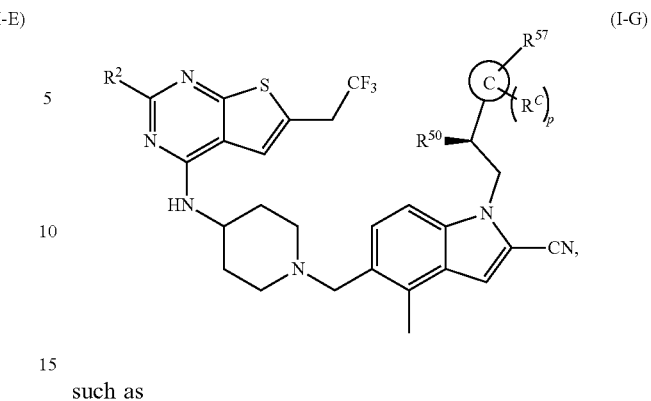

(I-G)

such as

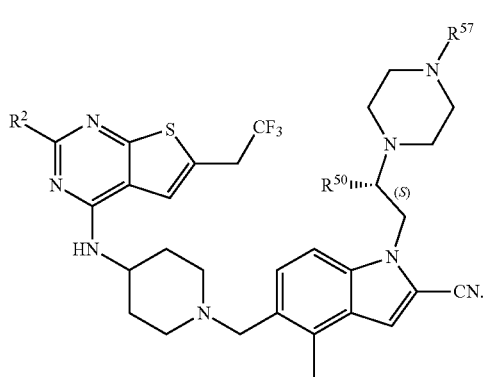

(I-F)

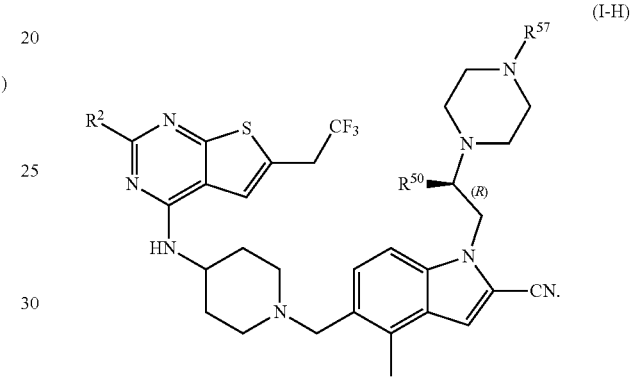

(I-H)

In some embodiments, C is selected from 5- to 7-membered monocyclic heterocycle, such as piperidinyl and piperazinyl. In some embodiments, $R^{50}$ is selected from deuterium, $C_{1-4}$ alkyl, $C_{1-4}$ haloalkyl, and $-OR^{52}$, such as $R^{50}$ is methyl. In some embodiments, $R^{57}$ is selected from $-S(=O)R^{52}$, $-S(=O)_2R^{58}$, $-S(=O)_2N(R^{52})_2$, and $-NR^{52}S(=O)_2R^{52}$, such as $R^{57}$ is selected from $-S(=O)CH_3$, $-S(=O)_2CH_3$, $-S(=O)_2NH_2$, $-NHS(=O)_2CH_3$, and $-S(=O)_2NHCH_3$. In some embodiments, $R^{57}$ is $-S(=O)_2CH_3$. In some embodiments, $R^{50}$ is methyl and $R^{57}$ is $-S(=O)_2CH_3$. In some embodiments, $R^2$ is selected from hydrogen, halogen, $-OH$, $-OR^{52}$, $-NH_2$, $-N(R^{52})_2$, $-CN$, $C_{1-3}$ alkyl, $-CH_2OH$, $-CH_2OR^{52}$, $-CH_2NH_2$, $-CH_2N(R^{52})_2$, $C_{1-3}$ alkyl-$N(R^{52})_2$, $C_{1-3}$ haloalkyl, $C_{2-3}$ alkenyl, and $C_{2-3}$ alkynyl, such as $R^2$ is selected from $-OH$, $-OR^{52}$, $-NH_2$, $-N(R^{52})_2$, $-CN$, and $C_{1-2}$ alkyl. In some embodiments, $R^2$ is methyl or $-NHCH_3$. In some embodiments, $R^2$ is H.

In certain aspects, a compound of Formula (II) may be represented by:

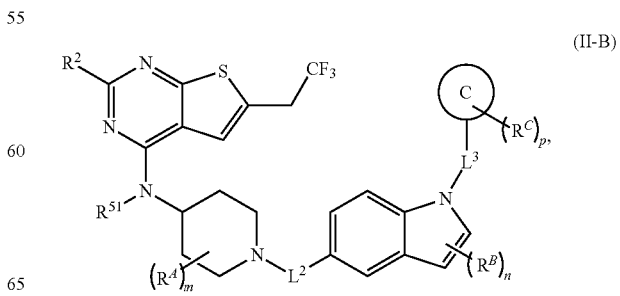

(II-B)

In some embodiments, C is selected from 5- to 7-membered monocyclic heterocycle, such as piperidinyl and piperazinyl. In some embodiments, $R^{50}$ is selected from deuterium, $C_{1-4}$ alkyl, $C_{1-4}$ haloalkyl, and $-OR^{52}$, such as $R^{50}$ is methyl. In some embodiments, $R^{57}$ is selected from $-S(=O)R^{52}$, $-S(=O)_2R^{58}$, $-S(=O)_2N(R^{52})_2$, and $-NR^{52}S(=O)_2R^{52}$, such as $R^{57}$ is selected from $-S(=O)CH_3$, $-S(=O)_2CH_3$, $-S(=O)_2NH_2$, $-NHS(=O)_2CH_3$, and $-S(=O)_2NHCH_3$. In some embodiments, $R^{57}$ is $-S(=O)_2CH_3$. In some embodiments, $R^{50}$ is methyl and $R^{57}$ is $-S(=O)_2CH_3$. In some embodiments, $R^2$ is selected from hydrogen, halogen, $-OH$, $-OR^{52}$, $-NH_2$, $-N(R^{52})_2$, $-CN$, $C_{1-3}$ alkyl, $-CH_2OH$, $-CH_2OR^{52}$, $-CH_2NH_2$, $-CH_2N(R^{52})_2$, $C_{1-3}$ alkyl-$N(R^{52})_2$, $C_{1-3}$ haloalkyl, $C_{2-3}$ alkenyl, and $C_{2-3}$ alkynyl, such as $R^2$ is selected from $-OH$, $-OR^{52}$, $-NH_2$, $-N(R^{52})_2$, $-CN$, and $C_{1-2}$ alkyl. In some embodiments, $R^2$ is methyl or $-NHCH_3$. In some embodiments, $R^2$ is H.

In certain aspects, a compound of Formula (I) may be represented by:

such as

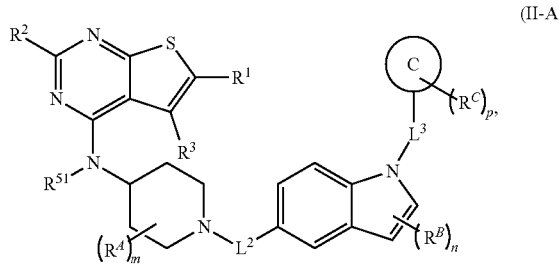

(II-A)

In some embodiments, $R^1$ is selected from $R^{50}$. In some embodiments, $R^1$ is $C_{1-3}$ haloalkyl, such as —$CH_2CF_3$. In some embodiments, $R^2$ is selected from $R^{50}$. In some embodiments, $R^2$ is selected from hydrogen, halogen, —OH, —$OR^{52}$, —$NH_2$, —$N(R^{52})_2$, —CN, $C_{1-3}$ alkyl, $C_{1-3}$ alkyl-$OR^{52}$, $C_{1-3}$ alkyl-$N(R^{52})_2$, $C_{1-3}$ haloalkyl, $C_{2-3}$ alkenyl, and $C_{2-3}$ alkynyl. In some embodiments, $R^2$ is selected from halogen, —OH, —$OR^{52}$, —$NH_2$, —$N(R^{52})_2$, —CN, $C_{1-3}$ alkyl, —$CH_2OH$, —$CH_2OR^{52}$, —$CH_2NH_2$, —$CH_2N(R^{52})_2$, $C_{1-3}$ alkyl-$N(R^{52})_2$, $C_{1-3}$ haloalkyl, $C_{2-3}$ alkenyl, and $C_{2-3}$ alkynyl, such as $R^2$ is selected from —OH, —$OR^{52}$, —$NH_2$, —$N(R^{52})_2$, —CN, and $C_{1-2}$ alkyl. Optionally, $R^2$ is selected from —$NH_2$, —$CH_3$, —$OCH_3$, —$CH_2OH$, and —$NHCH_3$. In some embodiments, $R^3$ is selected from hydrogen, halogen, —OH, —$N(R^{52})_2$, —CN, —$C(O)OR^{52}$, $C_{1-3}$ alkyl, and $C_{1-3}$ haloalkyl. In some embodiments, $R^{51}$ is selected from selected from hydrogen and alkyl, such as $R^{51}$ is hydrogen. In some embodiments, $R^A$ is selected from halogen, —CN, —$OR^{52}$, —$N(R^{52})_2$, —$NR^{53}R^{54}$, —$C(O)R^{52}$, —$C(O)OR^{52}$, —$OC(O)R^{52}$, —$NR^{52}C(O)R^{52}$, —$C(O)N(R^{52})_2$, —$C(O)NR^{53}R^{54}$, =O, $C_{1-10}$ alkyl, $C_{2-10}$ alkenyl, $C_{2-10}$ alkynyl, optionally substituted $C_{1-10}$ alkyl, optionally substituted $C_{2-10}$ alkenyl, and optionally substituted $C_{2-10}$ alkynyl. In some embodiments, m is 0. In some embodiments, $L^2$ is selected from —O—, —$N(R^{51})$—, —$N(R^{51})CH_2$—, —$C(O)N(R^{51})$—, —$N(R^{51})C(O)$—, —$N(R^{51})S(O)_2$—, —$S(O)_2N(R^{51})$—, $C_{1-4}$ alkylene and $C_{1-4}$ heteroalkylene. In some embodiments, $L^2$ is $C_{1-4}$ alkylene, optionally substituted with one or more $R^{50}$. In some embodiments, $L^2$ is $C_{1-2}$ alkylene, optionally substituted with one or more $R^{50}$. In some embodiments, $L^2$ is selected from —$CH_2$—, —$N(R^{51})$—, —$N(R^{51})CH_2$—, —$N(R^{51})C(O)$—, and —$N(R^{51})S(O)_2$—. In some embodiments, $L^2$ is —$CH_2$—. In some embodiments, $R^B$ is present at one or more positions of the indole, such as at position 2, 3, 4, or 6 of the indole. In some embodiments, $R^B$ is selected from halogen, —CN, —$OR^{52}$, —$N(R^{52})_2$, —$NR^{53}R^{54}$, —$C(O)R^{52}$, —$C(O)OR^{52}$, —$OC(O)R^{52}$, —$NR^{52}C(O)R^{52}$, —$C(O)N(R^{52})_2$, —$C(O)NR^{53}R^{54}$, =O, $C_{1-10}$ alkyl, $C_{2-10}$ alkenyl, $C_{2-10}$ alkynyl, optionally substituted $C_{1-10}$ alkyl, optionally substituted $C_{2-10}$ alkenyl, and optionally substituted $C_{2-10}$ alkynyl. In some embodiments, $R^B$ is selected from halogen, —CN, —$OR^{52}$, —$N(R^{52})_2$, —$NR^{53}R^{54}$, $C_{1-3}$ alkyl, and optionally substituted $C_{1-3}$ alkyl, such as $R^B$ is selected from halogen, —CN, —$OR^{52}$, —$N(R^{52})_2$, —$NR^{53}R^{54}$, and $C_{1-2}$ alkyl. In some embodiments, n is an integer from 1 to 4, such as an integer from 2 to 3. In some embodiments, n is 2. In some embodiments, $L^3$ is selected from alkylene, alkenylene, and alkynylene, each of which is substituted with one or more $R^{56}$ and optionally further substituted with one or more $R^{50}$. In some embodiments, $L^3$ is selected from $C_{1-6}$ alkylene, $C_{2-6}$ alkenylene, and $C_{2-6}$ alkynylene, each of which is substituted with one or more $R^{56}$ and optionally further substituted with one or more $R^{50}$. In some embodiments, $L^3$ is selected from $C_{1-6}$ alkylene, which is substituted with one or more $R^{56}$ and optionally further substituted with one or more $R^{50}$. In some embodiments, $L^3$ is $C_2$ alkylene substituted with at least one $C_{1-3}$ alkyl or $C_{1-3}$ haloalkyl, and optionally further substituted with one or more $R^{50}$. In some embodiments, $L^3$ is substituted with =O, $C_{1-6}$ alkyl, $C_{1-6}$ haloalkyl, $C_{1-3}$ alkyl(cyclopropyl), $C_{1-3}$ alkyl($NR^{52}C(O)R^{52}$) or —$O(C_{1-6}$ alkyl). In some embodiments, $L^3$ is substituted with —$CH_3$. In some embodiments, $L^3$ is selected from

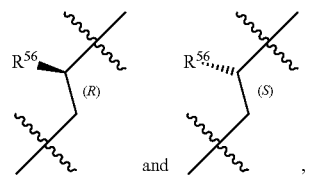

and where $R^{56}$ is optionally methyl. In some embodiments, C is selected from $C_{3-12}$ carbocycle and 3- to 12-membered heterocycle, such as 5- to 12-membered heterocycle. In some embodiments, the heterocycle is saturated. In some embodiments, C is selected from 5- to 7-membered monocyclic heterocycle, 8- to 10-membered fused bicyclic heterocycle, and 7- to 12-membered spirocyclic heterocycle. In some embodiments, the heterocycle comprises at least one nitrogen atom, such as one or two nitrogen atoms. In some embodiments, C comprises at least one ring nitrogen. In some embodiments, C is selected from piperidinyl and piperazinyl, such as

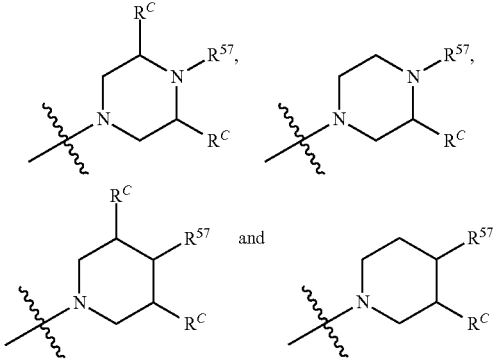

wherein $R^{57}$ is selected from hydrogen and $R^{50}$. In some embodiments, C is selected from

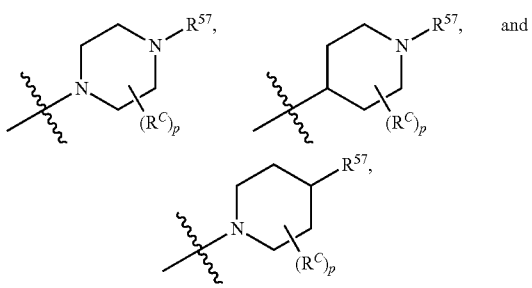

wherein $R^{57}$ is selected from hydrogen and $R^{50}$. In some embodiments, C is selected from

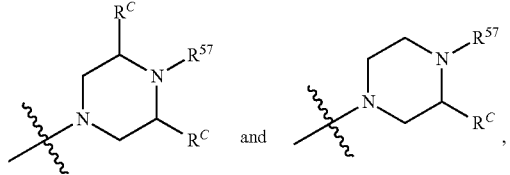 and 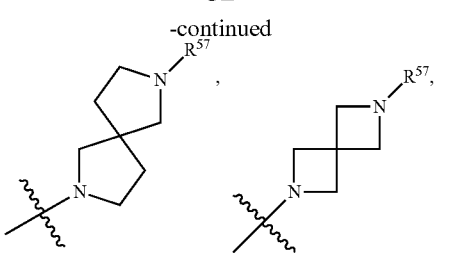

wherein $R^{57}$ is selected from hydrogen and $R^{50}$. In some embodiments, C is selected from

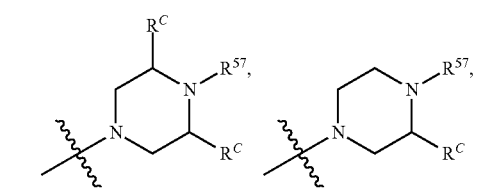

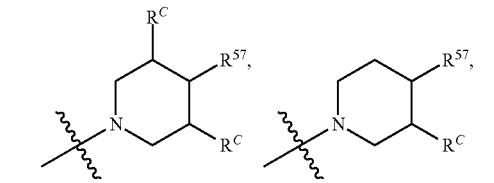

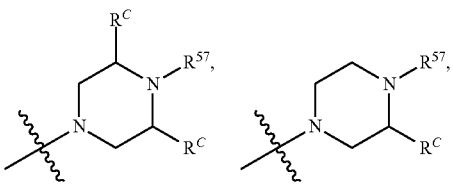 and

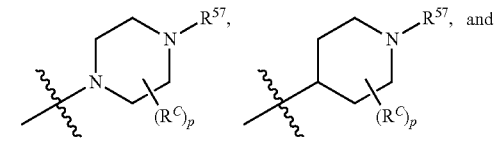

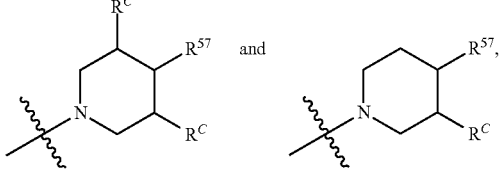

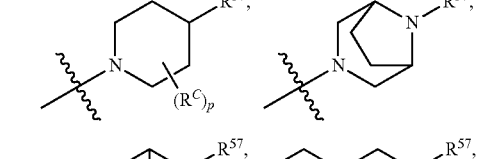

optionally substituted with one or more $R^C$, wherein $R^{57}$ is selected from hydrogen and $R^{50}$. In some embodiments, C is selected from

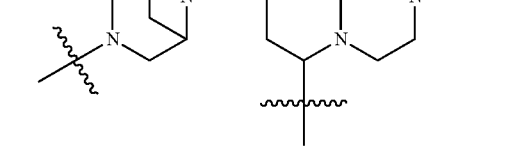

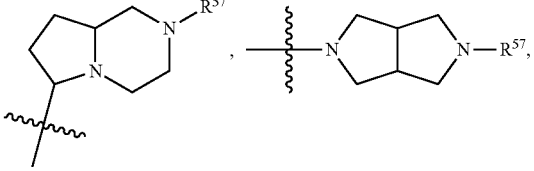

wherein $R^{57}$ is selected from $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$; and $C_{1-10}$ alkyl substituted with one or more substituents selected from $-S(=O)R^{52}$, $-S(=O)_2R^{52}$, $-S(=O)_2N(R^{52})_2$, $-S(=O)_2NR^{53}R^{54}$, and $-NR^{52}S(=O)_2R^{52}$. In some embodiments, $R^{57}$ is selected from $-S(=O)R^{52}$, $-S(=O)_2R^{52}$, $-S(=O)_2N(R^{52})_2$, and $-NR^{52}S(=O)_2R^{52}$, such as $R^{57}$ is selected from $-S(=O)CH_3$, $-S(=O)_2CH_3$, $-S(=O)_2NH_2$, $-NHS(=O)_2CH_3$, and $-S(=O)_2NHCH_3$. In some embodiments, C is selected from

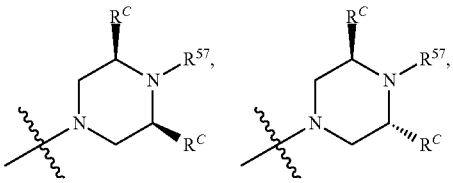

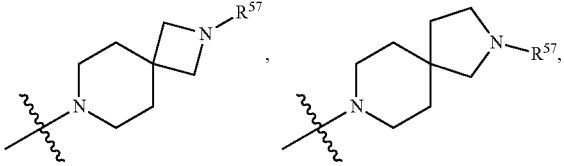

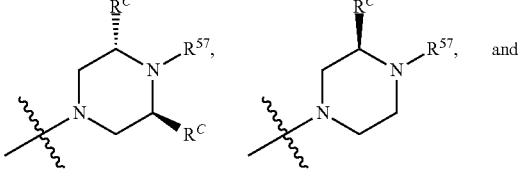

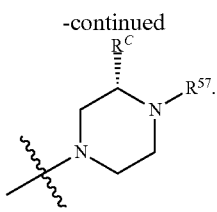

In some embodiments, $R^C$ is selected from —C(O)R$^{52}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, =O, C$_{1-3}$ alkyl, and C$_{1-3}$ haloalkyl, or two R$^C$ groups attached to different atoms can together form a C$_{1-3}$ bridge. In some embodiments, R$^C$ is selected from C$_{1-3}$ alkyl and C$_{1-3}$ haloalkyl, such as —CH$_3$. In some embodiments, p is selected from an integer 0 to 4, such as p is selected from an integer 0 to 2. In some embodiments, p is 0. In some embodiments, R$^C$ is selected from —N(R$^{52}$)$_2$, —NR$^{53}$R$^{54}$, —NR$^{52}$S(=O)$_2$R$^{52}$, —C(O)R$^{52}$, —C(O)OR$^{52}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, and —C(O)NR$^{53}$R$^{54}$. In some embodiments, R$^C$ is selected from —N(R$^{52}$)$_2$, —NR$^{53}$R$^{54}$, —NR$^{52}$S(=O)$_2$R$^{52}$, —C(O)R$^{52}$, —C(O)OR$^{52}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, C$_{1-6}$ alkyl, and C$_{1-6}$ alkyl substituted with —N(R$^{52}$)$_2$, —NR$^{53}$R$^{54}$, —NR$^{52}$S(=O)$_2$R$^{52}$, —C(O)R$^{52}$, —C(O)OR$^{52}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, or —C(O)NR$^{53}$R$^{54}$. In some embodiments, C is selected from

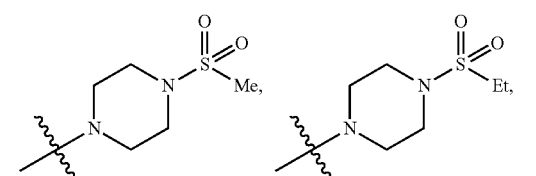

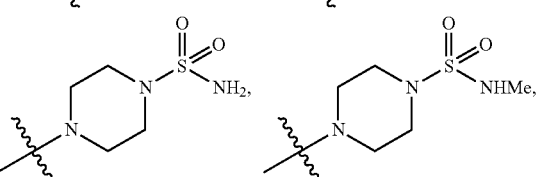

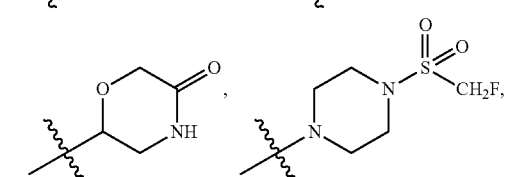

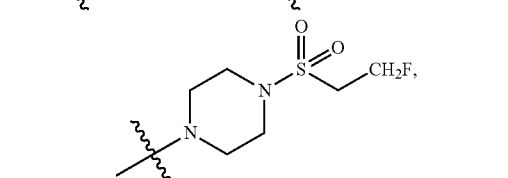

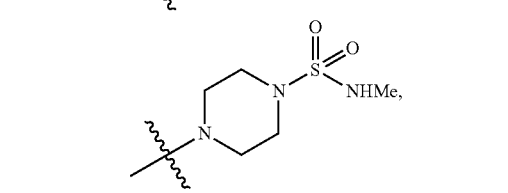

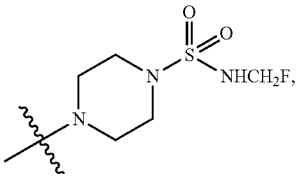

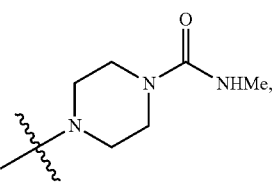

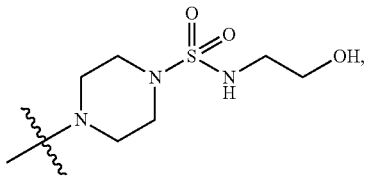

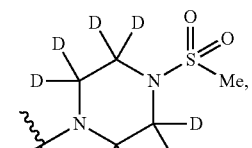 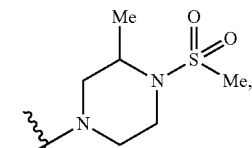

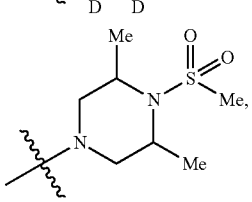 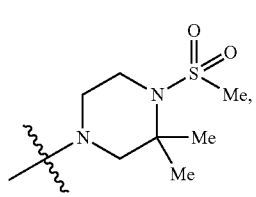

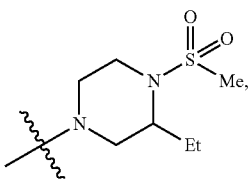 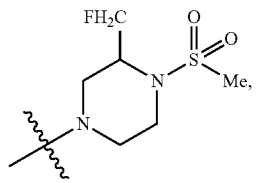

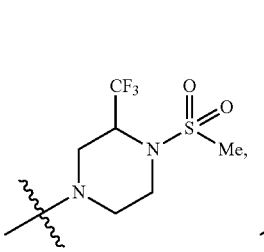 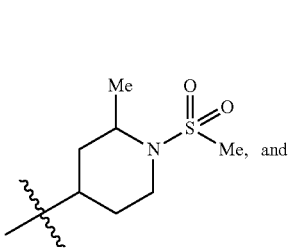

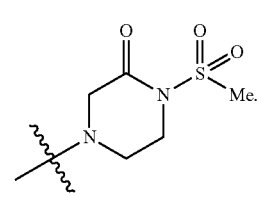

In certain aspects, a compound of Formula (II) may be represented by:

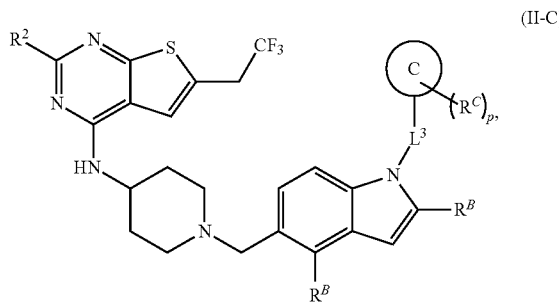

(II-C)

such as

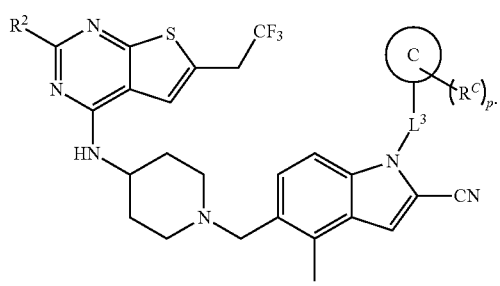

(II-D)

In some embodiments, $R^2$ is selected from $R^{50}$. In some embodiments, $R^2$ is selected from hydrogen, halogen, —OH, —OR$^{52}$, —NH$_2$, —N(R$^{52}$)$_2$, —CN, C$_{1-3}$ alkyl, C$_{1-3}$ alkyl-OR$^{52}$, C$_{1-3}$ alkyl-N(R$^{52}$)$_2$, C$_{1-3}$ haloalkyl, C$_{2-3}$ alkenyl, and C$_{2-3}$ alkynyl. In some embodiments, $R^2$ is selected from halogen, —OH, —OR$^{52}$, —NH$_2$, —N(R$^{52}$)$_2$, —CN, C$_{1-3}$ alkyl, —CH$_2$OH, —CH$_2$OR$^{52}$, —CH$_2$NH$_2$, —CH$_2$N(R$^{52}$)$_2$, C$_{1-3}$ alkyl-N(R$^{52}$)$_2$, C$_{1-3}$ haloalkyl, C$_{2-3}$ alkenyl, and C$_{2-3}$ alkynyl, such as $R^2$ is selected from —OH, —OR$^{52}$, —NH$_2$, —N(R$^{52}$)$_2$, —CN, and C$_{1-2}$ alkyl. Optionally, $R^2$ is selected from —NH$_2$, —CH$_3$, —OCH$_3$, —CH$_2$OH, and —NHCH$_3$. In some embodiments, $R^B$ is selected from halogen, —CN, —OR$^{52}$, —N(R$^{52}$)$_2$, —NR$^{53}$R$^{54}$, —C(O)R$^{52}$, —C(O)OR$^{52}$, —OC(O)R$^{52}$, —NR$^{52}$C(O)R$^{52}$, —C(O)N(R$^{52}$)$_2$, —C(O)NR$^{53}$R$^{54}$, =O, C$_{1-10}$ alkyl, C$_{2-10}$ alkenyl, C$_{2-10}$ alkynyl, optionally substituted C$_{1-10}$ alkyl, optionally substituted C$_{2-10}$ alkenyl, and optionally substituted C$_{2-10}$ alkynyl. In some embodiments, $R^B$ is selected from halogen, —CN, —OR$^{52}$, —N(R$^{52}$)$_2$, —NR$^{53}$R$^{54}$, C$_{1-3}$ alkyl, and optionally substituted C$_{1-3}$ alkyl, such as $R^B$ is selected from halogen, —CN, —OR$^{52}$, —N(R$^{52}$)$_2$, —NR$^{53}$R$^{54}$, and C$_{1-2}$ alkyl. In some embodiments, $L^3$ is selected from alkylene, alkenylene, and alkynylene, each of which is substituted with one or more R$^{56}$ and optionally further substituted with one or more R$^{50}$. In some embodiments, $L^3$ is selected from C$_{1-6}$ alkylene, C$_{2-6}$ alkenylene, and C$_{2-6}$ alkynylene, each of which is substituted with one or more R$^{56}$ and optionally further substituted with one or more R$^{50}$. In some embodiments, $L^3$ is selected from C$_{1-6}$ alkylene, which is substituted with one or more R$^{56}$ and optionally further substituted with one or more R$^{50}$. In some embodiments, $L^3$ is C$_2$ alkylene substituted with at least one C$_{1-3}$ alkyl or C$_{1-3}$ haloalkyl, and optionally further substituted with one or more R$^{50}$. In some embodiments, $L^3$ is substituted with =O, C$_{1-6}$ alkyl, C$_{1-6}$ haloalkyl, C$_{1-3}$ alkyl(cyclopropyl), C$_{1-3}$ alkyl(NR$^{52}$C(O) R$^{52}$) or —O(C$_{1-6}$ alkyl). In some embodiments $L^3$ is substituted with —CH$_3$. In some embodiments, $L^3$ is selected from

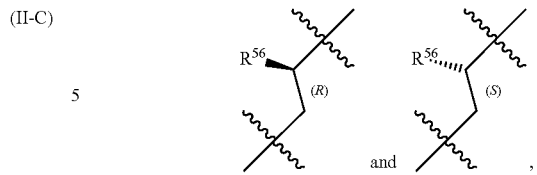

where $R^{56}$ is optionally methyl. In some embodiments, C is selected from C$_{3-12}$ carbocycle and 3- to 12-membered heterocycle, such as 5- to 12-membered heterocycle. In some embodiments, the heterocycle is saturated. In some embodiments, C is selected from 5- to 7-membered monocyclic heterocycle, 8- to 10-membered fused bicyclic heterocycle, and 7- to 12-membered spirocyclic heterocycle. In some embodiments, the heterocycle comprises at least one nitrogen atom, such as one or two nitrogen atoms. In some embodiments, C comprises at least one ring nitrogen. In some embodiments, C is selected from piperidinyl and piperazinyl, such as

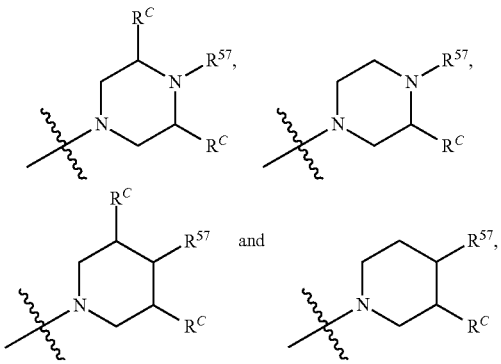

wherein $R^{57}$ is selected from hydrogen and $R^{50}$. In some embodiments, C is selected from

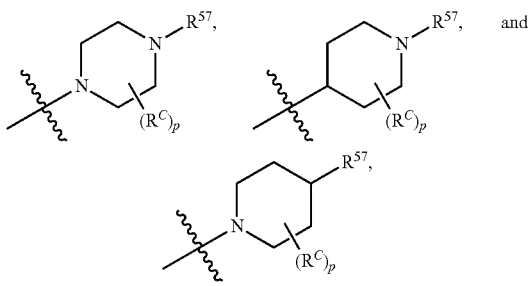

wherein $R^{57}$ is selected from hydrogen and $R^{50}$. In some embodiments, C is selected from

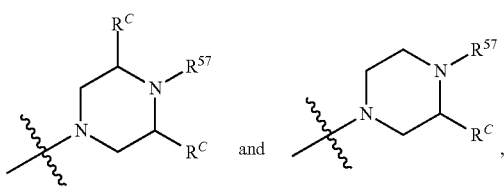

wherein $R^{57}$ is selected from hydrogen and $R^{50}$. In some embodiments, C is selected from

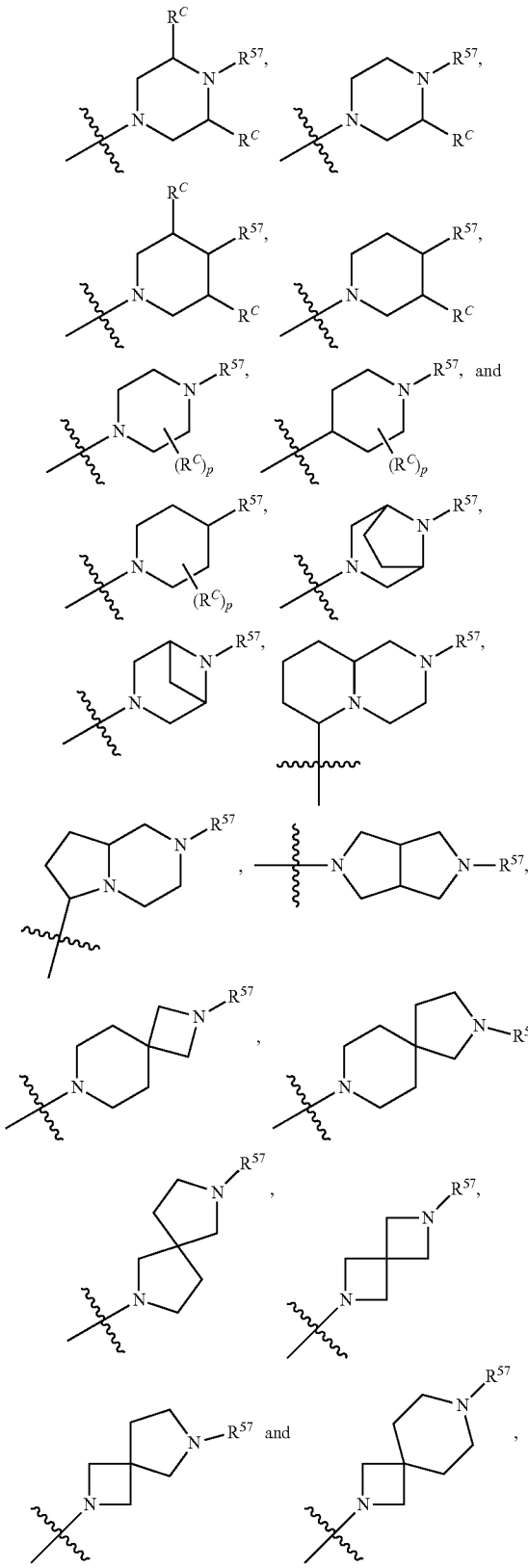

optionally substituted with one or more $R^C$, wherein $R^{57}$ is selected from hydrogen and $R^{50}$ In some embodiments, C is selected from

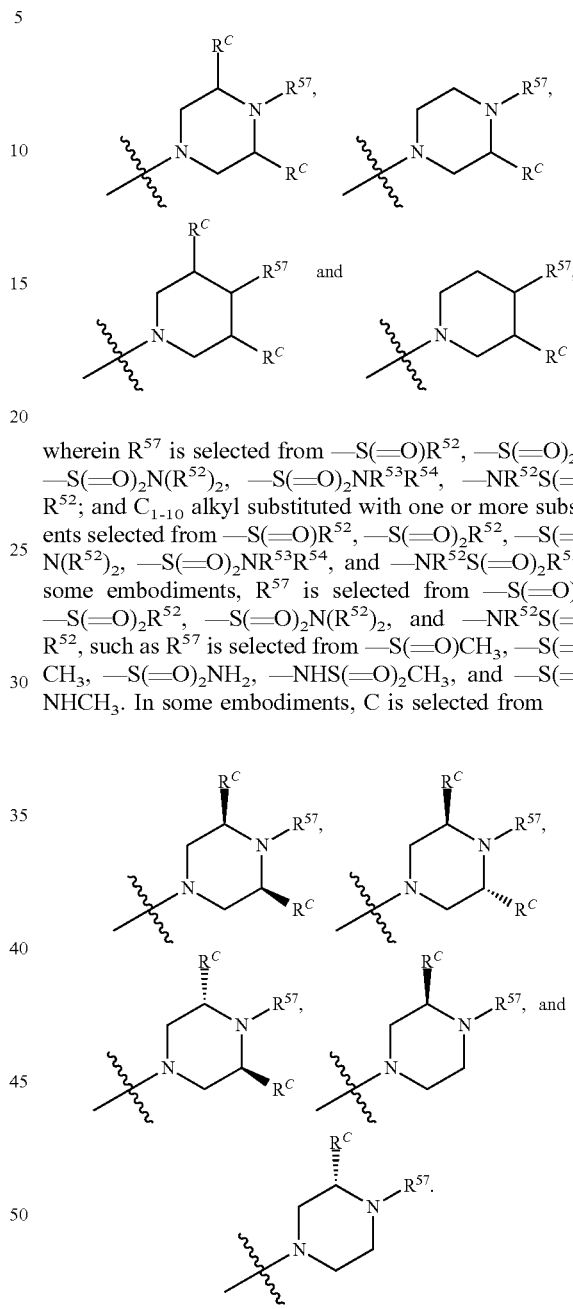

wherein $R^{57}$ is selected from —S(=O)$R^{52}$, —S(=O)$_2R^{52}$, —S(=O)$_2$N(R$^{52}$)$_2$, —S(=O)$_2$NR$^{53}$R$^{54}$, —NR$^{52}$S(=O)$_2$R$^{52}$; and C$_{1-10}$ alkyl substituted with one or more substituents selected from —S(=O)$R^{52}$, —S(=O)$_2R^{52}$, —S(=O)$_2$N(R$^{52}$)$_2$, —S(=O)$_2$NR$^{53}$R$^{54}$, and —NR$^{52}$S(=O)$_2$R$^{52}$. In some embodiments, $R^{57}$ is selected from —S(=O)$R^{52}$, —S(=O)$_2R^{52}$, —S(=O)$_2$N(R$^{52}$)$_2$, and —NR$^{52}$S(=O)$_2$R$^{52}$, such as $R^{57}$ is selected from —S(=O)CH$_3$, —S(=O)$_2$CH$_3$, —S(=O)$_2$NH$_2$, —NHS(=O)$_2$CH$_3$, and —S(=O)$_2$NHCH$_3$. In some embodiments, C is selected from In some embodiments, $R^C$ is selected from —C(O)R$^{52}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, =O, C$_{1-3}$ alkyl, and C$_{1-3}$ haloalkyl, or two $R^C$ groups attached to different atoms can together form a C$_{1-3}$ bridge. In some embodiments, $R^C$ is selected from C$_{1-3}$ alkyl and C$_{1-3}$ haloalkyl, such as —CH$_3$. In some embodiments, p is selected from an integer 0 to 4, such as p is selected from an integer 0 to 2. In some embodiments, p is 0. In some embodiments, $R^C$ is selected from —N(R$^{52}$)$_2$, —NR$^{53}$R$^{54}$, —NR$^{52}$S(=O)$_2$R$^{52}$, —C(O)R$^{52}$, —C(O)OR$^{52}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)

$N(R^{52})_2$, and $-C(O)NR^{53}R^{54}$. In some embodiments, $R^C$ is selected from $-N(R^{52})_2$, $-NR^{53}R^{54}$, $-NR^{52}S(=O)_2R^{52}$, $-C(O)R^{52}$, $-C(O)OR^{52}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $C_{1-6}$ alkyl, and $C_{1-6}$ alkyl substituted with $-N(R^{52})_2$, $-NR^{53}R^{54}$, $-NR^{52}S(=O)_2R^{52}$, $-C(O)R^{52}$, $-C(O)OR^{52}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, or $-C(O)NR^{53}R^{54}$. In some embodiments, C is selected from

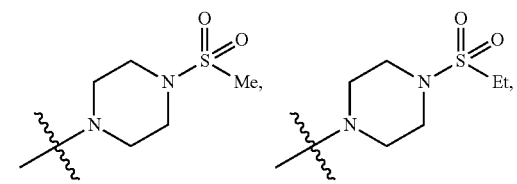

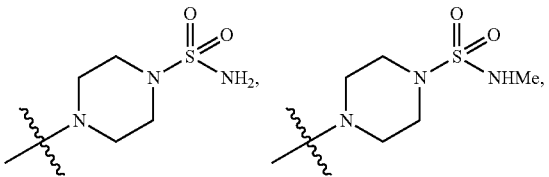

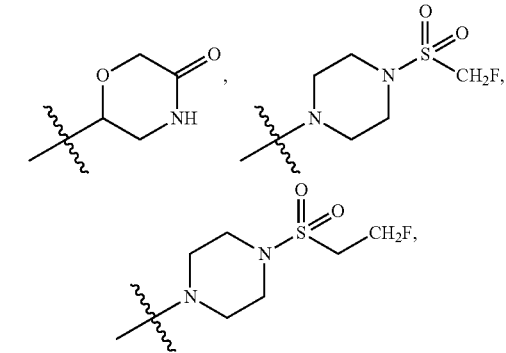

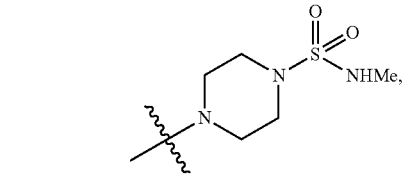

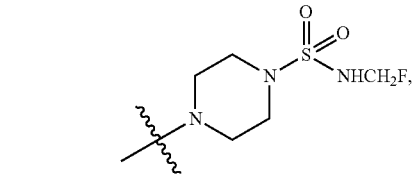

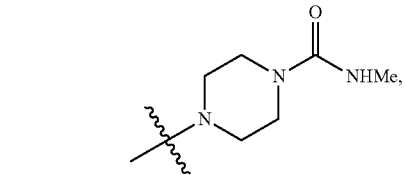

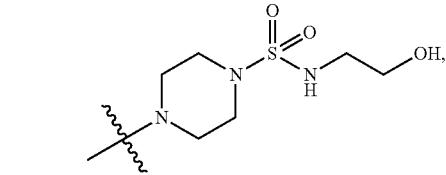

-continued

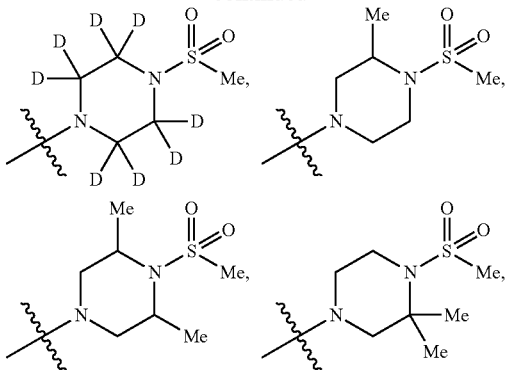

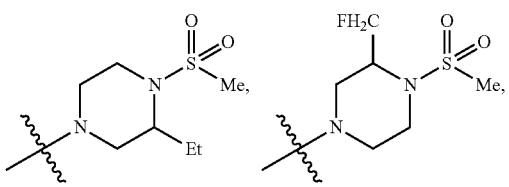

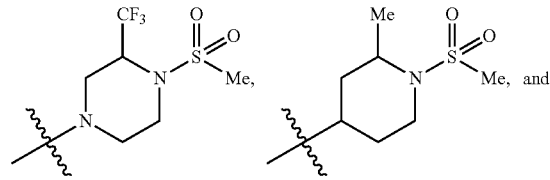

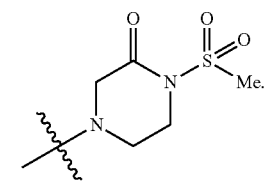

In certain aspects, a compound of Formula (II) may be represented by:

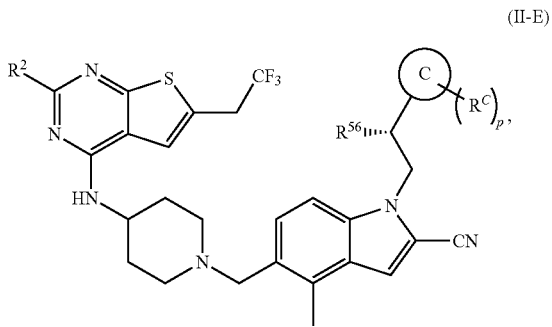

(II-E)

such as

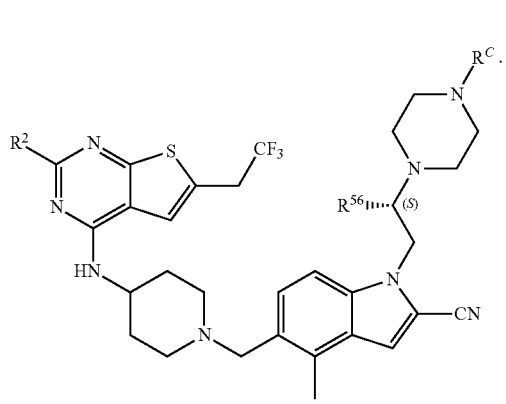

(II-F)

In some embodiments, C is selected from 5- to 7-membered monocyclic heterocycle, such as piperidinyl and piperazinyl. In some embodiments, $R^{56}$ is selected from deuterium, $C_{1-4}$ alkyl, $C_{1-4}$ haloalkyl, and $-OR^{59}$ such as $R^{56}$ is methyl. In some embodiments, $R^C$ is selected from $-S(=O)R^{52}$, $-S(=O)_2R^{52}$, $-S(=O)_2N(R^{52})_2$, and $-NR^{52}S(=O)_2R^{52}$, such as $R^C$ is selected from $-S(=O)CH_3$, $-S(=O)_2CH_3$, $-S(=O)_2NH_2$, $-NHS(=O)_2CH_3$, and $-S(=O)_2NHCH_3$. In some embodiments, p is an integer from 1 to 3, such as p is 1. In some embodiments, $R^C$ is $-S(=O)_2CH_3$. In some embodiments, $R^{56}$ is methyl and $R^C$ is $-S(=O)_2CH_3$. In some embodiments, $R^2$ is selected from hydrogen, halogen, $-OH$, $-OR^{52}$, $-NH_2$, $-N(R^{52})_2$, $-CN$, $C_{1-3}$ alkyl, $-CH_2OH$, $-CH_2OR^{52}$, $-CH_2NH_2$, $-CH_2N(R^{52})_2$, $C_{1-3}$ alkyl-$N(R^{52})_2$, $C_{1-3}$ haloalkyl, $C_{2-3}$ alkenyl, and $C_{2-3}$ alkynyl, such as $R^2$ is selected from $-OH$, $-OR^{52}$, $-NH_2$, $-N(R^{52})_2$, $-CN$, and $C_{1-2}$ alkyl. In some embodiments, $R^2$ is methyl or $-NHCH_3$. In some embodiments, $R^2$ is H.

In certain aspects, a compound of Formula (II) may be represented by:

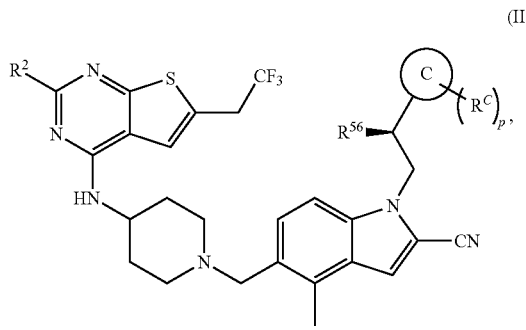

(II-G)

such as

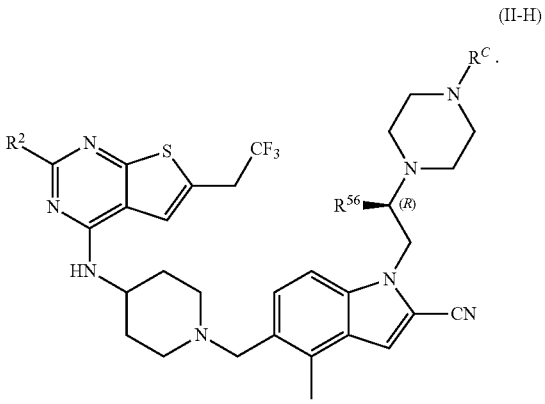

(II-H)

In some embodiments, C is selected from 5- to 7-membered monocyclic heterocycle, such as piperidinyl and piperazinyl. In some embodiments, $R^{56}$ is selected from deuterium, $C_{1-4}$ alkyl, $C_{1-4}$ haloalkyl, and $-OR^{59}$, such as $R^{56}$ is methyl. In some embodiments, $R^C$ is selected from $-S(=O)R^{52}$, $-S(=O)_2R^{52}$, $-S(=O)_2N(R^{52})_2$, and $-NR^{52}S(=O)_2R^{52}$, such as $R^C$ is selected from $-S(=O)CH_3$, $-S(=O)_2CH_3$, $-S(=O)_2NH_2$, $-NHS(=O)_2CH_3$, and $-S(=O)_2NHCH_3$. In some embodiments, p is an integer from 1 to 3, such as p is 1. In some embodiments, $R^C$ is $-S(=O)_2CH_3$. In some embodiments, $R^{56}$ is methyl and $R^C$ is $-S(=O)_2CH_3$. In some embodiments, $R^2$ is selected from hydrogen, halogen, $-OH$, $-OR^{52}$, $-NH_2$, $-N(R^{52})_2$, $-CN$, $C_{1-3}$ alkyl, $-CH_2OH$, $-CH_2OR^{52}$, $-CH_2NH_2$, $-CH_2N(R^{52})_2$, $C_{1-3}$ alkyl-$N(R^{52})_2$, $C_{1-3}$ haloalkyl, $C_{2-3}$ alkenyl, and $C_{2-3}$ alkynyl, such as $R^2$ is selected from $-OH$, $-OR^{52}$, $-NH_2$, $-N(R^{52})_2$, $-CN$, and $C_{1-2}$ alkyl. In some embodiments, $R^2$ is methyl or $-NHCH_3$. In some embodiments, $R^2$ is H.

In certain embodiments, the present disclosure provides a stereoisomer of a compound of Formula (I) or (II). In some embodiments, the stereoisomer is in enantiomeric excess. In some embodiments, the stereoisomer is provided in at least 20%, 30%, 40%, 50%, 55%, 60%, 65%, 70%, 75%, 80%, 85%, 88%, 90%, 91%, 92%, 93%, 94%, 95%, 96%, 97%, 98%, 99%, 99.5%, or 99.9%, enantiomeric excess. In some embodiments, the stereoisomer is provided in greater than 20%, 30%, 40%, 50%, 55%, 60%, 65%, 70%, 75%, 80%, 85%, 88%, 90%, 91%, 92%, 93%, 94%, 95%, 96%, 97%, 98%, 99%, 99.5%, or 99.9%, enantiomeric excess. In some embodiments, the stereoisomer is in greater than 95% enantiomeric excess, such as greater than 99% enantiomeric excess.

In certain embodiments, the present disclosure provides a stereoisomer of a compound of Formula (I) or (II). In some embodiments, the stereoisomer is in diastereomeric excess. In some embodiments, the stereoisomer is provided in at least 20%, 30%, 40%, 50%, 55%, 60%, 65%, 70%, 75%, 80%, 85%, 88%, 90%, 91%, 92%, 93%, 94%, 95%, 96%, 97%, 98%, 99%, 99.5%, or 99.9%, diastereomeric excess. In some embodiments, the stereoisomer is provided in greater than 20%, 30%, 40%, 50%, 55%, 60%, 65%, 70%, 75%, 80%, 85%, 88%, 90%, 91%, 92%, 93%, 94%, 95%, 96%, 97%, 98%, 99%, 99.5%, or 99.9%, diastereomeric excess. In some embodiments, the stereoisomer is in greater than 95% diastereomeric excess, such as greater than 99% diastereomeric excess.

In certain embodiments, the compound of Formula (I) or (II) is preferably used as a non-racemic mixture, wherein one enantiomer is present in excess of its corresponding enantiomer. Typically, such mixture will contain a mixture of the two isomers in a ratio of at least about 9:1, preferably at least 19:1. In some embodiments, the compound is provided in at least 96% enantiomeric excess, meaning the compound has less than 2% of the corresponding enantiomer. In some embodiments, the compound is provided in at least 96% diastereomeric excess, meaning the compound has less than 2% of the corresponding diastereomer.

In certain embodiments, the compound of Formula (I) or (II) is preferably used as a non-racemic mixture wherein the (+)-isomer is the major component of the mixture. Typically, such mixture will contain no more than about 10% of the (−)-isomer, meaning the ratio of (+)- to (−)-isomers is at least about 9:1, and preferably less than 5% of the (−)-isomer, meaning the ratio of (+)- to (−)-isomers is at least about 19:1. In some embodiments, the compound used has less than 2% of the (−)-isomer, meaning it has an enantiomeric excess of at least about 96%. In some embodiments, the compound has an enantiomeric excess of at least 98%. In some embodiments, the compound has an enantiomeric excess of at least 99%.

In certain embodiments, the compound of Formula (I) or (II) is preferably used as a non-racemic mixture wherein the (−)-isomer is the major component of the mixture. Typically, such mixture will contain no more than about 10% of the (+)-isomer, meaning the ratio of (−)- to (+)-isomers is at least about 9:1, and preferably less than 5% of the (+)-isomer, meaning the ratio of (−)- to (+)-isomers is at least about 19:1. In some embodiments, the compound used has less than 2% of the (+)-isomer, meaning it has an enantiomeric excess of at least about 96%. In some embodiments, the compound has an enantiomeric excess of at least 98%. In some embodiments, the compound has an enantiomeric excess of at least 99%.

In certain aspects, the present disclosure provides a stereoisomer of a compound of Formula (I):

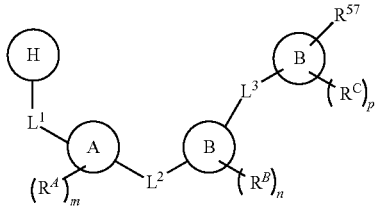

(I)

or a pharmaceutically acceptable salt, isotopic form, or prodrug thereof, wherein:

H is selected from $C_{5-12}$ carbocycle and 5- to 12-membered heterocycle, each of which is optionally substituted with one or more $R^{50}$;

A is selected from bond, $C_{3-12}$ carbocycle and 3- to 12-membered heterocycle;

B is selected from $C_{3-12}$ carbocycle and 3- to 12-membered heterocycle;

C is 3- to 12-membered heterocycle;

$L^1$, $L^2$ and $L^3$ are each independently selected from bond, —O—, —S—, —N($R^{51}$)—, —N($R^{51}$)CH$_2$—, —C(O)—, —C(O)O—, —OC(O)—, —OC(O)O—, —C(O)N($R^{51}$)—, —OC(O)N($R^{51}$)C(O)—, —C(O)N($R^{51}$)C(O)N($R^{51}$)—, —N($R^{51}$)C(O)—, —N($R^{51}$)C(O)N($R^{51}$)—, —N($R^{51}$)C(O)O—, —OC(O)N($R^{51}$)—, —C(N$R^{51}$)—, —N($R^{51}$)C(N$R^{51}$)—, —C(N$R^{51}$)N($R^{51}$)—, —N($R^{51}$)C(N$R^{51}$)N($R^{51}$)—, —S(O)$_2$—, —OS(O)—, —S(O)O—, —S(O)—, —OS(O)$_2$—, —S(O)$_2$O—, —N($R^{51}$)S(O)$_2$—, —S(O)$_2$N($R^{51}$)—, —N($R^{51}$)S(O)—, —S(O)N($R^{51}$)—, —N($R^{51}$)S(O)$_2$N($R^{51}$)—, —N($R^{51}$)S(O)N($R^{51}$)—; alkylene, alkenylene, alkynylene, heteroalkylene, heteroalkenylene, and heteroalkynylene, each of which is optionally substituted with one or more $R^{50}$, wherein two $R^{50}$ groups attached to the same atom or different atoms of any one of $L^1$, $L^2$ or $L^3$ can together optionally form a bridge or ring;

$R^A$, $R^B$ and $R^C$ are each independently selected at each occurrence from $R^{50}$, or two $R^A$ groups, two $R^B$ groups or two $R^C$ groups attached to the same atom or different atoms can together optionally form a bridge or ring;

m, n and p are each independently an integer from 0 to 6;

$R^{50}$ is independently selected at each occurrence from: halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$);

$C_{1-10}$ alkyl, $C_{2-10}$ alkenyl, and $C_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{50}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{1-6}$ alkyl, $C_{1-6}$ haloalkyl, $C_{2-6}$ alkenyl, and $C_{2-6}$ alkynyl;

$R^{51}$ is independently selected at each occurrence from: hydrogen, —C(O)R$^{52}$, —C(O)OR$^{52}$, —C(O)N(R$^{52}$)$_2$, —C(O)NR$^{53}$R$^{54}$;

$C_{1-6}$ alkyl, $C_{2-6}$ alkenyl, and $C_{2-6}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{3-12}$ carbocycle and 3- to 12-membered heterocycle; and C$_{3-12}$ carbocycle and 3- to 12-membered heterocycle, wherein each C$_{3-12}$ carbocycle and 3- to 12-membered heterocycle in R$^{51}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;

R$^{52}$ is independently selected at each occurrence from hydrogen; and C$_{1-20}$ alkyl, C$_{2-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle;

R$^{53}$ and R$^{54}$ are taken together with the nitrogen atom to which they are attached to form a heterocycle, optionally substituted with one or more R$^{50}$;

R$^{57}$ is selected from:
halogen, —NO$_2$, —CN, —SR$^{52}$, —NR$^{53}$R$^{54}$, —S(=O)R$^{52}$, —S(=O)$_2$R$^{58}$, —S(=O)$_2$N(R$^{52}$)$_2$, —S(=O)$_2$NR$^{53}$R$^{54}$, —NR$^{52}$S(=)$_2$R$^{52}$, —NR$^{52}$S(=O)$_2$N(R$^{52}$)$_2$, —NR$^{52}$S(=O)$_2$NR$^{53}$R$^{54}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)OR$^{52}$, —NR$^{52}$C(O)N(R$^{52}$)$_2$, —NR$^{52}$C(O)NR$^{53}$R$^{54}$, —C(O)NH(C$_{1-6}$ alkyl), —C(O)NR$^{53}$R$^{54}$, —P(O)(OR$^{52}$)$_2$, —P(O)(R$^{52}$)$_2$, =S, =N(R$^{52}$); and C$_{1-10}$ alkyl, C$_{2-10}$ alkenyl, and C$_{2-10}$ alkynyl, each of which is independently substituted at each occurrence with one or more substituents selected from —NO$_2$, —CN, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —P(O)(OR$^{52}$)$_2$, —P(O)(R$^{52}$)$_2$, =S, and =N(R$^{52}$); and R$^{58}$ is selected from hydrogen; and C$_{1-20}$ alkyl, C$_{3-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle.

In some embodiments, the stereoisomer of a compound of Formula (I) is provided in at least 20%, 30%, 40%, 50%, 55%, 60%, 65%, 70%, 75%, 80%, 85%, 88%, 90%, 91%, 92%, 93%, 94%, 95%, 96%, 97%, 98%, 99%, 99.5%, or 99.9%, enantiomeric excess. In some embodiments, the stereoisomer is provided in greater than 20%, 30%, 40%, 50%, 55%, 60%, 65%, 70%, 75%, 80%, 85%, 88%, 90%, 91%, 92%, 93%, 94%, 95%, 96%, 97%, 98%, 99%, 99.5%, or 99.9%, enantiomeric excess. In some embodiments, the stereoisomer is in greater than 95% enantiomeric excess, such as greater than 99% enantiomeric excess.

In some embodiments, for a stereoisomer of a compound of Formula (I), L$^3$ is selected from

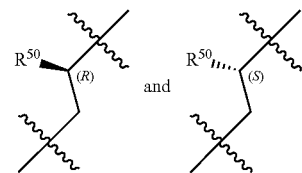

Optionally, R$^{50}$ is methyl. In some embodiments, L$^3$ is

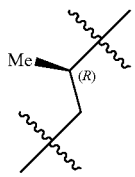

In some embodiments, L$^3$ is

In some embodiments, C is selected from

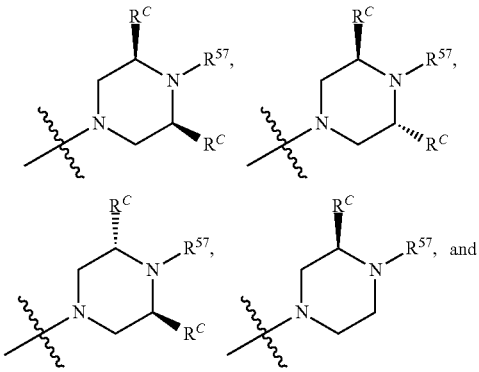

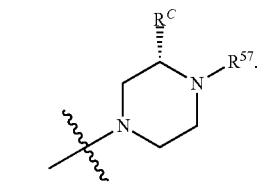

In some embodiments, L³ is selected from

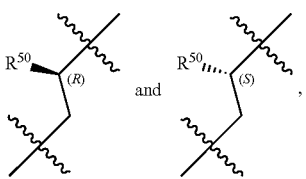

and C is selected from

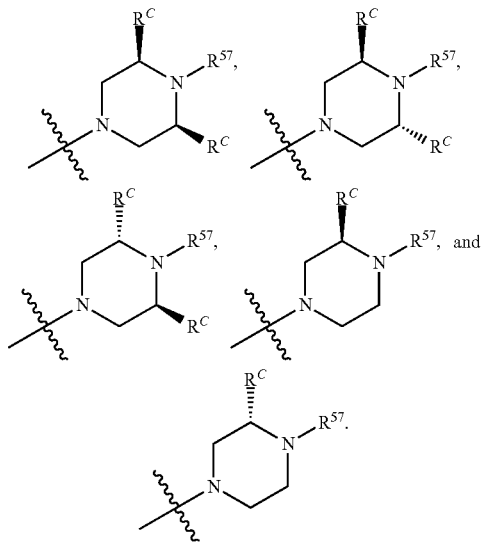

Any combination of the groups described above for the various variables of a compound of Formula (I) is contemplated herein for the stereoisomer of a compound of Formula (I).

In certain aspects, the present disclosure provides a stereoisomer of a compound of Formula (II):

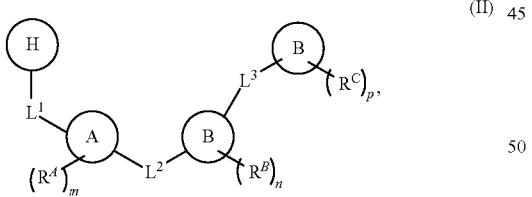

(II)

or a pharmaceutically acceptable salt thereof, wherein:

H is selected from $C_{5-12}$ carbocycle and 5- to 12-membered heterocycle, each of which is optionally substituted with one or more $R^{50}$;

A, B and C are each independently selected from $C_{3-12}$ carbocycle and 3- to 12-membered heterocycle;

$L^1$ and $L^2$ are each independently selected from bond, —O—, —S—, —N(R⁵¹)—, —N(R⁵¹)CH₂—, —C(O)—, —C(O)O—, —OC(O)—, —OC(O)O—, —C(O)N(R⁵¹)—, —C(O)N(R⁵¹)C(O)—, —C(O)N(R⁵¹)C(O)N(R⁵¹)—, —N(R⁵¹)C(O)—, —N(R⁵¹)C(O)N(R⁵¹)—, —N(R⁵¹)C(O)O—, —OC(O)N(R⁵¹)—, —C(NR⁵¹)—, —N(R⁵¹)C(NR⁵¹)—, —C(NR⁵¹)N(R⁵¹)—, —N(R⁵¹)C(NR⁵¹)N(R⁵¹)—, —S(O)₂—, —OS(O)—, —S(O)O—, —S(O)—, —OS(O)₂—, —S(O)₂O—, —N(R⁵¹)S(O)₂—, —S(O)₂N(R⁵¹)—, —N(R⁵¹)S(O)—, —S(O)N(R⁵¹)—, —N(R⁵¹)S(O)₂N(R⁵¹)—, —N(R⁵¹)S(O)N(R⁵¹)—; alkylene, alkenylene, alkynylene, heteroalkylene, heteroalkenylene, and heteroalkynylene, each of which is optionally substituted with one or more $R^{50}$, wherein two $R^{50}$ groups attached to the same atom or different atoms of L or L² can together optionally form a ring;

$L^3$ is selected from alkylene, alkenylene, and alkynylene, each of which is substituted with one or more $R^{56}$ and optionally further substituted with one or more $R^{50}$;

$R^A$, $R^B$ and $R^C$ are each independently selected at each occurrence from $R^{50}$, or two $R^A$ groups, two $R^B$ groups or two $R^C$ groups attached to the same atom or different atoms can together optionally form a bridge or ring;

m, n and p are each independently an integer from 0 to 6;

$R^{50}$ is independently selected at each occurrence from: halogen, —NO₂, —CN, —OR⁵², —SR⁵², —N(R⁵²)₂, —NR⁵³R⁵⁴, —S(=O)R⁵², —S(=O)₂R⁵², —S(=O)₂N(R⁵²)₂, —S(=O)₂NR⁵³R⁵⁴, —NR⁵²S(=O)₂R⁵², —NR⁵²S(=O)₂N(R⁵²)₂, —NR⁵²S(=O)₂NR⁵³R⁵⁴, —C(O)R⁵², —C(O)OR⁵², —OC(O)R⁵², —OC(O)OR⁵², —OC(O)N(R⁵²)₂, —OC(O)NR⁵³R⁵⁴, —NR⁵²C(O)R⁵², —NR⁵²C(O)OR⁵², —NR⁵²C(O)N(R⁵²)₂, —NR⁵²C(O)NR⁵³R⁵⁴, —C(O)N(R⁵²)₂, —C(O)NR⁵³R⁵⁴, —P(O)(OR⁵²)₂, —P(O)(R⁵²)₂, =O, =S, =N(R⁵²);

$C_{1-10}$ alkyl, $C_{2-10}$ alkenyl, and $C_{2-10}$ alkynyl, each of which is independently optionally substituted at each occurrence with one or more substituents selected from halogen, —NO₂, —CN, —OR⁵², —SR⁵², —N(R⁵²)₂, —NR⁵³R⁵⁴, —S(=O)R⁵², —S(=O)₂R⁵², —S(=O)₂N(R⁵²)₂, —S(=O)₂NR⁵³R⁵⁴, —NR⁵²S(=O)₂R⁵², —NR⁵²S(=O)₂N(R⁵²), —NR⁵²S(=O)₂NR⁵³R⁵⁴, —C(O)R⁵², —C(O)OR⁵², —OC(O)R⁵², —OC(O)OR⁵², —OC(O)N(R⁵²)₂, —OC(O)NR⁵³R⁵⁴, —NR⁵²C(O)R⁵², —NR⁵²C(O)OR⁵², —NR⁵²C(O)N(R⁵²)₂, —NR⁵²C(O)NR⁵³R⁵⁴, —C(O)N(R⁵²)₂, —C(O)NR⁵³R⁵⁴, —P(O)(OR⁵²)₂, —P(O)(R⁵²)₂, =O, =S, =N(R⁵²), $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{50}$ is independently optionally substituted with one or more substituents selected from halogen, —NO₂, —CN, —OR⁵², —SR⁵², —N(R⁵²)₂, —NR⁵³R⁵⁴, —S(=O)R⁵², —S(=O)₂R⁵², —S(=O)₂N(R⁵²)₂, —S(=O)₂NR⁵³R⁵⁴, —NR⁵²S(=O)₂R⁵², —NR⁵²S(=O)₂N(R⁵²)₂, —NR⁵²S(=O)₂NR⁵³R⁵⁴, —C(O)R⁵², —C(O)OR⁵², —OC(O)R⁵², —OC(O)OR⁵², —OC(O)N(R⁵²)₂, —OC(O)NR⁵³R⁵⁴, —NR⁵²C(O)R⁵², —NR⁵²C(O)OR⁵², —NR⁵²C(O)N(R⁵²)₂, —NR⁵²C(O)NR⁵³R⁵⁴, —C(O)N(R⁵²)₂, —C(O)NR⁵³R⁵⁴, —P(O)(OR⁵²)₂, —P(O)(R⁵²)₂, =O, =S, =N(R⁵²), $C_{1-6}$ alkyl, $C_{1-6}$ haloalkyl, $C_{2-6}$ alkenyl, and $C_{2-6}$ alkynyl;

$R^{51}$ is independently selected at each occurrence from: hydrogen, —C(O)R⁵², —C(O)OR⁵², —C(O)N(R⁵²)₂, —C(O)NR⁵³R⁵⁴;

$C_{1-6}$ alkyl, $C_{2-6}$ alkenyl, and $C_{2-6}$ alkynyl, each of which is independently optionally substituted at each occurrence with one or more substituents selected from halogen, —NO₂, —CN, —OR⁵², —SR⁵², —N(R⁵²)₂, —NR⁵³R⁵⁴, —S(=O)R⁵², —S(=O)₂R⁵², —S(=O)₂N(R⁵²)₂, —S(=O)₂NR⁵³R⁵⁴, —NR⁵²S(=O)₂N(R⁵²)₂, —NR⁵²S(=O)₂NR⁵³R⁵⁴, —C(O)R⁵², —C(O)OR⁵², —OC(O)R⁵², —OC(O)OR⁵², —OC(O)N(R⁵²)₂, —OC(O)NR⁵³R⁵⁴, —NR⁵²C (O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{3-12}$ carbocycle and 3- to 12-membered heterocycle; and C$_{3-12}$ carbocycle and 3- to 12-membered heterocycle,
wherein each C$_{3-12}$ carbocycle and 3- to 12-membered heterocycle in R$^{51}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;

R$^{52}$ is independently selected at each occurrence from hydrogen; and C$_{1-20}$ alkyl, C$_{2-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle;

R$^{53}$ and R$^{54}$ are taken together with the nitrogen atom to which they are attached to form a heterocycle, optionally substituted with one or more R$^{50}$;

R$^{56}$ is independently selected at each occurrence from:
—NO$_2$, —OR$^{59}$, —SR$^{52}$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{1-10}$ alkyl, C$_{2-10}$ alkenyl, C$_{2-10}$ alkynyl, C$_{3-12}$ carbocycle and 3- to 12-membered heterocycle, wherein each C$_{1-10}$ alkyl, C$_{2-10}$ alkenyl, and C$_{2-10}$ alkynyl in R$^{56}$ is independently optionally substituted at each occurrence with one or more substituents selected from halogen, —NO$_2$, —CN, —OR$^{59}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{3-12}$ carbocycle, and 3- to 12-membered heterocycle;

wherein each C$_{3-12}$ carbocycle and 3- to 12-membered heterocycle in R$^{56}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl; and further wherein R$^{56}$ optionally forms a bond to ring C; and R$^{59}$ is independently selected at each occurrence from C$_{1-20}$ alkyl, C$_{2-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle.

In some embodiments, the stereoisomer of a compound of Formula (II) is provided in at least 20%, 30%, 40%, 50%, 55%, 60%, 65%, 70%, 75%, 80%, 85%, 88%, 90%, 91%, 92%, 93%, 94%, 95%, 96%, 97%, 98%, 99%, 99.5%, or 99.9%, enantiomeric excess. In some embodiments, the stereoisomer is provided in greater than 20%, 30%, 40%, 50%, 55%, 60%, 65%, 70%, 75%, 80%, 85%, 88%, 90%, 91%, 92%, 93%, 94%, 95%, 96%, 97%, 98%, 99%, 99.5%, or 99.9%, enantiomeric excess. In some embodiments, the stereoisomer is in greater than 95% enantiomeric excess, such as greater than 99% enantiomeric excess.

In some embodiments, for a stereoisomer of a compound of Formula (II), L$^3$ is selected from

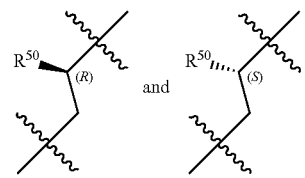

Optionally, R$^{56}$ is methyl. In some embodiments, L$^3$ is

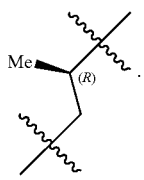

In some embodiments, L$^3$ is

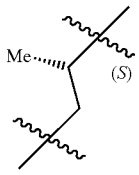

In some embodiments, C is selected from

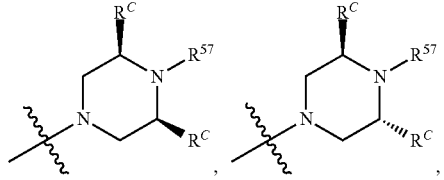

-continued

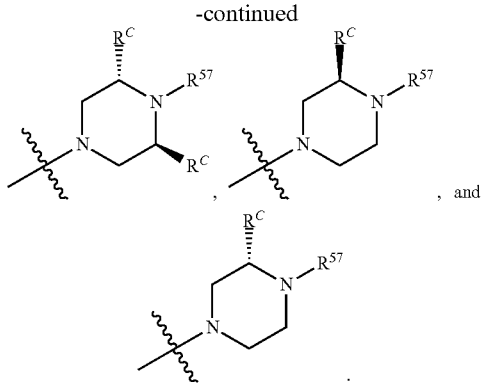

In some embodiments, L³ is selected from

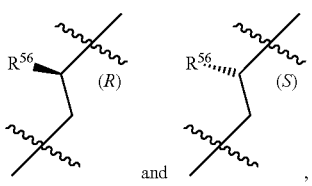

and C is selected from

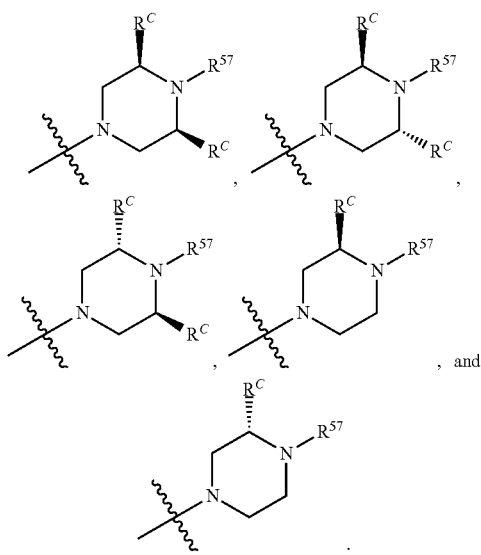

Any combination of the groups described above for the various variables of a compound of Formula (II) is contemplated herein for the stereoisomer of a compound of Formula (II).

In certain aspects, a compound of the disclosure covalently binds to menin and inhibits the interaction of menin with MLL. Such bonding may lead to an increase in the affinity of the compound for menin, which is an advantageous property in many applications, including therapeutic and diagnostic uses. In some embodiments, the compounds of the disclosure comprise electrophilic groups capable of reacting with a nucleophilic group present in a menin protein. Suitable electrophilic groups are described throughout the application, while suitable nucleophilic groups include, for example, cysteine moieties present in the binding domain of a menin protein. Without wishing to be bound by theory, a cysteine residue in the menin binding domain may react with the electrophilic group of a compound of the disclosure, leading to formation of a conjugate product. In some embodiments, the compounds of the disclosure are capable of covalently bonding to the cysteine residue at position 329 of a menin isoform 2 (SEQ ID NO: 2) or cysteine 334 in menin isoform 1 (SEQ ID NO: 1). In some embodiments, the disclosure provides a conjugate of a compound of the disclosure with a menin protein. For example, the disclosure provides a conjugate of a compound of the disclosure with menin, bound at the cysteine residue 329 of menin isoform 2 (SEQ ID NO: 2) or cysteine 334 in menin isoform 1 (SEQ ID NO: 1).

In some embodiments, for a compound of Formula (I) or (II), one or more of $R^A$, $R^B$ and $R^C$, when present, comprises a functional group that covalently reacts with one or more residues on menin. In some embodiments, the functional group covalently reacts with one or more cysteine residues on menin. In some embodiments, the functional group covalently reacts with a cysteine on menin at position 329 relative to SEQ ID NO: 2 when optimally aligned or position 334 relative to SEQ ID NO: 1 when optimally aligned. In some embodiments, the functional group covalently reacts with one or more residues on menin selected from cysteine 329, cysteine 241, and/or cysteine 230 on menin relative to SEQ ID NO: 2 when optimally aligned. In some embodiments, the functional group covalently reacts with cysteine 329 relative to SEQ ID NO: 2 when optimally aligned.

In some embodiments, for a compound of Formula (I) or (II), one or more of $R^A$, $R^B$ and $R^C$, when present, comprises a moiety that covalently reacts with one or more residues on menin. In some embodiments, one or more of $R^A$, $R^B$ and $R^C$, when present, comprises a moiety that covalently reacts with one or more isoforms of menin, for example, isoform 1 (SEQ ID NO: 1), isoform 2 (SEQ ID NO: 2) or isoform 3 (SEQ ID NO: 3) of menin. In certain embodiments, one or more of $R^A$, $R^B$ and $R^C$, when present, comprises a moiety that covalently reacts with menin, wherein the menin protein shares 60% or more, 70% or more, 75% or more, 80% or more, 85% or more, 90% or more, 95% or more, or 99% or more sequence identity with isoform 1 (SEQ ID NO: 1), isoform 2 (SEQ ID NO: 2) or isoform 3 (SEQ ID NO: 3).

In some embodiments, for a compound of Formula (I) or (II), one or more of $R^A$, $R^B$ and $R^C$, when present, comprises an electrophilic group that is susceptible to nuclephilic attack from a residue on menin. Any suitable electrophilic moiety known to one of skill in the art to bind to nuclephilic residues, for example, any electrophilic moiety known to bind to cysteine residues, is contemplated herein. In some embodiments, one or more of $R^A$, $R^B$ and $R^C$, when present, comprises a moiety other than an electrophile, wherein the moiety is capable of binding to or covalently reacting with a residue on menin. In some embodiments, a compound or salt of Formula (I) or (II) is capable of (a) binding covalently to menin and (b) inhibiting the interation of menin and MLL.

In some embodiments, for a compound of Formula (I) or (II), $R^C$ comprises a functional group that covalently reacts with one or more residues on menin. In some embodiments, the functional group covalently reacts with one or more cysteine residues on menin. In some embodiments, the functional group covalently reacts with a cysteine on menin at position 329 relative to SEQ ID NO: 2 when optimally aligned or position 334 relative to SEQ ID NO: 1 when optimally aligned.

In some embodiments, for a compound of Formula (I) or (II), $R^C$ is a moiety comprising an alpha, beta-unsaturated carbonyl; an alpha, beta-unsaturated sulfonyl; an epoxide; an aldehyde; sulfonyl fluoride; a halomethylcarbonyl, a dihalomethylcarbonyl, or a trihalomethylcarbonyl.

In some embodiments, for a compound of Formula (I) or (II), $R^C$ is selected from:

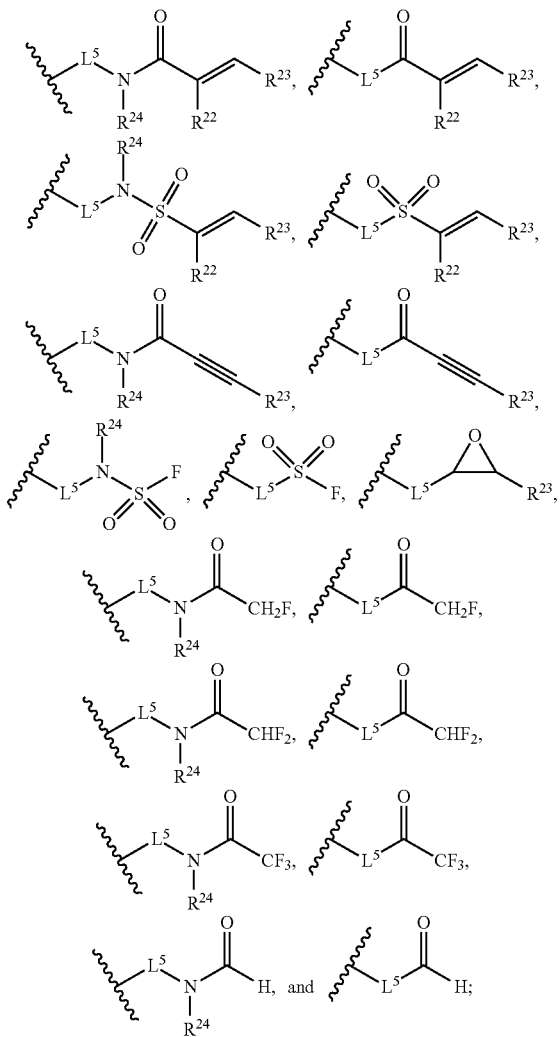

wherein:

$L^5$ is selected from a bond; and $C_{1-6}$ alkylene, $C_{1-6}$ heteroalkylene, $C_{2-6}$ alkenylene, and $C_{2-6}$ alkynylene, each of which is independently optionally substituted with one or more $R^{32}$;

$R^{22}$ and $R^{23}$ are each independently selected from:
hydrogen, halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, and $-CN$;

$C_{1-6}$ alkyl, $C_{2-6}$ alkenyl, and $C_{2-6}$ alkynyl, each of which is independently optionally substituted at each occurrence with one or more substituents selected from halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, $-CN$, $C_{3-10}$ carbocycle, and 3- to 10-membered heterocycle; and $C_{3-10}$ carbocycle and 3- to 10-membered heterocycle, wherein each $C_{3-10}$ carbocycle and 3- to 10-membered heterocycle of $R^{22}$ and $R^{23}$ is independently optionally substituted with one or more substituents selected from halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, $-CN$, $C_{1-6}$ alkyl, $C_{2-6}$ alkenyl, and $C_{2-6}$ alkynyl; or $R^{22}$ and $R^{23}$, together with the carbon atoms to which they are attached, form a carbocyclic ring;

$R^{24}$ is selected from:
hydrogen, $-C(O)R^{20}$, $-C(O)OR^{20}$, $-C(O)N(R^{20})_2$, $-OC(O)R^{20}$, $-S(O)_2R^{20}$, and $-S(O)_2N(R^{20})_2$;

$C_{1-6}$ alkyl, $C_{2-6}$ alkenyl, and $C_{2-6}$ alkynyl, each of which is independently optionally substituted at each occurrence with one or more substituents selected from halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, $-CN$, $C_{3-10}$ carbocycle, and 3- to 10-membered heterocycle; and $C_{3-10}$ carbocycle and 3- to 10-membered heterocycle, wherein each $C_{3-10}$ carbocycle and 3- to 10-membered heterocycle of $R^{24}$ is independently optionally substituted with one or more substituents selected from halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, $-CN$, $C_{1-6}$ alkyl, $C_{2-6}$ alkenyl, and $C_{2-6}$ alkynyl;

$R^{20}$ is independently selected at each occurrence from $R^{52}$; and $R^{32}$ is independently selected at each occurrence from $R^{50}$.

In some embodiments, $L^5$ is a bond. In some embodiments, $L^5$ is optionally substituted $C_{1-6}$ alkylene. In some embodiments, $L^5$ is selected from methylene, ethylene or propylene. In some embodiments, $L^5$ is substituted with one or more substituents selected from halogen, $-NO_2$, $=O$, $=S$, $-OR^{20}$, $-SR^{20}$, and $-N(R^{20})_2$.

In some embodiments, $R^{23}$ is selected from:
hydrogen;
$C_{1-6}$ alkyl, $C_{2-6}$ alkenyl, and $C_{2-6}$ alkynyl, each of which is independently optionally substituted at each occurrence with one or more substituents selected from halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, $-CN$, $C_{3-10}$ carbocycle and 3- to 10-membered heterocycle; and $C_{3-10}$ carbocycle, and 3- to 10-membered heterocycle, wherein each $C_{3-10}$ carbocycle and 3- to 10-membered heterocycle is independently optionally substituted with one or more substituents selected from halogen, $-OR^{20}$, $-SR^{20}$, $-N(R^{20})_2$, $-N(R^{20})C(O)R^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{1-6}$ alkyl, C$_{2-6}$ alkenyl, and C$_{2-6}$ alkynyl.

In some embodiments, R$^{23}$ is selected from:
hydrogen;
C$_{1-6}$ alkyl optionally substituted with one or more substituents selected from halogen, —OR$^{20}$, —SR$^{20}$, —N(R$^{20}$)$_2$, =O, =S, =N(R$^{20}$), and —CN; and
3- to 10-membered heterocycle optionally substituted with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{1-6}$ alkyl, C$_{2-6}$ alkenyl, and C$_{2-6}$ alkynyl.

In some embodiments, R$^{23}$ is selected from hydrogen and C$_{1-6}$ alkyl optionally substituted with one or more substituents selected from halogen, —OR$^{20}$, —SR$^{20}$, —N(R$^{20}$)$_2$, =O, =S, =N(R$^{20}$), and —CN.

In some embodiments, R$^{22}$ is selected from:
hydrogen and —CN;
C$_{1-6}$ alkyl, C$_{2-6}$ alkenyl, and C$_{2-6}$ alkynyl, each of which is independently optionally substituted at each occurrence with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{3-10}$ carbocycle and 3- to 10-membered heterocycle; and
C$_{3-10}$ carbocycle and 3- to 10-membered heterocycle, wherein each C$_{3-10}$ carbocycle and 3- to 10-membered heterocycle is independently optionally substituted with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{1-6}$ alkyl, C$_{2-6}$ alkenyl, and C$_{2-6}$ alkynyl.

In some embodiments, R$^{22}$ is selected from hydrogen, —CN; and C$_{1-6}$ alkyl optionally substituted with one or more substituents selected from halogen, —OR$^{20}$, —SR$^{20}$, and —N(R$^{20}$)$_2$.

In some embodiments, R$^{22}$ and R$^{23}$, together with the carbon atoms to which they are attached, form a 5-, 6-, or 7-membered carbocyclic ring.

In some embodiments, R$^{24}$ is selected from hydrogen and C$_{1-6}$ alkyl optionally substituted with one or more substituents selected from halogen, —OR$^{20}$, —SR$^{20}$, —N(R$^{20}$)$_2$, —NO$_2$, =O, and —CN.

In some embodiments, R$^{21}$ is selected from

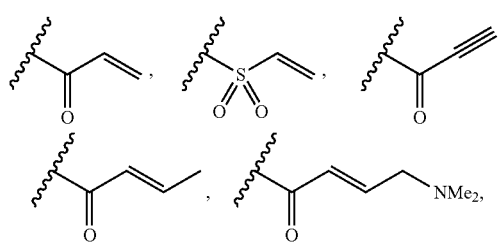

-continued

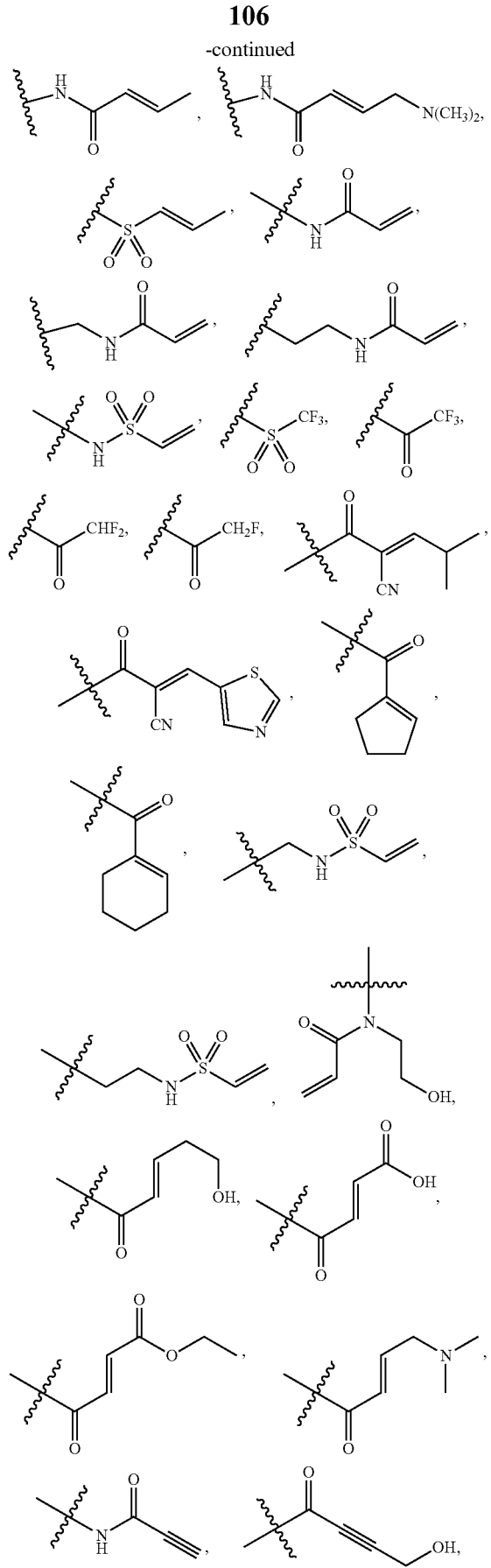

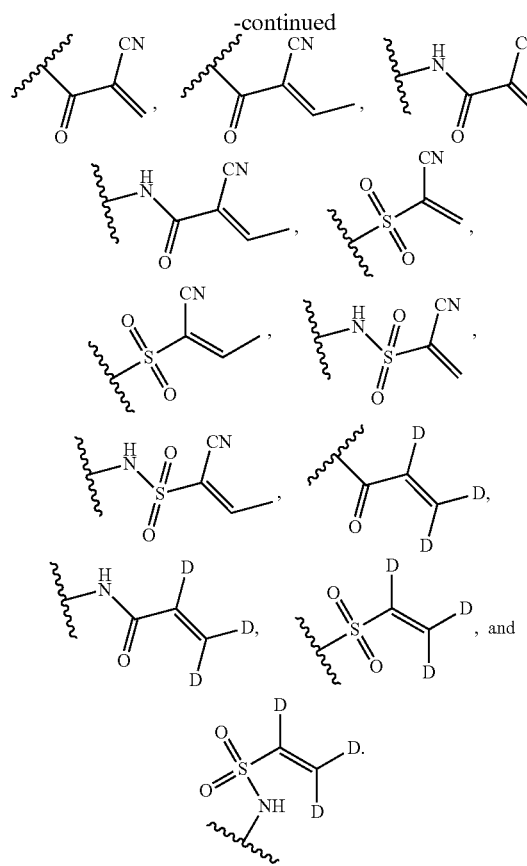

Any combination of the groups described above for the various variables is contemplated herein. Throughout the specification, groups and substituents thereof can be chosen to provide stable moieties and compounds.

The chemical entities described herein can be synthesized according to one or more illustrative schemes herein and/or techniques known in the art. Materials used herein are either commercially available or prepared by synthetic methods generally known in the art. These schemes are not limited to the compounds listed in the examples or by any particular substituents, which are employed for illustrative purposes. Although various steps are described and depicted in Scheme 1 and Examples 1-5, the steps in some cases may be performed in a different order than the order shown in Scheme 1 and Examples 1-5. Various modifications to these synthetic reaction schemes may be made and will be suggested to one skilled in the art having referred to the disclosure contained in this application. Numberings or R groups in each scheme do not necessarily correspond to that of the claims or other schemes or tables herein.

Unless specified to the contrary, the reactions described herein take place at atmospheric pressure, generally within a temperature range from −10° C. to 200° C. Further, except as otherwise specified, reaction times and conditions are intended to be approximate, e.g., taking place at about atmospheric pressure within a temperature range of about −10° C. to about 110° C. over a period of about 1 to about 24 hours; reactions left to run overnight average a period of about 16 hours.

In general, compounds of the disclosure may be prepared by the following reaction scheme:

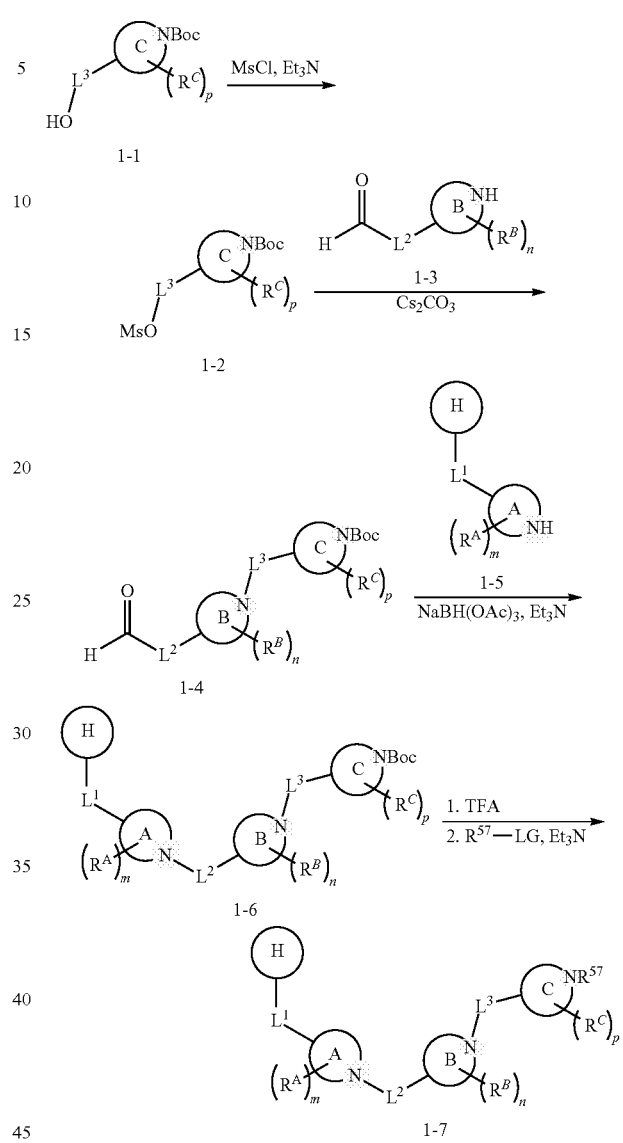

In some embodiments, a compound of Formula 1-7 may be prepared according to Scheme 1. For example, methanesulfonyl chloride can be added to a solution of alcohol 1-1 and triethylamine to afford mesylate 1-2. Addition of mesylate 1-2 to a solution of $Cs_2CO_3$ and amine 1-3 can provide a compound of Formula 1-4. Coupling of aldehyde 1-4 to amine 1-5 can proceed in the presence of a suitable reducing agent, such as $NaBH(OAc)_3$, to give a compound of Formula 1-6. Addition of TFA can reveal the free amine, which can optionally be reacted with $R^{57}$-LG, wherein LG is a suitable leaving group, to afford a compound of Formula 1-7.

In some embodiments, a compound of the present disclosure, for example, a compound of a formula given in Table 1 or 2, is synthesized according to one of the general routes outlined in Scheme 1, Examples 1-5, or by methods generally known in the art. In some embodiments, exemplary compounds may include, but are not limited to, a compound or salt thereof selected from Table 1.

TABLE 1
| No | Structure | MW (calc'd) | m/z (found) |
|----|-----------|-------------|-------------|
| 1 | 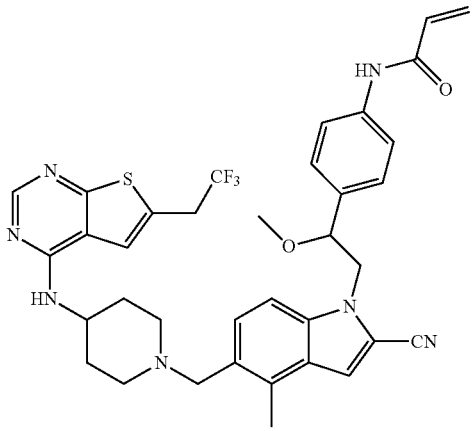 [SMILES: C=CC(=O)Nc1ccc(C(Cn2c(C#N)cc3c(C)c(CN4CCC(Nc5ncnc6sc(CC(F)(F)F)cc56)CC4)ccc32)OC)cc1] | 687.78 | 688.45 [M + H]+ |
| 2 | 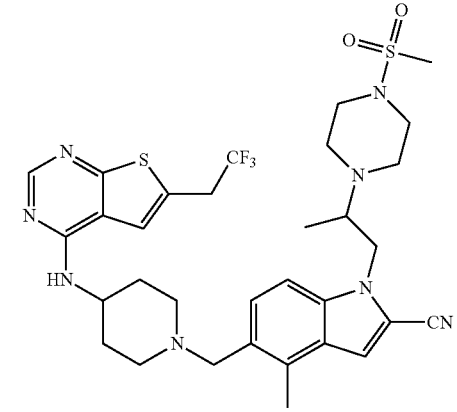 [SMILES: Cc1c(CN2CCC(Nc3ncnc4sc(CC(F)(F)F)cc34)CC2)ccc2c1cc(C#N)n2CC(C)N1CCN(S(C)(=O)=O)CC1] | 688.83 | 689.40 [M + H]+ |
| 3 | 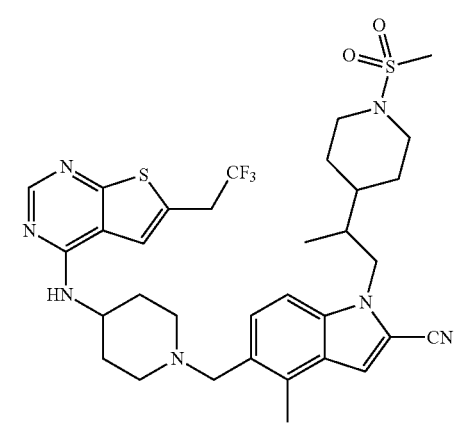 [SMILES: Cc1c(CN2CCC(Nc3ncnc4sc(CC(F)(F)F)cc34)CC2)ccc2c1cc(C#N)n2CC(C)C1CCN(S(C)(=O)=O)CC1] | 687.84 | 688.45 [M + H]+ |

TABLE 1-continued

| No | Structure | MW (calc'd) | m/z (found) |
|----|-----------|-------------|-------------|
| 4  | 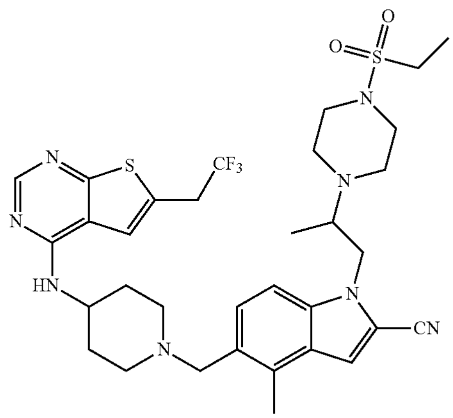 [SMILES: CCS(=O)(=O)N1CCN(C(C)Cn2c(C#N)cc3c(C)c(CN4CCC(Nc5ncnc6sc(CC(F)(F)F)cc56)CC4)ccc32)CC1]          | 702.86      | 703.55 [M + H]⁺ |
| 5  | 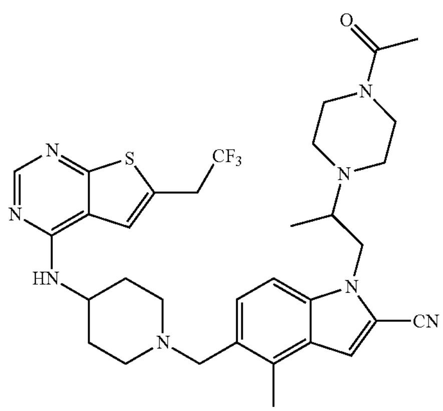 [SMILES: CC(=O)N1CCN(C(C)Cn2c(C#N)cc3c(C)c(CN4CCC(Nc5ncnc6sc(CC(F)(F)F)cc56)CC4)ccc32)CC1]          | 652.78      | 653.55 [M + H]⁺ |
| 6  | 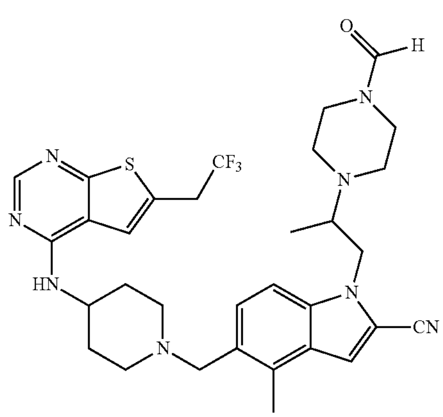          | 638.75      | 639.50 [M + H]⁺ |

TABLE 1-continued
| No | Structure | MW (calc'd) | m/z (found) |
|---|---|---|---|
| 7 | 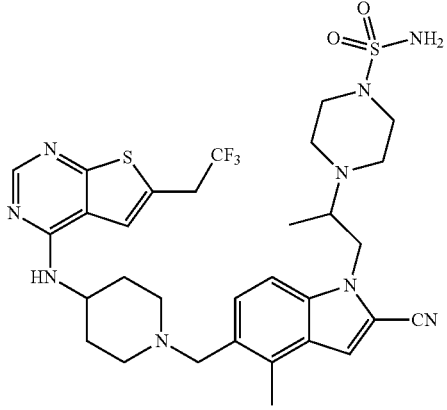 [SMILES: Cc1c(CN2CCC(Nc3ncnc4sc(CC(F)(F)F)cc34)CC2)ccc2c1cc(C#N)n2CC(C)N1CCN(S(N)(=O)=O)CC1] | 689.82 | 690.50 [M + H]+ |
| 8 | 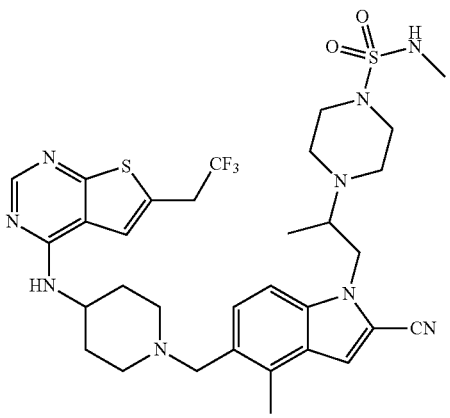 [SMILES: CNS(=O)(=O)N1CCN(C(C)Cn2c(C#N)cc3c(C)c(CN4CCC(Nc5ncnc6sc(CC(F)(F)F)cc56)CC4)ccc32)CC1] | 703.84 | 704.55 [M + H]+ |
| 9 | 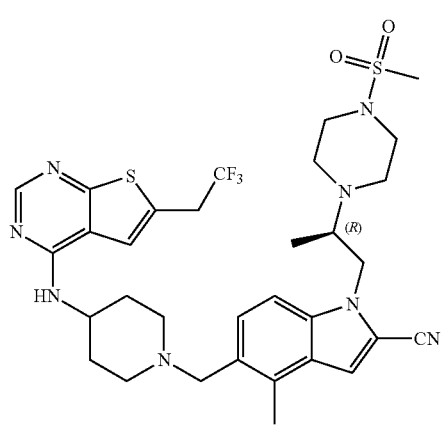 | 688.83 | 689.45 [M + H]+ |

TABLE 1-continued

| No | Structure | MW (calc'd) | m/z (found) |
|----|-----------|-------------|-------------|
| 10 | 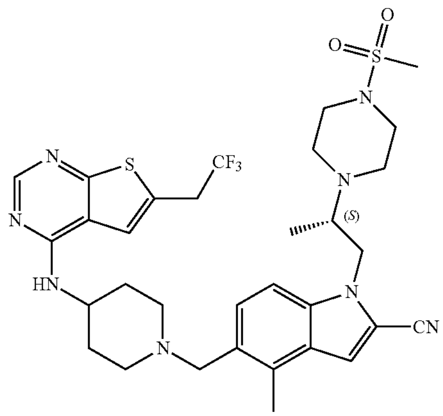 | 688.83 | 689.40 [M + H]⁺ |
| 11 | 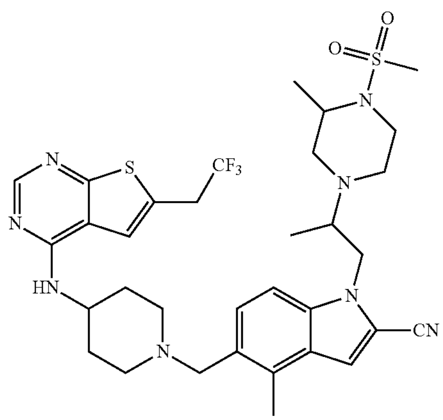 [SMILES: Cc1c(CN2CCC(Nc3ncnc4sc(CC(F)(F)F)cc34)CC2)ccc2c1cc(C#N)n2CC(C)N1CCN(S(C)(=O)=O)C(C)C1] | 702.86 | 703.55 [M + H]⁺ |
| 12 | 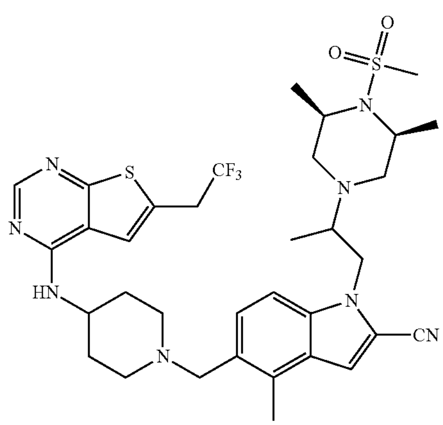 [SMILES: Cc1c(CN2CCC(Nc3ncnc4sc(CC(F)(F)F)cc34)CC2)ccc2c1cc(C#N)n2CC(C)N1C[C@@H](C)N(S(C)(=O)=O)[C@@H](C)C1] | 716.88 | 717.55 [M + H]⁺ |

TABLE 1-continued

| No | Structure | MW (calc'd) | m/z (found) |
|---|---|---|---|
| 13 | 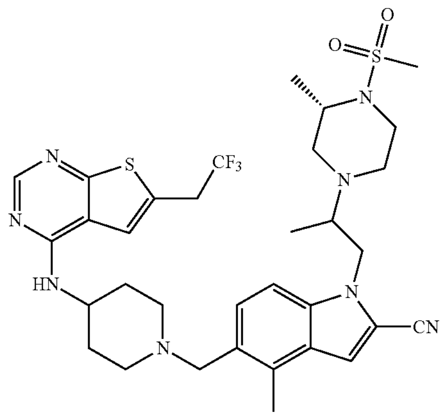 [SMILES: Cc1c(CN2CCC(Nc3ncnc4sc(CC(F)(F)F)cc34)CC2)ccc2c1cc(C#N)n2CC(C)N1CCN(S(C)(=O)=O)[C@@H](C)C1] | 702.86 | 703.55 [M + H]+ |
| 14 | 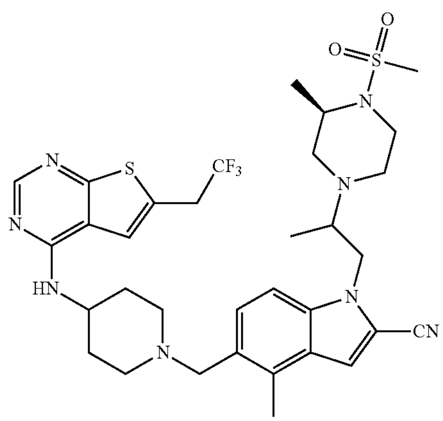 [SMILES: Cc1c(CN2CCC(Nc3ncnc4sc(CC(F)(F)F)cc34)CC2)ccc2c1cc(C#N)n2CC(C)N1CCN(S(C)(=O)=O)[C@H](C)C1] | 702.86 | 703.55 [M + H]+ |
| 15 | 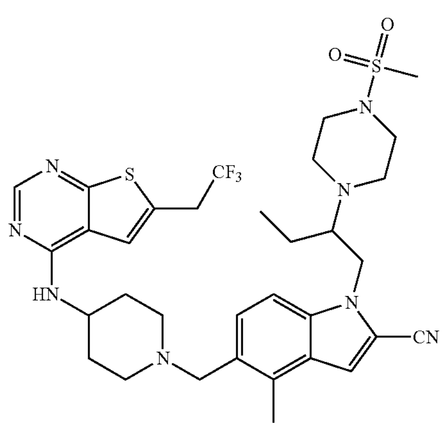 [SMILES: CCC(Cn1c(C#N)cc2c(C)c(CN3CCC(Nc4ncnc5sc(CC(F)(F)F)cc45)CC3)ccc21)N1CCN(S(C)(=O)=O)CC1] | 702.86 | 703.50 [M + H]+ |

TABLE 1-continued

| No | Structure | MW (calc'd) | m/z (found) |
|----|-----------|-------------|-------------|
| 16 | 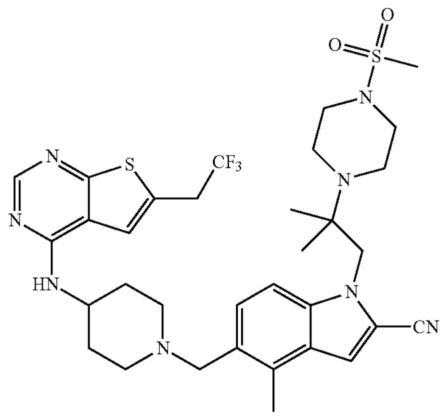 [SMILES: Cc1c(CN2CCC(Nc3ncnc4sc(CC(F)(F)F)cc34)CC2)ccc2c1cc(C#N)n2CC(C)(C)N1CCN(S(C)(=O)=O)CC1] | 702.86 | 703.60 [M + H]+ |
| 17 | 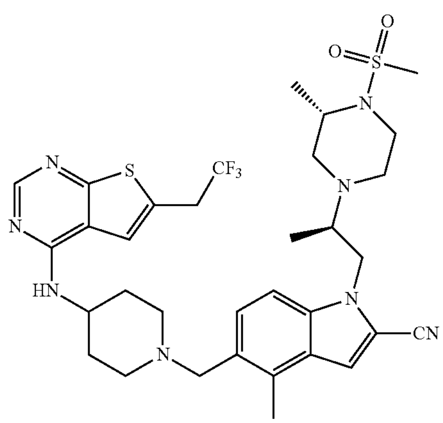 [SMILES: Cc1c(CN2CCC(Nc3ncnc4sc(CC(F)(F)F)cc34)CC2)ccc2c1cc(C#N)n2C[C@@H](C)N1CCN(S(C)(=O)=O)[C@@H](C)C1] | 702.86 | 703.35 [M + H]+ |
| 18 | 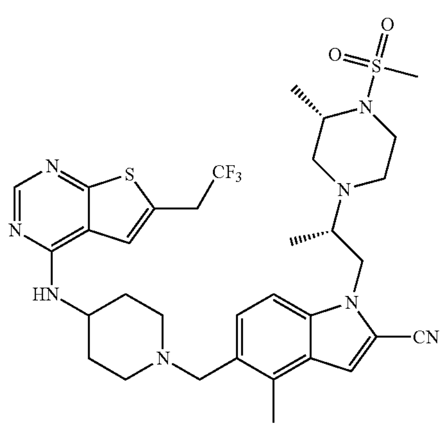 [SMILES: Cc1c(CN2CCC(Nc3ncnc4sc(CC(F)(F)F)cc34)CC2)ccc2c1cc(C#N)n2C[C@H](C)N1CCN(S(C)(=O)=O)[C@@H](C)C1] | 702.86 | 703.35 [M + H]+ |

TABLE 1-continued

| No | Structure | MW (calc'd) | m/z (found) |
|----|-----------|-------------|-------------|
| 19 | 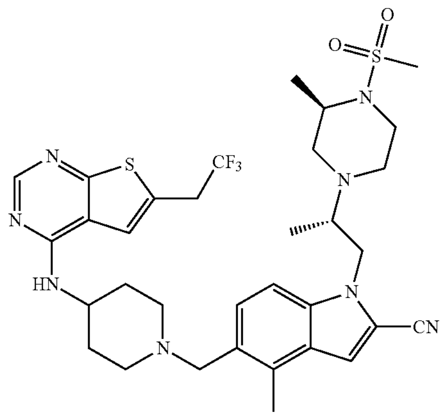 [SMILES: Cc1c(CN2CCC(Nc3ncnc4sc(CC(F)(F)F)cc34)CC2)ccc2c1cc(C#N)n2C[C@H](C)N1CCN(S(C)(=O)=O)[C@H](C)C1] | 702.86 | 703.35 [M + H]+ |
| 20 | 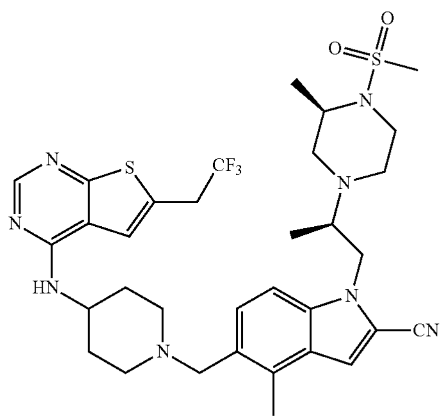 [SMILES: Cc1c(CN2CCC(Nc3ncnc4sc(CC(F)(F)F)cc34)CC2)ccc2c1cc(C#N)n2C[C@@H](C)N1CCN(S(C)(=O)=O)[C@H](C)C1] | 702.86 | 703.35 [M + H]+ |
| 21 | 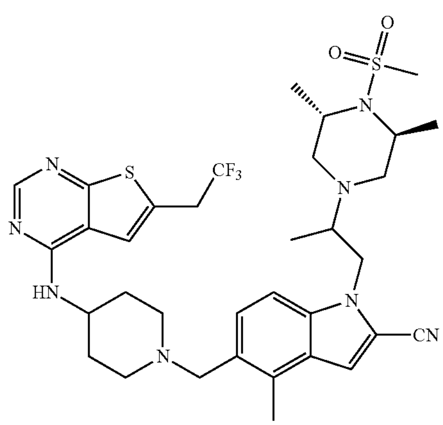 [SMILES: Cc1c(CN2CCC(Nc3ncnc4sc(CC(F)(F)F)cc34)CC2)ccc2c1cc(C#N)n2CC(C)N1C[C@H](C)N(S(C)(=O)=O)[C@@H](C)C1] | 716.88 | 717.35 [M + H]+ |

TABLE 1-continued

| No | Structure | MW (calc'd) | m/z (found) |
|---|---|---|---|
| 22 | 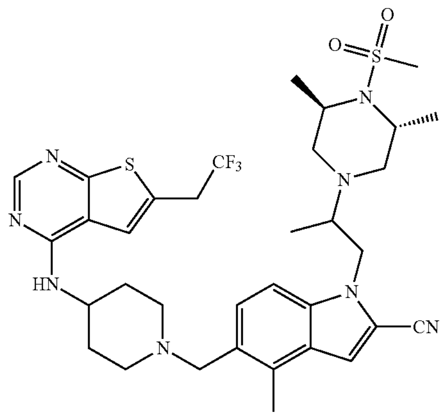 [SMILES: Cc1c(CN2CCC(Nc3ncnc4sc(CC(F)(F)F)cc34)CC2)ccc2c1cc(C#N)n2CC(C)N1C[C@@H](C)N(S(C)(=O)=O)[C@H](C)C1] | 716.88 | 717.35 [M + H]+ |
| 23 | 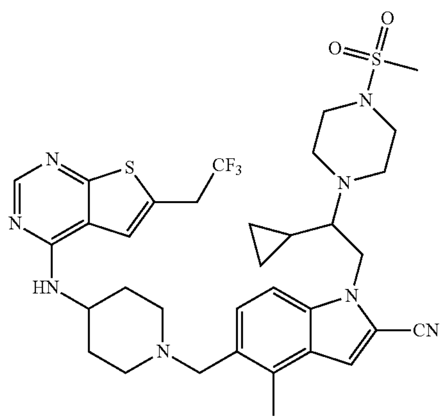 [SMILES: Cc1c(CN2CCC(Nc3ncnc4sc(CC(F)(F)F)cc34)CC2)ccc2c1cc(C#N)n2CC(C1CC1)N1CCN(S(C)(=O)=O)CC1] | 714.87 | 715.25 [M + H]+ |
| 24 | 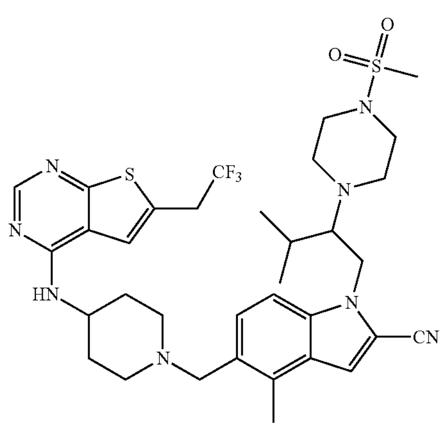 [SMILES: Cc1c(CN2CCC(Nc3ncnc4sc(CC(F)(F)F)cc34)CC2)ccc2c1cc(C#N)n2CC(C(C)C)N1CCN(S(C)(=O)=O)CC1] | 716.88 | 717.45 [M + H]+ |

TABLE 1-continued

| No | Structure | MW (calc'd) | m/z (found) |
|----|-----------|-------------|-------------|
| 25 | 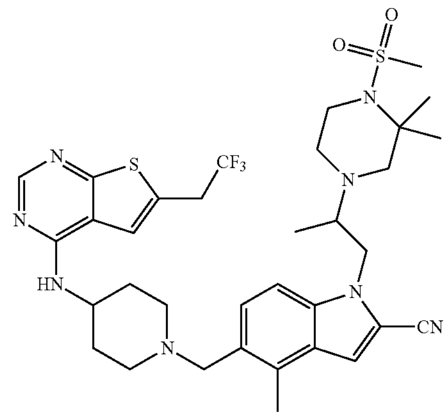 [SMILES: Cc1c(CN2CCC(Nc3ncnc4sc(CC(F)(F)F)cc34)CC2)ccc2c1cc(C#N)n2CC(C)N1CCN(S(C)(=O)=O)C(C)(C)C1] | 716.88 | 717.40 [M + H]+ |
| 26 | 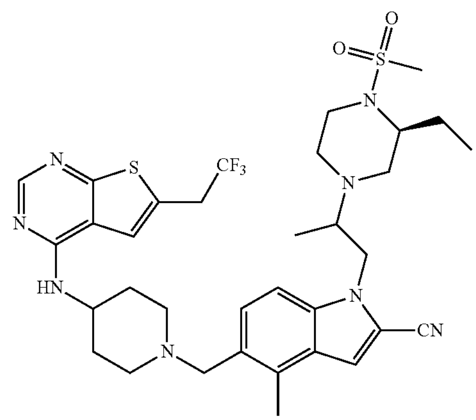 [SMILES: CC[C@H]1CN(C(C)Cn2c(C#N)cc3c(C)c(CN4CCC(Nc5ncnc6sc(CC(F)(F)F)cc56)CC4)ccc32)CCN1S(C)(=O)=O] | 716.88 | 717.40 [M + H]+ |
| 27 | 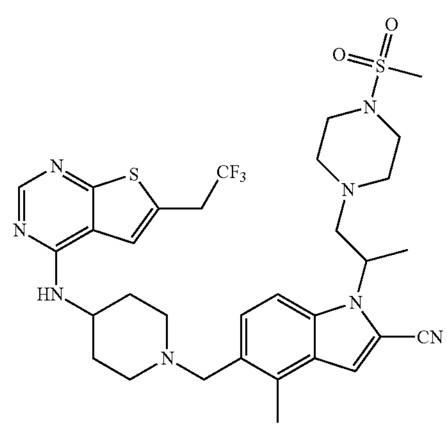 [SMILES: Cc1c(CN2CCC(Nc3ncnc4sc(CC(F)(F)F)cc34)CC2)ccc2c1cc(C#N)n2C(C)CN1CCN(S(C)(=O)=O)CC1] | | |

TABLE 1-continued

| No | Structure | MW (calc'd) | m/z (found) |
|----|-----------|-------------|-------------|
| 28 | 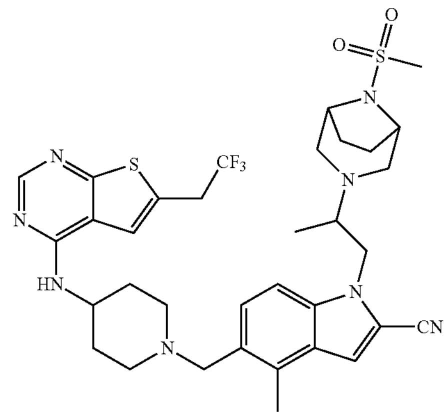 [SMILES: Cc1c(CN2CCC(Nc3ncnc4sc(CC(F)(F)F)cc34)CC2)ccc2c1cc(C#N)n2CC(C)N1CC2CCC(C1)N2S(C)(=O)=O] | 714.87 | 715.35 [M + H]+ |
| 29 | 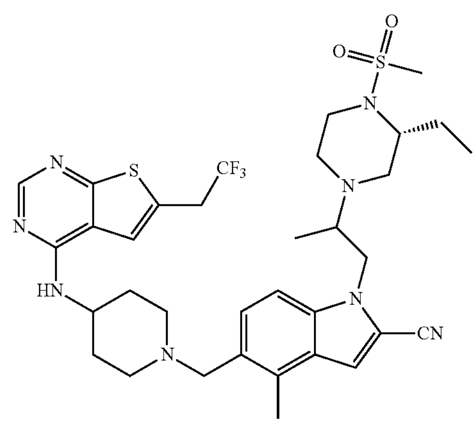 [SMILES: CC[C@@H]1CN(C(C)Cn2c(C#N)cc3c(C)c(CN4CCC(Nc5ncnc6sc(CC(F)(F)F)cc56)CC4)ccc32)CCN1S(C)(=O)=O] | 716.88 | 717.40 [M + H]+ |
| 30 | 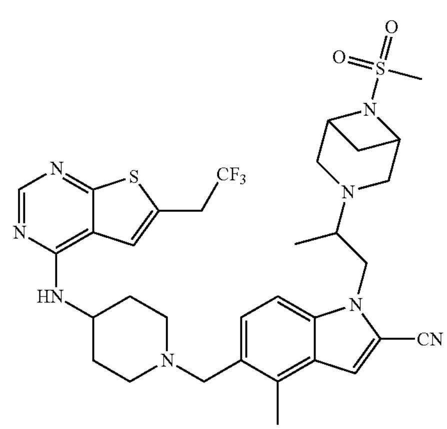 [SMILES: Cc1c(CN2CCC(Nc3ncnc4sc(CC(F)(F)F)cc34)CC2)ccc2c1cc(C#N)n2CC(C)N1CC2CC(C1)N2S(C)(=O)=O] | 700.84 | 701.35 [M + H]+ |

TABLE 1-continued

| No | Structure | MW (calc'd) | m/z (found) |
|----|-----------|-------------|-------------|
| 31 | 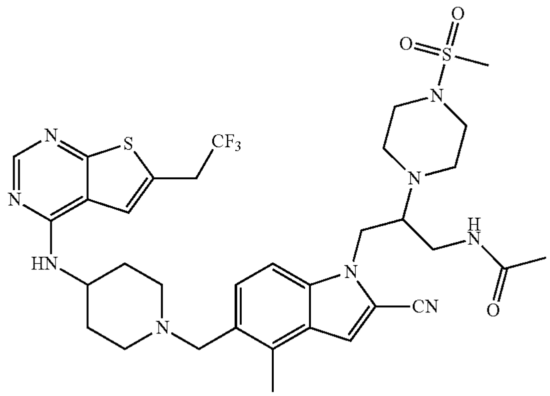 [SMILES: CC(=O)NCC(Cn1c(C#N)cc2c(C)c(CN3CCC(Nc4ncnc5sc(CC(F)(F)F)cc45)CC3)ccc21)N1CCN(S(C)(=O)=O)CC1] | | |
| 32 | 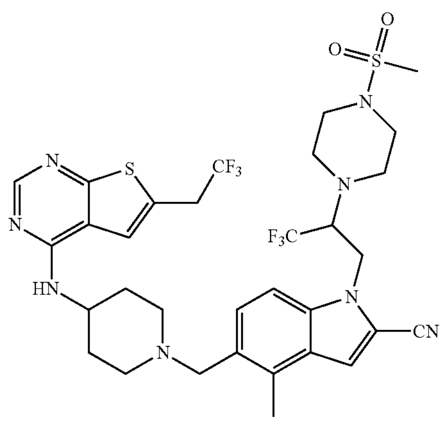 [SMILES: Cc1c(CN2CCC(Nc3ncnc4sc(CC(F)(F)F)cc34)CC2)ccc2c1cc(C#N)n2CC(N1CCN(S(C)(=O)=O)CC1)C(F)(F)F] | | |
| 33 | 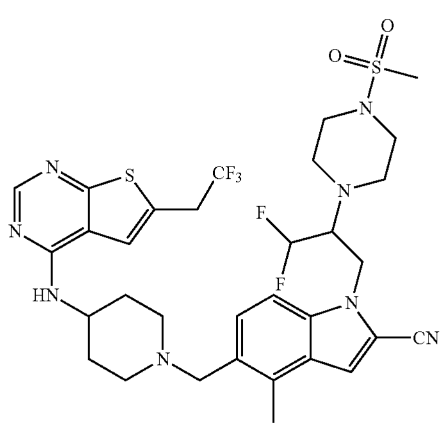 [SMILES: Cc1c(CN2CCC(Nc3ncnc4sc(CC(F)(F)F)cc34)CC2)ccc2c1cc(C#N)n2CC(C(F)F)N1CCN(S(C)(=O)=O)CC1] | | |

TABLE 1-continued
| No | Structure | MW (calc'd) | m/z (found) |
|---|---|---|---|
| 34 | 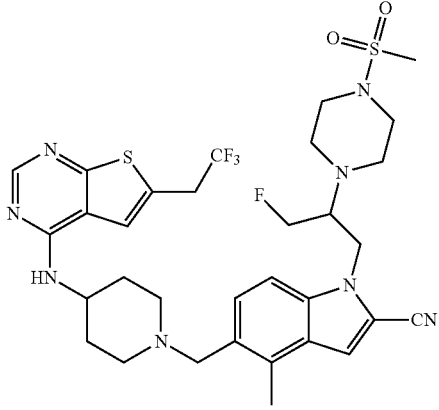 [SMILES: Cc1c(CN2CCC(Nc3ncnc4sc(CC(F)(F)F)cc34)CC2)ccc2c1cc(C#N)n2CC(CF)N1CCN(S(C)(=O)=O)CC1] | | |
| 35 | 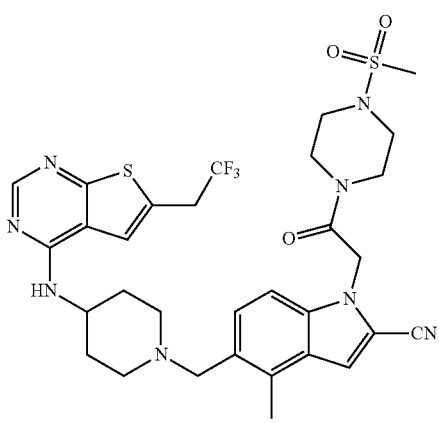 [SMILES: Cc1c(CN2CCC(Nc3ncnc4sc(CC(F)(F)F)cc34)CC2)ccc2c1cc(C#N)n2CC(=O)N1CCN(S(C)(=O)=O)CC1] | 688.79 | 689.15 [M + H]+ |
| 36 | 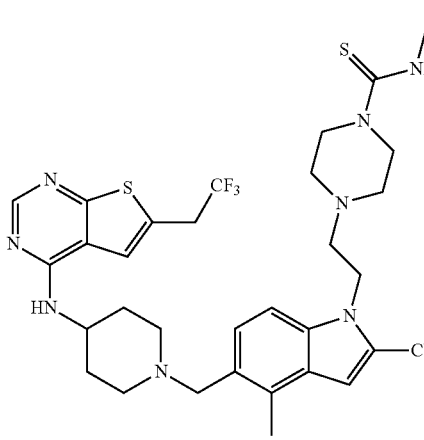 | | |
| 37 | 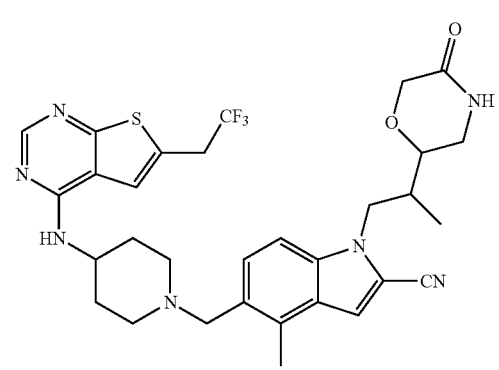 [SMILES: Cc1c(CN2CCC(Nc3ncnc4sc(CC(F)(F)F)cc34)CC2)ccc2c1cc(C#N)n2CC(C)C1CNC(=O)CO1] | | |

TABLE 1-continued

| No | Structure | MW (calc'd) | m/z (found) |
|---|---|---|---|
| 38 | 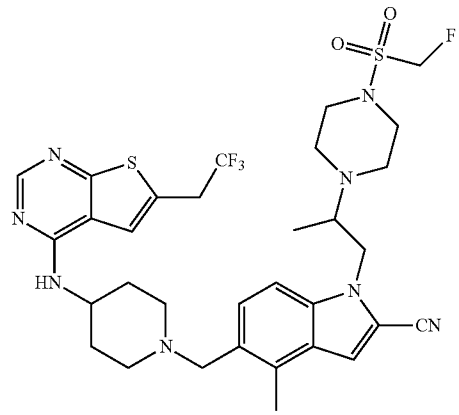 [SMILES: Cc1c(CN2CCC(Nc3ncnc4sc(CC(F)(F)F)cc34)CC2)ccc2c1cc(C#N)n2CC(C)N1CCN(S(=O)(=O)CF)CC1] | | |
| 39 | 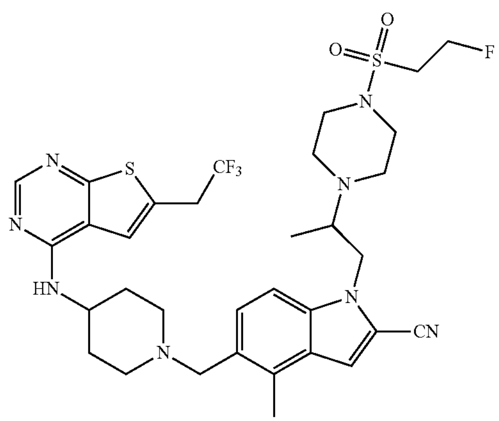 [SMILES: Cc1c(CN2CCC(Nc3ncnc4sc(CC(F)(F)F)cc34)CC2)ccc2c1cc(C#N)n2CC(C)N1CCN(S(=O)(=O)CCF)CC1] | | |
| 40 | 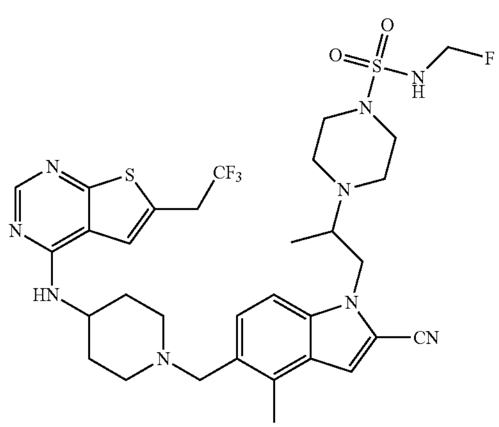 [SMILES: Cc1c(CN2CCC(Nc3ncnc4sc(CC(F)(F)F)cc34)CC2)ccc2c1cc(C#N)n2CC(C)N1CCN(S(=O)(=O)NCF)CC1] | | |

TABLE 1-continued
| No | Structure | MW (calc'd) | m/z (found) |
|----|-----------|-------------|-------------|
| 41 | 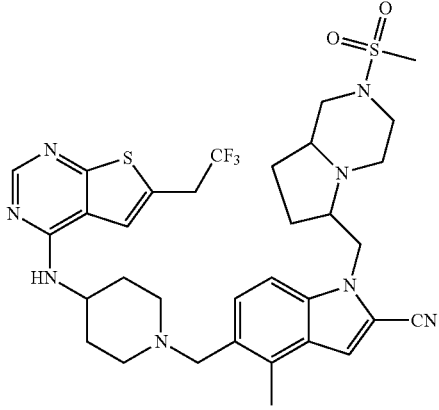 [SMILES: Cc1c(CN2CCC(Nc3ncnc4sc(CC(F)(F)F)cc34)CC2)ccc2c1cc(C#N)n2CC1CCC2CN(S(C)(=O)=O)CCN21] | | |
| 42 | 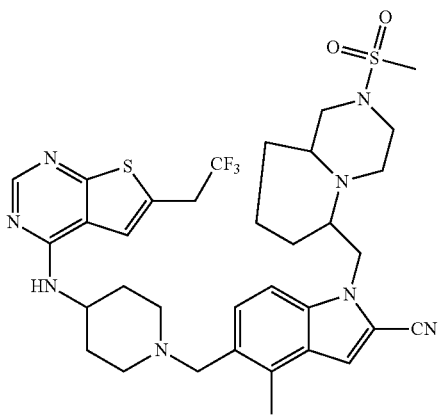 [SMILES: Cc1c(CN2CCC(Nc3ncnc4sc(CC(F)(F)F)cc34)CC2)ccc2c1cc(C#N)n2CC1CCCC2CN(S(C)(=O)=O)CCN21] | | |
| 43 | 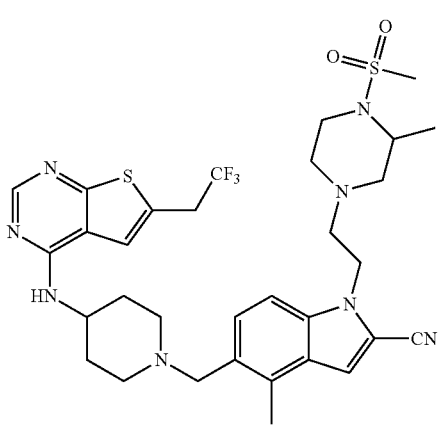 [SMILES: Cc1c(CN2CCC(Nc3ncnc4sc(CC(F)(F)F)cc34)CC2)ccc2c1cc(C#N)n2CCN1CCN(S(C)(=O)=O)C(C)C1] | 688.83 | 689.45 [M + H]+ |

TABLE 1-continued

| No | Structure | MW (calc'd) | m/z (found) |
|----|-----------|-------------|-------------|
| 44 | 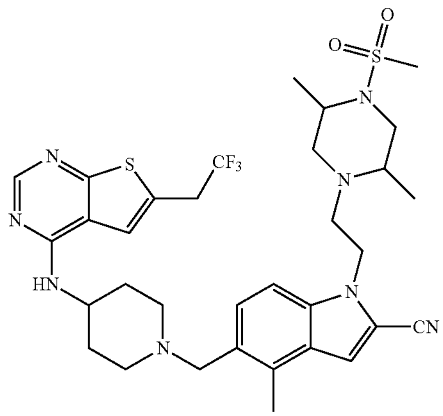 [SMILES: Cc1c(CN2CCC(Nc3ncnc4sc(CC(F)(F)F)cc34)CC2)ccc2c1cc(C#N)n2CCN1CC(C)N(S(C)(=O)=O)CC1C] | 702.86 | 703.45 [M + H]+ |
| 45 | 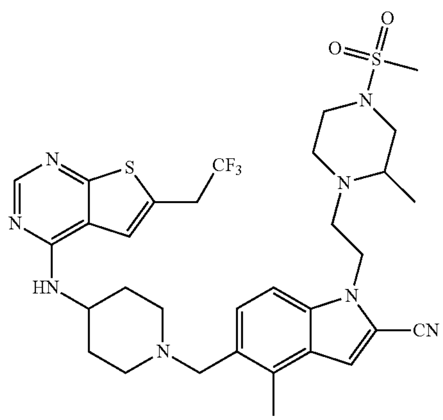 [SMILES: Cc1c(CN2CCC(Nc3ncnc4sc(CC(F)(F)F)cc34)CC2)ccc2c1cc(C#N)n2CCN1CCN(S(C)(=O)=O)CC1C] | 688.83 | 689.40 [M + H]+ |
| 46 | 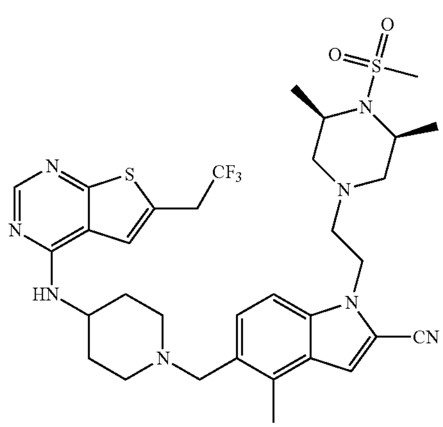 [SMILES: Cc1c(CN2CCC(Nc3ncnc4sc(CC(F)(F)F)cc34)CC2)ccc2c1cc(C#N)n2CCN1C[C@@H](C)N(S(C)(=O)=O)[C@@H](C)C1] | 702.86 | 703.45 [M + H]+ |

TABLE 1-continued

| No | Structure | MW (calc'd) | m/z (found) |
|---|---|---|---|
| 47 | 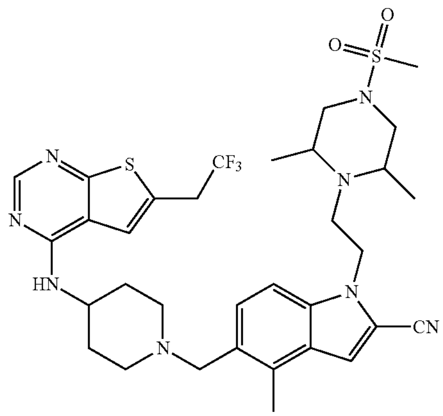 [SMILES: Cc1c(CN2CCC(Nc3ncnc4sc(CC(F)(F)F)cc34)CC2)ccc2c1cc(C#N)n2CCN1C(C)CN(S(C)(=O)=O)CC1C] | 702.86 | 703.50 [M + H]⁺ |
| 48 | 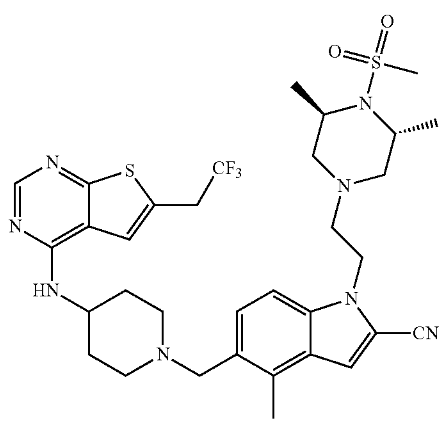 [SMILES: Cc1c(CN2CCC(Nc3ncnc4sc(CC(F)(F)F)cc34)CC2)ccc2c1cc(C#N)n2CCN1C[C@@H](C)N(S(C)(=O)=O)[C@H](C)C1] | 702.86 | 703.55 [M + H]⁺ |
| 49 | 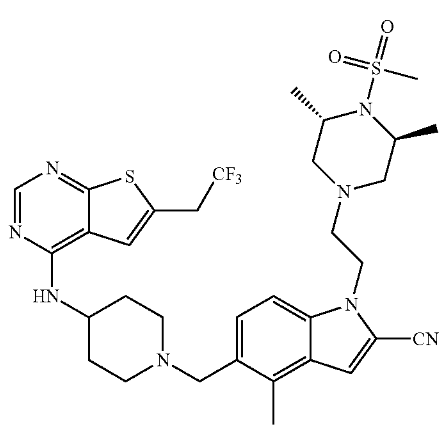 [SMILES: Cc1c(CN2CCC(Nc3ncnc4sc(CC(F)(F)F)cc34)CC2)ccc2c1cc(C#N)n2CCN1C[C@H](C)N(S(C)(=O)=O)[C@@H](C)C1] | 702.86 | 703.55 [M + H]⁺ |

TABLE 1-continued

| No | Structure | MW (calc'd) | m/z (found) |
|---|---|---|---|
| 50 | 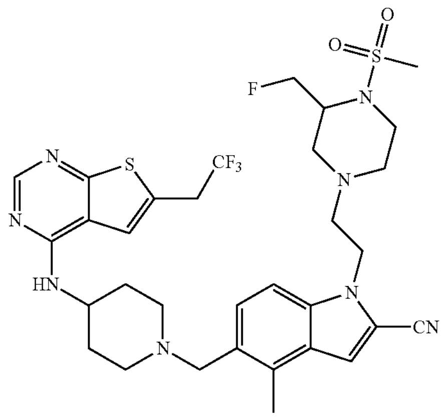 [SMILES: Cc1c(CN2CCC(Nc3ncnc4sc(CC(F)(F)F)cc34)CC2)ccc2c1cc(C#N)n2CCN1CCN(S(C)(=O)=O)C(CF)C1] | | |
| 51 | 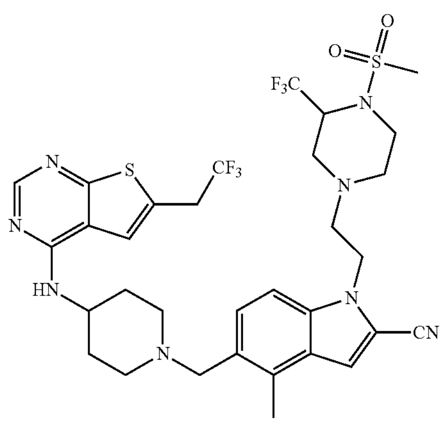 [SMILES: Cc1c(CN2CCC(Nc3ncnc4sc(CC(F)(F)F)cc34)CC2)ccc2c1cc(C#N)n2CCN1CCN(S(C)(=O)=O)C(C(F)(F)F)C1] | | |
| 52 | 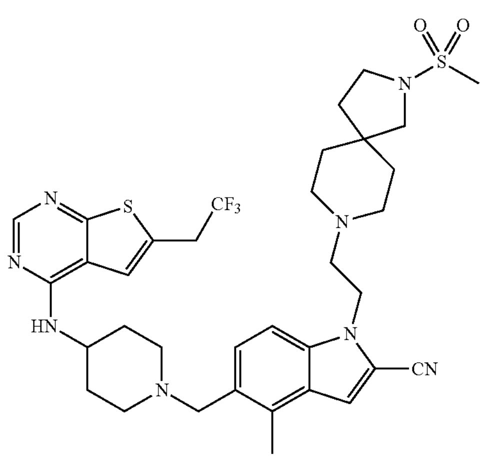 [SMILES: Cc1c(CN2CCC(Nc3ncnc4sc(CC(F)(F)F)cc34)CC2)ccc2c1cc(C#N)n2CCN1CCC2(CC1)CCN(S(C)(=O)=O)C2] | 728.89 | 729.55 [M + H]+ |

TABLE 1-continued

| No | Structure | MW (calc'd) | m/z (found) |
|---|---|---|---|
| 53 | 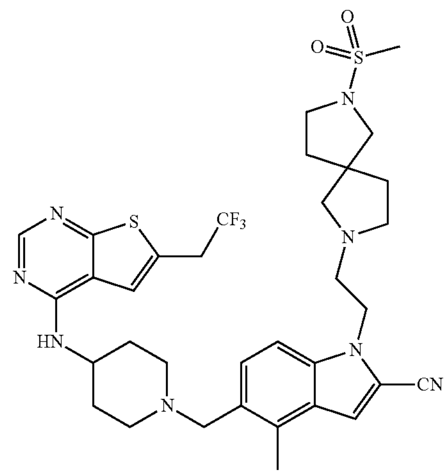 [SMILES: Cc1c(CN2CCC(Nc3ncnc4sc(CC(F)(F)F)cc34)CC2)ccc2c1cc(C#N)n2CCN1CCC2(CCN(S(C)(=O)=O)C2)C1] | 714.87 | 715.30 [M + H]+ |
| 54 | 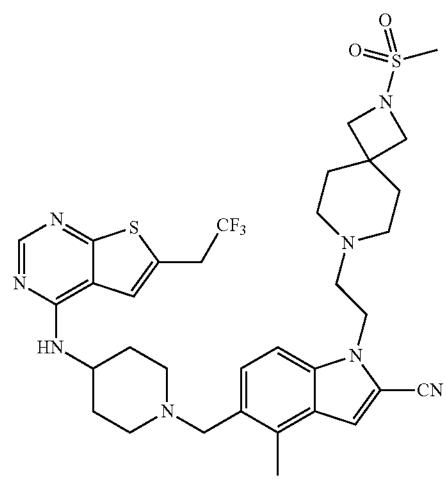 [SMILES: Cc1c(CN2CCC(Nc3ncnc4sc(CC(F)(F)F)cc34)CC2)ccc2c1cc(C#N)n2CCN1CCC2(CC1)CN(S(C)(=O)=O)C2] | 714.87 | 715.30 [M + H]+ |
| 55 | 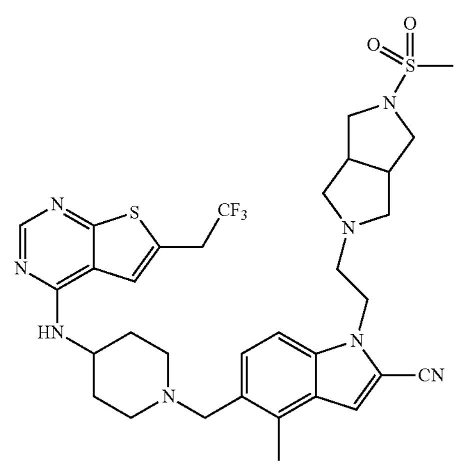 [SMILES: Cc1c(CN2CCC(Nc3ncnc4sc(CC(F)(F)F)cc34)CC2)ccc2c1cc(C#N)n2CCN1CC2CN(S(C)(=O)=O)CC2C1] | 700.84 | 701.30 [M + H]+ |

TABLE 1-continued

| No | Structure | MW (calc'd) | m/z (found) |
|---|---|---|---|
| 56 | 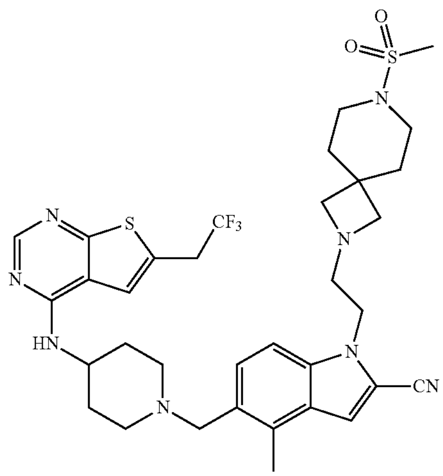 [SMILES: Cc1c(CN2CCC(Nc3ncnc4sc(CC(F)(F)F)cc34)CC2)ccc2c1cc(C#N)n2CCN1CC2(CCN(S(C)(=O)=O)CC2)C1] | 714.87 | 715.35 [M + H]+ |
| 57 | 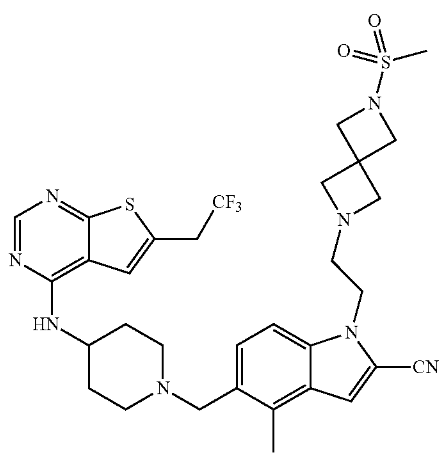 [SMILES: Cc1c(CN2CCC(Nc3ncnc4sc(CC(F)(F)F)cc34)CC2)ccc2c1cc(C#N)n2CCN1CC2(C1)CN(S(C)(=O)=O)C2] | 686.81 | 687.25 [M + H]+ |
| 58 | 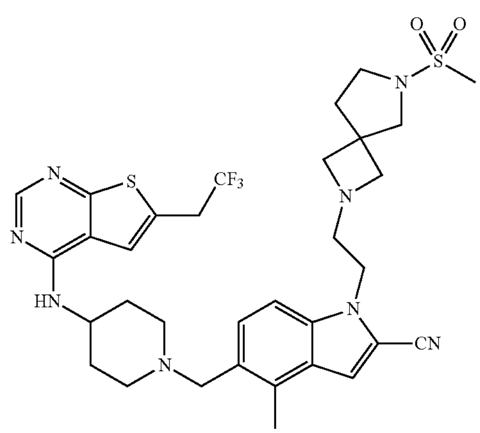 [SMILES: Cc1c(CN2CCC(Nc3ncnc4sc(CC(F)(F)F)cc34)CC2)ccc2c1cc(C#N)n2CCN1CC2(CCN(S(C)(=O)=O)C2)C1] | 700.84 | 701.35 [M + H]+ |

TABLE 1-continued

| No | Structure | MW (calc'd) | m/z (found) |
|---|---|---|---|
| 59 | 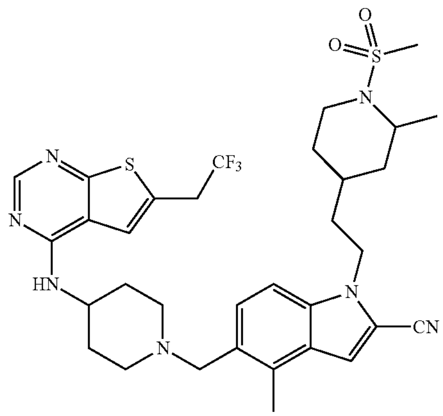 [SMILES: Cc1c(CN2CCC(Nc3ncnc4sc(CC(F)(F)F)cc34)CC2)ccc2c1cc(C#N)n2CCC1CCN(S(C)(=O)=O)C(C)C1] | 687.84 | 688.45 [M + H]+ |
| 60 | 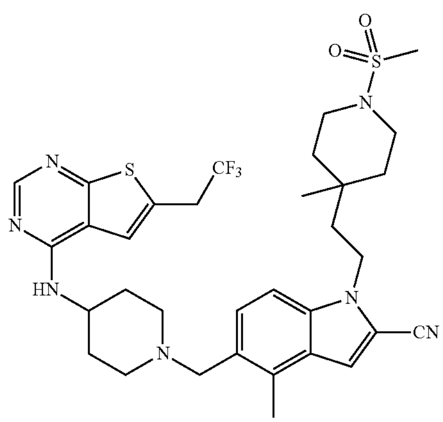 [SMILES: Cc1c(CN2CCC(Nc3ncnc4sc(CC(F)(F)F)cc34)CC2)ccc2c1cc(C#N)n2CCC1(C)CCN(S(C)(=O)=O)CC1] | 687.84 | 688.50 [M + H]+ |
| 61 | 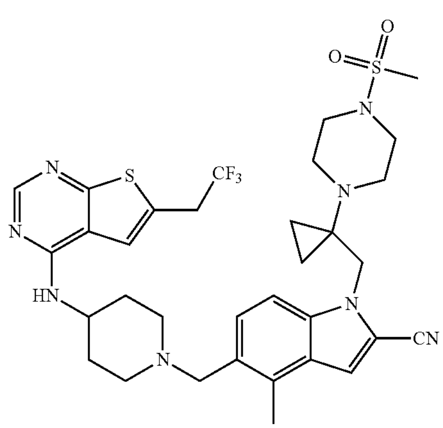 [SMILES: Cc1c(CN2CCC(Nc3ncnc4sc(CC(F)(F)F)cc34)CC2)ccc2c1cc(C#N)n2CC1(N2CCN(S(C)(=O)=O)CC2)CC1] | 700.84 | 701.30 [M + H]+ |

TABLE 1-continued
| No | Structure | MW (calc'd) | m/z (found) |
|---|---|---|---|
| 62 | 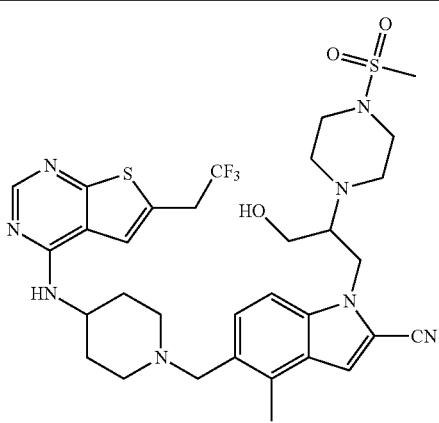 | | |
| 63 | 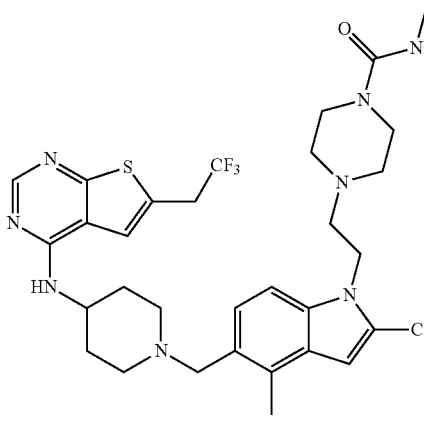 | | |
| 64 | 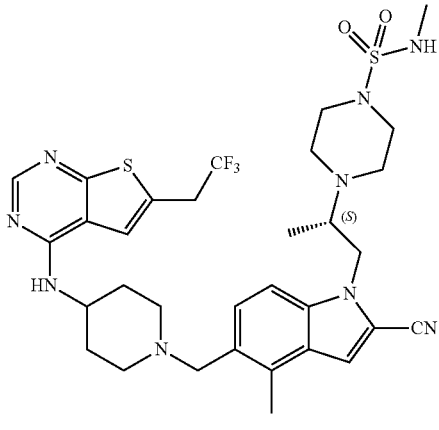 | 703.84 | 704.25 [M + H]+ |

TABLE 1-continued

| No | Structure | MW (calc'd) | m/z (found) |
|----|-----------|-------------|-------------|
| 65 | 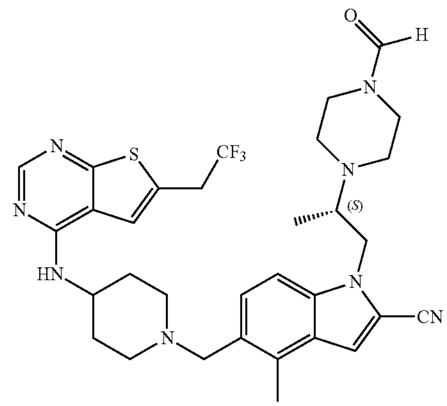 | 638.75 | 639.20 [M + H]+ |
| 66 | 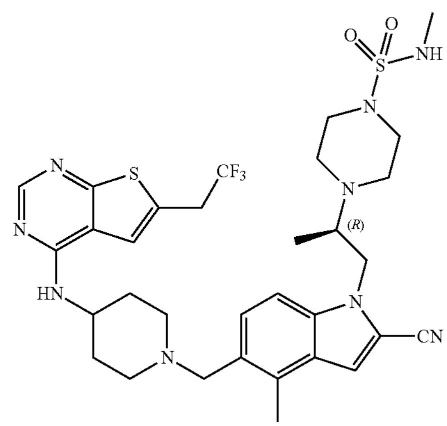 | 703.84 | 704.25 [M + H]+ |
| 67 | 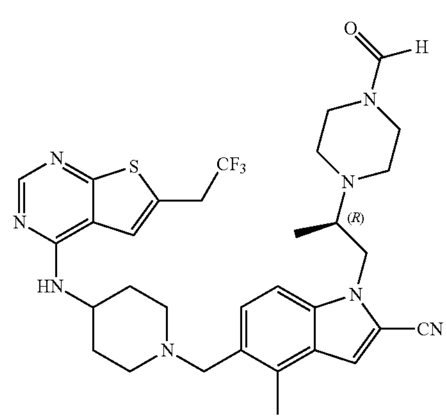 | 638.75 | 639.25 [M + H]+ |

TABLE 1-continued

| No | Structure | MW (calc'd) | m/z (found) |
|----|-----------|-------------|-------------|
| 68 | 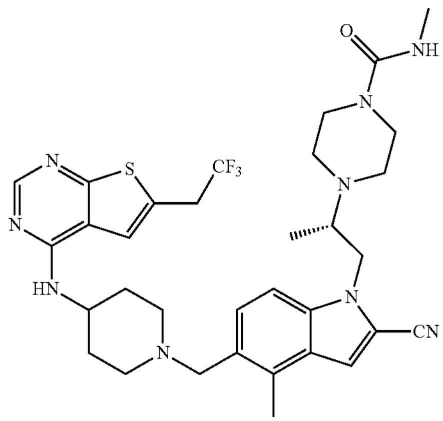 | 667.79 | 668.35 [M + H]+ |
| 69 | 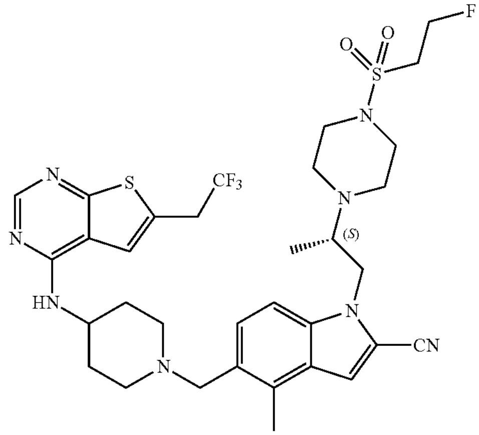 | 720.27 | 721.3 |
| 70 | 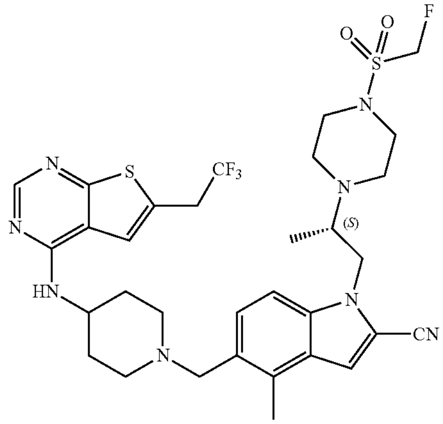 | 706.25 | 707.3 |

TABLE 1-continued

| No | Structure | MW (calc'd) | m/z (found) |
|---|---|---|---|
| 71 | 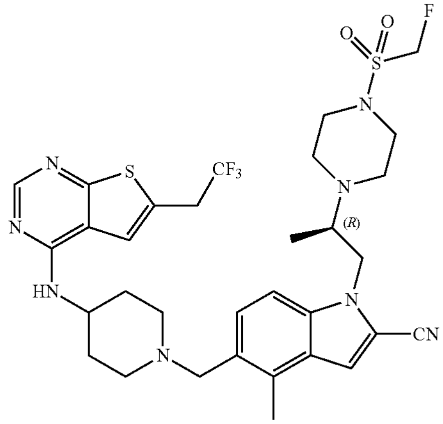 | 706.25 | 707.2 |
| 72 | 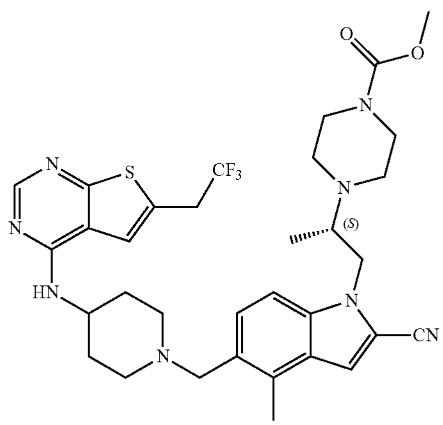 | 668.29 | 689.2 |
| 73 | 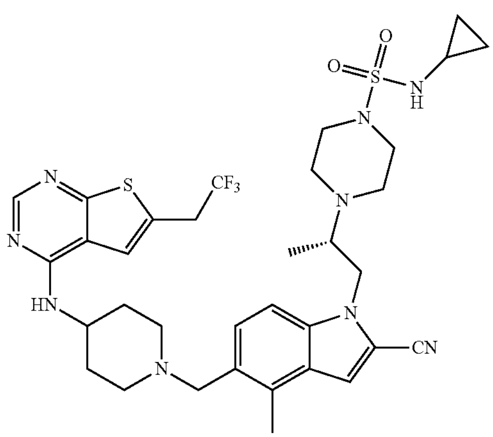 [SMILES: Cc1c(CN2CCC(Nc3ncnc4sc(CC(F)(F)F)cc34)CC2)ccc2c1cc(C#N)n2C[C@H](C)N1CCN(S(=O)(=O)NC2CC2)CC1] | 729.88 | 730.30 [M + H]+ |

TABLE 1-continued
| No | Structure | MW (calc'd) | m/z (found) |
|---|---|---|---|
| 74 | 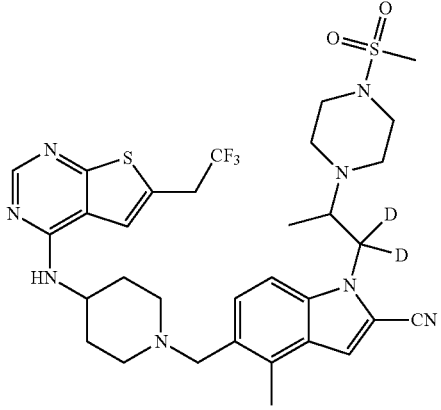 [SMILES: [2H]C([2H])(C(C)N1CCN(S(C)(=O)=O)CC1)n1c(C#N)cc2c(C)c(CN3CCC(Nc4ncnc5sc(CC(F)(F)F)cc45)CC3)ccc21] | | |
| 75 | 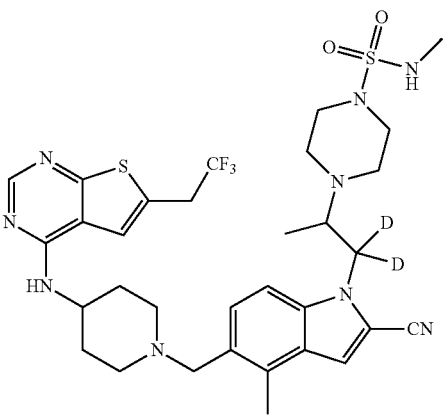 [SMILES: [2H]C([2H])(C(C)N1CCN(S(=O)(=O)NC)CC1)n1c(C#N)cc2c(C)c(CN3CCC(Nc4ncnc5sc(CC(F)(F)F)cc45)CC3)ccc21] | | |
| 76 | 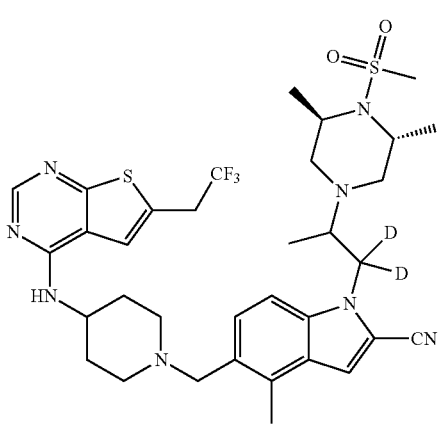 [SMILES: [2H]C([2H])(C(C)N1C[C@@H](C)N(S(C)(=O)=O)[C@H](C)C1)n1c(C#N)cc2c(C)c(CN3CCC(Nc4ncnc5sc(CC(F)(F)F)cc45)CC3)ccc21] | | |

TABLE 1-continued

| No | Structure | MW (calc'd) | m/z (found) |
|----|-----------|-------------|-------------|
| 77 | 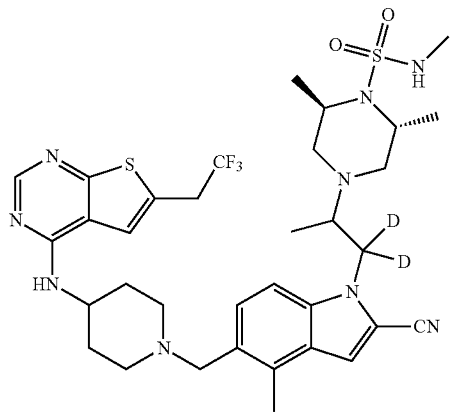 [SMILES: [2H]C([2H])(C(C)N1C[C@@H](C)N(S(=O)(=O)NC)[C@H](C)C1)n1c(C#N)cc2c(C)c(CN3CCC(Nc4ncnc5sc(CC(F)(F)F)cc45)CC3)ccc21] | | |
| 78 | 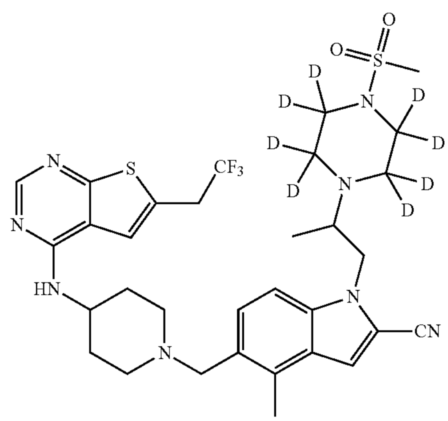 [SMILES: [2H]C1([2H])N(C(C)Cn2c(C#N)cc3c(C)c(CN4CCC(Nc5ncnc6sc(CC(F)(F)F)cc56)CC4)ccc32)C([2H])([2H])C([2H])([2H])N(S(C)(=O)=O)C1([2H])[2H]] | | |
| 79 | 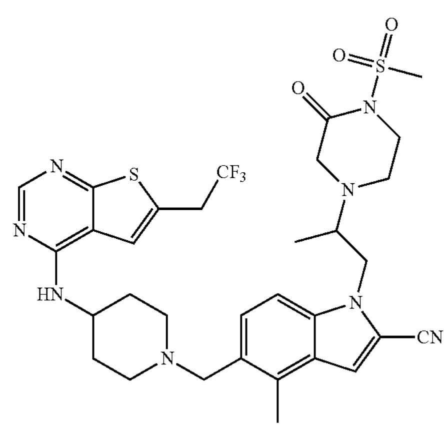 [SMILES: Cc1c(CN2CCC(Nc3ncnc4sc(CC(F)(F)F)cc34)CC2)ccc2c1cc(C#N)n2CC(C)N1CCN(S(C)(=O)=O)C(=O)C1] | | |

TABLE 1-continued

| No | Structure | MW (calc'd) | m/z (found) |
|----|-----------|-------------|-------------|
| 80 | 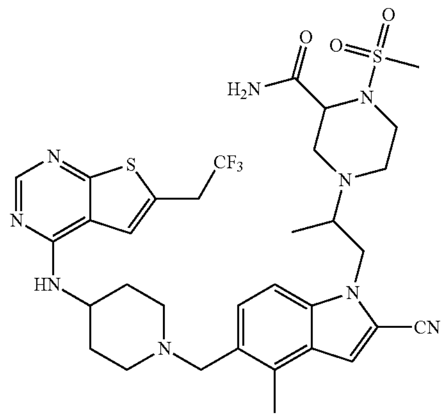 [SMILES: Cc1c(CN2CCC(Nc3ncnc4sc(CC(F)(F)F)cc34)CC2)ccc2c1cc(C#N)n2CC(C)N1CCN(S(C)(=O)=O)C(C(N)=O)C1] | | |
| 81 | 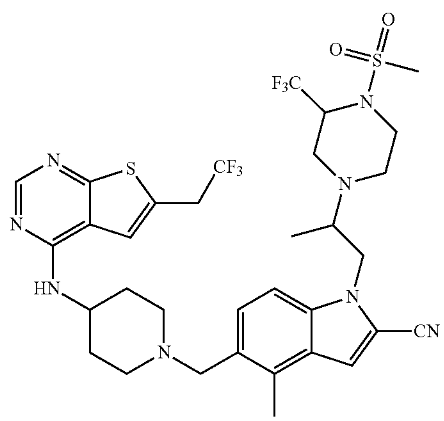 [SMILES: Cc1c(CN2CCC(Nc3ncnc4sc(CC(F)(F)F)cc34)CC2)ccc2c1cc(C#N)n2CC(C)N1CCN(S(C)(=O)=O)C(C(F)(F)F)C1] | | |
| 82 | 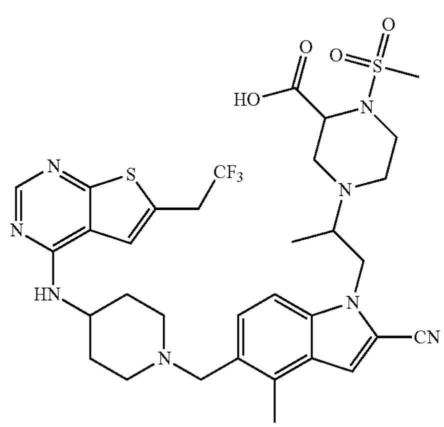 [SMILES: Cc1c(CN2CCC(Nc3ncnc4sc(CC(F)(F)F)cc34)CC2)ccc2c1cc(C#N)n2CC(C)N1CCN(S(C)(=O)=O)C(C(=O)O)C1] | | |

TABLE 1-continued
| No | Structure | MW (calc'd) | m/z (found) |
|---|---|---|---|
| 83 | 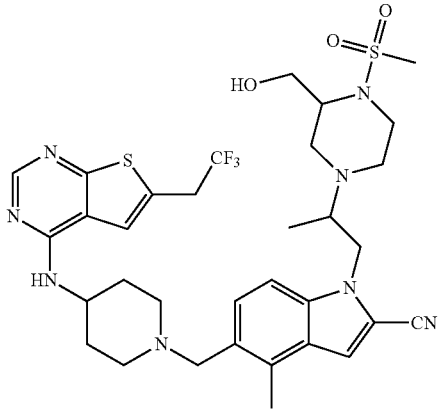 [SMILES: Cc1c(CN2CCC(Nc3ncnc4sc(CC(F)(F)F)cc34)CC2)ccc2c1cc(C#N)n2CC(C)N1CCN(S(C)(=O)=O)C(CO)C1] | | |
| 84 | 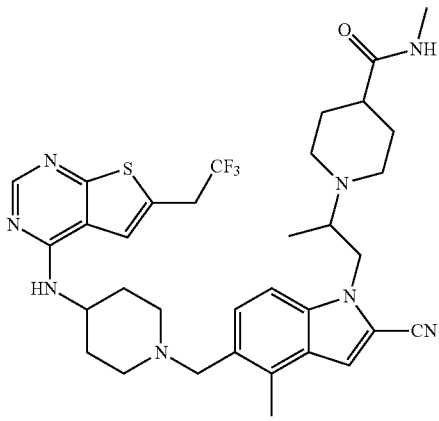 | | |
| 85 | 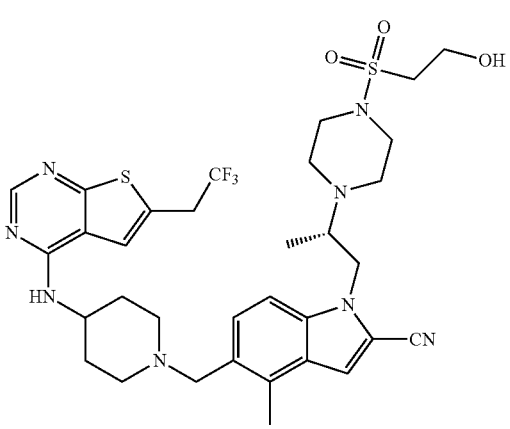 [SMILES: Cc1c(CN2CCC(Nc3ncnc4sc(CC(F)(F)F)cc34)CC2)ccc2c1cc(C#N)n2C[C@H](C)N1CCN(S(=O)(=O)CCO)CC1] | | |

TABLE 1-continued
| No | Structure | MW (calc'd) | m/z (found) |
|---|---|---|---|
| 86 | 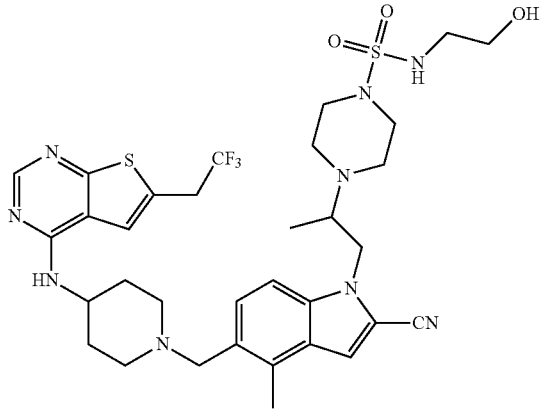 [SMILES: Cc1c(CN2CCC(Nc3ncnc4sc(CC(F)(F)F)cc34)CC2)ccc2c1cc(C#N)n2CC(C)N1CCN(S(=O)(=O)NCCO)CC1] | | |
| 87 | 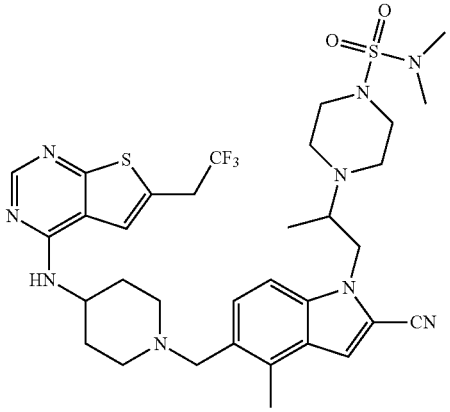 [SMILES: Cc1c(CN2CCC(Nc3ncnc4sc(CC(F)(F)F)cc34)CC2)ccc2c1cc(C#N)n2CC(C)N1CCN(S(=O)(=O)N(C)C)CC1] | 717.29 | 718.35 [M + H]+ |
| 88 | 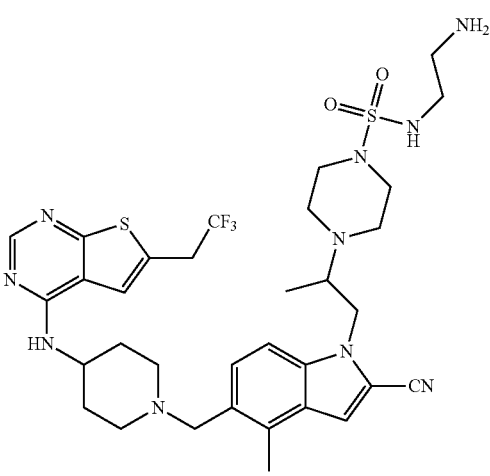 [SMILES: Cc1c(CN2CCC(Nc3ncnc4sc(CC(F)(F)F)cc34)CC2)ccc2c1cc(C#N)n2CC(C)N1CCN(S(=O)(=O)NCCN)CC1] | | |

TABLE 1-continued

| No | Structure | MW (calc'd) | m/z (found) |
|---|---|---|---|
| 89 | 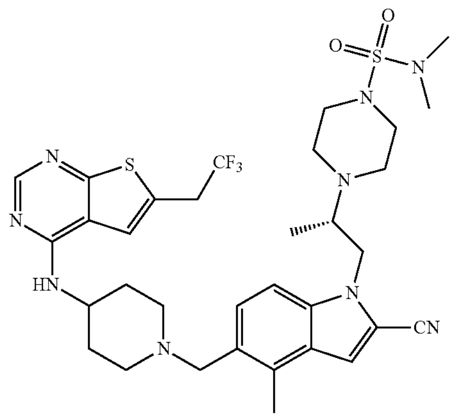 [SMILES: Cc1c(CN2CCC(Nc3ncnc4sc(CC(F)(F)F)cc34)CC2)ccc2c1cc(C#N)n2C[C@H](C)N1CCN(S(=O)(=O)N(C)C)CC1] | 717.29 | 718.25 [M + H]+ |
| 90 | 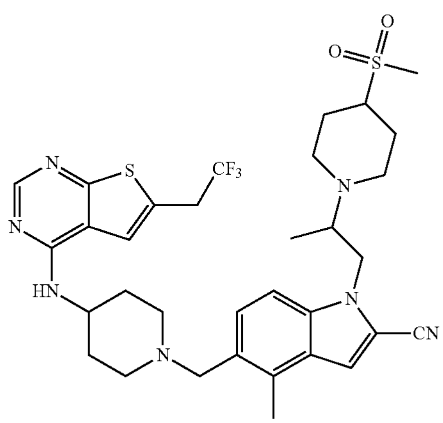 [SMILES: Cc1c(CN2CCC(Nc3ncnc4sc(CC(F)(F)F)cc34)CC2)ccc2c1cc(C#N)n2CC(C)N1CCC(S(C)(=O)=O)CC1] | | |
| 91 | 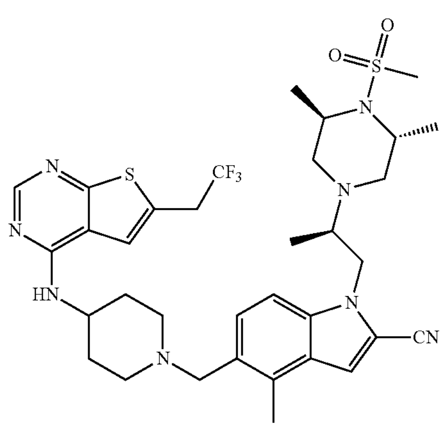 [SMILES: Cc1c(CN2CCC(Nc3ncnc4sc(CC(F)(F)F)cc34)CC2)ccc2c1cc(C#N)n2C[C@@H](C)N1C[C@@H](C)N(S(C)(=O)=O)[C@H](C)C1] | | |

TABLE 1-continued

| No | Structure | MW (calc'd) | m/z (found) |
|---|---|---|---|
| 92 | 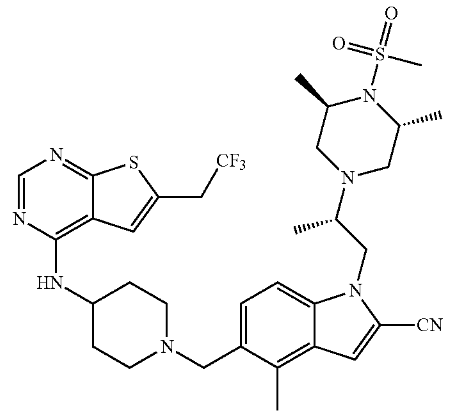 [SMILES: Cc1c(CN2CCC(Nc3ncnc4sc(CC(F)(F)F)cc34)CC2)ccc2c1cc(C#N)n2C[C@H](C)N1C[C@@H](C)N(S(C)(=O)=O)[C@H](C)C1] | | |
| 93 | 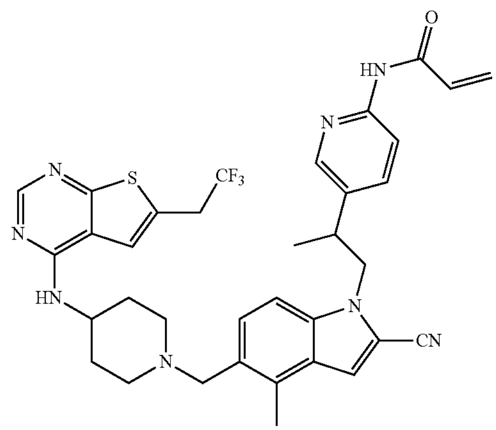 [SMILES: C=CC(=O)Nc1ccc(C(C)Cn2c(C#N)cc3c(C)c(CN4CCC(Nc5ncnc6sc(CC(F)(F)F)cc56)CC4)ccc32)cn1] | 672.26 | 673.2667 |
| 94 | 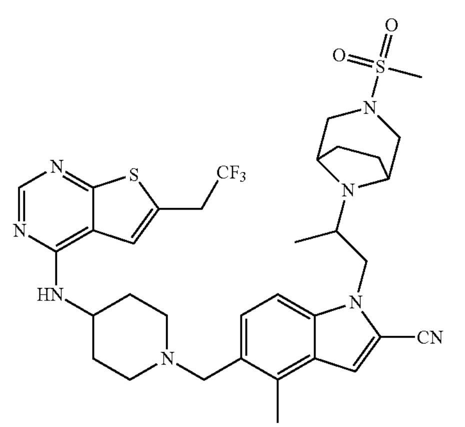 [SMILES: Cc1c(CN2CCC(Nc3ncnc4sc(CC(F)(F)F)cc34)CC2)ccc2c1cc(C#N)n2CC(C)N1C2CCC1CN(S(C)(=O)=O)C2] | 714.27 | 715.2 [M + H]+ |

TABLE 1-continued
| No | Structure | MW (calc'd) | m/z (found) |
|---|---|---|---|
| 95 | 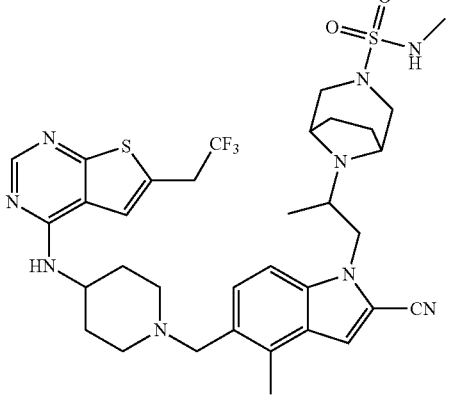 | | |
| 96 | 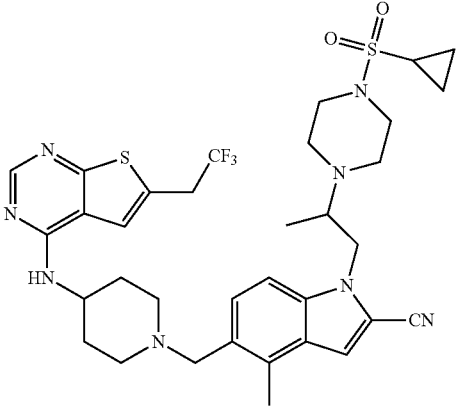 [SMILES: Cc1c(CN2CCC(Nc3ncnc4sc(CC(F)(F)F)cc34)CC2)ccc2c1cc(C#N)n2CC(C)N1CCN(S(=O)(=O)C2CC2)CC1] | | |
| 97 | 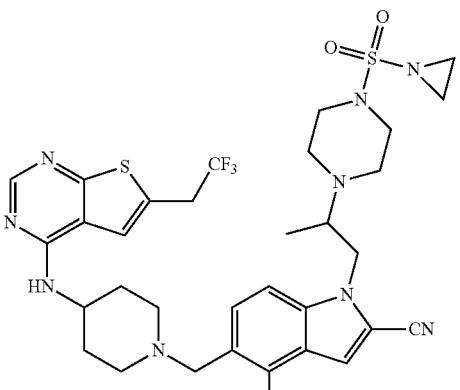 | | |

TABLE 1-continued

| No | Structure | MW (calc'd) | m/z (found) |
|---|---|---|---|
| 98 | 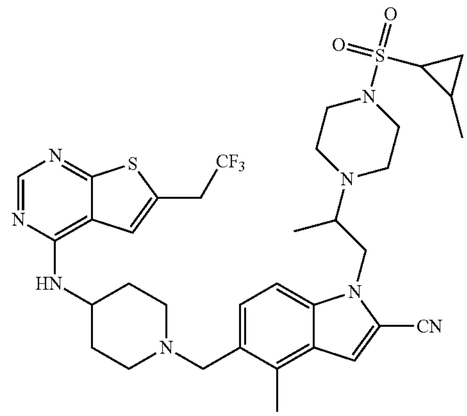 [SMILES: Cc1c(CN2CCC(Nc3ncnc4sc(CC(F)(F)F)cc34)CC2)ccc2c1cc(C#N)n2CC(C)N1CCN(S(=O)(=O)C2CC2C)CC1] | | |
| 99 | 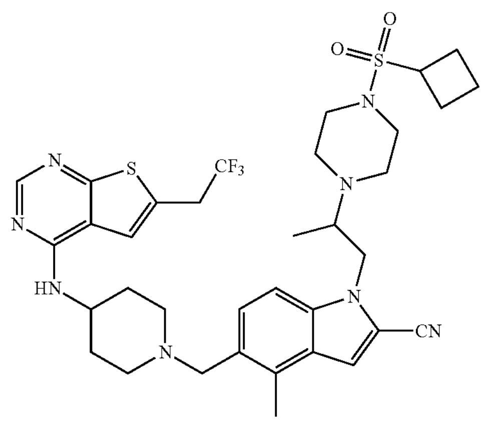 [SMILES: Cc1c(CN2CCC(Nc3ncnc4sc(CC(F)(F)F)cc34)CC2)ccc2c1cc(C#N)n2CC(C)N1CCN(S(=O)(=O)C2CCC2)CC1] | | |
| 100 | 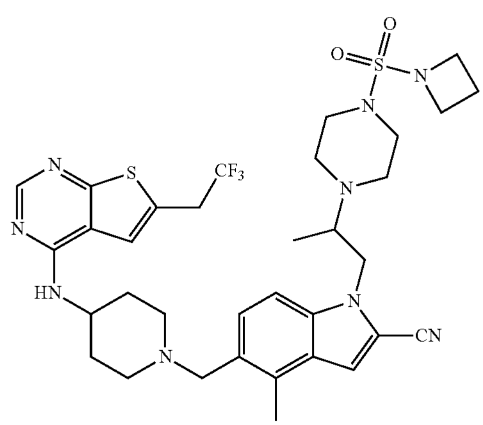 [SMILES: Cc1c(CN2CCC(Nc3ncnc4sc(CC(F)(F)F)cc34)CC2)ccc2c1cc(C#N)n2CC(C)N1CCN(S(=O)(=O)N2CCC2)CC1] | | |

TABLE 1-continued
| No | Structure | MW (calc'd) | m/z (found) |
|---|---|---|---|
| 101 | 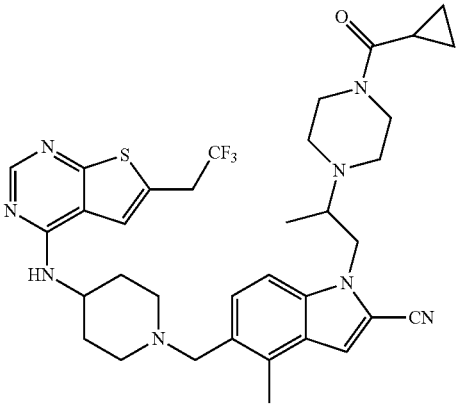 [SMILES: Cc1c(CN2CCC(Nc3ncnc4sc(CC(F)(F)F)cc34)CC2)ccc2c1cc(C#N)n2CC(C)N1CCN(C(=O)N2CC2)CC1] | | |
| 102 | 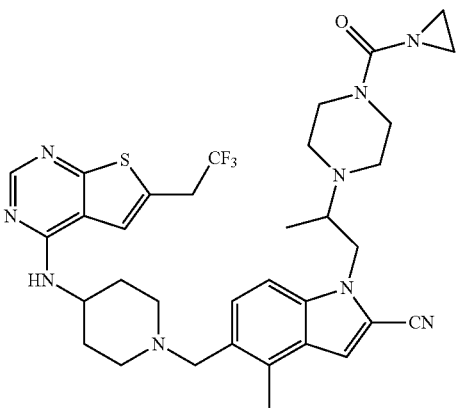 | | |
| 103 | 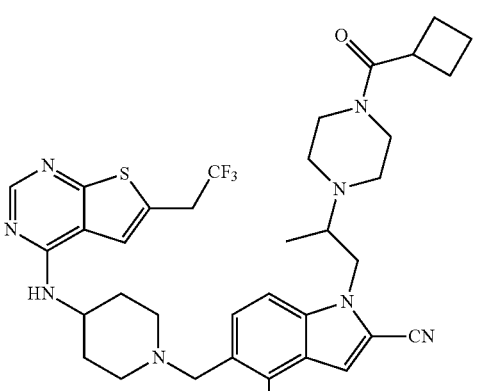 | | |

TABLE 1-continued

| No | Structure | MW (calc'd) | m/z (found) |
|----|-----------|-------------|-------------|
| 104 | 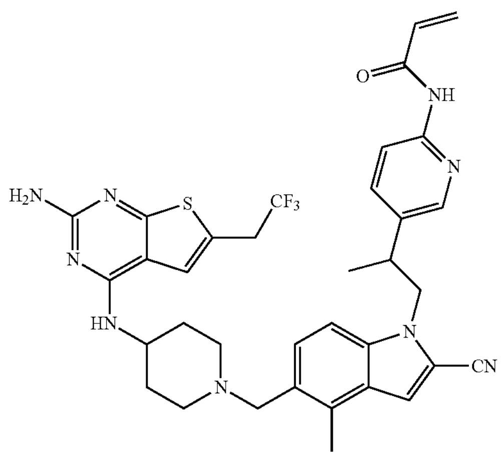 [SMILES: C=CC(=O)Nc1ccc(C(C)Cn2c(C#N)cc3c(C)c(CN4CCC(Nc5nc(N)nc6sc(CC(F)(F)F)cc56)CC4)ccc32)cn1] | | |
| 105 | 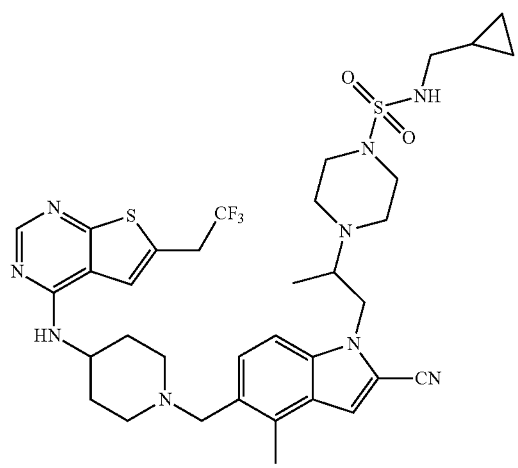 [SMILES: Cc1c(CN2CCC(Nc3ncnc4sc(CC(F)(F)F)cc34)CC2)ccc2c1cc(C#N)n2CC(C)N1CCN(S(=O)(=O)NCC2CC2)CC1] | | |
| 106 | 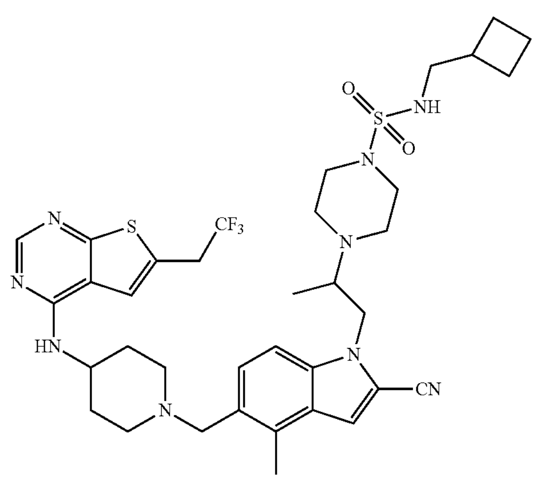 [SMILES: Cc1c(CN2CCC(Nc3ncnc4sc(CC(F)(F)F)cc34)CC2)ccc2c1cc(C#N)n2CC(C)N1CCN(S(=O)(=O)NCC2CCC2)CC1] | | |

TABLE 1-continued

| No | Structure | MW (calc'd) | m/z (found) |
|---|---|---|---|
| 107 | 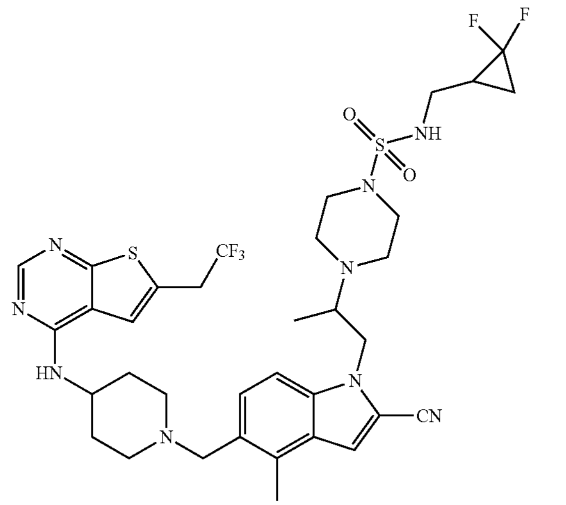 [SMILES: Cc1c(CN2CCC(Nc3ncnc4sc(CC(F)(F)F)cc34)CC2)ccc2c1cc(C#N)n2CC(C)N1CCN(S(=O)(=O)NCC2CC2(F)F)CC1] | | |
| 108 | 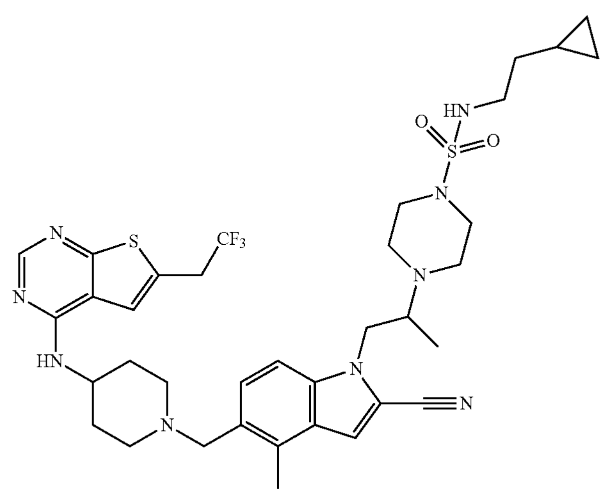 [SMILES: Cc1c(CN2CCC(Nc3ncnc4sc(CC(F)(F)F)cc34)CC2)ccc2c1cc(C#N)n2CC(C)N1CCN(S(=O)(=O)NCCC2CC2)CC1] | | |
| 109 | 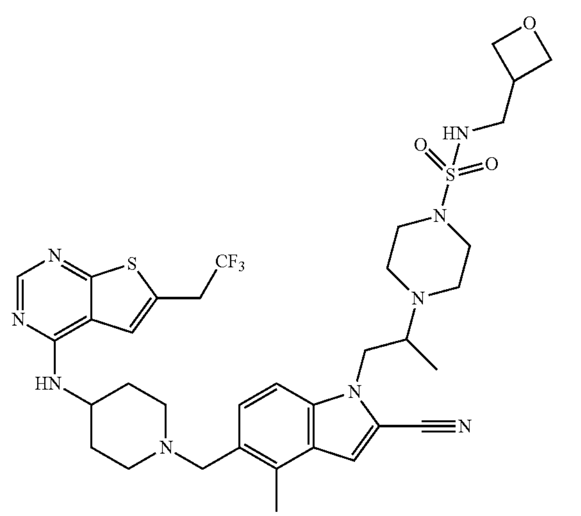 [SMILES: Cc1c(CN2CCC(Nc3ncnc4sc(CC(F)(F)F)cc34)CC2)ccc2c1cc(C#N)n2CC(C)N1CCN(S(=O)(=O)NCC2COC2)CC1] | | |

TABLE 1-continued
| No | Structure | MW (calc'd) | m/z (found) |
|---|---|---|---|
| 110 | 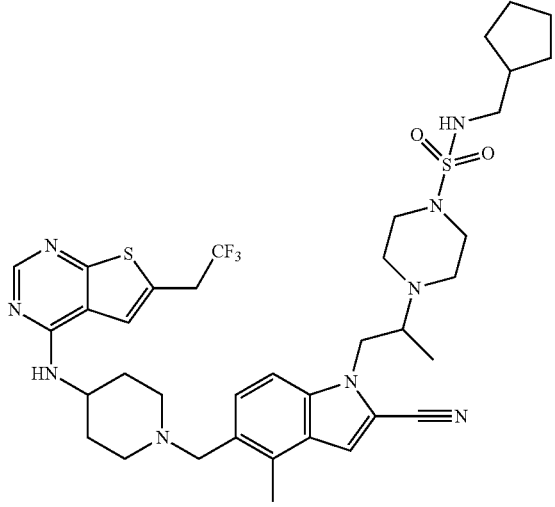 [SMILES: Cc1c(CN2CCC(Nc3ncnc4sc(CC(F)(F)F)cc34)CC2)ccc2c1cc(C#N)n2CC(C)N1CCN(S(=O)(=O)NCC2CCCC2)CC1] | | |
| 111 | 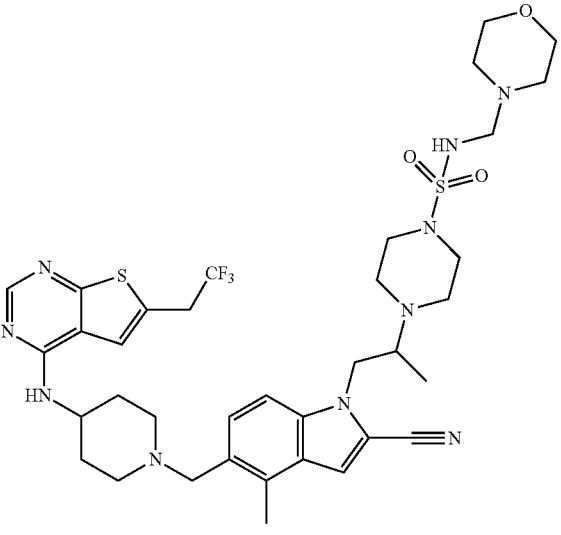 [SMILES: Cc1c(CN2CCC(Nc3ncnc4sc(CC(F)(F)F)cc34)CC2)ccc2c1cc(C#N)n2CC(C)N1CCN(S(=O)(=O)NCN2CCOCC2)CC1] | | |
| 112 | 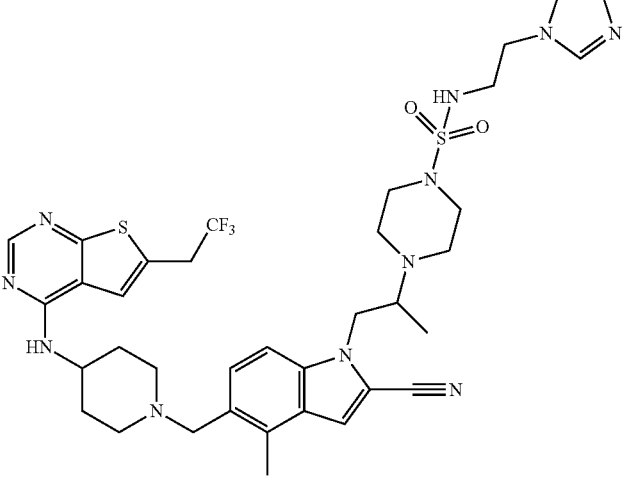 | | |

TABLE 1-continued
| No | Structure | MW (calc'd) | m/z (found) |
|---|---|---|---|
| 113 | 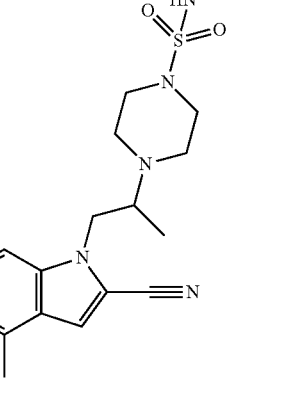 | | |
| 114 | 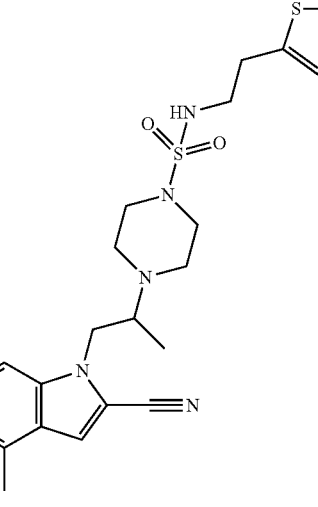 | | |
| 115 | 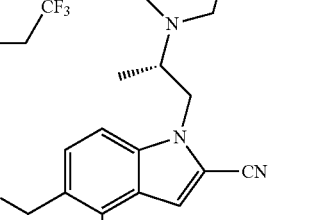 | 714.27 | 715.45 [M + H]+ |

TABLE 1-continued
| No | Structure | MW (calc'd) | m/z (found) |
|---|---|---|---|
| 116 | 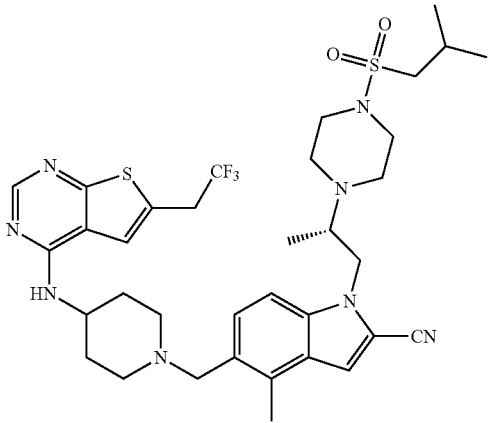 [SMILES: Cc1c(CN2CCC(Nc3ncnc4sc(CC(F)(F)F)cc34)CC2)ccc2c1cc(C#N)n2C[C@H](C)N1CCN(S(=O)(=O)CC(C)C)CC1] | 730.31 | 731.50 [M + H]+ |
| 117 | 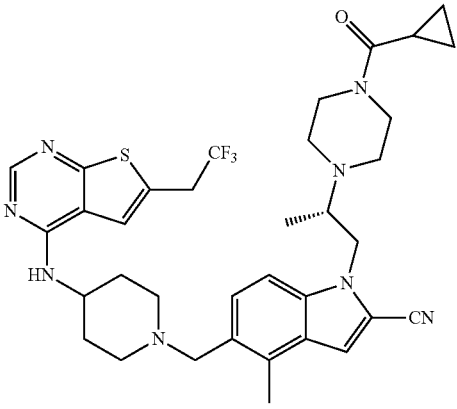 | 678.31 | 679.50 [M + H]+ |
| 118 | 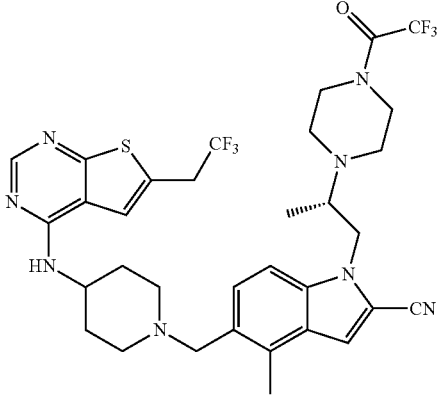 [SMILES: Cc1c(CN2CCC(Nc3ncnc4sc(CC(F)(F)F)cc34)CC2)ccc2c1cc(C#N)n2C[C@H](C)N1CCN(C(=O)C(F)(F)F)CC1] | 706.26 | 707.40 [M + H]+ |

TABLE 1-continued

| No | Structure | MW (calc'd) | m/z (found) |
|---|---|---|---|
| 119 | 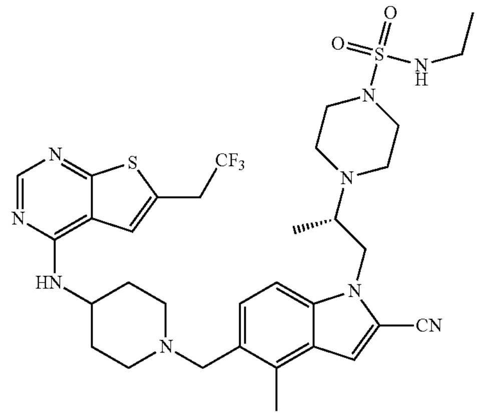 [SMILES: CCNS(=O)(=O)N1CCN([C@@H](C)Cn2c(C#N)cc3c(C)c(CN4CCC(Nc5ncnc6sc(CC(F)(F)F)cc56)CC4)ccc32)CC1] | 717.29 | 718.25 [M + H]+ |
| 120 | 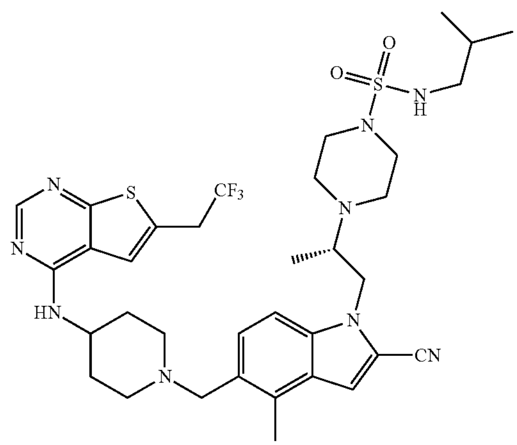 [SMILES: Cc1c(CN2CCC(Nc3ncnc4sc(CC(F)(F)F)cc34)CC2)ccc2c1cc(C#N)n2C[C@H](C)N1CCN(S(=O)(=O)NCC(C)C)CC1] | 745.32 | 746.30 [M + H]+ |
| 121 | 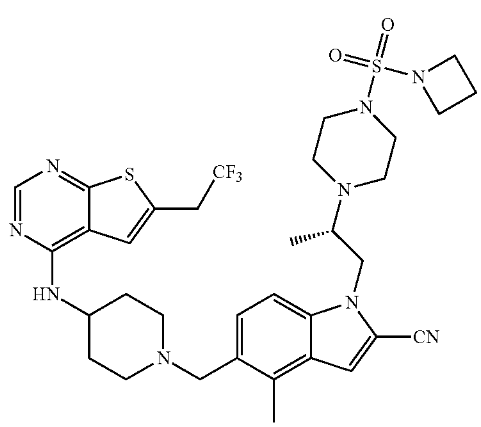 [SMILES: Cc1c(CN2CCC(Nc3ncnc4sc(CC(F)(F)F)cc34)CC2)ccc2c1cc(C#N)n2C[C@H](C)N1CCN(S(=O)(=O)N2CCC2)CC1] | 729.29 | 730.45 [M + H]+ |

TABLE 1-continued

| No | Structure | MW (calc'd) | m/z (found) |
|---|---|---|---|
| 122 | 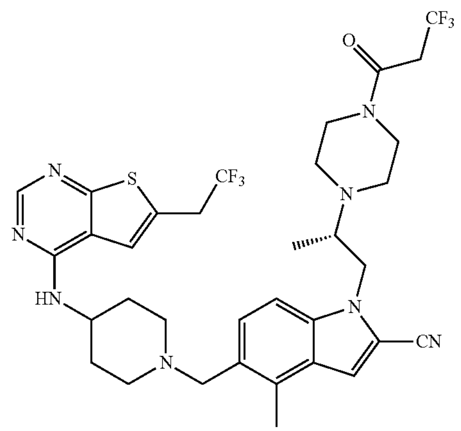 [SMILES: Cc1c(CN2CCC(Nc3ncnc4sc(CC(F)(F)F)cc34)CC2)ccc2c1cc(C#N)n2C[C@H](C)N1CCN(C(=O)CC(F)(F)F)CC1] | 720.28 | 721.40 [M + H]+ |
| 123 | 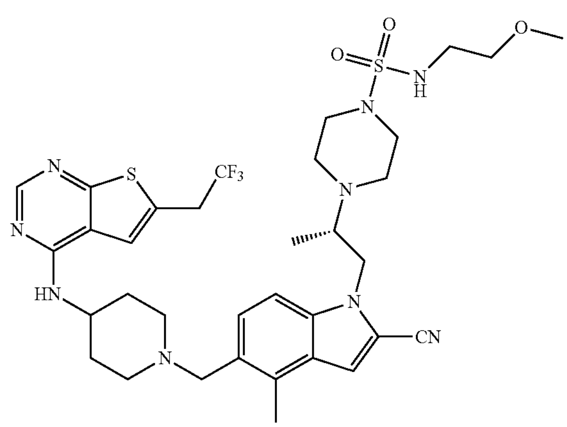 | 747.30 | 748.45 [M + H]+ |
| 124 | 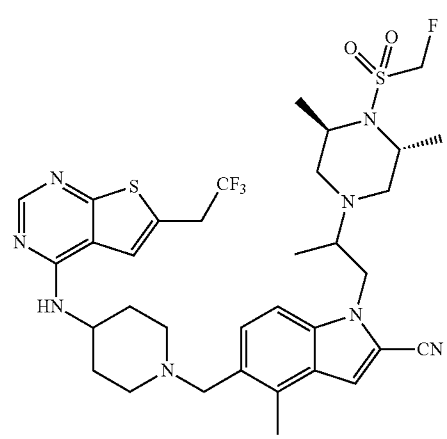 [SMILES: Cc1c(CN2CCC(Nc3ncnc4sc(CC(F)(F)F)cc34)CC2)ccc2c1cc(C#N)n2CC(C)N1C[C@@H](C)N(S(=O)(=O)CF)[C@H](C)C1] | 734.28 | 735.2 [M + H]+ |

TABLE 1-continued
| No | Structure | MW (calc'd) | m/z (found) |
|---|---|---|---|
| 125 | 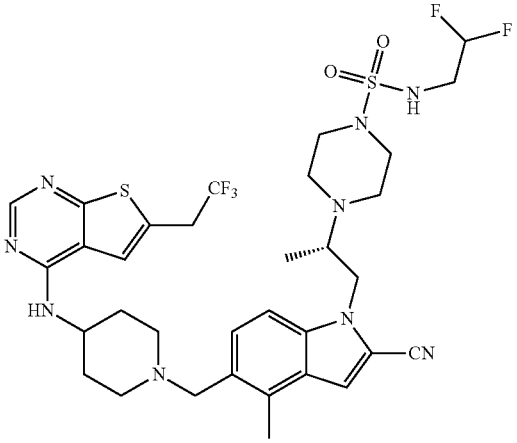 [SMILES: Cc1c(CN2CCC(Nc3ncnc4sc(CC(F)(F)F)cc34)CC2)ccc2c1cc(C#N)n2C[C@H](C)N1CCN(S(=O)(=O)NCC(F)F)CC1] | 753.27 | 754.45 [M + H]+ |
| 126 | 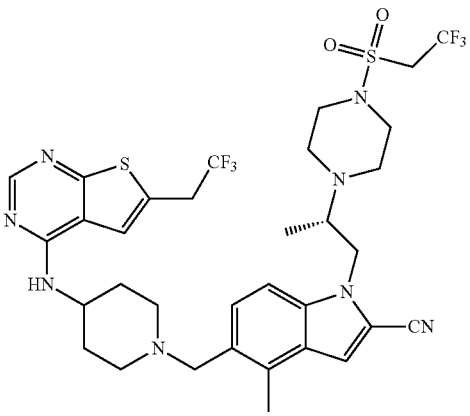 [SMILES: Cc1c(CN2CCC(Nc3ncnc4sc(CC(F)(F)F)cc34)CC2)ccc2c1cc(C#N)n2C[C@H](C)N1CCN(S(=O)(=O)CC(F)(F)F)CC1] | 756.25 | 757.35 [M + H]+ |
| 127 | 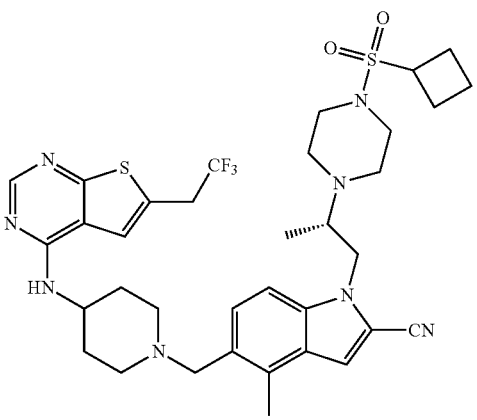 [SMILES: Cc1c(CN2CCC(Nc3ncnc4sc(CC(F)(F)F)cc34)CC2)ccc2c1cc(C#N)n2C[C@H](C)N1CCN(S(=O)(=O)C2CCC2)CC1] | 728.29 | 729.45 [M + H]+ |

TABLE 1-continued

| No | Structure | MW (calc'd) | m/z (found) |
|---|---|---|---|
| 128 | 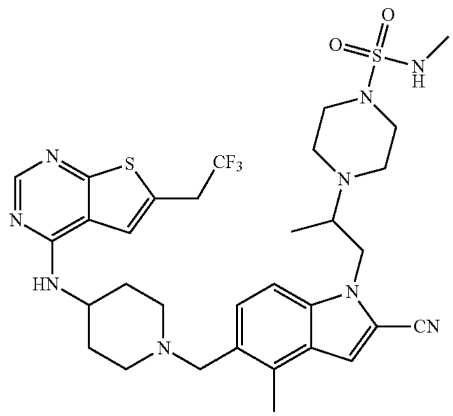 [SMILES: CNS(=O)(=O)N1CCN(C(C)Cn2c(C#N)cc3c(C)c(CN4CCC(Nc5ncnc6sc(CC(F)(F)F)cc56)CC4)ccc32)CC1] | 702.27 | 703.35 [M + H]+ |
| 129 | 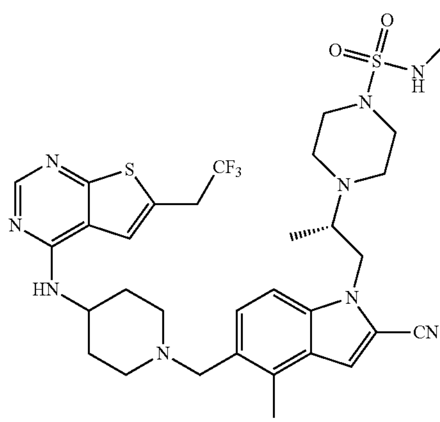 | 735.28 | 736.40 [M + H]+ |
| 130 | 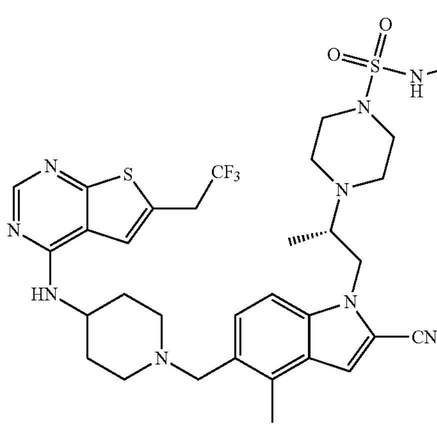 | 771.26 | 772.40 [M + H]+ |

TABLE 1-continued
| No | Structure | MW (calc'd) | m/z (found) |
|---|---|---|---|
| 131 | 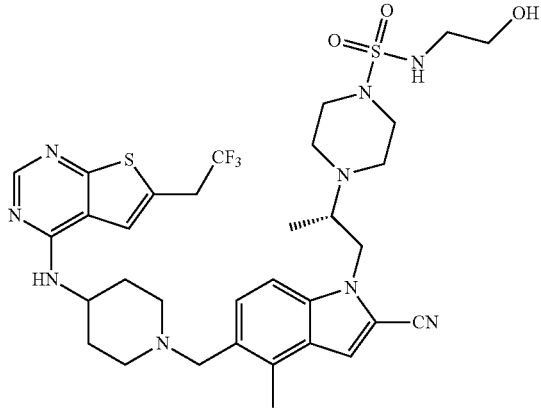 [SMILES: Cc1c(CN2CCC(Nc3ncnc4sc(CC(F)(F)F)cc34)CC2)ccc2c1cc(C#N)n2C[C@H](C)N1CCN(S(=O)(=O)NCCO)CC1] | 733.28 | 734.45 [M + H]+ |
| 132 | 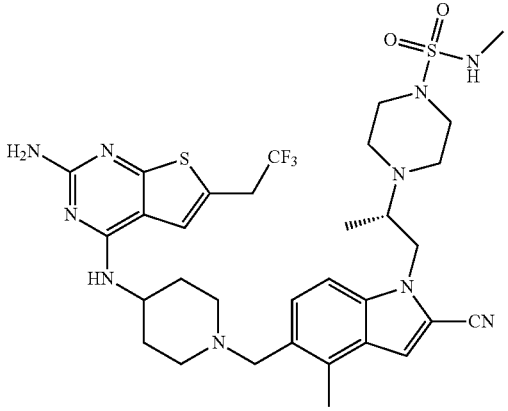 [SMILES: CNS(=O)(=O)N1CCN([C@@H](C)Cn2c(C#N)cc3c(C)c(CN4CCC(Nc5nc(N)nc6sc(CC(F)(F)F)cc56)CC4)ccc32)CC1] | 718.28 | 719.45 [M + H]+ |
| 133 | 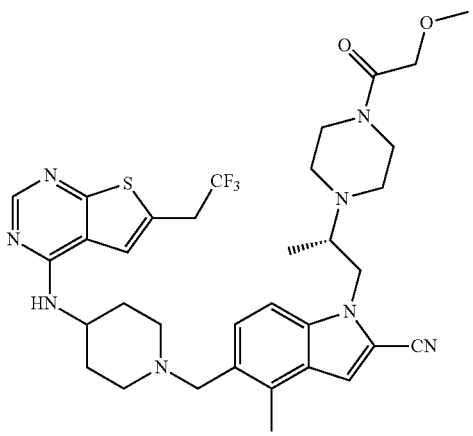 [SMILES: COCC(=O)N1CCN([C@@H](C)Cn2c(C#N)cc3c(C)c(CN4CCC(Nc5ncnc6sc(CC(F)(F)F)cc56)CC4)ccc32)CC1] | 682.30 | 683.50 [M + H]+ |

TABLE 1-continued

| No | Structure | MW (calc'd) | m/z (found) |
|----|-----------|-------------|-------------|
| 134 | 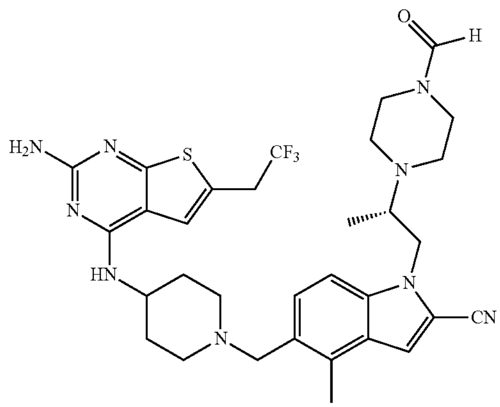 [SMILES: Cc1c(CN2CCC(Nc3nc(N)nc4sc(CC(F)(F)F)cc34)CC2)ccc2c1cc(C#N)n2C[C@H](C)N1CCN(C=O)CC1] | 653.29 | 654.40 [M + H]+ |
| 135 | 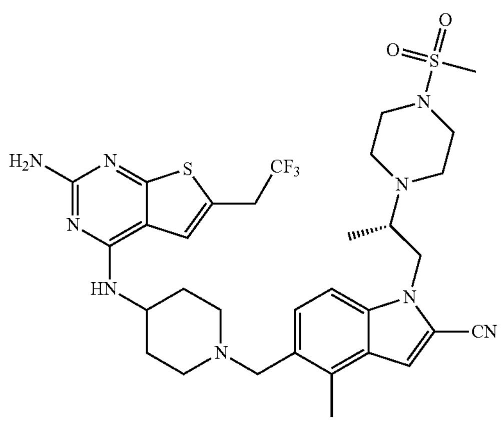 [SMILES: Cc1c(CN2CCC(Nc3nc(N)nc4sc(CC(F)(F)F)cc34)CC2)ccc2c1cc(C#N)n2C[C@H](C)N1CCN(S(C)(=O)=O)CC1] | 703.27 | 704.40 [M + H]+ |
| 136 | 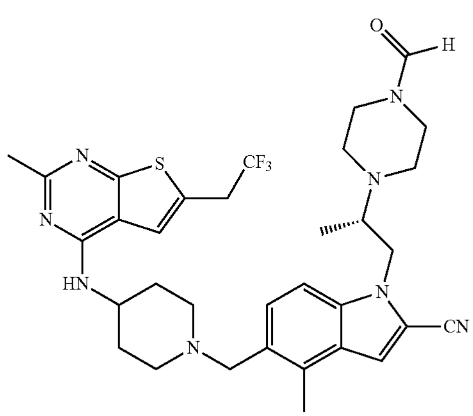 [SMILES: Cc1nc(NC2CCN(Cc3ccc4c(cc(C#N)n4C[C@H](C)N4CCN(C=O)CC4)c3C)CC2)c2cc(CC(F)(F)F)sc2n1] | 652.29 | 653.45 [M + H]+ |

TABLE 1-continued

| No | Structure | MW (calc'd) | m/z (found) |
|---|---|---|---|
| 137 | 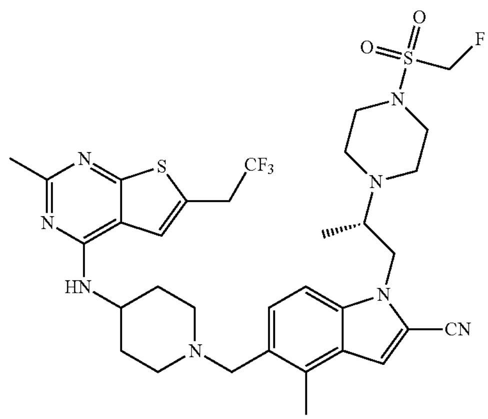 [SMILES: Cc1nc(NC2CCN(Cc3ccc4c(cc(C#N)n4C[C@H](C)N4CCN(S(=O)(=O)CF)CC4)c3C)CC2)c2cc(CC(F)(F)F)sc2n1] | 720.27 | 721.45 [M + H]+ |
| 138 | 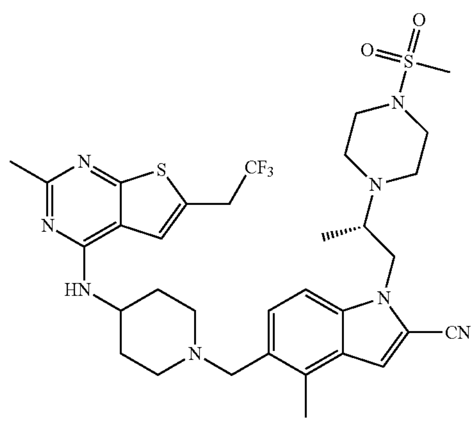 [SMILES: Cc1nc(NC2CCN(Cc3ccc4c(cc(C#N)n4C[C@H](C)N4CCN(S(C)(=O)=O)CC4)c3C)CC2)c2cc(CC(F)(F)F)sc2n1] | 702.27 | 703.50 [M + H]+ |
| 139 | 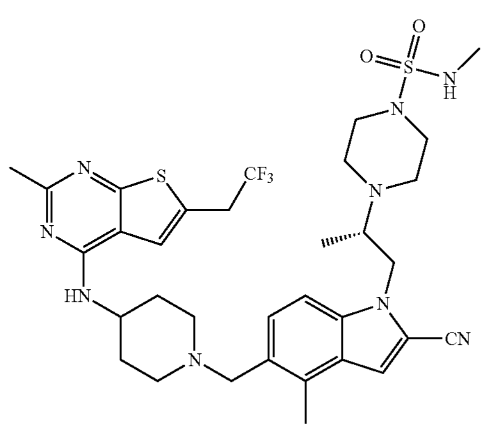 | 717.29 | 718.50 [M + H]+ |

TABLE 1-continued

| No | Structure | MW (calc'd) | m/z (found) |
|----|-----------|-------------|-------------|
| 140 | 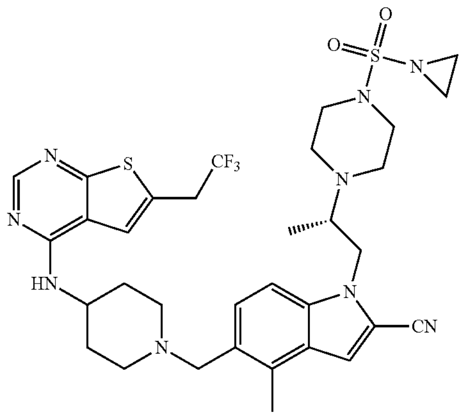 | 715.27 | 716.40 [M + H]+ |
| 141 | 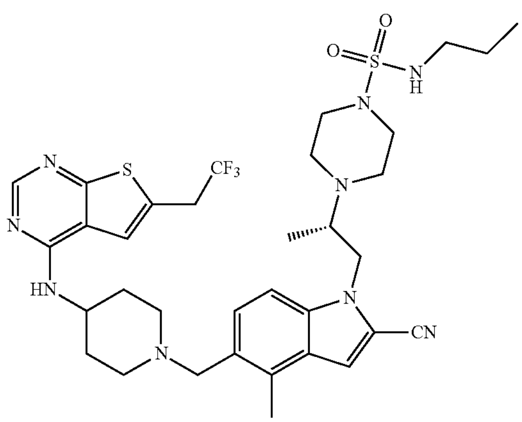 [SMILES: CCCNS(=O)(=O)N1CCN([C@@H](C)Cn2c(C#N)cc3c(C)c(CN4CCC(Nc5ncnc6sc(CC(F)(F)F)cc56)CC4)ccc32)CC1] | 731.30 | 732.45 [M + H]+ |
| 142 | 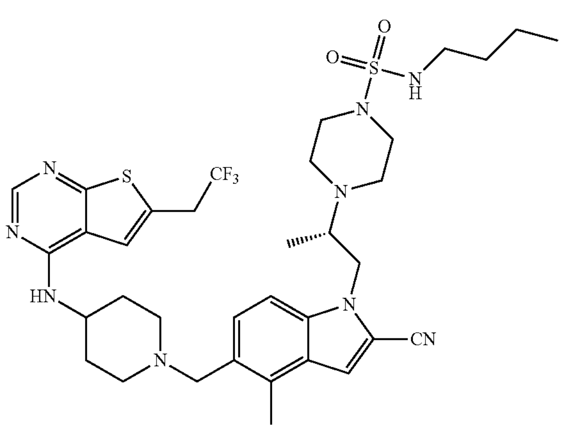 [SMILES: CCCCNS(=O)(=O)N1CCN([C@@H](C)Cn2c(C#N)cc3c(C)c(CN4CCC(Nc5ncnc6sc(CC(F)(F)F)cc56)CC4)ccc32)CC1] | 745.32 | 746.40 [M + H]+ |

TABLE 1-continued

| No | Structure | MW (calc'd) | m/z (found) |
|---|---|---|---|
| 143 | 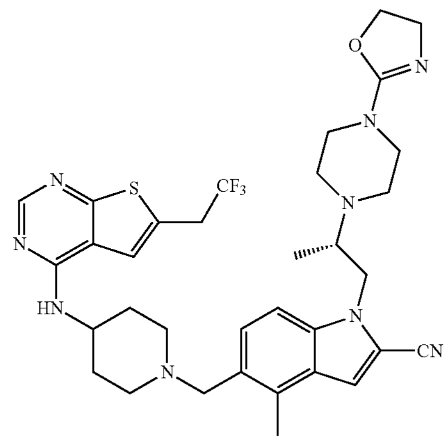 [SMILES: Cc1c(CN2CCC(Nc3ncnc4sc(CC(F)(F)F)cc34)CC2)ccc2c1cc(C#N)n2C[C@H](C)N1CCN(C2=NCCO2)CC1] | 679.30 | 680.50 [M + H]+ |
| 144 | 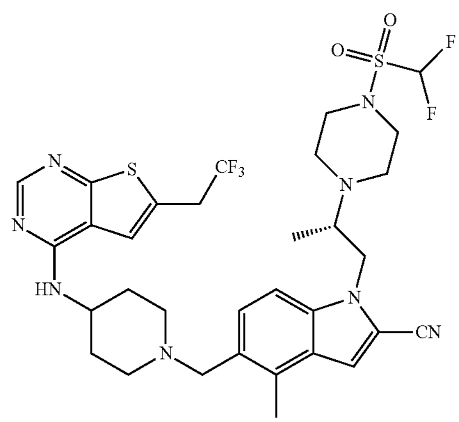 [SMILES: Cc1c(CN2CCC(Nc3ncnc4sc(CC(F)(F)F)cc34)CC2)ccc2c1cc(C#N)n2C[C@H](C)N1CCN(S(=O)(=O)C(F)F)CC1] | 724.24 | 725.40 [M + H]+ |
| 145 | 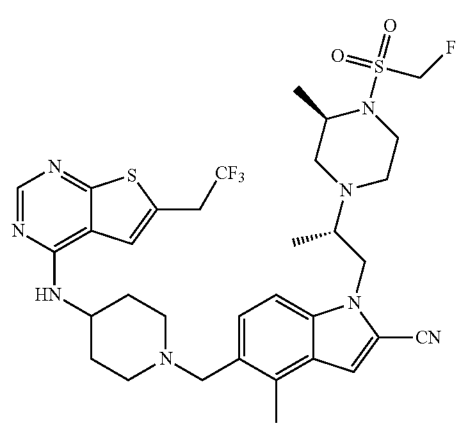 [SMILES: Cc1c(CN2CCC(Nc3ncnc4sc(CC(F)(F)F)cc34)CC2)ccc2c1cc(C#N)n2C[C@H](C)N1CCN(S(=O)(=O)CF)[C@H](C)C1] | 720.27 | 721.45 [M + H]+ |

TABLE 1-continued

| No | Structure | MW (calc'd) | m/z (found) |
|---|---|---|---|
| 146 | 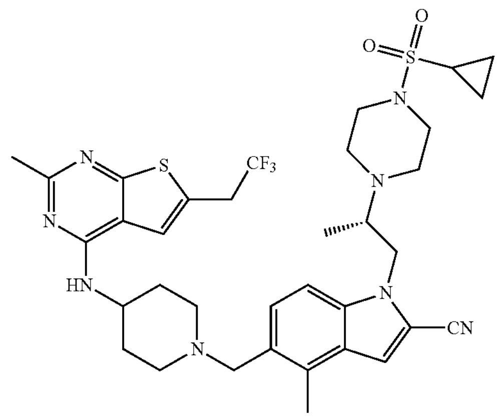 [SMILES: Cc1nc(NC2CCN(Cc3ccc4c(cc(C#N)n4C[C@H](C)N4CCN(S(=O)(=O)C5CC5)CC4)c3C)CC2)c2cc(CC(F)(F)F)sc2n1] | 728.29 | 729.45 [M + H]+ |
| 147 | 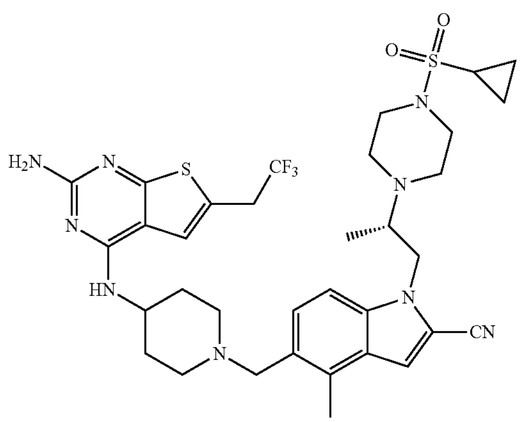 [SMILES: Cc1c(CN2CCC(Nc3nc(N)nc4sc(CC(F)(F)F)cc34)CC2)ccc2c1cc(C#N)n2C[C@H](C)N1CCN(S(=O)(=O)C2CC2)CC1] | 729.29 | 730.40 [M + H]+ |
| 148 | 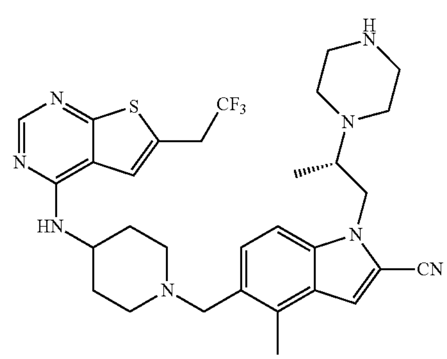 [SMILES: Cc1c(CN2CCC(Nc3ncnc4sc(CC(F)(F)F)cc34)CC2)ccc2c1cc(C#N)n2C[C@H](C)N1CCNCC1] | 610.28 | 611.3 [M + H]+ |
| 149 | 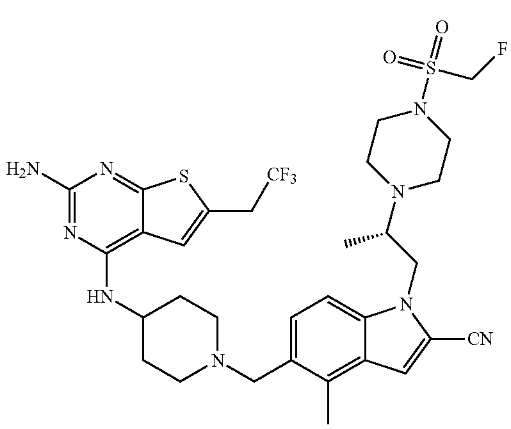 [SMILES: Cc1c(CN2CCC(Nc3nc(N)nc4sc(CC(F)(F)F)cc34)CC2)ccc2c1cc(C#N)n2C[C@H](C)N1CCN(S(=O)(=O)CF)CC1] | 721.26 | 722.45 [M + H]+ |

TABLE 1-continued

| No | Structure | MW (calc'd) | m/z (found) |
|---|---|---|---|
| 150 | 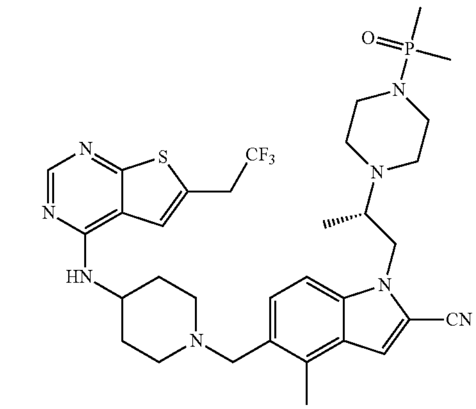 [SMILES: Cc1c(CN2CCC(Nc3ncnc4sc(CC(F)(F)F)cc34)CC2)ccc2c1cc(C#N)n2C[C@H](C)N1CCN(P(C)(C)=O)CC1] | 686.29 | 687.3 [M + H]+ |
| 151 | 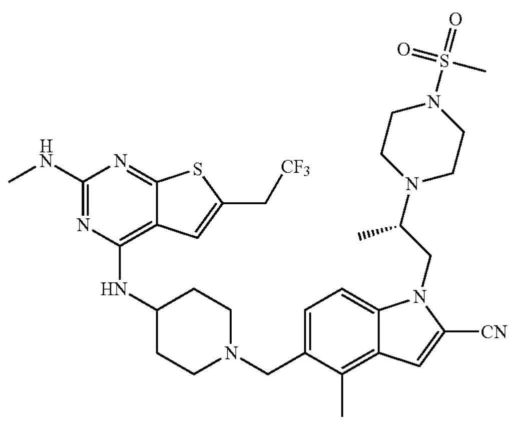 [SMILES: CNc1nc(NC2CCN(Cc3ccc4c(cc(C#N)n4C[C@H](C)N4CCN(S(C)(=O)=O)CC4)c3C)CC2)c2cc(CC(F)(F)F)sc2n1] | 717.29 | 718.55 [M + H]+ |
| 152 | 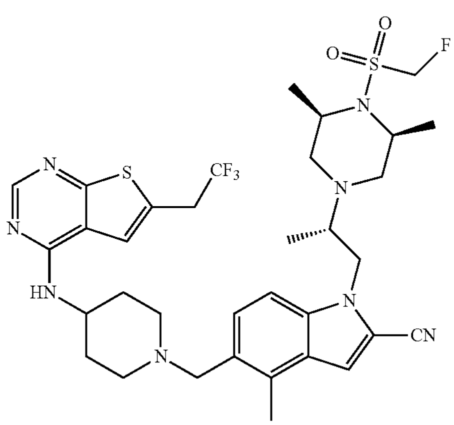 [SMILES: Cc1c(CN2CCC(Nc3ncnc4sc(CC(F)(F)F)cc34)CC2)ccc2c1cc(C#N)n2C[C@H](C)N1C[C@@H](C)N(S(=O)(=O)CF)[C@@H](C)C1] | 734.28 | 735.40 [M + H]+ |

TABLE 1-continued

| No | Structure | MW (calc'd) | m/z (found) |
|---|---|---|---|
| 153 | 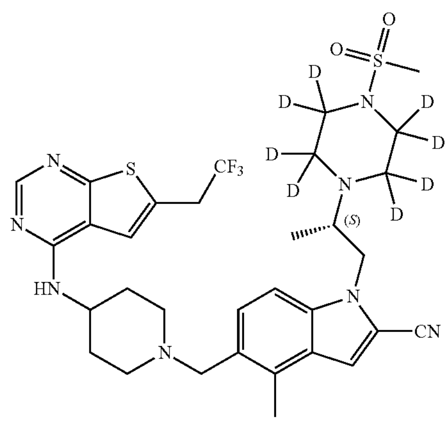 | 696.31 | |
| 154 | 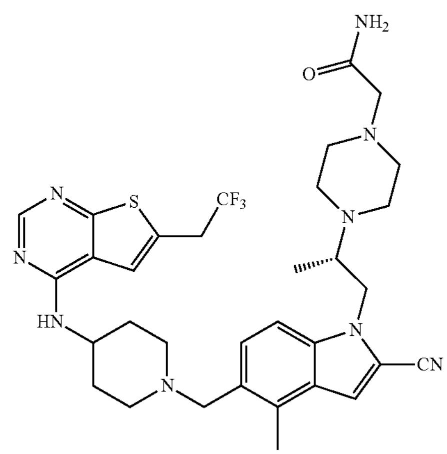 [SMILES: Cc1c(CN2CCC(Nc3ncnc4sc(CC(F)(F)F)cc34)CC2)ccc2c1cc(C#N)n2C[C@H](C)N1CCN(CC(N)=O)CC1] | 667.30 | 668.35 [M + H]+ |
| 155 | 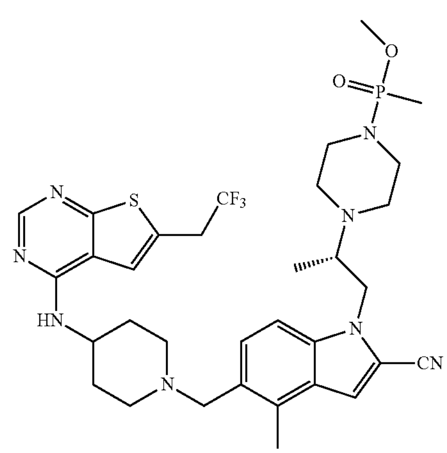 [SMILES: COP(C)(=O)N1CCN([C@@H](C)Cn2c(C#N)cc3c(C)c(CN4CCC(Nc5ncnc6sc(CC(F)(F)F)cc56)CC4)ccc32)CC1] | 702.28 | 703.35 [M + H]+ |

TABLE 1-continued

| No | Structure | MW (calc'd) | m/z (found) |
|---|---|---|---|
| 156 | 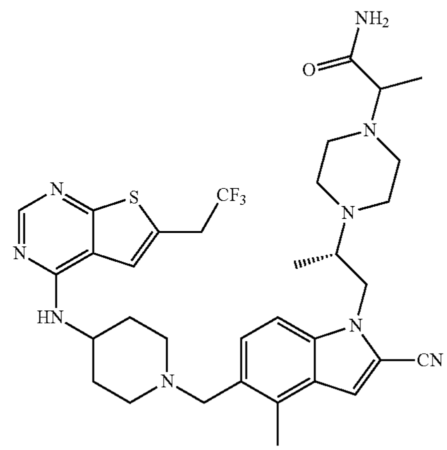 [SMILES: Cc1c(CN2CCC(Nc3ncnc4sc(CC(F)(F)F)cc34)CC2)ccc2c1cc(C#N)n2C[C@H](C)N1CCN(C(C)C(N)=O)CC1] | 681.32 | 682.45 [M + H]+ |
| 157 | 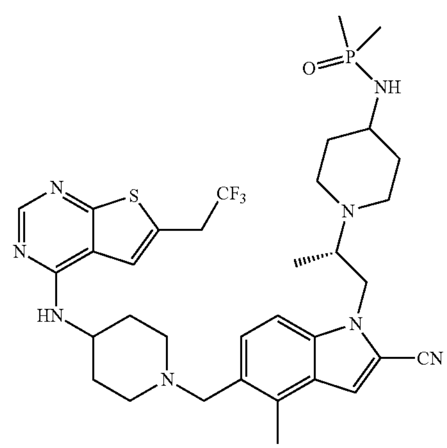 [SMILES: Cc1c(CN2CCC(Nc3ncnc4sc(CC(F)(F)F)cc34)CC2)ccc2c1cc(C#N)n2C[C@H](C)N1CCC(NP(C)(C)=O)CC1] | 700.30 | 701.40 [M + H]+ |
| 158 | 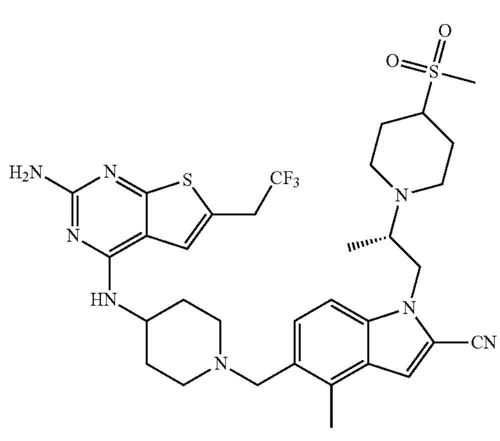 | 702.27 | 703.40 [M + H]+ |

TABLE 1-continued

| No | Structure | MW (calc'd) | m/z (found) |
|---|---|---|---|
| 159 | 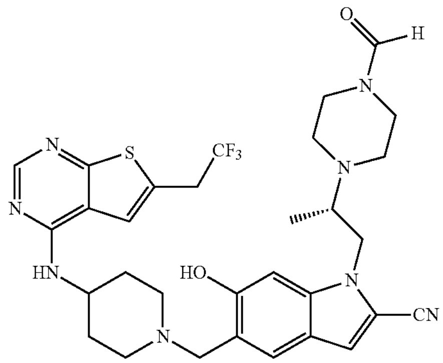 [SMILES: C[C@@H](Cn1c(C#N)cc2cc(CN3CCC(Nc4ncnc5sc(CC(F)(F)F)cc45)CC3)c(O)cc21)N1CCN(C=O)CC1] | 640.26 | 641.40 [M + H]+ |
| 160 | 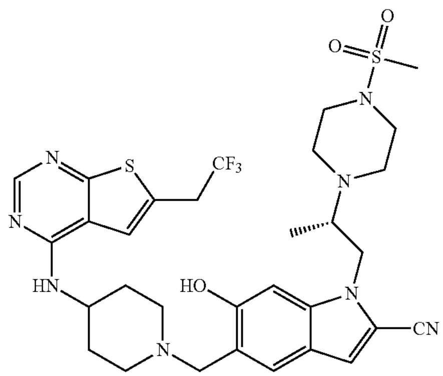 [SMILES: C[C@@H](Cn1c(C#N)cc2cc(CN3CCC(Nc4ncnc5sc(CC(F)(F)F)cc45)CC3)c(O)cc21)N1CCN(S(C)(=O)=O)CC1] | 690.24 | 691.35 [M + H]+ |
| 161 | 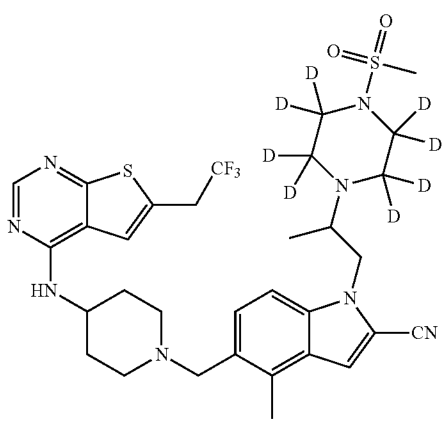 [SMILES: [2H]C1([2H])N(C(C)Cn2c(C#N)cc3c(C)c(CN4CCC(Nc5ncnc6sc(CC(F)(F)F)cc56)CC4)ccc32)C([2H])([2H])C([2H])([2H])N(S(C)(=O)=O)C1([2H])[2H]] | 696.31 | 697.3 [M + H]+ |
| 162 | 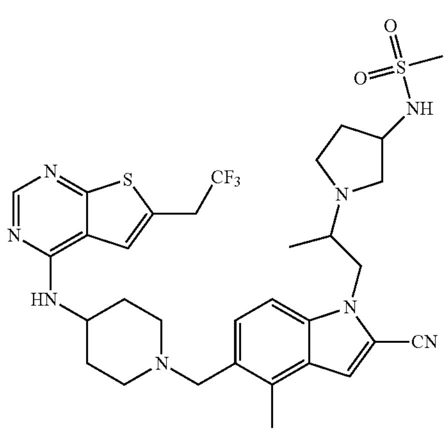 | 659.23 | 660.2 [M + H]+ |

TABLE 1-continued

| No | Structure | MW (calc'd) | m/z (found) |
|---|---|---|---|
| 163 | 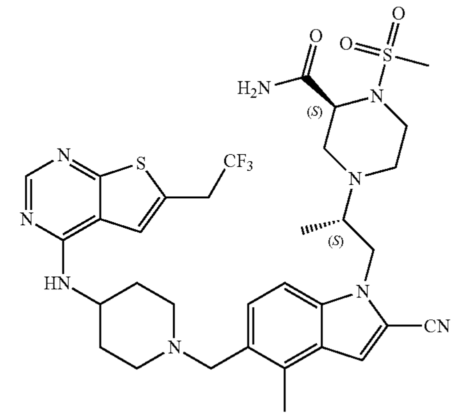 | 731.26 | 732.40 [M + ]+ |
| 164 | 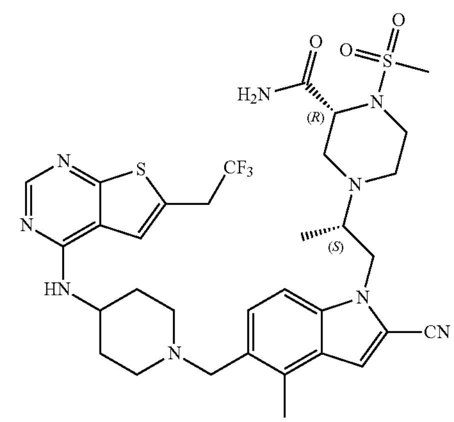 | 731.26 | 732.35 [M + H]+ |
| 165 | 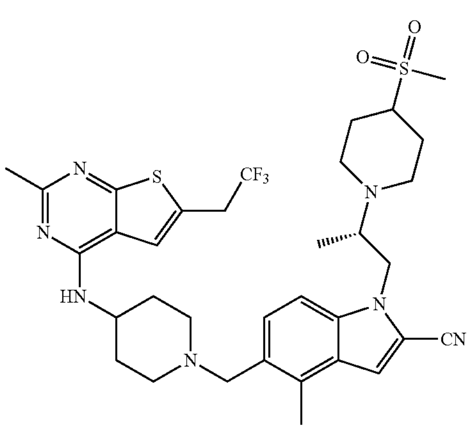 [SMILES: Cc1nc(NC2CCN(Cc3ccc4c(cc(C#N)n4C[C@H](C)N4CCC(S(C)(=O)=O)CC4)c3C)CC2)c2cc(CC(F)(F)F)sc2n1] | 701.28 | 702.40 [M + H]+ |

TABLE 1-continued

| No | Structure | MW (calc'd) | m/z (found) |
|---|---|---|---|
| 166 | 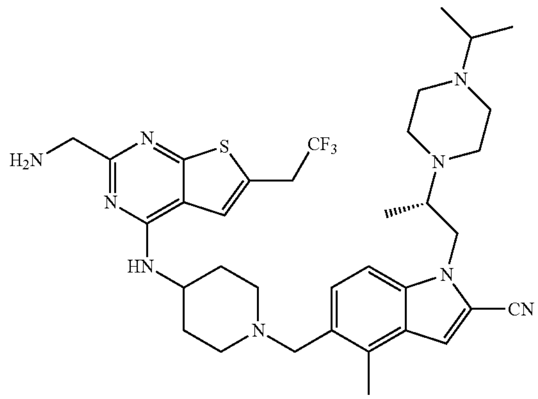 | 667.34 | 668.45 [M + H]⁺ |
| 167 | 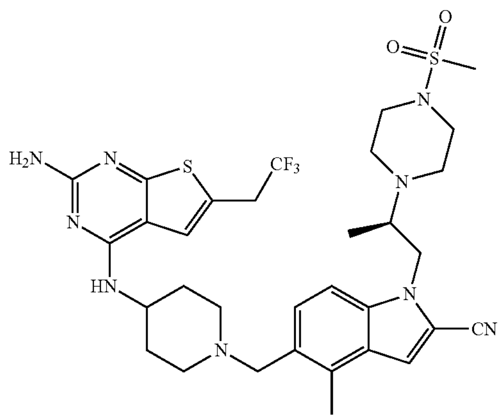 [SMILES: Cc1c(CN2CCC(Nc3nc(N)nc4sc(CC(F)(F)F)cc34)CC2)ccc2c1cc(C#N)n2C[C@@H](C)N1CCN(S(C)(=O)=O)CC1] | 703.27 | 704.40 [M + H]⁺ |
| 168 | 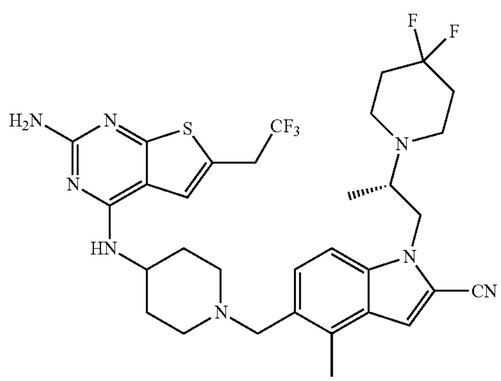 [SMILES: Cc1c(CN2CCC(Nc3nc(N)nc4sc(CC(F)(F)F)cc34)CC2)ccc2c1cc(C#N)n2C[C@H](C)N1CCC(F)(F)CC1] | 660.28 | 661.40 [M + H]⁺ |
| 169 | 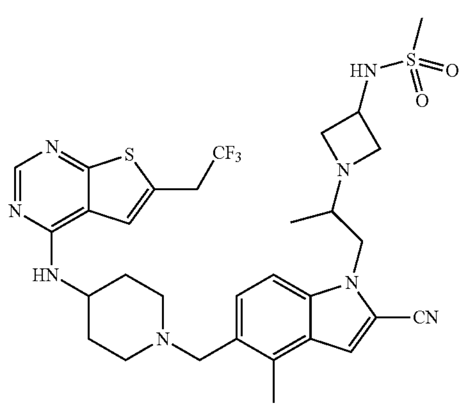 [SMILES: Cc1c(CN2CCC(Nc3ncnc4sc(CC(F)(F)F)cc34)CC2)ccc2c1cc(C#N)n2CC(C)N1CC(NS(C)(=O)=O)C1] | 674.24 | |

TABLE 1-continued

| No | Structure | MW (calc'd) | m/z (found) |
|----|-----------|-------------|-------------|
| 170 | 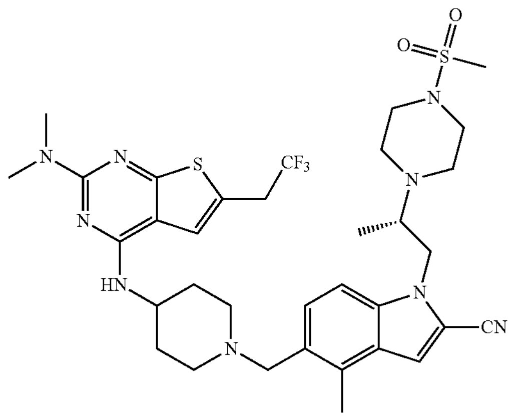 [SMILES: Cc1c(CN2CCC(Nc3nc(N(C)C)nc4sc(CC(F)(F)F)cc34)CC2)ccc2c1cc(C#N)n2C[C@H](C)N1CCN(S(C)(=O)=O)CC1] | 731.30 | 732.40 [M + H]⁺ |
| 171 | 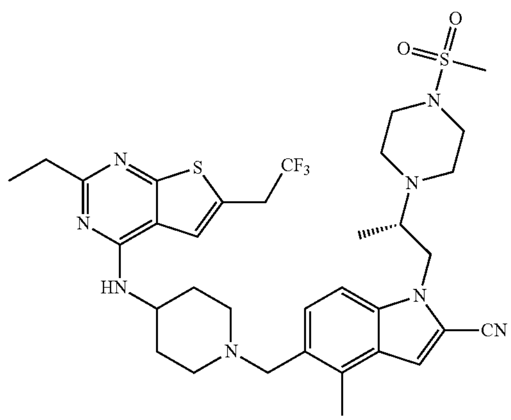 [SMILES: CCc1nc(NC2CCN(Cc3ccc4c(cc(C#N)n4C[C@H](C)N4CCN(S(C)(=O)=O)CC4)c3C)CC2)c2cc(CC(F)(F)F)sc2n1] | 716.29 | 717.45 [M + H]⁺ |
| 172 | 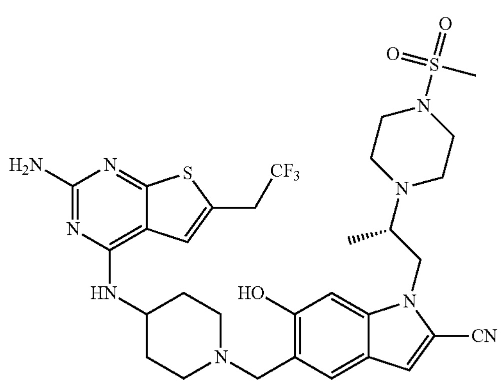 [SMILES: C[C@@H](Cn1c(C#N)cc2cc(CN3CCC(Nc4nc(N)nc5sc(CC(F)(F)F)cc45)CC3)c(O)cc21)N1CCN(S(C)(=O)=O)CC1] | 705.25 | 706.45 [M + H]⁺ |

TABLE 1-continued

| No | Structure | MW (calc'd) | m/z (found) |
|----|-----------|-------------|-------------|
| 173 | 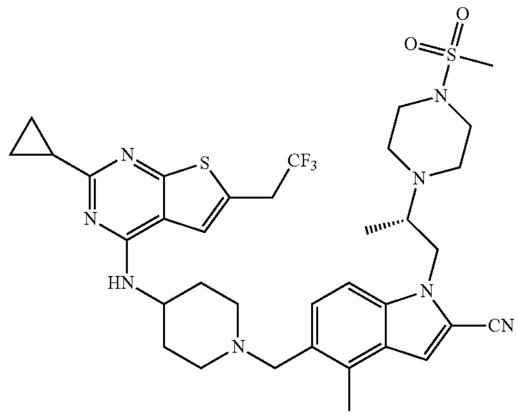 [SMILES: Cc1c(CN2CCC(Nc3nc(C4CC4)nc4sc(CC(F)(F)F)cc34)CC2)ccc2c1cc(C#N)n2C[C@H](C)N1CCN(S(C)(=O)=O)CC1] | 728.29 | 729.45 [M + H]+ |
| 174 | 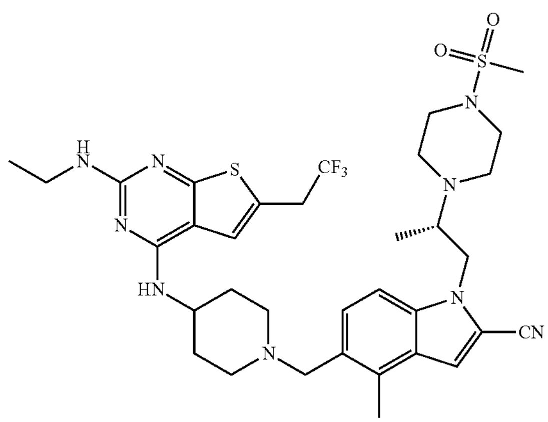 [SMILES: CCNc1nc(NC2CCN(Cc3ccc4c(cc(C#N)n4C[C@H](C)N4CCN(S(C)(=O)=O)CC4)c3C)CC2)c2cc(CC(F)(F)F)sc2n1] | 731.30 | 732.45 [M + H]+ |
| 175 | 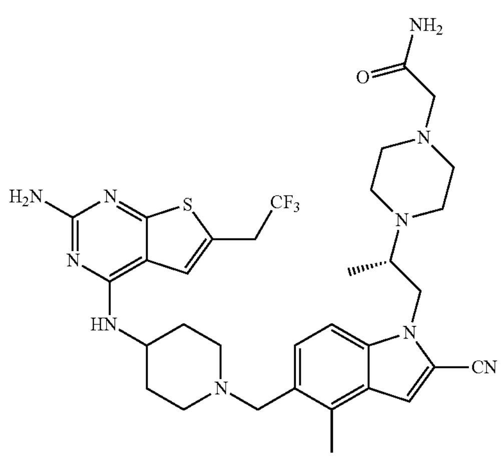 [SMILES: Cc1c(CN2CCC(Nc3nc(N)nc4sc(CC(F)(F)F)cc34)CC2)ccc2c1cc(C#N)n2C[C@H](C)N1CCN(CC(N)=O)CC1] | 682.31 | 683.45 [M + H]+ |

TABLE 1-continued

| No | Structure | MW (calc'd) | m/z (found) |
|---|---|---|---|
| 176 | 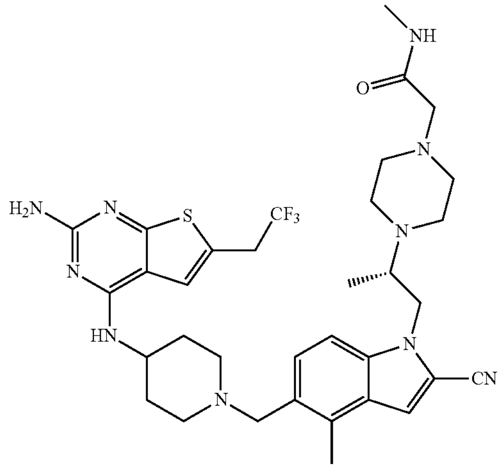 [SMILES: CNC(=O)CN1CCN([C@@H](C)Cn2c(C#N)cc3c(C)c(CN4CCC(Nc5nc(N)nc6sc(CC(F)(F)F)cc56)CC4)ccc32)CC1] | 696.33 | 697.60 [M + H]+ |
| 177 | 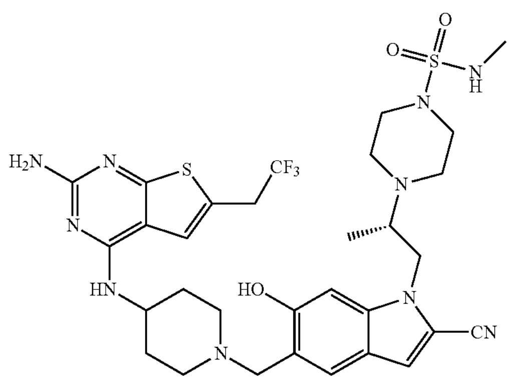 [SMILES: CNS(=O)(=O)N1CCN([C@@H](C)Cn2c(C#N)cc3cc(CN4CCC(Nc5nc(N)nc6sc(CC(F)(F)F)cc56)CC4)c(O)cc32)CC1] | 720.26 | 721.50 [M + H]+ |
| 178 | 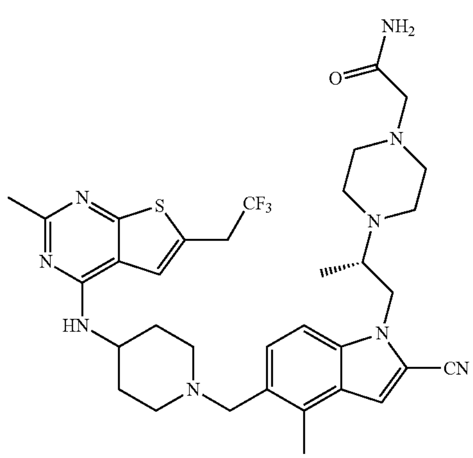 [SMILES: Cc1nc(NC2CCN(Cc3ccc4c(cc(C#N)n4C[C@H](C)N4CCN(CC(N)=O)CC4)c3C)CC2)c2cc(CC(F)(F)F)sc2n1] | 681.32 | 682.45 [M + H]+ |

TABLE 1-continued

| No | Structure | MW (calc'd) | m/z (found) |
|---|---|---|---|
| 179 | 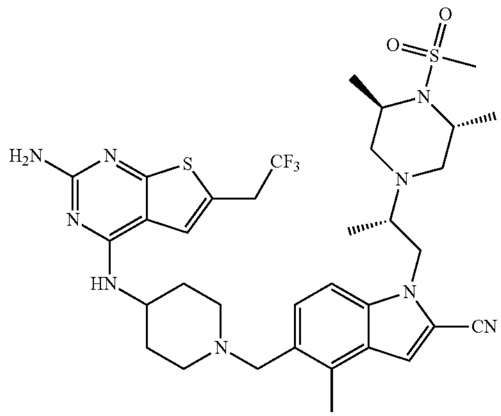 [SMILES: Cc1c(CN2CCC(Nc3nc(N)nc4sc(CC(F)(F)F)cc34)CC2)ccc2c1cc(C#N)n2C[C@H](C)N1C[C@@H](C)N(S(C)(=O)=O)[C@H](C)C1] | 731.30 | 732.50 [M + H]+ |
| 180 | 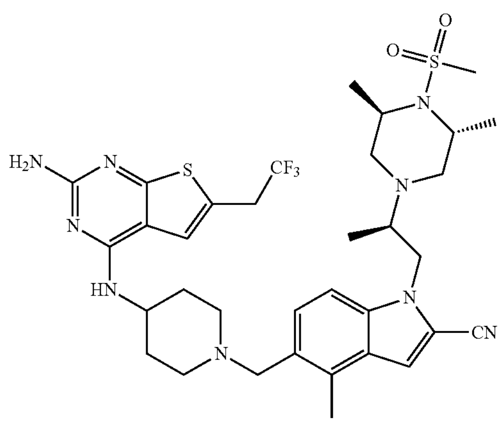 [SMILES: Cc1c(CN2CCC(Nc3nc(N)nc4sc(CC(F)(F)F)cc34)CC2)ccc2c1cc(C#N)n2C[C@@H](C)N1C[C@@H](C)N(S(C)(=O)=O)[C@H](C)C1] | 731.30 | 732.50 [M + H]+ |
| 181 | 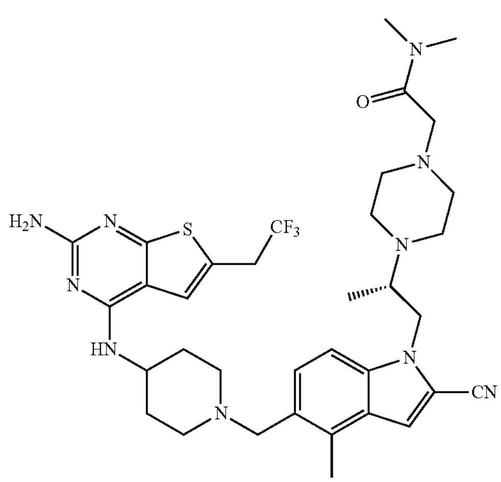 [SMILES: Cc1c(CN2CCC(Nc3nc(N)nc4sc(CC(F)(F)F)cc34)CC2)ccc2c1cc(C#N)n2C[C@H](C)N1CCN(CC(=O)N(C)C)CC1] | 710.35 | 711.50 [M + H]+ |

TABLE 1-continued

| No | Structure | MW (calc'd) | m/z (found) |
|---|---|---|---|
| 182 | 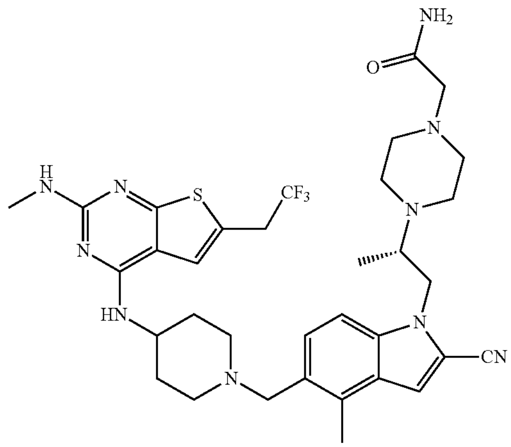 [SMILES: CNc1nc(NC2CCN(Cc3ccc4c(cc(C#N)n4C[C@H](C)N4CCN(CC(N)=O)CC4)c3C)CC2)c2cc(CC(F)(F)F)sc2n1] | 696.33 | 697.60 [M + H]+ |
| 183 | 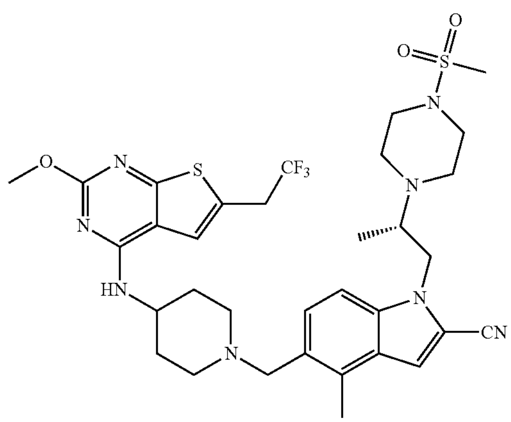 | 718.27 | 719.45 [M + H]+ |
| 184 | 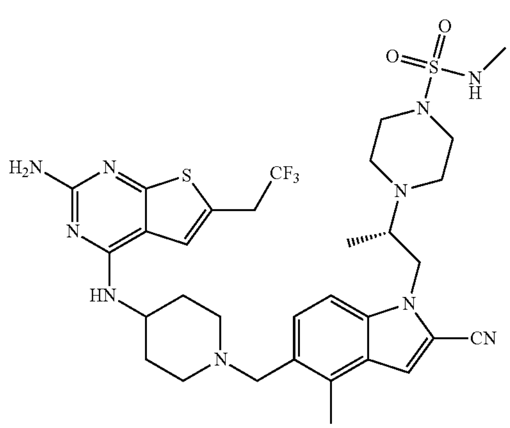 [SMILES: CNS(=O)(=O)N1CCN([C@@H](C)Cn2c(C#N)cc3c(C)c(CN4CCC(Nc5nc(N)nc6sc(CC(F)(F)F)cc56)CC4)ccc32)CC1] | 717.29 | 718.45 [M + H]+ |

TABLE 1-continued

| No | Structure | MW (calc'd) | m/z (found) |
|---|---|---|---|
| 185 | 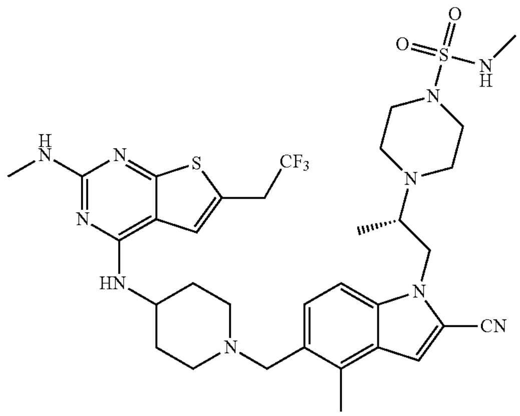 | 731.30 | 732.45 [M + H]+ |
| 186 | 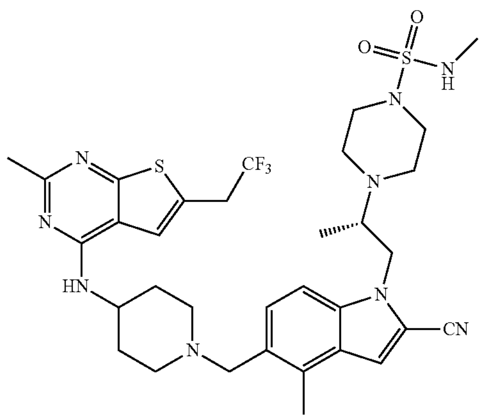 | 716.29 | 717.45 [M + H]+ |
| 187 | 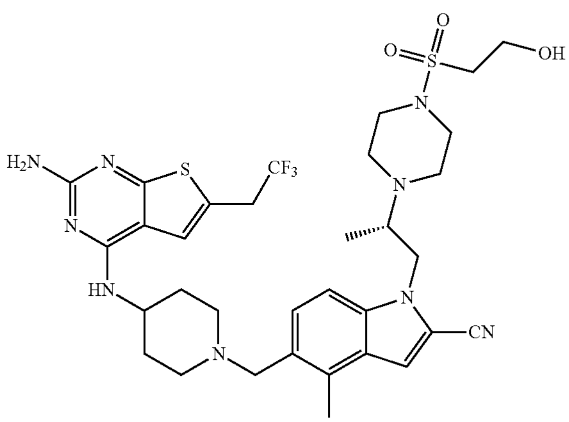 [SMILES: Cc1c(CN2CCC(Nc3nc(N)nc4sc(CC(F)(F)F)cc34)CC2)ccc2c1cc(C#N)n2C[C@H](C)N1CCN(S(=O)(=O)CCO)CC1] | 733.28 | 734.45 [M + H]+ |
| 188 | 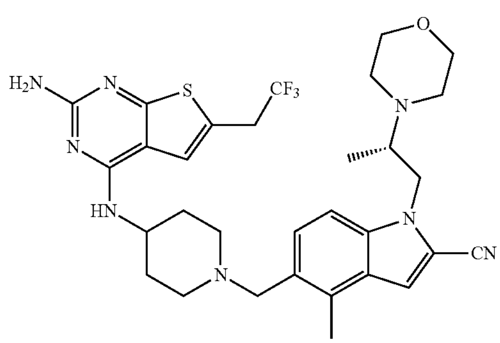 [SMILES: Cc1c(CN2CCC(Nc3nc(N)nc4sc(CC(F)(F)F)cc34)CC2)ccc2c1cc(C#N)n2C[C@H](C)N1CCOCC1] | 626.28 | 627.40 [M + H]+ |

TABLE 1-continued

| No | Structure | MW (calc'd) | m/z (found) |
|---|---|---|---|
| 189 | 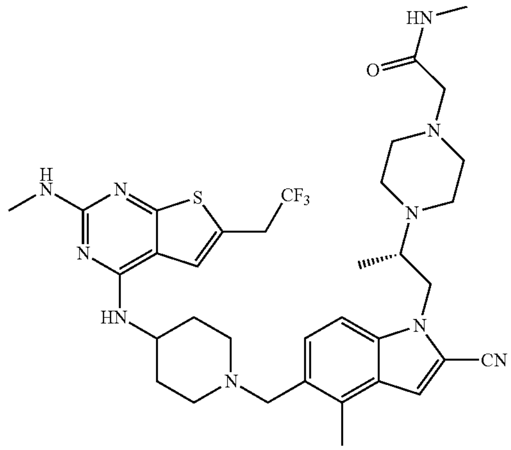 [SMILES: CNC(=O)CN1CCN([C@@H](C)Cn2c(C#N)cc3c(C)c(CN4CCC(Nc5nc(NC)nc6sc(CC(F)(F)F)cc56)CC4)ccc32)CC1] | 710.35 | 711.45 [M + H]+ |
| 190 | 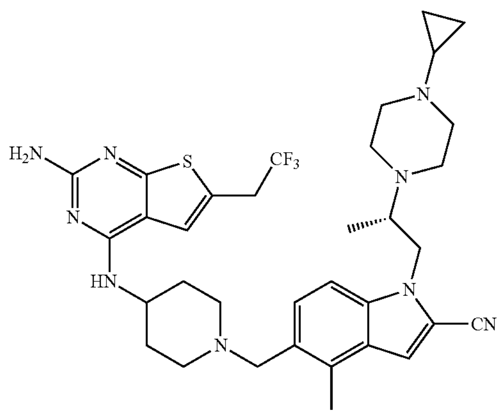 [SMILES: Cc1c(CN2CCC(Nc3nc(N)nc4sc(CC(F)(F)F)cc34)CC2)ccc2c1cc(C#N)n2C[C@H](C)N1CCN(C2CC2)CC1] | 665.32 | 666.45 [M + H]+ |
| 191 | 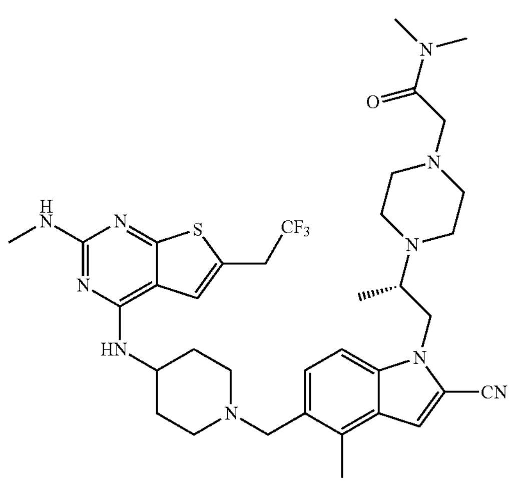 [SMILES: CNc1nc(NC2CCN(Cc3ccc4c(cc(C#N)n4C[C@H](C)N4CCN(CC(=O)N(C)C)CC4)c3C)CC2)c2cc(CC(F)(F)F)sc2n1] | 724.36 | 725.45 [M + H]+ |

TABLE 1-continued

| No | Structure | MW (calc'd) | m/z (found) |
|---|---|---|---|
| 192 | 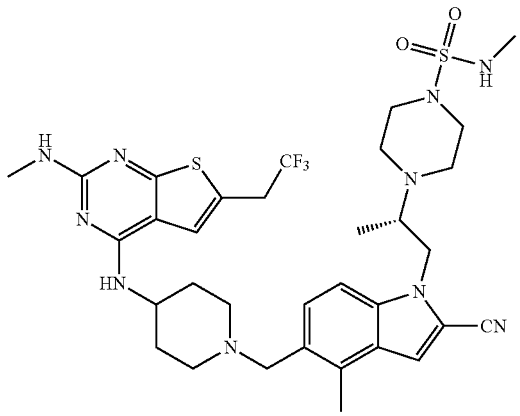 | 732.30 | 733.45 [M + H]⁺ |
| 193 | 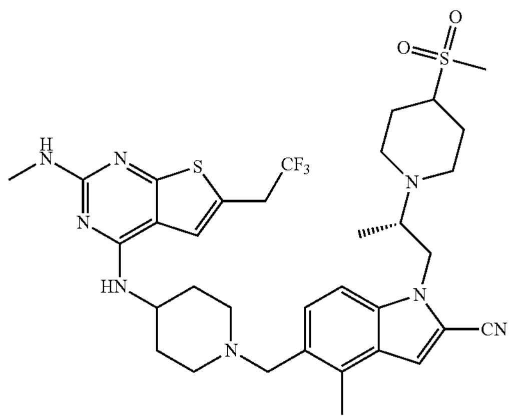 | 716.29 | 717.45 [M + H]⁺ |
| 194 | 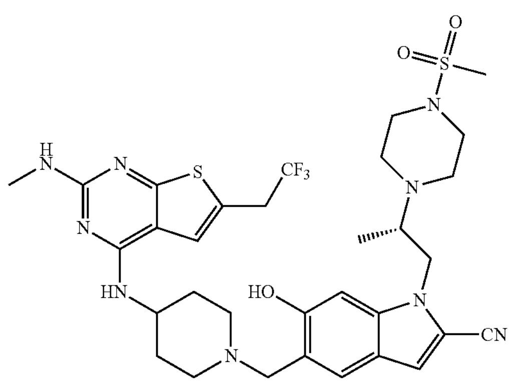 [SMILES: CNc1nc(NC2CCN(Cc3cc4cc(C#N)n(C[C@H](C)N5CCN(S(C)(=O)=O)CC5)c4cc3O)CC2)c2cc(CC(F)(F)F)sc2n1] | 719.26 | 720.55 [M + H]⁺ |
| 195 | 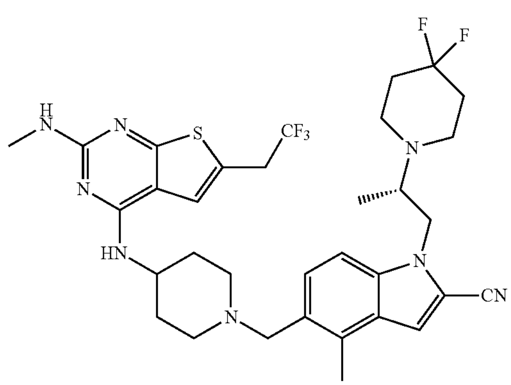 [SMILES: CNc1nc(NC2CCN(Cc3ccc4c(cc(C#N)n4C[C@H](C)N4CCC(F)(F)CC4)c3C)CC2)c2cc(CC(F)(F)F)sc2n1] | 674.29 | 675.50 [M + H]⁺ |

TABLE 1-continued
| No | Structure | MW (calc'd) | m/z (found) |
|---|---|---|---|
| 196 | 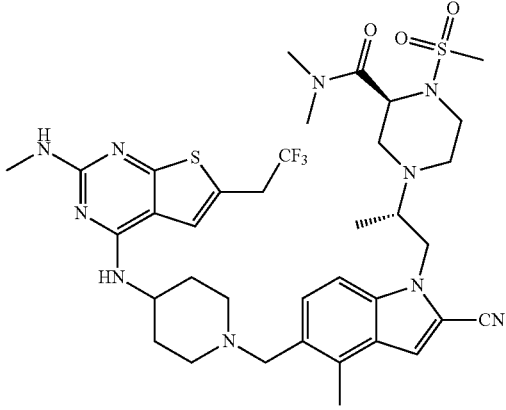 [SMILES: CNc1nc(NC2CCN(Cc3ccc4c(cc(C#N)n4C[C@H](C)N4CCN(S(C)(=O)=O)[C@H](C(=O)N(C)C)C4)c3C)CC2)c2cc(CC(F)(F)F)sc2n1] | 788.32 | 789.45 [M + H]+ |
| 197 | 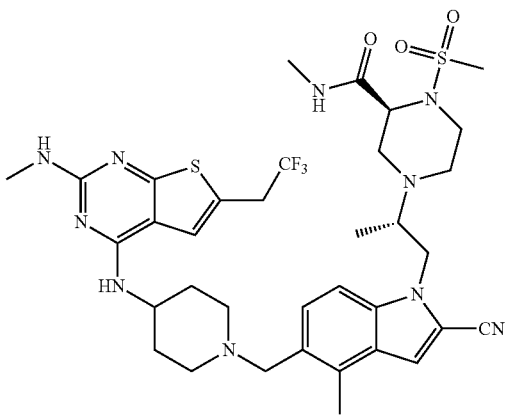 [SMILES: CNC(=O)[C@@H]1CN([C@@H](C)Cn2c(C#N)cc3c(C)c(CN4CCC(Nc5nc(NC)nc6sc(CC(F)(F)F)cc56)CC4)ccc32)CCN1S(C)(=O)=O] | 774.31 | 775.3 [M + H]+ |
| 198 | 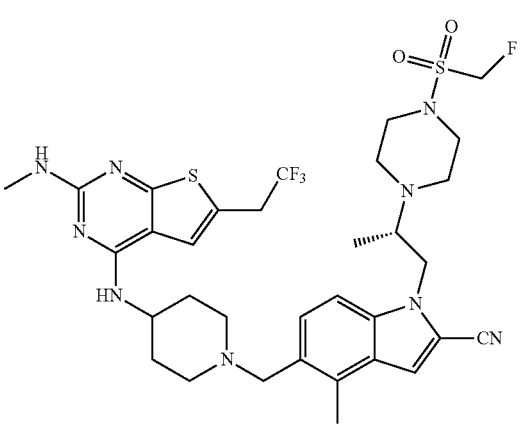 [SMILES: CNc1nc(NC2CCN(Cc3ccc4c(cc(C#N)n4C[C@H](C)N4CCN(S(=O)(=O)CF)CC4)c3C)CC2)c2cc(CC(F)(F)F)sc2n1] | 735.28 | 736.45 [M + H]+ |

TABLE 1-continued

| No | Structure | MW (calc'd) | m/z (found) |
|---|---|---|---|
| 199 | 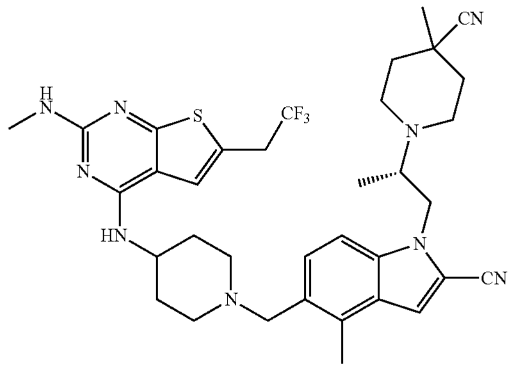 [SMILES: CNc1nc(NC2CCN(Cc3ccc4c(cc(C#N)n4C[C@H](C)N4CCC(C)(C#N)CC4)c3C)CC2)c2cc(CC(F)(F)F)sc2n1] | 677.32 | 678.55 [M + H]+ |
| 200 | 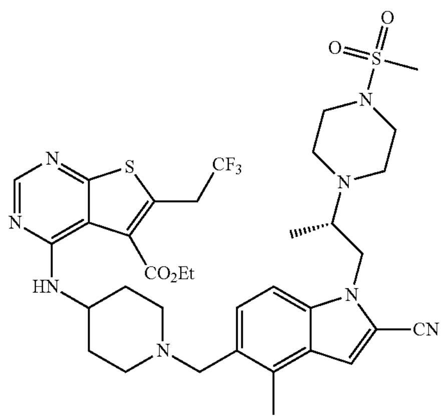 | 760.28 | 761.40 [M + H]+ |
| 201 | 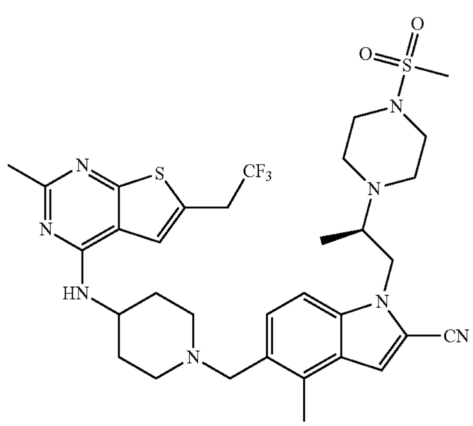 [SMILES: Cc1nc(NC2CCN(Cc3ccc4c(cc(C#N)n4C[C@@H](C)N4CCN(S(C)(=O)=O)CC4)c3C)CC2)c2cc(CC(F)(F)F)sc2n1] | 702.27 | 703.45 [M + H]+ |

TABLE 1-continued

| No | Structure | MW (calc'd) | m/z (found) |
|---|---|---|---|
| 202 | 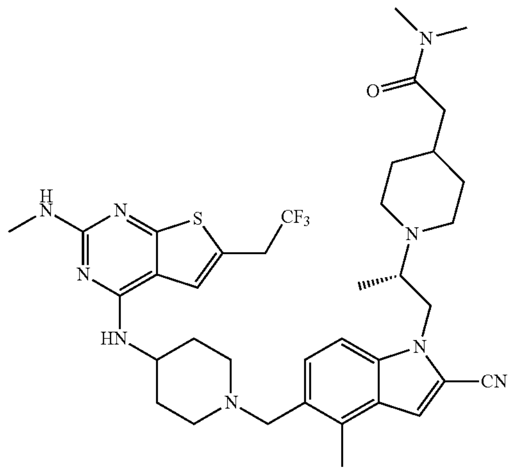 [SMILES: CNc1nc(NC2CCN(Cc3ccc4c(cc(C#N)n4C[C@H](C)N4CCC(CC(=O)N(C)C)CC4)c3C)CC2)c2cc(CC(F)(F)F)sc2n1] | 723.37 | 724.55 [M + H]+ |
| 203 | 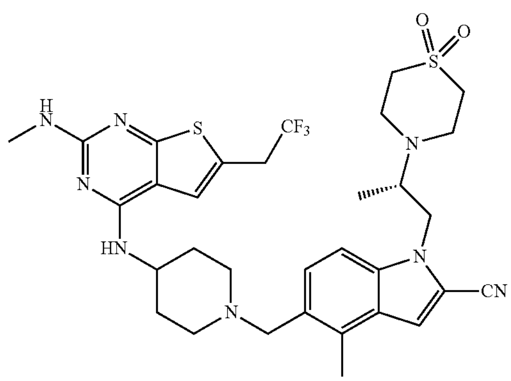 [SMILES: CNc1nc(NC2CCN(Cc3ccc4c(cc(C#N)n4C[C@H](C)N4CCS(=O)(=O)CC4)c3C)CC2)c2cc(CC(F)(F)F)sc2n1] | 688.26 | 689.40 [M + H]+ |
| 204 | 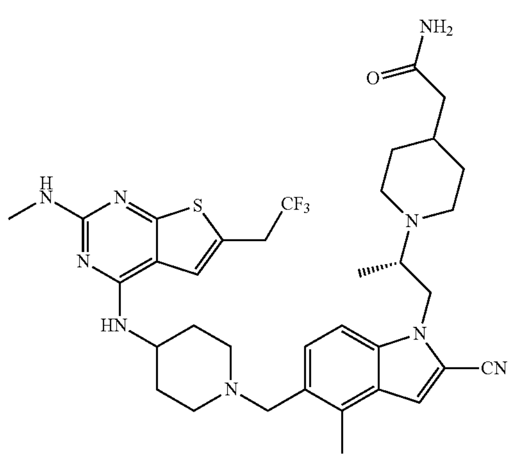 | 695.33 | 696.60 [M + H]+ |

TABLE 1-continued

| No | Structure | MW (calc'd) | m/z (found) |
|---|---|---|---|
| 205 | 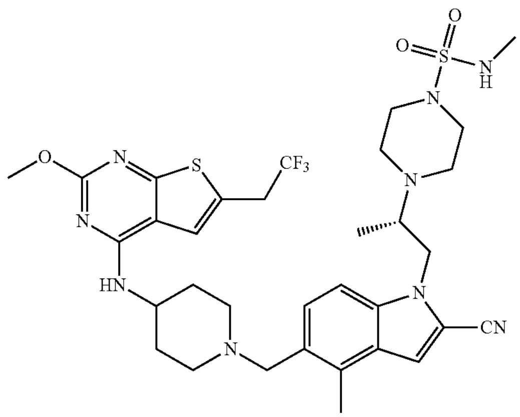 | 733.28 | 734.55 [M + H]+ |
| 206 | 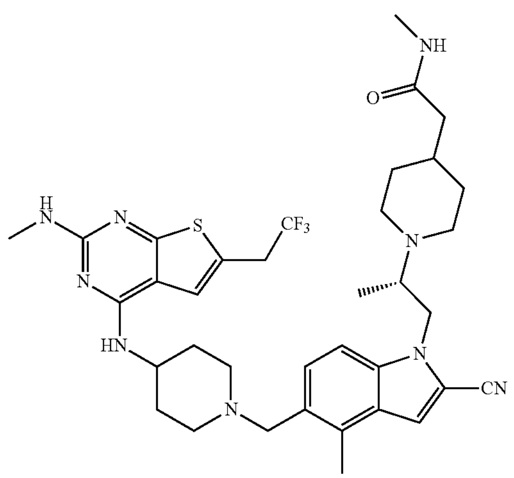 [SMILES: CNC(=O)CC1CCN([C@@H](C)Cn2c(C#N)cc3c(C)c(CN4CCC(Nc5nc(NC)nc6sc(CC(F)(F)F)cc56)CC4)ccc32)CC1] | 709.35 | 710.55 [M + H]+ |
| 207 | 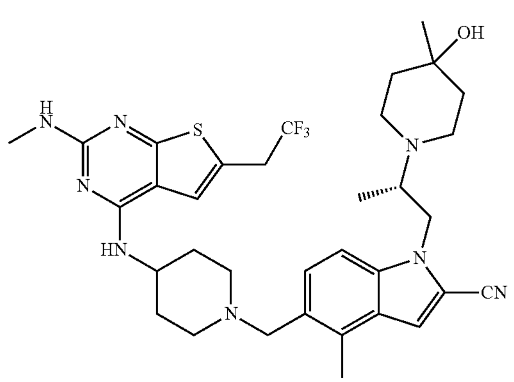 | 668.32 | 669.55 [M + H]+ |

TABLE 1-continued

| No | Structure | MW (calc'd) | m/z (found) |
|---|---|---|---|
| 208 | 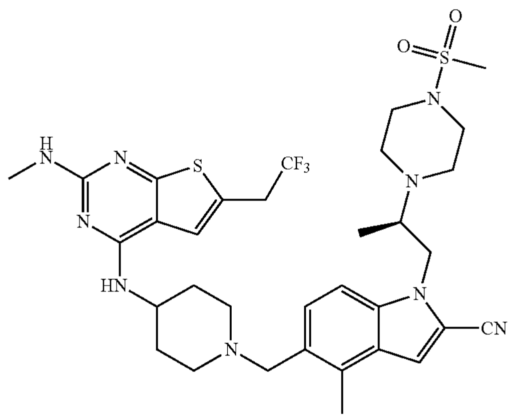 [SMILES: CNc1nc(NC2CCN(Cc3ccc4c(cc(C#N)n4C[C@@H](C)N4CCN(S(C)(=O)=O)CC4)c3C)CC2)c2cc(CC(F)(F)F)sc2n1] | 717.29 | 718.40 [M + H]+ |
| 209 | 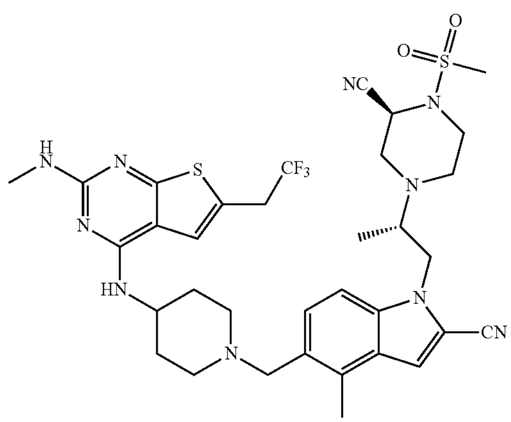 [SMILES: CNc1nc(NC2CCN(Cc3ccc4c(cc(C#N)n4C[C@H](C)N4CCN(S(C)(=O)=O)[C@H](C#N)C4)c3C)CC2)c2cc(CC(F)(F)F)sc2n1] | 742.28 | 743.40 [M + H]+ |
| 210 | 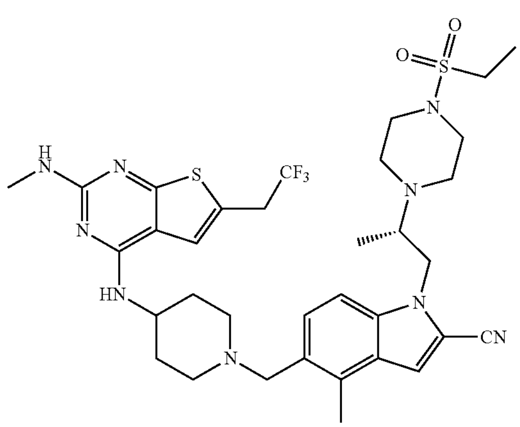 [SMILES: CCS(=O)(=O)N1CCN([C@@H](C)Cn2c(C#N)cc3c(C)c(CN4CCC(Nc5nc(NC)nc6sc(CC(F)(F)F)cc56)CC4)ccc32)CC1] | 731.30 | 732.40 [M + H]+ |

TABLE 1-continued

| No | Structure | MW (calc'd) | m/z (found) |
|---|---|---|---|
| 211 | 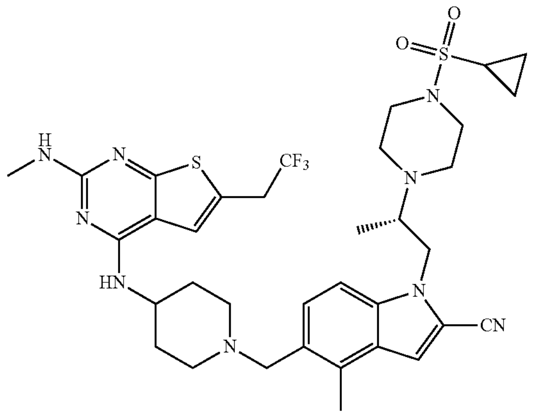 [SMILES: CNc1nc(NC2CCN(Cc3ccc4c(cc(C#N)n4C[C@H](C)N4CCN(S(=O)(=O)C5CC5)CC4)c3C)CC2)c2cc(CC(F)(F)F)sc2n1] | 743.30 | 744.40 [M + H]+ |
| 212 | 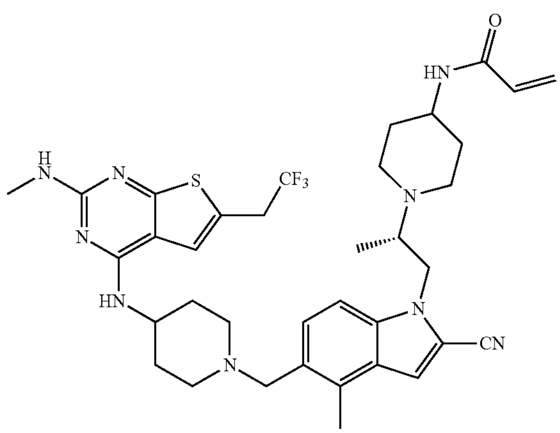 [SMILES: C=CC(=O)NC1CCN([C@@H](C)Cn2c(C#N)cc3c(C)c(CN4CCC(Nc5nc(NC)nc6sc(CC(F)(F)F)cc56)CC4)ccc32)CC1] | 707.33 | 708.45 [M + H]+ |
| 213 | 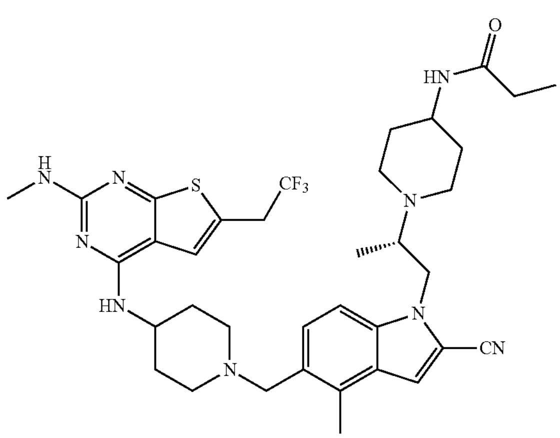 [SMILES: CCC(=O)NC1CCN([C@@H](C)Cn2c(C#N)cc3c(C)c(CN4CCC(Nc5nc(NC)nc6sc(CC(F)(F)F)cc56)CC4)ccc32)CC1] | 709.35 | 710.50 [M + H]+ |

TABLE 1-continued

| No | Structure | MW (calc'd) | m/z (found) |
|---|---|---|---|
| 214 | 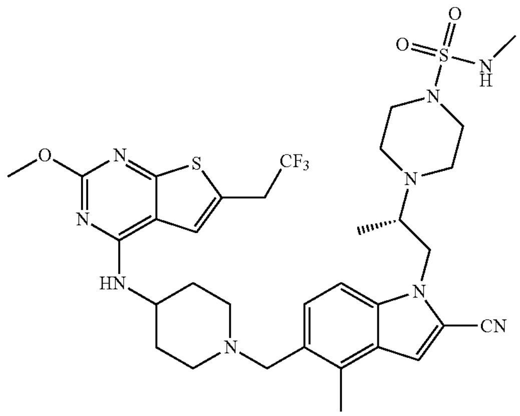 | 732.29 | 733.40 [M + H]+ |
| 215 | 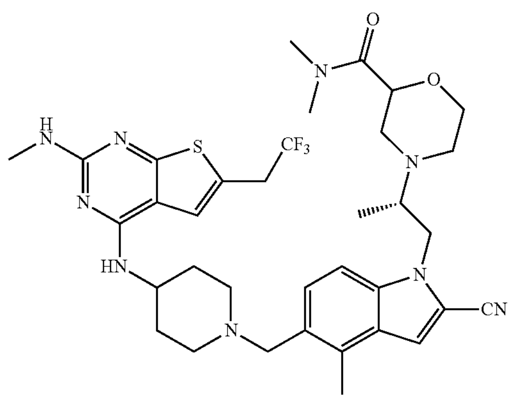 [SMILES: CNc1nc(NC2CCN(Cc3ccc4c(cc(C#N)n4C[C@H](C)N4CCOC(C(=O)N(C)C)C4)c3C)CC2)c2cc(CC(F)(F)F)sc2n1] | 711.33 | 712.45 [M + H]+ |
| 216 | 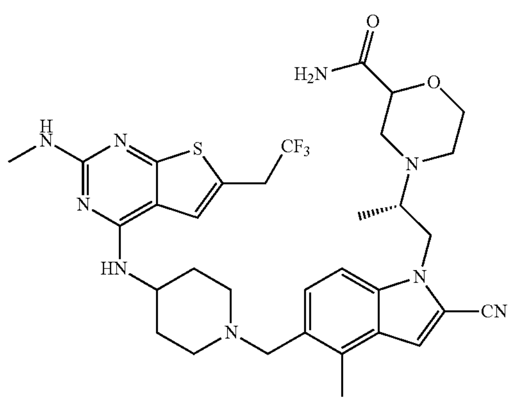 [SMILES: CNc1nc(NC2CCN(Cc3ccc4c(cc(C#N)n4C[C@H](C)N4CCOC(C(N)=O)C4)c3C)CC2)c2cc(CC(F)(F)F)sc2n1] | 683.30 | 684.45 [M + H]+ |
| 217 | 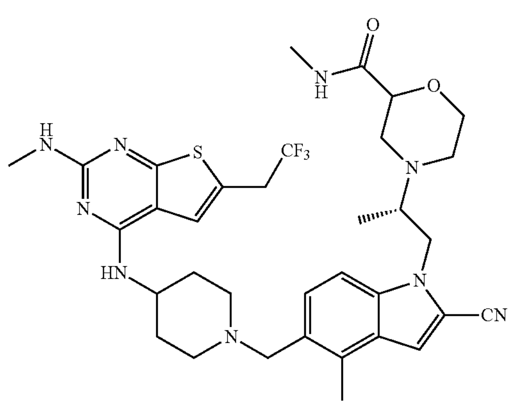 [SMILES: CNC(=O)C1CN([C@@H](C)Cn2c(C#N)cc3c(C)c(CN4CCC(Nc5nc(NC)nc6sc(CC(F)(F)F)cc56)CC4)ccc32)CCO1] | 697.31 | 698.3 [M + H]+ |

TABLE 1-continued

| No | Structure | MW (calc'd) | m/z (found) |
|---|---|---|---|
| 218 | 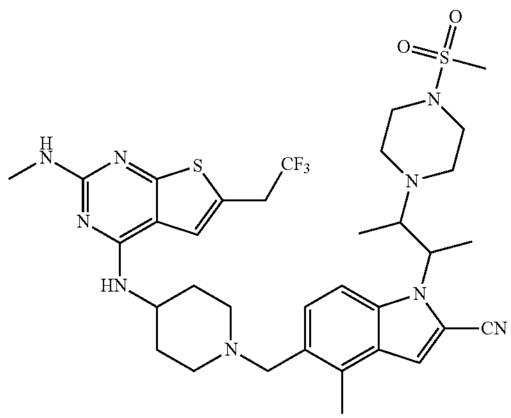 [SMILES: CNc1nc(NC2CCN(Cc3ccc4c(cc(C#N)n4C(C)C(C)N4CCN(S(C)(=O)=O)CC4)c3C)CC2)c2cc(CC(F)(F)F)sc2n1] | | |
| 219 | 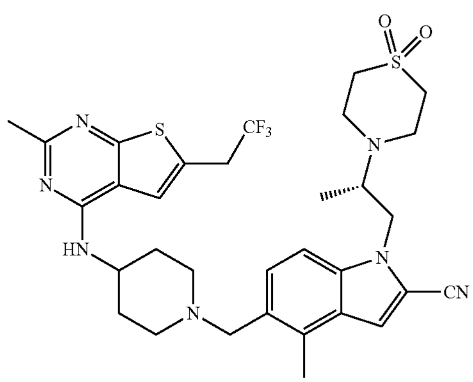 [SMILES: Cc1nc(NC2CCN(Cc3ccc4c(cc(C#N)n4C[C@H](C)N4CCS(=O)(=O)CC4)c3C)CC2)c2cc(CC(F)(F)F)sc2n1] | 673.25 | 674.2 [M + H]+ |
| 220 | 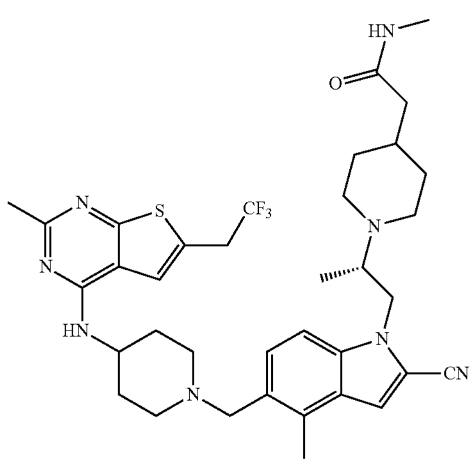 [SMILES: CNC(=O)CC1CCN([C@@H](C)Cn2c(C#N)cc3c(C)c(CN4CCC(Nc5nc(C)nc6sc(CC(F)(F)F)cc56)CC4)ccc32)CC1] | 694.34 | 695.50 [M + H]+ |

TABLE 1-continued
| No | Structure | MW (calc'd) | m/z (found) |
|---|---|---|---|
| 221 | 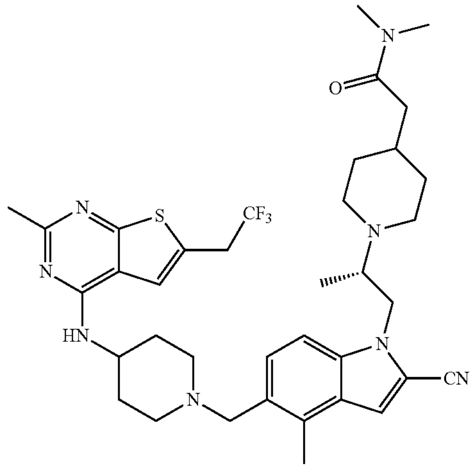 [SMILES: Cc1nc(NC2CCN(Cc3ccc4c(cc(C#N)n4C[C@H](C)N4CCC(CC(=O)N(C)C)CC4)c3C)CC2)c2cc(CC(F)(F)F)sc2n1] | 708.35 | 709.50 [M + H]+ |
| 222 | 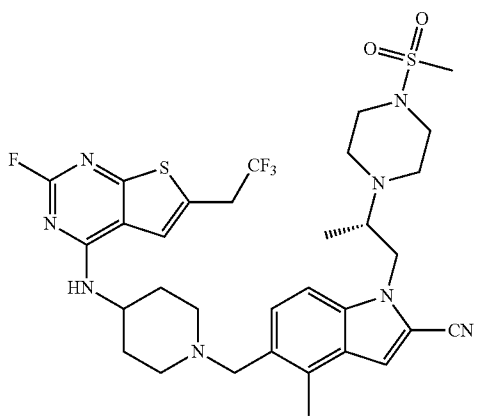 [SMILES: Cc1c(CN2CCC(Nc3nc(F)nc4sc(CC(F)(F)F)cc34)CC2)ccc2c1cc(C#N)n2C[C@H](C)N1CCN(S(C)(=O)=O)CC1] | 706.25 | 707.2561 |
| 225 | 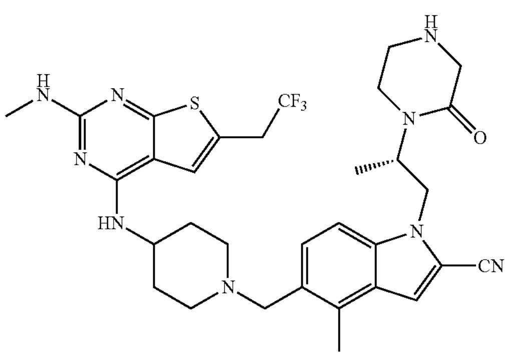 [SMILES: CNc1nc(NC2CCN(Cc3ccc4c(cc(C#N)n4C[C@H](C)N4CCNCC4=O)c3C)CC2)c2cc(CC(F)(F)F)sc2n1] | | |
| 226 | 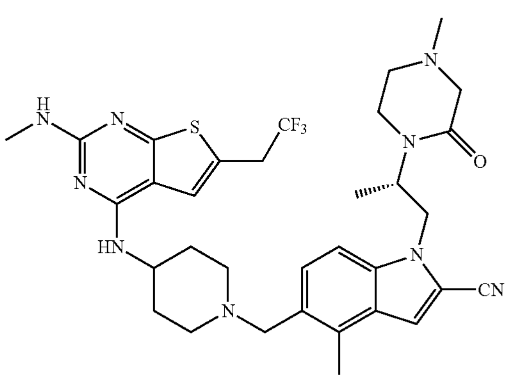 [SMILES: CNc1nc(NC2CCN(Cc3ccc4c(cc(C#N)n4C[C@H](C)N4CCN(C)CC4=O)c3C)CC2)c2cc(CC(F)(F)F)sc2n1] | | |

| No | Structure | MW (calc'd) | m/z (found) |
|----|-----------|-------------|-------------|
| 228 | 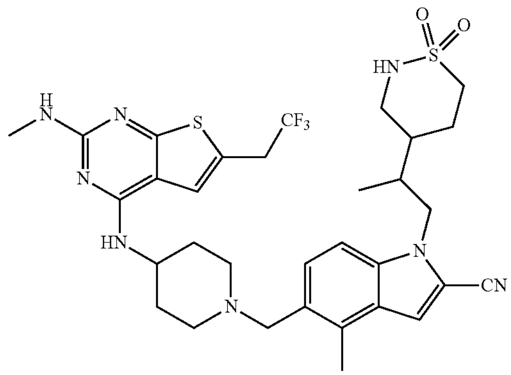 [SMILES: CNc1nc(NC2CCN(Cc3ccc4c(cc(C#N)n4CC(C)C4CCS(=O)(=O)NC4)c3C)CC2)c2cc(CC(F)(F)F)sc2n1] | | |
| 229 | 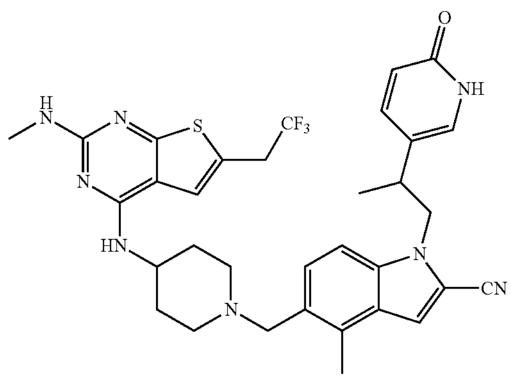 [SMILES: CNc1nc(NC2CCN(Cc3ccc4c(cc(C#N)n4CC(C)c4ccc(=O)[nH]c4)c3C)CC2)c2cc(CC(F)(F)F)sc2n1] | 648.26 | |
| 230 | 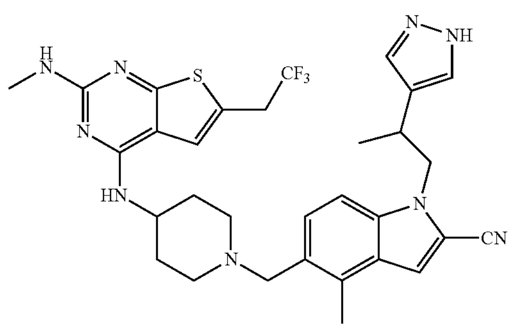 [SMILES: CNc1nc(NC2CCN(Cc3ccc4c(cc(C#N)n4CC(C)c4cn[nH]c4)c3C)CC2)c2cc(CC(F)(F)F)sc2n1] | 621.26 | 622.2 [M + H]+ |
| 231 | 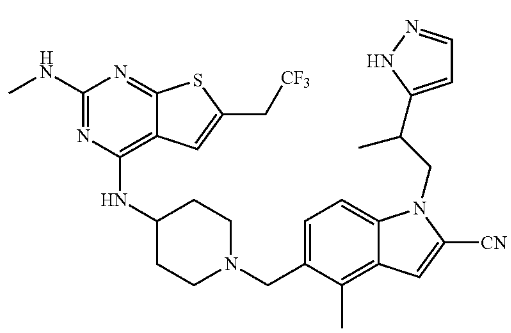 [SMILES: CNc1nc(NC2CCN(Cc3ccc4c(cc(C#N)n4CC(C)c4ccn[nH]4)c3C)CC2)c2cc(CC(F)(F)F)sc2n1] | | |

TABLE 1-continued

| No | Structure | MW (calc'd) | m/z (found) |
|---|---|---|---|
| 232 | 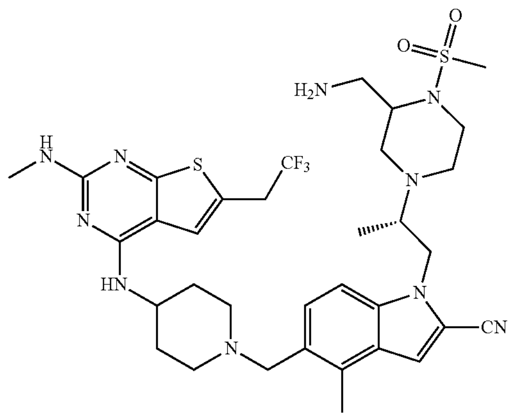 [SMILES: CNc1nc(NC2CCN(Cc3ccc4c(cc(C#N)n4C[C@H](C)N4CCN(S(C)(=O)=O)C(CN)C4)c3C)CC2)c2cc(CC(F)(F)F)sc2n1] | | |
| 233 | 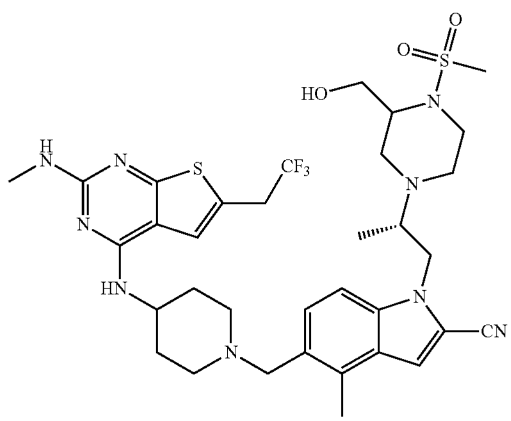 [SMILES: CNc1nc(NC2CCN(Cc3ccc4c(cc(C#N)n4C[C@H](C)N4CCN(S(C)(=O)=O)C(CO)C4)c3C)CC2)c2cc(CC(F)(F)F)sc2n1] | | |
| 234 | 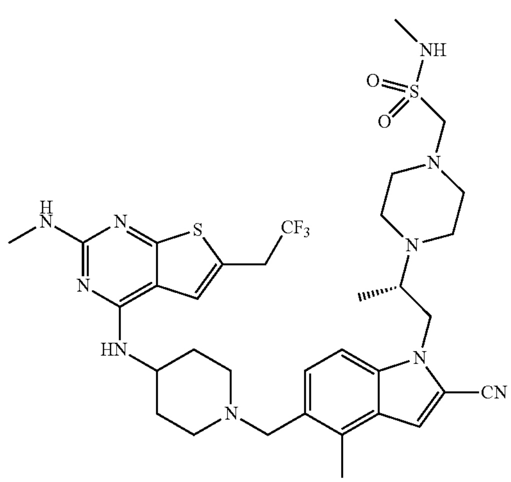 [SMILES: CNc1nc(NC2CCN(Cc3ccc4c(cc(C#N)n4C[C@H](C)N4CCN(CS(=O)(=O)NC)CC4)c3C)CC2)c2cc(CC(F)(F)F)sc2n1] | | |

TABLE 1-continued

| No | Structure | MW (calc'd) | m/z (found) |
|---|---|---|---|
| 235 | 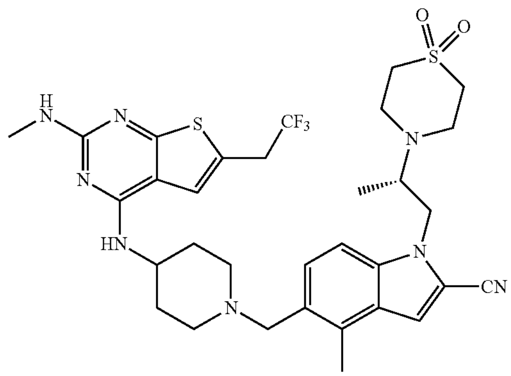 [SMILES: CNc1nc(NC2CCN(Cc3ccc4c(cc(C#N)n4C[C@H](C)N4CCS(=O)(=O)CC4)c3C)CC2)c2cc(CC(F)(F)F)sc2n1] | 688.26 | 689.40 [M + H]+ |
| 236 | 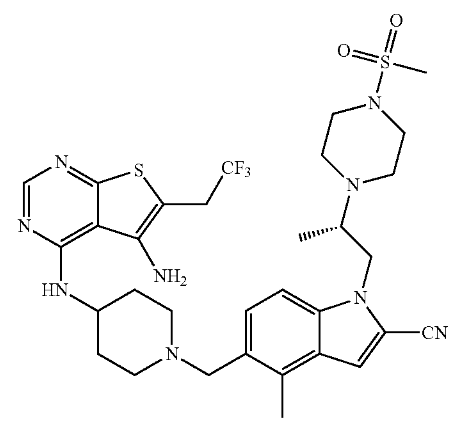 [SMILES: Cc1c(CN2CCC(Nc3ncnc4sc(CC(F)(F)F)c(N)c34)CC2)ccc2c1cc(C#N)n2C[C@H](C)N1CCN(S(C)(=O)=O)CC1] | | |
| 237 | 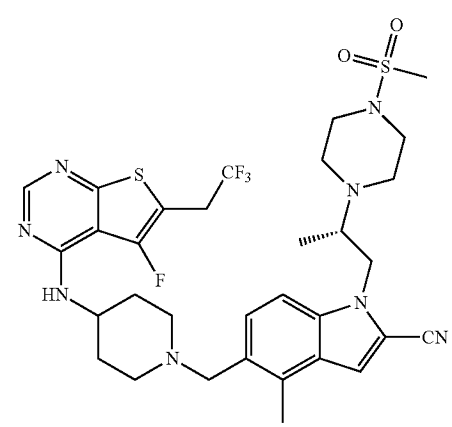 [SMILES: Cc1c(CN2CCC(Nc3ncnc4sc(CC(F)(F)F)c(F)c34)CC2)ccc2c1cc(C#N)n2C[C@H](C)N1CCN(S(C)(=O)=O)CC1] | | |

TABLE 1-continued

| No | Structure | MW (calc'd) | m/z (found) |
|---|---|---|---|
| 238 | 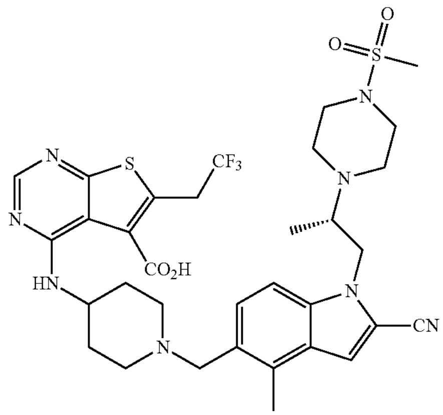 [SMILES: Cc1c(CN2CCC(Nc3ncnc4sc(CC(F)(F)F)c(C(=O)O)c34)CC2)ccc2c1cc(C#N)n2C[C@H](C)N1CCN(S(C)(=O)=O)CC1] | | |
| 239 | 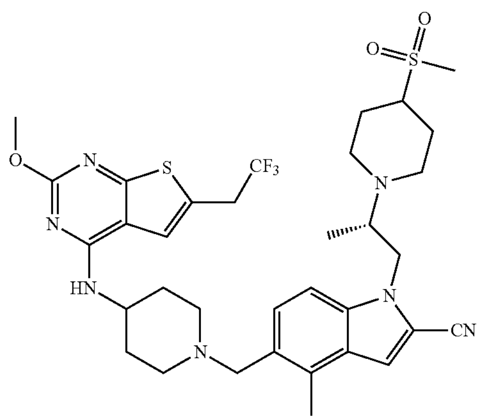 [SMILES: COc1nc(NC2CCN(Cc3ccc4c(cc(C#N)n4C[C@H](C)N4CCC(S(C)(=O)=O)CC4)c3C)CC2)c2cc(CC(F)(F)F)sc2n1] | 717.27 | 718.45 [M + H]+ |
| 240 | 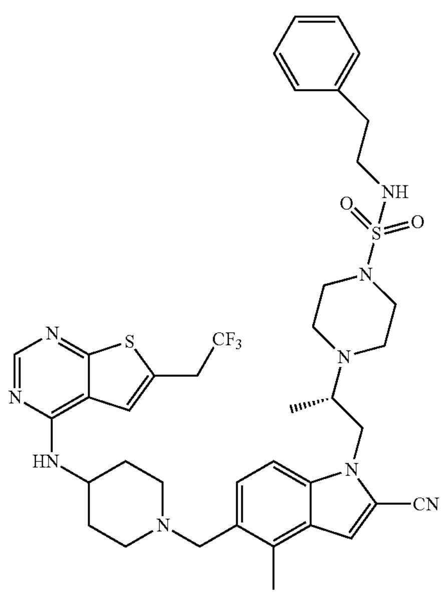 [SMILES: Cc1c(CN2CCC(Nc3ncnc4sc(CC(F)(F)F)cc34)CC2)ccc2c1cc(C#N)n2C[C@H](C)N1CCN(S(=O)(=O)NCCc2ccccc2)CC1] | 793.32 | 794.3244 |

TABLE 1-continued
| No | Structure | MW (calc'd) | m/z (found) |
|---|---|---|---|
| 241 | 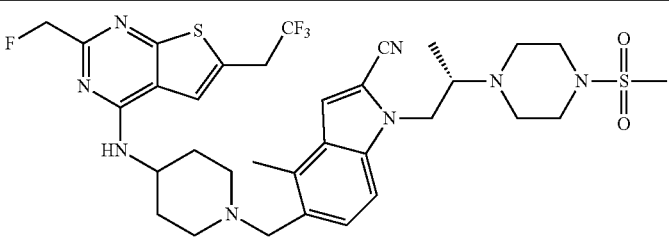 | 720.27 | 721.35 |
| 242 | 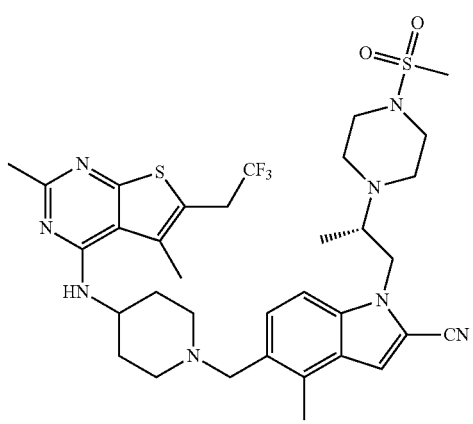 [SMILES: Cc1nc(NC2CCN(Cc3ccc4c(cc(C#N)n4C[C@H](C)N4CCN(S(C)(=O)=O)CC4)c3C)CC2)c2c(C)c(CC(F)(F)F)sc2n1] | 716.29 | 717.3 [M + H]+ |
| 243 | 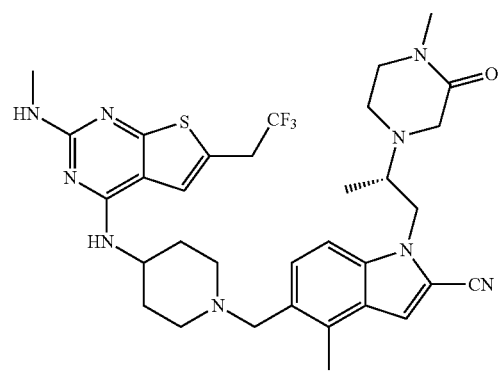 [SMILES: CNc1nc(NC2CCN(Cc3ccc4c(cc(C#N)n4C[C@H](C)N4CCN(C)C(=O)C4)c3C)CC2)c2cc(CC(F)(F)F)sc2n1] | 667.30 | 668.45 [M + H]+ |
| 244 | 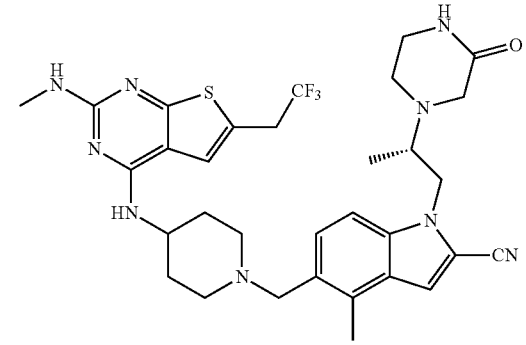 [SMILES: CNc1nc(NC2CCN(Cc3ccc4c(cc(C#N)n4C[C@H](C)N4CCNC(=O)C4)c3C)CC2)c2cc(CC(F)(F)F)sc2n1] | 653.29 | 654.45 [M + H]+ |

TABLE 1-continued

| No | Structure | MW (calc'd) | m/z (found) |
|---|---|---|---|
| 245 | 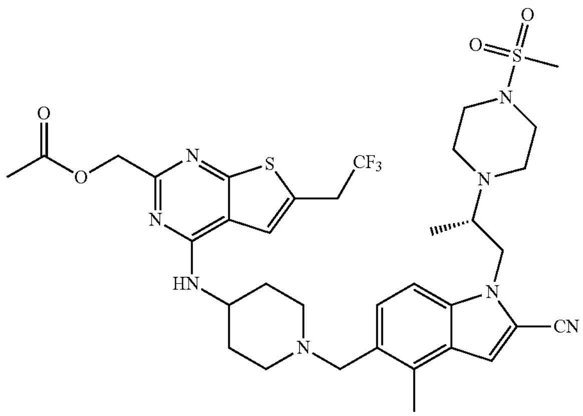 [SMILES: CC(=O)OCc1nc(NC2CCN(Cc3ccc4c(cc(C#N)n4C[C@H](C)N4CCN(S(C)(=O)=O)CC4)c3C)CC2)c2cc(CC(F)(F)F)sc2n1] | 760.28 | 761.2872 |
| 246 | 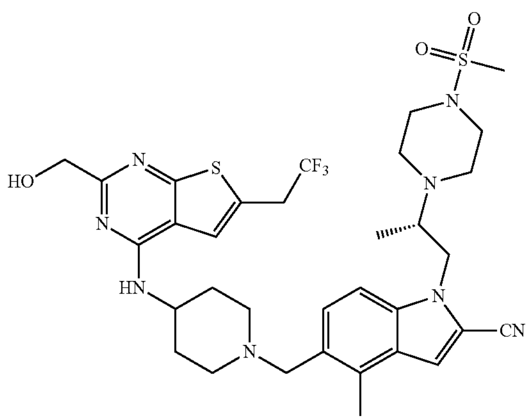 [SMILES: Cc1c(CN2CCC(Nc3nc(CO)nc4sc(CC(F)(F)F)cc34)CC2)ccc2c1cc(C#N)n2C[C@H](C)N1CCN(S(C)(=O)=O)CC1] | 718.27 | 719.2776 |
| 247 | 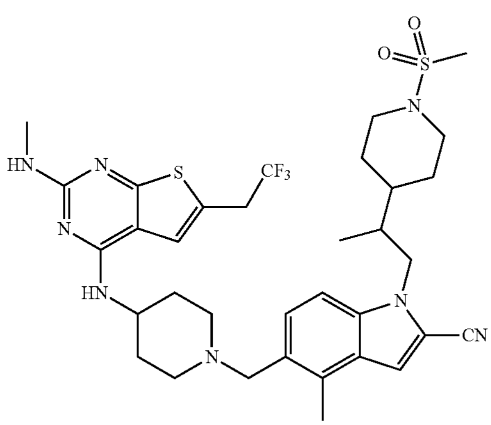 [SMILES: CNc1nc(NC2CCN(Cc3ccc4c(cc(C#N)n4CC(C)C4CCN(S(C)(=O)=O)CC4)c3C)CC2)c2cc(CC(F)(F)F)sc2n1] | 716.29 | 717.56 [M + H]+ |

TABLE 1-continued

| No | Structure | MW (calc'd) | m/z (found) |
|---|---|---|---|
| 248 | 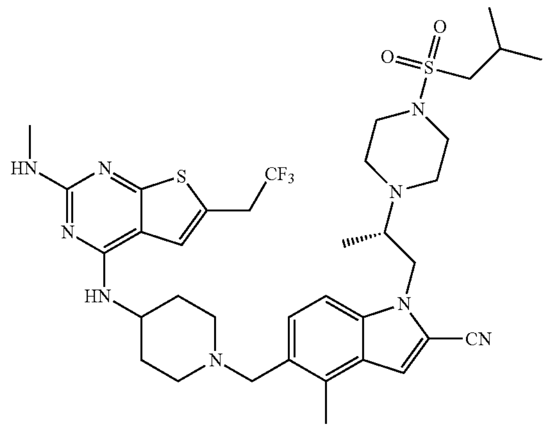 [SMILES: CNc1nc(NC2CCN(Cc3ccc4c(cc(C#N)n4C[C@H](C)N4CCN(S(=O)(=O)CC(C)C)CC4)c3C)CC2)c2cc(CC(F)(F)F)sc2n1] | 759.33 | 760.50 [M + H]+ |
| 249 | 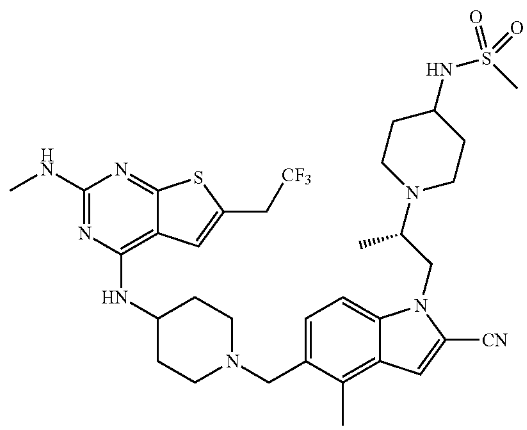 [SMILES: CNc1nc(NC2CCN(Cc3ccc4c(cc(C#N)n4C[C@H](C)N4CCC(NS(C)(=O)=O)CC4)c3C)CC2)c2cc(CC(F)(F)F)sc2n1] | 731.30 | 732.45 [M + H]+ |
| 250 | 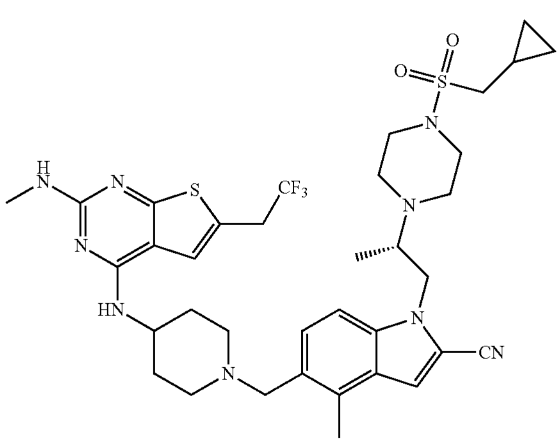 [SMILES: CNc1nc(NC2CCN(Cc3ccc4c(cc(C#N)n4C[C@H](C)N4CCN(S(=O)(=O)CC5CC5)CC4)c3C)CC2)c2cc(CC(F)(F)F)sc2n1] | | |

TABLE 1-continued

| No | Structure | MW (calc'd) | m/z (found) |
|---|---|---|---|
| 251 | 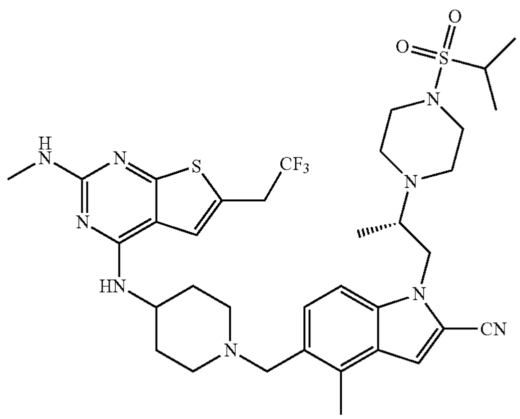 [SMILES: CNc1nc(NC2CCN(Cc3ccc4c(cc(C#N)n4C[C@H](C)N4CCN(S(=O)(=O)C(C)C)CC4)c3C)CC2)c2cc(CC(F)(F)F)sc2n1] | 745.32 | 746.3 [M + H]⁺ |
| 252 | 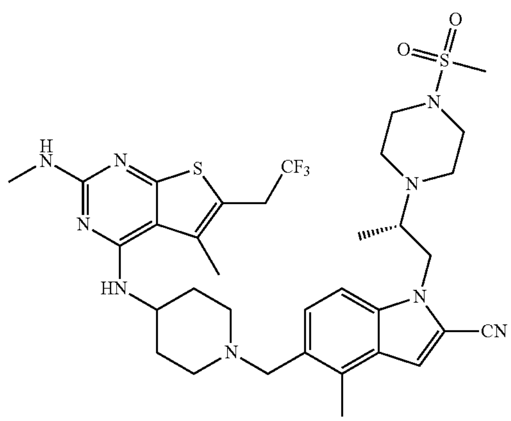 [SMILES: CNc1nc(NC2CCN(Cc3ccc4c(cc(C#N)n4C[C@H](C)N4CCN(S(C)(=O)=O)CC4)c3C)CC2)c2c(C)c(CC(F)(F)F)sc2n1] | 731.30 | 732.3 [M + H]⁺ |
| 253 | 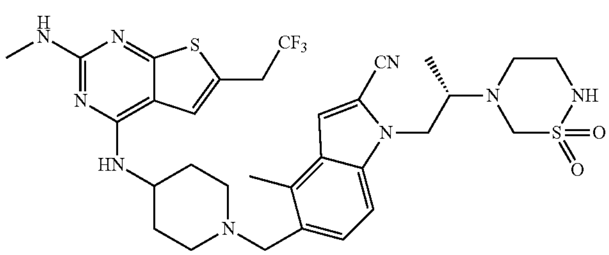 [SMILES: CNc1nc(NC2CCN(Cc3ccc4c(cc(C#N)n4C[C@H](C)N4CCNS(=O)(=O)C4)c3C)CC2)c2cc(CC(F)(F)F)sc2n1] | | |
| 254 | 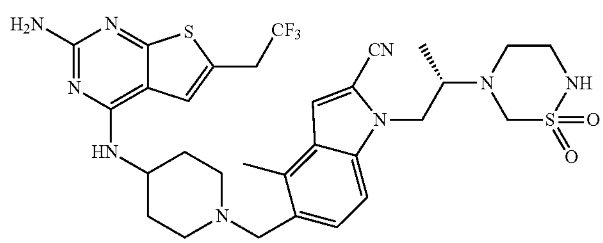 [SMILES: Cc1c(CN2CCC(Nc3nc(N)nc4sc(CC(F)(F)F)cc34)CC2)ccc2c1cc(C#N)n2C[C@H](C)N1CCNS(=O)(=O)C1] | | |
| 255 | 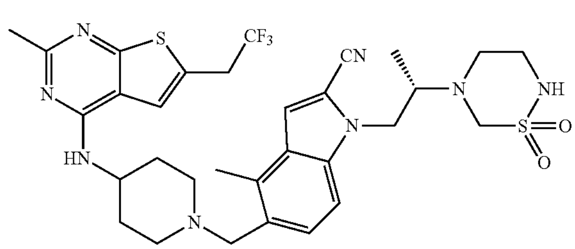 [SMILES: Cc1nc(NC2CCN(Cc3ccc4c(cc(C#N)n4C[C@H](C)N4CCNS(=O)(=O)C4)c3C)CC2)c2cc(CC(F)(F)F)sc2n1] | | |

TABLE 1-continued

| No | Structure | MW (calc'd) | m/z (found) |
|---|---|---|---|
| 256 | 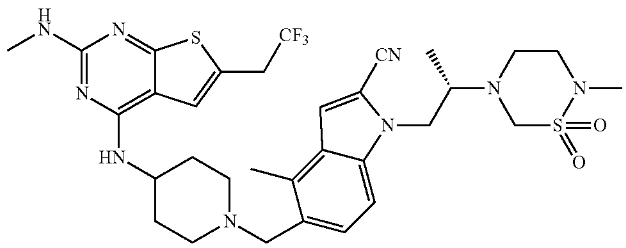 | | |
| 257 | 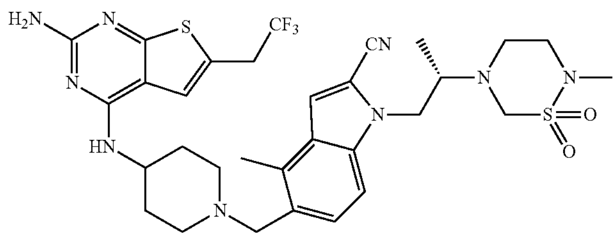 [SMILES: Cc1c(CN2CCC(Nc3nc(N)nc4sc(CC(F)(F)F)cc34)CC2)ccc2c1cc(C#N)n2C[C@H](C)N1CCN(C)S(=O)(=O)C1] | | |
| 258 | 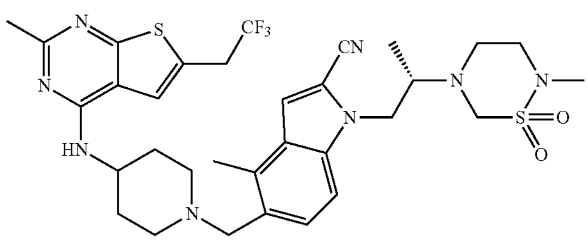 | | |
| 259 | 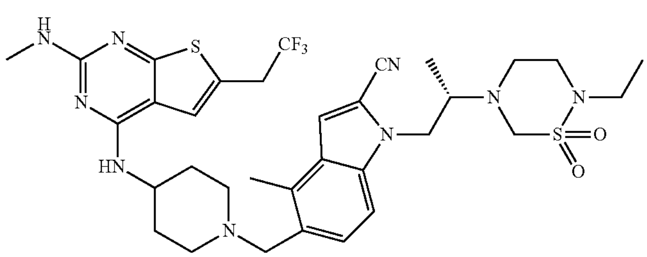 [SMILES: CCN1CCN([C@@H](C)Cn2c(C#N)cc3c(C)c(CN4CCC(Nc5nc(NC)nc6sc(CC(F)(F)F)cc56)CC4)ccc32)CS1(=O)=O] | | |
| 260 | 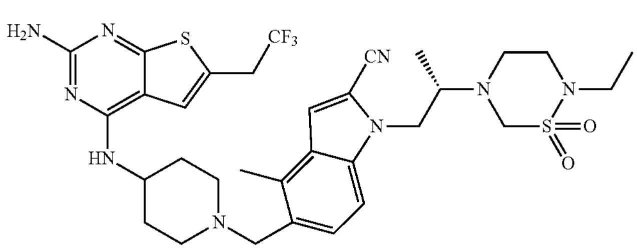 [SMILES: CCN1CCN([C@@H](C)Cn2c(C#N)cc3c(C)c(CN4CCC(Nc5nc(N)nc6sc(CC(F)(F)F)cc56)CC4)ccc32)CS1(=O)=O] | | |
| 261 | 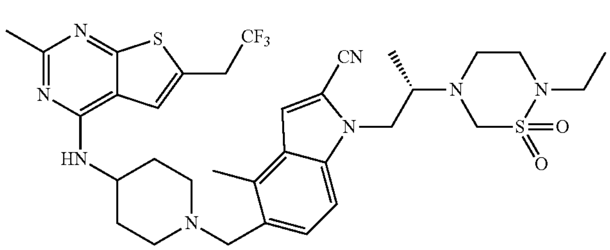 [SMILES: CCN1CCN([C@@H](C)Cn2c(C#N)cc3c(C)c(CN4CCC(Nc5nc(C)nc6sc(CC(F)(F)F)cc56)CC4)ccc32)CS1(=O)=O] | | |

TABLE 1-continued

| No | Structure | MW (calc'd) | m/z (found) |
|---|---|---|---|
| 262 | 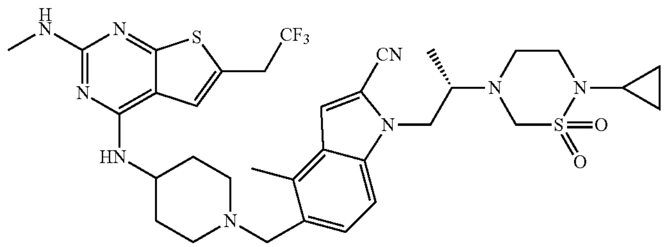 [SMILES: CNc1nc(NC2CCN(Cc3ccc4c(cc(C#N)n4C[C@H](C)N4CCN(C5CC5)S(=O)(=O)C4)c3C)CC2)c2cc(CC(F)(F)F)sc2n1] | | |
| 263 | 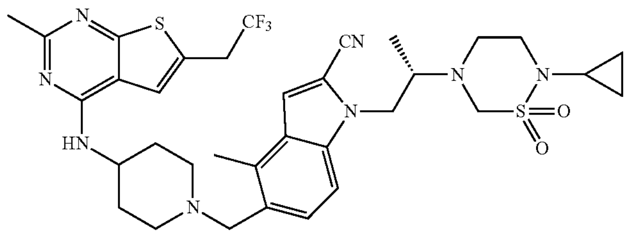 [SMILES: Cc1nc(NC2CCN(Cc3ccc4c(cc(C#N)n4C[C@H](C)N4CCN(C5CC5)S(=O)(=O)C4)c3C)CC2)c2cc(CC(F)(F)F)sc2n1] | | |
| 264 | 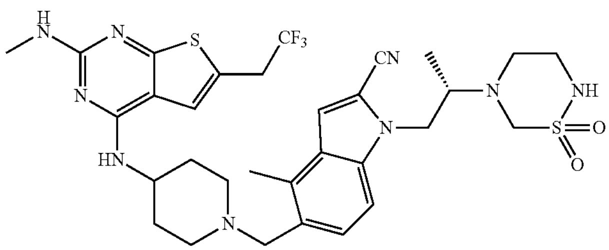 [SMILES: CNc1nc(NC2CCN(Cc3ccc4c(cc(C#N)n4C[C@H](C)N4CCNS(=O)(=O)C4)c3C)CC2)c2cc(CC(F)(F)F)sc2n1] | | |
| 265 | 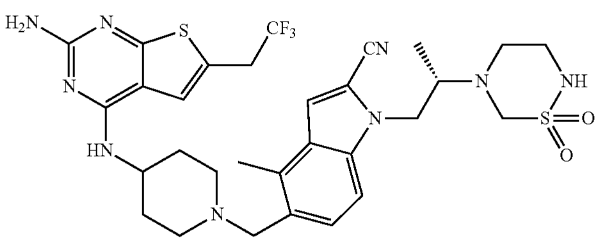 [SMILES: Cc1c(CN2CCC(Nc3nc(N)nc4sc(CC(F)(F)F)cc34)CC2)ccc2c1cc(C#N)n2C[C@H](C)N1CCNS(=O)(=O)C1] | | |
| 266 | 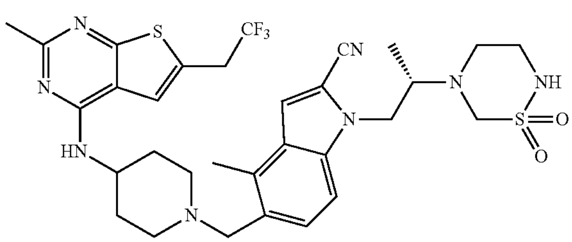 [SMILES: Cc1nc(NC2CCN(Cc3ccc4c(cc(C#N)n4C[C@H](C)N4CCNS(=O)(=O)C4)c3C)CC2)c2cc(CC(F)(F)F)sc2n1] | | |
| 267 | 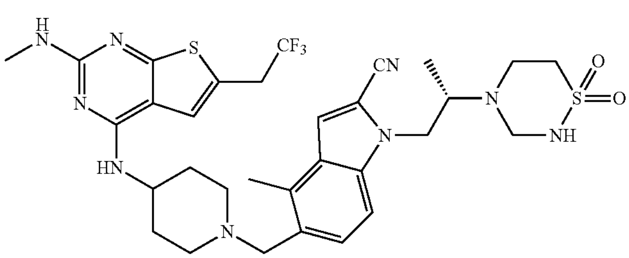 [SMILES: CNc1nc(NC2CCN(Cc3ccc4c(cc(C#N)n4C[C@H](C)N4CCS(=O)(=O)NC4)c3C)CC2)c2cc(CC(F)(F)F)sc2n1] | | |

TABLE 1-continued

| No | Structure | MW (calc'd) | m/z (found) |
|---|---|---|---|
| 268 | 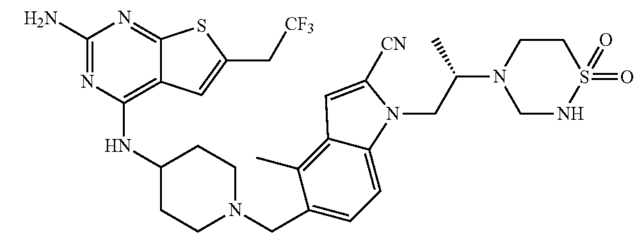 [SMILES: Cc1c(CN2CCC(Nc3nc(N)nc4sc(CC(F)(F)F)cc34)CC2)ccc2c1cc(C#N)n2C[C@H](C)N1CCS(=O)(=O)NC1] | | |
| 269 | 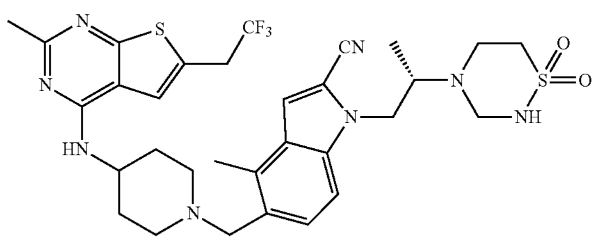 [SMILES: Cc1nc(NC2CCN(Cc3ccc4c(cc(C#N)n4C[C@H](C)N4CCS(=O)(=O)NC4)c3C)CC2)c2cc(CC(F)(F)F)sc2n1] | | |
| 270 | 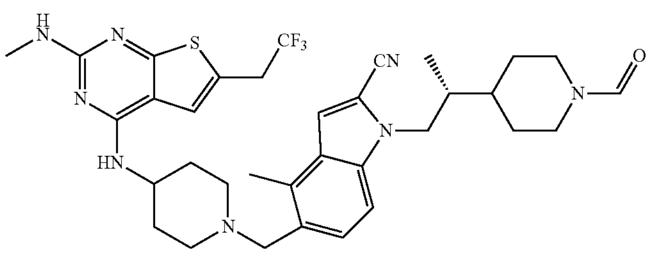 [SMILES: CNc1nc(NC2CCN(Cc3ccc4c(cc(C#N)n4C[C@H](C)C4CCN(C=O)CC4)c3C)CC2)c2cc(CC(F)(F)F)sc2n1] | | |
| 271 | 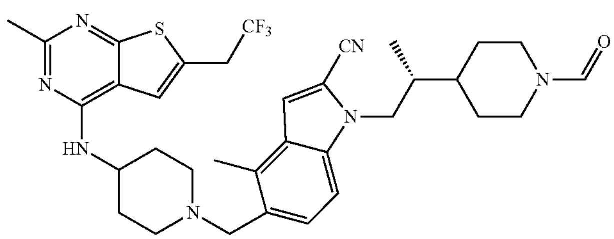 [SMILES: Cc1nc(NC2CCN(Cc3ccc4c(cc(C#N)n4C[C@H](C)C4CCN(C=O)CC4)c3C)CC2)c2cc(CC(F)(F)F)sc2n1] | | |
| 272 | 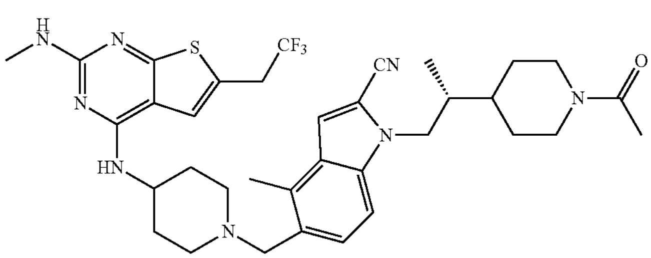 [SMILES: CNc1nc(NC2CCN(Cc3ccc4c(cc(C#N)n4C[C@H](C)C4CCN(C(C)=O)CC4)c3C)CC2)c2cc(CC(F)(F)F)sc2n1] | | |
| 273 | 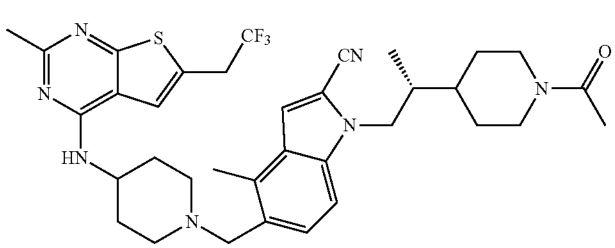 [SMILES: CC(=O)N1CCC([C@@H](C)Cn2c(C#N)cc3c(C)c(CN4CCC(Nc5nc(C)nc6sc(CC(F)(F)F)cc56)CC4)ccc32)CC1] | | |

TABLE 1-continued

| No | Structure | MW (calc'd) | m/z (found) |
|---|---|---|---|
| 274 | 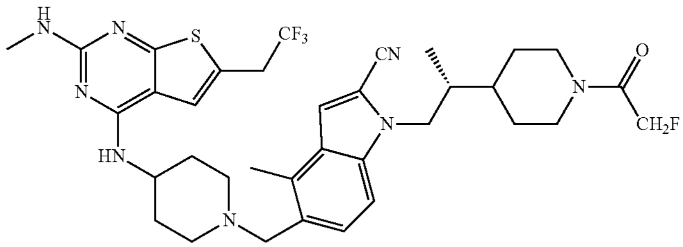 | | |
| 275 | 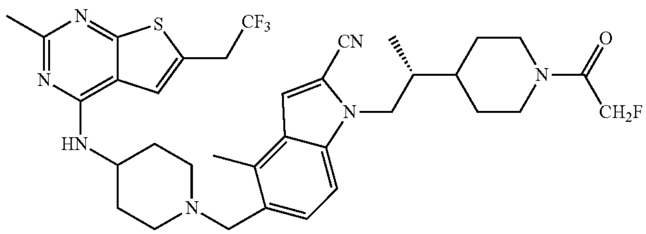 | | |
| 276 | 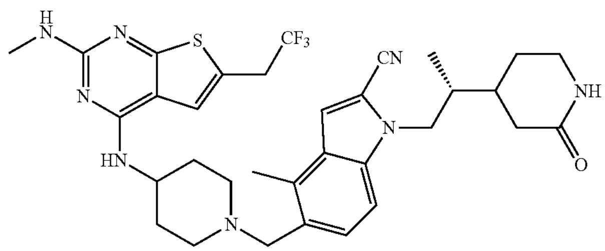 [SMILES: CNc1nc(NC2CCN(Cc3ccc4c(cc(C#N)n4C[C@H](C)C4CCNC(=O)C4)c3C)CC2)c2cc(CC(F)(F)F)sc2n1] | | |
| 277 | 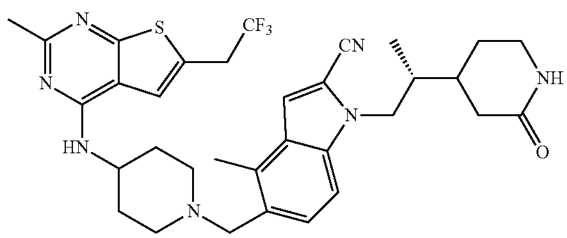 [SMILES: Cc1nc(NC2CCN(Cc3ccc4c(cc(C#N)n4C[C@H](C)C4CCNC(=O)C4)c3C)CC2)c2cc(CC(F)(F)F)sc2n1] | | |
| 278 | 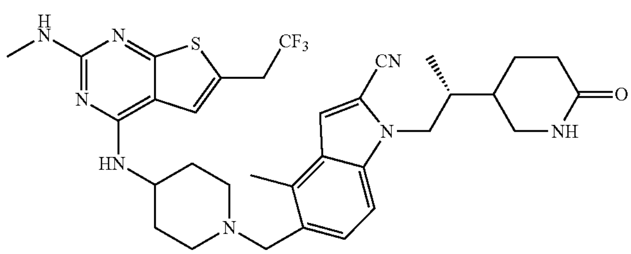 [SMILES: CNc1nc(NC2CCN(Cc3ccc4c(cc(C#N)n4C[C@H](C)C4CCC(=O)NC4)c3C)CC2)c2cc(CC(F)(F)F)sc2n1] | | |
| 279 | 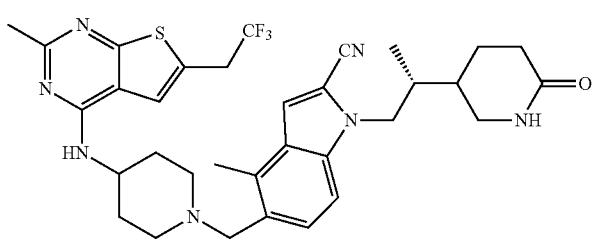 [SMILES: Cc1nc(NC2CCN(Cc3ccc4c(cc(C#N)n4C[C@H](C)C4CCC(=O)NC4)c3C)CC2)c2cc(CC(F)(F)F)sc2n1] | | |

TABLE 1-continued

| No | Structure | MW (calc'd) | m/z (found) |
|---|---|---|---|
| 280 | 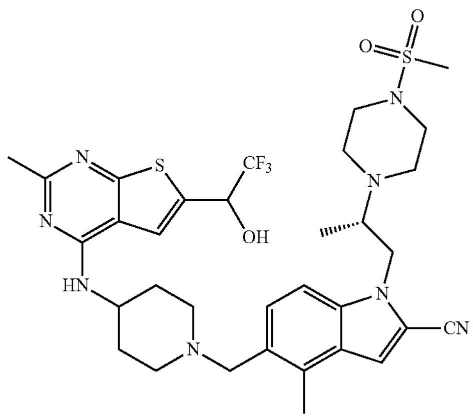 [SMILES: Cc1nc(NC2CCN(Cc3ccc4c(cc(C#N)n4C[C@H](C)N4CCN(S(C)(=O)=O)CC4)c3C)CC2)c2cc(C(O)C(F)(F)F)sc2n1] | 717.27 | 718.2 [M + H]+ |
| 281 | 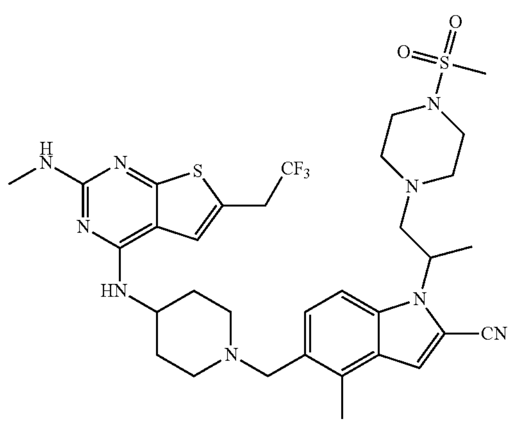 | 635.27 | 636.27 [M + H]+ |
| 282 | 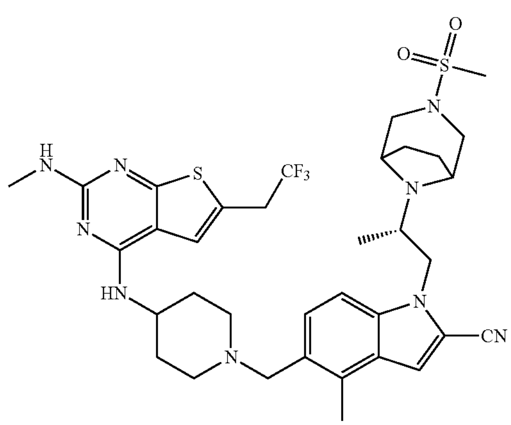 [SMILES: CNc1nc(NC2CCN(Cc3ccc4c(cc(C#N)n4C[C@H](C)N4C5CCC4CN(S(C)(=O)=O)C5)c3C)CC2)c2cc(CC(F)(F)F)sc2n1] | 743.30 | 744.31 [M + H]+ |

TABLE 1-continued

| No | Structure | MW (calc'd) | m/z (found) |
|---|---|---|---|
| 283 | 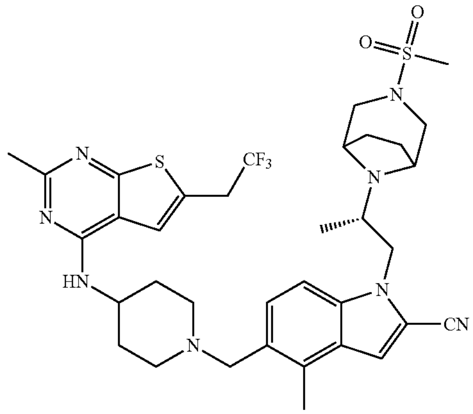 [SMILES: Cc1nc(NC2CCN(Cc3ccc4c(cc(C#N)n4C[C@H](C)N4C5CCC4CN(S(C)(=O)=O)C5)c3C)CC2)c2cc(CC(F)(F)F)sc2n1] | 728.29 | 729.30 [M + H]+ |
| 284 | 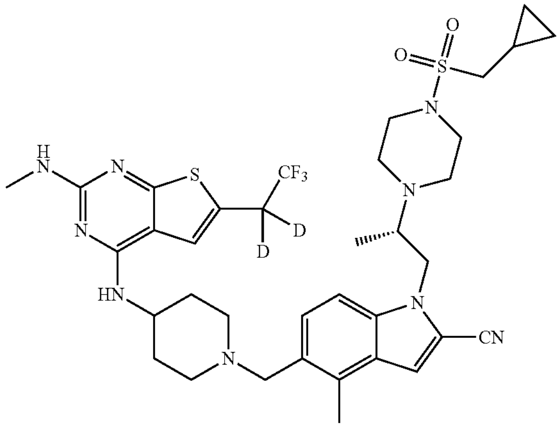 [SMILES: [2H]C([2H])(c1cc2c(NC3CCN(Cc4ccc5c(cc(C#N)n5C[C@H](C)N5CCN(S(=O)(=O)CC6CC6)CC5)c4C)CC3)nc(NC)nc2s1)C(F)(F)F] | | |
| 285 | 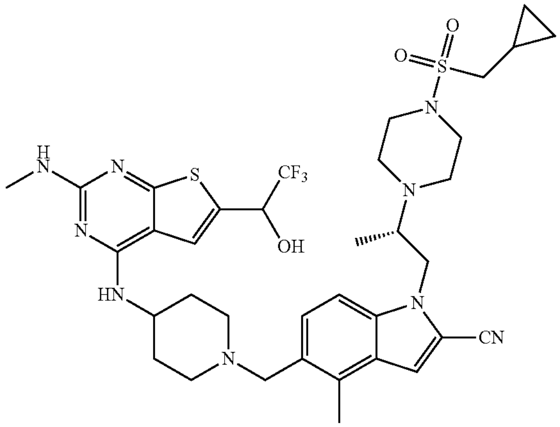 [SMILES: CNc1nc(NC2CCN(Cc3ccc4c(cc(C#N)n4C[C@H](C)N4CCN(S(=O)(=O)CC5CC5)CC4)c3C)CC2)c2cc(C(O)C(F)(F)F)sc2n1] | | |

| No | Structure | MW (calc'd) | m/z (found) |
|---|---|---|---|
| 286 | 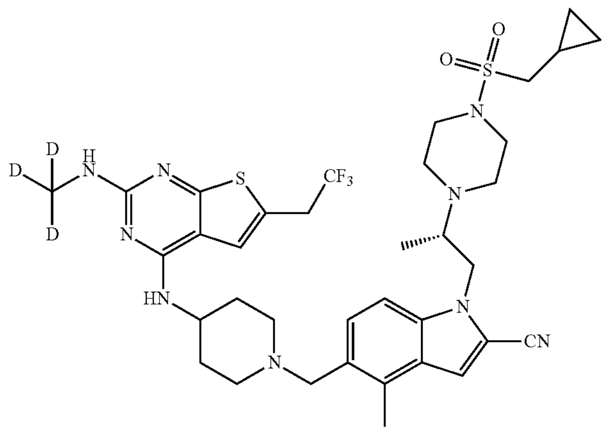 [SMILES: [2H]C([2H])([2H])Nc1nc(NC2CCN(Cc3ccc4c(cc(C#N)n4C[C@H](C)N4CCN(S(=O)(=O)CC5CC5)CC4)c3C)CC2)c2cc(CC(F)(F)F)sc2n1] | | |
| 287 | 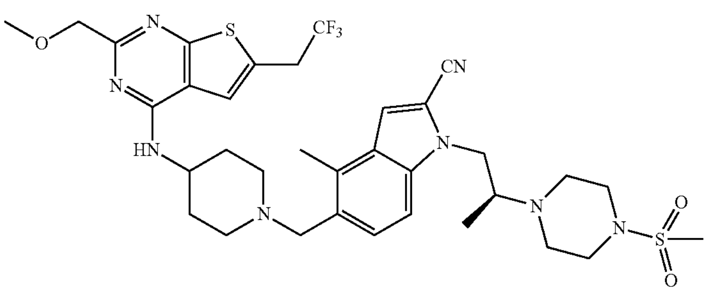 | | |
| 288 | 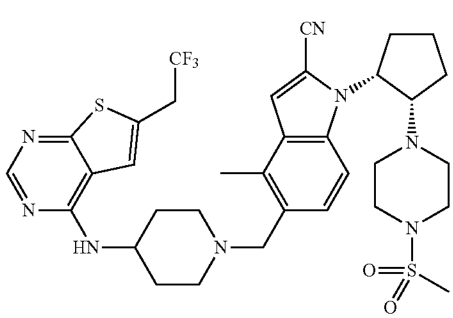 [SMILES: Cc1c(CN2CCC(Nc3ncnc4sc(CC(F)(F)F)cc34)CC2)ccc2c1cc(C#N)n2[C@@H]1CCC[C@@H]1N1CCN(S(C)(=O)=O)CC1] | | |

In some embodiments, exemplary compounds may include, but are not limited to, a compound or salt thereof selected from Table 2.

TABLE 2
| No | Structure | MW (cal'd) | m/z (found) |
|---|---|---|---|
| 1000 | 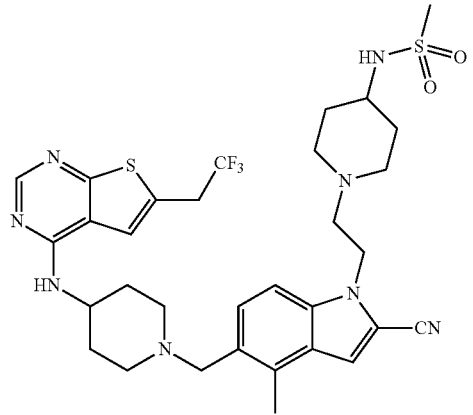 [SMILES: Cc1c(CN2CCC(Nc3ncnc4sc(CC(F)(F)F)cc34)CC2)ccc2c1cc(C#N)n2CCN1CCC(NS(C)(=O)=O)CC1] | | |
| 1001 | 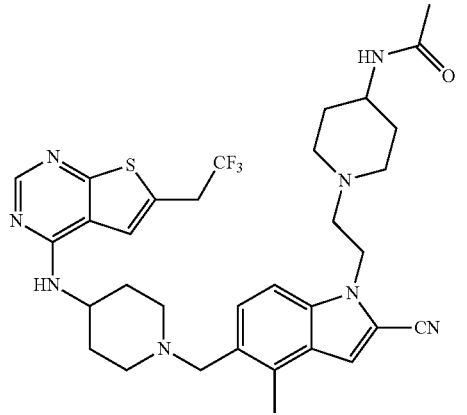 [SMILES: CC(=O)NC1CCN(CCn2c(C#N)cc3c(C)c(CN4CCC(Nc5ncnc6sc(CC(F)(F)F)cc56)CC4)ccc32)CC1] | | |
| 1002 | 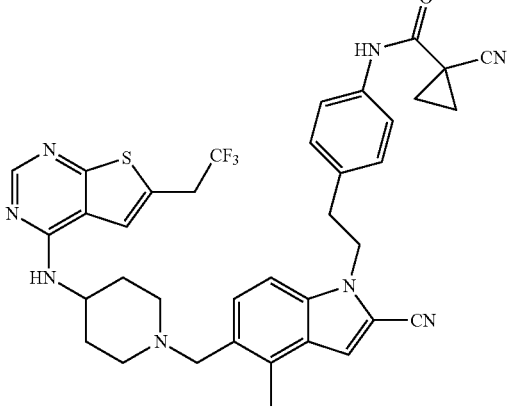 | | |

TABLE 2-continued
| No | Structure | MW (cal'd) | m/z (found) |
|---|---|---|---|
| 1003 | 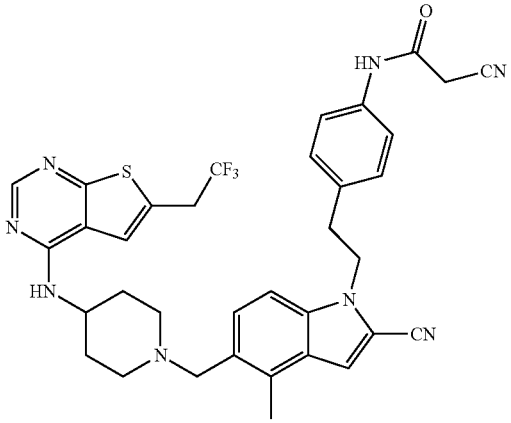 [SMILES: Cc1c(CN2CCC(Nc3ncnc4sc(CC(F)(F)F)cc34)CC2)ccc2c1cc(C#N)n2CCc1ccc(NC(=O)CC#N)cc1] | | |
| 1004 | 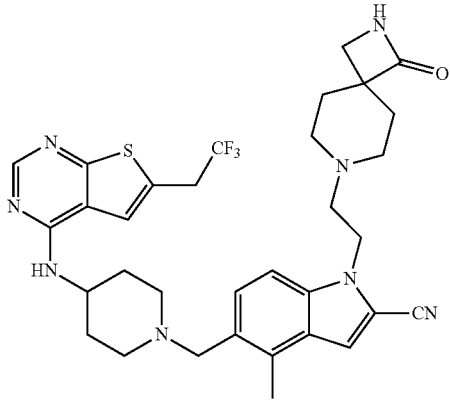 [SMILES: Cc1c(CN2CCC(Nc3ncnc4sc(CC(F)(F)F)cc34)CC2)ccc2c1cc(C#N)n2CCN1CCC2(CC1)CNC2=O] | | |
| 1005 | 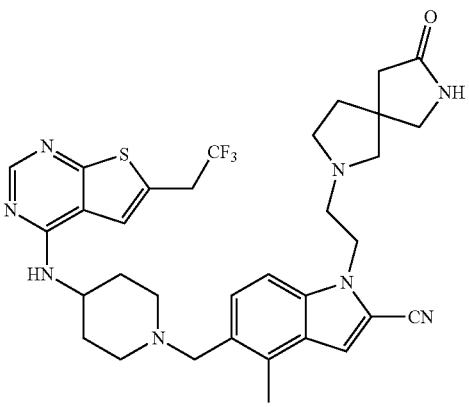 [SMILES: Cc1c(CN2CCC(Nc3ncnc4sc(CC(F)(F)F)cc34)CC2)ccc2c1cc(C#N)n2CCN1CCC2(CNC(=O)C2)C1] | | |

TABLE 2-continued

| No | Structure | MW (cal'd) | m/z (found) |
|---|---|---|---|
| 1006 | 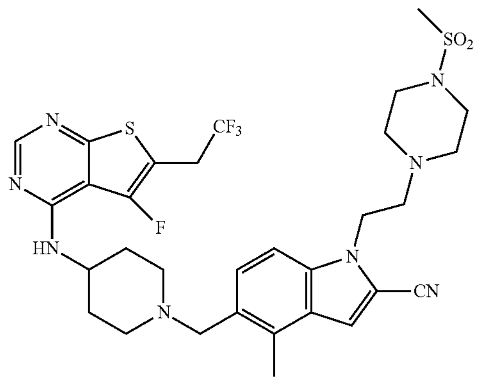 [SMILES: Cc1c(CN2CCC(Nc3ncnc4sc(CC(F)(F)F)c(F)c34)CC2)ccc2c1cc(C#N)n2CCN1CCN(S(C)(=O)=O)CC1] | | |
| 1007 | 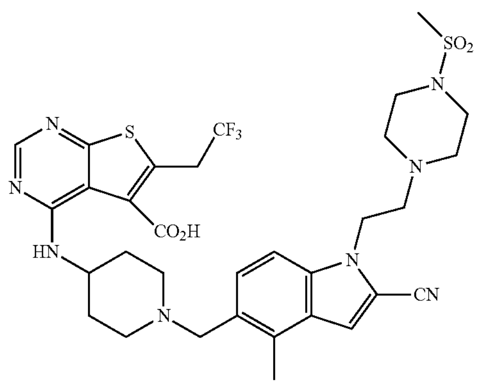 [SMILES: Cc1c(CN2CCC(Nc3ncnc4sc(CC(F)(F)F)c(C(=O)O)c34)CC2)ccc2c1cc(C#N)n2CCN1CCN(S(C)(=O)=O)CC1] | | |
| 1008 | 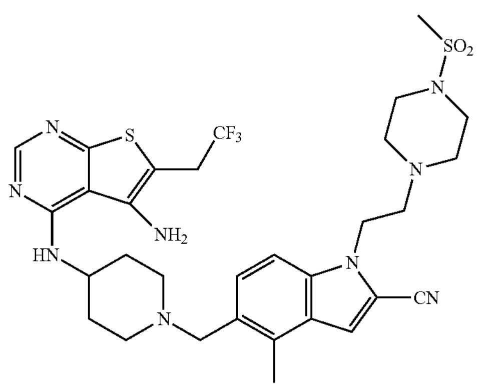 [SMILES: Cc1c(CN2CCC(Nc3ncnc4sc(CC(F)(F)F)c(N)c34)CC2)ccc2c1cc(C#N)n2CCN1CCN(S(C)(=O)=O)CC1] | | |
| 1009 | 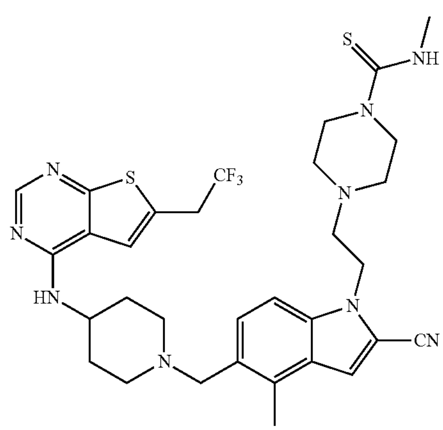 [SMILES: CNC(=S)N1CCN(CCn2c(C#N)cc3c(C)c(CN4CCC(Nc5ncnc6sc(CC(F)(F)F)cc56)CC4)ccc32)CC1] | | |

TABLE 2-continued

| No | Structure | MW (cal'd) | m/z (found) |
|---|---|---|---|
| 1010 | 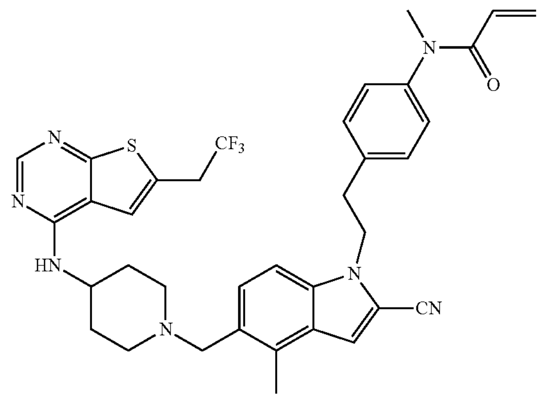 [SMILES: C=CC(=O)N(C)c1ccc(CCn2c(C#N)cc3c(C)c(CN4CCC(Nc5ncnc6sc(CC(F)(F)F)cc56)CC4)ccc32)cc1] | | |
| 1011 | 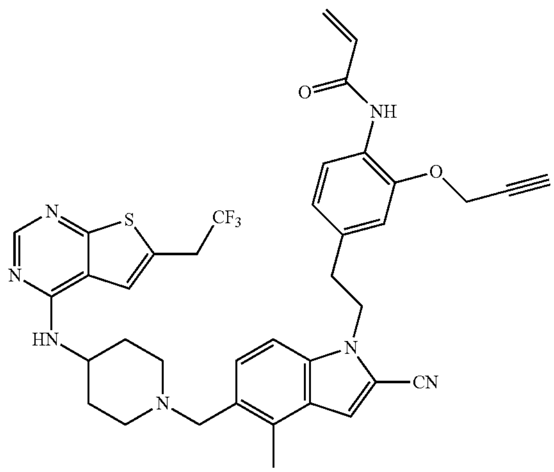 [SMILES: C#CCOc1cc(CCn2c(C#N)cc3c(C)c(CN4CCC(Nc5ncnc6sc(CC(F)(F)F)cc56)CC4)ccc32)ccc1NC(=O)C=C] | | |
| 1012 | 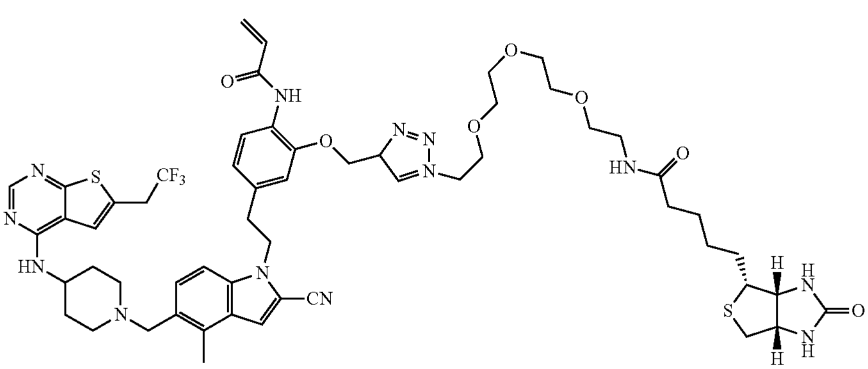 | | |

TABLE 2-continued

| No | Structure | MW (cal'd) | m/z (found) |
|---|---|---|---|
| 1013 | 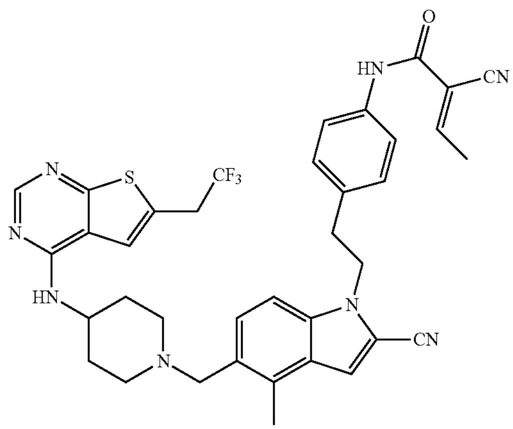 [SMILES: C/C=C(\C#N)C(=O)Nc1ccc(CCn2c(C#N)cc3c(C)c(CN4CCC(Nc5ncnc6sc(CC(F)(F)F)cc56)CC4)ccc32)cc1] | | |
| 1014 | 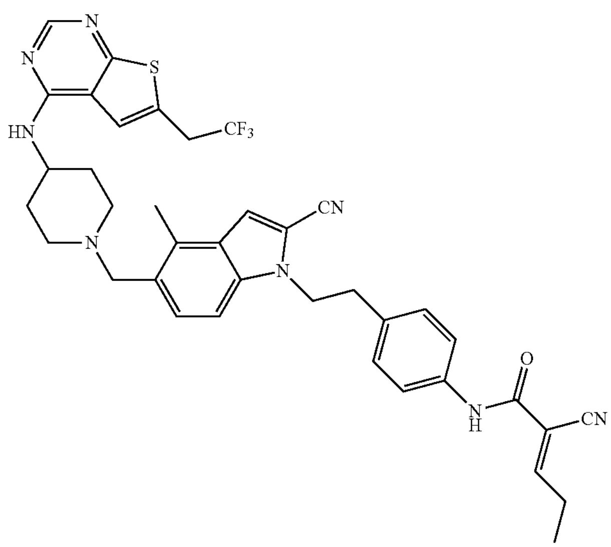 [SMILES: CC/C=C(\C#N)C(=O)Nc1ccc(CCn2c(C#N)cc3c(C)c(CN4CCC(Nc5ncnc6sc(CC(F)(F)F)cc56)CC4)ccc32)cc1] | | |
| 1015 | 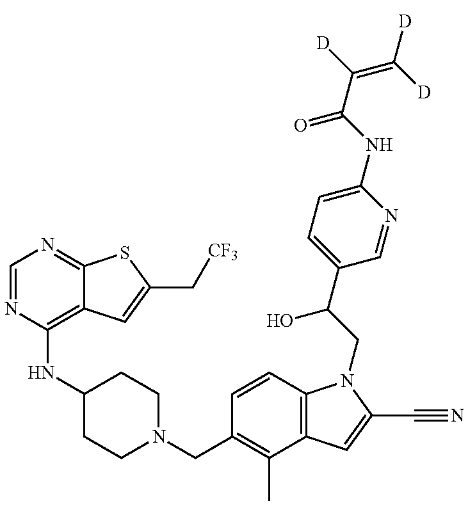 [SMILES: [2H]C([2H])=C([2H])C(=O)Nc1ccc(C(O)Cn2c(C#N)cc3c(C)c(CN4CCC(Nc5ncnc6sc(CC(F)(F)F)cc56)CC4)ccc32)cn1] | | |

TABLE 2-continued

| No | Structure | MW (cal'd) | m/z (found) |
|---|---|---|---|
| 1016 | 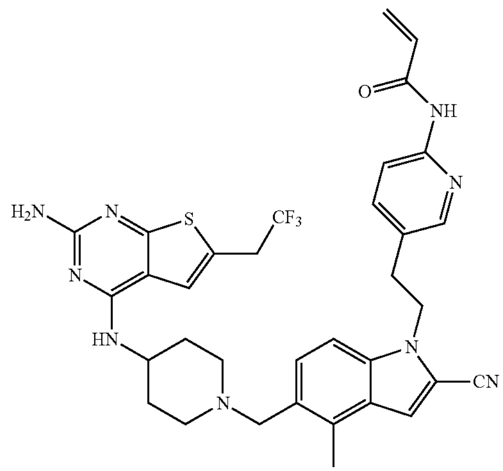 [SMILES: C=CC(=O)Nc1ccc(CCn2c(C#N)cc3c(C)c(CN4CCC(Nc5nc(N)nc6sc(CC(F)(F)F)cc56)CC4)ccc32)cn1] | 673.26 | 337.6 [M + 2H]²⁺ |
| 1017 | 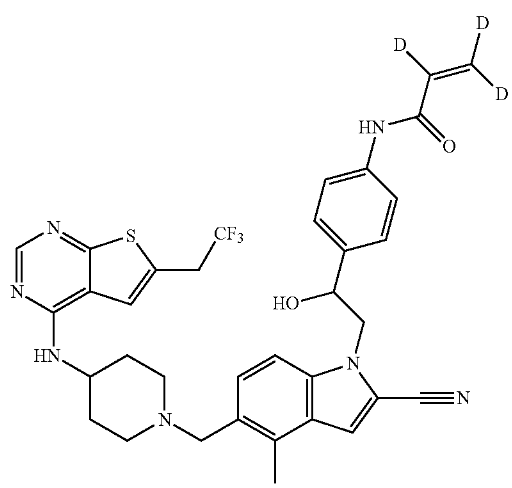 [SMILES: [2H]C([2H])=C([2H])C(=O)Nc1ccc(C(O)Cn2c(C#N)cc3c(C)c(CN4CCC(Nc5ncnc6sc(CC(F)(F)F)cc56)CC4)ccc32)cc1] | | |
| 1018 | 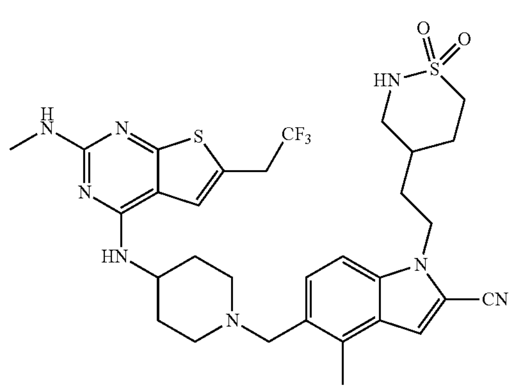 [SMILES: CNc1nc(NC2CCN(Cc3ccc4c(cc(C#N)n4CCC4CCS(=O)(=O)NC4)c3C)CC2)c2cc(CC(F)(F)F)sc2n1] | | |

TABLE 2-continued
| No | Structure | MW (cal'd) | m/z (found) |
|---|---|---|---|
| 1019 | 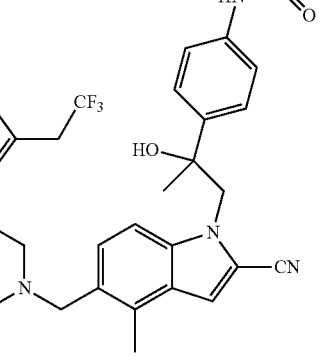 | | |
| 1020 | 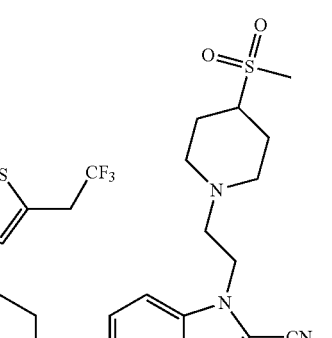 | | |
| 1021 | 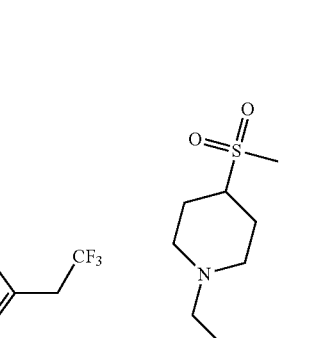 | | |

TABLE 2-continued

| No | Structure | MW (cal'd) | m/z (found) |
|---|---|---|---|
| 1022 | 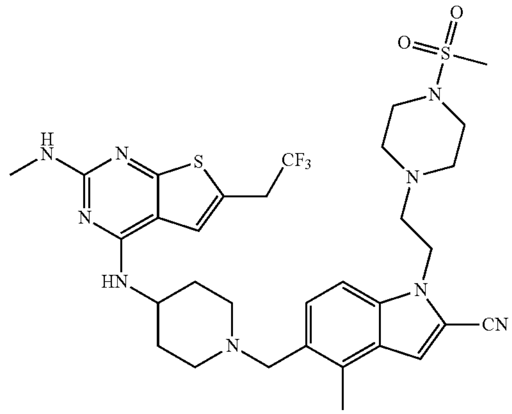 [SMILES: CNc1nc(NC2CCN(Cc3ccc4c(cc(C#N)n4CCN4CCN(S(C)(=O)=O)CC4)c3C)CC2)c2cc(CC(F)(F)F)sc2n1] | | |
| 1023 | 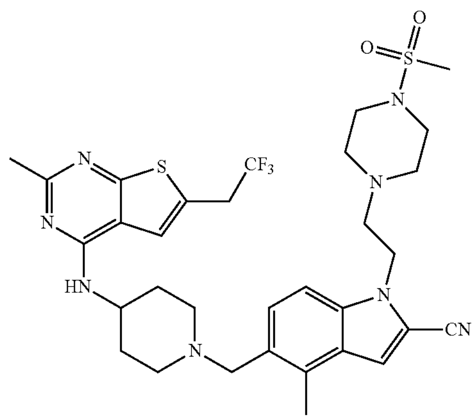 [SMILES: Cc1nc(NC2CCN(Cc3ccc4c(cc(C#N)n4CCN4CCN(S(C)(=O)=O)CC4)c3C)CC2)c2cc(CC(F)(F)F)sc2n1] | | |
| 1024 | 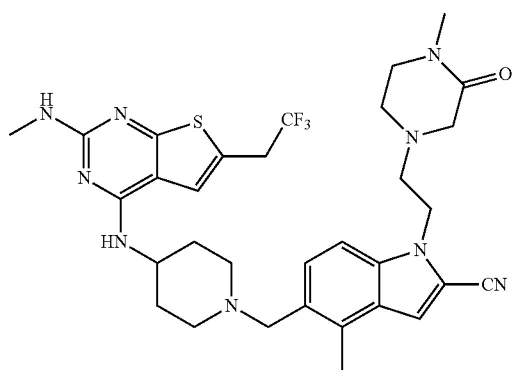 [SMILES: CNc1nc(NC2CCN(Cc3ccc4c(cc(C#N)n4CCN4CCN(C)C(=O)C4)c3C)CC2)c2cc(CC(F)(F)F)sc2n1] | | |
| 1025 | 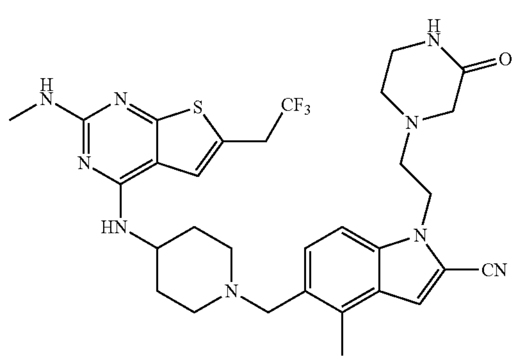 [SMILES: CNc1nc(NC2CCN(Cc3ccc4c(cc(C#N)n4CCN4CCNC(=O)C4)c3C)CC2)c2cc(CC(F)(F)F)sc2n1] | | |

| No | Structure | MW (cal'd) | m/z (found) |
|----|-----------|------------|-------------|
| 1026 | 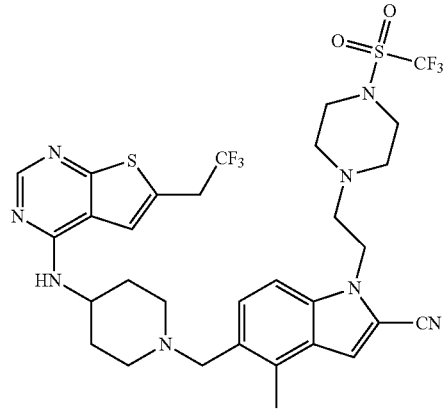 [SMILES: Cc1c(CN2CCC(Nc3ncnc4sc(CC(F)(F)F)cc34)CC2)ccc2c1cc(C#N)n2CCN1CCN(S(=O)(=O)C(F)(F)F)CC1] | | |
| 1027 | 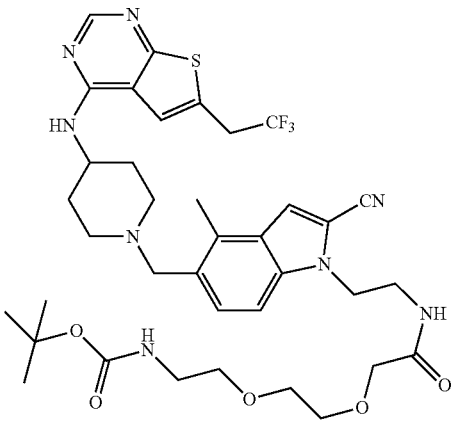 [SMILES: Cc1c(CN2CCC(Nc3ncnc4sc(CC(F)(F)F)cc34)CC2)ccc2c1cc(C#N)n2CCNC(=O)COCCOCCNC(=O)OC(C)(C)C] | | |

Pharmaceutical Compositions

The compositions and methods of the present disclosure may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound or salt of Formula (I) or (II) and a pharmaceutically acceptable carrier.

In some embodiments, the pharmaceutical composition is formulated for oral administration. In other embodiments, the pharmaceutical composition is formulated for injection. In still more embodiments, the pharmaceutical compositions comprise a compound as disclosed herein and an additional therapeutic agent (e.g., anticancer agent). Non-limiting examples of such therapeutic agents are described herein below.

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a composition of a compound or salt of Formula (I) or (II) is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, a compound or salt of Formula (I) or (II) is delivered in a targeted drug delivery system, for example, in a liposome coated with organ-specific antibody. In such embodiments, the liposomes are targeted to and taken up selectively by the organ. In yet other embodiments, the composition is provided in the form of a rapid release formulation, in the form of an extended release formulation, or in the form of an intermediate release formulation. In yet other embodiments, the composition is administered topically.

The compound of Formula (I) or (II), or a pharmaceutically acceptable salt thereof, may be effective over a wide dosage range. For example, in the treatment of adult humans, dosages from 0.01 to 1000 mg per day, from 0.5 to 100 mg per day, from 1 to 50 mg per day, and from 5 to 40 mg per day are examples of dosages that may be used in some embodiments. The exact dosage will depend upon the route of administration, the form in which the compound is administered, the subject to be treated, the body weight of the subject to be treated, and the preference and experience of the attending physician.

In some embodiments, a compound or salt of Formula (I) or (II) is administered in a single dose. Typically, such administration will be by injection, e.g., intravenous injection, in order to introduce the agent quickly. However, other routes are used as appropriate. In some embodiments, a single dose of a compound or salt of Formula (I) or (II) is used for treatment of an acute condition.

In some embodiments, a compound or salt of Formula (I) or (II) is administered in multiple doses. In some embodiments, dosing is about once, twice, three times, four times, five times, six times, or more than six times per day. In other embodiments, dosing is about once a month, once every two weeks, once a week, or once every other day. In another embodiment, a compound or salt of Formula (I) or (II) and another agent are administered together about once per day to about 6 times per day. In another embodiment, the administration of a compound or salt of Formula (I) or (II) and an agent continues for less than about 7 days. In yet another embodiment, the administration continues for more than about 6 days, more than about 10 days, more than about 14 days, more than about 28 days, more than about two months, more than about six months, or one year or more. In some cases, continuous dosing is achieved and maintained as long as necessary.

Administration of a compound or salt of Formula (I) or (II) may continue as long as necessary. In some embodiments, a compound of the disclosure is administered for more than 1, more than 2, more than 3, more than 4, more than 5, more than 6, more than 7, more than 14, or more than 28 days. In some embodiments, a compound of the disclosure is administered 28 days or less, 14 days or less, 7 days or less, 6 days or less, 5 days or less, 4 days or less, 3 days or less, 2 days or less, or 1 day or a part thereof. In some embodiments, a compound or salt of Formula (I) or (II) is administered chronically on an ongoing basis, e.g., for the treatment of chronic effects.

In some embodiments, a compound or salt of Formula (I) or (II) is administered in dosages. It is known in the art that due to intersubject variability in compound pharmacokinetics, individualization of dosing regimen is necessary for optimal therapy. Dosing for a compound or salt of Formula (I) or (II) may be found by routine experimentation in light of the instant disclosure.

In some embodiments, a compound or salt of Formula (I) or (II) is formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Provided herein are pharmaceutical compositions comprising a compound or salt of Formula (I) or (II) and a pharmaceutically acceptable diluent(s), excipient(s), or carrier(s). In certain embodiments, the compounds or salts described are administered as pharmaceutical compositions in which a compound or salt of Formula (I) or (II) is mixed with other active ingredients, as in combination therapy. Encompassed herein are all combinations of active ingredients set forth in the combination therapies section below and throughout this disclosure. In specific embodiments, the pharmaceutical compositions include one or more compounds of Formula (I) or (II), or a pharmaceutically acceptable salt thereof.

A pharmaceutical composition, as used herein, refers to a mixture of a compound or salt of Formula (I) or (II) with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of a compound or salt of Formula (I) or (II) are administered in a pharmaceutical composition to a mammal having a disease, disorder or medical condition to be treated. In specific embodiments, the mammal is a human. In certain embodiments, therapeutically effective amounts vary depending on the severity of the disease, the age and relative health of the subject, the potency of the compound used and other factors. A compound or salt of Formula (I) or (II) may be used singly or in combination with one or more therapeutic agents as components of mixtures.

In one embodiment, a compound or salt of Formula (I) or (II) is formulated in an aqueous solution. In specific embodiments, the aqueous solution is selected from, by way of example only, a physiologically compatible buffer, such as Hank's solution, Ringer's solution, or physiological saline buffer. In other embodiments, a compound or salt of Formula (I) or (II) is formulated for transmucosal administration. In specific embodiments, transmucosal formulations include penetrants that are appropriate to the barrier to be permeated. In still other embodiments wherein a compound or salt of Formula (I) or (II) is formulated for other parenteral injections, appropriate formulations include aqueous or nonaqueous solutions. In specific embodiments, such solutions include physiologically compatible buffers and/or excipients.

In another embodiment, a compound or salt of Formula (I) or (II) is formulated for oral administration. A compound or salt of Formula (I) or (II) may be formulated by combining the active compounds with, e.g., pharmaceutically acceptable carriers or excipients. In various embodiments, a compound or salt of Formula (I) or (II) is formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with a compound or salt of Formula (I) or (II), optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating.

In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, a therapeutically effective amount of a compound or salt of Formula (I) or (II) is formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, a therapeutically effective amount of a compound or salt of Formula (I) or (II) is formulated for buccal or sublingual administration. Formulations suitable for buccal or sublingual administration include, by way of example only, tablets, lozenges, or gels. In still other embodiments, a compound or salt of Formula (I) or (II) is formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions are formulated in a form suitable for parenteral injection as sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, a suspension of a compound or salt of Formula (I) or (II) is prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. In certain embodiments, the active agent is in powder form for constitution with a suitable vehicle, e.g., sterile pyrogen-free water, before use.

In still other embodiments, a compound or salt of Formula (I) or (II) is administered topically. A compound or salt of Formula (I) or (II) may be formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, a compound or salt of Formula (I) or (II) is formulated for transdermal administration. Transdermal formulations may employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of a compound or salt of Formula (I) or (II) is accomplished by means of iontophoretic patches and the like. In certain embodiments, transdermal patches provide controlled delivery of a compound or salt of Formula (I) or (II). In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing a compound or salt of Formula (I) or (II), optionally with carriers, optionally a rate controlling barrier to deliver the compound to the skin of the host at a controlled and predetermined rate over a prolonged period of time, and means to secure the device to the skin.

In other embodiments, a compound or salt of Formula (I) or (II) is formulated for administration by inhalation. Various forms suitable for administration by inhalation include, but are not limited to, aerosols, mists or powders. Pharmaceutical compositions of a compound or salt of Formula (I) or (II) are conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatin for use in an inhaler or insufflator are formulated containing a powder mix of a compound or salt of Formula (I) or (II) and a suitable powder base such as lactose or starch.

In still other embodiments, a compound or salt of Formula (I) or (II) is formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients may be optionally used as suitable. Pharmaceutical compositions comprising a compound or salt of Formula (I) or (II) are manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and a compound or salt of Formula (I) or (II), sometimes referred to herein as an active agent or ingredient. The active ingredient may be in free-acid or free-base form, or in a pharmaceutically acceptable salt form. Additionally, a compound or salt of Formula (I) or (II) may be in unsolvated or solvated forms with pharmaceutically acceptable solvents such as water and ethanol. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising a compound or salt of Formula (I) or (II) include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound or salt of Formula (I) or (II). Semi-solid compositions include, but are not limited to, gels, suspensions and creams. The form of the pharmaceutical compositions of a compound or salt of Formula (I) or (II) include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, a pharmaceutical composition comprising a compound or salt of Formula (I) or (II) takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, aqueous suspensions contain one or more polymers as suspending agents. Polymers include water-soluble polymers such as cellulosic polymers, e.g., hydroxypropyl methylcellulose, and water-insoluble polymers such as cross-linked carboxy-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Pharmaceutical compositions also, optionally, include solubilizing agents to aid in the solubility of a compound described herein. The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, useful compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Pharmaceutical compositions may include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Pharmaceutical compositions may include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose reclosable containers are used, in which case it is typical to include a preservative in the composition.

In certain embodiments, delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, a compound or salt of Formula (I) or (II) is delivered using a sustained-release system, such as semipermeable matrices of solid hydrophobic polymers containing the therapeutic agent. Various sustained-release materials may be used herein. In some embodiments, sustained-release capsules release the compounds for a few weeks up to over 100 days. Depending on the chemical nature and the biological stability of the therapeutic reagent, additional strategies for protein stabilization are employed.

In certain embodiments, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l)

pentosan polysulfate and other heparinoids, (m) divalent cations such as magnesium and zinc; or (n) combinations thereof.

In some embodiments, the concentration of a compound or salt of Formula (I) or (II) provided in a pharmaceutical compositions is less than about: 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of a compound or salt of Formula (I) or (II) provided in a pharmaceutical composition is greater than about: 90%, 80%, 70%, 60%, 50%, 40%, 30%, 20%, 19.75%, 19.50%, 19.25%, 19%, 18.75%, 18.50%, 18.25%, 18%, 17.75%, 17.50%, 17.25%, 17%, 16.75%, 16.50%, 16.25%, 16%, 15.75%, 15.50%, 15.25%, 15%, 14.75%, 14.50%, 14.25%, 14%, 13.75%, 13.50%, 13.25%, 13%, 12.75%, 12.50%, 12.25%, 12%, 11.75%, 11.50%, 11.25%, 11%, 10.75%, 10.50%, 10.25%, 10%, 9.75%, 9.50%, 9.25%, 9%, 8.75%, 8.50%, 8.25%, 8%, 7.75%, 7.50%, 7.25%, 7%, 6.75%, 6.50%, 6.25%, 6%, 5.75%, 5.50%, 5.25%, 5%, 4.75%, 4.50%, 4.25%, 4%, 3.75%, 3.50%, 3.25%, 3%, 2.75%, 2.50%, 2.25%, 2%, 1.75%, 1.50%, 1.25%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of a compound or salt of Formula (I) or (II) is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of a compound or salt of Formula (I) or (II) is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of a compound or salt of Formula (I) or (II) is equal to or less than about: 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of a compound or salt of Formula (I) or (II) is more than about: 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of one or more compounds of the disclosure is in the range of 0.0001-10 g, 0.0005-9 g, 0.001-8 g, 0.005-7 g, 0.01-6 g, 0.05-5 g, 0.1-4 g, 0.5-4 g, or 1-3 g.

For use in the therapeutic applications described herein, kits and articles of manufacture are also provided. In some embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from a variety of materials such as glass or plastic.

The articles of manufacture provided herein contain packaging materials. Packaging materials for use in packaging pharmaceutical products include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) includes a compound or salt of Formula (I) or (II), optionally in a composition or in combination with another agent as disclosed herein. The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical composition is presented in a pack or dispenser device which contains one or more unit dosage forms containing a compound provided herein. The pack, for example, contains metal or plastic foil, such as a blister pack. Or, the pack or dispenser device is accompanied by instructions for administration. Or, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are prepared, placed in an appropriate container, and labeled for treatment of an indicated condition.

Methods

The present disclosure provides a method of inhibiting the interaction of menin and one or more proteins (e.g., MLL1, MLL2, an MLL fusion protein, or an MLL Partial Tandem Duplication) comprising contacting a cell with an effective amount of a compound or salt of Formula (I) or (II). Inhibition of the interaction of menin and one or more proteins (e.g., MLL1, MLL2, an MLL fusion protein, or an MLL Partial Tandem Duplication) can be assessed and demonstrated by a wide variety of ways known in the art. Non-limiting examples include a showing of (a) a decrease in menin binding to one or more proteins or protein fragments (e.g., MLL1, MLL2, an MLL fusion protein, an MLL Partial Tandem Duplication, or a peptide fragment thereof); (b) a decrease in cell proliferation and/or cell viability; (c) an increase in cell differentiation; (d) a decrease in the levels of downstream targets of MLL1, MLL2, an MLL fusion protein, and/or an MLL Partial Tandem Duplication (e.g., Hoxa9, DLX2, and Meis1); and/or (e) decrease in tumor volume and/or tumor volume growth rate. Kits and commercially available assays can be utilized for determining one or more of the above.

The disclosure also provides methods of using the compounds or pharmaceutical compositions of the present disclosure to treat disease conditions, including but not limited to conditions implicated by menin, MLL, MLL1, MLL2, and/or MLL fusion proteins (e.g., cancer).

In some embodiments, a method for treatment of cancer is provided, the method comprising administering an effective amount of any of the foregoing pharmaceutical compositions comprising a compound or salt of Formula (I) or (II) to a subject in need thereof. In some embodiments, the cancer is mediated by an MLL fusion protein. In other embodiments, the cancer is leukemia, breast cancer, prostate cancer, pancreatic cancer, lung cancer, liver cancer, skin cancer, or a brain tumor. In certain embodiments, the cancer is leukemia. In some embodiments, the cancer comprises a solid tumor.

In some embodiments, the disclosure provides a method of treating a disorder in a subject in need thereof, wherein the method comprises determining if the subject has an MLL fusion protein and, if the subject is determined to have an MLL fusion protein, administering to the subject a therapeutically effective dose of a compound or salt of Formula (I) or (II).

MLL fusion proteins have also been identified in hematological malignancies (e.g., cancers that affect blood, bone marrow and/or lymph nodes). Accordingly, certain embodiments are directed to administration of a compound or salt of Formula (I) or (II) to a patient in need of treatment of a hematological malignancy. Such malignancies include, but are not limited to leukemias and lymphomas. For example, the presently disclosed compounds can be used for treatment of diseases such as Acute lymphoblastic leukemia (ALL), Acute myelogenous leukemia (AML), Chronic lymphocytic leukemia (CLL), small lymphocytic lymphoma (SLL), Chronic myelogenous leukemia (CML), Acute monocytic leukemia (AMoL), hairy cell leukemia, and/or other leukemias. In other embodiments, the compounds are can be used for treatment of lymphomas such as all subtypes of Hodgkins lymphoma or non-Hodgkins lymphoma.

Determining whether a tumor or cancer comprises an MLL fusion protein can be undertaken by assessing the nucleotide sequence encoding the MLL fusion protein, by assessing the amino acid sequence of the MLL fusion protein, or by assessing the characteristics of a putative MLL fusion protein.

Methods for detecting an MLL fusion protein nucleotide sequence are known by those of skill in the art. These methods include, but are not limited to, polymerase chain reaction-restriction fragment length polymorphism (PCR-RFLP) assays, polymerase chain reaction-single strand conformation polymorphism (PCR-SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. In some embodiments, the MLL fusion protein is identified using a direct sequencing method of specific regions (e.g., exon 2 and/or exon 3) in the MLL or fusion partner gene, for example. This technique will identify all possible mutations in the region sequenced.

Methods for detecting an MLL fusion protein are known by those of skill in the art. These methods include, but are not limited to, detection of an MLL fusion protein using a binding agent (e.g., an antibody) specific for the fusion protein, protein electrophoresis and Western blotting, and direct peptide sequencing.

Methods for determining whether a tumor or cancer comprises an MLL fusion protein can use a variety of samples. In some embodiments, the sample is taken from a subject having a tumor or cancer. In some embodiments, the sample is taken from a subject having a cancer or tumor. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is processed to a cell lysate. In some embodiments, the sample is processed to DNA or RNA.

The disclosure also relates to a method of treating a hyperproliferative disorder in a mammal that comprises administering to the mammal a therapeutically effective amount of a compound or salt of Formula (I) or (II). In some embodiments, the method relates to the treatment of cancer such as acute myeloid leukemia, cancer in adolescents, adrenocortical carcinoma childhood, AIDS-related cancers (e.g., Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or Viral-Induced cancer. In some embodiments, the method relates to the treatment of a non-cancerous hyperproliferative disorder such as benign hyperplasia of the skin (e.g., psoriasis), restenosis, or prostate (e.g., benign prostatic hypertrophy (BPH)). In some cases, the method relates to the treatment of leukemia, hematologic malignancy, solid tumor cancer, prostate cancer (e.g., castration-resistant prostate cancer), breast cancer, Ewing's sarcoma, bone sarcoma, primary bone sarcoma, T-cell prolymphocyte leukemia, glioma, glioblastoma, liver cancer (e.g., hepatocellular carcinoma), or diabetes. In some cases, the leukemia comprises AML, ALL, Mixed Lineage Leukemia or leukemias with Partial Tandem Duplications of MLL.

In certain particular embodiments, the disclosure relates to methods for treatment of lung cancers, the methods comprise administering an effective amount of any of the above described compound (or a pharmaceutical composition comprising the same) to a subject in need thereof. In certain embodiments the lung cancer is a non-small cell lung carcinoma (NSCLC), for example adenocarcinoma, squamous-cell lung carcinoma or large-cell lung carcinoma. In other embodiments, the lung cancer is a small cell lung carcinoma. Other lung cancers treatable with the disclosed compounds include, but are not limited to, glandular tumors, carcinoid tumors and undifferentiated carcinomas.

Subjects that can be treated with a compound of the disclosure, or a pharmaceutically acceptable salt, ester, prodrug, solvate, tautomer, stereoisomer, isotopologue, hydrate or derivative of the compound, according to the methods of this disclosure include, for example, subjects that have been diagnosed as having acute myeloid leukemia, acute myeloid leukemia, cancer in adolescents, adrenocortical carcinoma childhood, AIDS-related cancers (e.g., Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, Viral-Induced cancer, leukemia, hematologic malignancy, solid tumor cancer, prostate cancer, castration-resistant prostate cancer, breast cancer, Ewing's sarcoma, bone sarcoma, primary bone sarcoma, T-cell prolymphocyte leukemia, glioma, glioblastoma, hepatocellular carcinoma, liver cancer, or diabetes. In some embodiments subjects that are treated with the compounds of the disclosure include subjects that have been diagnosed as having a non-cancerous hyperproliferative disorder such as benign hyperplasia of the skin (e.g., psoriasis), restenosis, or prostate (e.g., benign prostatic hypertrophy (BPH)).

The disclosure further provides methods of modulating the interaction of menin and one or more proteins (e.g., MLL1, MLL2, an MLL fusion protein, or an MLL Partial Tandem Duplication) by contacting the menin with an effective amount of a compound or salt of Formula (I) or (II). Modulation can be inhibiting or activating protein activity of menin, one or more of its binding partners, and/or one or more of the downstream targets of menin or one or more of its binding partners. In some embodiments, the disclosure provides methods of inhibiting the interaction of menin and one or more proteins (e.g., MLL1, MLL2, an MLL fusion protein, or an MLL Partial Tandem Duplication) by contacting menin with an effective amount of a compound or salt of Formula (I) or (II). In some embodiments, the disclosure provides methods of inhibiting the interaction of menin and one or more proteins (e.g., MLL1, MLL2, an MLL fusion protein, or an MLL Partial Tandem Duplication) by contacting a cell, tissue, or organ that expresses menin, MLL1, MLL2, an MLL fusion protein, and/or an MLL Partial Tandem Duplication. In some embodiments, the disclosure provides methods of inhibiting protein activity in subject including but not limited to rodents and mammal (e.g., human) by administering to the subject an effective amount of a compound or salt of Formula (I) or (II). In some embodiments, the percentage modulation exceeds 25%, 30%, 40%, 50%, 60%, 70%, 80%, or 90%. In some embodiments, the percentage of inhibiting exceeds 25%, 30%, 40%, 50%, 60%, 70%, 80%, or 90%.

In some embodiments, the disclosure provides methods of inhibiting the interaction of menin and one or more proteins (e.g., MLL1, MLL2, an MLL fusion protein, or an MLL Partial Tandem Duplication) in a cell by contacting the cell with an amount of a compound of the disclosure sufficient to inhibit the interaction of menin and one or more proteins (e.g., MLL1, MLL2, an MLL fusion protein, or an MLL Partial Tandem Duplication) in the cell. In some embodiments, the disclosure provides methods of inhibiting the interaction of menin and one or more proteins (e.g., MLL1, MLL2, an MLL fusion protein, or an MLL Partial Tandem Duplication) in a tissue by contacting the tissue with an amount of a compound or salt of Formula (I) or (II) sufficient to inhibit the interaction of menin and one or more proteins (e.g., MLL1, MLL2, an MLL fusion protein, or an MLL Partial Tandem Duplication) in the tissue. In some embodiments, the disclosure provides methods of inhibiting the interaction of menin and one or more proteins (e.g., MLL1, MLL2, an MLL fusion protein, or an MLL Partial Tandem Duplication) in an organism by contacting the organism with an amount of a compound or salt of Formula (I) or (II) sufficient to inhibit the interaction of menin and one or more proteins (e.g., MLL1, MLL2, an MLL fusion protein, or an MLL Partial Tandem Duplication) in the organism. In some embodiments, the disclosure provides methods of inhibiting the interaction of menin and one or more proteins (e.g., MLL1, MLL2, an MLL fusion protein, or an MLL Partial Tandem Duplication) in an animal by contacting the animal with an amount of a compound of the disclosure sufficient to inhibit the interaction of menin and one or more proteins (e.g., MLL1, MLL2, an MLL fusion protein, or an MLL Partial Tandem Duplication) in the animal. In some embodiments, the disclosure provides methods of inhibiting the interaction of menin and one or more proteins (e.g., MLL1, MLL2, an MLL fusion protein, or an MLL Partial Tandem Duplication) in a mammal by contacting the mammal with an amount of a compound of the disclosure sufficient to inhibit the interaction of menin and one or more proteins (e.g., MLL1, MLL2, an MLL fusion protein, or an MLL Partial Tandem Duplication) in the mammal. In some embodiments, the disclosure provides methods of inhibiting the interaction of menin and one or more proteins (e.g., MLL1, MLL2, an MLL fusion protein, or an MLL Partial Tandem Duplication) in a human by contacting the human with an amount of a compound of the disclosure sufficient to inhibit the interaction of menin and one or more proteins (e.g., MLL1, MLL2, an MLL fusion protein, or an MLL Partial Tandem Duplication) in the human. The present disclosure provides methods of treating a disease mediated by the interaction of menin and one or more proteins (e.g., MLL1, MLL2, an MLL fusion protein, or an MLL Partial Tandem Duplication) in a subject in need of such treatment.

The disclosure also provides methods of treating a disorder mediated by menin interaction with one or more proteins (e.g., MLL1, MLL2, an MLL fusion protein, or an MLL Partial Tandem Duplication) by administering to a subject in need thereof a therapeutically effective amount of a compound or salt of Formula (I) or (II).

The disclosure further provides methods of treating a disorder mediated by chromosomal rearrangement on chromosome 11q23 in a subject in need thereof by administering to the subject a therapeutically effective amount of a compound or salt of Formula (I) or (II).

The disclosure also provides methods for the treatment of a disease or condition by administering an effective amount of a compound or salt of Formula (I) or (II) to a subject suffering from the disease or condition.

The disclosure further provides methods for the treatment of a disease or condition by administering a compound or salt of Formula (I) or (II) to a subject suffering from the disease or condition, wherein the compound binds to menin and inhibits the interaction of menin with one or more proteins (e.g., MLL1, MLL2, an MLL fusion protein, or an MLL Partial Tandem Duplication).

The disclosure further provides methods of stabilizing menin, comprising contacting menin with a compound or salt of Formula (I) or (II). In some embodiments, the contacting step comprises contacting menin with an amount of the compound sufficient to stabilize menin. In some embodiments, the contacting step takes place in vivo. In some embodiments, the contacting step takes place in vitro. In some embodiments, the contacting step takes place in a cell.

The present disclosure also provides methods for combination therapies in which an agent known to modulate other pathways, or other components of the same pathway, or even overlapping sets of target enzymes are used in combination with a compound or salt of Formula (I) or (II). In one aspect, such therapy includes but is not limited to the combination of one or more compounds of the disclosure with chemotherapeutic agents, therapeutic antibodies, and radiation treatment, to provide a synergistic or additive therapeutic effect.

Where desired, a compound or pharmaceutical composition of the present disclosure can be used in combination with Notch inhibitors and/or c-Myb inhibitors. Where desired, a compound or pharmaceutical composition of the present disclosure can be used in combination with MLL-WDR5 inhibitors and/or Dot 11 inhibitors.

Many chemotherapeutics are presently known in the art and can be used in combination with a compound of the disclosure. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

Non-limiting examples are chemotherapeutic agents, cytotoxic agents, and non-peptide small molecules such as Gleevec® (Imatinib Mesylate), Velcade® (bortezomib), Casodex (bicalutamide), Iressa® (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO). Where desired, the compounds or pharmaceutical composition of the present disclosure can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

This disclosure further relates to a method for using a compound or salt of Formula (I) or (II) or a pharmaceutical composition provided herein, in combination with radiation therapy for inhibiting abnormal cell growth or treating the hyperproliferative disorder in the mammal. Techniques for administering radiation therapy are known in the art, and these techniques can be used in the combination therapy described herein. The administration of the compound of the disclosure in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner of the present disclosure include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

The compounds or pharmaceutical compositions of the disclosure can be used in combination with an amount of one or more substances selected from anti-angiogenesis agents, signal transduction inhibitors, antiproliferative agents, glycolysis inhibitors, or autophagy inhibitors.

Anti-angiogenesis agents, such as MMP-2 (matrix-metalloproteinase 2) inhibitors, MMP-9 (matrix-metalloproteinase 9) inhibitors, and COX-11 (cyclooxygenase 11) inhibitors, can be used in conjunction with a compound of the disclosure and pharmaceutical compositions described herein. Anti-angiogenesis agents include, for example, rapamycin, temsirolimus (CCI-779), everolimus (RAD001), sorafenib, sunitinib, and bevacizumab. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (e.g., MAP-1, MMP-3, MMP-4, MMP-5, MMP-6, MMP-7, MMP-8, MMP-10, MMP-11, MMP-12, and MMP-13). Some specific examples of MMP inhibitors useful in the disclosure are AG-3340, RO 32-3555, and RS 13-0830.

Autophagy inhibitors include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

In some embodiments, the compounds described herein are formulated or administered in conjunction with liquid or solid tissue barriers also known as lubricants. Examples of tissue barriers include, but are not limited to, polysaccharides, polyglycans, seprafilm, interceed and hyaluronic acid.

In some embodiments, medicaments which are administered in conjunction with the compounds described herein include any suitable drugs usefully delivered by inhalation for example, analgesics, e.g., codeine, dihydromorphine, ergotamine, fentanyl or morphine; anginal preparations, e.g., diltiazem; antiallergics, e.g., cromoglycate, ketotifen or nedocromil; anti-infectives, e.g., cephalosporins, penicillins, streptomycin, sulphonamides, tetracyclines or pentamidine; antihistamines, e.g., methapyrilene; anti-inflammatories, e.g., beclomethasone, flunisolide, budesonide, tipredane, triamcinolone acetonide or fluticasone; antitussives, e.g., noscapine; bronchodilators, e.g., ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g., amiloride; anticholinergics e.g., ipratropium, atropine or oxitropium; hormones, e.g., cortisone, hydrocortisone or prednisolone; xanthines e.g., aminophylline, choline theophyllinate, lysine theophyllinate or theophylline; and therapeutic proteins and peptides, e.g., insulin or glucagon. It will be clear to a person skilled in the art that, where appropriate, the medicaments are used in the form of salts (e.g., as alkali metal or amine salts or as acid addition salts) or as esters (e.g., lower alkyl esters) or as solvates (e.g., hydrates) to optimize the activity and/or stability of the medicament.

Other exemplary therapeutic agents useful for a combination therapy include but are not limited to agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include antimicrobial agents, sulfonamides, trimethoprim-sulfamethoxazole quinolones, and agents for urinary tract infections, penicillins, cephalosporins, and other, β-lactam antibiotics, an agent comprising an aminoglycoside, protein synthesis inhibitors, drugs used in the chemotherapy of tuberculosis, *Mycobacterium avium* complex disease, and leprosy, antifungal agents, antiviral agents including nonretroviral agents and antiretroviral agents.

Examples of therapeutic antibodies that can be combined with a compound of the disclosure include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

For treating renal carcinoma, one may combine a compound of the present disclosure with sorafenib and/or avastin. For treating an endometrial disorder, one may combine a compound of the present disclosure with doxorubincin, taxotere (taxol), and/or cisplatin (carboplatin). For treating ovarian cancer, one may combine a compound of the present disclosure with cisplatin (carboplatin), taxotere, doxorubincin, topotecan, and/or tamoxifen. For treating breast cancer, one may combine a compound of the present disclosure with taxotere (taxol), gemcitabine (capecitabine), tamoxifen, letrozole, tarceva, lapatinib, PD0325901, avastin, herceptin, OSI-906, and/or OSI-930. For treating lung cancer, one may combine a compound of the present disclosure with taxotere (taxol), gemcitabine, cisplatin, pemetrexed, Tarceva, PD0325901, and/or avastin.

Further therapeutic agents that can be combined with a compound of the disclosure are found in Goodman and Gilman's "The Pharmacological Basis of Therapeutics" Tenth Edition edited by Hardman, Limbird and Gilman or the Physician's Desk Reference, both of which are incorporated herein by reference in their entirety.

The compounds described herein can be used in combination with the agents disclosed herein or other suitable agents, depending on the condition being treated. Hence, in some embodiments the one or more compounds of the disclosure will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the disclosure and any of the agents described above can be simultaneously administered, wherein both the agents are present in separate formulations. In another alternative, a compound of the present disclosure can be administered just followed by and any of the agents described above, or vice versa. In some embodiments of the separate administration protocol, a compound of the disclosure and any of the agents described above are administered a few minutes apart, or a few hours apart, or a few days apart.

The following examples are given for the purpose of illustrating various embodiments of the disclosure and are not meant to limit the present disclosure in any fashion. The present examples, along with the methods and compositions described herein, are presently representative of preferred embodiments, are exemplary, and are not intended as limitations on the scope of the disclosure. Changes therein and other uses which are encompassed within the spirit of the disclosure as defined by the scope of the claims will occur to those skilled in the art.

EXAMPLES

Example 1: Synthesis of Compound 59 in Table 1

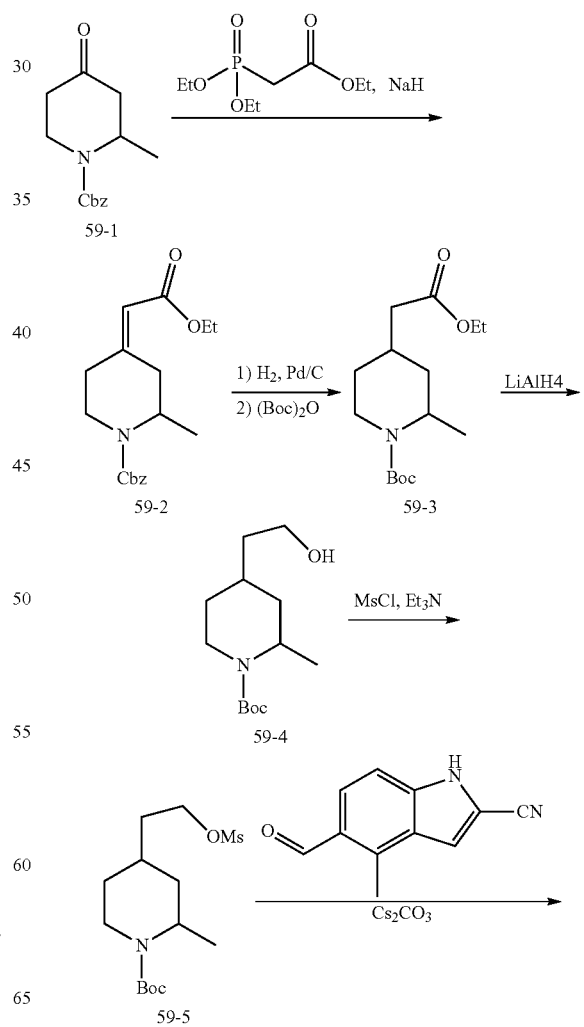

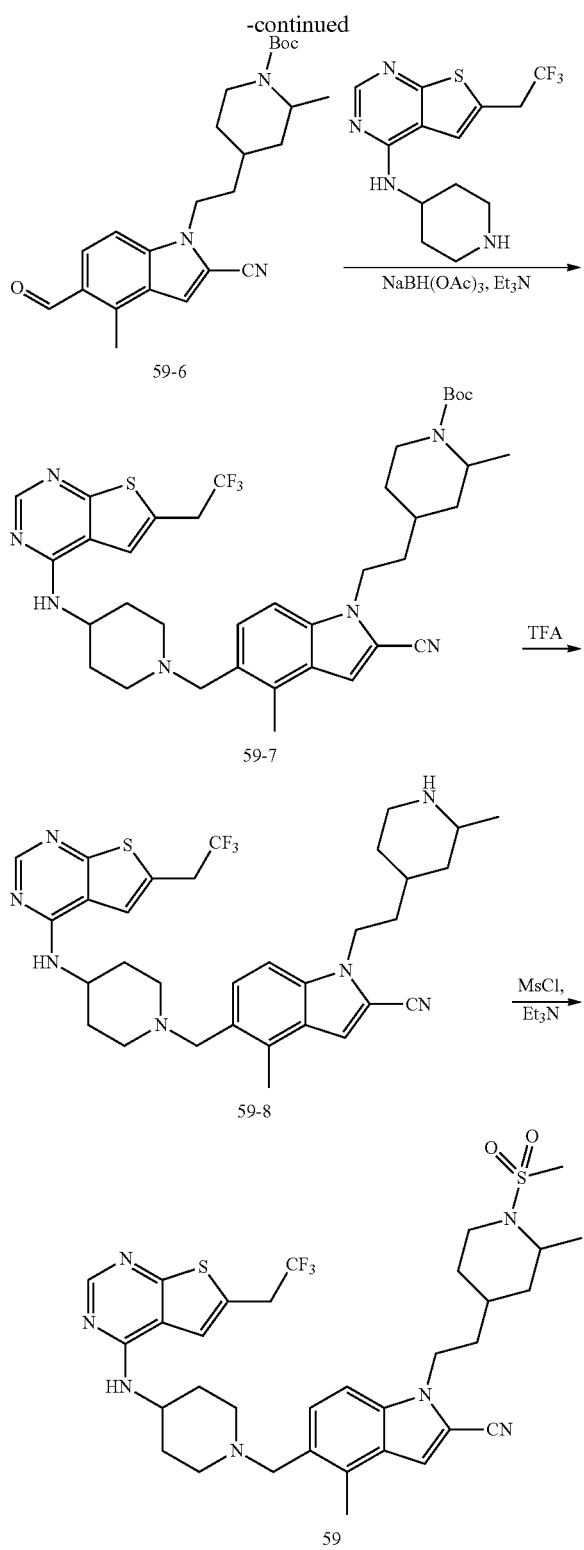

acetate (50 mL×2). The combined organic layer was washed with brine (50 mL), dried over sodium sulfate and concentrated in vacuo. The residue was purified by flash chromatography (eluted 20% EtOAc in pet. ether) to afford 2.15 g of 59-2 as a white solid (yield: 85%).

Step B: Preparation of Compound 59-3:

To a solution of 59-2 (905 mg, 2.85 mmol) in MeOH (20 mL) was added (Boc)$_2$O (1.24 g, 5.71 mmol) and Pd/C catalyst. The reaction mixture was stirred at room temperature for 8 hours under H$_2$. TLC showed the reaction was complete. The reaction was filtered and concentrated. The residue was purified by silica gel column chromatography (eluted 20% EtOAc in pet. ether) to give 59-3 as a solid (740 mg, yield: 91%).

Step C: Preparation of Compound 59-4:

To a solution of 59-3 (670 mg, 2.35 mmol) in THF (20 mL) was added LiAlH$_4$ (179 mg, 4.7 mmol) at 0° C. The reaction was stirred at 0° C. for 2 h, then 0.2 mL H$_2$O, 0.2 mL 15% NaOH, and 0.5 mL H$_2$O added. The mixture was stirred at room temperature for 1 h. The mixture was filtered and the organic solution was concentrated. The residue was purified by silica gel column chromatography (eluted 40% EtOAc in pet. ether) to give 59-4 as a solid (525 mg, yield: 92%).

Step D: Preparation of Compound 59-5:

To a solution of 59-4 (486 mg, 2 mmol) and Et$_3$N (404 mg, 4 mmol) in CH$_2$Cl$_2$ (20 mL) was added MsCl (344 mg, 3 mmol) at 0° C. The reaction was stirred at room temperature for 1 h. TLC showed the reaction was complete. The combined organic layer was washed with H$_2$O and brine, dried over sodium sulfate and concentrated in vacuo to afford 500 mg of 59-5 as a white solid (yield: 78%).

Step E: Preparation of Compound 59-6:

A mixture of 59-5 (500 mg, 1.56 mmol), Cs$_2$CO$_3$ (846 mg, 2.33 mmol), and 5-formyl-4-methyl-1H-indole-2-carbonitrile (143 mg, 0.78 mmol) was mixed in DMF (20 mL). The reaction mixture was heated at 85° C. for 3 h. EtOAc (200 mL) was added into the resulting mixture. The combined organic layer was washed with H$_2$O and brine, dried over sodium sulfate and concentrated. The residue was purified by flash column (eluted 30% EtOAc in pet. ether) to afford 278 mg of 59-6 as a white solid (yield: 43%).

Step F: Preparation of Compound 59-7:

A mixture of 59-6 (278 mg, 0.68 mmol), N-(piperidin-4-yl)-6-(2,2,2-trifluoroethyl)thieno[2,3-d]pyrimidin-4-amine (280 mg, 0.88 mmol) and Et$_3$N (412 mg, 4.08 mmol) in CH$_2$Cl$_2$ (20 mL) was stirred at room temperature for 1 hour. NaBH(OAc)$_3$ (865 mg, 4.08 mmol) was added to the reaction under ice bath and the reaction mixture stirred at room temperature overnight. The solvent was removed by vacuum and the residue was purified by silica gel column chromatography (eluted 2.5% MeOH in dichloromethane) to give 59-7 as a white solid (400 mg, yield: 82%).

Step G: Preparation of Compound 59-8:

A solution of 59-7 (200 mg, 0.28 mmol) in TFA (15 mL) was stirred at room temperature for 2 hours. Solvent was removed and a solution of NH$_3$ (7N) in MeOH (10 mL) was added. The resulting mixture was concentrated and the residue was purified by silica gel column chromatography (eluted 10% MeOH in dichloromethane) to give 59-8 as an oil (164 mg, yield: 96%).

Step H: Preparation of Compound 59:

To a solution of 59-8 (127 mg, 0.21 mmol) and Et$_3$N (43 mg, 0.42 mmol) in CH$_2$Cl$_2$ (20 mL) was added MsCl (29 mg, 0.25 mmol) at 0° C. The reaction was stirred at room temperature for 1 h. TLC showed the reaction was complete. The combined organic layer was washed with H$_2$O and Step A: Preparation of Compound 59-2:

To a solution of ethyl-2-(diethoxylphosphoryl) acetate (1.91 g, 8.5 mmol) in THF (30 mL) was added NaH (421 mg, 10.5 mmol) at 0° C. The reaction was stirred at 0° C. for 0.5 hour before 59-1 (2 g, 8 mmol) was added. The reaction mixture was stirred at room temperature for 5 h. Ice-water (50 mL) was added, and the product extracted with ethyl brine, dried over sodium sulfate, and concentrated in vacuo to afford 45 mg of 59 as a white solid (yield: 31%). $^1$HNMR (400 MHz, DMSO) δ: 8.33 (s, 1H), 7.87 (s, 1H), 7.67 (s, 1H) 7.45-7.56 (m, 3H), 4.35-4.32 (m, 2H), 4.08-4.02 (m, 4H), 3.57-3.54 (m, 3H), 3.17 (m, 1H, 2.88-2.83 (m, 6H), 2.54 (s, 3H), 2.20-1.47 (m, 12H), 1.25 (d, 3H). ESI-MS m/z: 688.84 (M+H).

Example 2: Synthesis of Compound 48 in Table 1

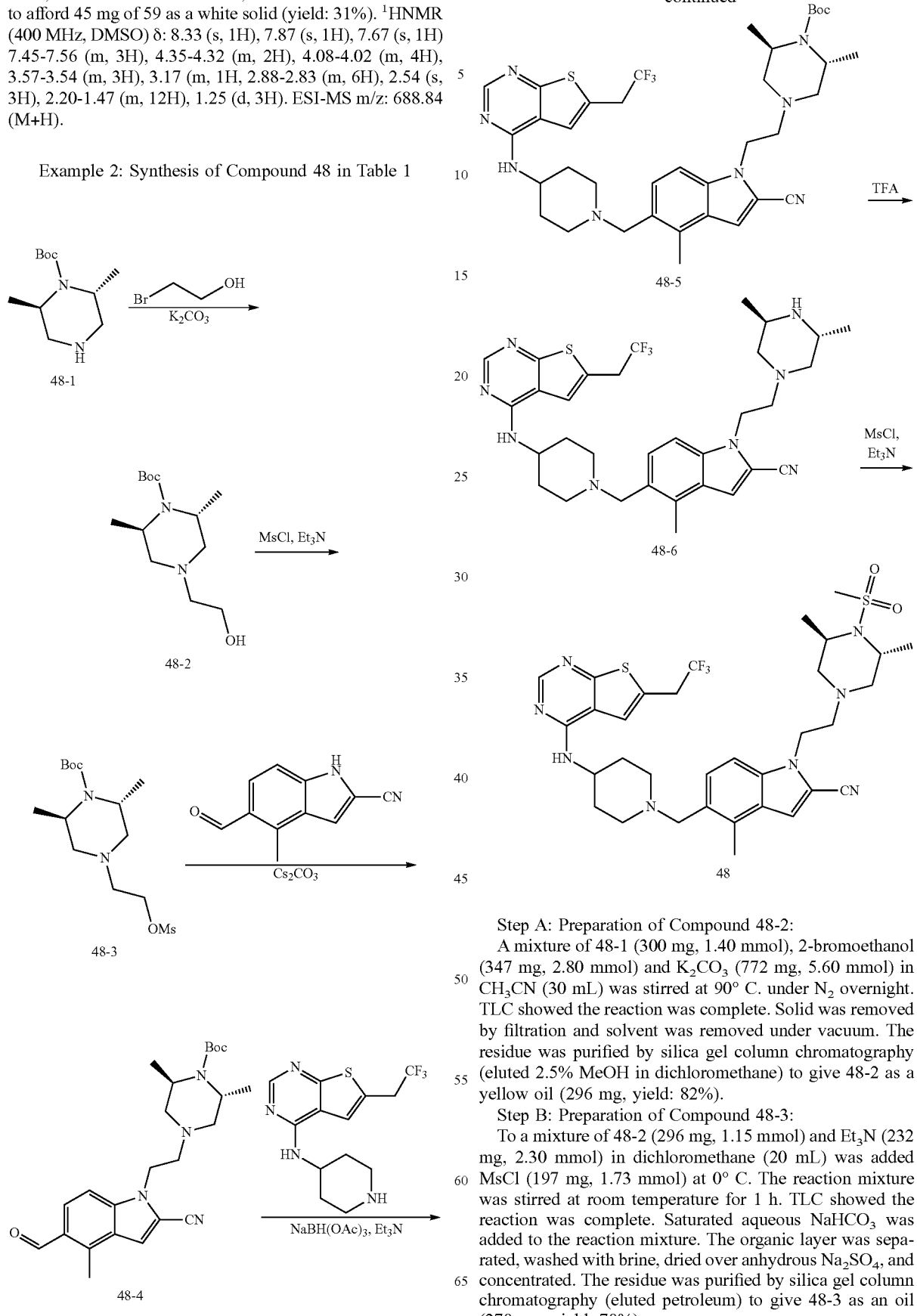

Step A: Preparation of Compound 48-2:

A mixture of 48-1 (300 mg, 1.40 mmol), 2-bromoethanol (347 mg, 2.80 mmol) and K$_2$CO$_3$ (772 mg, 5.60 mmol) in CH$_3$CN (30 mL) was stirred at 90° C. under N$_2$ overnight. TLC showed the reaction was complete. Solid was removed by filtration and solvent was removed under vacuum. The residue was purified by silica gel column chromatography (eluted 2.5% MeOH in dichloromethane) to give 48-2 as a yellow oil (296 mg, yield: 82%).

Step B: Preparation of Compound 48-3:

To a mixture of 48-2 (296 mg, 1.15 mmol) and Et$_3$N (232 mg, 2.30 mmol) in dichloromethane (20 mL) was added MsCl (197 mg, 1.73 mmol) at 0° C. The reaction mixture was stirred at room temperature for 1 h. TLC showed the reaction was complete. Saturated aqueous NaHCO$_3$ was added to the reaction mixture. The organic layer was separated, washed with brine, dried over anhydrous Na$_2$SO$_4$, and concentrated. The residue was purified by silica gel column chromatography (eluted petroleum) to give 48-3 as an oil (270 mg, yield: 70%).

Step C: Preparation of Compound 48-4:

A mixture of 48-3 (270 mg, 0.8 mmol), 5-formyl-4-methyl-1H-indole-2-carbonitrile (123 mg, 0.67 mmol) and $Cs_2CO_3$ (524 mg, 1.6 mmol) in DMF (10 mL) was stirred at 80° C. under $N_2$ overnight. Solid was removed by filtration before the reaction mixture was diluted with water and ethyl acetate. The organic layer was separated, washed with brine, dried over anhydrous $Na_2SO_4$, concentrated and purified by silica gel column chromatography (eluted 20% ethyl acetate in petroleum) to give 48-4 as an oil (169 mg, yield: 50%). ESI-MS m/z: 424.54 (M+H).

Step D: Preparation of Compound 48-5:

A mixture of 48-4 (169 mg, 0.4 mmol), N-(piperidin-4-yl)-6-(2,2,2-trifluoroethyl)thieno[2,3-d]pyrimidin-4-amine (190 mg, 0.6 mmol) and $Et_3N$ (242 mg, 2.4 mmol) in $CH_2Cl_2$ (20 mL) was stirred at room temperature for 1 hour. $NaBH(OAc)_3$ (508 mg, 2.4 mmol) was added to the reaction under ice bath cooling and the mixture reaction was stirred at room temperature overnight. Solvent was removed by vacuum and the residue was purified by silica gel column chromatography (eluted 2.5% MeOH in dichloromethane) to give 48-5 as an oil (174 mg, yield: 60%). ESI-MS m/z: 724.88 (M+H).

Step E: Preparation of Compound 48-6:

To a solution of 48-5 (174 mg, 0.24 mmol) in $CH_2Cl_2$ (15 mL) was added TFA (5 mL). The reaction was stirred at room temperature for 2 hours before solvent was removed. A solution of $NH_3$/MeOH (7N, 10 mL) was added and the resulting mixture was concentrated. The residue and purified by silica gel column chromatography (eluted 10% MeOH in dichloromethane) to give 48-6 as an oil (120 mg, yield: 80%). ESI-MS m/z: 624.30 (M+H).

Step F: Preparation of Compound 48:

To a mixture of 48-6 (120 mg, 0.192 mmol) and $Et_3N$ (39 mg, 0.384 mmol) in $CH_2Cl_2$ (10 mL) was added slowly methanesulfonyl chloride (33 mg, 0.288 mmol) in $CH_2Cl_2$ (5 mL) at −20° C. under $N_2$. The reaction mixture was stirred at room temperature for 2 hours. TLC showed the reaction was complete. Saturated aqueous $NaHCO_3$ was added to the reaction mixture. The organic layer was separated, washed with brine, dried over anhydrous $Na_2SO_4$, concentrated and purified by silica gel column chromatography (eluted 10% MeOH in dichloromethane) to give final product 48 as a solid (54 mg, yield: 40%). $^1$H NMR (400 MHz, $CDCl_3$) δ: 8.48 (s, 1H), 7.38 (d, 1H), 7.21 (s, 1H), 7.15 (d, 1H), 7.08 (s, 1H), 5.10 (d, 1H), 4.34 (m, 2H), 4.24 (m, 1H), 3.87 (m, 2H), 3.65 (m, 4H), 2.93 (m, 5H), 2.71 (m, 2H), 2.63 (m, 2H), 2.57 (s, 3H), 2.29 (m, 2H), 2.21 (m, 2H), 2.10 (d, 2H), 1.61 (m, 2H), 1.31 (d, 6H); ESI-MS m/z: 702.27 (M+H).

Example 3: Synthesis of Compound 2 in Table 1

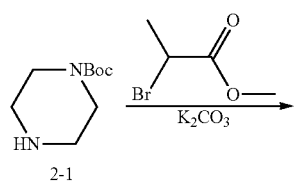

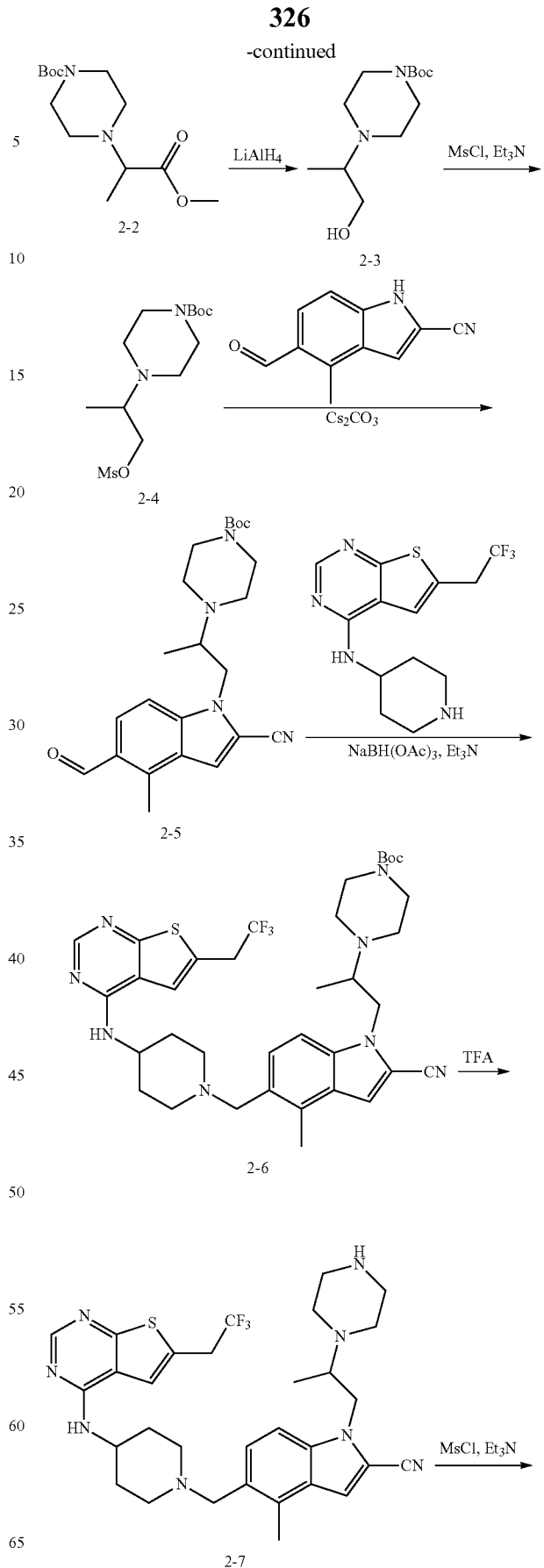

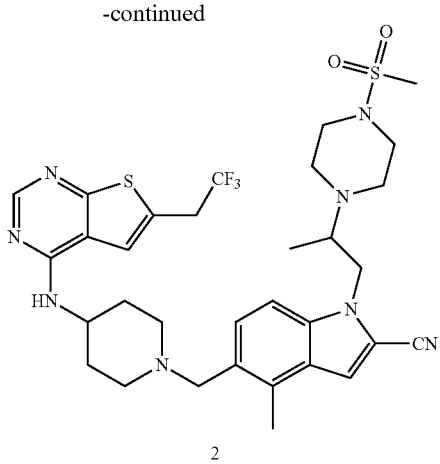

2

Step A: Preparation of Compound 2-2:

To a suspension of K₂CO₃ (3.6 g, 26.5 mmol) and tert-butyl piperazine-1-carboxylate (1.0 g, 5.3 mmol) in CH₃CN (15 mL) was added methyl 2-bromopropanoate (2.2 g, 13.4 mmol). The reaction was stirred at 80° C. for 10 hours. TLC showed that the reaction was complete. The reaction mixture was allowed to cool to room temperature, then the solid filtered off and solvent removed under vacuum. The residue was purified by silica gel column chromatography (CH₂Cl₂/MeOH=50:1) to give tert-butyl 4-(1-methoxy-1-oxopropan-2-yl)piperazine-1-carboxylate (2-2) as a brown oil (1.4 g, yield: 99%).

Step B: Preparation of Compound 2-3:

To a solution of tert-butyl 4-(1-methoxy-1-oxopropan-2-yl)piperazine-1-carboxylate (540 mg, 2 mmol) in THF (10 mL) was added LiAlH₄ (1.0 mL, 2.5 mol in THF) at 0° C. dropwise. The reaction mixture was stirred at the same temperature for 2 hours. TLC showed that the reaction was complete. The reaction was quenched with EtOAc. The reaction was partitioned between EtOAc and H₂O, and the organic layer was washed with brine and dried over Na₂SO₄. Solvent was removed under vacuum and the residue was purified by silica gel column chromatography (CH₂Cl₂/MeOH=20:1) to give tert-butyl 4-(1-hydroxypropan-2-yl)piperazine-1-carboxylate (2-3) as a brown oil (300 mg, yield: 65%).

Step C: Preparation of Compound 2-5:

To a solution of tert-butyl 4-(1-hydroxypropan-2-yl)piperazine-1-carboxylate (200 mg, 0.82 mmol) and Et₃N (171 mg, 1.64 mmol) in CH₂Cl₂ (10 mL) was added MsCl (112 mg, 0.98 mmol) at 0° C. The reaction was stirred at room temperature for 30 min. The reaction was quenched with NaHCO₃, washed with brine and dried over Na₂SO₄. Solvent was removed under vacuum to give tert-butyl 4-(1-((methylsulfonyl)oxy)propan-2-yl)piperazine-1-carboxylate (2-4), used in the next step without further purification.

To a mixture of Cs₂CO₃ (682 mg, 2.1 mmol) and 5-formyl-4-methyl-1H-indole-2-carbonitrile (77 mg, 0.42 mmol) in DMF was added tert-butyl 4-(1-((methylsulfonyl)oxy)propan-2-yl)piperazine-1-carboxylate in DMF. The reaction was stirred at 100° C. for 10 hours. The reaction mixture was partitioned between EtOAc and H₂O, and the organic layer was washed with brine and dried over Na₂SO₄. Solvent was removed under vacuum and the residue was purified by silica gel column chromatography (pet. ether/EtOAc=5:1~3:1) to give tert-butyl 4-(1-(2-cyano-5-formyl-4-methyl-1H-indol-1-yl)propan-2-yl)piperazine-1-carboxylate (2-5) as a yellow solid (90 mg, yield: 53%).

Step D: Preparation of Compound 2-6:

A mixture of tert-butyl 4-(1-(2-cyano-5-formyl-4-methyl-1H-indol-1-yl)propan-2-yl)piperazine-1-carboxylate (90 mg, 0.22 mmol), 6-(2,2,2-trifluoroethyl)-N-(piperidin-4-yl)thieno-[2,3-d]pyrimidin-4-amine (100 mg, 0.26 mmol) and Et₃N (130 mg, 1.32 mmol) in CH₂Cl₂ (10 mL) was stirred at room temperature for 1 hour before NaBH(OAc)₃ (280 mg, 1.32 mmol) was added. The reaction mixture was stirred at room temperature overnight, then partitioned between CH—₂Cl₂ and NaHCO₃. The organic layer was washed with brine and dried over Na₂SO₄. Solvent was removed under vacuum and the residue was purified by silica gel column chromatography (CH₂Cl₂:MeOH=50:1~20:1) to give tert-butyl 4-(1-(2-cyano-4-methyl-5-((4-((6-(2,2,2-trifluoroethyl)thieno[2,3-d]pyrimidin-4-yl)amino)piperidin-1-yl)methyl)-1H-indol-1-yl)propan-2-yl)piperazine-1-carboxylate (2-6) as a yellow solid (130 mg, yield: 81%).

Step E: Preparation of Compound 2-7:

To a solution of tert-butyl 4-(2-(2-cyano-4-methyl-5-((4-((6-(2,2,2-trifluoroethyl)thieno[2,3-d]pyrimidin-4-yl)amino)piperidin-1-yl)methyl)-1H-indol-1-yl)-1-hydroxyethyl)piperidine-1-carboxylate (130 mg, 0.21 mmol) in CH₂Cl₂ (3 mL) was added TFA (2 mL). The reaction was stirred for 4 hours before solvent was removed under vacuum. The residue was diluted with CH₂Cl₂ and washed with NaHCO₃. The organic layer was washed with brine and dried over Na₂SO₄. Solvent was removed under vacuum and the residue (2-7) was used without further purification as a yellow foam (100 mg, yield: 98%).

Step F: Preparation of Compound 2:

To a solution of 4-methyl-1-(2-(piperazin-1-yl)propyl)-5-((4-((6-(2,2,2-trifluoroethyl)thieno[2,3-d]pyrimidin-4-yl)amino)piperidin-1-yl)methyl)-1H-indole-2-carbonitrile (60 mg, 0.1 mmol) and Et₃N (36 mg, 0.4 mmol) in CH₂Cl₂ (10 mL) was added MsCl (21 mg, 0.2 mmol) at 0° C. The reaction was stirred at room temperature for 30 min. The reaction was quenched by NaHCO₃, washed with brine and dried over Na₂SO₄. Solvent was removed and the residue was purified by Prep-TLC (CH₂Cl₂:MeOH=15:1) to give 4-methyl-1-(2-(4-(methylsulfonyl)piperazin-1-yl)propyl)-5-((4-((6-(2,2,2-trifluoroethyl)thieno[2,3-d]pyrimidin-4-yl)amino)piperidin-1-yl)methyl)-1H-indole-2-carbonitrile (compound 2) as a white solid (10 mg, yield: 20%). ¹H NMR (400 MHz, CDCl₃) 8.48 (s, 1H), 7.36 (d, 1H), 7.20 (s, 1H), 7.00-7.15 (m, 2H), 5.16 (d, 1H), 4.20-4.40 (m, 2H), 4.00-4.10 (m, 1H), 3.60-3.70 (m, 4H), 3.10-3.30 (m, 5H), 2.80-2.90 (m, 4H), 2.77 (s, 3H), 2.57 (s, 3H), 1.56-2.53 (m, 8H), 1.08 (d, 3H). ESI-MS m/z: 689.25 (M+H).

Example 4: Synthesis of Compound 61 in Table 1

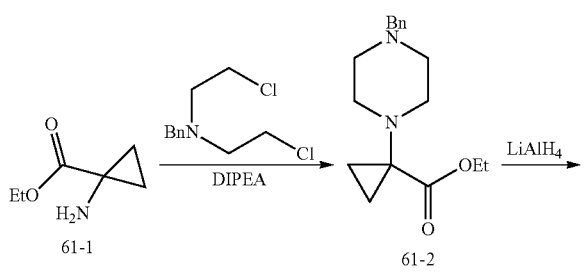

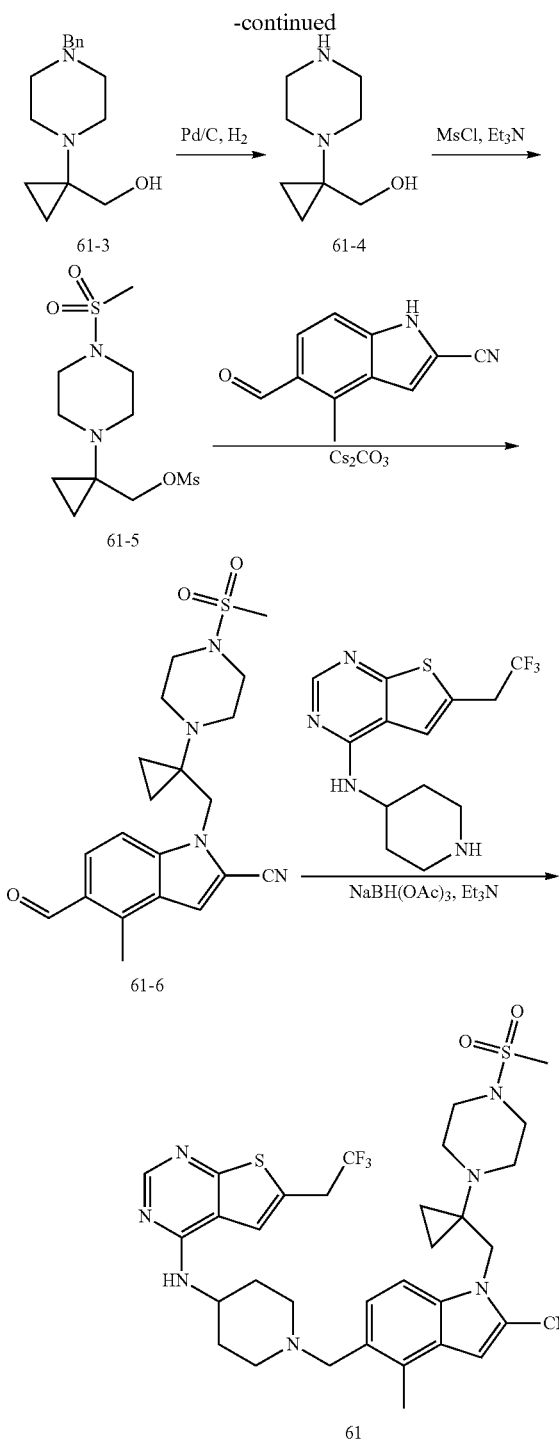

Step A: Preparation of Compound 61-2:

A mixture of ethyl 1-aminocyclopropanecarboxylate hydrochloride (2.4 g, 14.5 mmol), N-benzyl-2-chloro-N-(2-chloroethyl)ethanamine hydrochloride (4.26 g, 15.8 mmol), and N,N-Diisopropylethylamine (25 mL) in ethanol (32 mL) was stirred at reflux for 16 hours. The reaction mixture was concentrated to dryness. The residue was partitioned between dichloromethane and water. Two layers were separated, and the aqueous layer was extracted with dichloromethane. The combined organic layers were concentrated. The residue was purified by silica gel column (pet. ether/ EtOAc=1:0~10:1) to give ethyl 1-(4-benzylpiperazin-1-yl)cyclopropanecarboxylate (61-2, 1.8 g, yield: 43%) as a yellow oil. $^1$H NMR (400 MHz, CDCl$_3$) δ: 7.37-7.27 (m, 5H), 4.19-4.13 (m, 2H), 3.54 (s, 2H), 3.00 (brs, 2H), 2.39 (brs, 2H), 1.31-1.26 (m, 5H), 7.52 (m, 1H), 0.93-0.91 (m, 2H).

Step B: Preparation of Compound 61-3:

To a mixture of ethyl 1-(4-benzylpiperazin-1-yl)cyclopropanecarboxylate (880 mg, 3 mmol) in THF (12 mL) was added LiAlH$_4$ (290 mg, 6 mmol) slowly at 0° C. The resulting mixture was stirred at 0° C. for 1 h. Water (0.5 mL) was added, followed by ethyl acetate (20 mL). Solid was filtered off and solvent was removed. The residue was purified by silica gel column (pet. ether/EtOAc=3:1) to give (1-(4-benzylpiperazin-1-yl)cyclopropyl)methanol (61-3, 660 mg, yield: 88%) as a white solid.

Step C: Preparation of Compound 61-4:

A mixture of (1-(4-benzylpiperazin-1-yl)cyclopropyl) methanol (600 mg, 2.4 mmol) and Pd/C (10%, 50 mg) in ethanol (10 mL) was stirred at 50° C. overnight under H$_2$. The reaction mixture was filtered and the filtrate concentrated to give (1-(piperazin-1-yl)cyclopropyl)methanol (61-4) as an oil (400 mg, yield: 96%). The crude product was used in the next step without further purification.

Step D: Preparation of Compound 61-5:

To a mixture of (1-(piperazin-1-yl)cyclopropyl)methanol (400 mg, 2.5 mmol) in dichloromethane (10 mL) was added Et$_3$N (1.1 mL, 7.5 mmol), followed by a mixture of methanesulfonyl chloride (925 mg, 7.5 mmol) in dichloromethane (5 mL). The resulting mixture was stirred at room temperature for 4 h. The reaction mixture was diluted with water and CH$_2$Cl$_2$. The organic layer was dried over Na$_2$SO$_4$, and concentrated to give a crude product (1-(4-(methylsulfonyl)piperazin-1-yl)cyclopropyl)methyl methanesulfonate (61-5) as a brown oil (500 mg).

Step E: Preparation of Compound 61-6:

A mixture of crude (1-(4-(methylsulfonyl)piperazin-1-yl) cyclopropyl)methyl methanesulfonate (500 mg), 5-formyl-4-methyl-1H-indole-2-carbonitrile (200 mg, 1.1 mmol), and K$_2$CO$_3$ (800 mg, 5.8 mmol) in acetonitrile was stirred at 80° C. overnight. The mixture was filtered and the filtrate was concentrated to dryness. The residue was purified by silica gel column (pet. ether/EtOAc=3:1) to give 5-formyl-4-methyl-1-((1-(4-(methylsulfonyl)piperazin-1-yl)cyclopropyl)methyl)-1H-indole-2-carbonitrile (61-6, 330 mg) as a brown solid. ESI-MS m/z: 401 (M+H).

Step F: Preparation of Compound 61:

A mixture of 5-formyl-4-methyl-1-((1-(4-(methylsulfonyl)piperazin-1-yl)cyclopropyl)methyl)-1H-indole-2-carbonitrile (330 mg, crude), N-(piperidin-4-yl)-6-(2,2,2-trifluoroethyl)thieno[2,3-d]pyrimidin-4-amine hydrochloride (391 mg, 1.1 mmol), and Et$_3$N (0.5 mL) in dichloromethane (12 mL) was stirred at room temperature overnight. The reaction mixture was diluted with water and CH$_2$Cl$_2$. The organic layer was separated, dried over Na$_2$SO$_4$, and concentrated. The residue was purified by silica gel column (dichloromethane/methanol=50:1~30:1) to give a crude product. The crude product was purified by Prep-TLC with dichloromethane/methanol (7N NH$_3$/MeOH)=50:1 to give the product (compound 61) as a colorless solid (12 mg). ESI-MS m/z: 701 (M+H). $^1$H NMR (400 MHz, CDCl$_3$) δ: 8.46 (s, 1H), 7.20-7.28 (m, 3H), 4.30-4.36 (m, 3H), 3.84 (brs, 2H), 3.61-3.68 (m, 2H), 3.09-3.13 (m, 6H), 2.76 (s, 3H), 2.64-2.66 (m, 4H), 2.59 (s, 3H), 2.40-2.48 (m, 2H), 2.14-2.18 (m, 2H), 1.87-1.90 (m, 2H), 0.79-0.82 (t, 2H), 0.61-0.64 (t, 2H).

Example 5: Synthesis of Compound 35 in Table 1

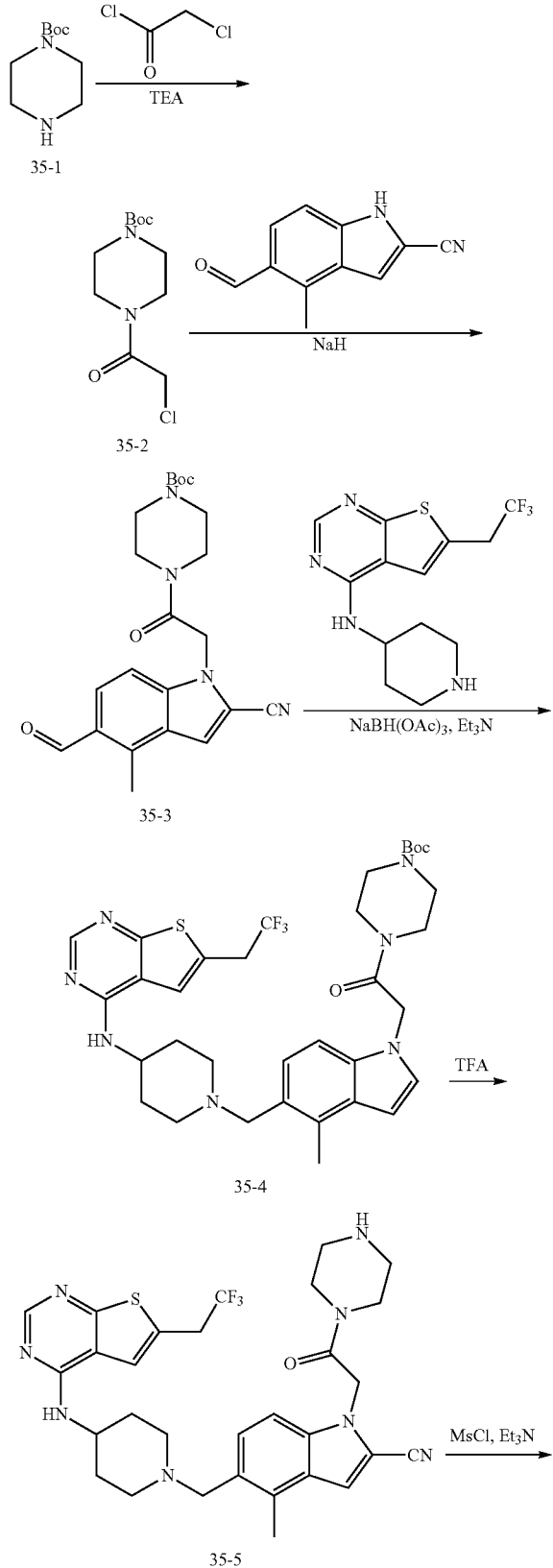

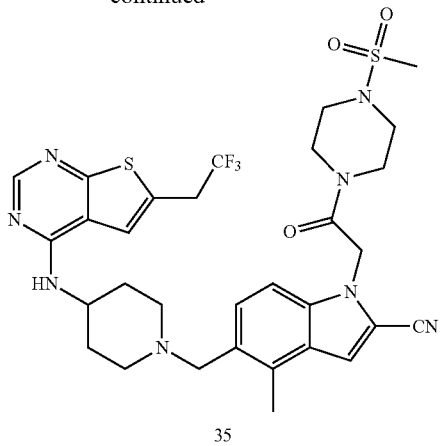

Step A: Preparation of Compound 35-2:

A mixture of tert-butyl piperazine-1-carboxylate (1.9 g, 10 mmol) and Et$_3$N (3 g, 30 mmol) in CH$_2$Cl$_2$ (40 mL) was stirred at 0° C. before 2-chloroacetyl chloride (2.2 g, 20 mmol) was added slowly. The reaction mixture was stirred at 0° C. under N$_2$ for 4 hr. TLC showed that the reaction was complete. The reaction mixture was partitioned between CH$_2$Cl$_2$ and H$_2$O, and the organic layer was washed with brine and dried over Na$_2$SO$_4$. Solvent was removed under vacuum and the residue (35-2) was used without further purifications as light yellow oil (2.5 g, yield: 95%).

Step B: Preparation of Compound 35-3:

To a mixture of N-(piperidin-4-yl)-6-(2,2,2-trifluoroethyl)thieno[2,3-d]pyrimidin-4-amine (1 g, 4 mmol), and 5-formyl-4-methyl-1H-indole-2-carbonitrile (540 mg, 3 mmol) in THF (10 mL) was added NaH (180 mg, 4.5 mmol) at 0° C. The reaction mixture was stirred at room temperature for 16 hours. The reaction mixture was then partitioned between EtOAc and H$_2$O, and the organic layer was washed with brine and dried over Na$_2$SO$_4$. Solvent was removed under vacuum and the residue purified by silica gel column chromatography (pet. ether:EtOAc=10:1~1:1) to give tert-butyl 4-(2-(2-cyano-5-formyl-4-methyl-1H-indol-1-yl)acetyl)piperazine-1-carboxylate (35-3) as a light yellow solid (60 mg, yield: 4%).

Step C: Preparation of Compound 35-4:

A mixture of methyl tert-butyl 4-(2-(2-cyano-5-formyl-4-methyl-1H-indol-1-yl)acetyl)piperazine-1-carboxylate (40 mg, 0.1 mmol), N-(piperidin-4-yl)-6-(2,2,2-trifluoroethyl)thieno[2,3-d]pyrimidin-4-amine hydrochloride (60 mg, 0.2 mmol) and Et$_3$N (60 mg, 0.6 mmol) in CH$_2$Cl$_2$ (5 mL) was stirred at room temperature for 2 hours. NaBH(OAc)$_3$ (120 mg, 0.6 mmol) was then added to the reaction with ice bath cooling. The reaction mixture was stirred at room temperature overnight. The reaction was partitioned between CH$_2$Cl$_2$ and NaHCO$_3$, and the organic layer was washed with brine and dried over Na$_2$SO$_4$. Solvent was removed under vacuum and the residue was purified by silica gel column chromatography (CH$_2$Cl$_2$:MeOH=100:1~20:1) to give tert-butyl 4-(2-(2-cyano-4-methyl-5-((4-((6-(2,2,2-trifluoroethyl)thieno[2,3-d]pyrimidin-4-yl)amino)piperidin-1-yl)methyl)-1H-indol-1-yl)acetyl)piperazine-1-carboxylate (35-4) as a yellow solid (40 mg, yield: 55%).

Step D: Preparation of Compound 35-5:

A solution of tert-butyl 4-(2-(2-cyano-4-methyl-5-((4-((6-(2,2,2-trifluoroethyl)thieno[2,3-d]pyrimidin-4-yl)amino)piperidin-1-yl)methyl)-1H-indol-1-yl)acetyl)piperazine-1- carboxylate (40 mg, 0.06 mmol) in HCl-MeOH (10 mL) was stirred at room temperature for 16 h. TLC showed that the reaction was complete. Solvent was removed under vacuum and the residue (35-5) was used without further purification in next step as a yellow solid (35 mg, yield: 85%).

Step E: Preparation of Compound 35:

To a mixture of 4-methyl-1-(2-oxo-2-(piperazin-1-yl) ethyl)-5-((4-((6-(2,2,2-trifluoroethyl)thieno[2,3-d]pyrimidin-4-yl)amino)piperidin-1-yl)methyl)-1H-indole-2-carbonitrile (35 mg, 0.05 mmol) and $Et_3N$ (15 mg, 0.15 mmol) in $CH_2Cl_2$ (10 mL) was slowly added MsCl (12 mg, 0.1 mmol) at 0° C. The reaction mixture was stirred at room temperature for 4 hours and then partitioned between $CH_2Cl_2$ and $NaHCO_3$. The organic layer was washed with brine and dried over $Na_2SO_4$. Solvent was removed under vacuum and the residue was purified by Prep-TLC ($CH_2Cl_2$:MeOH=20: 1) to give 4-methyl-1-(2-(4-(methylsulfonyl)piperazin-1-yl)-2-oxoethyl)-5-((4-((6-(2,2,2-trifluoroethyl)thieno[2,3-d] pyrimidin-4-yl)amino)piperidin-1-yl)methyl)-1H-indole-2-carbonitrile (compound 35) as a white solid (16 mg, yield: 56%). $^1$HNMR (400 MHz, $CDCl_3$) 8.42 (s, 1H), 7.84-7.76 (m, 1H), 7.33~7.22 (m, 3H), 5.15 (s, 2H), 4.37~4.08 (m, 2H), 3.78 (s, 3H), 3.69~3.61 (m, 2H), 3.44~3.30 (m, 5H), 2.86 (s, 3H), 2.70~2.54 (m, 4H), 2.15~2.06 (m, 3H), 1.35~1.23 (m, 4H), 0.91~0.85 (m, 2H).

Example 6: Fluorescence Polarization Assay

This example illustrates an assay effective in monitoring the binding of MLL to menin. Fluorescence polarization (FP) competition experiments were performed to determine the effectiveness with which a compound inhibits the menin-MLL interaction, reported as an $IC_{50}$ value. A fluorescein-labeled peptide containing the high affinity menin binding motif found in MLL was produced according to Yokoyama et al. (*Cell*, 2005, 123(2): 207-218), herein incorporated by reference in its entirety. Binding of the labeled peptide (1.7 kDa) to the much larger menin (~67 kDa) is accompanied by a significant change in the rotational correlation time of the fluorophore, resulting in a substantial increase in the fluorescence polarization and fluorescence anisotropy (excitation at 500 nm, emission at 525 nm). The effectiveness with which a compound inhibits the menin-MLL interaction was measured in an FP competition experiment, wherein a decrease in fluorescence anisotropy correlates with inhibition of the interaction and was used as a read-out for $IC_{50}$ determination.

Table 3 shows biological activities of selected compounds in a fluorescence polarization assay. Compound numbers correspond to the numbers and structures provided in Tables 1 and 2 and Examples 1-5.

TABLE 3

| | Less than 50 nM (++++) | 50 nM to less than 250 nM (+++) | 250 nM to 1000 nM (++) | Greater than 1000 nM (+) |
|---|---|---|---|---|
| Menin MLL 4-43 $IC_{50}$ (nM) | 6, 8, 10, 12, 13, 14, 18, 20, 22, 27, 28, 64, 65, 73, 80, 85, 88, 89, 90, 92, 93, 115, 119, 123, 129, 131, 132, 134, 135, 136, 138, 139, 141, 147, 148, 149, 151, 154, 158, 163, 165, 166, 172, 175, 176, 177, 178, 181, 182, 183, 184, 186, 187, 189, 191, 192, 193, 194, 196, 197, 202, 203, 204, 205, 206, 207, 209, 210, 212, 213, 214, 215, 216, 217, 219, 220, 221, 222, 225, 226, 229, 233, 239, 243, 244, 246, 247, 248, 249, 250, 251, 281, 282, 283, 1020, 1021, 1022, 1024, 1025, 1026, 1027 | 2, 4, 5, 7, 11, 17, 19, 21, 25, 29, 30, 43, 46, 48, 49, 54, 61, 68, 69, 70, 72, 74, 84, 87, 91, 94, 116, 117, 120, 121, 122, 124, 125, 126, 127, 128, 130, 133, 137, 140, 142, 143, 144, 145, 146, 150, 152, 153, 155, 156, 159, 160, 161, 162, 164, 167, 168, 171, 174, 179, 180, 185, 188, 190, 195, 198, 199, 208, 211, 230, 241, 245, 280, 1002, 1003, 1013, 1023 | 1, 3, 24, 26, 44, 45, 52, 53, 55, 56, 57, 58, 59, 66, 67, 82, 118, 157, 169, 173, 201, 1000, 1001, 1011 | 9, 15, 16, 23, 35, 47, 60, 62, 71, 170, 200, 242, 252, 1010, 1012 |

Example 7: Homogenous Time-Resolve Fluorescence (HTRF) Assay

A homogeneous time-resolve fluorescence (HTRF) assay is utilized as a secondary assay to confirm the results of the FP assay. In some embodiments, the HTRF assay is the primary assay and the FP assay is used as a secondary assay to confirm results. HTRF is based on the non-radiative energy transfer of the long-lived emission from the Europium cryptate ($Eu^{3+}$-cryptate) donor to the allophycocyanin (XL665) acceptor, combined with time-resolved detection. An $Eu^{3+}$-cryptate donor is conjugated with mouse anti-6His monoclonal antibody (which binds His-tagged menin) and XL665-acceptor is conjugate to streptavidin (which binds biotinylated MLL peptide). When these two fluorophores are brought together by the interaction of menin with the MLL peptide, energy transfer to the acceptor results in an increase in fluorescence emission at 665 nm and increased HTRF ratio (emission intensity at 665 nm/emission intensity at 620 nm). Inhibition of the menin-MLL interaction separates the donor from the acceptor, resulting in a decrease in emission at 665 nm and decreased HTRF ratio.

Example 8: Menin Engagement Assay

Sample Preparation: 2.5 µL of 100 µM compound is added to 47.5 µL of 526 nM menin in PBS (5 µM compound 500 nM menin in 5% DMSO final concentration). The reaction is incubated at room temperature for variable lengths of time and quenched with 2.5 µL of 4% formic acid (FA, 0.2% final concentration). Method: A Thermo Finnigan Surveyor Autosampler, PDA Plus UV detector and MS Pump along with an LTQ linear ion trap mass spectrometer were used to collect sample data under XCalibur software control. A 5 µL sample in "no waste" mode was injected onto a Phenomenex Jupiter 5u 300A C5 (guard column) 2×4.00 mm at 45° C. Mobile phase composition: Buffer A (95:5 water:acetonitrile, 0.1% FA) and Buffer B (acetonitrile, 0.1% FA). Gradient elution was used with an initial mobile phase of 85:15 (Buffer A:B) and a flow rate of 250 µL/min. Upon injection, 85:15 A:B was held for 1.3 min, Buffer B was increased to 90% over 3.2 min, held for 1 min, and then returned to initial conditions in 0.1 min and held for 2.4 min. The total run time is 8 min. A post-column divert valve employed to direct void volume salts to waste was used for the first 2 min of the sample method. Blank injection of Buffer A is used in between each of the sample injections. A needle wash of 1:1 acetonitrile:water with 0.1% FA was used. The electrospray ionization (ESI) source used a 300° C. capillary temperature, 40 units sheath gas flow, 20 units aux gas flow, 3 units sweep gas flow, 3.5 kV spray voltage, 120 V tube lens. Data Collection: Data collection was performed in the positive ion full scan mode 550-1500 Da, 10 microscans, 200 ms max ion time. Data analysis: Protein mass spectra were acquired as XCalibur datafiles. The best scans were added together using XCalibur Qual Browser. The spectra were displayed using "View/Spectrum List with a Display option to display all peaks. The Edit/Copy cell menu was used to copy the mass spectrum into the PC clipboard. The spectrum in the PC clipboard was pasted into Excel. The first two columns (m/z and Intensity were kept and the third column (Relative) was deleted. The remaining two columns were then saved as a tab delimited file (m/z and intensity) as filename.txt from Excel. The Masslynx Databridge program was then used to convert the filename.txt tab delimited file to Masslynx format. In some cases, an external calibration using a (similarly converted) myoglobin spectrum was applied in Masslynx to correct the m/z values of the menin protein m/z data. MaxEnt1 software from the MassLynx software suite was used for deconvolution of the mass spectrum to yield the average MW of the protein(s). The percentage of covalent adduct formation was determined from the deconvoluted spectrum and used to calculate the reaction rate (k) of the covalent reaction.

Example 9: Cell Proliferation Assay

The ability of a compound of the present disclosure to inhibit the growth of cells, such as human leukemia cell, acute myeloid leukemia cell, cells with an MLL fusion, control cells without an MLL fusion, VCaP, LNCaP, 22RV1, DU145, LNCaP-AR, MV4;11, KOPN-8, ML-2, MOLM-13, RS4;11, SEM, bone marrow cells (BMCs), MLL-AF9, MLL-AF4, MLL-ENL, MLL-CBP, MLL-GAS7, MLL-AF1p, MLL-AF6, HM-2, E2A-HLF, REH, U937, K562, KG-1, HL-60 and NB4 cells, is tested using a cell viability assay, such as the Promega CellTiter-Glo® Luminescent Cell Viability Assay (Promega Technical Bulletin, 2015, "CellTiter-Glo® Luminescent Cell Viability Assay": 1-15, herein incorporated by reference in its entirety). Cells are plated at relevant concentrations, for example about $1 \times 10^5$-$2 \times 10^5$ cells per well in a 96-well plate. A compound of the present disclosure is added at a concentration up to about 2 µM with eight, 2-fold serial dilutions for each compound. Cells are incubated at 37° C. for a period of time, for example, 72 hours, then cells in the control wells are counted. Media is changed to restore viable cell numbers to the original concentration, and compounds are re-supplied. Proliferation is measured about 72 hours later using Promega CellTiter-Glo® reagents, as per kit instructions. Certain compounds disclosed herein exhibited $GI_{50}$ values of less than 250 nM or less than 50 nM when tested in MV4;11 cells. As used in the Examples, the $GI_{50}$ value of a compound is the concentration of the compound for 50% of maximal inhibition of cell proliferation.

Table 4 shows biological activities of selected compounds in a cell proliferation assay. Compound numbers correspond to the numbers and structures provided in Tables 1 and 2 and Examples 1-5.

TABLE 4

| | Less than 10 nM (++++) | 10 nM to less than 50 nM (+++) | 50 nM to less than 250 nM (++) | 250 nM to 1000 nM (+) |
|---|---|---|---|---|
| MLL-AF9 BMC $GI_{50}$ (nM) | 132, 135, 151, 163, 165, 172, 177, 183, 199, 203, 205, 207, 214 | 10, 80, 138, 139, 171, 174, 175, 176, 181, 217 | | 9 |

Example 10: RT-PCR Analysis of MLL Fusion Protein Downstream Targets

The effect of a compound of the present disclosure on expression of one or more MLL fusion protein downstream targets is assessed by RT-PCR. Cells, such as human leukemia cell, acute myeloid leukemia cell, cells with an MLL fusion, control cells without an MLL fusion, VCaP, LNCaP, 22RV1, DU145, LNCaP-AR, MV4;11, KOPN-8, ML-2, MOLM-13, RS4;11, SEM, bone marrow cells (BMCs), MLL-AF9, MLL-AF4, MLL-ENL, MLL-CBP, MLL-GAS7, MLL-AF1p, MLL-AF6, HM-2, E2A-HLF, REH, U937, K562, KG-1, HL-60 and NB4 cells, are treated with an effective concentration of a compound disclosed herein for about 7 days or less, then total RNA is extracted from cells using any available kit such as an RNeasy mini kit (QIAGEN) according to the manufacturer's instructions. Total RNA is reverse transcribed using a High Capacity cDNA Reverse Transcription Kit (Applied Biosystems), and relative quantification of relevant gene transcripts (e.g., Hoxa9, DLX2, and Meis1) is determined by real-time PCR. Effective inhibition of the menin-MLL interaction is expected to result in the downregulation of downstream targets of MLL, including Hoxa9, DLX2, and Meis1.

Example 11: Pharmacokinetic Studies in Mice

The pharmacokinetics of menin-MLL inhibitors are determined in female C57BL/6 mice following intravenous (iv) dosing at 15 mg/kg and oral dosing (po) at 30 mg/kg. Compounds are dissolved in the vehicle containing 25%

(v/v) DMSO, 25% (v/v) PEG-400 and 50% (v/v) PBS. Serial blood samples (50 µL) are collected over 24 h, centrifuged at 15,000 rpm for 10 min and saved for analysis. Plasma concentrations of the compounds are determined by the LC-MS/MS method developed and validated for this study. The LC-MS/MS method consists of an Agilent 1200 HPLC system and chromatographic separation of tested compound is achieved using an Agilent Zorbax Extend-C18 column (5 cm×2.1 mm, 3.5 µm; Waters). An AB Sciex QTrap 3200 mass spectrometer equipped with an electrospray ionization source (ABI-Sciex, Toronto, Canada) in the positive-ion multiple reaction monitoring (MRM) mode is used for detection. All pharmacokinetic parameters are calculated by noncompartmental methods using WinNonlin® version 3.2 (Pharsight Corporation, Mountain View, Calif., USA).

Example 12: Efficacy Study in Mouse Xenograft Tumor Model

Immunodeficient mice, such as 8-10 week-old female nude (nu/nu) mice, are used for in vivo efficacy studies in accordance with the guidelines approved by IACUC. Leukemia cells, such as human MV4-11 leukemia cells available from ATCC, are implanted subcutaneously via needle into female nude mice ($5\times10^6$ cells/mouse). When the tumor reaches a size of approximately 150 to 250 mm$^3$ in mice, the tumor-bearing mice are randomly assigned to a vehicle control or compound treatment group (8 animals per group). Animals are treated with a compound of the present disclosure by oral gavage or intraperitoneal injection in an appropriate amount and frequency as can be determined by the skilled artisan without undue experimentation. Subcutaneous tumor volume in nude mice and mice body weight are measured twice weekly. Tumor volumes are calculated by measuring two perpendicular diameters with calipers (V=(length×width$^2$)/2). Percentage tumor growth inhibition (% TGI=1−[change of tumor volume in treatment group/change of tumor volume in control group]*100) is used to evaluate anti-tumor efficacy. Statistical significance is evaluated using a one-tailed, two sample t test. P<0.05 is considered statistically significant.

Example 13: Efficacy Study in Prostate Tumor Xenograft Model

Immunodeficient mice, such as 4-6 week-old male CB17 severe combined immunodeficiency (SCID) mice, are used for in vivo efficacy studies in accordance with the guidelines approved by IACUC. Parental prostate cancer cells, such as VCaP or LNCaP-AR cells, are implanted subcutaneously into male CB.17.SCID mice ($3-4\times10^6$ cells in 50% Matrigel). When the tumor reaches a palpable size of approximately 80 mm$^3$, the tumor-bearing mice are randomly assigned to a vehicle control or compound treatment group (6 or more animals per group). Animals are treated with a compound of the present disclosure by intraperitoneal injection in an appropriate amount and frequency as can be determined by the skilled artisan without undue experimentation. In one example, mice are treated with 40 mg/kg of a compound of the present disclosure daily by i.p. injection for two weeks, then 5 days per week thereafter. Subcutaneous tumor volume and mice body weight are measured twice weekly. Tumor volumes are calculated by measuring two perpendicular diameters with calipers (V=(length×width$^2$)/2).

Example 14: Efficacy Study in Castration-Resistant Prostate Tumor Xenograft Model (VCaP)

Immunodeficient mice, such as 4-6 week-old male CB17 severe combined immunodeficiency (SCID) mice, are used for in vivo efficacy studies in accordance with the guidelines approved by IACUC. Parental prostate cancer cells, such as VCaP cells, are implanted subcutaneously into male CB.17.SCID mice ($3-4\times10^6$ cells in 50% Matrigel). When the tumor reaches a size of approximately 200-300 mm$^3$, the tumor-bearing mice are physically castrated and tumors observed for regression and regrowth to approximately 150 mm$^3$. The tumor-bearing mice are randomly assigned to a vehicle control or compound treatment group (6 or more animals per group). Animals are treated with a compound of the present disclosure by intraperitoneal injection in an appropriate amount and frequency as can be determined by the skilled artisan without undue experimentation. In one example, mice are treated with 40 mg/kg of a compound of the present disclosure daily by i.p. injection. Subcutaneous tumor volume and mice body weight are measured twice weekly. Tumor volumes are calculated by measuring two perpendicular diameters with calipers (V=(length×width$^2$)/2).

Example 15: Efficacy Study in Castration-Resistant Prostate Tumor Xenograft Model (LNCaP-AR)

Immunodeficient mice, such as 4-6 week-old male CB17 severe combined immunodeficiency (SCID) mice, are used for in vivo efficacy studies in accordance with the guidelines approved by IACUC. CB.17.SCID mice are surgically castrated and allowed to recover for 2-3 weeks before implanting parental prostate cancer cells, such as LNCaP-AR cells, subcutaneously into ($3-4\times10^6$ cells in 50% Matrigel). When the tumor reaches a size of approximately 80-100 mm$^3$, the tumor-bearing mice are randomly assigned to a vehicle control or compound treatment group (6 or more animals per group). Animals are treated with a compound of the present disclosure by intraperitoneal injection in an appropriate amount and frequency as can be determined by the skilled artisan without undue experimentation. In one example, mice are treated with 60 mg/kg of a compound of the present disclosure daily by i.p. injection for 27 days. Subcutaneous tumor volume and mice body weight are measured twice weekly. Tumor volumes are calculated by measuring two perpendicular diameters with calipers (V=(length×width$^2$)/2).

Example 16: Cellular Thermal Shift Assay (CETSA)

For the cell lysate CETSA experiments, cultured cells from cell lines (e.g., HEK293, bone marrow samples) are harvested and washed with PBS. The cells are diluted in kinase buffer (KB) (25 mM Tris(hydroxymethyl)-aminomethane hydrochloride (Tris-HCl, pH 7.5), 5 mM beta-glycerophosphate, 2 mM dithiothreitol (DTT), 0.1 mM sodium vanadium oxide, 10 mM magnesium chloride) or in phosphate-buffered saline (PBS) (10 mM phosphate buffer (pH 7.4), 2.7 mM potassium chloride and 137 mM sodium chloride). All buffers are supplemented with Complete protease inhibitor cocktail. The cell suspensions are freeze-thawed three times using liquid nitrogen. The soluble fraction (lysate) is separated from the cell debris by centrifugation at 20000×g for 20 minutes at 4° C. The cell lysates are diluted with appropriate buffer and divided into two aliquots, with one aliquot being treated with drug and the other aliquot with the diluent of the inhibitor (control). After 10-30 minute incubation at room temperature the respective lysates are divided into smaller (50 µL) aliquots and heated individually at different temperatures for 3 minutes followed by cooling for 3 minutes at room temperature. The appropriate temperatures are determined in preliminary CETSA experiments. The heated lysates are centrifuged at 20000×g for 20 minutes at 4° C. in order to separate the soluble fractions from precipitates. The supernatants are transferred to new microtubes and analyzed by sodium dodecyl sulfate polyacrylamide gel electrophoresis (SDS-PAGE) followed by western blot analysis.

For the intact cell experiments the drug-treated cells from the in vitro experiments above are heated as previously described followed by addition of KB (30 µL) and lysed using 2 cycles of freeze-thawing with liquid nitrogen. The soluble fractions are isolated and analyzed by western blot.

For the in vivo mice experiments, lysates of frozen tissues are used. The frozen organs (e.g., liver or kidney) are thawed on ice and briefly rinsed with PBS. The organs are homogenized in cold PBS using tissue grinders followed by 3 cycles of freeze-thawing using liquid nitrogen. Tissue lysates are separated from the cellular debris and lipids. The tissue lysates are diluted with PBS containing protease inhibitors, divided into 50 µL aliquots and heated at different temperatures. Soluble fractions are isolated and analyzed by western blot.

It is expected that the aliquots treated with one or more of the compounds disclosed herein exhibit increased thermal stabilization of menin compared to the control aliquots.

Example 17: CETSA-Like Dot-Blot Experiments on Purified Proteins

Purified protein (0.5 µg) is added to the wells of a PCR plate and the volume adjusted to 50 µL by addition of buffer or cell lysates and ligands depending on the experimental setup. The samples are heated for the designated time and temperature in a thermocycler. After heating, the samples are immediately centrifuged for 15 min at 3000×g and filtered using a 0.65 µm Multiscreen HTS 96 well filter plate. 3 µL of each filtrate are blotted onto a nitrocellulose membrane. Primary antibody and secondary conjugate are used for immunoblotting. All membranes are blocked with blocking buffer; standard transfer and western blot protocols recommended by the manufacturers are used. All antibodies are diluted in blocking buffer. The dot-blot is developed. Chemiluminescence intensities are detected and imaged. Raw dot blot images are processed. The background is subtracted and intensities are quantified. Graphs are plotted and fitted using sigmoidal dose-response (variable slope).

Example 18: Cell Proliferation Assays

The ability of a compound of the present disclosure to inhibit the growth of cells was tested in both MLL leukemia cell lines (e.g., MV4;11, MOLM13 and/or KOPN8) and control cell lines (e.g., K562, REH, U937, KG-1, and/or HL-60) using the MTT cell proliferation assay (ATCC® 30-1010K). One or more compounds disclosed herein, e.g., a compound provided in Table 3 having an $IC_{50}$ value of less than 1 µM, preferably less than 50 nM (a measurement reflecting the ability of the compound to disrupt the menin-MLL interaction, measured in accordance with Example 6), inhibit the proliferation of MLL leukemia cell lines (MV4; 11 and MOLM13 cells) while having a much weaker inhibitory effect on the proliferation of control cell lines (e.g., K562 and REH cells) at the same concentration. Cells were plated at about 1×10⁵ cells per well in a 96-well plate. A compound of the present disclosure was added at a concentration up to about 2 µM with seven, 2-fold serial dilutions for each compound. Cells were incubated at 37° C. for 72 hours, then cells in the control wells were counted. Media was changed to restore viable cell numbers to the original concentration, and compounds were re-supplied. Proliferation was measured 96 hours later using MTT reagents, as per kit instructions. The $GI_{50}$ value of a compound of the present disclosure, such as Compound B of FIG. 4, was 35 nM in MV4;11 cells (MLL-AF4 AML), 75 nM in MOLM13 cells (MLL-AF9 AML), 1500 nM in K562 cells, and 2000 nM in REH cells, as measured by the MTT cell proliferation assay. The $GI_{50}$ value of a compound of the present disclosure, such as Compound C of FIG. 8, was 15 nM in MV4;11 cells (MLL-AF4 AML), 16 nM in MOLM13 cells (MLL-AF9 AML), 20 nM in KOPN8 (MLL-ENL AML) cells, 1500 nM in REH cells, greater than 6000 nM in K562 cells, and greater than 6000 nM in U937 cells, as measured by the MTT cell proliferation assay. The $GI_{50}$ value of a compound of the present disclosure, such as Compound D of FIG. 11, was 10 nM in MV4;11 cells (MLL-AF4 AML), 17 nM in MOLM13 cells (MLL-AF9 AML), 18 nM in KOPN8 (MLL-ENL AML) cells, greater than 2000 nM in HL-60 cells, and greater than 2000 nM in U937 cells. REH, K562, KG-1, and U937 cells are control cell lines without MLL fusions. Certain compounds disclosed herein exhibited $GI_{50}$ values in the range of 1500 nM to greater than 6000 nM when tested in REH, K562, KG-1, and U937 cells. Certain compounds disclosed herein exhibited $GI_{50}$ values in the range of 5 nM to 25 nM when tested in MV4;11 cells (MLL-AF4 AML), MOLM13 cells (MLL-AF9 AML), murine bone marrow cells (rMML-AF9 AML), KOPN8 (MLL-ENL AML) cells, RS4;11 cells (MLL-AF4 ALL), or SEM (MLL-AF4 ALL) cells.

Example 19: Efficacy Study in Mouse Xenograft Tumor Model

Figure 8:
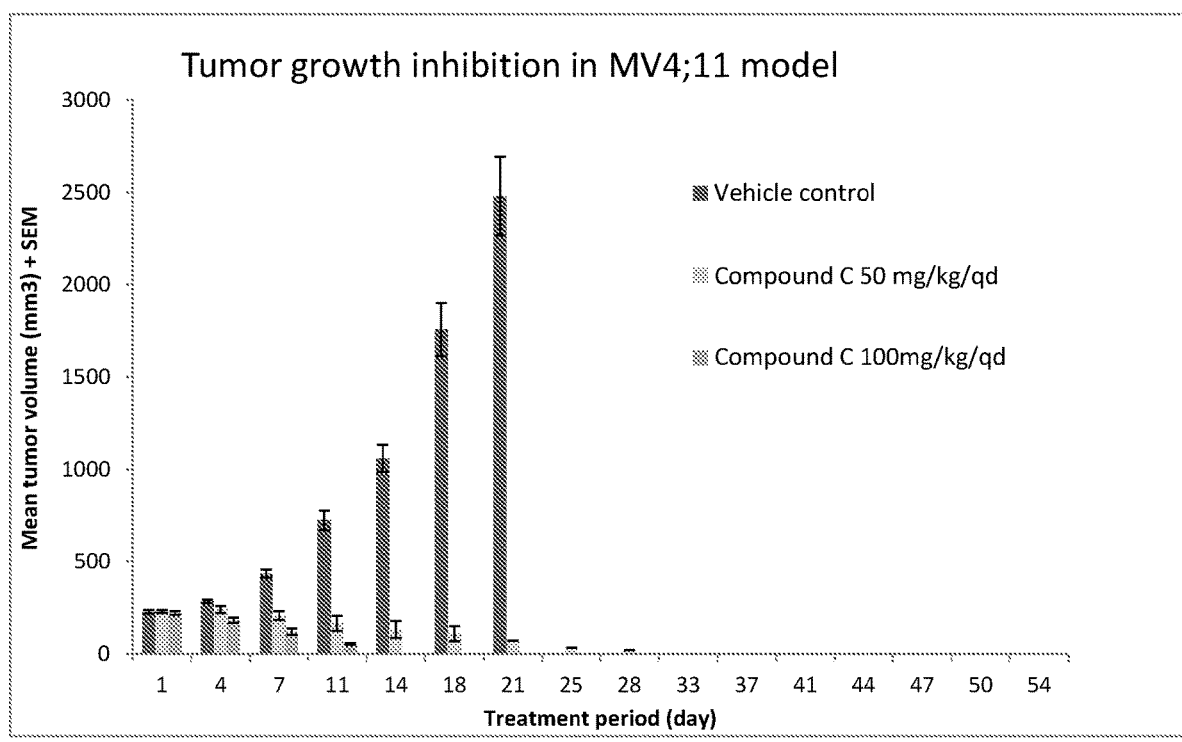
FIG. 8 depicts the change in volume of MV4;11 tumors in vehicle and compound treated mice.

One or more compounds disclosed herein, e.g., a compound provided in Table 3 having an $IC_{50}$ value of less than 1 µM, preferably less than 50 nM (a measurement reflecting the ability of the compound to disrupt the menin-MLL interaction, measured in accordance with Example 6), provide suppression of MV4;11 (human leukemia) tumor growth in mouse xenograft models. Immunocompromised 8-10 week-old female nude (nu/nu) mice were used for in vivo efficacy studies in accordance with IACUC guidelines. Human MV4;11 leukemia cells available from ATCC were implanted subcutaneously into female nude mice (5×10⁶ cells/mouse). When the tumor reached a size of approximately 150 to 250 mm³, the tumor-bearing mice were randomly assigned to a vehicle control or a compound treatment group (8 mice per group). Mice in each treatment group were administered a compound of the present disclosure by oral gavage at the dosage indicated (50 mg/kg, bid; 50 gm/kg, qd; 100 mg/kg, bid; 100 mg/kg, qd; 200 mg/kg, qd.; or 200 mg/kg, bid). Subcutaneous tumor volume and mouse body weight were measured twice weekly. Tumor volumes were calculated by measuring two perpendicular diameters with calipers (V=(length×width²)/2). As shown in FIG. 4, a compound provided in Table 3 having an $IC_{50}$ value of less than 50 nM (a measurement reflecting the ability of the compound to disrupt the menin-MLL interaction, measured in accordance with Example 6), labeled Compound B in the figure, inhibited tumor growth and induced tumor regression relative to the vehicle control group in a dose-dependent manner. As shown in FIG. 8, a compound provided in Table 3 having an $IC_{50}$ value of less than 50 nM (a measurement reflecting the ability of the compound to disrupt the menin-MLL interaction, measured in accordance with Example 6), labeled Compound C in the figure, inhibited tumor growth and induced tumor regression relative to the vehicle control group in a dose-dependent manner.

Example 20: Efficacy Study in Xenotransplantation Mouse Model of MLL Leukemia One or more compounds disclosed herein, e.g., a compound provided in Table 3 having an $IC_{50}$ value of less than 1 µM, preferably less than 50 nM (a measurement reflecting the ability of the compound to disrupt the menin-MLL interaction, measured in accordance with Example 6), provide suppression of MV4;11 tumor growth in a xenotransplantation mouse model of MLL leukemia. Immunocompromised 8-10 week-old female NSG mice were used for in vivo efficacy studies in accordance with IACUC guidelines. Luciferase expressing human MV4;11 leukemia cells (MV4; 11-luc) were engrafted intravenously via tail vein injection ($1 \times 10^7$ cells/animal). When the mean luminescence of the cells reached approximately $1.5 \times 10^6$, the tumor-bearing mice were randomly assigned to a vehicle control or a compound treatment group (5 animals per group). Animals in each of the treatment groups were administered a different compound of the present disclosure by oral gavage (120 mg/kg b.i.d, 150 mg/kg b.i.d., 200 mg/kg b.i.d., or 200 mg/kg q.d.). Body weight was measured daily, while mean luminescence was measured 6 days after initiating the treatment with compound or vehicle.

Figure 5:
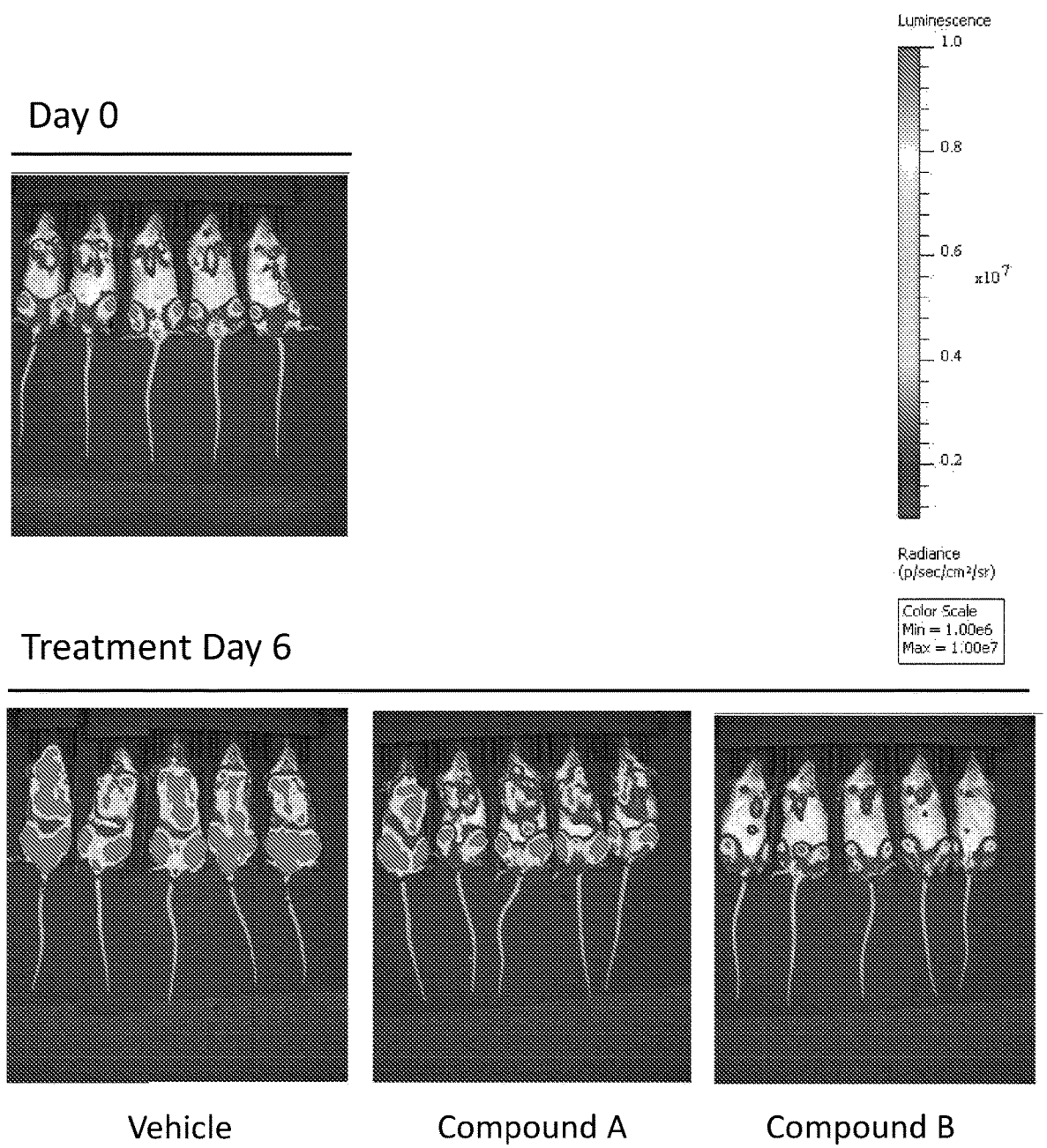
FIG. 5 depicts the luminescence of MV4;11-luc tumors in vehicle and compound treated xenotransplantation mouse models of MLL leukemia after 6 days of treatment.

As shown in FIG. 5, a 200 mg/kg b.i.d. treatment regimen of Compound B of the present disclosure inhibited tumor growth and induced tumor regression relative to the vehicle control group. By contrast, a compound provided in Table 3 having an $IC_{50}$ value of greater than 1 µM (a measurement reflecting the ability of the compound to disrupt the menin-MLL interaction, measured in accordance with Example 6), labeled Compound A in FIG. 5, inhibited tumor growth but did not induce tumor regression relative to the vehicle control group when administered at 200 mg/kg b.i.d. As shown in FIG. 11, a 120 mg/kg b.i.d. treatment regimen of Compound 165—a compound provided in Table 3 having an $IC_{50}$ value of less than 50 nM (a measurement reflecting the ability of the compound to disrupt the menin-MLL interaction, measured in accordance with Example 6) and labeled Compound D in the figures—inhibited tumor growth and induced tumor regression relative to the vehicle control group.

Figure 6:
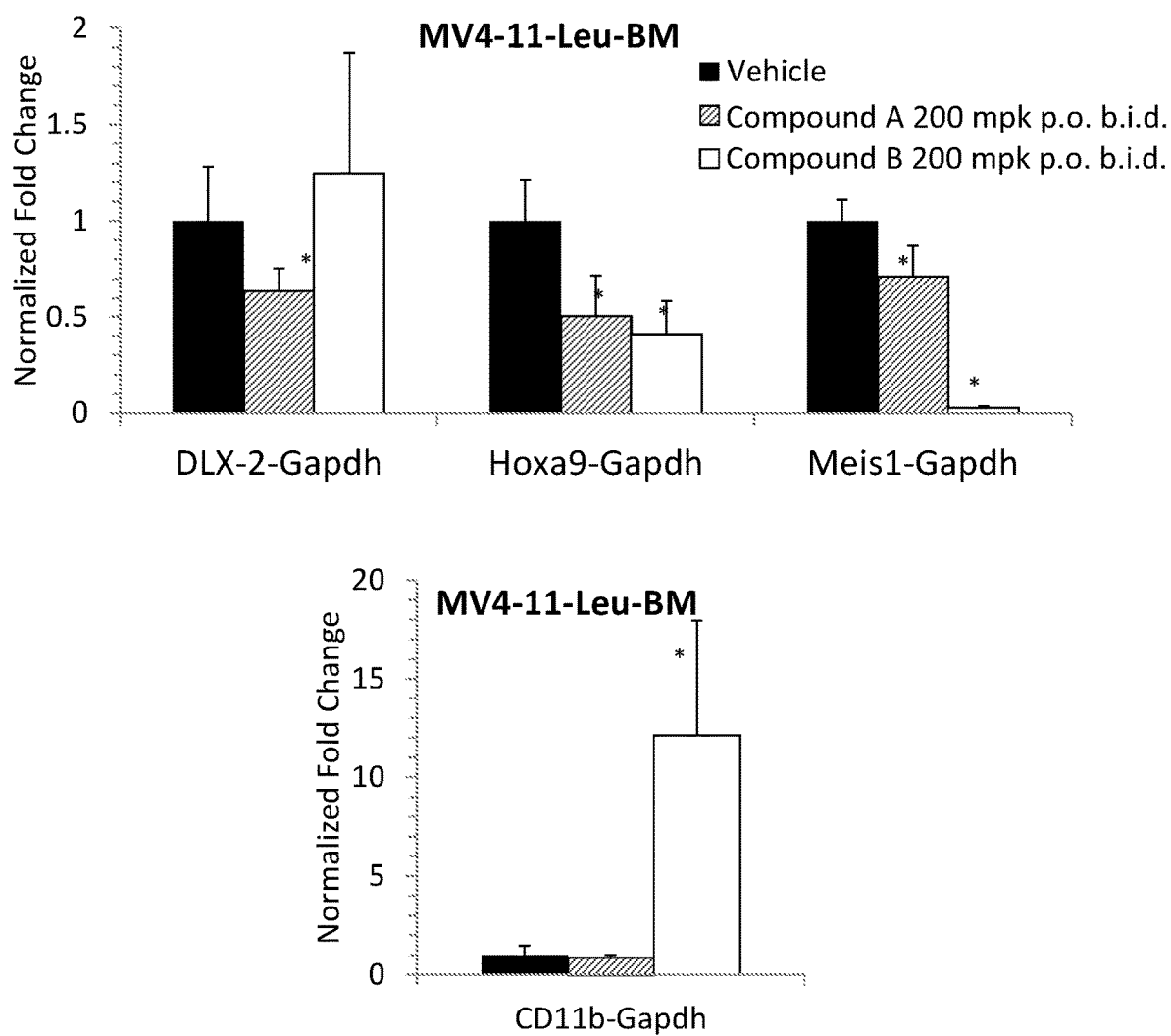
FIG. 6 depicts gene expression changes of DLX2, HOXA9, MEIS1 and CD11B in bone marrow samples taken from the vehicle and compound treated mice shown in FIG. 5.
Figure 9:
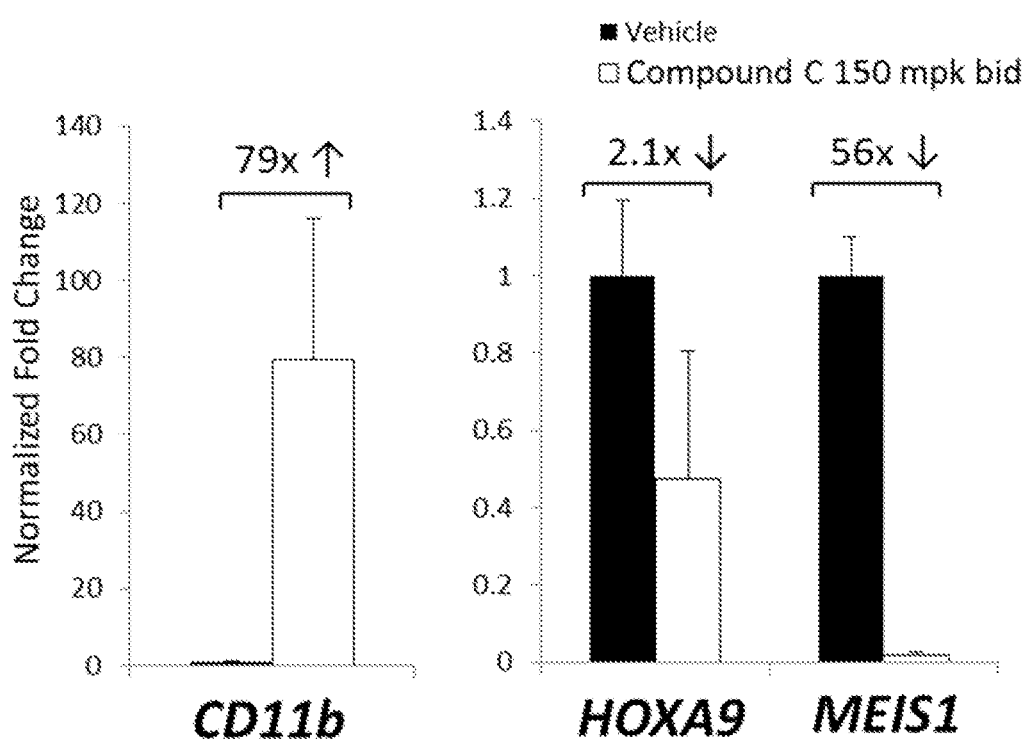
FIG. 9 depicts gene expression changes of HOXA9, MEIS1 and CD11B in bone marrow samples taken from vehicle and compound treated mice.
Figure 12:
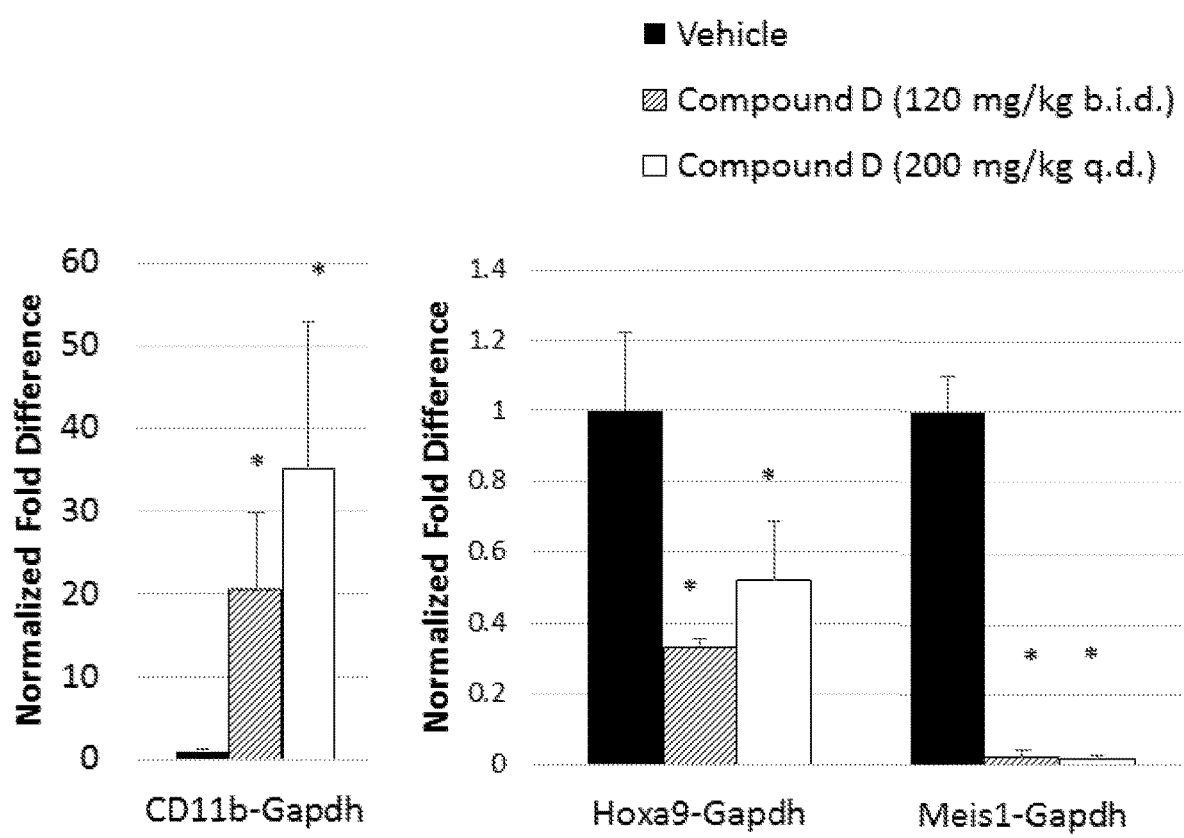
FIG. 12 depicts gene expression changes of HOXA9, MEIS1 and CD11B in bone marrow samples taken from the vehicle and compound treated mice shown in FIG. 11.

Animals were sacrificed on Day 7 of treatment and bone marrow samples collected and prepared for gene expression analysis. Expression levels of MLL fusion protein target genes HOXA9, DLX2, and/or MEIS1 were measured by qRT-PCR and are presented in FIG. 6, FIG. 9 and FIG. 12 as fold changes normalized to GAPDH expression. Expression of differentiation marker CD11b was elevated in bone marrow samples from Compound B-treated animals, Compound C-treated animals and Compound D-treated animals, suggesting that these cells undergo differentiation. In addition, the expression levels of MEIS1 and HOXA9 were substantially reduced upon treatment with Compound B, Compound C or Compound D, consistent with inhibition of leukemia progression induced by this compound.

Figure 7:
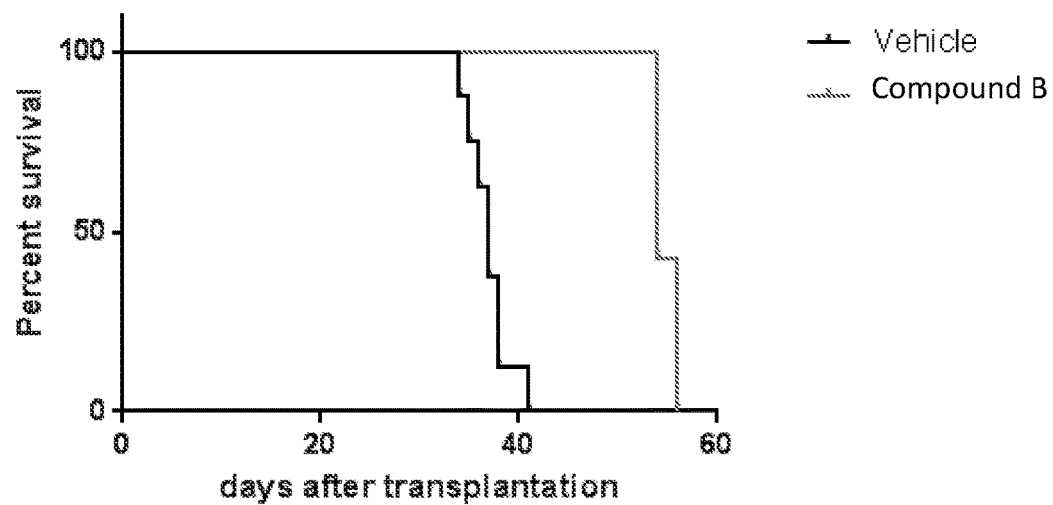
FIG. 7 depicts the survival curve of vehicle and compound treated mice with MV4;11-luc tumors.

Example 21: Survival Study in Xenotransplantation Mouse Model of MLL Leukemia For survival studies in the xenotransplantation MNV4;11 xenograft model, 6 to 8-week old female NSG mice were intravenously injected with $1 \times 10^7$ luciferase-expressing MV4;11 cells harboring MLL-AF4 translocation. At day 12 after transplantation, treatment was initiated with Compound B, 120 mg/kg b.i.d., p.o. or vehicle (20% 2-hydroxypropyl-b-cyclodextrin with 5% cremophore) and was continued for 22 consecutive days. As shown in FIG. 7, Compound B of the present disclosure extended median survival time relative to the vehicle control group. Mice treated with Compound B had a median survival time of 54 days, while mice in the vehicle control group had a median survival time of 37 days, indicating a survival benefit of 17 days (46%) for compound-treated mice.

Figure 10:
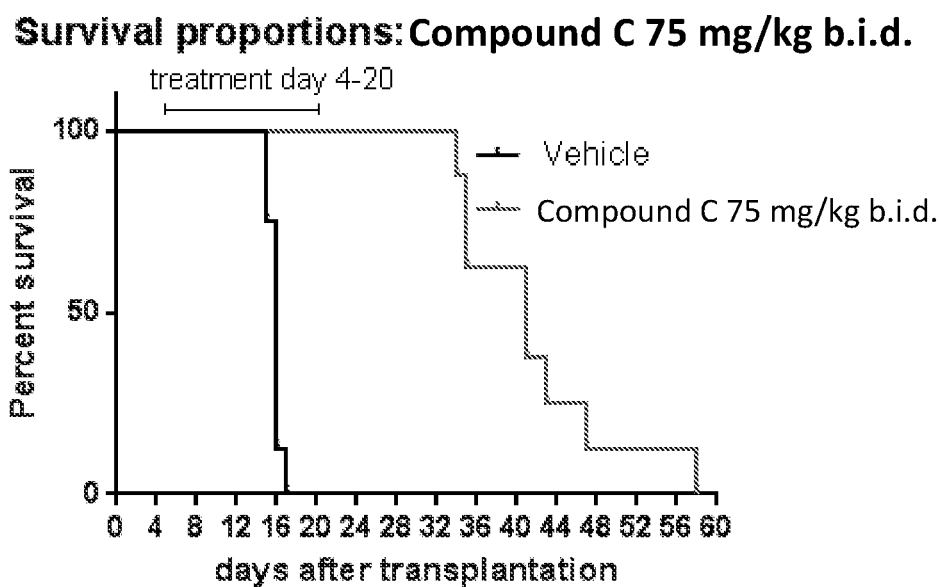
FIG. 10 depicts the survival curve of vehicle and compound treated mice with MOLM13 tumors.

For survival studies in the xenotransplantation MOLM13 xenograft model, 6 to 8-week old female NSG mice were intravenously injected with $0.5 \times 10^6$ MOLM13 cells harboring MLL-AF9 translocation. At day 4 after transplantation, treatment was initiated with Compound C, 75 mg/kg, b.i.d., p.o. or vehicle (20% 2-hydroxypropy-b-cyclodextrin with 5% cremophore) and was continued for 16 consecutive days in the compound treated mice or until terminal leukemia developed in the vehicle-treated mice. As shown in FIG. 10, Compound C of the present disclosure extended median survival time relative to the vehicle control group.

Figure 13:
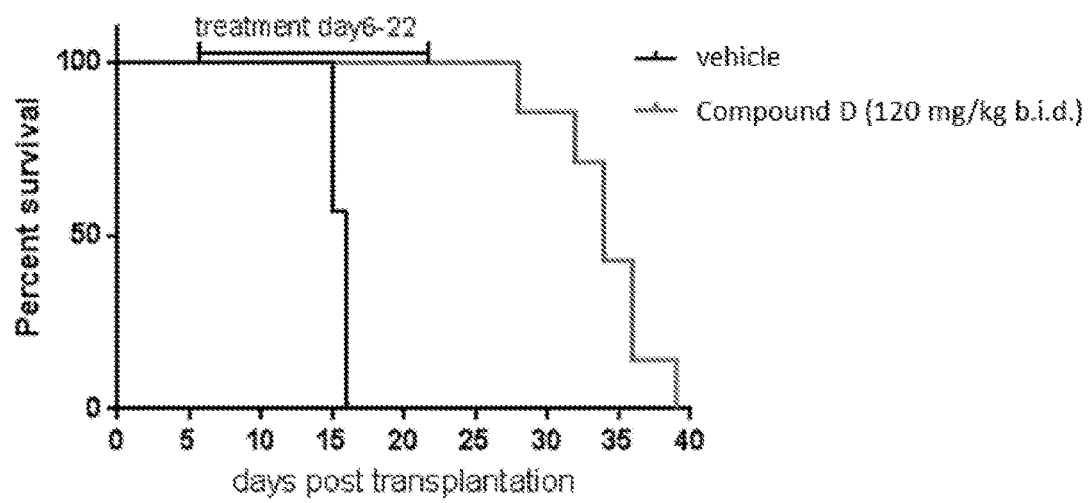
FIG. 13 depicts the survival curve of vehicle and compound treated mice with MOLM13 tumors.

Similarly, a 120 mg/kg b.i.d. treatment regimen of Compound D was initiated on day 6 after MOLM13 transplantation and continued for 16 consecutive days in the compound treated mice or until terminal leukemia developed in the vehicle-treated mice. As shown in FIG. 13, Compound D of the present disclosure extended the median survival time to 24 days, relative to a median survival time of 16 days for mice in the vehicle control group, indicating a survival benefit of 18 days (75%) for compound-treated mice.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the invention. It is intended that the following claims define the scope of the invention and that methods and structures within the scope of these claims and their equivalents be covered thereby.

What is claimed is:

1. A compound of Formula (II-A):

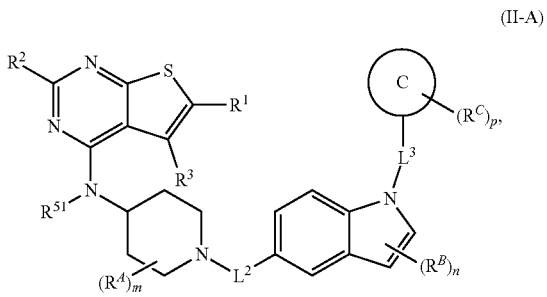

(II-A)

or a pharmaceutically acceptable salt thereof, wherein:

C is selected from $C_{3-12}$ carbocycle and 3- to 12-membered heterocycle;

$L^2$ is selected from bond, —O—, —S—, —N($R^{51}$)—, —N($R^{51}$)CH$_2$—, —C(O)—, —C(O)O—, —OC(O)—, —OC(O)O—, —C(O)N($R^{51}$)—, —C(O)N($R^{51}$)C(O)—, —C(O)N($R^{51}$)C(O)N($R^{51}$)—, —N($R^{51}$)C(O)—, —N($R^{51}$)C(O)N($R^{51}$)—, —N($R^{51}$)C(O)O—, —OC(O)N($R^{51}$)—, —C(N$R^{51}$)—, —N($R^{51}$)C(NR$^{51}$)—, —C(NR$^{51}$)N(R$^{51}$)—, —N($R^{51}$)C(NR$^{51}$)N(R$^{51}$)—, —S(O)$_2$-, —OS(O)—, —S(O)O—, —S(O)—, —OS(O)$_2$—, —S(O)$_2$O—, —N($R^{51}$)S(O)$_2$—, —S(O)$_2$N($R^{51}$)—, —N($R^{51}$)S(O)—, —S(O)N($R^{51}$)—, —N($R^{51}$)S(O)$_2$N($R^{51}$)—, —N($R^{51}$)S(O)N($R^{51}$)—, alkylene, alkenylene, alkynylene, heteroalkylene, heteroalkenylene, and heteroalkynylene, each of which is optionally substituted with one or more $R^{50}$;

$L^3$ is selected from alkylene, alkenylene, and alkynylene, each of which is substituted with one or more $R^{56}$ and optionally further substituted with one or more $R^{50}$;

$R^1$ and $R^3$ are each independently selected from hydrogen and $R^{50}$;

$R^2$ is $R^{50}$;

$R^A$, $R^B$, and $R^C$ are each independently selected at each occurrence from $R^{50}$, or two $R^A$ groups, two $R^B$ groups, or two $R^C$ groups attached to the same atom or different atoms can together optionally form a bridge or ring;

m, n, and p are each independently an integer from 0 to 6;

$R^{50}$ is independently selected at each occurrence from:
halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$ NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, and =N(R$^{52}$);

$C_{1-10}$ alkyl, $C_{2-10}$ alkenyl, and $C_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{3-12}$ carbocycle, and 3- to 12-membered heterocycle; and $C_{3-12}$ carbocycle and 3- to 12-membered heterocycle,
wherein each $C_{3-12}$ carbocycle and 3- to 12-membered heterocycle in $R^{50}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$ NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{1-6}$ alkyl, $C_{1-6}$ haloalkyl, $C_{2-6}$ alkenyl, and $C_{2-6}$ alkynyl;

$R^{51}$ is independently selected at each occurrence from: hydrogen, —C(O)R$^{52}$, —C(O)OR$^{52}$, —C(O)N(R$^{52}$)$_2$, and —C(O)NR$^{53}$R$^{54}$; and $C_{1-6}$ alkyl, $C_{2-6}$ alkenyl, and $C_{2-6}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{3-12}$ carbocycle, and 3- to 12-membered heterocycle; and $C_{3-12}$ carbocycle and 3- to 12-membered heterocycle,
wherein each $C_{3-12}$ carbocycle and 3- to 12-membered heterocycle in $R^{51}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{1-6}$ alkyl, $C_{1-6}$ haloalkyl, $C_{2-6}$ alkenyl, and $C_{2-6}$ alkynyl;

$R^{52}$ is independently selected at each occurrence from hydrogen; and $C_{1-20}$ alkyl, $C_{2-20}$ alkenyl, $C_{2-20}$ alkynyl, $C_{1-6}$ heteroalkyl, $C_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, $C_{3-12}$ carbocycle, or 3- to 6-membered heterocycle;

$R^{53}$ and $R^{54}$ are taken together with the nitrogen atom to which they are attached to form a heterocycle, optionally substituted with one or more $R^{50}$;

$R^{56}$ is independently selected at each occurrence from: —NO$_2$, —SR$^{52}$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{1-10}$ alkyl, $C_{2-10}$ alkenyl, $C_{2-10}$ alkynyl, $C_{3-12}$ carbocycle, and 3- to 12-membered heterocycle, wherein each C$_{1-10}$ alkyl, C$_{2-10}$ alkenyl, and C$_{2-10}$ alkynyl in R$^{56}$ is independently optionally substituted at each occurrence with one or more substituents selected from halogen, —NO$_2$, —CN, —OR$^{59}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{3-12}$ carbocycle, and 3- to 12-membered heterocycle;

wherein each C$_{3-12}$ carbocycle and 3- to 12-membered heterocycle in R$^{56}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl; and further wherein R$^{56}$ optionally forms a bond to ring C; and R$^{59}$ is independently selected at each occurrence from C$_{1-20}$ alkyl, C$_{2-20}$ alkenyl, C$_{2-20}$ alkynyl, C$_{1-6}$ heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle, wherein for a compound or salt of Formula (II-A), when R$^{56}$ is —CH$_3$, L$^3$ is not further substituted with —OH, —NH$_2$, or —CN.

2. The compound of claim 1, wherein R$^c$ is selected from —C(O)R$^{52}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, =O, C$_{1-3}$ alkyl, and C$_{1-3}$ haloalkyl, or two R$^C$ groups attached to different atoms can together form a C$_{1-3}$ bridge.

3. The compound of claim 1, wherein C is 5- to 12-membered saturated heterocycle, wherein the heterocycle comprises at least one nitrogen atom.

4. The compound of claim 1, wherein C is selected from:

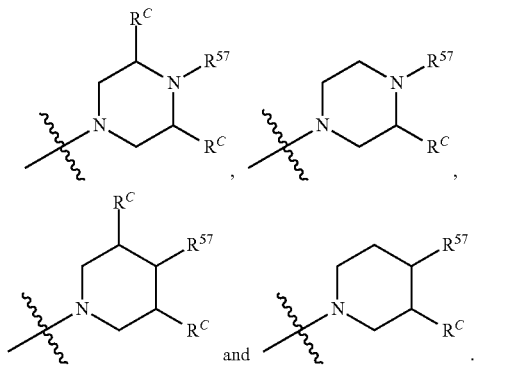

, wherein R$^{57}$ is selected from —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, and C$_{1-10}$ alkyl substituted with one or more substituents selected from —S(=O)R$^{52}$, —S(=O)$_2$R$^{52}$, —S(=O)$_2$N(R$^{52}$)$_2$, —S(=O)$_2$NR$^{53}$R$^{54}$, and —NR$^{52}$S(=O)$_2$R$^{52}$.

5. The compound of claim 1, wherein:
R$^2$ is selected from hydrogen, halogen, —OH, —OR$^{52}$, —NH$_2$, —N(R$^{52}$)$_2$, —CN, C$_{1-3}$ alkyl, C$_{1-3}$ alkyl-N(R$^{52}$)$_2$, C$_{1-3}$ haloalkyl, C$_{2-3}$ alkenyl, and C$_{2-3}$ alkynyl; and R$^3$ is selected from hydrogen, halogen, —OH, —N(R$^{52}$)$_2$, —CN, —C(O)OR$^{52}$, C$_{1-3}$ alkyl, and C$_{1-3}$ haloalkyl.

6. The compound of claim 1, wherein R$^1$ is C$_{1-3}$ haloalkyl.

7. The compound of claim 1, wherein m is 0.

8. The compound of claim 1, wherein n is an integer from 1 to 3.

9. The compound of claim 1, wherein L$^2$ is C$_{1-4}$ alkylene, optionally substituted with one or more R$^{50}$.

10. The compound of claim 1, wherein L$^3$ is substituted with =O, C$_{1-6}$ alkyl, C$_{1-6}$ haloalkyl, C$_{1-3}$ alkyl(cyclopropyl), C$_{1-3}$ alkyl(NR$^{52}$C(O)R$^{52}$) or —O(C$_{1-6}$ alkyl).

11. The compound of claim 1, wherein L$^3$ is selected from

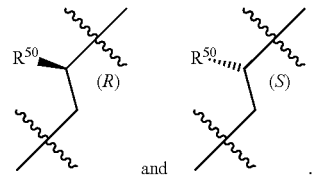

12. The compound of claim 11, wherein R$^{56}$ is methyl.
13. The compound of claim 1, wherein:
L$^2$ is selected from —O—, —S—, —NH—, and —CH$_2$—;

L$^3$ is selected from C$_{1-6}$ alkylene, C$_{2-6}$ alkenylene, and C$_{2-6}$ alkynylene, each of which is substituted with one or more R$^{56}$ and optionally further substituted with one or more R$^{50}$;

R$^A$, R$^B$, and R$^C$ are each independently selected at each occurrence from R$^{50}$, or two R$^A$ groups, two R$^B$ groups, or two R$^C$ groups attached to the same atom or different atoms can together optionally form a bridge or ring;
m is an integer from 0 to 3;
n is an integer from 1 to 3;
p is an integer from 0 to 6;
R$^{56}$ is independently selected at each occurrence from:
—OR$^{59}$, =O, C$_{1-10}$ alkyl, C$_{2-10}$ alkenyl, and C$_{2-10}$ alkynyl,
wherein each C$_{1-10}$ alkyl, C$_{2-10}$ alkenyl, and C$_{2-10}$ alkynyl in R$^{56}$ is independently optionally substituted at each occurrence with one or more substituents selected from halogen, —NO$_2$, —CN, —OR$^{59}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$_{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{3-12}$ carbocycle, and 3- to 12-membered heterocycle;

wherein each $C_{3-12}$ carbocycle and 3- to 12-membered heterocycle in $R^{56}$ is independently optionally substituted with one or more substituents selected from halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $=O$, $=S$, $=N(R^{52})$, $C_{1-6}$ alkyl, $C_{1-6}$ haloalkyl, $C_{2-6}$ alkenyl, and $C_{2-6}$ alkynyl; and further wherein $R^{56}$ optionally forms a bond to ring C; and $R^{59}$ is independently selected at each occurrence from $C_{1-20}$ alkyl, $C_{2-20}$ alkenyl, $C_{2-20}$ alkynyl, $C_{1-6}$ heteroalkyl, $C_{3-12}$ carbocycle, and 3- to 12-membered heterocycle, each of which is optionally substituted by halogen, $-CN$, $-NO_2$, $-NH_2$, $-NHCH_3$, $-NHCH_2CH_3$, $=O$, $-OH$, $-OCH_3$, $-OCH_2CH_3$, $C_{3-12}$ carbocycle, or 3- to 6-membered heterocycle.

14. The compound of claim 13, wherein p is 1 and $R^C$ is $-S(=O)_2R^{52}$, $-S(=O)_2N(R^{52})_2$, or $-S(=O)_2NR^{53}R^{54}$.

15. The compound of claim 13, wherein the compound is a stereoisomer provided in at least 90% enantiomeric excess.

16. The compound of claim 1, wherein the compound has the structure of Formula (II-C):

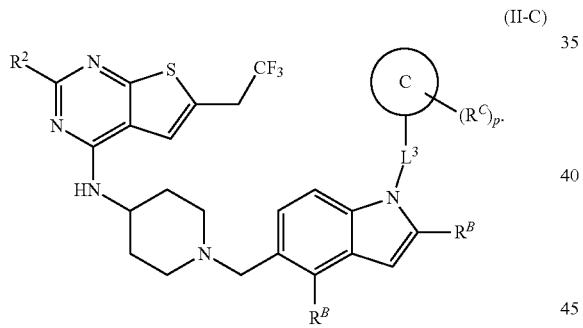

(II-C)

17. The compound of claim 1, wherein the compound has the structure of Formula (II-F) or Formula (II-H):

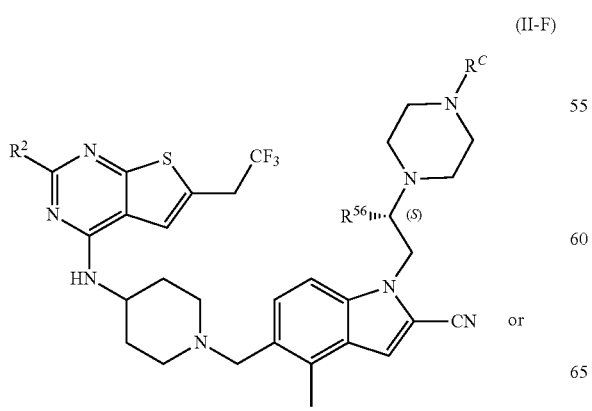

(II-F)

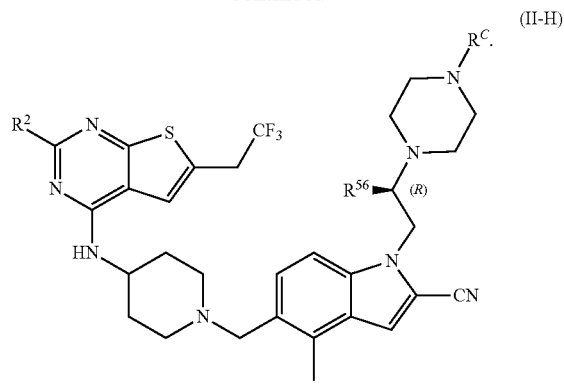

(II-H)

18. The compound of claim 1, wherein the compound is selected from the group consisting of:

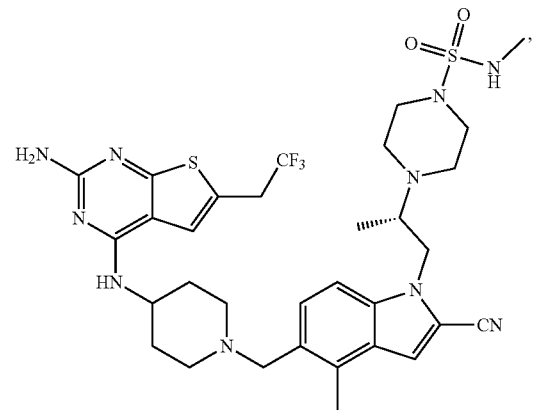

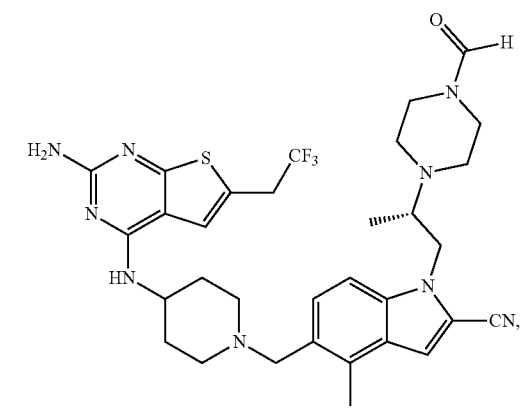

349
-continued
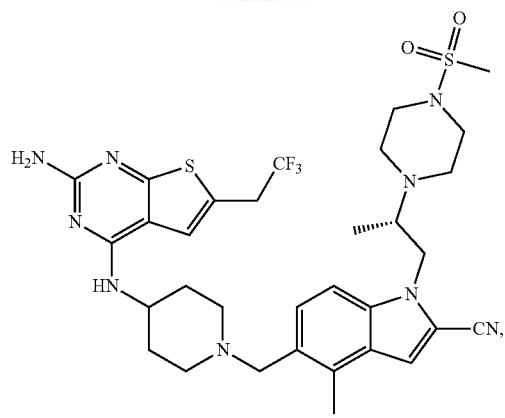
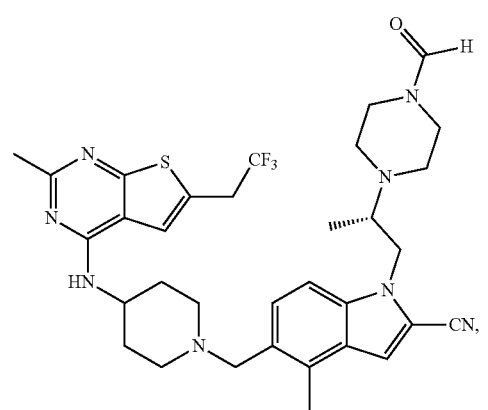
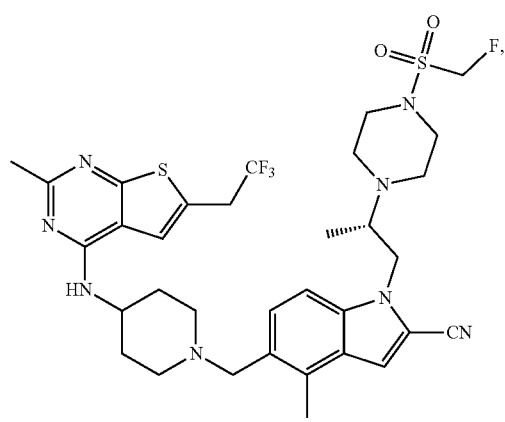
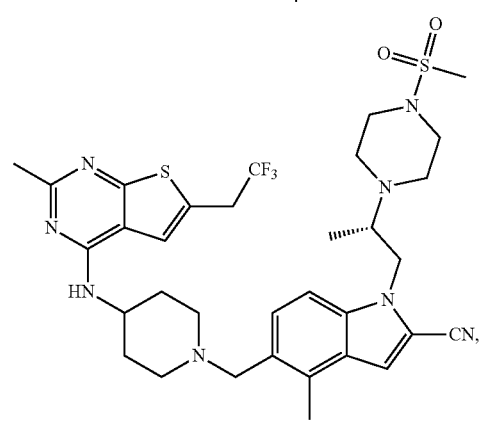
350
-continued
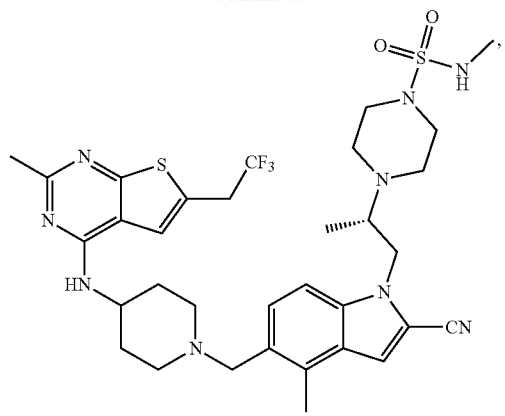
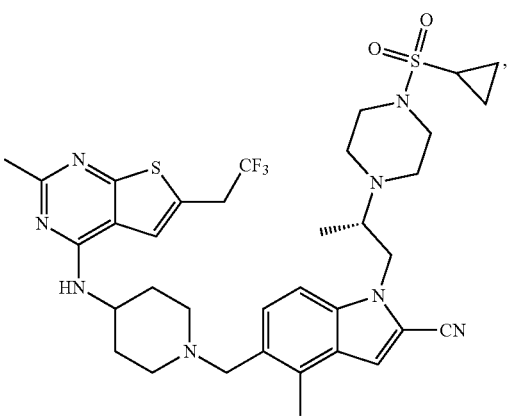
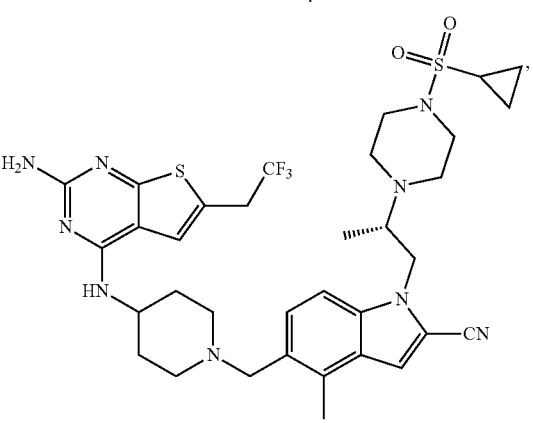
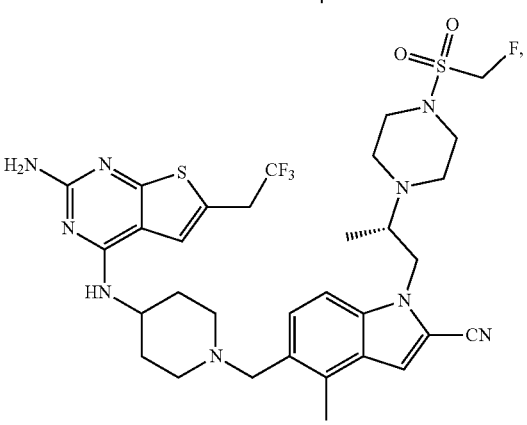

-continued
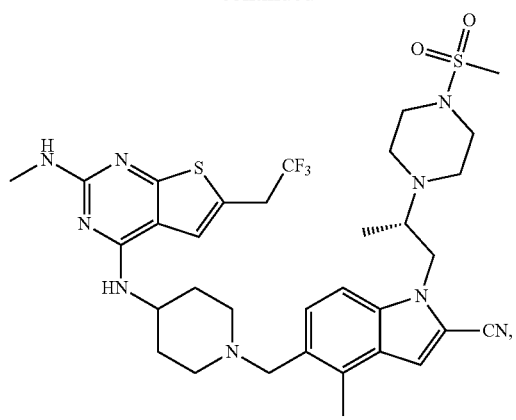
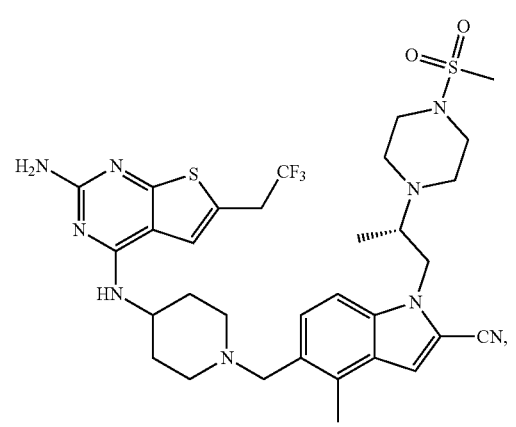
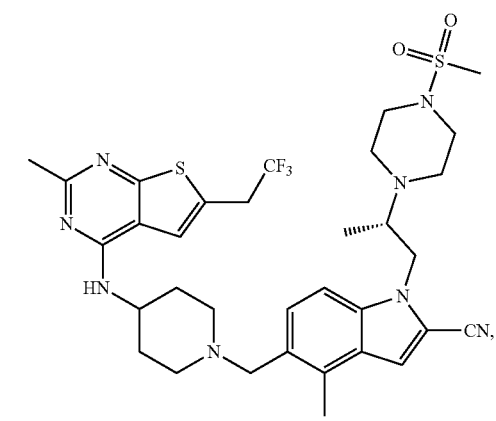
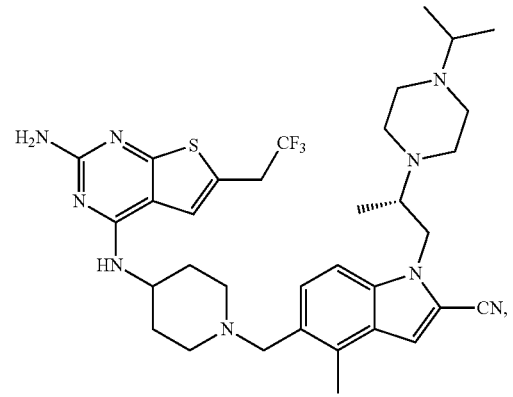
-continued
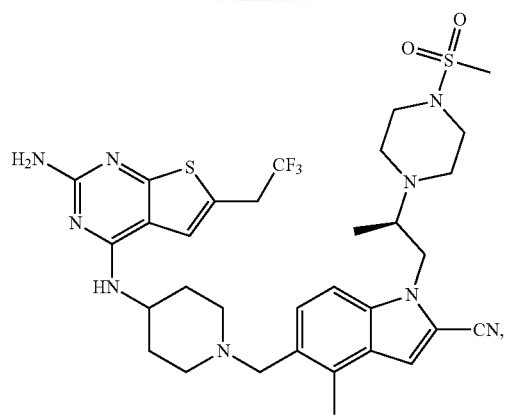
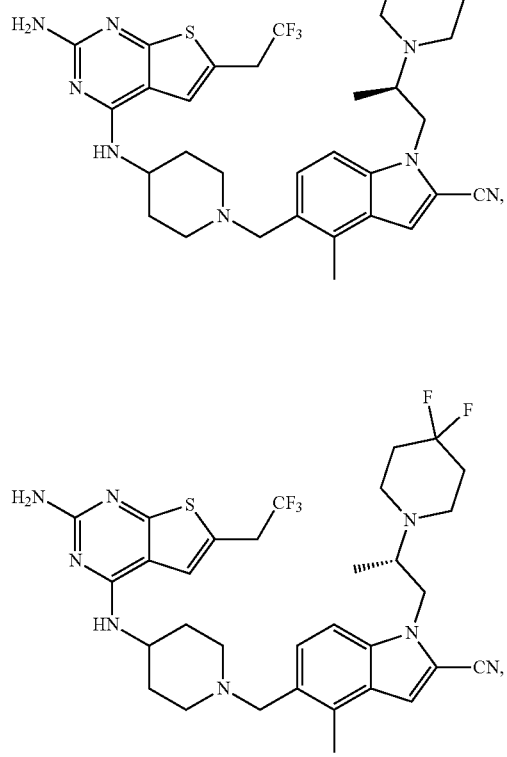
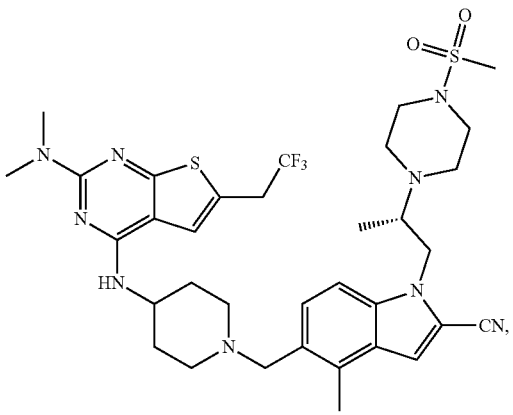
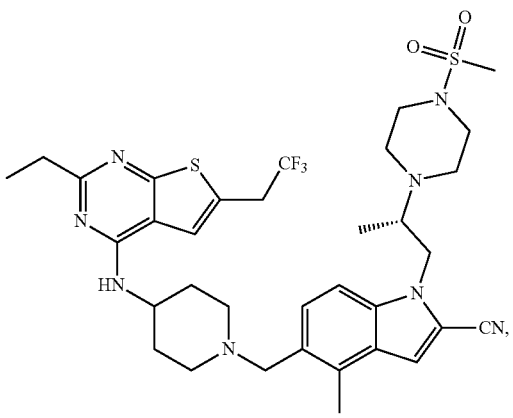

353
-continued
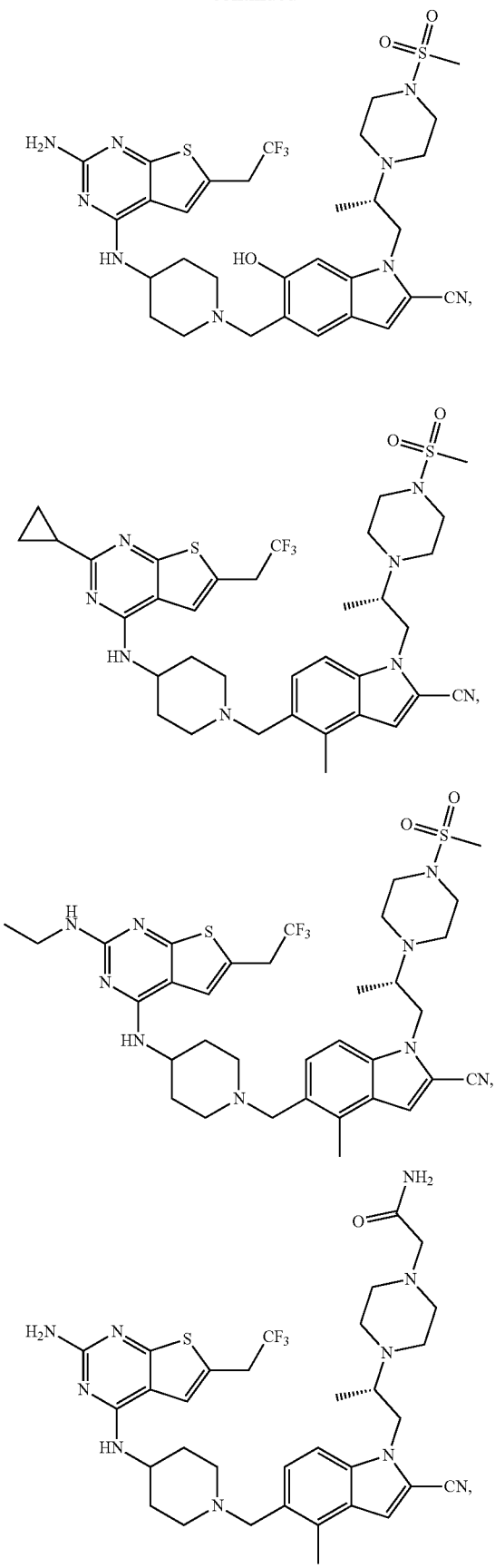
354
-continued
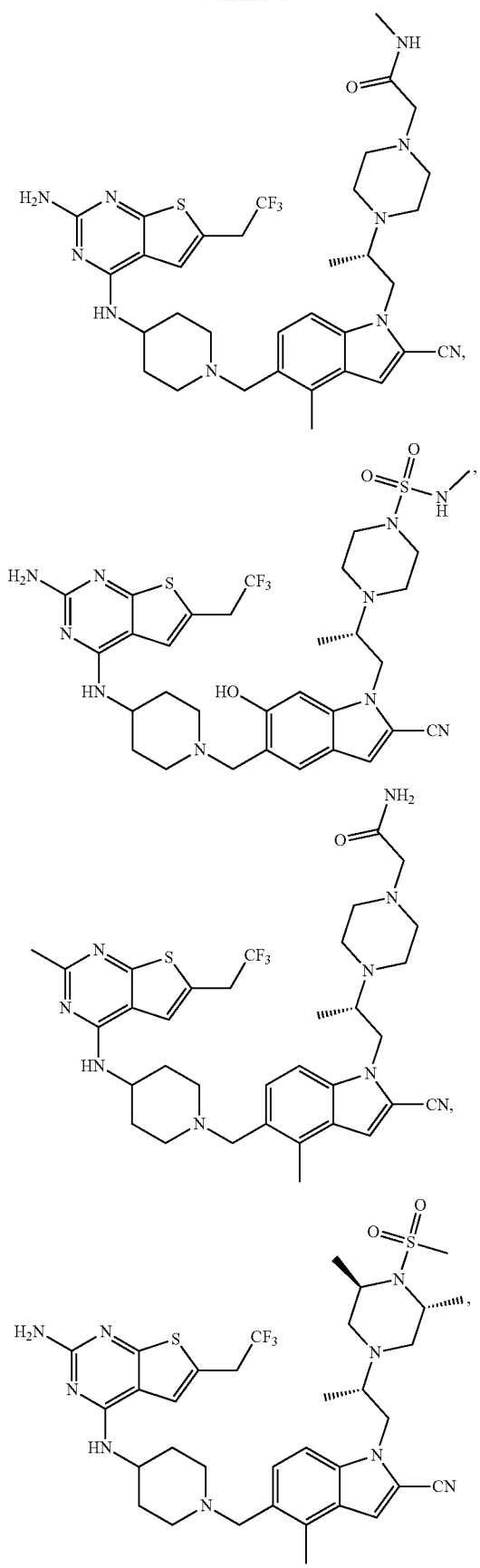

355
-continued
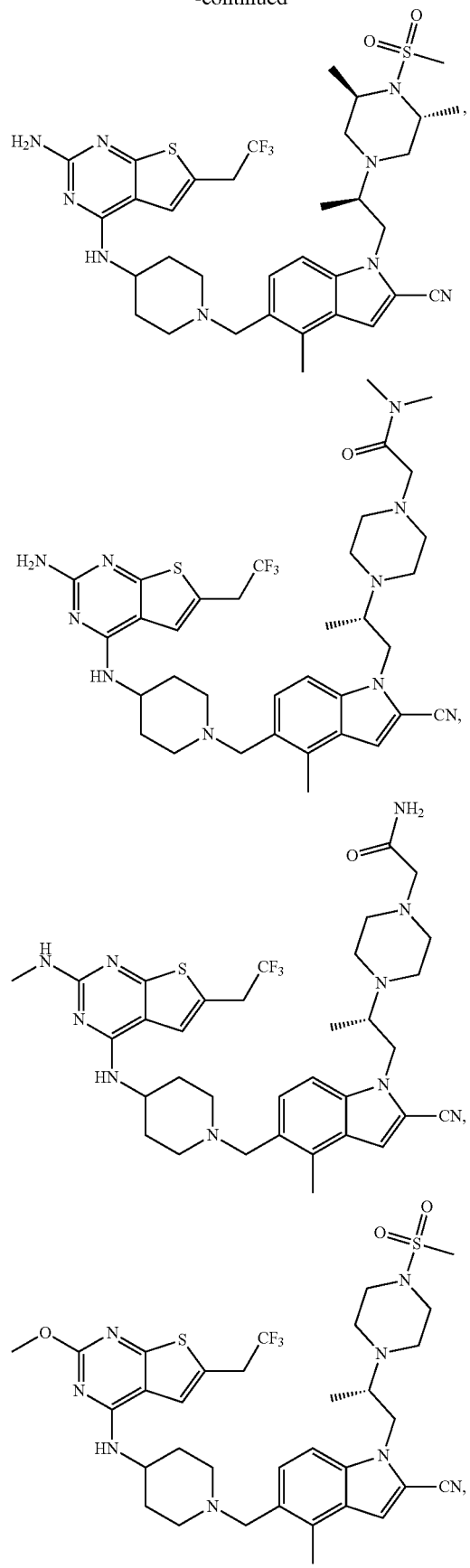
356
-continued
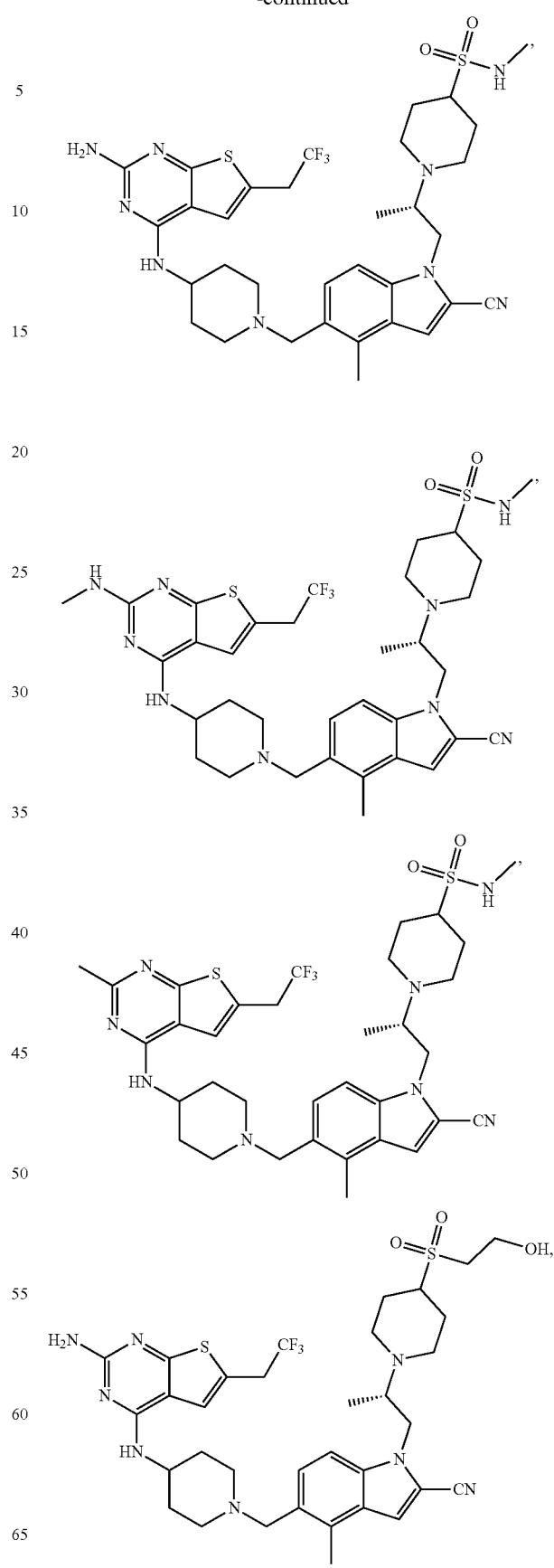

357
-continued
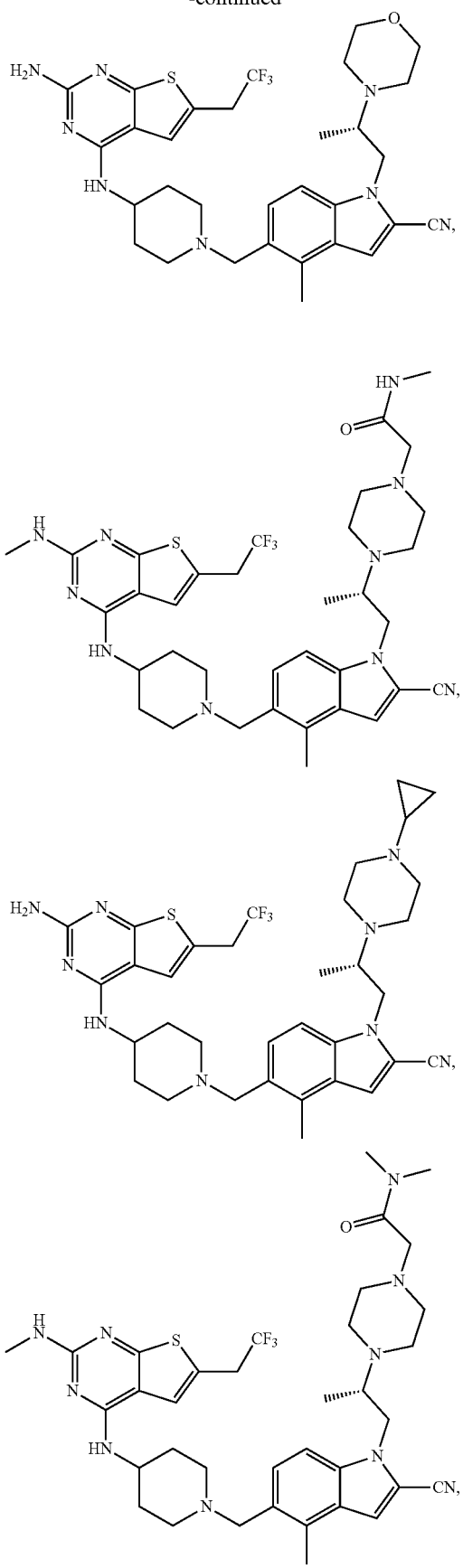
358
-continued
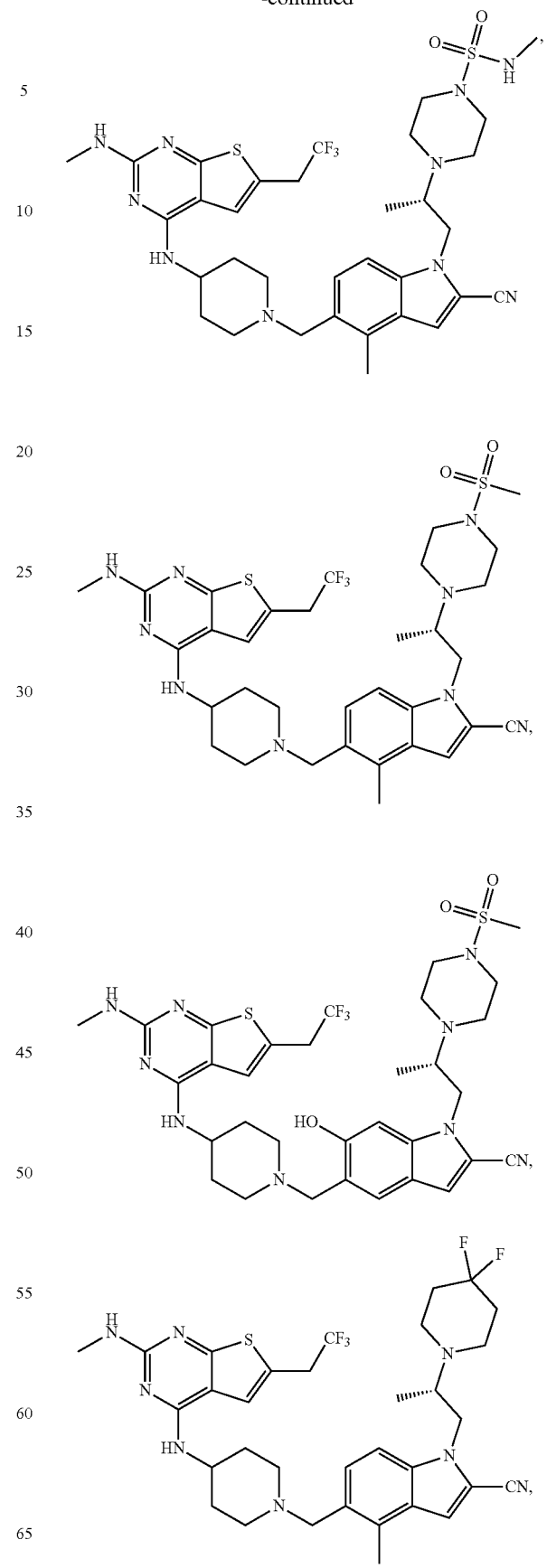

359
-continued
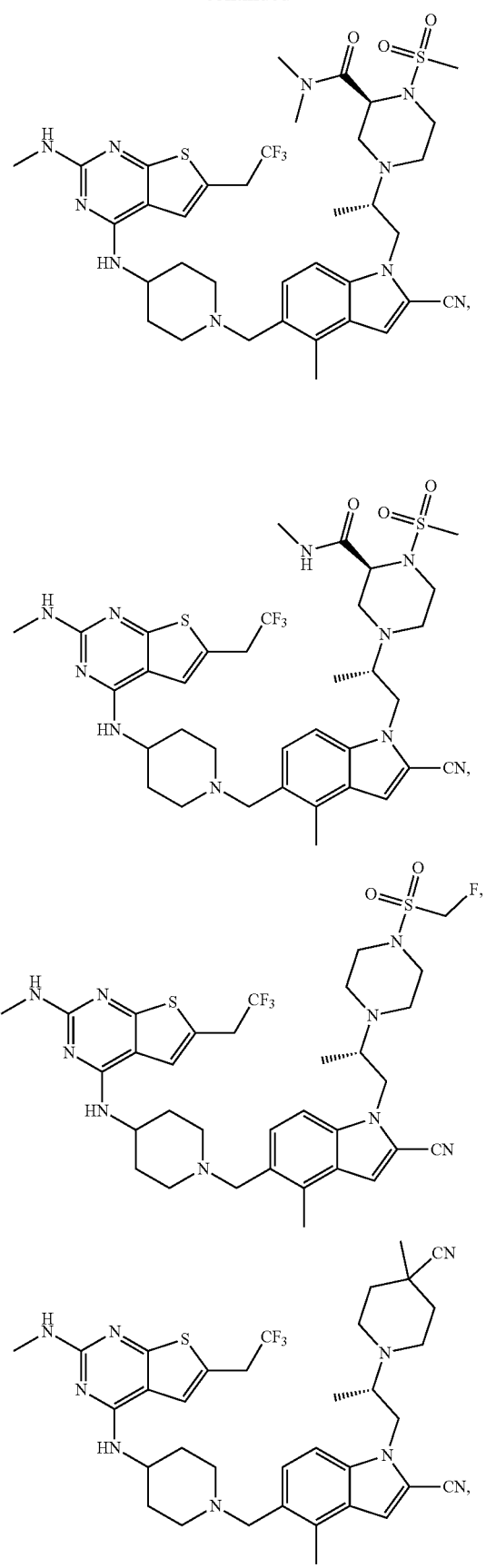
360
-continued
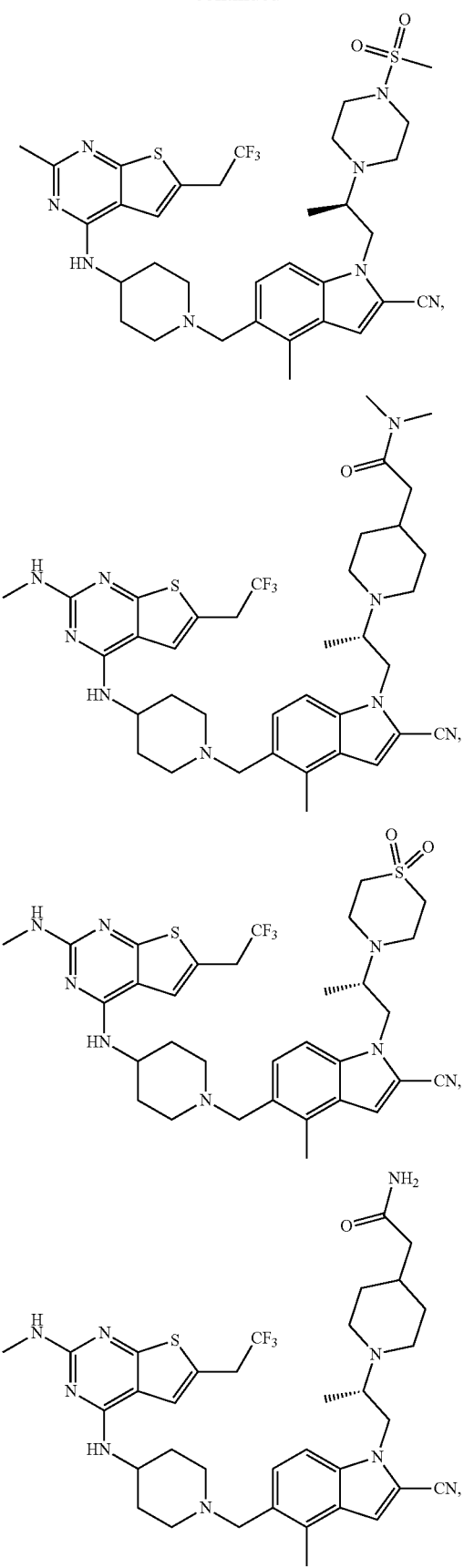

361
-continued
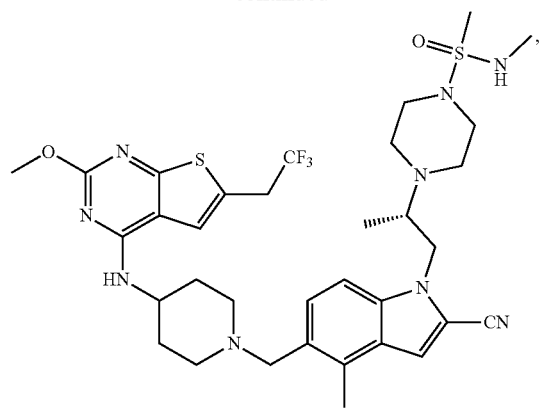
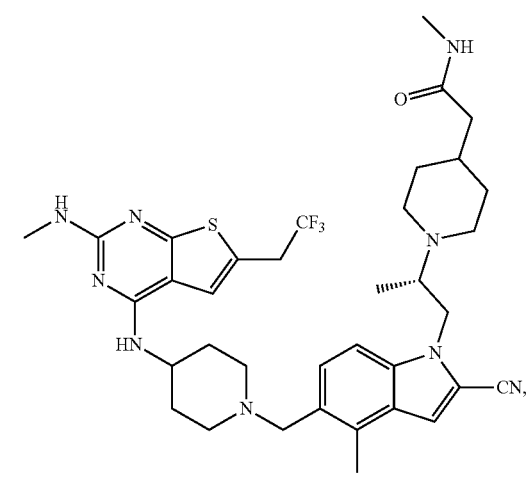
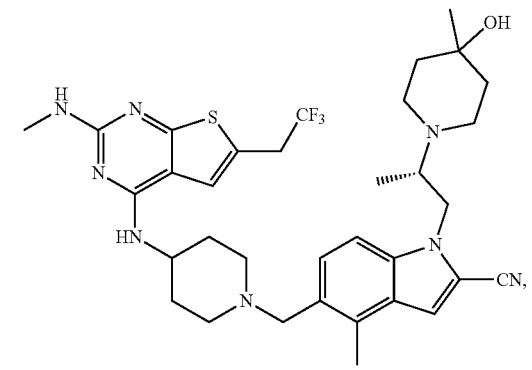
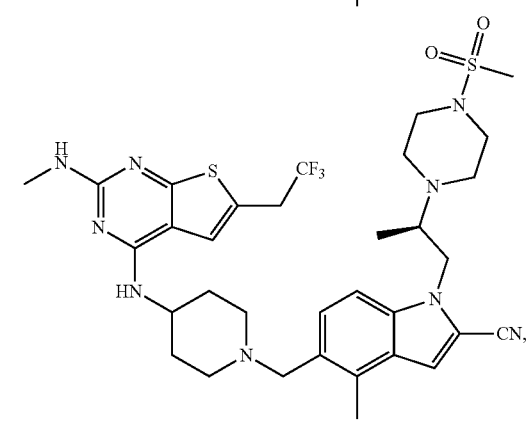
362
-continued
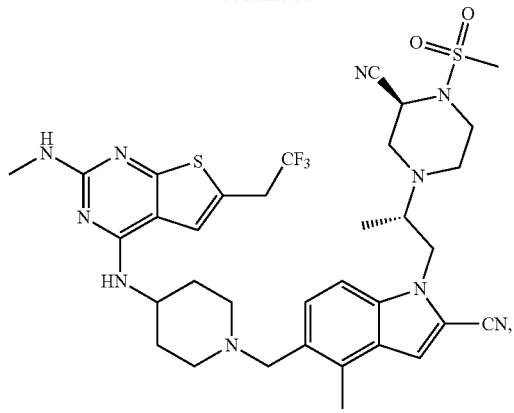
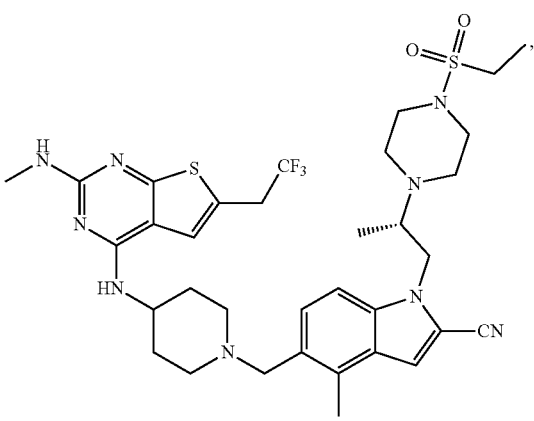
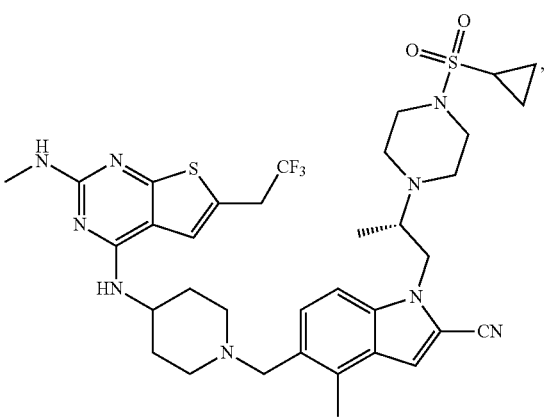
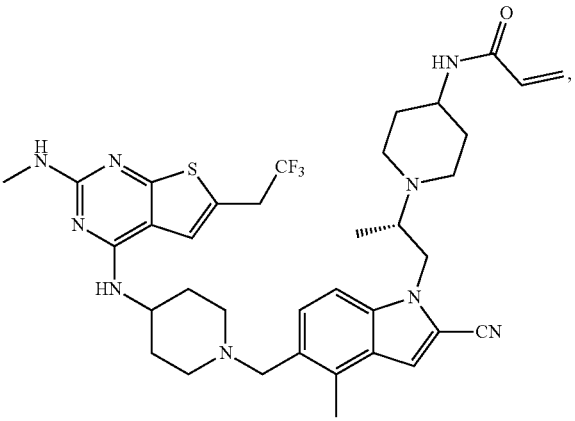

363
-continued
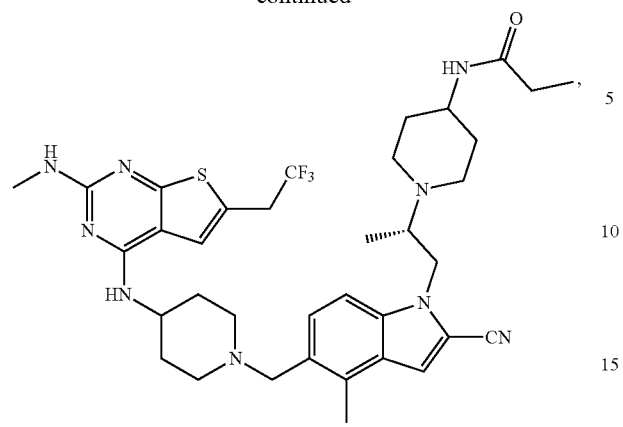
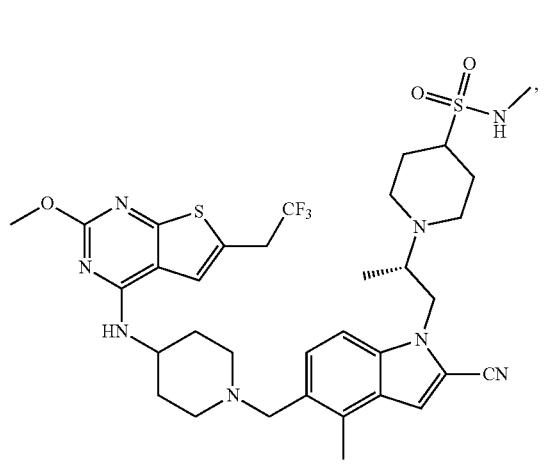
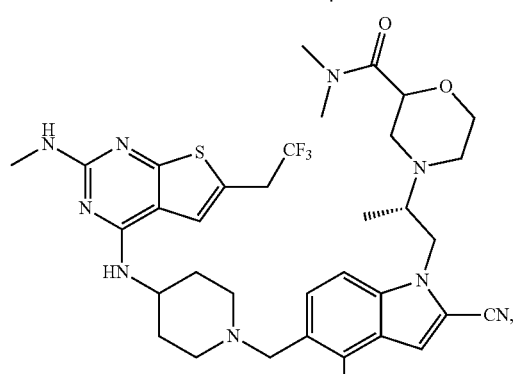
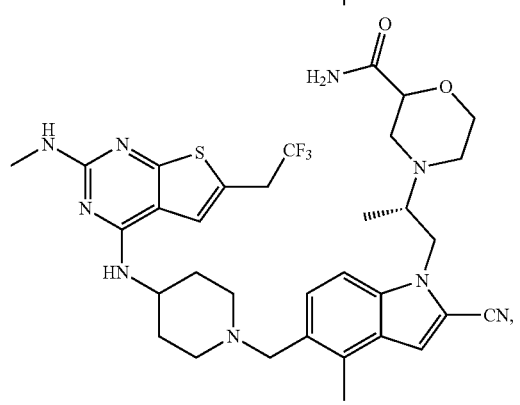
364
-continued
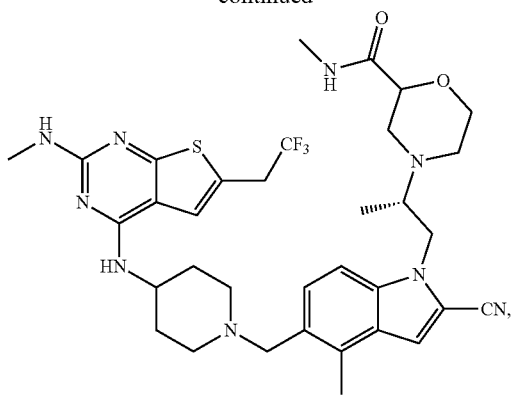
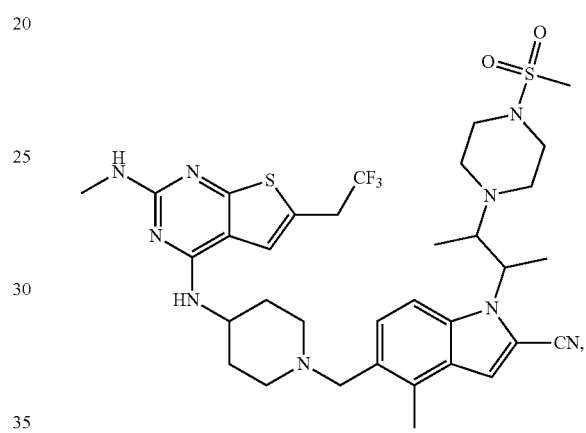
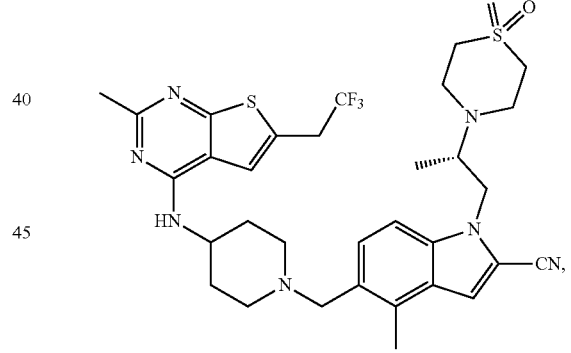
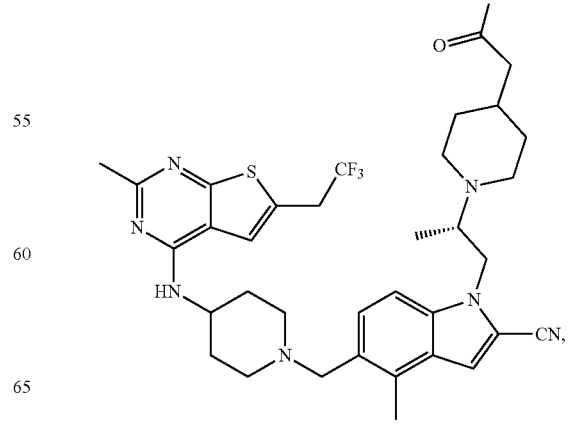

365
-continued
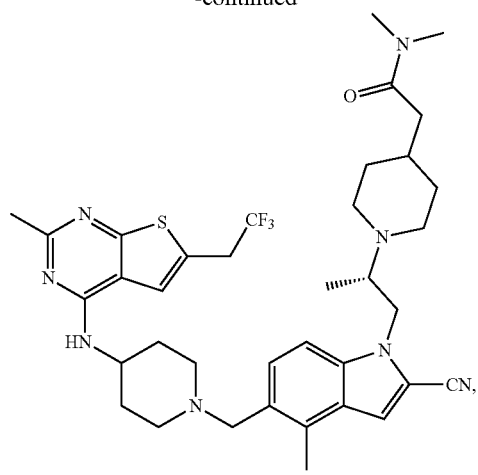
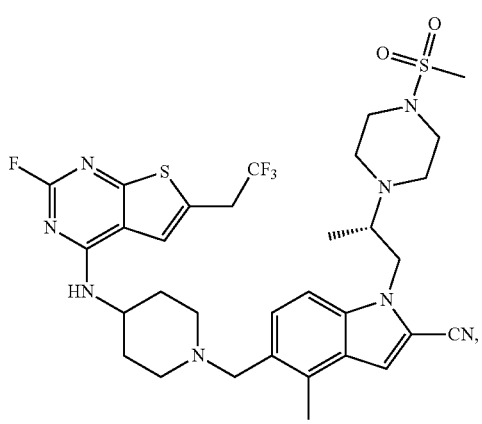
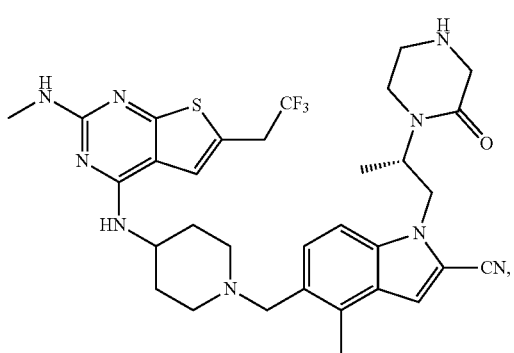
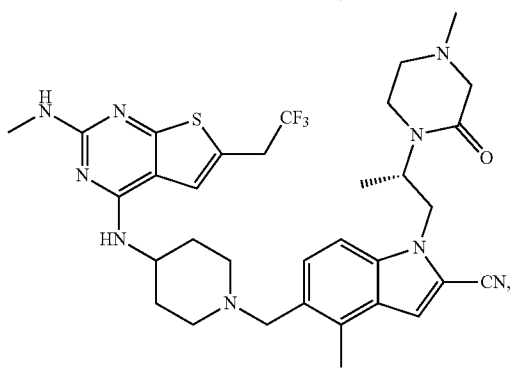
366
-continued
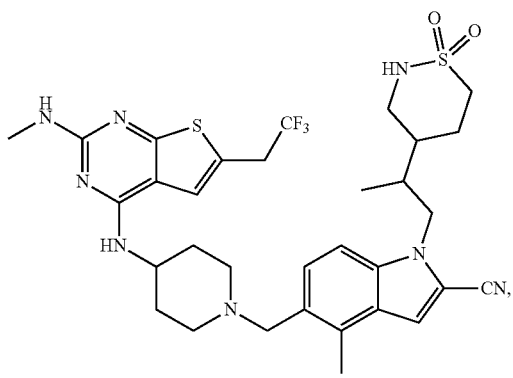
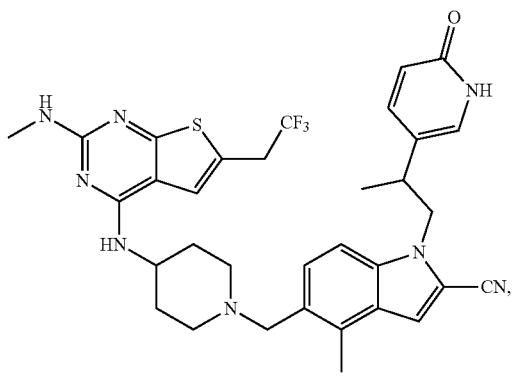
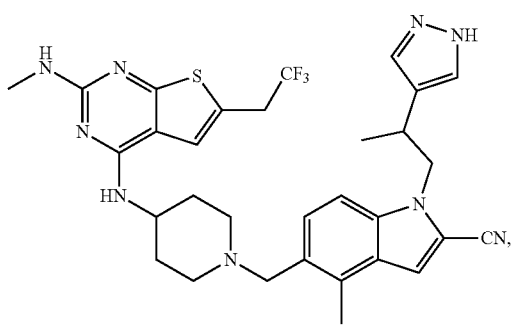
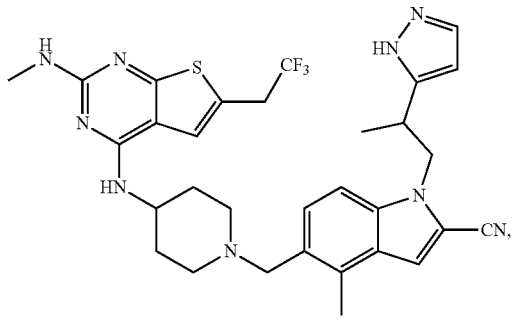

367
-continued
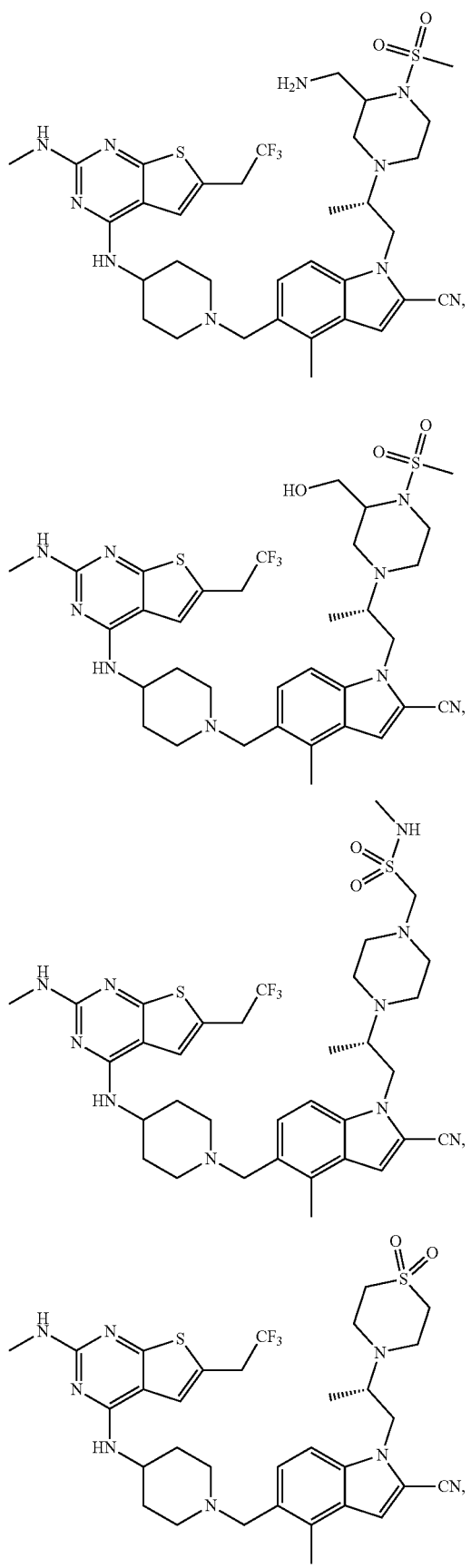
368
-continued
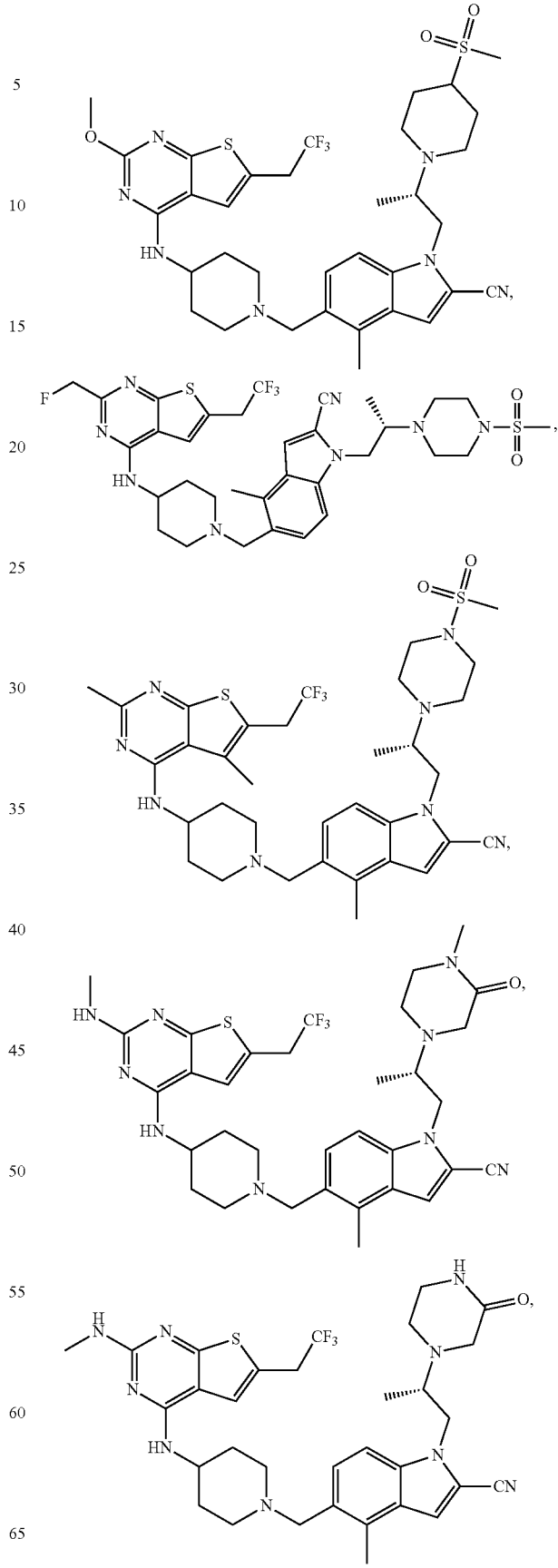

369
-continued
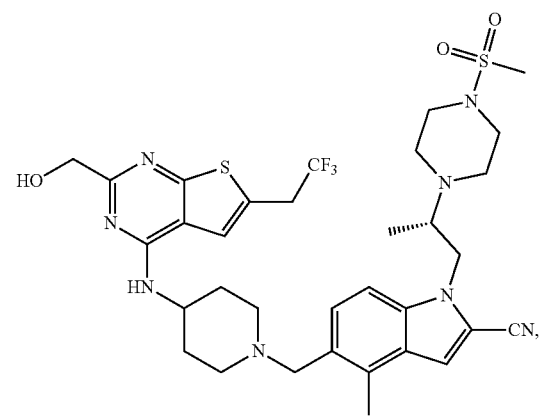
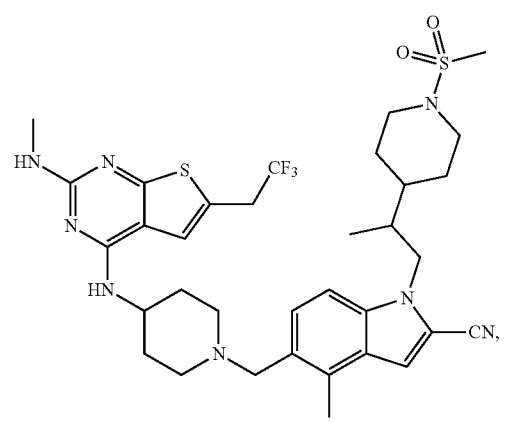
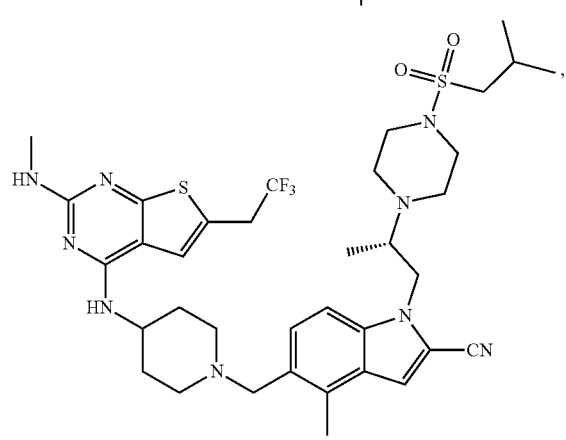
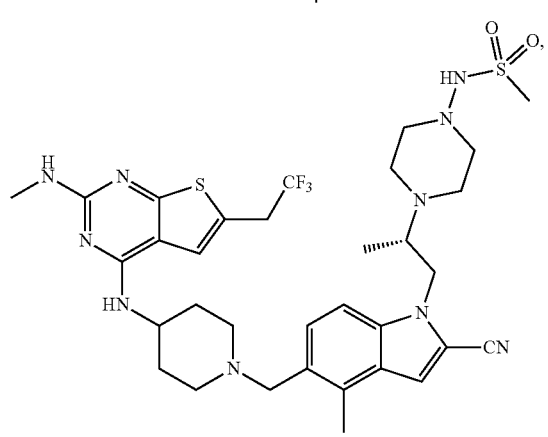
370
-continued
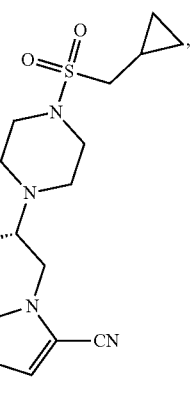
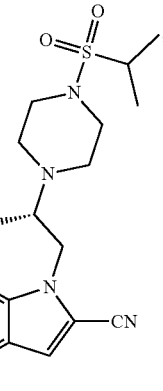
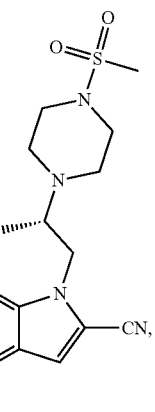
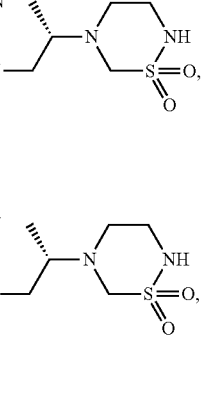

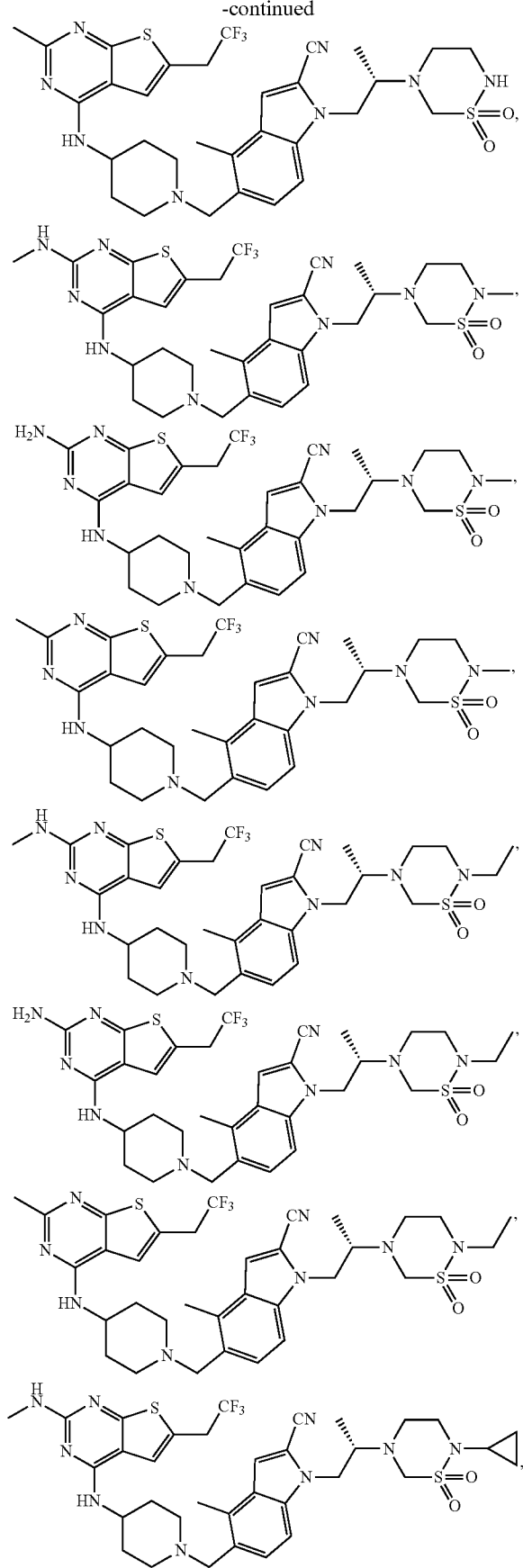
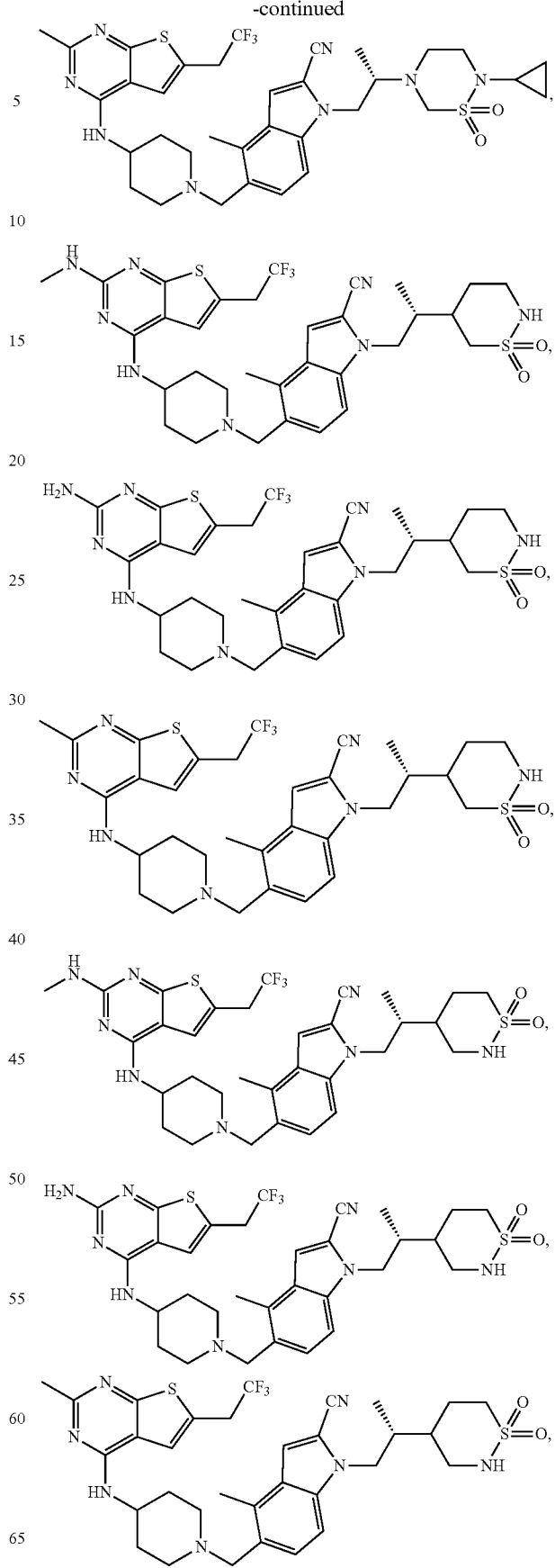

373
-continued
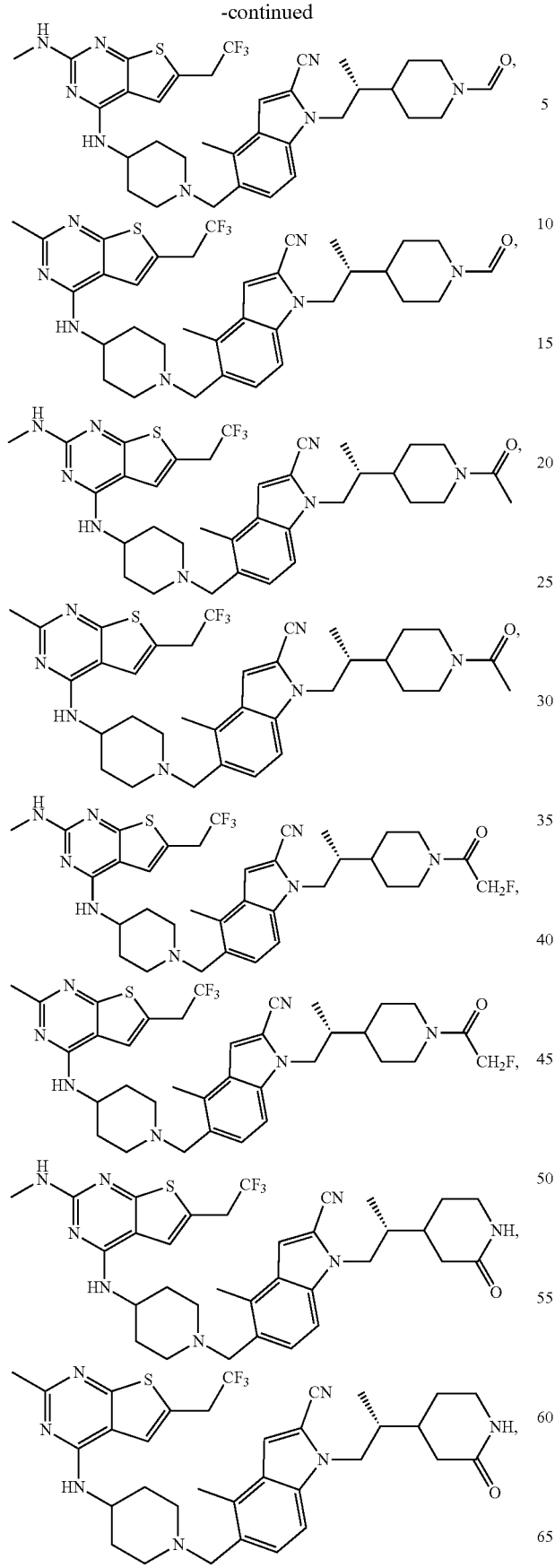
374
-continued
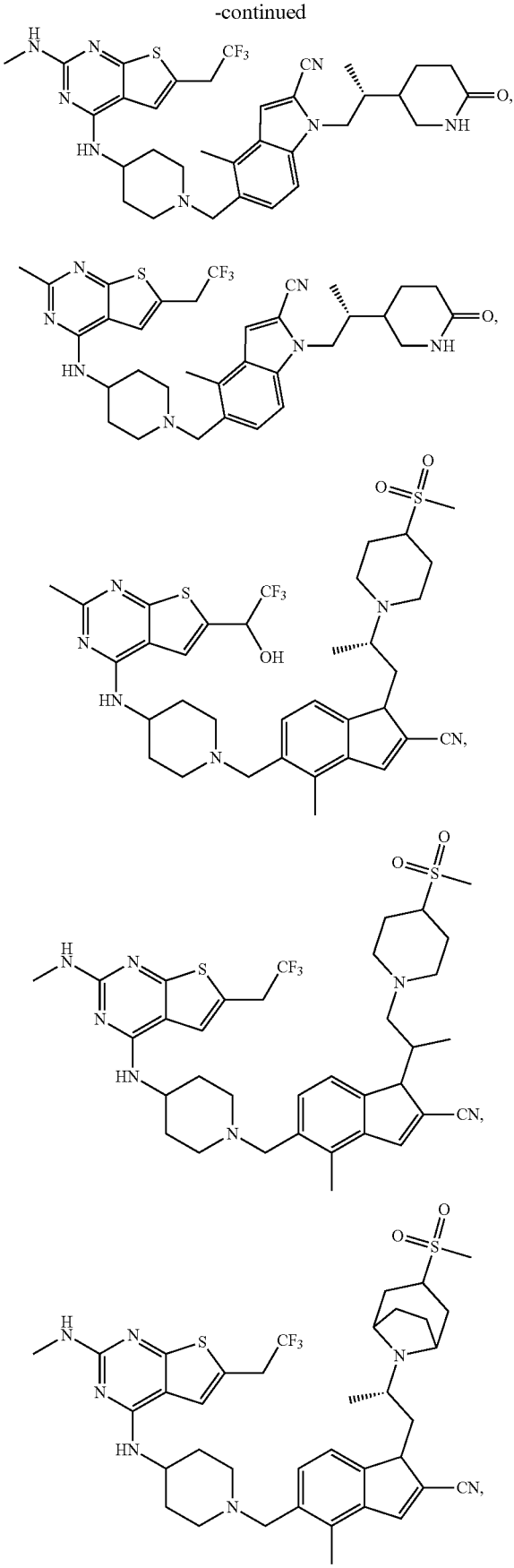

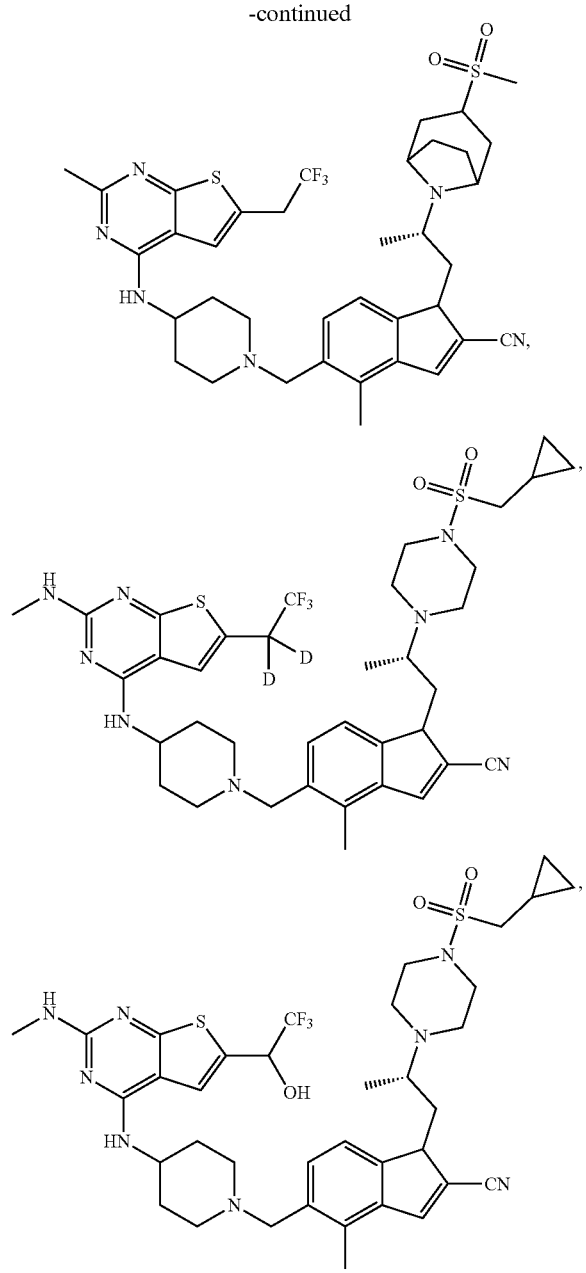
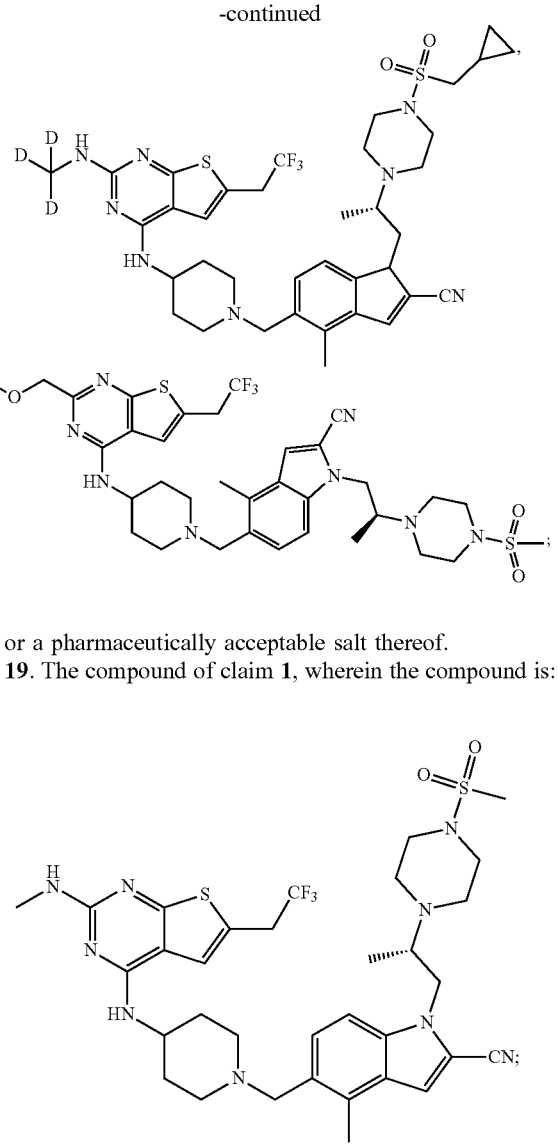
or a pharmaceutically acceptable salt thereof.
19. The compound of claim 1, wherein the compound is:
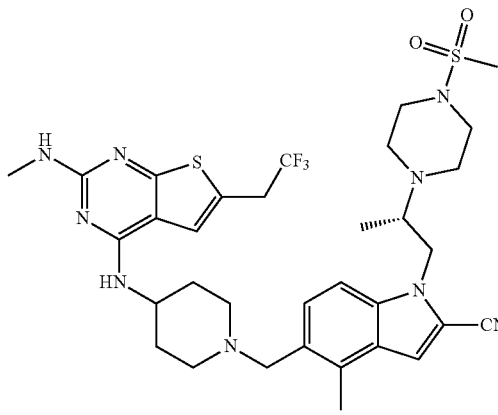
or a pharmaceutically acceptable salt thereof.
20. A pharmaceutical composition comprising a compound of claim 1 and a pharmaceutically acceptable carrier.
* * * * *